(12) United States Patent
Van Dien et al.

(10) Patent No.: US 11,401,534 B2
(45) Date of Patent: *Aug. 2, 2022

(54) MICROORGANISMS FOR THE PRODUCTION OF 1,4- BUTANEDIOL AND RELATED METHODS

(71) Applicant: Genomatica, Inc., San Diego, CA (US)

(72) Inventors: Stephen J. Van Dien, Encinitas, CA (US); Anthony P. Burgard, Elizabeth, PA (US); Robert Haselbeck, San Diego, CA (US); Catherine J. Pujol-Baxley, Santee, CA (US); Wei Niu, Lincoln, NE (US); John D. Trawick, La Mesa, CA (US); Harry Yim, Vista, CA (US); Mark J. Burk, San Diego, CA (US); Robin E. Osterhout, San Diego, CA (US); Jun Sun, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/294,753

(22) Filed: Mar. 6, 2019

(65) Prior Publication Data

US 2019/0376095 A1 Dec. 12, 2019

Related U.S. Application Data

(63) Continuation of application No. 15/148,759, filed on May 6, 2016, now Pat. No. 10,273,508, which is a continuation of application No. 13/361,799, filed on Jan. 30, 2012, now Pat. No. 9,434,964, which is a continuation of application No. 12/794,700, filed on Jun. 4, 2010, now Pat. No. 8,129,169.

(60) Provisional application No. 61/184,311, filed on Jun. 4, 2009.

(51) Int. Cl.

| C12P 7/18 | (2006.01) |
|---|---|
| C07D 307/33 | (2006.01) |
| C12P 17/04 | (2006.01) |
| C07D 307/08 | (2006.01) |
| C07D 207/267 | (2006.01) |
| C12P 17/10 | (2006.01) |
| C12N 9/04 | (2006.01) |
| C12N 9/02 | (2006.01) |
| C12N 9/10 | (2006.01) |
| C12N 9/16 | (2006.01) |
| C12N 9/88 | (2006.01) |
| C12N 9/00 | (2006.01) |
| C12N 15/52 | (2006.01) |

(52) U.S. Cl.
CPC .......... *C12P 7/18* (2013.01); *C07D 207/267* (2013.01); *C07D 307/08* (2013.01); *C07D 307/33* (2013.01); *C12N 9/001* (2013.01); *C12N 9/0006* (2013.01); *C12N 9/0008* (2013.01); *C12N 9/13* (2013.01); *C12N 9/16* (2013.01); *C12N 9/88* (2013.01); *C12N 9/93* (2013.01); *C12N 15/52* (2013.01); *C12P 17/04* (2013.01); *C12P 17/10* (2013.01)

(58) Field of Classification Search
None
See application file for complete search history.

(56) References Cited

U.S. PATENT DOCUMENTS

| 4,048,196 A | 9/1977 | Broecker et al. |
|---|---|---|
| 4,301,077 A | 11/1981 | Pesa et al. |
| 4,430,430 A | 2/1984 | Momose et al. |
| 4,652,685 A | 3/1987 | Cawse et al. |
| 4,876,331 A | 10/1989 | Doi |
| 5,164,309 A | 11/1992 | Gottschalk et al. |
| 5,245,023 A | 9/1993 | Peoples et al. |
| 5,250,430 A | 10/1993 | Peoples et al. |
| 5,286,842 A | 2/1994 | Kimura |
| 5,292,860 A | 3/1994 | Shiotani et al. |
| 5,378,616 A | 1/1995 | Tujimoto et al. |
| 5,413,922 A | 5/1995 | Matsuyama et al. |
| 5,461,139 A | 10/1995 | Gonda et al. |
| 5,475,086 A | 12/1995 | Tobin et al. |
| 5,478,952 A | 12/1995 | Schwartz |
| 5,502,273 A | 3/1996 | Bright et al. |
| 5,516,883 A | 5/1996 | Hori et al. |
| 5,534,432 A | 7/1996 | Peoples et al. |
| 5,563,239 A | 10/1996 | Hubbs et al. |

(Continued)

FOREIGN PATENT DOCUMENTS

| AU | 2010256428 B2 | 2/2016 |
|---|---|---|
| AU | 2013203177 B2 | 2/2016 |

(Continued)

OTHER PUBLICATIONS

Kizer L et al. Application of Functional Genomics to Pathway Optimization for Increased Isoprenoid Production. Applied and Environmental Microbiology, May 2008, p. 3229-3241. Vol. 74, No. 10 (Year: 2008).*

(Continued)

*Primary Examiner* — Paul J Holland

(74) *Attorney, Agent, or Firm* — Greenberg Traurig

(57) ABSTRACT

The invention provides non-naturally occurring microbial organisms comprising a 1,4-butanediol (BDO) pathway comprising at least one exogenous nucleic acid encoding a BDO pathway enzyme expressed in a sufficient amount to produce BDO and further optimized for expression of BDO. The invention additionally provides methods of using such microbial organisms to produce BDO.

20 Claims, 61 Drawing Sheets

Specification includes a Sequence Listing.

(56) References Cited

U.S. PATENT DOCUMENTS

| | | |
|---|---|---|
| 5,602,321 A | 2/1997 | John |
| 5,608,146 A | 3/1997 | Frommer et al. |
| 5,610,041 A | 3/1997 | Somerville et al. |
| 5,650,555 A | 7/1997 | Somerville et al. |
| 5,663,063 A | 9/1997 | Peoples et al. |
| 5,674,978 A | 10/1997 | Tobin et al. |
| 5,705,626 A | 1/1998 | Tobin et al. |
| 5,747,311 A | 5/1998 | Jewell |
| 5,750,848 A | 5/1998 | Krüger et al. |
| 5,770,435 A | 6/1998 | Donnelly et al. |
| 5,830,716 A | 11/1998 | Kojima et al. |
| 5,846,740 A | 12/1998 | Tobin et al. |
| 5,849,894 A | 12/1998 | Clemente et al. |
| 5,869,301 A | 2/1999 | Nghiem et al. |
| 5,908,924 A | 6/1999 | Burdette et al. |
| 5,942,660 A | 8/1999 | Gruys et al. |
| 5,958,745 A | 9/1999 | Gruys et al. |
| 5,994,478 A | 11/1999 | Asrar et al. |
| 5,998,366 A | 12/1999 | Tobin et al. |
| 6,010,870 A | 1/2000 | Pelzer et al. |
| 6,011,139 A | 1/2000 | Tobin et al. |
| 6,011,144 A | 1/2000 | Steinbuchel et al. |
| 6,022,729 A | 2/2000 | Steinbuchel et al. |
| 6,080,562 A | 6/2000 | Byrom et al. |
| 6,091,002 A | 7/2000 | Asrar et al. |
| 6,111,658 A | 8/2000 | Tabata |
| 6,117,658 A | 9/2000 | Dennis et al. |
| 6,156,852 A | 12/2000 | Asrar et al. |
| 6,159,738 A | 12/2000 | Donnelly et al. |
| 6,204,341 B1 | 3/2001 | Asrar et al. |
| 6,228,579 B1 | 5/2001 | Zyskind et al. |
| 6,228,623 B1 | 5/2001 | Asrar et al. |
| 6,248,862 B1 | 6/2001 | Asrar et al. |
| 6,277,586 B1 | 8/2001 | Tobin et al. |
| 6,280,986 B1 | 8/2001 | Hespell et al. |
| 6,316,262 B1 | 11/2001 | Huisman et al. |
| 6,329,183 B1 | 12/2001 | Skraly et al. |
| RE37,543 E | 2/2002 | Krüger et al. |
| 6,361,983 B1 | 3/2002 | Ames |
| 6,448,061 B1 | 9/2002 | Pan et al. |
| 6,448,473 B1 | 9/2002 | Mitsky et al. |
| 6,455,267 B1 | 9/2002 | Tobin et al. |
| 6,495,152 B2 | 12/2002 | Steinbuchel et al. |
| 6,515,205 B1 | 2/2003 | Liebergesell et al. |
| 6,576,450 B2 | 6/2003 | Skraly et al. |
| 6,593,116 B1 | 7/2003 | Huisman et al. |
| 6,596,521 B1 | 7/2003 | Chang et al. |
| 6,623,946 B1 | 9/2003 | Möckel et al. |
| 6,682,906 B1 | 1/2004 | Tobin et al. |
| 6,686,310 B1 | 2/2004 | Kourtakis et al. |
| 6,689,589 B2 | 2/2004 | Huisman et al. |
| 6,730,503 B1 | 5/2004 | Asakura et al. |
| 6,759,219 B2 | 7/2004 | Hein et al. |
| 6,770,464 B2 | 8/2004 | Steinbuchel et al. |
| 6,835,820 B2 | 12/2004 | Cannon et al. |
| 6,838,276 B2 | 1/2005 | Falco et al. |
| 6,897,055 B2 | 5/2005 | Nickel et al. |
| 6,913,911 B2 | 7/2005 | Huisman et al. |
| 6,916,637 B2 | 7/2005 | Rieping et al. |
| 7,052,883 B2 | 5/2006 | Rieping et al. |
| 7,067,300 B2 | 6/2006 | Emptage et al. |
| 7,081,357 B2 | 7/2006 | Huisman et al. |
| 7,125,693 B2 | 10/2006 | Davis et al. |
| 7,127,379 B2 | 10/2006 | Palsson et al. |
| 7,132,267 B2 | 11/2006 | Davis et al. |
| 7,135,315 B2 | 11/2006 | Hoshino et al. |
| 7,186,541 B2 | 3/2007 | Gokarn et al. |
| 7,223,567 B2 | 5/2007 | Ka-Yiu et al. |
| 7,229,804 B2 | 6/2007 | Huisman et al. |
| 7,256,021 B2 | 8/2007 | Hermann |
| 7,309,597 B2 | 12/2007 | Liao et al. |
| 7,314,974 B2 | 1/2008 | Cao et al. |
| 7,393,676 B2 | 7/2008 | Gokman et al. |
| 7,504,250 B2 | 3/2009 | Emptage et al. |
| 7,858,350 B2 | 12/2010 | Burk et al. |
| 7,947,483 B2 | 5/2011 | Burgard et al. |
| 8,067,214 B2 | 11/2011 | Burk et al. |
| 8,178,327 B2 | 5/2012 | Burk et al. |
| 8,357,520 B2 | 1/2013 | Burk et al. |
| 8,969,054 B2 | 3/2015 | Burk et al. |
| 9,487,803 B2 | 11/2016 | Burk et al. |
| 2002/0012939 A1 | 1/2002 | Palsson |
| 2002/0164729 A1 | 11/2002 | Skraly et al. |
| 2002/0168654 A1 | 11/2002 | Maranas et al. |
| 2003/0059792 A1 | 3/2003 | Palsson et al. |
| 2003/0203459 A1 | 10/2003 | Chen et al. |
| 2003/0224363 A1 | 12/2003 | Park et al. |
| 2003/0233218 A1 | 12/2003 | Schilling |
| 2003/0233675 A1 | 12/2003 | Cao et al. |
| 2004/0009466 A1 | 1/2004 | Maranas et al. |
| 2004/0023347 A1 | 2/2004 | Skraly |
| 2004/0029149 A1 | 2/2004 | Palsson et al. |
| 2004/0072723 A1 | 4/2004 | Palsson et al. |
| 2004/0096946 A1 | 5/2004 | Kealey et al. |
| 2004/0106176 A1 | 6/2004 | Skraly |
| 2004/0152159 A1 | 8/2004 | Causey et al. |
| 2004/0152166 A1 | 8/2004 | Mockel |
| 2005/0042736 A1 | 2/2005 | San et al. |
| 2005/0090645 A1 | 4/2005 | Asakura |
| 2005/0164342 A1 | 7/2005 | Tobin |
| 2005/0170480 A1 | 8/2005 | Huisman |
| 2005/0221466 A1 | 10/2005 | Liao et al. |
| 2005/0239179 A1 | 10/2005 | Skraly et al. |
| 2005/0287655 A1 | 12/2005 | Tabata et al. |
| 2006/0041152 A1 | 2/2006 | Cantrell et al. |
| 2006/0046288 A1 | 3/2006 | Ka-Yiu et al. |
| 2006/0084155 A1 | 4/2006 | Huisman et al. |
| 2006/0134760 A1 | 6/2006 | Rieping |
| 2006/0141594 A1 | 6/2006 | San et al. |
| 2007/0072279 A1 | 3/2007 | Meynial-Salles et al. |
| 2007/0087425 A1 | 4/2007 | Ohto |
| 2007/0184539 A1 | 8/2007 | San et al. |
| 2007/0190605 A1 | 8/2007 | Bessler et al. |
| 2007/0259410 A1 | 11/2007 | Donaldson et al. |
| 2007/0292927 A1 | 12/2007 | Donaldson et al. |
| 2008/0120732 A1 | 5/2008 | Elliot |
| 2008/0138870 A1 | 6/2008 | Bramucci et al. |
| 2008/0171371 A1 | 7/2008 | Yukawa et al. |
| 2008/0182308 A1 | 7/2008 | Donaldson et al. |
| 2008/0229451 A1 | 9/2008 | Cao et al. |
| 2008/0261230 A1 | 10/2008 | Liao et al. |
| 2008/0274524 A1 | 11/2008 | Bramucci et al. |
| 2008/0274525 A1 | 11/2008 | Bramucci et al. |
| 2008/0274526 A1 | 11/2008 | Bramucci et al. |
| 2008/0293125 A1 | 11/2008 | Subbian et al. |
| 2009/0023182 A1 | 1/2009 | Schilling |
| 2009/0047719 A1 | 2/2009 | Burgard et al. |
| 2009/0075351 A1 | 3/2009 | Burk et al. |
| 2009/0100536 A1 | 4/2009 | Adams et al. |
| 2009/0158452 A1 | 6/2009 | Johnson et al. |
| 2009/0246842 A1 | 10/2009 | Hawkins et al. |
| 2009/0253192 A1 | 10/2009 | Emptage et al. |
| 2009/0275096 A1 | 11/2009 | Burgard et al. |
| 2010/0099925 A1 | 4/2010 | Kharas |
| 2010/0112654 A1 | 5/2010 | Burk et al. |
| 2010/0184171 A1 | 7/2010 | Jantama et al. |
| 2010/0304453 A1 | 12/2010 | Trawick et al. |
| 2010/0330634 A1 | 12/2010 | Park et al. |
| 2011/0014669 A1 | 1/2011 | Madden et al. |
| 2011/0045575 A1 | 2/2011 | Van Dien et al. |
| 2011/0129904 A1 | 6/2011 | Burgard et al. |
| 2011/0190513 A1 | 8/2011 | Lynch |
| 2011/0294178 A1 | 12/2011 | Soucaille et al. |
| 2013/0109069 A1 | 5/2013 | Burk et al. |
| 2014/0120595 A1 | 5/2014 | Lynch |

FOREIGN PATENT DOCUMENTS

| | | |
|---|---|---|
| EP | 1710302 A1 | 10/2006 |
| EP | 2438178 B1 | 3/2018 |
| GB | 1230276 | 4/1971 |
| GB | 1314126 | 4/1973 |
| GB | 1344557 | 1/1974 |
| GB | 1512751 | 6/1978 |

(56) References Cited

FOREIGN PATENT DOCUMENTS

| | | |
|---|---|---|
| JP | 62285779 | 12/1987 |
| JP | 5530057 | 4/2014 |
| KR | 1020060011345 A | 2/2006 |
| KR | 100676160 B1 | 1/2007 |
| KR | 100679638 B1 | 1/2007 |
| KR | 1020070021732 A | 2/2007 |
| KR | 1020070096348 A | 2/2007 |
| KR | 10-2009-0025902 | 3/2009 |
| WO | WO 1982/003854 | 11/1982 |
| WO | WO 1991/000917 | 1/1991 |
| WO | WO 1992/019747 | 11/1992 |
| WO | WO 1993/002187 | 2/1993 |
| WO | WO 1993/002194 | 4/1993 |
| WO | WO 1993/006225 | 4/1993 |
| WO | WO 1994/011519 | 5/1994 |
| WO | WO 1994/012014 | 6/1994 |
| WO | WO 1995/011985 | 5/1995 |
| WO | WO 1999/006532 | 2/1999 |
| WO | WO 1999/014313 | 3/1999 |
| WO | WO 2000/061763 | 10/2000 |
| WO | WO 2002/055995 | 7/2002 |
| WO | WO 2002/061115 | 8/2002 |
| WO | WO 2003/008603 | 1/2003 |
| WO | WO 2003/106998 | 12/2003 |
| WO | WO 2004/018621 | 3/2004 |
| WO | WO 2004/029235 | 4/2004 |
| WO | WO 2005/026338 | 3/2005 |
| WO | WO 2005/052135 | 6/2005 |
| WO | WO 2006/031424 | 3/2006 |
| WO | WO 2007/030830 | 3/2007 |
| WO | WO 2007/141208 | 12/2007 |
| WO | WO 2008/018930 | 2/2008 |
| WO | WO 2008/027742 | 6/2008 |
| WO | WO 2008/115840 | 9/2008 |
| WO | WO 2008/116848 | 10/2008 |
| WO | WO 2008/116852 | 10/2008 |
| WO | WO 2008/131286 | 10/2008 |
| WO | WO 2008/144626 | 11/2008 |
| WO | WO 2009/011974 | 1/2009 |
| WO | WO 2009/023493 | 2/2009 |
| WO | WO 2009/031766 | 3/2009 |
| WO | WO 2009/049274 | 4/2009 |
| WO | WO 2009/094485 | 7/2009 |
| WO | WO 2009/103026 | 8/2009 |
| WO | WO 2009/111513 | 9/2009 |
| WO | WO 2009/131040 | 10/2009 |
| WO | WO 2010/006076 | 1/2010 |
| WO | WO 2010/030711 | 3/2010 |
| WO | WO 2010/085731 | 7/2010 |
| WO | WO 2011/137192 | 11/2011 |

OTHER PUBLICATIONS

Prather KLJ et al. De novo biosynthetic pathways: rational design of microbial chemical factories. Current Opinion in Biotechnology 2008, 19:468-474. (Year: 2008).*

Abe et al., "Biosynthesis from gluconate of a random copolyester consisting of 3-hydroxybutyrate and medium-chain-length 3-hydroxyalkanoates by Pseudomonas sp. 61-3," Int. J. Biol. Macromol., 16(3):115-119 (1994).

Aberhart et al., "Stereospecific hydrogen loss in the conversion of [PH7]isobutyrate to beta-hydroxyisobutyrate in Pseudomonas putida. The stereochemistry of beta-hydroxyisobutyrate dehydrogenase," *J. Chem. Soc. Perkin1* ., 6:1404-1406 (1979).

Abiko et al., "Localization of NAD-isocitrate dehydrogenase and glutamate dehydrogenase in rice roots: candidates for providing carbon skeletons to NADH-glutamate synthase," *Plant Cell Physiol.*, 46(10):1724-1734 (2005).

Adams et al., "Oxidoreductase-type enzymes and redox proteins involved in fermentative metabolisms of hyperthermophilic Archaea," *Adv. Protein Chem.*, 48:101-180 (1996).

Aevarsson et al., "Crystal structure of 2-oxoisovalerate and dehydrogenase and the architecture of 2-oxo acid dehydrogenase multienzyme complexes," *Nat. Struct. Biol.*, 6:785-792 (1999).

Aidoo et al., "Cloning, sequencing and disruption of a gene from Streptomyces clavuligerus Involved in clavulanic acid biosynthesis," *Gene*, 147(1):41-46 (1994).

Alber et al., "Malonyl-coenzyme a reductase in the modified 3-hydroxypropionate cycle for autotrophic carbon fixation in archaeal Metallosphaera and Sulfolobus spp.," *J. Bacteriol.*, 188:8551-8559 (2006).

Alberty, "Biochemical thermodynamics," *Biochim. Biophys. Acta*, 1207:1-11 (1994).

Alhapel et al., "Molecular and functional analysis of nicotinate catabolism in Eubacterium barkeri," *Proc. Natl. Acad. Sci. U.S.A,*. 103(33)12341-12346 (2006).

Allen et al., "DNA sequence of the putA gene from Salmonella typhimurium: a bifunctional membrane-associated dehydrogenase that binds Dna," *Nucleic Acids Res.*, 21:1676 (1993).

Amarasingham et al., "Regulation of alpha-ketoglutarate dehydrogenase formation in *Escherichia coli,*" *J. Biol. Chem.*, 240: 3664-3668 (1965).

Amos et al., "Composition of poly-.beta.-hydroxyalkanoate from Syntrophomonas wottei grown on unsaturated fatty acid substrates," *Arch. Microbiol.*, 155:103-106 (1991).

Amuro et al., "Isolation and characterization of the two distinct genes for human glutamate dehydrogenase," *iochem. Biophys. Acta.*, 1049:216-218 (1990).

Andersen et al., "A gene duplication led to specialized gamma-aminobutyrate and beta-alaine aminotransferase in yeast," *FEBS J*, 274(7):1804-1817 (2007).

Andersen et al., "Cloning of the lysA gene from *Mycobacterium tuberculosis,*" *Gene*, 124:105-109 (1993).

Andre et al., "Nucleotide sequence of the yeast UGA1 gene encoding GABA transaminase," *Nucleic Acids Res.*, 18:3049 (1990).

Aneja et al., "Poly-3-hydroxybutyrate degradation in Rhizobium (Sinorhizobium) meliloti: isolation and characterization of a gene encoding 3-hydroxybutryate dehydrogenase," *J. Bacteriol.*, 181(3):849-857 (1999).

Ansorge et al., "Production of Recombinant L-Leucine Dehydrogenase from Bacillus cereus in Pilot Scale Using the Runaway Replication System *E. coli*[pIET98]," *Biotechnol. Bioeng.*, 68(5):557-562 (2000).

Aoshima et al., "A novel biotin protein required for reductive carboxylation of 2-oxoglutarate by isocitrate dehydrogenase in Hydrogenobacter thermophilus TK-6,"*Mol. Microbiol.*, 51(3):791798 (2004).

Aoshima et al., "A novel oxalosuccinate-forming enzyme involved in the reductive carboxylation of 2-oxoglutarate in Hydrogenobacter thermophilus TK-6," *Mol. Microbiol.,*. 62(3):748-759 (2006).

Aragon et al., "A survey of enzymes which generate or use acetoacetyl thioesters in rat liver," *J Biol. Chem.*, 258(8):4725-4733 (1983).

Arikawa et al., "Soluble fumarate reductase isoenzymes from *Saccharomyces cerevisiae* are required for anaerobic growth," *FEMS Microbiol. Lett.*, 165:111-116 (1998).

Arps et al., "Genetics of Serine Pathway Enzymes in Methylobacterium extorquens AM1: Phosphoenolpyruvate Carboxylase and Malyl Coenzyme ALyase," *J Bacteriol.*, 175(12):3776-3783 (1993).

Asano et al., "Alteration of substrate specificity of aspartase by directed evolution," *Biomol. Eng.*, 22:95-101 (2005).

Asano et al., "Crystalline 3-methylaspartase from a facultative anaerobe, *Escherichia coli* strain YG1002," *FEMS Microbiol. Lett.*, 118(3):255-258 (1994).

Asaoka et al., "Production of 1,4-butanediol from bacillus which is fermented on sugar substrate, from which production is recovered," *Chiyoda Chem. Eng. Constr. Co.*, (Official Publication Date 1987). Database WPI Week 198804 Thomson Scientific, London, GB; AN 1988-025175.

Asuncion et al., "Overexpression, purification, crystallization and data collection of 3-methylaspartase from Clostridium tetanomorphum," *Acta Crystallogr.D. Biol. Crystallogr.*, 57:731-733 (2001).

Asuncion et al., "The Structure of 3-Methylaspartase from Clostridium tetanomorphum Functions via the Common Enolase Chemical Step," *J Biol. Chem.*, 277(10):8306-8311 (2002).

(56) References Cited

OTHER PUBLICATIONS

Atsumi et al., "Non-fermentative pathways for synthesis of branched-chain higher alcohols as biofuels," Nature, 451(7174):86-89 (2008).
Baba et al., "Construction of Escherichia coli K-12 in-frame, single-gene knockout mutants: the Keio collection," Mol. Syst. Biol., 2:2006.0008 (2006).
Baker et al., "Purification and properties of L-erythro-3,5-diaminohexanoate dehydrogenase from Clostridium sticklandii," Biochemistry, 13(2):292-299 (1974).
Baker et al., "Purification and properties of L-erythro-3,5-diaminohexanoate dehydrogenase from a lysine-fermenting Clostirdium," J Biol. Chem., 247(23):7724-7734 (1972).
Barker et al., "Butyryl-CoA:acetoacetate CoA-transferase from a lysine-fermenting Clostridium," J Biol. Chem., 253(4):1219-1225 (1978).
Barker et al., "Pathway of Lysine Degradation in Fusobacterium nucleatum," J Bacteriol., 152(1):201-207 (1982).
Barrowman et al "Immunological comparison of microbial TPP-dependent non-oxidative alpha-keto acid decarboxylase," FEMS Microbiology Lett., 34:57-60 (1986).
Barthelmebs et al., "Expression of Escherichia coli of Native and Chimeric Phenolic Acid Decarboxylases with Modified Enzymatic activites and Method for Scrreening recombinant E. coli Strains Expressing These Enzymes," Appl. Environ. Microbiol., 67:1063-1069 (2001).
Bartsch et al., "Molecular analysis of two genes of the Escherichia coli gab cluster: nucleotide sequence of the glutamate:succinic semialdehyde transaminase gene (gabT) and characterization of the succinic semialdehyde dehydrogenase gene (gabD)," J Bacteriol., 172:7035-7042 (1990).
Baum et al., "A plant glutamate decarboxylase containing a calmodulin binding domain, Cloning, sequence, and functional analysis," J. Biol. Chem., 268:19610-19617 (1993).
Benachenhou-Lahfa et al., "PCR-mediated cloning and sequencing of the gene encoding glutamate dehydrogenase from the archaeon Sulfolobus shilbatae: Identification of putative amino-acid signatures for extremophilic adaptation," Gene, 140:17-24 (1994).
Berg et al., "A 3-Hydroxypropionate/4-Hydroxybutyrate Autotrophic Carbon Dioxide Assimilation Pathway in Archaea," Science, 318:1782-1786 (2007).
Bergquist et al., "Degenerate oligonucleotide gene shuffling (DOGS) and random drift mutagenesis (RNDN): two complementary techniques for enzyme evolution," Biomol. Eng., 22:63-72 (2005).
Bergquist et al., "Degenerate oligonucleotide gene shuffling," Methods Mol. Biol., 352:191-204 (2007).
Berkovitch et al., "A locking mechanism preventing radical damage in the absence of substrate, as revealed by the x-ray structure of lysine 5,6-aminomutase," Proc. Natl. Acad. Sci. U.S.A., 101:15870-15875 (2004).
Bermejo et al., "Expression of Clostridium acetobutylicum ATCC 824 Genes in Escherichia coli for Acetone Production and Acetate Detoxification," Appl. Environ. Microbiol., 64(3):1079-1085 (1998).
Biellmann et al., "Aspartate-beta-semialdehyde dehydrogenase from Escherichia coli. Purification and general properties," Eur. J Biochem., 104(1):53-58 (1980).
Biello, "Turning Bacteria into Plastic Factories," cientific American, 1-2 (2008). (Printed Feb. 17, 2011).
Binstock et al., "Fatty acid oxidation complex from Escherichia coli," Methods Enzymol., 71 Pt C:403-411 (1981).
Birrer et al., "Electro-transformation of Clostridium beijerinckii NRRL B-592 with shuttle plasmid pHR106 and recombinant derivatives," Appl. Microbiol. Biotechnol., 41(1):32-38 (1994).
Bisswanger, "Substrate Specificity of the Pyruvate Dehydrogenase Complex from Escherichi coli," J Biol. Chem., 256(2):815-822 (1981).
Blanco et al., "Critical catalytic functional groups in the mechanims of aspartate-β-semialdehyde dehydrogenase," Acta Crystallogr. D. Biol. Crystallogr., 60:1808-1815 (2004).

Blanco et al., "The role of substrate-binding roups in the mechanism of asparte-β-semialdehyde dehydrogenase," Acta Crystallogr. D. Biol. Crystallog., 60:1388-1395 (2004).
Blattner et al., "The complete genome sequence of Escherichia coli K-12," Science, 277:1453-1462 (1997).
Boles et al., "Characterization of a glucose-repressed pyruvate kinase (Pyk2p) in Saccharomyces cerevisiae that is catalytically insensitive to fructose-1,6-bisphosphate," J. Bacteriol., 179:2987-2993 (1997).
Bonnarme et al., "Itaconate biosynthesis in Aspergillus terreus," J. Bacteriol., 177(12):3573-3578 (1995).
Bonner et al., "Purification and Properties of Fatty Acyl Thiesterase I from Escherichia coli," J Biol. Chem., 247(10) 3123-3133 (1972).
Botsford et al., "Accumulation of glutamate by Salmonella typhimurium in response to osmotic stress," Appl. Environ. Microbiol., 60:2568-2574 (1994).
Botting et al., "Substrate Specificity of the 3-Methylaspartate Ammonia-Lyase Reaction: Observation of Differential Relative Reaction rates for Substrate-Product Pairs," Biochemistry, 27:2953-2955 (1988).
Bower et al., "Cloning, Sequencing, and Characterization of the Bacillus subtilis Biotin Biosynthetic Operon," J Bacteriol., 178(14):4122-4130 (1996).
Boynton et al., "Cloning, sequencing, and expression of clustered genes encoding beta-hydroxybutyryl-coenzyme A (CoA) dehydrogenase, crotonase, and butyryl-CoA dehydrogenase from Clostridium acetobutylicum ATCC 824," J Bateriol., 178(11):3015-3024 (1996).
Branden et al., "Introduction to Protein Structure," Garland Publishing Inc., New York, p. 247 (1991).
Brandl et al., "Ability of the phototrophic bacterium Rhodospirillum rubrum to produce various poly (beta-hydroxyalkanoates): potential sources for biodegradable polyesters," Int. J Biol. Macromol., 11:49-55 (1989).
Branlant et al., "Nucleotide sequence of the Escherichia coli gap gene. Differente evolutionay behaviour of the Nad+-binding domain and of the catalytic domain of D-glyceraldehyde-3-phosphate dehydrogenase," Eur. J. Biochem., 150(1):61-66 (1985).
Brasen et al., "Unusual ADP-forming acetyl-coenzyme A synthetases from the mesophilic halophilic eurarchaeon Haloarcula marismortui and from the hyperthermophilic crenarchaeon Pyrobaculum aerophilum," Arch. Microbiol., 182:277-287 (2004).
Bravo et al., "Reliable, sensitive, rapid and quantitative enzyme-based assay for gamma-hydroxybutyric acid (GHB)," J. Forensic Sci., 49:379-387 (2004).
Breitkreuz et al., "A novel gamma-hydroxybutyrate dehydrogenase: identification and expression of an Arabidopsis cDNA and potential role under oxygen deficiency," J. Biol. Chem., 278:41552-41556 (2003).
Bremer, "Pyruvate Dehydrogenase, Substrate Specificity and Product Inhibition," Eur. J Biochem., 8:535-540 (1969).
Bridger et al., "The subunits of succinyl-coenzyme. A synthetase—function and assembly," in Krebs Citric Acid Cycle- Half a Century and Still Turning, Biochem. Soc. Symp., 54:103-111 (1987).
Brosch et al., "Genome plasticity of BCG and impact on vaccine efficacy," Proc. Natl. Acad. Sci. U.S.A., 104(13):5596-5601 (2007).
Bu et al., "Two human glutamate decarboxylases, 65-kDa Gad and 67-kDa Gad, are each encoded by a single gene," Proc. Natl. Acad. Sci. U.S.A., 89(6):2115-2119 (1992).
Bu, et al., "The exon-intron organization of the genes (GAD1 and GAD2) encoding two human glutamate decarboxylases (GAD67 and GAD65) suggests that they derive from a common ancestral Gad," Genomics, 21:222-228 (1994).
Buck et al., "Primary Structure of the Succinyl-CoA Synthetase of Escherichia coli," Biochemistry, 24:6245-6252 (1985).
Buck et al., "Cloning and expression of the succinyl-CoA synthetase genes of Escherichia coli K12," J. Gen. Microbiol., 132(6):1753-1762 (1986).
Buck et al., "Overexpression and site-directed mutagenesis of the succinyl-CoA synthetase of Escherichia coli and nucleotide sequence of a gene (g30) that is adjacent to the suc operon," Biochem. J., 260(3):737-747 (1989).
Buckel et al., "Glutaconate CoA-Transferase from Acidaminococcus fermentans," Eur. J. Biochem., 118:315-321 (1981).

(56) References Cited

OTHER PUBLICATIONS

Bult et al., "Complete genome sequence of the methanogenic archaeon, Methanococcus jannaschii," *Science*, 273:1058-1073 (1996).
Burgard et al., "Minimal Reaction Sets for *Escherichia coli* Metabolism under Different Growth Requirements and Uptake Environments," *Biotechnol. Prog.*, 17:791-797 (2001).
Burgard et al., "Optknock: a bilevel programming framework for identifying gene knockout strategies for microbial strain optimization," *Biotechnol. Bioeng.*, 84(6):647-657 (2003).
Burgard et al., "Probing the Performance Limits of the *Escherichia coli* Metabolic Network Subject to Gene Additions or Deletions," *Biotechnol. Bioeng.*, 74(5):364-375 (2001).
Burke et al, "The Isolation, Characterization, and Sequence of the Pyruvate Kinase Gene of *Saccharomyces cerevisiae*," *J Biol. Chem.*, 258(4):2193-2201 (1983).
Buu et al., "Functional Characterization and Localization of Acetyl-CoA Hydrolase, Ach1p, in *Saccharomyces cerevisiae*," *J. Biol. Chem.*, 278(19):17203-17209 (2003).
Campbell et al., "A new *Escherichia coli* metabolic competency: growth on fatty acids by a novel anaerobic 13-oxidation pathway," *Mol. Microbiol.*, 47(3):793-805 (2003).
Cary et al., "Cloning and expression of Clostridium acetobutylicum ATCC 824 acetoacetyl-coenzyme A:acetate/butyrate:coenzyme A-transferase in *Escherichia coli*," *Appl. Environ. Microbiol.*, 56(6):1576-1583 (1990).
Cary et al., "Cloning and expression of Clostridium acetobutylicum phosphotransbutyrylase and butyrate kinase genes in *Escherichia coli*," *J Bacteriol.*, 170(10):4613-4618 (1988).
Caspi et al., "MetaCyc: a multiorganism database of metabolic pathways and enzymes," *Nucleic Acids Res.*, 34(Database issue):D511-D516 (2006).
Causey et al., "Engineering *Escherichia coli* for efficient conversion of glucose to pyruvate," *Proc. Natl. Acad. Sci. U.S.A.*, 101:2235-2240 (2004).
Cha et al., "Succinic Thiokinase. I. Purification of the Enzyme from Pig Heart," *J. Biol. Chem.*, 239:1961-1967 (1964).
Chandra Raj et al., "Pyruvate decarboxylase: a key enzyme for the oxidative metabolism of lactic acid by Acetobacter pasteurianus," *Arch. Microbiol.*, 176:443-451 (2001).
Chavez et al., "The NADP-glutamate dehydrogenase of the cyanobacterium Synechocystis 6803: cloning, transcriptional analysis and disruption of the gdhA gene," *Plant Mol. Biol.*, 28:173-188 (1995).
Chen et al., "A novel lysine 2,3-aminomutase encoded by the yodO gene of Bacillus subtilis: characterization and the observation of organic radical intermediates," *Biochem. J*, 348:539-549 (2000).
Chen et al., "Cloning, Sequencing, Heterologous Expression, Purification, and Characterization of Adenosylcobalamin-dependent D-Ornithine Aminomutase from Clostridium sticklandii," *J. Biol. Chem.*, 276:44744-44750 (2001).
Chen et al., "Acetone-Butanol-Isopropanol Production by *Clostridium beijerinckii* (Synonym, Clostridium Butylicum)," *Biotechnology Letters*, 8(5):371-376 (1986).
Chen et al., "Regulation of the adhE gene, which encodes ethanol dehydrogenase in *Escherichia coli*," *J. Bacteriol.*, 173(24):8009-8013 (1991).
Chicco et al., "Regulation of Gene Expression of Branched-chain Keto Acid Dehydrogenase Complex in Primary Cultured Hepatocytes by Dexamethasone and cAMP Analog," *J. Biol. Chem.*, 269(30):19427-19434 (1994).
Chirpich et al., "Lysine 2,3-Aminomutase. Purification and properties of a pyridoxal phosphate and S-adenosylmethionine-activated enzyme," *J Biol. Chem.*, 245(7):1778-1789 (1970).
Cho et al., "Critical residues for the coenzyme specificity of NAD+-deptendent 15- hydroxyprtaglandin dehydrogenase," *Arch. Biochem. Biophys.*, 419(2): 139-146 (2003).
Chowdhury et al., "Cloning and Overexpression of the 3-Hydroxyisobutyrate Dehydrogenase Gene from Pseudomonas putida E23," *Biosci. Biotechnol. Biochem.*, 67(2):438-441 (2003).

Chowdhury et al., "3-Hydroxyisobutyrate dehydrogenase from Pseudomonas putida E23: purification and characterization," *Biosci. Biotechnol. Biochem.*, 60(12):2043-2047 (1996).
Christenson et al., "Kinetic analysis of the 4-methylideneimidazole-5-one-containing tyrosine aminomutase in enediyne antitumor antibiotic C-1027 biosynthesis," *Biochemistry*, 42(43):12708-12718 (2003).
Chu et al., "Enzymatically active truncated cat brain glutamate decarboxylase: expression, purification, and absorption spectrum," *Arch. Biochem. Biophys.*, 313:287-295 (1994).
Clark, Progress Report for Department of Energy Grant DE-FG02-88ER13941, "Regulation of Alcohol Fermentation in *Escherichia coli*," pp. 1-7 for the period: Jul. 1991-Jun. 1994.
Clarke et al., "Rational construction of a 2-hydroxyacid dehydrogenase with new substrate specificity," *Biochem. Biophys. Res. Commun.*, 148:15-23 (1987).
Clausen et al., "PAD1 encodes phenylacrylic acid decarboxylase which confers resistance to . cinnamic acid in *Saccharomyces cerevisiae*," *Gene*, 142:107-112 (1994).
Cock et al., "A nuclear gene with many introns encoding ammonium-inductible chloroplastic NADP-specific glutamate dehydrogenase(s) in Chlorella sorokiniana," *Plant Mol. Biol.*, 17:1023-1044 (1991).
Coco et al., "DNA shuffling method for generating highly recombined genes and evolved enzymes," *Nat. Biotechnol.*, 19(4):354-359 (2001).
Cogoni et al., "*Saccharomyces cerevisiae* has a single glutamate synthase gene coding for a plant-like high-molecular-weight polypeptide," *J Bacteriol.*, 177:792-798 (1995).
Colby and Chen, "Purification and properties of 3-Hydroxybutyryl-Coenzyme A Dehydrogenase from Clostridium beijerinckii (Clostridium butylicum:) NRRL B593, "*Appl. Environ. Microbiol.*, 58:3297-3302 (1992).
Cole et al., "Deciphering the biology of *Mycobacterium tuberculosis* from the complete genome sequence," *Nature*, 393:537-544 (1998).
Coleman et al., "Expression of a glutamate decarboxylase homologue is required for normal oxidative stress tolerance in *Saccharomyces cerevisiae*," *J Biol. Chem.*, 276:244-250 (2001).
Cooper, "Glutamate-γ-aminobutyrate transaminase," *Methods Enzymol.*, 113:80-82 (1985).
Corthesy-Theulaz et al., "Cloning and characterization of Helicobacter pylori succinyl CoA:acetoacetate CoA-transferase, a novel prokaryotic member of the CoA-transferase family," *J. Biol. Chem.*, 272(41):25659-25667 (1997).
Creaghan et al., "Succinate dehydrogenase-dependent nutritional requirement for succinate in mutants of *Escherichia coli* K12," *J. Gen. Microbiol.* 107(1):1-13 (1978).
Cukalovic et al., "Feasibility of production method for succinic acid derivatives: a marriage of renewable resources and chemical technology," *Biofuels Bioprod. Bioref.* 2:505-529 (2008).
Cunningham et al., "Transcription and transcript processing in the sdhCDAB-sucABCD operon of *Escherichia coli*,"*Microbiology*, 144:2113-2123 (1998).
Darlison et al., "Nucleotide sequence of the sucA gene encoding the 2-oxoglutarate dehydrogenase of *Escherichia coli* K12,"*0 Eur. J Biochem.*, 141(2):351-359 (1984).
Datsenko et al., "One-step inactivation of chromosomal genes in *Escherichia coli* K-12 using PCR products," *Proc. Natl. Acad. Sci. U.S.A.*, 97(12):6640-6645 (2000).
Davie et al., "Expression and Assembly of a Functional E1 Component (α2β2) of Mammalian Branched-Chain α-Ketoacid Dehydrogenase Complex in *Escherichia coli*," *J. Biol. Chem.*, 267:16601-16606 (1992).
De Blase et al., "Isolation, overexpression, and biochemical characterization of the two isoforms of glutamic acid decarboxylase from *Escherichia coli*," *Protein Expr. Purif.*, 8:430-438 (1996).
De La Torre et al., "Identification and functional analysis of prokaryotic-type aspartate aminotransferase: implications for plant amino acid metabolism," *Plant J.*, 46(3):414-425 (2006).
Deana, "Substrate specificity of a dicarboxyl-CoA: dicarboxylic acid coenzyme A transferase from rat liver mitochondria," *Biochem. Int.*, 26(4):767-773 (1992).

(56) References Cited

OTHER PUBLICATIONS

Deckert et al., "The complete genome of the hyperthermophilic bacterium Aquifex aeolicus," *Nature*, 392:353-358 (1998).
Diao et al., "Crystal Structure of Butyrate Kinase 2 from Thermotoga maritima, a Member of the ASKHA Superfamily of Phosphotransferases," *J Bacteriol.*, 191(8):2521-2529 (2009).
Diao et al., "Crystallization of butyrate kinase 2 from Thermotoga maritima medicated by varpor diffusion of acetic acid," *Acta Crystallogr. D. Crystallogr.*, 59:1100-1102 (2003).
Diaz et al., "Gene cloning, heterologous overexpression and optimized refolding of the NAD-glutamate dehydrogenase from haloferax mediterranei," *Extremophiles*, 10(2):105-115 (2006).
Diderichsen et al., "Cloning of aldB, which encodes alpha-acetolactate decarboxylase, an exoenzyme from Bacillus brevis," *J Bacteriol.*, 172(8):4315-4321 (1990).
Diruggiero et al., "Expression and in vitro assembly of recombinant glutamate dehydrogenase from the hyperthermophilic archaeon Pyrococcus turiosus," *Appl. Environ. Microbiol.*, 61:159-164 (1995).
Doi et al., "Biosynthesis and characterization of poly(3-hydroxybutyrate-co-4-hydroxybutyrate) in Alcaligenes eutrophus," *Int. J Biol. Macromol.*, 12:106-111 (1990).
Doi et al., "Nuclear Magnetic Resonance Studies on Unusual Bacterial Copolyesters of 3-Hydroxybutyrate and 4-Hydroxybutyrate,"*Macromolecules*, 21:2722-2727 (1988).
Doi, "Microbial Synthesis, Physical Properties, and Biodegradability of Polyhydroxyalkanoates," *Macromol. Symp.*, 98:585-599 (1995).
Dombek et al., "Ethanol production during batch fermentation with Saccharomyces cerevisiae: changes in glycolytic enzymes and internal pH," *Appl. Environ. Microbiol.*, 53:1286-1291 (1987).
Donnelly et al., "Succinic semialdehyde dehydrogenases of *Escherichia coli*: Their role in the degradation of p-hydroxyphenylacetate and γ-aminobutyrate," *Eur. J. Biochem.*, 113:555-561 (1981).
Donnelly. et al., "Two succinic semialdehyde dehydrogenases are induced when *Escherichia coli* K-12 is grown on gamma-aminobutyrate,"*J. Bacteriol.*, 145:1425-1427 (1981).
Dover et al., "Genetic analysis of the gamma-aminobutyrate utilization pathway in *Escherichia coli* K-12," *J. Bacteriol.*, 117(2):494-501 (1974).
Doyle et al., "Structural basis for a change in substrate specificity: crystal structure of S113E isocitrate dehydrogenase in a complex with isopropylmalate, Mg2+, and NADP,"*Biochemistry*, 40(14):4234-4241 (2001).
Drake, "Acetogenesis, acetogenic bacteria, and the acetyl-CoA "Wood/Ljungdahl" pathway: past and current perspectives," in H.L. Drake (ed.), *Acetogenesis*, pp. 3-60 Chapman and Hall, New York (1994).
Drewke et al., "4-O-Phosphoryl-L-threonine, a substrate of the pdxC(serC) gene product involved in vitamin $B_6$ biosynthesis," *FEBS Lett.*, 390:179-182 (1996).
Duncan et al., "Acetate utilization and butyryl coenzyme A (CoA):acetate-CoA transferase in butyrate-producing bacteria from the human large intestine," *Appl. Environ. Microbiol.*, 68(10):5186-5190 (2002).
Duncan et al., "Purification and properties of NADP-dependent glutamate dehydrogenase from Ruminococcus flavefaciens FD-1," *Appl. Environ. Microbiol.*, 58:4032-4037 (1992).
Durre et al., "Solventogenic enzymes of Clostridium acetobutylicum: catalytic properties, genetic organization, and transcriptional regulation," *FEMS Microbiol. Rev.*, 17(3):251-262 (1995).
Edwards et al., "In Silico Predictions of *Escherichia coli* metabolic capabilities are Consistent with Experimental Data," *Nat. Biotechnol.*, 19(2):125-130 (2001).
Edwards et al., "Systems properties of the Haemophilus influenzae Rd metabolic genotype," *J. Biol. Chem.*, 274(25):17410-17416 (1999).
Edwards et al., "The *Escherichia coli* MG1655 in silico Metabolic Genotype: Its Definition, Characteristics, and Capabilities," *Proc. Natl. Acad. Sci. U.S.A.*, 97(10):5528-5533 (2000).

Efe et al., "Options for biochemical production of 4-hydroxybutyrate and its lactone as a substitute for petrochemical production," *Biotechnol. Bioeng.*, 99:1392-1406 (2008).
Eggen et al., "The glutamate dehydrogenase-encoding gene of the hyperthermophilic archaeon Pyrococcus furiosus: sequence, transcription and analysis of the deduced amino acid sequence," *Gene1*, 132:143-148 (1993).
Enomoto et al., "Cloning and sequencing of the gene encoding the soluble fumarate reductase from *Saccharomyces cerevisiae,*" *DNA Res.*, 3:263-267 (1996).
Estevez et al., "X-ray crystallographic and kinetic correlation of a clinically observed human fumarase mutation," *Protein Sci.*, 11:1552-1557 (2002).
Faehnle et al., "A New Branch in the Family: Structure of Aspartate-β-semialdehyde dehydrogenase from Methanococcus jannaschii," *J Mol. Biol.*, 353:1055-1068 (2005).
Feist et al., "The growing scope of applications of genome-scale metabolic reconstructions using *Escherichia coli,*" *Nat. Biotechnol.*, 26(6):659-667 (2008).
Fell et al., "Fat Synthesis in Adipose Tissue. An Examination of Stoichiometric Constraints," *Biochem. J*, 238(3):781-786 (1986).
Fernandez-Valverde et al., "Purification of Pseudomonas putida Acyl coenzyme a Ligase Active with a Range of Aliphatic and Aromatic Substrates," *Appl. Environ. Microbiol.*, 59:1149-1154 (1993).
Fidler et al., "Polyhydroxyalkanoate production in recombinant *Escherichia coli,*" FEMS Microbiol. Rev., 9(2-4):231-235 (1992).
Filetici et al., "Sequence of the GLT1 gene from *Saccharomyces cerevisiae* reveals the domain structure of yeast glutamate synthase," *Yeast*, 12:1359-1366 (1996).
Fischer et al., "Metabolic flux profiling of *Escherichi coli* mutants in central carbon metabolism using GC-MS," *Eur. J Biochem.*, 270(5) 880-891 (2003).
Fishbein et al., "Purification and properties of an enzyme in human blood and rat liver microsomes catalyzing the formation and hydrolysis of gamma-lactones. I. Tissue localization, stoichiometry, specificity, distinction from esterase," *J Biol. Chem.*, 241(21):4835-4841 (1966).
Fishbein et al., "Purification and properties of an enzyme in human blood and rat liver microsomes catalyzing the formation and hydrolysis of γ-lactones. II. Metal ion effects, kinetics, and equilibra," *J Biol. Chem.*, 241(21):4842-4847 (1966).
Föllner et al., "Analysis of the PHA granule-associate proteins GA20 and GA11 in Methylobacterium extorquens and Methylobacterium rhodesianum," *J. Basic Microbiol.*, 37(1):11-21 (1997).
Fong et al., "Description and interpretation of adaptive evolution of *Escherichia coli* K-12 MG1655 by using a genome-scale in silico metabolic model," *J. Bacteriol.*, 185(21):6400-6408 (2003).
Fong et al., "Metabolic gene-deletion strains of *Escherichia coli* evolve to computationally predicted growth phenotypes," *Nat. Genet.*, 36(10):1056-1058 (2004).
Fontaine et al, "A New Type of Glucose Fermentation by Clostridium thermoaceticum N.sp.," *J Bacteriol.*, 43:701-715 (1943).
Fontaine et al., "Molecular characterization and transcriptional analysis of adhE2, the gene encoding the NADH-dependent aldehyde/alcohol dehydrogenase responsible for butanol production in alcohologenic cultures of Clostridium acetobutylicum ATCC 824," *J. Bacteriol.*, 184(3):821-830 (2002).
Ford, et al., "Molecular properties of the lysl+ gene and the regulation of alpha-aminoadipate reductase in Schizosaccharomyces pombe," *Curr. Genet.*, 28(2):131-137 (1995).
Forster et al., "Genome-scale reconstruction of the *Saccharomyces cerevisiae* metabolic network," *Genome Res.*, 13(2):244-253 (2003).
Four pages from URL: shigen.mg.acJp/ecoli/pec/genes.List. DetailAction.do (Printed Dec. 21, 2009).
Friedrich et al., "The complete stereochemistry of the enzymatic dehydration of 4-hydroxybutyryl coenzyme A to crotonyl coenzyme A," *Angew. Chem. Int. Ed. Engl.*, 47:3254-3257 (2008).
Fries et al., "Reaction Mechanism of the Heteroameric (α2β2) E1 Component of 2-Oxo Acid Dehydrogenase Multienzyme Complexes," *Biochemistry*, 42:6996-7002 (2003).

(56) References Cited

OTHER PUBLICATIONS

Fuhrer et al., "Computational prediction and experimental verification of the gene encoding the NAD+/NADP+-dependent succinate semialdehyde dehydrogenase in *Escherichia coli*," *J. Bacteriol.*, 189:8073-8078 (2007).
Fujii et al., "Characterization of L-lysine 6-aminotransferase and its structural gene from Favobacterium lutescens IFO3084," *J. Biochem.*, 128(3):391-397 (2000).
Fujii et al., "Error-prone rolling circle amplification: the simplest random mutagenesis protocol," *Nat. Protoc.*, 1(5):2493-2497 (2006).
Fujii et al., "One-step random mutagenesis by error-prone rolling circle amplification," *Nucleic Acids Res.*, 32(19):e145 (2004).
Fujita et al., "Novel Substrate Specificity of designer3-Isopropylmalate Dehydrogenase Derived from thermus thermophilus Hbi," *Biosci. Biotechnol. Biochem.*, 65(12):2695-2700 (2001).
Fukao et al., "Succinyl-coA:3-Ketoacid CoA Transferase (SCOT): Cloning of the Human SCOT Gene, Tertiary Structural Modeling of the Human SCOT Monomer, and Characterization of Three Pathogenic Mutations," *Genomics*, 68:144-151 (2000).
Fukuda et al., "Role of a highly conserved YPITP motif in 2-oxoacid:ferredoxin oxidoreductase," *Eur. J Biochem.*, 268:5639-5646 (2001).
Fukuda et al., "Substrate recognition by 2-oxoacid:ferredoxin oxidoreductase from *Sulfolobus* sp. Strain 7," *Biochim. Biophys. Acta*, 1597:74-80 (2002).
Gallego et al., "A role for glutamate decarboxylase during tomato ripening: the characterisation of a cDNA encoding a putative glutamate decarboxylase with a calmodulin-binding site," *Plant Mol. Biol.*, 27:1143-1151 (1995).
Gay et al., "Cloning Structural Gene sacB, Which codes for Exoenzyme Levansucrase of . . Bacillus subtilis: Epxresion of the Gene in *Escherichia coli*," *J Bacteriol.*, 153:1424-1431 (1983).
Genbank Accession No. AAA23199.2; GI:60592974 (Mar. 9, 2005).
Genbank Accession No. AAA25892.1; GI:151363 (Apr. 26, 1993).
Genbank Accession No. AAA58352.1; GI:177198 (Dec. 31, 1994).
Genbank Accession No. AAB24070.1; GI:259429 (May 8, 1993).
Genbank Accession No. AAC24333.2; GI:22711873 (Feb. 2, 1993).
Genbank Accession No. AAC45217; GI:1684886 (Dec. 20, 2007).
Genbank Accession No. AAC73823.1; GI:1786949 (May 14, 2010).
Genbank Accession No. AAC76268.1; GI:1789632 (May 14, 2010).
Genbank Accession No. AAC79717.1; GI:3928904 (Jan. 3, 2000).
Genbank Accession No. AAC79718.1; GI:3928905 (Jan. 3, 2000).
Genbank Accession No. AAD38039.1; GI:5020215 (Mar. 30, 2000).
Genbank Accession No. AAK09379.1; GI:12958626 (Jan. 17, 2002).
Genbank Accession No. AAK72501; GI:17223684 (Dec. 1, 2001).
Genbank Accession No. AAK72502; GI:17223685 (Dec. 1, 2001).
Genbank Accession No. AAL26884; GI:16588720 (Nov. 2, 2001).
Genbank Accession No. AAM14586.1; GI:20162442 (Apr. 17, 2002).
Genbank Accession No. AAR19757.1; GI:38425288 (Mar. 18, 2004).
Genbank Accession No. AAS20429.1; GI:42561982 (Feb. 22, 2004).
Genbank Accession No. AAV66076.1; GI:55818563 (Jun. 8, 2005).
Genbank Accession No. AB052732; GI:13429869 (Feb. 26, 2004).
Genbank Accession No. AB330293; GI:149941607 (Mar. 18, 2008).
Genbank Accession No. AB368798; GI: 188496948 ( May 16, 2008).
Genbank Accession No. ABC88407.1; GI:86278275 (Aug. 18, 2006).
Genbank Accession No. ABE07970.1; GI:91073089 (Apr. 30, 2010).
Genbank Accession No. ABE07971.1; GI:91073090 (Apr. 30, 2010).
Genbank Accession No. ABF58893.1; GI:98626772 (Apr. 30, 2007).
Genbank Accession No. ABF58894.1; GI:98626792 (Apr. 30, 2007).
Genbank Accession No. ABF82233.1; GI:106636093 (Aug. 2, 2007).
Genbank Accession No. ABF82234.1; GI:106636094 (Aug. 2, 2007).
Genbank Accession No. ABN80423.1; GI:126202187 (Oct. 9, 2007).
Genbank Accession No. ABS19624.1; GI:152002983 (Jul. 21, 2007).
Genbank Accession No. ACA54153.1; GI:169405742 (Feb. 18, 2010).
Genbank Accession No. AF017117; GI:2394281 (Apr. 14, 1998).
Genbank Accession No. AJ276891; GI:11322456 (Nov. 21, 2000).
Genbank Accession No. AJ278683; GI:11691809 (Mar. 11, 2001).
Genbank Accession No. BAA03892.1; GI:425213 (Feb. 16, 2008).
Genbank Accession No. BAA28709.1; GI:3184397 (Feb. 1, 2000).
Genbank Accession No. BAB12273.1; GI:9967138 (Mar. 18, 2005).
Genbank Accession No. BAB34184.1; GI:13360220 (Jan. 18, 2008).
Genbank Accession No. BAB85476.1; GI:18857901 (Mar. 18, 2005).
Genbank Accession No. CAA15502; GI:3191970 (Jan. 13, 2009).
Genbank Accession No. CAA43225.1; GI:45682 (Apr. 18, 2005).
Genbank Accession No. CAA43228.1; GI:45685 (Apr. 18, 2005).
Genbank Accession No. CAA57199.1; GI:559392 (Mar. 22, 1995).
Genbank Accession No. CAA57200.1; GI:559393 (Mar. 22, 1995).
Genbank Accession No. CAA71086.1; GI:2765041 (Apr. 18, 2005).
Genbank Accession No. CAA76083.1; GI:3402834 (Apr. 18, 2005).
Genbank Accession No. CAC07932.1; GI:10046659 (Jun. 9, 2001).
Genbank Accession No. CAG29274.1; GI:47496502 (Feb. 3, 2005).
Genbank Accession No. CAG29275.1; GI:47496504 (Feb. 3, 2005).
Genbank Accession No. CAJ15517.1; GI:77019264 (Nov. 14, 2006).
Genbank Accession No. EDK35586.1; GI:146349050 (Feb. 21, 2008).
Genbank Accession No. JC7926; GI:60729613 (Jul. 14, 2003).
Genbank Accession No. L21902.1; GI:1228100 (Mar. 15, 1996).
Genbank Accession No. NC_000907.1; GI:16271976 (May 24, 2010).
Genbank Accession No. NC_002950.2; GI:34539880 (Mar. 31, 2010).
Genbank Accession No. NP_001004072.2; GI:124430510 (Feb. 14, 2010).
Genbank Accession No. NP_010432.1; GI:6320352 (May 17, 2010).
Genbank Accession No. NP_011533.1; GI:6321456 (May 17, 2010).
Genbank Accession No. NP_012141.1; GI:6322066 (May 17, 2010).
Genbank Accession No. NP_014032.1; GI:6323961 (May 17, 2010).
Genbank Accession No. NP_036914.1; GI:77736548 (Mar. 4, 2010).
Genbank Accession No. NP_062140.1; GI:158749538 (Mar. 5, 2010).
Genbank Accession No. NP_112287.1; GI:78365255 (Apr. 30, 2010).
Genbank Accession No. NP_116635.1; GI:14318501 (May 17, 2010).
Genbank Accession No. NP_147035.1; GI:14602185 (May 5, 2010).
Genbank Accession No. NP_229443.1; GI:15644391 (Mar. 31, 2010).
Genbank Accession No. NP_252259.1; GI:15598765 (May 24, 2010).
Genbank Accession No. NP_267384.1; GI:15673210 (Apr. 1, 2010).
Genbank Accession No. NP_279651.1; GI:15789827 (May 5, 2010).
Genbank Accession No. NP_343563.1; GI:15898958 (May 5, 2010).
Genbank Accession No. NP_349314.1; GI:15895965 (Apr. 14, 2010).
Genbank Accession No. NP_349315.1; GI:15895966 (Apr. 14, 2010).
Genbank Accession No. NP_349316.1; GI:15895967 (Apr. 14, 2010).
Genbank Accession No. NP_349317.1; GI:15895968 (Apr. 14, 2010).
Genbank Accession No. NP_349318.1; GI:15895969 (Apr. 14, 2010).
Genbank Accession No. NP_349675; GI:15896326 (Apr. 14, 2010).
Genbank Accession No. NP_349676; GI:15896327 (Apr. 14, 2010).
Genbank Accession No. NP_349891.1; GI:15896542 (Apr. 14, 2010).
Genbank Accession No. NP_349892.1; GI:15896543 (Apr. 14, 2010).
Genbank Accession No. NP_378167.1; GI:15922498 (May 5, 2010).
Genbank Accession No. NP_378302.1; GI:15922633 (May 5, 2010).
Genbank Accession No. NP_390283.1; GI:16079459 (Mar. 31, 2010).
Genbank Accession No. NP_390284.1; GI:16079460 (Mar. 31, 2010).

(56) References Cited

OTHER PUBLICATIONS

Genbank Accession No. NP_390285.1; GI:16079461 (Mar. 31, 2010).
Genbank Accession No. NP_390902.2; GI:50812281 (Apr. 25, 2009).
Genbank Accession No. NP_414656.1; GI:16128107 (May 14, 2010).
Genbank Accession No. NP_414657.1; GI:16128108 (May 14, 2010).
Genbank Accession No. NP_414658.1; GI:16128109 (May 14, 2010).
Genbank Accession No. NP_414777.1; GI:16128228 (May 14, 2010).
Genbank Accession No. NP_414778.1; GI:16128229 (May 14, 2010).
Genbank Accession No. NP_414986; GI:16128437 (May 14, 2010).
Genbank Accession No. NP_415027; GI:16128478 (May 14, 2010).
Genbank Accession No. NP_415129; GI:16128580 (May 14, 2010).
Genbank Accession No. NP_415254.1; GI:16128701 (May 14, 2010).
Genbank Accession No. NP_415255.1; GI:16128702 (May 14, 2010).
Genbank Accession No. NP_415256.1; GI:16128703 (May 14, 2010).
Genbank Accession No. NP_415264; GI:16128711 (May 14, 2010).
Genbank Accession No. NP_415427.1; GI:16128874 (May 14, 2010).
Genbank Accession No. NP_415448.1; GI:16128895 (May 14, 2010).
Genbank Accession No. NP_415705.1; GI:16129150 (May 14, 2010).
Genbank Accession No. NP_415757.1; GI:16129202 (May 14, 2010).
Genbank Accession No. NP_415818.1; GI:16129263 (May 14, 2010).
Genbank Accession No. NP_415898.1; GI:16129341 (May 14, 2010).
Genbank Accession No. NP_415905.1; GI:16129348 (May 14, 2010).
Genbank Accession No. NP_415911.1; GI:16129354 (May 14, 2010).
Genbank Accession No. NP_415912.1; GI:16129355 (May 14, 2010).
Genbank Accession No. NP_415914; GI:16129357 (May 14, 2010).
Genbank Accession No. NP_416010; GI:16129452 (May 14, 2010).
Genbank Accession No. NP_416799.1; GI:16130231 (May 14, 2010).
Genbank Accession No. NP_416800.1; GI:16130232 (May 14, 2010).
Genbank Accession No. NP_416843.1; GI:16130274 (May 14, 2010).
Genbank Accession No. NP_416844.1; GI:16130275 (May 14, 2010).
Genbank Accession No. NP_417484.1; GI:16130909 (May 14, 2010).
Genbank Accession No. NP_417552.1; GI:16130976 (May 14, 2010).
Genbank Accession No. NP_417891.1; GI:16131307 (May 14, 2010).
Genbank Accession No. NP_417974; GI:16131389 (May 14, 2010).
Genbank Accession No. NP_418288.1; GI:16131692 (May 14, 2010).
Genbank Accession No. NP_418393.1; GI:16131796 (May 14, 2010).
Genbank Accession No. NP_418562; GI:90111690 (May 14, 2010).
Genbank Accession No. NP_445764.1; GI:158749632 (Aug. 5, 2008).
Genbank Accession No. NP_446446.1; GI:16758900 (Apr. 30, 2010).
Genbank Accession No. NP_570103.1; GI:18543355 (Apr. 30, 2010).
Genbank Accession No. NP_570112; GI:51036669 (Apr. 30, 2010).
Genbank Accession No. NP_745426.1; GI:26990001 (May 24, 2010).
Genbank Accession No. NP_745427.1; GI:26990002 (May 24, 2010).
Genbank Accession No. NP_746515.1; GI:26991090 (May 24, 2010).
Genbank Accession No. NP_746516.1; GI:26991091 (May 24, 2010).
Genbank Accession No. NP_746775.1; GI:26991350 (May 24, 2010).
Genbank Accession No. NP_783085.1; GI:28212141 (Mar. 31, 2010).
Genbank Accession No. NP_904963.1; GI:34540484 (Mar. 31, 2010).
Genbank Accession No. NP_955417.1; GI:40786469 (Apr. 30, 2010).
Genbank Accession No. NP_971211.1; GI:42526113 (Mar. 31, 2010).
Genbank Accession No. 034676.1; GI:4033499 (May 18, 2010).
Genbank Accession No. 050463.4; GI:160395583 (Apr. 20, 2010).
Genbank Accession No. 069294.1; GI:9789756 (Mar. 2, 2010).
Genbank Accession No. P00370; GI:118547 (Mar. 2, 2010).
Genbank Accession No. P05042.1; GI:120601 (Mar. 2, 2010).
Genbank Accession No. P05361.1; GI:113593 (Feb. 9, 2010).
Genbank Accession No. P06169; GI:30923172 (Apr. 20, 2010).
Genbank Accession No. P06672.1; GI:118391 (Apr. 20, 2010).
Genbank Accession No. P07346.1; GI:114273 (Mar. 2, 2010).
Genbank Accession No. P09062.1; GI:129044 (Mar. 2, 2010).
Genbank Accession No. P09063.1; GI:118677 (Mar. 2, 2010).
Genbank Accession No. P0A393; GI:61222614 (Mar. 2, 2010).
Genbank Accession No. P0A9B2.2; GI:71159358 (Mar. 23, 2010).
Genbank Accession No. P14408.1; GI:120605 (Mar. 2, 2010).
Genbank Accession No. P14941.1; GI:113443 (Apr. 20, 2010).
Genbank Accession No. P16263.1; GI:129041 (Jun. 16, 2009).
Genbank Accession No. P20906.2; GI:3915757 (Apr. 20, 2010).
Genbank Accession No. P21880.1; GI:118672 (Mar. 23, 2010).
Genbank Accession No. P21883.2; GI:129054 (Mar. 23, 2010).
Genbank Accession No. P22256.1; GI:120779 (Mar. 2, 2010).
Genbank Accession No. P23129.2; GI:51704265 (Jun. 16, 2009).
Genbank Accession No. P23542.3; GI:1703040 (May 18, 2010).
Genbank Accession No. P23616.1; GI:113592 (Feb. 9, 2010).
Genbank Accession No. P26899.1; GI:114271 (Jun. 16, 2009).
Genbank Accession No. P28811.1; GI:127211 (Mar. 2, 2010).
Genbank Accession No. P28817.2; GI:2506374 (Mar. 23, 2010).
Genbank Accession No. P31937.2; GI:12643395 (May 18, 2010).
Genbank Accession No. P32185.1; GI:416872 (Mar. 2, 2010).
Genbank Accession No. P33109.1; GI:416661 (Mar. 2, 2010).
Genbank Accession No. P38942.2; GI:1705614 (Feb. 5, 2008).
Genbank Accession No. P38946.1; GI:729048 (Mar. 2, 2010).
Genbank Accession No. P38947.1; GI:730847 (Feb. 5, 2008).
Genbank Accession No. P44324.1; GI:1168534 (Apr. 20, 2010).
Genbank Accession No. P46248.2; GI:20532373 (Apr. 20, 2010).
Genbank Accession No. P50554.3; GI:122065191 (Apr. 20, 2010).
Genbank Accession No. P55792; GI:84028213 (Jan. 19, 2010).
Genbank Accession No. P76458.1; GI:2492990 (Mar. 2, 2010).
Genbank Accession No. P76459.1; GI:2492994 (Mar. 2, 2010).
Genbank Accession No. P80147.2; GI:120968 (Mar. 2, 2010).
Genbank Accession No. P84067; GI:75345323 (Oct. 31, 2006).
Genbank Accession No. P84127; GI:75427690 (Oct. 31, 2006).
Genbank Accession No. P93033.2; GI:39931311 (Mar. 2, 2010).
Genbank Accession No. P94427.1; GI:6016090 (Mar. 23, 2010).
Genbank Accession No. P96110.4; GI:6226595 (Mar. 2, 2010).
Genbank Accession No. Q12629; GI:52788279 (Apr. 20, 2010).
Genbank Accession No. Q21217.1; GI:6016091 (Apr. 20, 2010).
Genbank Accession No. Q59477.1; GI:2842618 (Apr. 20, 2010).
Genbank Accession No. Q5EU90.1; GI:62287512 (Nov. 24, 2009).
Genbank Accession No. Q5XIE6.2; GI:146324906 (Mar. 2, 2010).
Genbank Accession No. Q6NVY1.2; GI:146324905 (May 18, 2010).
Genbank Accession No. Q81DR3; GI:81434808 (Oct. 31, 2006).
Genbank Accession No. Q8L208; GI:75401480 (Oct. 31, 2006).

(56) References Cited

OTHER PUBLICATIONS

Genbank Accession No. Q8L388; GI:75401616 (Oct. 31, 2006).
Genbank Accession No. Q8NRN8.1; GI:39931596 (Apr. 20, 2010).
Genbank Accession No. Q8RHX4; GI:81485301 (Nov. 28, 2006).
Genbank Accession No. Q94B07; GI:75249805 (Oct. 31, 2006).
Genbank Accession No. Q97111; GI:20137415 (Mar. 2, 2010).
Genbank Accession No. Q9HUR2.1; GI:81539678 (Apr. 20, 2010).
Genbank Accession No. Q9XBQ8.1; GI:75423266 (May 18, 2010).
Genbank Accession No. U63827; GI:1762615 (May 14, 1997).
Genbank Accession No. YP_001190490; GI:146303174 (May 6, 2010).
Genbank Accession No. YP_001190500; GI:146303184 (May 6, 2010).
Genbank Accession No. YP_001190808.1; GI:146303492 (May 6, 2010).
Genbank Accession No. YP_001191505; GI:146304189 (May 6, 2010).
Genbank Accession No. YP_001192057; GI:146304741 (May 6, 2010).
Genbank Accession No. YP_001333808.1; GI:152968699 (May 25, 2010).
Genbank Accession No. YP_001333809.1; GI:152968700 (May 25, 2010).
Genbank Accession No. YP_001333810.1; GI:152968701 (May 25, 2010).
Genbank Accession No. YP_001343536.1; GI:152977907 (May 27, 2010).
Genbank Accession No. YP_001396399.1; GI:153955634 (May 6, 2010).
Genbank Accession No. YP_001433009.1; GI:156742880 (Apr. 12, 2010).
Genbank Accession No. YP_001928843; GI:188994591 (Apr. 28, 2010).
Genbank Accession No. YP_026231.1; GI:49176374 (May 14, 2010).
Genbank Accession No. YP_026272.1; GI:49176430 (May 14, 2010).
Genbank Accession No. YP_047869.1; GI:50086359 (May 24, 2010).
Genbank Accession No. YP_089485.1; GI:52426348 (May 24, 2010).
Genbank Accession No. YP_224801.1; GI:62389399 (Mar. 31, 2010).
Genbank Accession No. YP_226809.1; GI:62391407 (Mar. 31, 2010).
Genbank Accession No. YP_256941.1; GI:70608071 (May 6, 2010).
Genbank Accession No. YP_260581.1; GI:70730840 (May 24, 2010).
Genbank Accession No. YP_299880.1; GI:73539513 (Mar. 31, 2010).
Genbank Accession No. YP_299881.1; GI:73539514 (Mar. 31, 2010).
Genbank Accession No. YP_430895.1; GI:83590886 (Apr. 1, 2010).
Genbank Accession No. YP_632558.1; GI:108756898 (Apr. 27, 2010).
Genbank Accession No. YP_709328.1; GI:111116444 (Mar. 2, 2010).
Genbank Accession No. YP_709353.1; GI:111116469 (Mar. 2, 2010).
Genbank Accession No. YP_725182.1; GI:113866693 (Apr. 12, 2010).
Genbank Accession No. YP_726053.1; GI:113867564 (Apr. 12, 2010).
Genbank Accession No. ZP_01039179.1; GI:85708113 (Jan. 25, 2006).
Genbank Accession No. ZP_01626393.1; GI:119504313 (Dec. 15, 2006).
Genbank Accession No. ZP_02036683.1; GI:154498305 (Aug. 2, 2007).
Genbank Accession No. ZP_02443222.1; GI:167771169 (Feb. 13, 2008).
Genbank Accession No. ZP_02852366.1; GI:169192667 (Feb. 29, 2008).
Gerhardt et al., "Fermentation of 4-aminobutyrate by Clostridium aminobutyricum: cloning of two genes involved in the formation and dehydration of 4-hydroxybutyryl-CoA," *Arch. Microbiol.*, 174:189-199 (2000).
Gerngross et al., "Enzyme-catalyzed synthesis of poly((R)-(-)-3-hydroxybutyrate): formation of macroscopic granules in vitro," *Proc. Natl. Acad. Sci. U.S.A.*, 92:6279-6783 (1995).
Gerngross, et al., "Overexpression and purification of the soluble polyhydroxyalkanoate synthase from Alcalligenes eutrophus: evidence for a required posttranslational modification for catalytic activity," *Biochemistry*, 33:9311-9320 (1994).
Gibbs et al., "Degenerate oligonucleotide gene shuffling (DOGS): a method for enhancing the frequency of recombination with family shuffling," *Gene*, 271:13-20 (2001).
Giesel et al., "On the occurrence of enoate reductase and 2-oxo-carboxylate reductase in clostridia and some observations on the amino acid fermentation by Peptostreptococcus anaerobius," *Arch. Microbiol.*, 135(1):51-57 (1983).
Girbal, et al., "Regulation of metabolic shifts in Clostridium acetobutylicum ATCC 824," *FEMS Microbiol. Rev.*, 17:287-297 (1995).
Goda et al., "Cloning, Sequencing, and Expression in *Escherichia coli* of the Clostridium tetanomorphum Gene Encoding β-Methylaspartase and Characterization of the Recombinant Protein," *Biochemistry*, 31:10747-10756 (1992).
Gong et al., "Specificity Determinants for the Pyruvate Dehydrogenase Component Reaction Mapped with Mutated and Prosthetic Group Modified Lipoyl Domains," *J. Biol. Chem.*, 275(18):13645-13653 (2000).
Gonzalez et al., "Cloning of a yeast gene coding for the glutamate synthase small subunit (GUS2) by complementation of *Saccharomyces cerevisiae* and *Escherichia coli* glutamate auxotrophs," *Mol. Microbiol.*, 6:301-308 (1992).
Gonzalez-Pajuelo et al., "Metabolic engineering of Clostridium acetobutylicum for the industrial production of 1,3-propanediol from glycerol," *Met. Eng.*, 7:329-336 (2005).
Goupil et al., "Imbalance of leucine flux in Lactoccus lactis and its use for the isolation of diacetyl-overproducing strains," *Appl. Environ. Microbiol.*, 62(7):2636-2640 (1996).
Goupil-Feuillerat et al., "Transcriptional and translational regulation of alpha-acetolactate decarboxylase of Lactococcus lactis subsp. Lactis," *J Bacteriol.*, 182(19):5399-5408 (2000).
Green et al., "Catabolism of aα-Ketoglutarate by a sucA Mutant of Bradyrhizobium japonicum: Evidence for an Alternative Tricarboxylic Acid Cycle," *J. Bacteriol.*, 182(10):2838-2844 (2000).
Gregerson et al., "Molecular characterization of NADH-dependent glutamate synthase from alfalfa nodules," *Plant Cell*, 5:215-226 (1993).
Guirard et al., "Purification and properties of ornithine decarboxylase from Lactobacillus sp. 30a," *. Biol. Chem.*, 255(12):5960-5964 (1980).
Guo et al., "Posttranslational activation, site-directed mutation and phylogenetic analyses of lysine biosynthesis enzymes alpha-aminoadipate reductase Lys1P (AARO and the phosphopantetheinyl transferase Lys7p (PPTase) from Schizosaccharomyces pombe," *Yeast*, 21(15):1279-1288 (2004).
Guo et al., "Site-directed mutational analysis of the novel catalytic domains of alpha- aminoadipate reductase (Lys2p) from Candida albicans," *Mol. Genet. Genomics*, 269(2):271-279 (2003).
Guzman et al., "Tight regulation, modulation, and high-level expression by vectors containing the arabinose Pbad promoter," *J. Bacteriol.*, 177:4121-4130 (1995).
Hadfield et al., "Active site analysis of the potential antimicrobial target aspartate semialdehyde dehydrogenase," *Biochemistry*, 40(48):14475-14483 (2001).
Hadfield et al., "Structure of aspartate-beta-semialdehyde dehydrogenase from *Escherichia coli*, a key enzyme in the aspartate family of amino acid biosynthesis," *J. Mol. Biol.*, 289(4):991-1002 (1999).

(56) References Cited

OTHER PUBLICATIONS

Hammer et al., "Purification and characterization of an inducible L-lysine:2-oxoglutarate 6-aminostransferase from Dandida utilis," *J. Basic Microbiol.*, 32:21-27 (1992).

Hanai et al., "Engineered synthetic pathway for isopropanol production in *Escherichia coli*," *Appl. Environ. Microbiol.*, 73:7814-7818 (2007).

Hansford, "Control of mitochondrial substrate oxidation," *Curr. Top. Bioenerg.*, 10:217-278 (1980).

Hasegawa et al., "Transcriptional regulation of ketone body-utilizing enzyme, acetoacetyl-CoA synthetase, by C/EBPα during adipocyte differentiation," *Biochim. Biophys. Acta*, 1779:414-419 (2008).

Hashidoko et al., "Cloning of a DNA Fragment Carrying the 4-Hydroxycinnamate Decarboxylase (pofK) Gene from Klebsiella oxtoca, and Its Constitutive Expression in *Escherichia coli* JM109 Cells," *Biosci. Biotech. Biochem.*, 58(1):217-218 (1994).

Hashimoto et al., "Activation of L-Lysine E-Dehydrogenase from Agrobacterium tumefaciens by Several Amino Acids and Monocarboxylates," *J. Biochem.*, 106:76-80 (1989).

Hasson et al., "The Crystal Structure of Benzoylformate Decarboxylase at 1.6 a Resolution: Diversity of Catalytic Residues in thiamin Diphosphate-Dependent Enzymes," *Biochemistry*, 37:9918-9930 (1998).

Hawes et al., "Mammalian 3-hydroxyisobutyrate dehydrogenase," *Methods Enzymol.*, 324:218-228 (2000).

Hayden et al., "Glutamate dehydrogenase of Halobacterium salinarum: evidence that the gene sequence currently assigned to the NADP+-dependent enzyme is in fact that of the NAD+-dependent glutamate dehydrogenase," *FEMS Microbiol. Lett.*, 211:37-41 (2002).

Hayes et al., "Combining computational and experimental screening for rapid optimization of protein properties," *Proc. Natl. Acad. Sci. U.S.A.*, 99(25):15926-15931 (2002).

Hein et al., "Biosynthesis of poly(4-hydroxybutyric acid) by recombinant strains of *Escherichia coli*," *FEMS Microbiol. Lett.*, 153(2):411-418 (1997).

Henne et al., "Construction of environmental DNA libraries in *Escherichia coli* and screening for the presence of genes conferring utilization of 4-hydroxybutyrate,"*Appl. Environ. Microbiol.*, 65(9):3901-3907 (1999).

Hennessy et al., "The reactivity of gamma-hydroxybutyric acid (GHB) and gamma-butyrolactone (GBL) in alcoholic solutions," *J. Forensic. Sci.*, 49(6):1220-1229 (2004). (provided electronically by publisher as pp. 1-10).

Henning et al., "Identification of Novel enzoylformate Decarboxlyases by Growth Selection," *App. Environ. Microbiol.*, 72(12)7510-7517 (2006).

Hermes et al., "Searching sequence space by definably random mutagenesis: Improving the catalytic potency of an enzyme," *J. Proc. Natl. Acad. Sci. U.S.A.*, 87:696-700 (1990).

Herrmann et al., "Two beta-alanyl-CoA.ammonia lyases in Clostridium propionicum," *FEBS J.*, 272:813-821 (2005).

Hesslinger et al., "Novel keto acid formate-lyase and propionate kinase enzymes are components of an anaerobic pathway in *Escherichia coli* that degrades L-threonine to propionate," *Mol. Microbiol.*, 27:477-492 (1998).

Hester et al., "Purification of active E1 alpha 2 beta 2 of Pseudomonas putida branched-chain-oxoacid dehydrogenase," *Eur. J Biochem.*, 233(3):828-836 (1995).

Heydari et al., "Highly Stable L-Lysine 6-Dehydrogenase from the Thermophile Geobacillus stearothemophilus Isolated from a Japanese Hot Spring: Characterization, gene Cloning and Sequencing, and Expression," *Appl. Environ. Microbiol.*, 70:937-942 (2004).

Hezayen et al., "Biochemical and enzymological properties of the polyhydroxybutyrate synthase from the extremely halophilic archaeon strain 56," *Arch. Biochem. Biophys.*, 403(2):284291 (2002).

Hibbert et al. "Directed evolution of biocatalytic processes," *Biomol. Eng.*, 22:11-19 (2005).

Hijarrubia et al., "Domain Structure characterization of the Multifunctional α-Aminoadipate Reductase from Penicillium chrysogenum by Limited Proteolysis," *J. Biol. Chem.*, 278:8250-8256 (2003).

Hillmer et al., "Solubilization and partial characterization of particulate dehydrogenases from Clostridium kluyveri," *Biochim. Biophys. Acta*, 334:12-23 (1974).

Hiramitsu, et al., "Production of Poly(3-hydroxybutyrate-co-4-hydroxybutyrate) by Alcallgenes latus," *Biotechnol Lett.*, 15:461-464 (1993).

Hirano et al., "Purification and Characterization of the alcohol dehydrogenase with a broad substrate specificity originated from 2-phenylethanol-assimilating Brevibacterium sp. KU 1390," *J Biosci. Bioeng.*, 100(3):318-322 (2005).

Hiser et al., "ERG10 from Saccharomyces cerevisiae encodes acetoacetyl-CoA thiolase," *J. Biol. Chem.*, 269:31383-31389 (1994).

Hoffmeister et al., "Mitochondrial trans-2-enoyl-CoA reductase of wax ester fermentation from Euglena gracilis defines a new family of enzymes involved in lipid synthesis,"*J. Biol. Chem.*, 280:4329-4338 (2005).

Hogan et al., "Improved specificity toward substrates with ositively charged side chains by site-directed mutagenesis of the L-lactate dehydrogenase of Bacillus stearothermophilus," *Biochemistry*, 34(13):4225-4230 (1995).

Hong and Lee, "Enhanced Production of Succinic Acid by Metabolically Engineered *Escherichia coli* with Amplified Activities of Malic Enzyme and Fumarase," *Biotechnol. Bioprocess Eng.*, 9:252-255 (2004).

Hong et al., "The genome sequence of the capnophilic rumen bacterium Mannheimia succiniciproducens," *Nat. Biotechnol.*, 22(10):1275-1281 (2004).

Huang et al., "Identification and Characterization of a Second Butyrate Kinase from Clostridium acetobutylicum ATCC 824, " *J Mol. Microbiol. Biotechnol.*, 2(1):33-38 (2000).

Huang et al., "Purification and Characterization of a Ferulic Acid Decarboxylase from Pseudomonas fluorescens," *J Bacteriol.*, 176(19):5912-5918 (1994).

Hughes et al., "Evidence for Isofunctional Enzymes in the Degradation of Phenol, m- and p-Toulate, and p-Cresol via Catechol meta-Cleavage Pathways in Alcaligenes eutrophus," *J. Bacteriol.*, 158:79-83 (1984).

Hugler et al., "Malonyl-coenzyme A reductase from Chloroflexus aurantiacus, a key enzyme of the 3-hydroxypropionate cycle for autotrophic Co(2) fixation," *J Bacteriol.*, 184:2404-2410 (2002).

Huh et al., "Global analysis of protein localization in budding yeast," *Nature*, 425:686-691 (2003).

Huisman et al., "Ch. 30: Enzyme Evolution for Chemical Process Applications," In R N. Patel (ed.), *Biocatalysis in the pharmaceutical and biotechnology industries*, CRC Press, Boca Raton, FL, p. 717-742 (2007).

Huo et al., "Substrate specificity and identification of functional groups of homoserine kinase from *Escherichia col*," *Biochemistry*, 35(50):16180-16185 (1996).

Ibarra et al., "*Escherichia coli* K-12 undergoes adaptive evolution to achieve in silico predicted optimal growth," *Nature*, 420(6912):186-189 (2002).

Iffland et al., "Directed molecular evolution of cytochrome c peroxidase," *Biochemistry*, 39(25):10790-10798 (2000).

Ikai et al., "Identification and Analysis of a Gene Encoding L-2,4-Diaminobutyrate:2-Ketoglutarate 4-Aminotransferase Invloved in the 1,3-Diaminopropane Production Pathway in Acinetobacter baumanni," *J Bacteriol.*, 179(16):5118-5125 (1997).

Imai et al., "Measurement of yeast intracellular pH by image processing and the change it undergoes during growth phase," *J. Biotechnol.*, 38:165-172 (1995).

Ingoldsby et al., "The discovery of four distinct glutamate dehydrogenase genes in a strain of Halobacterium salinarum," *Gene*, 349:237-244 (2005).

Ishida et al., "Efficient production of L-Lactic acid by metabolically engineered *Saccharomyces cerevisiae* with a genome-integrated L-lactate dehydrogenase gene." *Appl. Envirom. Microbiol.*, 71:1964-1970 (2005).

(56) References Cited

OTHER PUBLICATIONS

Ishige et al., "Wax ester production from n-alkanes by Acinetobacter sp. strain M-1: ultrastructure of cellular inclusions and role of acyl coenzyme a reductase," *Appl. Environ. Microbiol.*, 68(3):1192-1195 (2002).
Ismaiel et al., "Purification and characterization of a primary-secondary alcohol dehydrogenase from two strains of Clostridium beijerinckii," *J Bacteriol.*, 175(16):5097-5105 (1993).
Ismail et al., "Functional genomics by NMR spectroscopy Phenylacetate catabolism in *Escherichia coli*," *Eur. J Biochem.*, 270:3047-3054 (2003).
Ito et al., "D-3-hydroxybutyrate dehydrogenase from Pseudomonas fragi: molecular cloning of the enzyme gene and crystal structure of the enzyme," *J Mol. Biol.*, 355(4):722-733 (2006).
Iverson et al., "Structure of the *Escherichia coli* fumarate reductase respiratory complex," *Science*, 284(5422):1961-1966 (1999).
Jeon et al., "Heterologous expression of the alcohol dehydrogenase (adhI) gene from Geobacillus thermoglucosidasius strain M10EXG," *J Biotechnol.*, 135:127-133 (2008).
Jesudason et al., "Synthetic Poly[(R,S)-.beta.-hydroxyalkanoates] with Butyl and Hexyl Side Chains," *Macromolecules*, 27:2595-2602 (1994).
Jewell et al., "Bioconversion of propionic, valeric and 4-hydroxybutyric acids into the corresponding alcohols by Clostridium acetobutylicum Nrrl 527," *Curr. Microbiol.*, 13(4):215-219 (1986).
Jiang et al., "De novo computational design of retro-aldol enzymes," *Science*, 319(5868):1387-1391 (2008).
Johnson et al., "Alteration of a single amino acid changes the substrate specificity of dihydroflavonol 4-reductase," *Plant J.*, 25(3):325-333 (2001).
Johnston et al., "Complete nucleotide sequence of Saccharomyces cerevisiae chromosome VIII, " *Science*, 265:2077-2082 (1994).
Jones et al.,"Acetone-butanol fermentation revisited," *Microbiol. Rev.*, 50(4):484-524 (1986).
Jones et al., "Purification and characterization of D-b-hydroxybutyrate dehydrogenase expressed in *Escherichia coli*," *Biochem. Cell Biol.*, 71(7-8):406-410 (1993).
Kakimoto et al., "β-Aminoisobutyrate-α-ketoglutarate transaminase in relation to α-ammoisobutyric aciduria," *Biochim. Biophys. Acta.*, 156(2):374-380 (1968).
Kaneko et al., "Sequence analysis of the genome of the unicellular cyanobacterium Synechocystis sp. strain PCC6803, Ii. Sequence determination of the entire genome and assignment of potential protein-coding regions," *DNA Res.*, 3:109-136 (1996).
Kapatral et al., "Genome Sequence and Analysis of the Oral Bacterium Fusobacterium nucleatum Strain ATCC 25586," *J Bacteriol.*, 184(7):2005-2018 (2002).
Kato et al., "3-Methylaspartate ammonia-lyase as a marker enzyme of the mesaconate pathway for (S)-glutamate fermentation in Enterobacteriaceae," *Arch. Microbiol.*, 168(6):457-463 (1997).
Kato et al., "Open reading frame 3 of the barotolerant bacterium strain DSS12 is complementary with cydD in Escherichia coli: cydD functions are required for cell stability at high pressure," I Biochem., 120:301-305 (1996).
Kato et al., "Production of a novel copolyester of 3-hydroxybutyric acid with a medium-chain-length 3-hydroxyalkanoic acids by Pseudomonas sp. 61-3 from sugars," *Appl. Microbiol. Biotechnol.*, 45:363-370 (1996).
Kazahaya et al, "Aerobic Dissimilation of Glucose by Heterolactic Bacteria," *J. Gen. Appl. Microbiol.*, 18(1):43-55 (1972).
Keng et al., "Specificity of Aspartakinase III from *Escherichia coli* and an Examination of Important Catalytic Residues," *Arch. Biochem. Biophys.*, 335:73-81 (1996).
Kessler et al., "Pyruvate-formate-lyase-deactivase and acetyl-CoA reductase activities of *Escherichia coli* reside on a polymeric protein particle encoded by adhE," *FEBS. Lett.*, 281:59-63 (1991).
Khan et al., "Molecular properties and enhancement of thermostability by random mutagenesis of glutamate ehydrogenase from Bacillus subtilis," *Biosci. Biotechnol. Biochem.*, 69(10):1861-1870 (2005).

Killenberg-Jabs et al., "Active oligomeric states of pyruvate decarboxylase and their functional characterization," *Eur. J Biochem.*, 268:1698-1704 (2001).
Kim et al., "Construction of an *Escherichia coli* K-12 Mutant for Homoethanologenic Fermentation of glucose or Xylose without Foreign Genes," *Appl. Environ. Microbiol.*, 73:1766-1771 (2007).
Kim et al., "Dihydrolipoamide Dehydrogenase Mutation Alters the NADH Sensitivity of Pyruvate Dehydrogenase Complex of *Escherichi coli* K-12," *J Bacteriol.*, 190:3851-3858 (2008).
Kim et al., "Effect of overexpression of Actinobacillus succinogenes phosphoenolpyruvate carboxykinase on succinate production in *Escherichia coli*," *Appl. Environ. Microbiol.*, 70:1238-1241 (2004).
Kim, "Purification and Propertis of a mine α-Ketoglutarate Transaminase from *Escherichia coli*," *J Biol. Chem.*, 239:783-786 (1964).
Kimura et al., "Production of Poly(3-hydroxybutyrate-co-4-hydroxybutyrate) by Pseudomonas acidovorans," *Biotechnol. Lett.*, 14(6):445-450 (1992).
Kinnaird et al., "The complete nucleotide sequence of the Neurospora crassa am (NADP-specific glutamate dehydrogenase) gene," *Gene*, 26:253-260 (1983).
Kino et al., "Synthesis of DL-tryptophan by modified broad specificity amino acid racemase from Pseudomonas putida IFO 12996," *Appl. Microbiol. Biotechnol.*, 73(6):1299-1305 (2007).
Kinoshita, "Purification of two alcohol dehydrogenases from Zymomonas mobilis and their properties," *Appl. Microbiol. Biotechnol.*, 22:249-254 (1985).
Kirby et al., "Purification and properties of rabbit brain and liver 4-aminobutyrate aminotransferases isolated by monoclonal-antibody Immunoadsorbent chromatography," *Biochem J.*, 230:481-488 (1985).
Kizer et al., "Application of Functional Genomics to Pathway Optimization for Increased Isoprenoid Production," *Appl. Environ. Microbiol.*, 74(10):3229-3241 (2008).
Klatt et al., "Comparative genomics provides evidence for the 3-hydroxypropionate autotrophic pathway in filamentous anoxygenic phototrophic bacteria and in hot spring microbial mats," *Environ. Microbiol.*, 9(8):2067-2078 (2007).
Klenk et al., "The complete genome sequence of the hyperthermophilic, sulphate-reducing archaeon Archaeoglobus fulgidus," *Nature*, 390:364-370 (1997).
Knapp et al., "Crystal Structure of the Truncated Cubic Core Component of the *Escherichia coli* 2-Oxoglutarate Dehydrogenase Multienzyme Complex," *J. Mol. Biol.*, 289:655-668 (1998).
Knappe et al., "A radical-chemical route to acetyl-CoA: the anaerobically induced pyruvate formate-lyase system of *Escherichia coli*," *FEMS Microbiol. Rev.*, 75:383-398 (1990).
Kobayashi et al., "Frementative Production of 1,4-Butanediol from Sugars by Bacillus sp.," *Agric. Biol. Chem.*, 51(6):1689-1690 (1987).
Kobayashi et al., "Physiochemical, Catalytic, and Immunochemical Properties of Fumarases Crystallized Separately from Mitochondrial and Cytosolic Fractions of Rat Liver," *J. Biochem.*, 89:1923-1931 (1981).
Koo et al., "Cloning and characterization of the bifunctional alcohol/acetaldehyde dehydrogenase gene (adhE) in Leuconostoc mesenteroides isolated from kimchi," *Biotechnol. Lett.*, 27(7):505-510 (2005).
Korbert et al., "Crystallization of the NADP+-dependent Glutamate Dehydrogenase from *Escherichia coli*," *J Mol. Biol.*, 234:1270-1273 (1993).
Korolev et al., "Autotracing of *Escherichia coli* acetate CoA-transferase α-subunit structure using 3.4 Å MAD and 1.9 Å native data," *Acta. Cryst.*, D58:2116-2121 (2002).
Kort et al., "Glutamate dehydrogenase from the hyperthermophilic bacterium Thermotoga maritima: molecular characterization and phylogenetic implications," *Extremophiles*, 1:52-60 (1997).
Kosaka et al., "Characterization of the sol operon in butanol-hyperproducing Clostridium saccharoperbutylacetonicum strain N1-4 and its degeneration mechanism," *Biosci. Biotechnol. Biochem.*, 71:58-68 (2007).
Kosjek et al., "Purification and characterization of a chemotolerant alcohol dehydrogenase applicable to coupled redox reactions," *Biotechnol. Bioeng.*, 86(1):55-62 (2004).

(56) References Cited

OTHER PUBLICATIONS

Kreimeyer et al., "Indentification of the Last Unknown Genes in the fermentation Pathway of . Lysme," *J. Biol. Chem.*, 282:7191-7197 (2007).
Kretz et al., "Gene site saturation mutagenesis: a comprehensive mutagenesis approach," Methods Enzymol., 388:3-11 (2004).
Krieger et al., "Pyruvate decarboxylase from Kluyveromyces lactis an enzyme with an extraordinary substrate activation behaviour," *Eur. J Biochem.*, 269:3256-3263 (2002).
Kumamaru et al., "Enhanced degradation of polychlorinated biphenyls by directed evolution of biphenyl dioxgenase," *Nat. Biotechnol.*, 16(7)663-666 (1998).
Kunioka et al., "New bacterial copolyesters produced in Alcaligenes eutrophus from organic acids," *Polym. Commun.*, 29:174-176 (1988).
Kurihara et al., "A Novel Putrescine Utilization Pathway Involves γ-Glutamylated Intermediates of Escherichia coli K-12," *J Biol. Chem.*, 280(6) 4602-4608 (2005).
Kuznetsova et al., "Enzyme genomics: Application of general enzymatic screens to discover new enzymes," *FEMS Microbiol. Rev.*, 29:263-279 (2005).
Kwok et al., "GFP-labelled Rubisco and aspartate aminotransferase are present in plastid stromules and traffic between plastids," *J. Exp. Bot.*, 55:(397)595-604 (2004).
Kwon et al., "Brain 4-aminobutyrate aminotransferase. Isolation and sequence of a cDNA encoding the enzyme," *J. Biol. Chem.*, 267:7215-7216 (1992).
Kwon et al., "Influence of gluconeogenic phosphoenolpyruvate carboxykinase (PCK) expression on succinic acid fermentation in Escherichia coli under high bicarbonate condition," *J. Microbiol. Biotechnol.*, 16(9):1448-1452 (2006).
Lageveen et al., "Formation of Polyesters by Pseudomonas oleovorans: Effect of Substrates on Formation and Composition of Poly-(R)-3-Hydroxyalkanoates and Poly-(R)-3-Hydroxyalkenoates,"Appl. Environ. Microbiol., 54:2924-2932 (1988).
Laivenieks et al., "Cloning sequencing, and overexpression of the Anaerobiospirillum succinicproducens phosphoenolpyruvate carboxykinase (pckA) gene," *Appl. Environ. Microbiol.*, 63:2273-2280 (1997).
Lam et al., "Metabolic Relationships between Pyridoxine (vitamin B6) and Serine Biosynthesis in Escherichia coli K-12," *J Bacteriol.*, 172(11):6518-6528 (1990).
Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J*, 395:147-155 (2006).
Lamed et al., "Novel NAP-linked alcohol-aldehyde/ketone oxidoreductase in thermophilic ethanologenic bacteria," *Biochem. J.*, 195:183-190 (1981).
Lebbink et al., "Engineering activity and stability of Thermotoga maritima glutamate dehydrogenase. II: construction of a 16-residue ion-pair network at the subunit interface," *J. Mol. Biol.*, 289(2):357-369 (1999).
Lebbink et al., "Engineering activity and stability of Thermotoga maritima Glutamate Dydrogenase. I. Introduction of a Six-residue Ion-pair Network in the Hinge Region," J. Mol. Biol., 280:287-296 (1998).
Leduc et al., "The Hotdog Thiesterase EntH (YbdB) Plays a Role in Vivo in Optimal Enterobactin biosynthesis by Interacting with the ArCP Domain of EntB," *J Bacteriol.*, 189(19):7112-7126 (2007).
Lee et al., "Biosynthesis of enantiopure (s)-3-hydroxybutyric acid in metabolically engineered Escherichia coli," *Appl. Microbiol. Biotechnol.*, 79(4):633-641 (2008).
Lee et al., "Cloning and Characterization of Mannheimia succiniciproducens MBEL55E Phosphoenolpyruvate Carboxykinase (pckA) Gene," *Biotechnol. Bioprocess Eng.*, 7:95-99 (2002).
Lee et al., "Identification of essential active-site residues in ornithine decarboxylase of Nicotiana glutmosa decarboxylating both L-ornithine and L-lysine," *Biochem. J.*, 360(Pt 3):657-665 (2001).
Lee et al., "Phylogenetic diversity and the structural basis of substrate specificity in the beta/alpha-barrel fold basic amino acid decarboxylases," *J Biol. Chem.*, 282(37):27115-27125 (2007).
Lee et al., "A new approach to directed gene evolution by recombined extension on truncated templates (RETT)," *J. Molec. Catalysis*, 26:119-129 (2003).
Lee et al., "Biosynthesis of copolyesters consisting of 3-hydroxybutyric acid and medium-chain-length 3-hydroxyalkanoic acids from 1,3-butanediol or from 3-hydroxybutyrate by Pseudomonas sp. A33," *Appl. Microbiol. Biotechnol.*, 42: 901-909 (1995).
Lee et al., "Enhanced biosynthesis of P(3HB-3HV) and P(3HB-4HB) by amplification of the cloned PHB biosynthesis genes in Alcatigenes eutrophus," *Biotechnol. Lett.*, 19:771-774 (1997).
Lemoigne et al., "Fermentation b-Hydroxybutyrique,"*Annales des Fermentations*, 5:527-536 (1925).
Lemonnier et al., "Expression of the second lysine decarboxylase gene of Escherichia coli," *Microbiology*, 144(Pt 3):751-760 (1998).
Lepore et al., "The x-ray crystal structure of lysine-2,3-aminomutase from Clostridium subterminale," *Proc. Natl. Acad. Sci. U.S.A.*, 102:13819-13824 (2005).
Li et al., "Effecrts of Substitution of Tryptophan 412 in the Substrate Activation Pathway of Yeast Pyruvate Decarboxylase," *Biochemistry* 38:10004-10012 (1999).
Li, "Development of a reporter system for the study of gene expression for solvent production in Clostridium beijerinckii NRRL B592 and Clostridium acetobutylicum ATCC 824," Dissertation, Department of Biochemestry, Virginia Polytechnic Institute and State University (Sep. 1998).
Lian et al., "Sterochemical and Isotopic Labeling Studies of 4-Oxalocrotonate Decarboxylase and Vinylpyruvate Hydratase: Analysis and Mechanistic Implications," *J. Am. Chem. Soc.*, 116:10403-10411 (1994).
Liebergesell et al., "Cloning and nucleotide sequences of genes relevant for biosynthesis of poly(3-hydroxybutyric acid) in Chromatium vinosum strain D," *Eur. J Biochem.*, 209(1):135-150 (1992).
Lin et al., "Fed-batch culture of a metabolically engineered Escherichia coli strain designed for high-level succinate production and yield under aerobic conditions," *Biotechnol. Bioeng.*, 90(6):775-779 (2005).
Lin et al., "Functional expression of horseradish peroxidase in E. coli by directed evolution," *Biotechnol. Prog.*, 15(3):467-471 (1999).
Lingen et al., "Alteration of the Substrate Specificity of Benzoylformate Decarboxylase from Pseudomonas putida by Directed Evolution," *Chembiochem*, 4:721-726 (2003).
Lingen et al., "Improving the carboligase activity of benzoylformate decarboxylase from Pseudomonas putida by a combination of directed evolution and site-directed mutagenesis," *Protein Eng.*, 15:585-593 (2002).
Link et al., "Methods for generating precise deletions and insertions in the genome of wild-type Escherichia coli: application to open reading frame characterization," *J. Bacteriol.*, 179:6228-6237 (1997).
Liu et al., "Crystal Structures of Unbound and Aminoxyacetate-Bound Eschericiha coli Y-Aminobutyrate Aminotransferase," *Biochem.*, 43:10896-10905 (2004).
Liu et al., "Kinetic and crystallographic analysis of active site mutants of Escherichia coli gamma-aminobutyrate aminotransferase," *Biochemistry*, 44:(8):2982-2992 (2005).
Liu et al., "A novel genetically engineered pathway for synthesis of poly(hydroxyalkanoic acids) in Escherichia coli," Appl. Environ. Microbiol., 66(2):739-743 (2000).
Liu et al., "Exploitation of butyrate kinase and phosphotransbutyrylase from Clostridium acetobutylicum for the in vitro biosynthesis of poly (hydroxyalkanoic acid),"*Appl. Microbiol. Biotechnol.*, 53(5):545-552 (2000).
Ljungdahl et al., "Formate dehydrogenase, a selenium—tungsten enzyme from Clostridium thermoaceticum," *Methods Enzymol.*, 53:360-372 (1978).
Lokanath et al., "Crystal Structure of novel NADP-dependent 3-Hydroxyisobutyrate Dehydrogenase from Thermus thermophilus HB8," *J. Mol Biol.*, 352:905-917 (2005).
Louie et al., "Cloning and characterization of the gamma-glutamyl phosphate reductase gene of Campylobacter jejuni," *Mol. Gen. Genet.*, 240:29-35 (1993).

(56) References Cited

OTHER PUBLICATIONS

Louis et al., "Restricted Distribution of the Butyrate Kinase Pathway among Butyrate-Producing Bacteria from the Human Colon," *J. Bacteriol.*, 186(7):2099-2106 (2004).

Low et al., "Mimicking somatic hypermutation: affinity maturation of antibodies displayed on baceriophage using a bacterial mutator strain," *J. Mol. Biol.*, 260(3):359-368 (1996).

Lu et al, "Functional analysis and regulation of the divergent spuABCDEFG-spuI operons for polyamine uptake and utilization in Pseudomonas aeruginosa PA01," *J. Bacteriol.*, 184:3765-3773 (2002).

Lu et al., "Enhanced production of poly(3-hydroxybutyrate-co-3-hydroxyhexanoate) via manipulating the fatty acid beta-oxidation pathway in *E. coli*," *FEMS Microbiol. Lett.*, 221(1):97101 (2003).

Lu et al., "Molecular cloning of polyhydroxyalkanoate synthesis operon from Aeromonas hydrophilia and its expression in *Escherichia coli*," *Biotechnol. Prog.*, 20(5):1332-1336 (2004).

Lutke-Eversloh et al., "Biochemical and molecular characterization of a succinate semialdehyde dehydrogenase involved in the catabolism of 4-hydroxybutyric acid in Ralstonia eutropha," *FEMS Microbiol. Lett.*, 181:63-71 (1999).

Lutz et al., "Creating multiple-crossover DNA libraries independent of sequence identity," *Proc. Natl. Acad. Sci. U.S.A.*, 98(20):11248-11253 (2001).

Lutz et al., "Independent and tight regulation of transcriptional units in *Escherichia coli* via the LacR/O, the TetR/O and AraC/I1-I2 regulatory elements," *Nucleic Acids Res.*, 25:1203-1210 (1997).

Lutz et al., "Rapid generation of incremental truncation libraries for protein engineering using α-phosphothioate nucleotides," *Nucleic Acids Res.*, 15:29(4):e16 (2001).

Ma et al., "Induced Rebuilding of Aspartase Confromation," *Ann. N.Y. Acad. Sci.* 672:60-65 (1992).

Mack et al., "Conversion of glutaconate CoA-transferase from Acidaminococcus fermentas into an acyl-CoA hydrolase by site-directed mutagenesis," *FEBS Lett.*, 405:209-212 (1997).

Mack et al., "Location of the two genes encoding glutaconate coenzyme A-transferase at the beginning of the hydroxyglutarate operon in Acidaminococcus fermentans," *Eur. J. Biochem.*, 226:41-51 (1994).

Mahadevan et al., "Applications of metabolic modeling to drive bioprocess development for the production of value-added chemicals," *Biotechnol. Bioprocess Eng.*, 10(5):408-417 (2005).

Mahadevan et al., "The effects of alternate optimal solutions in constraint-based genome-scale metabolic models," *Metab. Eng.*, 5(4):264-276 (2003).

Mahan et al, "Genetic analysis of the proBA genes of *Salmonella typhimurium*: physical and genetic analyses of the cloned proB+ A+ genes of *Escherichia coli* and of a mutant allele that confers proline overproduction and enhanced osmotolerance," *J. Bacteriol.*, 156(3):1249-1262.

Majewski et al., "Simple Constrained-Optimization View of Acete Overflow in *E. coli*," *Biotechnol. Bioeng.*, 35(7):732-738 (1990).

Majumdar et al., "Functional consequences of substitution in the active site (phosphor) histidine residue of *Escherichia coli* succinyl-CoA synthetase," *Biochim. Biophys. Acta.*, 1076:8690 (1991).

Mandal et al., "Isolation of a glutamate synthase (GOGAT)-negative, pleiotropically N utilization-defective mutant of Azospirillum brasilense: cloning and partial characterization of GOGAT structural gene," *J. Bacteriol.*, 175:8024-8029 (1993).

Manning et al., "Tracer studies of the interconversion of R- and S-methylmalonic semialdehydes in man," *Biochem J.*, 231:481-484 (1985).

Marco-Marin et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," *J. Mol. Biol.*, 334:459-476 (2003).

Marek et al., "Cloning and expression of the *Escherichia coli* K-12 sad gene," *J. Bacteriol.*, 170(2):991-994 (1988).

Marks et al., "Molecular Cloning and Characterization of (R)-3-Hydroxybutyrate Dehydrogenase from Human Heart," *J. Biol. Chem.*, 267:15459-15463 (1992).

Martin et al., "Engineering a mevalonate pathway in *Escherichia coli* for production of terpenoids," *Nat. Biotechnol.*, 21:796-802 (2003).

Martinez-Blanco et al., "Purification and Biochemical Characterization of Phenylacetyl-CoA Ligase from Pseudomonas putida," *J. Biol. Chem.*, 265(12):7084-7090 (1990).

Mat-Jan et al., "Anaerobic growth defects resulting from gene fusions affecting succinyl-CoA synthetase in *Escherichia coli* K12," *Mol. Gen. Genet.*, 215:276-280 (1989).

Mattevi et al., "Atomic structure of the cubic core of the pyruvate dehydrogenase multienzyme complex," *Science*, 255:1544-1550 (1992).

Matthies et al., "Reciprocal Isomerization of Butyrate and Isobutyrate by the Strictly Anaerobic Bacterium Strain WoG13 and Methanogenic Isobutyrate Degradation by a Devined Triculture," *Appl. Environ. Microbiol.*, 58(5):1435-1439 (1992).

Mavrovouniotis,"Estimation of standard Gibbs energy changes of biotransformations," *J. Biol. Chem.*, 266:14440-14445 (1991).

McKinlay et al., "Prospects for a bio-based succinate industry," *Appl. Microbiol. Biotechnol.*, 76(4):727-740 (2007).

McLaggan et al., "Interdependence of K+ and glutamate accumulation during osmotic adaptation of *Escherichia coli*," *J Biol. Chem.*, 269:1911-1917 (1994).

McPherson et al., "Complete nucleotide sequence of the *Escherichia coli* gdhA gene," *Nucleic Acids Res.*, 11(15):5257-5266 (1983).

Melchiorsen et al., "The level of pyruvate-formate lyase controls the shift from homolactic to mixed-acid product formation in Lactoccus lactis," *Appl. Microbiol. Biotechnol.*, 58(3):338-344 (2002).

Meng et al., "Site-Directed Mutagenesis and functional Analysis of the Active-Site Residues of the E2 Component of Bovine Branched-Chain α-Keto Acid Dehydrogenase Complex," *Biochem.*, 33:12879-12885 (1994).

Menzel et al., "Enzymatic evidence for an involvement of pyruvate dehydrogenase in the anaerobic glycerol metabolism of Klebsiella pneumoniae," *J Biotechnol.*, 56:135-142 (1997).

Menzel et al., "Kinetic, dynamic, and pathway studies of glycerol metabolism by Klebsiella pneumoniae in anaerobic continuous culsutre: Iv. Enzynmes and fluxes of pyruvate metabolism," *Biotechnol. Bioeng.*, 60(5):617-626 (1998).

Mermelstein et al., "Metabolic Engineering of Clostridium acetobutylicum Atcc 824 for Increased Solvent Production by Enhancement of Acetone Formation Enzyme Activities Using a Synthetic Acetone Operon," *Biotechnol. Bioeng.*, 42(9):1053-1060 (1993).

Metz et al., "Purification of a jojoba embryo fatty acyl-coenzyme a reductase and expression of its cDNA in high erucic acid rapeseed," *Plant Physiol.*, 122(3):635-644 (2000).

Metzer et al., "In vivo cloning and characterization of the gabCTDP gene cluster of *Escherichia coli* K-12," *J. Bacteriol.*, 172:3250-3256 (1990).

Metzer et al., "Isolation and properties of *Escherichia coli* K-12 mutants impaired in the . utilization of gamma-aminobutyrate," *J. Bacteriol.*, 137(3):1111-1118 (1979).

Miles et al., "Molecular genetic aspects of the citric acid cycle of *Escherichia coli*," *Biochem. Soc. Symp.*, 54:45-65 (1987).

Miller et al., "Cloning and characterization of gdhA, the structural gene for glutamate dehydrogenase of Salmonella typhimurium," *J Bacteriol.*, 157:171-178 (1984).

Misono et al., "Occurrence of L-Lysine ε-Dehydrogenase in Agrobacterium tumefaciens," *J. Bacteriol.*, 150(1):398-401 (1982).

Miyamoto et al., "Possible physiological roles of aspartase, NAD- and NADP-requiring glutamate dehydrogenases of Pseudomonas fluorescens," *J Biochem.*, 112:52-56 (1992).

Miyazaki et al., "α-Aminoadipate aminotransferase from an extremely thermophilic bacterium, Thermus thermophilus," *Microbiology*, 150:2327-2334 (2004).

Mizobata et al., "Purification and Characterization of a thermostable Class II Fumarase from Thermus thermophilus," *Arch. Biochem. Biophys.*, 355:49-55 (1998).

(56) References Cited

OTHER PUBLICATIONS

Momany et al., "Crystallographic Structures of a PLP-Dependent Ornithine Decarboxylase from Lactobacillus 30a to 3.0 Å Resolution," *J. Mol. Biol.*, 242:643-655 (1995).
Monnet et al., "Regulation of branched-chain amino acid biosynthesis by α-acetolactate decarboxylase in Streptococcus thermophilus," *Lett. Appl. Microbiol.*, 36(6):399-405 (2003).
Moore et al., "Expression and Purification of Aspartate β-Semialdehyde Dehydrogenase from Infectious Microorganisms," *Protein Expr. Purif.*, 25:189-194 (2002).
Morris et al., "Nucleotide sequence of the LYS2 gene of Saccharomyces cerevisiae: homology to Bacillus brevis tyrocidine synthetaseI," *Gene*, 98:141-145 (1991).
Mountain et al., "The Klebsiella aerogenes glutamate dehydrogenase (gdnA) gene: cloning, high-level expression and hybrid enzyme formation in *Escherichia coli*,"*Mol. Gen. Genet.*, 199:141-145 (1985).
Muh et al., "4-Hydroxybutyryl-CoA dehydratase from Clostridium aminobutyricum: characterization of FAD and iron-sulfur clusters involved in an overall non-redox reaction," *Biochemistry*, 35:11710-11718 (1996).
Muh et al., "Mossbauer study of 4-hydroxybyl-CoA dehydratase--probing the role of an iron-sulfur cluster in an overall non-redox reaction," *Eur. J Biochem.*, 248:380-384 (1997).
Muller et al., "Nucleotide exchange and excision technology (NExT) DNA shuffling: a robust method for DNA fragmentation and directed evolution," *Nucleic Acids Res.*, 33(13):e117 (2005).
Mullins et al., "A specialized citric acid cycle requiring succinyl-coenzyme A (CoA):acetate CoA-transferase (AarC) confers acetic acid resistance on the acidophile Acetobacter aceti," *J. Bacteriol.*, 190:4933-4940 (2008).
Muratsubaki et al., "One of the fumarate reductase isoenzymes from *Saccharomyces cerevisiae* is encoded by the OSM1 gene," *Arch. Biochem. Biophys.*, 352(2):175-181 (1998).
Musfeldt et al., "Novel Type of ADP-Forming Acetyl Coenzyme a Synthetase in Hyperthermophilic Archaea: Heterologous Expression and Characterization of Isoenzymes from the Sulfate Reducer Archaeoglobus fulgidus and the Methanogen Methanococcus jannaschii," *J. Bacteriol.*, 184(3):636-644 (2002).
Nagasu et al., "Nucleotide Sequence of the GDH gene coding for the NADP-specific glutamate dehydrogenase of *Saccharomyces cerevisiae,*" *Gene*, 37:247-253 (1985).
Naggert et al., "Cloning, Sequencing, and Characterization of *Escherichia coli* thioesteraseII," *J. Biol. Chem.*, 266(17):11044-11050 (1991).
Najmudin et al., "Purification, crystallization and preliminary X-ray crystallographic studies on Acetolactate decarboxylase," *Acta. Crystallogr. D. Biol. Crystallog.*, 59:1073-1075 (2003).
Nakahigashi et al., "Nucleotide sequence of the fadA and fadB genes from *Escherichia coli,"* *Nucleic Acids Res.*, 18(16):4937 (1990).
Nakano et al., "Characterization of Anaerobic Fermentative Growth of *Bacillus subtilis*: Identification of Fermentation End Products and Genes Required for Growth," *J Bacteriol.*, 179(21):6749-6755 (1997).
Namba et al., "Coenzyme A and Nicotinamide Adenine dinucleotide-deptendent Branched Chain α-Keto Acid Dehydrogenase," *J Biol. Chem.*, 244:4437-4447 (1969).
Ness et al., "Synthetic shuffling expands functional protein diversity by allowing amino acids to recombine independently," *Nat. Biotechnol.*, 20(12):1251-1255 (2002).
Nexant, "1,4-Butanediol/THF—PERP Program New Report Alert," Nexant ChemSystems PERP Report 02/03-7, p. 1-5 (Jan. 2004).
Niegemann et al., "Molecular organization of the *Escherichia coli* gab cluster: nucleotide sequence of the structural genes gabD and gabP and expression of the GABA permease gene," *Arch. Microbiol.*, 160:454-460 (1993).
Nishizawa et al., "Gene expression and characterization of two 2-oxoacid:ferredoxin oxidoreductases from *Aeropyrum pernix* K1," *FEBS. Lett.*, 579:2319-2322 (2005).
Niu et al., "Benzene-free synthesis of adipic acid," *Biotechnol. Prog.*, 18:201-211 (2002).
Nolling et al., "Genome sequence and comparative analysis of the solvent-producing bacterium Clostridium acetobutylicum,"*J Bacteriol.*, 183(16):4823-4838 (2001).
Nowicki et al., "Recombinant tyrosine aminotransferase from Trypanosoma cruzi: structural characterization and site directed mutagenesis of a broad substrate specificity enzyme," *Biochim. Biophys. Acta*, 1546(2):268-281 (2001).
Ohgami et al., "Expression of acetoacetyl-CoA synthetase, a novel cytosolic ketone body-utilizing enzyme, in human brain," *Biochem. Pharmacol.*, 65:989-994 (2003).
Ohsugi et al., "Metabolism of L-β-Lysine by a Pseudomonas, Purification and Properties of a Deacetylase-Thiolesterase utilizing 4-Acetamidobutyrl CoA and Related Compounds," *J. Biol. Chem.*, 256:7642-7651 (1981).
Okino et al., "An efficient succinic acid production process in a metabolically engineered Corynebacterium glutamicum strain," *Appl. Microbiol. Biotechnol.*, 81(3):459-464 (2008).
Oku et al., "Biosynthesis of Branched-chain Fatty Acids in Bacillis subtilis," *J. Biol. Chem.*, 263:18386-18396 (1988).
Okuno et al., "2-Aminoadipate-2-oxoglutarate aminotransferase isoenzymes in human liver: a plausible physiological role in lysine and tryptophan metabolism," *Enzyme Protein*, 47(3):136-148 (1993).
Oliver et al., "Determination of the nucleotide sequence for the glutamate synthase structural genes of *Escherichia coli* K-12," *Gene*, 60:1-11 (1987).
Olivera et al., "Molecular characterization of the phenylacetic acid catabolic pathway in Pseudomonas putida U: the phenylacetyl-CoA catabolon," *Proc. Natl. Acad. Sci. U.S.A.*, 95:6419-6424 (1998).
Onuffer et al., "Redesign of the substrate specificity of *Escherichia coli* aspartate aminotransferase to that of *Escherichia coli* tyrosine aminotransferase by homology modeling and site-directed mutagenesis," *Protein Sci.*, 4:1750-1757 (1995).
O'Reilly et al., "Sequence and analysis of the citrulline biosynthetic operon argC-F from Bacillus subtilis," *Microbiology*, 140:1023-1025 (1994).
Orencio-Trejo et al., "Metabolic regulation analysis of an ethanologenic *Escherichia coli* strain based on RT-PCR and enzymatic activities," *Biotechnol. Biofuels*, 1:8 (2008).
Ostermeier et al., "A combinatorial approach to hybrid enzymes independent of DNA homology," *Nat. Biotechnol.*, 17(12):1205-1209 (1999).
Ostermeier et al., "Combinatorial protein engineering by incremental truncation," *Proc. Natl. Acad. Sci. U.S.A.*, 96(7):3562-3567 (1999).
O'Sullivan et al., "Purification and characterisation of acetolactate decarboxylase from Leuconostoc lactis NCW1," *FEMS Microbiol. Lett.*, 194(2):245-249 (2001).
Otten et al., "Directed evolution: selecting today's biocatalysts," *Biomol. Eng.*, (22):1-9 (2005).
Palosaari et al., "Purification and properties of the inducible coenzyme A-linked butyraldehyde dehydrogenase from Clostridium acetobutylicum," *J. Bacteriol.*, 170(7):2971-2976 (1988).
Park et al., "Biosynthesis of poly(3-hydroxybutyrate- co-3-hydroxyalkanoates) by metabolically engineered *Escherichia coli* strains," *Appl. Biochem. Biotechnol.*, 113-116:335-346 (2004).
Park et al., "Identification and Characterization of a New Enoyl coenzyme A Hydratase involved in biosynthesis of Medium-Chain-Length Polyhdroxyalkanoates in recombinant *Escherichia coli,"* *J Bacteriol.*, 185(18):5391-5397 (2003).
Park et al., "New FadB homologous enzymes and their use in enhanced biosynthesis of medium-chain-length polyhydroxyalkanoates in FadB mutant *Escherichia coli,"* *Biotechnol. Bioeng.*, 86:681-686 (2004).
Park et al., "Regulation of succinate dehydrogenase (sdhCDAB) operon expression ion *Escherichia coli* in response to carbon supply and anaerobiosis: role of ArcA and Fnr," *Mol. Microbiol.*, 15:473-482 (1995).
Park et al., "Aerobic regulation of the sucABCD genes of *Escherichia coli*, which encode alpha-ketoglutarate dehydrogenase and succinyl coenzyme a synthetase: roles of ArcA, Fnr, and the upstream sdhCDAB promoter," *J Bacteriol.*, 179:4138-4142 (1997).

(56) References Cited

OTHER PUBLICATIONS

Park et al., "Isolation and characterization of recombinant mitochondrial 4-aminobutyrate aminotransferase," *J. Biol. Chem.*, 268:7636-7639 (1993).
Park et al., "Regulation of the Citrate Synthase (gltA) Gene of *Escherichia coli* in response to Anaerobiosis and Carbon Supply: Role of the arcA Gene Product," *J Bacteriology*, 176(16):5086-5092 (1994).
Parsot et al., "Nucleotide sequence of *Escherichia coli* argB and argC genes: comparison of N-acetylglutamate kinase and N-acetylglutamate-gamma-semialdehyde dehydrogenase with homologous and analogous enzymes," *Gene*, 68(2): 275-283 (1988).
Pauwels et al., "The N-acetylglutamate synthase? N-acetylglutamate kinase metabolon of Saccharomyces cerevisiae allows cor-ordinated feedback regulation of the first two steps in arginine biosynthesis," *Eur. J Biochem.*, 270:1014-1024 (2003).
Paxton et al., "Role of branched-chain 2-oxo acid dehydrogenase and pyruvate dehydrogenase in 2-oxobutyrate metabolism," *Biochem. J.*, 234:295-303 (1986).
Pelanda et al., "Glutamate synthase genes of the diazotroph Azospirillum brasillense. Cloning, sequencing, and analysis of functional domains," *J. Biol. Chem.*, 268:3099-3106 (1993).
Peoples et al., "Fine structural analysis of the Zoogloea ramigera phhA-phhB locus encoding beta-ketothiolase and acetoacetyl-CoA reductase: nucleotide sequence of phbB," *Mol. Microbiol.*, 3:349-357 (1989).
Pereira et al., "Active site mutants of *Escherichia coli* citrate synthase. Effects of mutations on catalytic and allosteric properties," *J Biol. Chem.*, 269:412-417 (1994).
Peretz et al., "Amino Acid Sequence of Alcohol Dehydrogenase from the Thermophilic Bacterium Thermoanaerobium brockii," *Biochem.*, 28:6549-6555 (1989).
Peretz et al., "Molecular cloning, nucleotide sequencing, and expression of genes encoding alcohol dehydrogenases from the thermophile Thermoanaerobacter brockii and the mesophile Clostridium beijerinckii," *Anaerobe*, 3:259-270 (1997).
Perez et al., "*Escherichia coli* YqhD exhibits aldehyde reductase activity and protects from the harmful effect of lipid peroxidation-derived aldehydes," *J Biol. Chem.*, 283(12):7346-7353 (2008).
Perez-Prior et al., "Reactivity of lactones and Ghb formation," *J Org. Chem.*, 70(2):420-426 (2005).
Petitdemange et al., "Regulation of the NADH and NADPH-ferredoxin oxidoreductases in clostridia of the butyric group," *Biochim. Biophys. Acta.*, 421(2):334-337 (1976).
Phalip et al., "Purification and properties of the alpha-acetolactate decarboxylase from Lactococcus lactis subsp. Lactis Ncdo 2118," *FEBS Lett.*, 351:95-99 (1994).
Pharkya et al., "Exploring the overproduction of amino acids using the bilevel optimization framework OptKnock," *Biotechnol. Bioeng.*, 84(7):887-899 (2003).
Ploux et al., "The Nadph-linked acetoacetyl-CoA reductase from Zoogloea ramigera, Characterization and mechanistic studies of the cloned enzyme over-produced in *Escherichia coli*," *Eur. J Biochem.*, 174:177-182 (1988).
Pohl et al., "Remarkably broad substrate tolerance of malonyl-CoA synthetase, an enzyme capable of intracellular synthesis of polyketide precursors," *J. Am. Chem Soc.*, 123(24): 5822-5823 (2001).
Pohlmann et al., "Genome sequence of the bioplastic-producing "Knallgas" bacterium Ralstonia eutropha H16," *Nat. Biotechnol.*, 24(10):1257-1262 (2006).
Poirier et al., "Polyhydroxybutyrate, a Biodegradable Thermoplastic Produced in Transgenic Plants," *Science*, 256:520-523 (1992).
Polovnikova et al., "Structural and Kinetic Analysis of Catalysis by a thiamin diphosphate-Dependent Enzyme, Benzoylformate Decarboxylase," *Biochemistry*, 42:1820-1830 (2003).
Poston, "Assay of leucine 2,3-aminomutase," *Methods Enzymol.*, 166:130-135 (1988).
Powlowski et al., "Purification and properties of the physically associated meta-cleavage pathway enzymes 4-hydroxy-2-ketovalerate aldolase and aldehyde dehydrogenase (acylating) from Pseudomonas sp. strain CF600," *J. Bacteriol.*, 175:377-385 (1993).
Prather et al., "De novo biosynthetic pathways: rational design of microbial chemical factories," *Current Opinion in Biotechnology*, 19:468-474 (2008).
Presecan et al., "The Bacillus subtillis genome from gerBC (311 degrees) to licR (334 degrees)," *Microbiology*, 143:3313-3328 (1997).
Price et al., "Genome-scale models of microbial cells: evaluating the consequences of constraints," *Nat. Rev. Microbiol.*, 2(11):886-897 (2004).
Pritchard et al., "A general model of error-prone PCR," *J Theor. Biol.*, 234:497-509 (2005).
Purnell et al., "Modulation of higher-plant NAD(H)-dependent glutamate dehydrogenase activity in transgenic tobacco via alteration of beta subunit levels," *Planta*, 222:167-180 (2005).
Qi et al., "Functional expression of prokaryotic and eukaryotic genes in *Escherichia coli* for conversion of glucose to p-hydroxystyrene," *Metab. Eng.*, 9:268-276 (2007).
Qian et al., "Metabolic engineering of *Escherichia coli* for the production of putrescine: a four carbon diamine," *Biotechnol. Bioeng.*, 104(4)651-662 (2009).
Qiu et al., "Metabolic engineering for the production of copolyesters consisting of 3hydroxybutyrate and 3-hydroxyhexanoate by Aeromonas hydrophilia," *Macromol. Biosci.*, 4(3):255-261 (2004).
Radhakrishnan et al., "Applications of metabolic modeling to drive bioprocess development for the production of value-aded chemicals," *Biotechnol. Bioprocess. Eng.*, 10:408-417 (2005).
Rajpal et al., "A general method for greatly improving the affinity of antibodies by using combinatorial libraries," *Proc. Natl. Acad. Sci. U.S.A.,*_102(24):8466-8471 (2005).
Ramon-Maiques et al., "Structure of Acetylglutamate Kinase, a Key Enzyme for Arginine Biosynthesis and a Prototype for the Amino Acid Kinase Enzyme Family, during Catalysis," *Structure*, 10:329-342 (2002).
Ramos et al., "Mutations affecting the enzymes involved in the utilization of 4-aminobutyric acid as nitrogen source by the yeast *Saccharomyces cerevisiae*," *Eur. J. Biochem.*, 149:401-404 (1985).
Rathinasabapathi, "Propionate, a source of β-alanine, is an inhibitor of β-alanine methylation in Limonium latifolium, Plumbaginaceae," *J. Plant Physiol*, 159:671-674 (2002).
Recasens et al., "Cysteine Sulfinate Aminotransferase and Aspartate Aminotransferase Isoenzymes of Rat Brain. Purification, Characterization, and Further Evidence for Identity," *Biochemistry*, 19:4583-4589 (1980).
Redenbach et al., "A set of ordered cosmids and a detailed genetic and physical map for the 8 Mb Streptomyces coelicolor A3(2) chromosome," *Mol. Microbiol.*, 21:77-96 (1996).
Reed et al., "An expanded genome-scale model of *Escherichia coli* K-12 (iJR904 GSM/GPR)," *Genome. Biol.*, 4(9):R54 (2003).
Reetz et al., "Creation of Enantioselective biocatalysts for Organic Chemistry by In Vitro Evolution," *Agnew. Chem. Int. Ed. Engl.*, 36:2830-2832 (1997).
Reetz et al., "Directed Evolution of an Enantioselective Enzyme through Combinatorial Multiple-Cassette Mutagenesis," *Agnew. Chem. Int. Ed. Engl.*, 40:3589-3591 (2001).
Reetz et al., "Iterative saturation mutagenesis (ISM) for rapid directed evolution of functional enzymes," *Nat. Protoc.*, 2(4):891-903 (2007).
Reetz et al., "Iterative Saturation Mutagenesis on the Basis of B Factors as a Strategy for Increasing Protein Thermostability," *Agnew. Chem. Int. Ed. Engl.*, 45:7745-7751 (2006).
Reetz et al., Expanding the range of substrate acceptance of enzymes: combinatorial active-site saturation test, *Angew. Chem. Int. Ed. Engl.*, 44(27):4192-4196 (2005).
Reidhaar-Olson et al., "Combinatorial cassette mutagenesis as a probe of the informational content of protein sequences," *Science*, 241(4861):53-57 (1988).
Reidhaar-Olson et al., "Random mutagenesis of protein sequences using oligonucleotide cassettes," *Methods Enzymol.*, 208:564-586 (1991).
Reiser et al., "Isolation of mutants of Acinetobacter calcoaceticus deficient in wax ester synthesis and complementation of one muta-

(56) References Cited

OTHER PUBLICATIONS tion with a gene encoding a fatty acyl coenzyme A reductase," *J Bacteriol.*, 179(9):2969-2975 (1997).

Reitzer, "Ammonia Assimillation and the Biosynthesis of Glutamine, Glutamate, Aspartate, Asparagine, l-Alanine, and d-Alanine," in Neidhardt (Ed.), *Escherichia coli and Salmonella: Cellular and Molecular Biology*, ASM Press: Washington, DC, p. 391-407 (1996).

Repetto et al., "Structure and Regulation of KGD1, the Structural Gene for Yeast α-Ketoglutarate Dehydrogenase," *Mol. Cell.*, 9:2695-2705 (1989).

Resnekov et al., "Organization and regulation of the Bacillus subtilis odhAB operon, which encodes two of the subenzymes of the 2-oxoglutarate dehydrogenase complex," *Mol. Gen. Genet.*, 234(2):285-296 (1992).

Ribeiro et al., "Microbial reduction of α-acetyl-γ-butyrolactone," *Tetrahedron: Asymmetry*, 17(6):984-988 (2006).

Rigden et al., "A cofactor-dependent phosphoglycerate mutase homolog from Bacillus stearothermophilus is actually a broad specificity phosphatase," *Protein Sci.*,10:1835-1846 (2001).

Riondet et al., "Measurement of the intracellular pH in *Escherichia coli* with the internally conjugated fluorescent probe 5- (and 6-)carboxyfluorescein succinimidyl ester," *iBiotechnol. Tech.*, 11:735-738 (1997).

Riviere et al., "Acetyl:Succinate CoA-transferase in Procyclic Trypanosoma brucei," *J. Biol Chem.*, 279(44):45337-45346 (2004).

Robinson et al., "Studies on Rat Brain Acyl-Coenzyme a Hydrolase (Short Chain)," *Biochem. Biophys. Res. Commun.*, 71:959-965 (1976).

Roca et al., "Metabolic engineering of ammonium assimilation in xylose-fermenting *Saccharmyces cerevisiae* improves ethanol production," *Appl. Environ. Microbiol.*, 69(8):4732-4736 (2003).

Rodriguez et al., "Characterization of the p-coumaric acid decarboxylase from Lactobacillus plantarum CECT 748(T)," *J Agric. Food Chem.*, 56(9):3068-3072 (2008).

Rohdich et al., "Enoate reductases of Clostridia. Cloning, sequencing, and expression," *J. Biol. Chem.*, 276(8):5779-5787 (2001).

Romero et al., "Partial purification, characterization and nitrogen regulation of the lysine epsilon-aminotransferase of Streptomyces clavuligerus," *J. Ind. Microbiol. Biotechnol.*, 18(4):241-246 (1997).

Rose et al., "The role of the allosteric B site in the fumarase reaction," *Proc. Natl. Acad. Sci. U.S.A.*, 101:3393-3397 (2004).

Rose et al., "Enzymatic phosphorylation of acetate," *J. Biol. Chem.*, 211(2):737-756 (1954).

Roy et al., "Cloning and Characterization of the Gene Encoding Lipamide Dehydrogenase in *Saccharomyces cerevisiae*," *J Gen. Microbiol.*, 133:925-933 (1987).

Ruldeekulthamrong et al., "Molecular characterization of lysine 6-dehydrogenase from Achromobacter denitrificans," *BMB Rep.*, 41:790-795 (2008).

Sabo et al., "Purification and Physical Properties of Inducible Escherichia coli Lysine Decarboxylase," *Biochemistry*, 13(4):662-670 (1974).

Sadowski et al., "The sequence-structure relatiohsip and protein function prediction," *Curr. Op. Struct. Biol.*, 19:357-362 (2009).

Saito et al., "Microbial synthesis and properties of poly(3-hydroxybutyrate-co-4- hydroxybutyrate) in Comamonas acidovorans,"*Int. J Biol. Macromol.*, 16:99-104 (1994).

Saito et al., "Microbial Synthesis and properties of Poly(3-hydroxybutyrate-co-4- hydroxybutyrate)," *Polym. Int.*, 39:169-174 (1996).

Sakakibara et al., "Isolation and characterization of a cDNA that encodes maize glutamate dehydrogenase," *Plant Cell Physiol.*, 36:789-797 (1995).

Salmon et al., "Global gene expression profiling in *Escherichia coli* K12: effects of oxygen availability and ArcA," *J. Biol. Chem.*, 280(15):15084-15096 (2005).

Samsonova et al., "Molecular cloning and characterization of *Escherichia coli* K12 ygjG gene," *BMC Microbiol.*, 3:2 (2003).

Sanchez et al., "Properties and functions of two succinic-semialdehyde dehydrogenases from Pseudomonas putida," *Biochim. Biophys. Acta.*, 953(3):249-257 (1988).

Sanchez et al., "Purification and properties of two succinic semialdehyde dehydrogenases from Klebsiella pneumoniae," *Biochim. Biophys. Acta.*, 990(3):225-231 (1989).

Sato et al., "Poly[(R)-3-Hydroxybutyrate] Formation in *Escherichia coli* from Glucose through an Enoyl-CoA Hydratase-Mediated Pathway," *J Biosci. Bioeng.*, 103(1):38-44 (2007).

Scherf et al., "Purification and properties of an iron-sulfur and Fad-containing 4hydroxybuturyl-CoA dehydratase/vinylacetyl-CoA Δ3-Δ2-isomerase from Clostridium aminobutyricum," *Eur. J Biochem.*, 215:421-429 (1993).

Scherf et al., "Purification and properties of 4-hydroxybutyrate coenzyme a transferase from Clostridium aminobutyricum," *Appl. Environ. Microbiol.*, 57(9):2699-2702 (1991).

Scherf et al., "Suffinate-ethanol fermentation in Clostridium kluyveri: purification and characterisation of 4-hydroxybutyryl-CoA dehydratase/vinylacetyl-CoA delta 3-delta 2-isomerase," *Arch. Microbiol.*, 161:239-245 (1994).

Schilling et al., "Combining Pathway Analysis with Flux Balance Analysis for the Comprehensive Study of Metabolic Systems," *Biotechnol. Bioeng.*, 71(4):286-306 (2000-2001).

Schilling et al., "Theory for the Systematic Definition of Metabolic Pathways and Their Use in Interpreting Metabolic Function from a Pathway-Oriented Perspective," *J Theor. Biol.*, 203(3):229-248 (2000).

Schilling et al., "Toward Metabolic Phenomics: Analysis of Genomic Data Using Flux Balances," *Biotechnol. Prog.*, 15(3):288-295 (1999).

Schneider et al., "The *Escherichia coli* gabDTPC operon: specific γ-aminobutyrate catabolism and nonspecific induction," *J Bacteriol.*, 184:6976-6986 (2002).

Schulz et al., "Stereopsecific Production of the Herbicide Phosphinothricin (Glufosinate) by Transamination: Isolation and Characterization of a Phosphinothricin-Specific Transaminase from *Escherichia coli*," *Appl. Environ. Microbiol.*, 56:1-6 (1990).

Scott et al., "Soluble γ-Aminobutyric-Glutamic Transaminase from Pseudomonas fluorescens," *J Biol. Chem.*, 234:932-936 (1959).

Seedorf et al., "The genome of Clostridium kluyveri, a strict anaerobe with unique metabolic features," *Proc. Natl. Acad. Sci. U.S.A.*, 105(6):2128-2133 (2008).

Seffernick et al., "Melamine deaminase and atrazine chlorohydrolase: 98 percent identical but functionally different," *J Bacteriol.*, 183(3):2405-2410 (2001).

Selifonova et al., "Rapid evolution of novel traits in microorganisms," *Appl. Environ. Microbiol.*, 67(8):3645-3649 (2001).

Sen et al., "Developments in directed evolution for improving enzyme functions," *Appl. Biochem. Biotechnol.*, 143(3):212-223 (2007).

Shafiani et al., "Cloning and characterization of aspartate-β-semialdehyde dehydrogenase from *Mycobacterium tuberculosis* H37 Rv," *J Appl. Microbiol.*, 98:832-838 (2005).

Shalel-Levanon et al., "Effect of ArcA and FNR on the expression of genes related to the oxygen rregulation and the glycolysis pathway in *Escherichiha coli* under microaerobic growth conditions," *Biotechnol. Bioeng.*, 92(2):147-159 (2005).

Shames et al., "Interaction of aspartate and aspartate-derived antimetabolites with the enzymes of the threonine biosynthetic pathway of *Escherichia ecoli*," *J Biol. Chem.*, 259(24):15331-15339 (1984).

Shao et al., "Random-Priming in Vitro Recombination: an Effective Tool for Directed Evolution," *Nucleic Acids Res.*, 26(2):681-683 (1998).

Shi et al., "The structure of L-aspartate ammonia-lyase from *Escherichia coli*," *Biochem.*, 36(30):9136-9144 (1997).

Shigeoka et al., "Characterization and molecular properties of 2-oxoglutarate decarboxylase from Euglena gracilis," *Arch. Biochem. Biophys.*, 288:22-28 (1991).

Shigeoka et al., "Effect of L-glutamate on 2-oxoglutarate decarboxylase in Euglena gracilis," *Biochem. J.*, 282 (Pt 2):319-323 (1992).

Shigeoka et al., "The effect of thiamin on the activation of thiamin pyrophosphate-dependent 2-oxoglutarate decarboxylase in Euglena gracilis," *Biochem. J*, 292 (Pt 2):463-467 (1993).

(56) References Cited

OTHER PUBLICATIONS

Shimomura et al., "3-Hydroxyisobu 1-CoA Hydrolase," *Meth. Enzymol.*, 324:229-240 (2000).
Shimomura et al., "Purification and Partial Characterization of 3-Hydroxyisobutyryl-coenzyme a Hydrolase of Rat Liver," *J Biol. Chem.*, 269:14248-14253 (1994).
Shingler et al., "Nucleotide Sequence and Functional Analysis of the Complete Phenol/3,4-Dimethylphenol Catabolic Pathway of Pseudomonas sp. Strain CF600," *J Bacteriol.*, 174(3):711724 (1992).
Shiraki et al., "Fermentative production of (R)-(-)-(3) hydroxybutyrate using 3-hydroxybutyrate dehydrogenase null mutant of Ralstonia eutropha and recombinant *Escherichia coli*," *J. Biosci. Bioeng.*, 102(6):529-534 (2006).
Shukla et al., "Production of D(-)-lactate from sucrose and molasses," *Biotechnol. Lett.*, 26(9):689-693 (2004).
Sieber et al., "Libraries of hybrid proteins from distantly related sequences," *Nat. Biotechnol.*, 19(5):456-460 (2001).
Siegert et al., "Exchanging the substrate specificities of pyruvate decarboxylase from Zymomonas mobilis and benzoylase from *Pseudomonas putida*," *Protein Eng. Des. Sel.*, 18:345-357 (2005).
Simonov et al., "Application of Gas Chromatography and Gas Chromatography-Mass Spectrometry to the Detection of γ-Hydroxybutyric Acid and Its Precursors in Various Materials," *J Anal. Chem.*, 59:965-971 (2004).
Sinclair et al, "Purification and characterization of the branched chain α-ketoacid dehydrogenase complex from *Saccharomyces cerevisiae*," *Biochem. Mol. Biol. Int.*, 31(5):911-922 (1993).
Sivaraman et al., "Codon choice in genes depends on flanking sequence information—implications for theoretical reverse translation," *Nucleic Acids Res.*, 36(3):e16 (2008).
Sjostrom et al., "Purfication and characterisation of a plasminogen-binding protein from Haemophilus influenzae. Sequence determination reveals identity with aspartase," *Biochim. Biophys. Acta.*, 1324:182-190 (1997).
Skarstedt et al., "*Escherichia coli* Acetate Kinase Mechanism Studied by Net Initial Rate, Equilibriu, and Independent Isotopic Exchange Kinetics," *J Biol. Chem.*, 251:6775-6783 (1976).
Skinner et al., "An *Escherichia coli* mutant defective in the Nad-dependent succinate semialdehyde dehydrogenase," *Arch. Microbiol.*, 132(3):270-275 (1982).
Smit et al., "Identification, Cloning, and Characterization of a Lactococcus lactis Branched-Chain α-Keto Acid Decarboxylase Involved in Flavor Formation," *Appl. Environ. Microbiol.*, 71:303-311 (2005).
Smith et al., "Fumarate metabolism and the microaerophily of Campylobacter species," *Int. J. Biochem. Cell Biol.*, 31:961-975 (1999).
Smith et al., "Purification and characteristics of a gamma-glutamyl kinase involved in *Escherichia coli* proline biosynthesis," *J Bacteriol.*, 157:545-551 (1984).
Smith et al., "Complete genome sequence of Methanobacterium thermoautotrophicum deltaH: functional analysis and comparative genomics," *J Bacteriol.*, 179:7135-7155 (1997).
Snedecor et al., "Selection, expression, and nucleotide sequencing of the glutamate dehydrogenase gene of Peptostreptococcus asaccharolyticus," *J Bacteriol.*, 173:6162-6167 (1991).
Soda et al., "L-Lysine:alpha-ketoglutarate aminotransferase. II. Purification, crystallization, and properties," *Biochemistry*, 7(11):4110-4119 (1968).
Sohling et al., "Molecular analysis of the anaerobic succinate degradation pathway in Clostridium kluyveri.," *J Bacteriol.*, 178(3):871-880 (1996).
Söhling et al., "Purification and characterization of a Coenzyme-A-dependent succinate-semialdehyde dehydrogenase from Clostridium kluyveri," *Eur. J Biochem.*, 212:121-127 (1993).
Sokatch et al., "Purification of a Branched-Chain Keto Acid Dehydrogenase from Pseudomonas putida," *J Bacteriol.*, 647-652 (1981).
Song et al., "Structure, Function, and Mechanism of the Phenylacetate Pathway Hot Dog-fold Thioesterase PaaI," *J Biol. Chem.*, 281(16):11028-11038 (2006).
Song et al., "Construction of recombinant *Escherichia coli* strains producing poly (4-hydroxybutyric acid) homopolyester from glucose," *Wei Sheng Wu Xtte Bao*, 45(3):382-386 (2005). (in Chinese, includes English abstract).
Spencer et al., "Nucleotide sequence of the sucB gene encoding the dihydrolipoamide succinyltransferase of *Escherichia coli* K12 and homology with the corresponding acetyltransferase," *Eur. J Biochem.*, 141(2):361-374 (1984).
Spencer et al., "Transcription analysis of the sucAB, aceEF and 1pd genes of *Escherichia coli*," *Mol. Gen. Genetics*, 200:145-154 (1985).
Stadtman, "The enzymatic synthesis of β-alanyl coenzyme A," *J Am. Chem. Soc.*, 77:5765-5766 (1955).
Stanley et al., "Expression and stereochemical and isotope effect studies of active 4-oxalocrotonate decarboxylase," *Biochemistry*, 39(12):3514 (2000).
Stanley et al., "Expression and Sterochemical and Isotope Effect Studies of Active 4-Oxalocrotonate Decarboxylase," *Biochem.*, 39:(4):718-726 (2000).
Starai et al., "Acetate excretion during growth of Salmonella enterica on ethanolamine requires phosphotransacetylase (EutD) activity, and acetate recapture requires acetyl-CoA synthetase (Acs) and phosphotransacetylase (Pta) activities," *Microbiology*, 151(Pt 11):3793-3801 (2005).
Starai et al., "Residue Leu-641 of Acetyl-CoA synthetase is critical for the acetylation of residue Lys-609 by the Protein acetyltransferase enzyme of Salmonella enterica," *Biol. Chem.*, 280(28):26200-26205 (2005). (Epub May 17, 2005).
Steinbuchel et al., "A multifunctional fermentative alcohol dehydrogenase from the strict aerobe Alcaligenes eutrophus: purification and properties," *Eur. J Biochem.*, 141:555-564 (1984).
Steinbuchel et al., "A Pseudomonas strain accumulating polyesters of 3-hydroxybutyric acid and medium-chain-length 3-hydroxyalkanoic acids," *Appl. Microbiol. Biotechnol.*, 37:691-697 (1992).
Steinbuchel et al., "Diversity of bacterial polyhydroxyalkanoic acids," *FEMS Microbiol. Lett*, 128:219-228 (1995).
Steinbüchel et al., "NAD-linked L(+)-lactate dehydrogenase from the strict aerobe alcaligenes eutrophus. 2. Kinetic properties and inhibition by oxaloacetate," *Eur. J. Biochem.*, 130(2):329-334 (1983).
Steinbuchel et al., "Physiology and molecular genetics of poly(beta-hydroxy-alkanoic acid) synthesis in Alcaligenes eutrophus," *Mol. Microbiol.*, 5(3):535-542 (1991).
Stemmer, "Dna Shuffling by random fragmentation and reassembly: in vitro recombination for molecular evolution," *Proc. Natl. Acad. Sci. U.S.A.*, 91(22):10747-10751 (1994).
Stemmer, "Rapid evolution of a protein in vitro by DNA shuffling," *Nature*, 370:389-391 (1994).
Stokell et al., "Probing the roles of key residues in the unique regulatory NADH binding site of type Ii citrate synthase of *Escherichia coli*," *J Biol. Chem.*, 278(37):35435-35443 (2003).
Stols et al., "New vectors for co-expression of proteins: Structure of Bacillus subtilis ScoAB obtained by high-throughput protocols," *Protein Expr. Purif.*, 53:396-403 (2007).
Stoyan et al., "Cloning, sequencing and overexpression of the leucine dehydrogenase gene from *Bacillus cereus*," *J Biotechnol.*, 54:77-80 (1997).
Strauss et al., "Enzymes of a novel autotrophic CO2 fixation pathway in the phototrophic bacterium Chloroflexus aurantiacus, the 3-hydroxypropionate cycle," *Eur. J. Biochem.*, 215:633-643 (1993).
Suda et al., "Purification and properties of alpha-keoadipate reductase, a newly discovered enzyme from human placenta," *Arch. Biochem. Biophys.*, 176(2):610-620 (1976).
Suda et al., "Subcellular Localization and tissue Distribution of α-Ketodaipate Reduction and Oxidation in the Rat," *Biochem. Biophys. Res. Commun.*, 77:586-591 (1977).
Suematsu et al., "Molecular cloning and functional expression of rat liver cytosolic acetyl-CoA hydrolase," *Eur. J Biochem.*, 268(9):2700-2709 (2001).

(56) References Cited

OTHER PUBLICATIONS

Sulzenbacher et al., "Crystal structure E. coli dehydrogenase Yqhd: evidence of a covalently modified NADP coenzyme," *J. Mol. Biol.*, 342(2):489-502 (2004).

Suthers et al., "Metabolic flux elucidation for large-scale models using 13C labeled isotopes," *Metab. Eng.*, 9(5-6):387-405 (2007).

Suzuki et al., "GriC and GriD Constitute a carboxylic acid reductase involved in grixazone biosynthesis in Streptomyces griseus," *J. Antibiot.*, 60(6):380-387 (2007).

Suzuki, "Phosphotransacetylase of *Escherichia coli* B, activation by pyruvate and inhibition by NADH and certain nucleotides," *Biochim. Biophys. Acta*, 191(3):559-569 (1969).

Syntichaki et al., "The amino-acid sequence similarity of plant glutamate dehydrogenase to the extremophilic archaeal enzyme conforms to its stress-related function," *Gene.*, 168:87-92 (1996).

Takagi et al., "Isolation of a Versatile Serratia marcescens Mutant as a Host and Molecular Cloning of the Aspartase Gene," *J. Bacteriol.*, 161(1):1-6 (1985).

Takagi et al., "Purfication, Crystallization, and Molecular Properties of Aspartase from Pseudomonas fluorescens," *J. Biochem.*, 96:545-552 (1984).

Takahashi et al., "Metabolic Pathways for Cytoxic End Product Formation from Glutamate-and Aspartate-Containing Peptides by Porphyromonas gingivalis," *J. Bacteriol.*, 182(17):4704-4710 (2000).

Takahashi-Abbe et al., "Biochemical and functional properties of a pyruvate formate-lyase (Pfl)-activating system in Streptococcus mutans," *Oral Microbiol. Immunol.*, 18(5)293-297 (2003).

Takanashi et al., "Characterization of a novel 3-hydroxybutyrate dehydrogenase from Ralstonia pickettii T1," *Antonie van Leeuwnhoek*, 95(3):249-262 (2009).

Takatsuka et al., "Gene cloning and molecular characterization of lysine decarboxylase from Selenomonas ruminantium delineate its evolutionary relationship to ornithine decarboxylases from eukaryotes," *J. Bacteriol.*, 182(23):6732-6741 (2000).

Takatsuka et al., "Identification of the amino acid residues conferring substrate specificity upon selenomonas ruminantium lysine decarboxylase," *Biosci. Biotechnol. Biochem.*, 63(10):1843-1846 (1999).

Takigawa et al., "Probabilistic path ranking based on adjacent pairwise coexpression for metabolic transcripts analysis," *Bioinformatics*, 24(2):250-257 (2008).

Tamaki et al., "Purification, Properties, and Sequencing of Aminisobutyrate Aminotransferases from Rat Liver," *Meth. Enzymol.*, 324:376-389 (2000).

Tanaka et al., "Cloning and characterization of a human orthologue of testis-specific succinyl CoA:3-oxo acid CoA transferase (Scot-t) cDNA," *Mol. Hum. Reprod.*, 8:16-23 (2001.).

Tanaka et al., "Lysine decarboxylase of Vibrio parahaemolyticus: kinetics of transcription and role in acid resistance," *J. Appl. Microbiol.*, 104(5):1283-1293 (2007).

Tang et al., "Identification of a novel pyridoxal 5'-phosphaste binding site in adenosylcobalamin-dependent lysine 5,6-aminomutase from Porphyromonas gingivalis," *Biochemistry*, 41(27):8767-8776 (2002).

Tani et al., "Thermostable NADP(+)-dependent medium-chain alcohol dehydrogenase from Acinetobacter sp strain M-1: Purification and characterization and gene expression in *Escherichia coli*," *Appl. Environ. Microbiol.*, 66:5231-5235 (2000).

Teller et al., "The glutamate dehydrogenase gene of Clostridium symbiosum, Cloning by polymerase chain reaction sequence analysis and over-expression in *Escherichia coli*," *Eur. J. Biochem.*, 206:151-159 (1992).

Ter Schure et al., "Pyruvate Decarboxylase Catalyzes Decarboxylation of Branched-Chaing 2-Oxo Acids but Is Not Essential for Fusel Alcohol Production by *Saccharomyces cerevisiae*," *Appl. Environ. Microbiol.*, 64(4):1303-1307 (1998).

Thakur et al., "Changes in the Electroencephalographic and gamma.-Aminobutyric Acid Transaminsase and Succinic Semialdehyde Dehydrogenase in the Allergen Induced Rat Brain," *Biochem. Int.*, 16:235-243 (1998).

Thauer, "Microbiology. A fifth pathway of carbon fixation," *Science*, 318:1732-1733 (2007).

Tian et al., "Variant tricarboxylic acid cycle in Mycobacterium tuberculosis: identification of alpha-ketoglutarate decarboxylase," *Proc. Natl. Acad. Sci. U.S.A.*, 102(30):10670-10675 (2005).

Tobin et al., "Localization of the lysine epsilon-aminotransferase (lat) and delta- (L-alpha-aminoadipyl)-L-cysteinyl-D-Valine synthetase (pcbAB) genes from Streptomyces clavuligerus and production of lysine epsilon-aminotransferase activity in *Escherichia coli*," *J. Bacteriol.*, 173(19):6223-6229 (1991).

Tomb et al., "The complete genome sequence of the gastric pathogen Helicobacter pylori," *Nature*, 388:539 (1997).

Toth et al., "The ald gene, encoding a coenzyme A-acylating aldehyde dehydrogenase, distinguishes Clostridium beijerinckii and two other solvent-producing clostridia from Clostridium acetobutylicum," *Appl. Environ. Microbiol.*, 65(11):4973-4980 (1999).

Tretter et al., "Alpha-ketoglutarate dehydrogenase: a target and generator of oxidative stress," *Philos. Trans. R. Soc. Lond B. Biol. Sci.*, 360:2335-2345 (2005).

Tseng et al., "Metabolic engineering of *Escherichia coli* for enhanced production of (R)- and (S)-3-hydroxybutyrate," *Appl. Environ. Microbiol.* m 75(10):3137-3145 (2009).

Tsuji et al., "The effects of temperature and pH on the growth of eight enteric and nine glucose non-fermenting species of gram-negative rods," *Microbiol. Immunol.*, 26(1):15-24 (1982).

Tucci et al., "A novel prokaryotic trans-2-enoyl-CoA reductase from the spirochete Treponema denticola," *FEBS Lett.*, 581:1561-1566 (2007).

Twarog et al., "Role of Buyryl Phosphate in the Energy Metabolism of Clostridium Tetanomorphum," *J Bacteriol.*, 86:112-117 (1963).

Two pages from URL: www.genome.jp/dbget-bin/www_bget?cdf:CD2966 (Printed Dec. 21, 2009).

Two pages from URL: www.genome.jp/dbget-bin/www_bget?cpe:CPE2531 (Printed Dec. 21, 2009).

Two pages from URL: www.genome.jp/dbget-bin/www_bget?ctc:CTC01366 (Printed Dec. 21, 2009).

Two pages from URL: www.genome.jp/dbget-bin/www_bget?cth:Cthe_0423 (Printed Mar. 04, 2010).

Two pages from URL: Openwetware.org/wiki/Synthetic_Biology:BioBricks, Synthetic Biology:BioBricks, portal for information relating to the Resistry of Standard Biological Parts (Printed Dec. 21, 2009).

Tzimagiorgis et al., "Molecular cloning, structure and expression analysis of a full-length mouse brain glutamate dehydrogenase cDNA," *Biochem. Biophys. Acta.*, 1089:250-253 (1991).

Tzimagiorgis et al., "Structure and expression analysis of a member of the human glutamate dehydrogenase (GLUD) gene gamily mapped to chromosome 10p11.2," *Hum. Genet.*, 91:433-438 (1993).

Uchiyama et al., "Identification of the4-Hydroxycinnamate Decarboxylase (PAD) Gene of Klebsiella oxytoca," *Biosci. Biotechnol. Biochem.*, 72:116-123 (2008).

Umeda et al., "Cloning and sequence analysis of the poly(3-hydroxyalkanoic acid)-synthesis genes of Pseudomonas acidophila," *Appl. Biochem. Biotechnol.*, 70-72:341-352 (1998).

UniProt Accession No. P21881 (document last modified Jun. 28, 2011; Sequence last modified Jan. 23, 2007).

UniProt Accession No. P21882 (document last modified Jun. 28, 2011; Sequence last modified Jan. 23, 2007).

Uttaro et al., "Purification and characterisation of a novel iso-propanol dehydrogenase from Phytomonas sp," *Mol. Biochem. Parasitol.*, 85:213-219 (1997).

Valdes-Hevia et al., "Isolation and characterization of the gene encoding phosphoenolpyruvate carboxykinase from *Saccharomyces cerevisiae*," *FEBS Lett.*, 258(2):313316 (1989).

Valentin et al., "Identification of 4-hydroxyvaleric acid as a constituent of biosynthetic polyhydroxyalkanoic acids from bacteria," *Appl. Microbiol. Biotechnol.*, 36:507-514 (1992).

Valentin et al., "Identification of 5-hydroxyhexanoic acid, 4-hydroxyaheptanoic acid and 4hydroxyoctanoic acid as new constituents of bacterial polyhydroxyalkanoic acids," *Appl. Microbiol. Biotechnol.*, 46:261-267 (1996).

(56) References Cited

OTHER PUBLICATIONS

Valentin et al., "Indentication of 4-hydroxyhexanoic acid as a new constituent of biosynthetic polyhydroxyalkanoic acids from bacteria," *Appl. Microbiol. Biotechnol.*, 40:710-716 (1994).
Valentin et al., "Metabolic pathway for biosynthesis of poly(3-hydroxybutyrate-co-4-hydroxybutyrate) from 4-hydroxybutyrate by Alcaligenes eutrophus," *Eur. J Biochem.*, 227(12):43-60 (1995).
Valentin et al., "Poly(3-hydroxybutyrate-co-4-hydroxybutyrate) formation from gamma-aminobutyrate and glutamate," *Biotechnol Bioeng.*, 67(3):291-299 (2000).
Valentin et al., "Production of poly(3-hydroxybutyrate-co-4-hydroxybutyrate) in recombinant *Escherichia coli* grown on glucose," *J. Biotechnol.*, 58:33-38 (1997).
Valentine et al., "Purification and role of phosphotransbutyrylase," *J. Biol. Chem.*, 235:1948-1952 (1960).
Valle et al., "Complete nucleotide sequence of the glutamate dehydrogenase gene from *Escherichia coli* K-12," *Gene*, 27:193-199 (1984).
Valle et al., "Nucleotide sequence of the promotor and amino-terminal coding region of the glutamate dehydrogenase structural gene of *Escherichia coli,*" *Gene*, 23:199-209 (1983).
Vamecq et al., "The microsomal dicarboxylyl-CoA synthetase," *Biochem. J.*, 230:683-693 (1985).
Van Der Rest et al., "Functions of the membrane-associated and cytoplasmic malate dehydrogenases in the citric acid cycle of *Escherichia coli,*" *J Bacteriol.*, 182(24):6892-6899 (2000).
Van Der Voorhorst et al., "Genetic and biochemcial characterization of a short-chain alcohol dehydrogenase from the hyperthermophilic archaeon Pyrococcus furiosus," *Eur. J. Biochem.*, 268:3062-3068 (2001).
Van Grinsven et al., "Acetate:Succinate CoA-transferase in the Hydrogenosomes of Trichomonas vaginalis," *J. Biol. Chem.*, 283:1411-1418 (2008).
Vanderwinkel et al., "Growth of *Escherichia coli* on Fatty Acids: Requirement for Coenzyme a Transferase Activity," *Biochem. Biophys. Res. Commun.*, 33:902-908 (1968).
Vanrolleghem et al., "Validation of a Metabolic Network for *Saccharomyces cerevisiae* Using Mixed Substrate Studies," *Biotechnol. Prog.*, 12(4):434-448 (1996).
Varma et al., "Metabolic Flux Balancing: Basic Concepts, Scientific and Practical Use," *Biotechnology*, 12:994-998 (1994).
Varma et al., "Stoichiometric flux balance models quantitatively predict growth and metabolic by-product secretion in wild-type *Escherichia coli* W3110," *Appl. Environ. Microbiol.*, 60:3724-3731 (1994).
Vazquez et al., "Phosphotransbutyrylase Expression in Bacillus megaterium," *Curr. Microbiol.*, 42:345-349 (2001).
Venkitasubramanian et al. Biocatalysis in the Pharmaceutical and Biotechnology Industries, ed. R.N. Patel, Chapter 15, pp. 425-440, Crc Press Llc, Boca Raton, Fl. 2007.
Venkitasubramanian et al., "Reduction of Carboxylic Acids by Nocardia Aldehyde Oxidoreductase Requires a Phosphopantetheinylated Enzyme," *J. Biol Chem.*, 282:478-485 (2007).
Vernal et al., "Cloning and heterologous expression of a broad specificity aminotransferase of leishmania mexicana promastigotes 1," *FEMS Microbiol. Lett.*, 229(2):217-222 (2003).
Vernal et al., "Isolation and partial characterization of a broad specificity aminotransferase from Leishmania mexicana promastigotes," *Mol. Biochem. Parasitol.*, 96(1-2):83-92 (1998).
Vey et al., "Structural basis for glycyl radical formation by pyruvate formate-lyase activating enzyme," *Proc. Natl. Acad. Sci. U.S.A.*, 105(42):16137-16141 (2008).
Viola, "L-aspartase: new tricks from an old enzyme," *Adv. Enzymol. Relat. Areas. Mol. Biol.*, 74:295-341 (2000).
Vita et al., "Disulfide bond-dependent mechanism of protection against oxidative stress in pyruvate-ferredoxin oxidoreductase of anaerobic Desulfovibrio bacteria," *Biochemistry*, 47(3):957-964 (2008).
Volkov et al., "Random chimeragenesis by heteroduplex recombination," *Methods Enzymol.*, 328:456-463 (2000).
Volkov et al., "Recombination and chimeragenesis by in vitro heteroduplex formation and in vivo repair," *Nucleic Acids Res.*, 27(18):e18 (1999).
Wakil et al., "Studies on the Fatty Acid Oxidizing System of Animal Tissues," *J. Biol. Chem.*, 207:631-638 (1954).
Walter et al., "Sequence and arrangement of two genes of the butyrate-synthesis pathway of Clostridium acetobutylicum ATCC 824," *Gene*, 134:107-111 (1993).
Walter et al., "Molecular characterization of two Clostridium acetobutylicum ATCC 824 butanol dehydrogenase isozyme genes," *J. Bacteriol.*, 174(22):7149-7158 (1992).
Wang et al., "Molecular cloning and functional identification of a novel phenylacetyl-CoA ligase gene from Penicillium chrysogenum," *Biochem. Biophys. Res. Commun.*, 360(2):453-458 (2007).
Wang et al., "The primary structure of branched-chain α-oxo acid dehydrogenase from Bacillus subtilis and its similarity to other a-oxo acid dehydrogenases," *Eur. J Biochem.*, 213:1091-1099 (1993).
Wang et al., "Isolation of poly-3-hydroxybutyrate metabolism genes from complex microbial communities by phenotypic complementation of bacterial mutants," *Appl. Environ. Microbiol.*, 72(1):384-391 (2006).
Wang et al., "Screening microorganisms for utilization of furfural and possible intermediates in its degradative pathway," *Biotechnol. Lett.*, 16(9):977-982 (1994).
Ward et al., "Molecular analysis of the role of two aromatic aminotransferases and a broad-specificity aspartate aminotransferase in the aromatic amino acid metabolism of Pyrococcus furiosus," *Archaea*, 1:133-141 (2002).
Weaver, "Structure of free fumarase C from *Eschericiha coli,*" *Acta. Crystallog. D. Biol. Crystallogr.*, 61:1395-1401 (2005).
Weidner et al., "Molecular Characterization of the Genes Encoding Pyruvate Formate-Lyase and Its Activating Enzyme of Clostridium pasteruianum," *J Bacteriol.*, 178(8):2440-2444 (1996).
Welch et al., "Purification and characterization of the NADH-dependent butanol dehydrogenase from Clostridium acetobutylicum (ATCC 824)," *Arch. Biochem. Biophys.*, 273(2):309-318 (1989).
Werpy et al., "Top Value Added Chemicals from Biomass. vol. I—Results of Screening for Potential Candidates from Sugars and Synthesis Gas," DOE Report (2004).
Westin et al., "The Identification of Succinyl-CoA Thioesterase Suggests a Novel Pathway for Succinate Production in Peroxisomes," *J Biol. Chem.*, 280(46):38125-38132 (2005).
Wexler et al., "A wide host-range metagenomic library from a waste water treatment plant yields a novel alcohol/aldehyde dehdrogenase," *Environ. Microbiol.*, 7:1917-1926 (2005).
Whalen et al., "Analysis of an avtA::Mu dl(Ap lac) Mutant: Metabolic role of Transaminase C," *J Bacteriol.*, 150(2):739-746 (1982).
Whalen et al., "Gratuitous Repression of avtA in *Escherichia coli* and Salmonella typhimurium," *J Bacteriol.*, 158(2):571-574 (1984).
Wiesenborn et al., "Coenzyme A Transferase from Clostridium acetobutylicum ATC 824 and Its Role in the Uptake of Acids," *Appl. Environ. Microbiol.*, 55:323-329 (1989).
Wilkie et al., "Recombinant Expression, Purification, and Characterization of Three Isoenzymes of Aspartate Aminotrannsferase from *Arabidopsis thaliana,*" Protein Expr. Purif., 12:381-389 (1998).
Wilks et al., "A specific, highly active malate dehydrogenase by redesign of a lactate dehydrogenase framework," *Science*, 242(4885):1541-1544 (1988).
Wilks et al., "Design for a broad substrate specificity keto acid dehydrogenase," *Biochemistry*, 29(37)8587-8591 (1990).
Wilks et al., "Design of a specific phenyllactate dehydrogenase by peptide loop exchange on the Bacillus stearothermophilus lactate dehydrogenase framework," *Biochemistry*, 31(34):7802-7806 (1992).
Willadsen et al., "Assay of 4-hydroxybu 1-CoA dehydrasate from Clostridium . ammobutyricum," *FEMS Microbiol. Lett.*, 70:187-191 (1990).
Williams et al., "Biodegradable plastics from plants," *CHEMTECH*, 26:38-44 (1996).
Willke et al., "Biotechnological production of itaconic acid," *Appl. Microbiol. Biotechnol.*, 56:289-295 (2001).

(56) References Cited

OTHER PUBLICATIONS

Winzer et al., "Differential regulation of two thiolase genes from Clostridium acetobutylicum Dsm 792," *J Mol. Microbiol. Biotechnol.*, 2:531-541 (2000).
Witkowski et al., "Conversion of a 13-ketoacyl synthase to a malonyl decarboxylase by replacement of the active-site cysteine with glutamine," *Biochemistry*, 38(36):11643-11650 (1999).
Wolff et al., "Dehydrogenases involved in the conversion of succinate to 4-hydroxybutanoate by Clostridium kluyven," *Appl. Environ. Microbiol.*, 59:1876-1882 (1993).
Wolff et al., "Purification and characterization of the oxygen-sensitive 4-hydroxybutanoate dehydrogenase from Clostridium kluyveri," *Protein Expr. Purif.*, 6:206-212 (1995).
Wong et al., "Sequence satruation mutagenesis with tunable mutation frequencies," *Anal. Biochem.*, 341:187-189 (2005).
Wong et al., "Sequence saturation mutagenesis (SeSaM): a novel method for directed evolution," *Nucleic Acids Res.*, 32(3):e26 (2004).
Wong et al., "Transversion-enriched sequence saturation mutagenesis (SeSaM-Tv+): a random mutagenesis method with consecutive nucleotide exchanges that complements the bias of error-prone PCR," *Biotechnol. J.*, 3:74-82 (2008).
Wynn et al., "Chaperonins GroEL and GroES Promote Assembly of Heterotramers ($\alpha 2\beta 2$) of Mammalian Mitochondrial Branched-chain $\alpha$-Keto Acid Decarboxylase in *Escherichia coli*," *J. Biol. Chem.*, 267(18):12400-12403 (1992).
Wynn et al., "Cloning and Expression in *Escherichia coli* of a Mature E1$\beta$ Subunit of Bovine Mitochondrial Branched-chain $\alpha$-Keto Acid Dehydrogenase Complex," *J. Biol Chem.*, 267(3):1881-1887 (1992).
Yagi et al., "Aspartate: 2-Oxoglutarate Aminotransferase from Bakers' Yeast: Crystallization and Charactierization," *J Biochem.*, 92:35-43 (1982).
Yagi et al., "Crystallization and Properties of Aspartate Aminotransferase from *Escherichi Coli B*," *FEBS Lett*, 100(1)81-84 (1979).
Yagi et al., "Glutamate-Aspartate Transaminase from Microorganisms," *Meth. Enzymol.*, 113:83- 89 (1985).
Yakunin et al., "Purification and characterization of pyruvate oxidoreductase from the photosynthetic bacterium Rhodobacter capsulatus," *Biochim. Biophys. Acta.*, 1409(1):39-49 (1998).
Yamamoto et al., "Carboxylation reaction catalyzed by 2-oxoglutarate:ferredoxin oxidoreductases from Hydrogenobacter thermophilus," *Extremophiles*, 14:79-85 (2010).
Yamamoto et al., "Purification and properties of Nadp-dependent formate dehydrogenase from Clostridium thermoaceticum, a tungsten-selenium-iron protein," *J. Biol. Chem.*, 258(3):1826-1832 (1983).
Yang et al, "Nucleotide Sequence of the fadA Gene. Primary structure of 3-ketoacyl-coenzyme A thiolase from *Escherichia coli* and the structural organization of the fadAB operon," *J. Biol. Chem.*, 265(18):10424-10429 (1990) with correction in *J. Biol. Chem.*, 266(24):16255 (1991).
Yang et al., "Aspartate Dehydrogenase, a Novel Enszyme Idnetified from Structural and Functional Studies of TM16343," *J. Biol. Chem.*, 278:8804-8808 (2003).
Yang et al., "Nucleotide sequence of the promoter and fadB gene of the fadBA operon and primary structure of the multifunctional fatty acid oxidation protein from *Escherichia coli*," *Biochemistry*, 30(27):6788-6795 (1991).
Yano et al., "Directed evolution of an aspartate aminotransferase with new substrate specificities," *Proc. Natl. Acad. Sci. U.S.A.*, 95:5511-5515 (1998).
Yarlett et al., "Trichomonas vaginalis: characterization of ornithine decarboxylase," *Biochem. J.*, 293:487-493 (1993).
Yee et al., "Isolation and characterization of a NADP-dependent glutamate dehydrogenase gene from the primitive eucaryote Giardia lamblia," *J Biol. Chem.*, 267:7539-7544 (1992).
Yim et al., "Metabolic engineering of *Escherichia coli* for direct production of 1,4-butanediol," *Nature Chemical Biology*, 7(7):445-452 (2011).
Yoshida et al., "The structures of L-rhamnose isomerase from Pseudomonas stutzeri in complexes with L-rhamnose and D-allose provide insights into broad substrate specificity," *J. Mol. Biol.*, 365(5): 1505-1516 (2007).
Youngleson et al., "Homology between hydroxybutyryl and hydroxyacyl coenzyme a dehydrogenase enzymes from Clostridium acetobutylicum fermentation and vertebrate fatty acid beta-oxidation pathways," *J Bacteriol.*, 171(12):6800-6807 (1989).
Yu et al., "sucAB and sucCD are mutually essential genes in *Escherichia coli*," *FEMS Microbiol. Lett.*, 254(2):245-250 (2006).
Yun et al., "The genes for anabolic 2-oxoglutarate: ferredoxin oxidoreductse from hydrogenobacter thermophilus TK-6," *Biochem. Biophys. Res. Commun.*, 282(2):589-594 (2001).
Yun et al., "$\omega$-Amino acid:pyruvate transaminase from Alcaligenes denitrificans Y2k-2: a new catalyst for kinetic resolution of ($\beta$-amino acids and amines," *Appl. Environ. Microbiol.*, 70(4):2529-2534 (2004).
Zeiher et al., "Identification and Characterization of Mitochondrial Acetyl-Coenzyme A Hydrolase from Pisum sativum L. Seedlings," *Plant Physiol.*, 94:20-27 (1990).
Zhang et al., "2-Oxoacid: Ferredoxin Oxidoreductase from the Thermoacidophilic Archaeon, Sulfolobus sp. Strain 7," *J Biochem.*, 120:587-599 (1996).
Zhang et al., "Directed evolution of a fucosidase from a galactosidase by DNA shuffling and screening," *Proc. Natl. Acad. Sci. U.S.A.*, 94:4504-4509 (1997).
Zhang et al., "Isolation and Properties of a levo-lactonase from Fusarium proliferatum ECD2002: a robust biocatalyst for production of chiral lactones," *App. Microbiol. Biotechnol.*, 75(5):1087-1094 (2007).
Zhang et al., "Kinetic and mechanistic characterization of the polyhydroxybutyrate synthase from Ralstonia eutropha," *Biomacromolecules*, 1(2):244-251 (2000).
Zhao et al., "Molecular evolution by staggered extension process (StEP) in vitro recombination," *Nat. Biotechnol.*, 16(3):258-261 (1998).
Zhou et al., "Engineering a native homoethanol pathway in *Escherichia coli* B for ethanol production," *Biotechnol. Lett.*, 30:335-342 (2008).
Zhou et al., "The remarkable structural and functional organization of the eukaryotic pyruvate dehydrogenase complexes," *Proc. Natl. Acad. Sci. U.S.A.*, 98:14802-14807 (2001).
Zhou et al., "Functional replacement of the *Escherichia coli* D-(-)-lactate dehydrogenase gene (ldhA) with the L-(+)-lactate dehydrogenase gene (ldhL) from Pediococcus acidilactici," *Appl. Environ. Micro.*, 69:2237-2244 (2003).
Zhu, "The Effects of pH and Temperature on the Growth of *Escherichia coli* DH5a," California State Science Fair, Apr. 2, 2007, Project No. J1440.
Zhuang et al., "The YbgC protein encoded by the ybgC gene of the tol-pal gene cluster of Haemophilus influenzae catalyzes acyl-coenzyme A thioester hydrolysis," *FEBS Lett*., 516:161163 (2002).
U.S. Appl. No. 12/049,256, 20090075351, filed Mar. 14, 2008, Mahatan, C. S., Compositions and Methods for the Biosynthesis of 1,4-Butanediol and Its Precursors, Patented.
U.S. Appl. No. 12/830,238, filed Jul. 2, 2010, Unassigned, Compositions and Methods for the Biosynthesis of 1,4-Butanediol and Its Precursors, Abandoned.
U.S. Appl. No. 13/286,135, 20120094345, filed Oct. 31, 2011, Mahatan, C., Compositions and Methods for the Biosynthesis of 1,4-Butanediol and Its Precursors, Patented.
U.S. Appl. No. 13/248,564, 20120122171, filed Jan. 11, 2012, Mahatan, C. S., Compositions and Methods for the Biosynthesis of 1,4-Butanediol and Its Precursors, Patented.
U.S. Appl. No. 13/717,350, 20130196397, filed Dec. 17, 2012, Mahatan, C. S., Compositions and Methods for the Biosynthesis of 1,4-Butanediol and Its Precursors, Patented.
U.S. Appl. No. 14/530,530, 20150267229, filed Oct. 31, 2014, Mahatan, C. S., Compositions and Methods for the Biosynthesis of 1,4-Butanediol and Its Precursors, Abandoned.
U.S. Appl. No. 15/056,914, 20170022524, filed Feb. 29, 2016, Mahatan, C. S., Compositions and Methods for the Biosynthesis of 1,4-Butanediol and Its Precursors, Abandoned.

(56) References Cited

OTHER PUBLICATIONS

U.S. Appl. No. 15/925,301, 20190062758, filed Mar. 19, 2018, Mahatan, C. S., Compositions and Methods for the Biosynthesis of 1,4-Butanediol and Its Precursors, Abandoned.
U.S. Appl. No. 14/603,174, 20150368676, filed Jan. 22, 2015, Mahatan, C. S., Compositions and Methods for the Biosynthesis of 1,4-Butanediol and Its Precursors, Patented.
U.S. Appl. No. 15/270,578. 20170088840 Sep. 20, 2016 Mahatan, C Compositions and Methods for the Biosynthesis of 1,4-Butanediol and Its Precursors, Pending.
U.S. Appl. No. 11/891,602, 20090047719, filed Aug. 10, 2007 Joike, M. K. Methods and Organisms for the Growth-Coupled Production of 1,4-Butanediol, Patented.
U.S. Appl. No. 13/065,303, 20110201071, filed Mar. 18, 2011 Joike, M. K. Methods and Organisms for the Growth-Coupled Production of 1,4-Butanediol, Patented.
U.S. Appl. No. 13/914,422, 20140030780, filed Jun. 10, 2013 Gussow, A., Methods and Organisms for the Growth-Coupled Production of 1,4-Butanediol, Abandoned.
U.S. Appl. No. 15/424,723, 20170240931, filed Feb. 3, 2017 Calamita, H., Methods and Organisms for the Growth-Coupled Production of 1,4-Butanediol, Abandoned.
U.S. Appl. No. 16/428,627, 20200095616, filed May 31, 2019, Mohammad, M. Y., Methods and Organisms for the Growth-Coupled Production of 1,4-Butanediol, Pending.
U.S. Appl. No. 12/556,550, 20100112654, filed Sep. 9, 2009, Kam, C. M., Microorganisms for the Production of 1,4-Butanediol, Patented.
U.S. Appl. No. 12/947,790, 20110159572, filed Nov. 16, 2010, Kam, C. M., Microorganisms for the Production of 1,4-Butanediol, Patented.
U.S. Appl. No. 13/009,813, 20110281337, filed Jan. 19, 2011, Kam, C. M., Microorganisms for the Production of 1,4-Butanediol, Patented.
U.S. Appl. No. 13/449,187, 20130109069, filed Apr. 17, 2012, Moore, W. W.,Microorganisms for the Production of 1,4-Butanediol, Patented.
U.S. Appl. No. 13/566,826, 20130071886, filed Aug. 3, 2012, Meah, M. Y., Microorganisms for the Production of 1,4-Butanediol, Abandoned.
U.S. Appl. No. 14/700,096, 20160053287, filed Apr. 29, 2015, Tsay, M. M., Microorganisms for the Production of 1,4-Butanediol, Abandoned.
U.S. Appl. No. 15/682,349, 20180142269, filed Aug. 21, 2017, Tsay, M. M., Microorganisms for the Production of 1,4-Butanediol, Pending.
U.S. Appl. No. 12/793,623, 20110003355, filed Jun. 3, 2010, Lacourciere, G. M., Process of Separating Components of a Fermentation Broth, Patented.
U.S. Appl. No. 14/066,598, 20140322777, filed Oct. 29, 2013, Holland, P. J., Process of Separating Components of a Fermentation Broth, Patented.
U.S. Appl. No. 15/975,630, 20190112247, filed May 9, 2018, Holland, P. J., Process of Separating Components of a Fermentation Broth, Patented.
U.S. Appl. No. 16/848,430, 20210002194, filed Apr. 14, 2020, Holland, P. J., Process of Separating Components of a Fermentation Broth, Pending.
U.S. Appl. No. 12/794,700, 20110045575, filed Jun. 4, 2010, Gangle, B. J., Microorganisms for the Production of 1,4-Butanediol and Relayed Methods, Patented.
U.S. Appl. No. 13/361,799, 20120225463, filed Jan. 30, 2012, Holland, P. J., Microorganisms for the Production of 1,4-Butanediol and Relayed Methods, Patented.
U.S. Appl. No. 15/148,759, 20160355846, filed May 6, 2016, Holland, P. J., Microorganisms for the Production of 1,4-Butanediol and Relayed Methods, Patented.

U.S. Appl. No. 12/878,980, 20110201068, filed Sep. 9, 2010, Robinson, H. A., Microorganisms and Methods for the Co-Production of Isopropanol With Primary Alcohols, Diols and Acids, Patented.
U.S. Appl. No. 14/167,693, 20140377820, filed Jan. 29, 2014, Robinson, H. A. Microorganisms and Methods for the Co-Production of Isopropanol With Primary Alcohols, Diols and Acids, Abandoned.
U.S. Appl. No. 12/904,130, 20110129899, filed Oct. 13, 2010, Ramirez, D. M., Microorganisms for the Production of 1,4-Butanediol, 4-Hydroxybutanal, 4-Hydroxybutyryl-Coa, Putrescine and Related Compounds, and Methods Related Thereto, Patented.
U.S. Appl. No. 13/109,732, 20110229946, filed May 17, 2011, Ramirez, D. M., Microorganisms for the Production of 1,4-Butanediol, 4-Hydroxybutanal, 4-Hydroxybutyryl-Coa, Putrescine and Relayed Compounds, and Methods Related Thereto, Patented.
U.S. Appl. No. 13/477,094, 20130029381, filed Apr. 13, 2012, Ramirez, D. M., Microorganisms for the Production of 1,4-Butanediol, 4-Hydroxybutanal, 4-Hydroxybutyryl-Coa, Putrescine and Related Compounds, and Methods Related Thereto, Abandoned.
U.S. Appl. No. 13/737,866, 20130189751, filed Jan. 9, 2013, Ramirez, D. M., Microorganisms for the Production of 1,4-Butanediol, 4-Hydroxybutanal, 4-Hydroxybutyryl-Coa, Putrescine and Relayed Compounds, and Methods Related Thereto, Abandoned.
U.S. Appl. No. 15/173,427, 20160376614, filed Jun. 3, 2016, Ramirez, D. M., Microorganisms for the Production of 1,4-Butanediol, 4-Hydroxybutanal, 4-Hydroxybutyryl-Coa, Putrescine and Related Compounds, and Methods Related Thereto, Abandoned.
U.S. Appl. No. 16/216,865, 20190264240, filed Dec. 11, 2018, Ramirez, D. M., Microorganisms for the Production of 1,4-Butanediol, 4-Hydroxybutanal, 4-Hydroxybutyryl-Coa, Putrescine and Relayed Compounds, and Methods Related Thereto, Pending.
U.S. Appl. No. 13/530,053, 20130034884, filed Jun. 21, 2012, Liu, S. W., Microorganisms for Producing 1,4-Butanediol and Methods Relayed Thereto, Abandoned.
U.S. Appl. No. 15/018,736, 20160264978, filed Feb. 8, 2016, Liu, S. W., Microorganisms for Producing 1,4-Butanediol and Methods Relayed Thereto, Pending.
U.S. Appl. No. 13/908,907, 20140030779, filed Jun. 3, 2013, Ekstrom, R. C., Microorganisms and Methods for Production of 4-Hydroxybutyrate, 1,4-Butanediol and Related Compounds, Patented.
U.S. Appl. No. 15/585,079, 20170362565, filed May 2, 2017 Ekstrom, R. C., Microorganisms and Methods for Production of 4-Hydroxybutyrate, 1,4- Butanediol and Related Compounds, Patented.
U.S. Appl. No. 17/369,871, filed Jul. 7, 2021, Unassigned Microorganisms and Methods for Production of 4-Hydroxybutyrate, 1,4-Butanediol and Related Compounds, Pending.
U.S. Appl. No. 14/405,390, 20150148513, filed Dec. 3, 2014, Steadman, J. Microorganisms and Methods for Production of 4-Hydroxybutyrate, 1,4-Butanediol and Related Compounds, Pending.
U.S. Appl. No. 13/975,678, 20140058056, filed Aug. 26, 2013, Mesh, G., Microorganisms and Methods for Enhancing the Availability of Reducing Equivalents in the Presence of Methanol, and for Producing 1,4-Butanediol Relayed Thereto, Patented.
U.S. Appl. No. 14/424,404, 20150203875, filed Feb. 26, 2015, Saidha, T., Microorganisms and Methods for Enhancing the Availability of Reducing Equivalents in the Presence of Methanol, and for Producing 1,4-Butanediol Relayed Thereto, Patented.
U.S. Appl. No. 16/816,064, 20210087591, filed Mar. 11, 2020, Chowdhury, I. H., Microorganisms and Methods for Enhancing the Availability of Reducing Equivalents in the Presence of Methanol, and for Producing 1.4-Butanediol Relayed Thereto, Pending.
U.S. Appl. No. 15/488,320, 20180030484, filed Apr. 14, 2017, Chowdhury, I. H., Microorganisms and Methods for Enhancing the Availability of Reducing Equivalents in the Presence of Methanol, and for Producing 1,4-Butanediol Relayed Thereto, Pending.

(56) References Cited

OTHER PUBLICATIONS

U.S. Appl. No. 14/211,863, 20140275465, filed Mar. 14, 2014, Bullock, I.S.C., Process and Systems for Obtaining 1,4-Butanediol From Fermentation Broths, Abandoned.
U.S. Appl. No. 15/651,929, 20180065907, filed Jul. 17, 2017, Hobson, S., Process and Systems for Obtaining 1,4-Butanediol From Fermentation Broths, Pending.
U.S. Appl. No. 15/696,098, 20170362149, filed Sep. 5, 2017, Luderer M. R., Process and Sys 1EMS for Obtaining 1,4-Butanediol From Fermentation Broths, Abandoned.
U.S. Appl. No. 16/216,965, 20190177255, filed Dec. 11, 2018, Keys, R.. A., Process and Systems for Obtaining 1,4-Butanediol From Fermentation Broths, Abandoned.
U.S. Appl. No. 16/799,743, 20210002195, filed Feb. 24, 2020, Keys, R.. A., Process and Systems for Obtaining 1,4-Butanediol From Fermentation Broths, Pending.
U.S. Appl. No. 14/262,461, 20140371417, filed Apr. 25, 2014, Liu, S.W., Microorganisms and Methods for Production of 4-Hydroxybutyrate, 1,4-Butanediol and Related Compounds, Abandoned.
U.S. Appl. No. 15/191,421, 20170183694, filed Jun. 23, 2016, Liu, S.W. Microorganisms and Methods for Production of 4-Hydroxybutyrate, 1,4-Butanediol and Related Compounds, Pending.
U.S. Appl. No. 13/011,796, 20110201089, filed Jan. 21, 2011, Carlson, K. C., Methods for Increasing Product Yields, Patented.
U.S. Appl. No. 13/011,788, 20110207189, filed Jan. 21, 2011, Carslon, K. C., Methods for Increasing Product Yields, Patented.
U.S. Appl. No. 13/011,818, 20110212507, filed Jan. 21, 2011, Desai, A. U., Methods for Increasing Product Yields, Patented.
U.S. Appl. No. 13/889,056, 20140011249, filed May 7, 2013, Carslon, K. C., Methods for Increasing Product Yields, Abandoned.
U.S. Appl. No. 14/806,435, 20160145652, filed Jul. 22, 2015, Carslon, K. C., Methods for Increasing Product Yields, Patented.
U.S. Appl. No. 16/137,264, 20190264242, filed Sep. 20, 2018, Carslon, K. C., Methods for Increasing Product Yields, Abandoned.
U.S. Appl. No. 12/940,021, 20110217742, filed Nov. 4, 2010, Kosson, R., Microorganisms and Methods for the Coproduction 1,4-Butanediol and Gamma-Butyrolactone, Patented.
U.S. Appl. No. 13/936,878, 20140162327, filed Jul. 8, 2013, Kosson, R., Microorganisms and Methods for the Coproduction 1,4-Butanediol and Gamma-Butyrolactone, Patented.
U.S. Appl. No. 14/954,487, 20160319313, filed Nov. 30, 2015, Kosson, R. Microorganisms and Methods for the Coproduction 1,4-Butanediol and Gamma-Butyrolactone, Patented.
U.S. Appl. No. 15/971,878, 20190276863, filed May 4, 2018, Kosson, R. Microorganisms and Methods for the Coproduction 1,4-Butanediol and Gamma-Butyrolactone, Patented.
U.S. Appl. No. 12/538,217, 20090191593, filed Jan. 22, 2009, Saidha, T., Methods and Organisms for Utilizing Synthesis Gas or Other Gaseous Carbon Sources and Methanol, Patented.
U.S. Appl. No. 12/963,978, 20110195461, filed Apr. 15, 2011, Chowdhury, I. H., Methods and Organisms for Utilizing Synthesis Gas or Other Gaseous Carbon Sources and Methanol, Patented.
U.S. Appl. No. 12/875,068, 20110003344, filed Sep. 2, 2010, Saidha, T. Methods and Organisms for Utilizing Synthesis Gas or Other Gaseous Carbon Sources and Methanol, Patented.
U.S. Appl. No. 13/106,764, 20110223637, filed May 12, 2011, Chowdhury, I. H., Methods and Organisms for Utilizing Synthesis Gas or Other Gaseous Carbon Sources and Methanol, Patented.
U.S. Appl. No. 13/615,168, 20130071883, filed Sep. 13, 2012, Chowdhury, I. H., Methods and Organisms for Utilizing Synthesis Gas or Other Gaseous Carbon Sources and Methanol, Patented.
U.S. Appl. No. 14/185,709, 20150024468, filed Feb. 20, 2014, Chowdhury, I. H., Methods and Organisms for Utilizing Synthesis Gas or Other Gaseous Carbon Sources and Methanol, Patented.
U.S. Appl. No. 14/700,103, 20160053288, filed Apr. 29, 2015, Chowdhury, I. H., Methods and Organisms for Utilizing Synthesis Gas or Other Gaseous Carbon Sources and Methanol, Abandoned.
U.S. Appl. No. 15/889,788, 20180334690, filed Feb. 6, 2018, Chowdhury, I. H., Methods and Organisms for Utilizing Synthesis Gas or Other Gaseous Carbon Sources and Methanol, Patented.
U.S. Appl. No. 16/780,548, 20200385765, filed Feb. 3, 2020, Chowdhury, I. H., Methods and Organisms for Utilizing Synthesis Gas or Other Gaseous Carbon Sources and Methanol, Pending.
U.S. Appl. No. 12/639,977, 20100304453, filed Dec. 16, 2009, Raghu, G., Microorganisms and Methods for Conversion of Syngas and Other Carbon Sources to Useful Products, Patented.
U.S. Appl. No. 13/371,278, 20120208249, filed Feb. 10, 2012, Raghu, G. Microorganisms and Methods for Conversion of Syngas and Other Carbon Sources to Useful Products, Patented.
U.S. Appl. No. 13/920,927, 20140147900, filed Jun. 18, 2013, Raghu, G. Microorganisms and Methods for Conversion of Syngas and Other Carbon Sources to Useful Products, Patented.

* cited by examiner

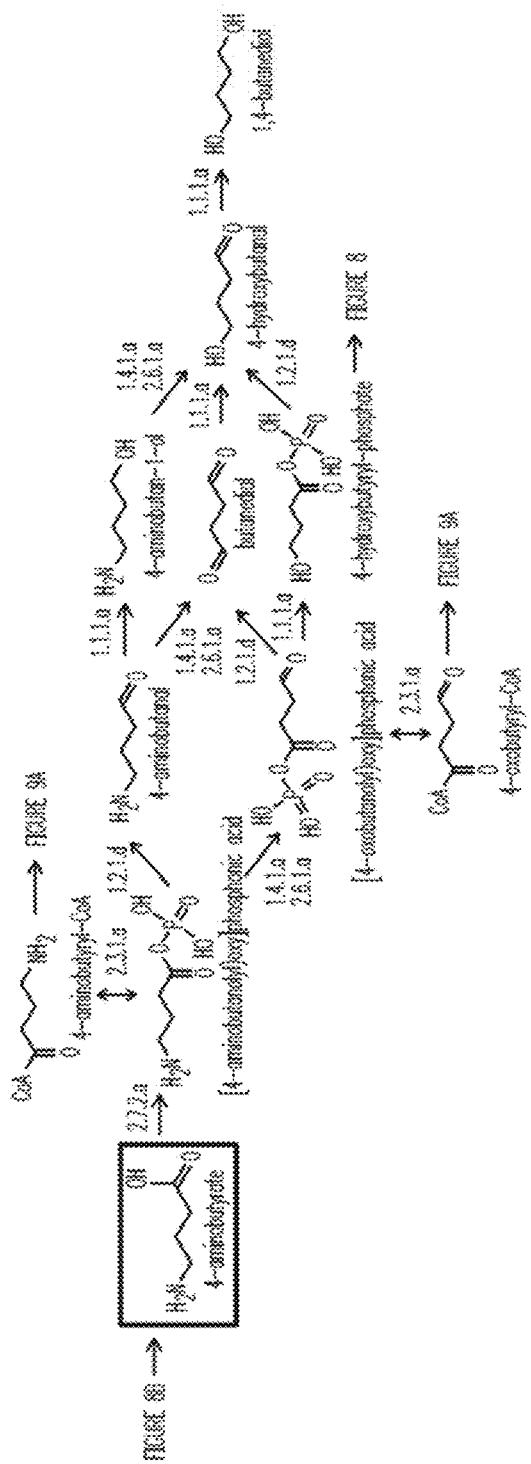
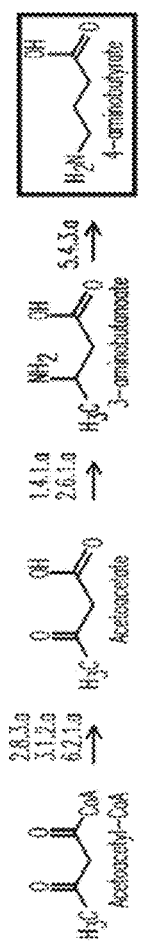
FIG. 9B
FIG. 9C

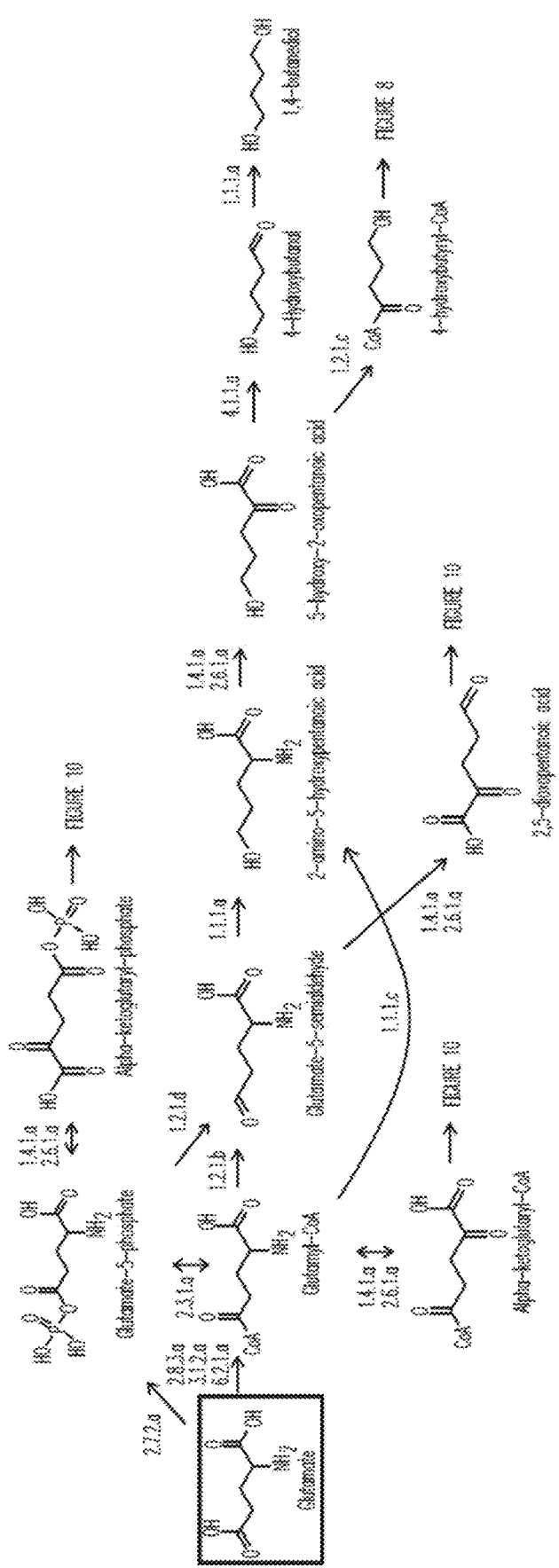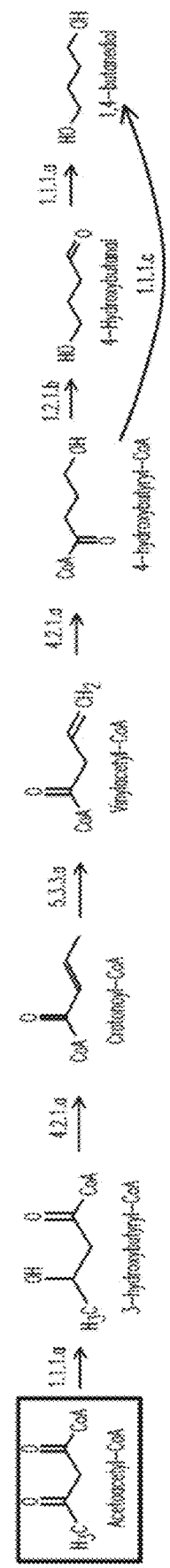
FIG. 11
FIG. 12

FIG. 14A

ATGAACTTACATGAATATCAGGCAAAACAACTTTTTGCCCGCTATGGCTTACCAGCACCGGTGGGTTATG
CCTGTACTACTCCGCGCGAAGCAGAAGAAGCCGCTTCAAAAATCGGTGCCGGTCCGTGGGTAGTGAAAT
GTCAGGTTCACGCTGGTGGCCGCGGTAAAGCGGGCGGTGTGAAAGTTGTAAACAGCAAAGAAGACATC
CGTGCTTTTGCAGAAAACTGGCTGGGCAAGCGTCTGGTAACGTATCAAACAGATGCCAATGGCCAACCG
GTTAACCAGATTCTGGTTGAAGCAGCGACCGATATCGCTAAAGAGCTGTATCTCGGTGCCGTTGTTGAC
CGTAGTTCCGTCGTGTGGTCTTTATGGCCTCCACCGAAGGCGGCGTGGAAATCGAAAAGTGGCGGA
AGAAACTCCGCACCTGATCCATAAAGTTGCGCTTGATCCGCTGACTGGCCCGATGCCGTATCAGGGACG
CGAGCTGGCGTTCAAACTGGGTCTGGAAGGTAAACTGGTTCAGCAGTTCACCAAAATCTTCATGGGCCT
GGCGACCATTTTCCTGGAGCGCGACCTGGCGTTGATCGAAATCAACCCGCTGGTCATCACCAAACAGGG
CGATCTGATTTGCCTCGACGGCAAACTGGGCGCTGACGGCAACGCACTGTTCCGCCAGCCTGATCTGCG
CGAAATGCGTGACCAGTCGCAGGAAGATCCGCGTGAAGCACAGGCTGCACAGTGGGAACTGAACTACG
TTGCGCTGGACGGTAACATCGGTTGTATGGTTAACGGCGCAGGTCTGGCGATGGGTACGATGGACATC
GTTAAACTGCACGGCGGCGAACCGGCTAACTTCCTTGACGTTGGCGGCGGCGCAACCAAAGAACGTGT
AACCGAAGCGTTCAAAATCATCCTCTCTGACGACAAAGTGAAAGCCGTTCTGGTTAACATCTTCGGCGGT
ATCGTTCGTTGCGACCTGATCGCTGACGGTATCATCGGCGCGGTAGCAGAAGTGGGTGTTAACGTACCG
GTCGTGGTACGTCTGGAAGGTAACAACGCCGAACTCGGCGCGAAGAAACTGGCTGACAGCGGCCTGAA
TATTATTGCAGCAAAAGGTCTGACGGATGCAGCTCAGCAGGTTGTTGCCGCAGTGGAGGGGAAATAAT
GTCCATTTTAATCGATAAAAACACCAAGGTTATCTGCCAGGGCTTTACCGGTAGCCAGGGGACTTTCCAC
TCAGAACAGGCCATTGCATACGGCACTAAAATGGTTGGCGGCGTAACCCCAGGTAAAGGCGGCACCAC
CCACCTCGGCCTGCCGGTGTTCAACACCGTGCGTGAAGCCGTTGCTGCCACTGGCGCTACCGCTTCTGTT
ATCTACGTACCAGCACCGTTCTGCAAAGACTCCATTCTGGAAGCCATCGACGCAGGCATCAAACTGATTA
TCACCATCACTGAAGGCATCCCGACGCTGGATATGCTGACCGTGAAAGTGAAGCTGGATGAAGCAGGC
GTTCGTATGATCGGCCCGAACTGCCCAGGCGTTATCACTCCGGGTGAATGCAAAATCGGTATCCAGCCT
GGTCACATTCACAAACCGGGTAAAGTGGGTATCGTTTCCCGTTCCGGTACACTGACCTATGAAGCGGTT
AAACAGACCACGGATTACGGTTTCGGTCAGTCGACCTGTGTCGGTATCGGCGGTGACCCGATCCCGGGC
TCTAACTTTATCGACATTCTCGAAATGTTCGAAAAAGATCCGCAGACCGAAGCGATCGTGATGATCGGT
GAGATCGGCGGTAGCGCTGAAGAAGAAGCAGCTGCGTACATCAAAGAGCACGTTACCAAGCCAGTTGT
GGGTTACATCGCTGGTGTGACTGCGCCGAAAGGCAAACGTATGGGCCACGCGGGTGCCATCATTGCCG
GTGGGAAAGGGACTGCGGATGAGAAATTCGCTGCTCTGGAAGCCGCAGGCGTGAAAACCGTTCGCAGC
CTGGCGGATATCGGTGAAGCACTGAAAACTGTTCTGAAATAA

FIG. 14B

MNLHEYQAKQLFARYGLPAPVGYACTTPREAEEAASKIGAGPWVVKCQVHAGGRGKAGGVKVVNSKEDIR
AFAENWLGKRLVTYQTDANGQPVNQILVEAATDIAKELYLGAVVDRSSRRVVFMASTEGGVEIEKVAEETPH
LIHKVALDPLTGPMPYQGRELAFKLGLEGKLVQQFTKIFMGLATIFLERDLALIEINPLVITKQGDLICLDGKLGA
DGNALFRQPDLREMRDQSQEDPREAQAAQWELNYVALDGNIGCMVNGAGLAMGTMDIVKLHGGEPAN
FLDVGGGATKERVTEAFKIILSDDKVKAVLVNIFGGIVRCDLIADGIIGAVAEVGVNVPVVVRLEGNNAELGAK
KLADSGLNIIAAKGLTDAAQQVVAAVEGK

FIG. 14C

MSILIDKNTKVICQGFTGSQGTFHSEQAIAYGTKMVGGVTPGKGGTTHLGLPVFNTVREAVAATGATASVIY
VPAPFCKDSILEAIDAGIKLIITITEGIPTLDMLTVKVKLDEAGVRMIGPNCPGVITPGECKIGIQPGHIHKPGKV
GIVSRSGTLTYEAVKQTTDYGFGQSTCVGIGGDPIPGSNFIDILEMFEKDPQTEAIVMIGEIGGSAEEEAAAYIK
EHVTKPVVGYIAGVTAPKGKRMGHAGAIIAGGKGTADEKFAALEAAGVKTVRSLADIGEALKTVLK

FIG. 15A

```
ATGGCCAACATAAGTTCACCATTCGGGCAAAACGAATGGCTGGTTGAAGAGATGTACCGCAAGTTCCGC
GACGACCCCTCCTCGGTCGATCCCAGCTGGCACGAGTTCCTGGTTGACTACAGCCCCGAACCCACCTCCC
AACCAGCTGCCGAACCAACCCGGGTTACCTCGCCACTCGTTGCCGAGCGGGCCGCTGCGGCCGCCCCGC
AGGCACCCCCAAGCCGGCCGACACCGCGGCCGCGGGCAACGGCGTGGTCGCCGCACTGGCCGCCAAA
ACTGCCGTTCCCCCGCCAGCCGAAGGTGACGAGGTAGCGGTGCTGCGCGGCGCCGCCGCGGCCGTCGT
CAAGAACATGTCCGCGTCGTTGGAGGTGCCGACGGCGACCAGCGTCCGGGCGGTCCCGGCCAAGCTAC
TGATCGACAACCGGATCGTCATCAACAACCAGTTGAAGCGGACCCGCGGCGGCAAGATCTCGTTCACGC
ATTTGCTGGGCTACGCCCTGGTGCAGGCGGTGAAGAAATTCCCGAACATGAACCGGCACTACACCGAA
GTCGACGGCAAGCCCACCGCGGTCACGCCGGCGCACACCAATCTCGGCCTGGCGATCGACCTGCAAGG
CAAGGACGGGAAGCGTTCCCTGGTGGTGGCCGGCATCAAGCGGTGCGAGACCATGCGATTCGCGCAGT
TCGTCACGGCCTACGAAGACATCGTACGCCGGGCCCGCGACGGCAAGCTGACCACTGAAGACTTTGCCG
GCGTGACGATTTCGCTGACCAATCCCGGAACCATCGGCACCGTGCATTCGGTGCCGCGGCTGATGCCCG
GCCAGGGCGCCATCATCGGCGTGGGCGCCATGGAATACCCCGCCGAGTTTCAAGGCGCCAGCGAGGAA
CGCATCGCCGAGCTGGGCATCGGCAAATTGATCACTTTGACCTCCACCTACGACCACCGCATCATCCAGG
GCGCGGAATCGGGCGACTTCCTGCGCACCATCCACGAGTTGCTGCTCTCGGATGGCTTCTGGGACGAGG
TCTTCCGCGAACTGAGCATCCCATATCTGCCGGTGCGCTGGAGCACCGACAACCCCGACTCGATCGTCG
ACAAGAACGCTCGCGTCATGAACTTGATCGCGGCCTACCGCAACCGCGGCCATCTGATGGCCGATACCG
ACCCGCTGCGGTTGGACAAAGCTCGGTTCCGCAGTCACCCCGACCTCGAAGTGCTGACCCACGGCCTGA
CGCTGTGGGATCTCGATCGGGTGTTCAAGGTCGACGGCTTTGCCGGTGCGCAGTACAAGAAACTGCGC
GACGTGCTGGGCTTGCTGCGCGATGCCTACTGCCGCCACATCGGCGTGGAGTACGCCCATATCCTCGAC
CCCGAACAAAAGGAGTGGCTCGAACAACGGGTCGAGACCAAGCACGTCAAACCCACTGTGGCCCAACA
GAAATACATCCTCAGCAAGCTCAACGCCGCCGAGGCCTTTGAAACGTTCCTACAGACCAAGTACGTCGG
CCAGAAGCGGTTCTCGCTGGAAGGCGCCGAAAGCGTGATCCCGATGATGGACGCGGCGATCGACCAGT
GCGCTGAGCACGGCCTCGACGAGGTGGTCATCGGGATGCCGCACCGGGGCCGGCTCAACGTGCTGGCC
AACATCGTCGGCAAGCCGTACTCGCAGATCTTCACCGAGTTCGAGGGCAACCTGAATCCGTCGCAGGCG
CACGGCTCCGGTGACGTCAAGTACCACCTGGGCGCCACCGGGCTGTACCTGCAGATGTTCGGCGACAAC
GACATTCAGGTGTCGCTGACCGCCAACCCGTCGCATCTGGAGGCCGTCGACCCGGTGCTGGAGGGATT
GGTGCGGGCCAAGCAGGATCTGCTCGACCACGAAGCATCGACAGCGACGGCCAACGGGCGTTCTCGG
TGGTGCCGCTGATGTTGCATGGCGATGCCGCGTTCGCCGGTCAGGGTGTGGTCGCCGAGACGCTGAAC
CTGGCGAATCTGCCGGGCTACCGCGTCGGCGGCACCATCCACATCATCGTCAACAACCAGATCGGCTTC
ACCACCGCGCCCGAGTATTCCAGGTCCAGCGAGTACTGCACCGACGTCGCAAAGATGATCGGGGCACC
GATCTTTCACGTCAACGGCGACGACCCGGAGGCGTGTGTCTGGGTGGCGCGGTTGGCGGTGGACTTCC
GACAACGGTTCAAGAAGGACGTCGTCATCGACATGCTGTGCTACCGCCGCCGCGGGCACAACGAGGGT
GACGACCCGTCGATGACCAACCCCTACATGTACGACGTCGTCGACACCAAGCGCGGGGCCCGCAAAAG
CTACACCGAAGCCCTGATCGGACGTGGCGACATCTCGATGAAGGAGGCCGAGGACGCGCTGCGCGACT
ACCAGGGCCAGCTGGAACGGGTGTTCAACGAAGTGCGCGAGCTGGAGAAGCACGGTGTGCAGCCGAG
CGAGTCGGTCGAGTCCGACCAGATGATTCCCGCGGGGCTGGCCACTGCGGTGGACAAGTCGCTGCTGG
CCCGGATCGGCGATGCGTTCCTCGCCTTGCCGAACGGCTTCACCGCGCACCCGCGAGTCCAACCGGTGC
TGGAGAAGCGCCGGGAGATGGCCTATGAAGGCAAGATCGACTGGGCCTTTGGCGAGCTGCTGGCGCT
GGGCTCGCTGGTGGCCGAAGGCAAGCTGGTGCGCTTGTCGGGGCAGGACAGCCGCCGCGGCACCTTCT
CCCAGCGGCATTCGGTTCTCATCGACCGCCACACTGGCGAGGAGTTCACACCACTGCAGCTGCTGGCGA
CCAACTCCGACGGCAGCCCGACCGGCGGAAAGTTCCTGGTCTACGACTCGCCACTGTCGGAGTACGCCG
CCGTCGGCTTCGAGTACGGCTACACTGTGGGCAATCCGGACGCCGTGGTGCTCTGGGAGGCGCAGTTC
```

FIG. 15A continued

GGCGACTTCGTCAACGGCGCACAGTCGATCATCGACGAGTTCATCAGCTCCGGTGAGGCCAAGTGGGG
CCAATTGTCCAACGTCGTGCTGCTGTTACCGCACGGGCACGAGGGGCAGGGACCCGACCACACTTCTGC
CCGGATCGAACGCTTCTTGCAGTTGTGGGCGGAAGGTTCGATGACCATCGCGATGCCGTCGACTCCGTC
GAACTACTTCCACCTGCTACGCCGGCATGCCCTGGACGGCATCCAACGCCCGCTGATCGTGTTCACGCCC
AAGTCGATGTTGCGTCACAAGGCCGCCGTCAGCGAAATCAAGGACTTCACCGAGATCAAGTTCCGCTCA
GTGCTGGAGGAACCCACCTATGAGGACGGCATCGGAGACCGCAACAAGGTCAGCCGGATCCTGCTGAC
CAGTGGCAAGCTGTATTACGAGCTGGCCGCCCGCAAGGCCAAGGACAACCGCAATGACCTCGCGATCG
TGCGGCTTGAACAGCTCGCCCCGCTGCCCAGGCGTCGACTGCGTGAAACGCTGGACCGCTACGAGAAC
GTCAAGGAGTTCTTCTGGGTCCAAGAGGAACCGGCCAACCAGGGTGCGTGGCCGCGATTCGGGCTCGA
ACTACCCGAGCTGCTGCCTGACAAGTTGGCCGGGATCAAGCGAATCTCGCGCCGGGCGATGTCAGCCCC
GTCGTCAGGCTCGTCGAAGGTGCACGCCGTCGAACAGCAGGAGATCCTCGACGAGGCGTTCGGCTAA

FIG. 15B

MANISSPFGQNEWLVEEMYRKFRDDPSSVDPSWHEFLVDYSPEPTSQPAAEPTRVTSPLVAERAAAAAPQA
PPKPADTAAAGNGVVAALAAKTAVPPPAEGDEVAVLRGAAAAVVKNMSASLEVPTATSVRAVPAKLLIDNR
IVINNQLKRTRGGKISFTHLLGYALVQAVKKFPNMNRHYTEVDGKPTAVTPAHTNLGLAIDLQGKDGKRSLV
VAGIKRCETMRFAQFVTAYEDIVRRARDGKLTTEDFAGVTISLTNPGTIGTVHSVPRLMPGQGAIIGVGAME
YPAEFQGASEERIAELGIGKLITLTSTYDHRIIQGAESGDFLRTIHELLLSDGFWDEVFRELSIPYLPVRWSTDNP
DSIVDKNARVMNLIAAYRNRGHLMADTDPLRLDKARFRSHPDLEVLTHGLTLWDLDRVFKVDGFAGAQYKK
LRDVLGLLRDAYCRHIGVEYAHILDPEQKEWLEQRVETKHVKPTVAQQKYILSKLNAAEAFETFLQTKYVGQK
RFSLEGAESVIPMMDAAIDQCAEHGLDEVVIGMPHRGRLNVLANIVGKPYSQIFTEFEGNLNPSQAHGSGD
VKYHLGATGLYLQMFGDNDIQVSLTANPSHLEAVDPVLEGLVRAKQDLLDHGSIDSDGQRAFSVVPLMLHG
DAAFAGQGVVAETLNLANLPGYRVGGTIHIIVNNQIGFTTAPEYSRSSEYCTDVAKMIGAPIFHVNGDDPEAC
VWVARLAVDFRQRFKKDVVIDMLCYRRRGHNEGDDPSMTNPYMYDVVDTKRGARKSYTEALIGRGDISM
KEAEDALRDYQGQLERVFNEVRELEKHGVQPSESVESDQMIPAGLATAVDKSLLARIGDAFLALPNGFTAHP
RVQPVLEKRREMAYEGKIDWAFGELLALGSLVAEGKLVRLSGQDSRRGTFSQRHSVLIDRHTGEEFTPLQLLA
TNSDGSPTGGKFLVYDSPLSEYAAVGFEYGYTVGNPDAVVLWEAQFGDFVNGAQSIIDEFISSGEAKWGQLS
NVVLLPHGHEGQGPDHTSARIERFLQLWAEGSMTIAMPSTPSNYFHLLRRHALDGIQRPLIVFTPKSMLRH
KAAVSEIKDFTEIKFRSVLEEPTYEDGIGDRNKVSRILLTSGKLYYELAARKAKDNRNDLAIVRLEQLAPLPRRRL
RETLDRYENVKEFFWVQEEPANQGAWPRFGLELPELLPDKLAGIKRISRRAMSAPSSGSSKVHAVEQQEILDE
AFG

FIG. 18A

ATGGAAATCAAAGAAATGGTGAGCCTTGCACGCAAGGCTCAGAAGGAGTATCAAGCTACCCATAACCA
AGAAGCAGTTGACAACATTTGCCGAGCTGCAGCAAAAGTTATTTATGAAAATGCAGCTATTCTGGCTCG
CGAAGCAGTAGACGAAACCGGCATGGGCGTTTACGAACACAAAGTGGCCAAGAATCAAGGCAAATCCA
AAGGTGTTTGGTACAACCTCCACAATAAAAAATCGATTGGTATCCTCAATATAGACGAGCGTACCGGTAT
GATCGAGATTGCAAAGCCTATCGGAGTTGTAGGAGCCGTAACGCCGACGACCAACCCGATCGTTACTCC
GATGAGCAATATCATCTTTGCTCTTAAGACCTGCAATGCCATCATTATTGCCCCCCACCCCAGATCCAAAA
AATGCTCTGCACACGCAGTTCGTCTGATCAAAGAAGCTATCGCTCCGTTCAACGTACCGGAAGGTATGG
TTCAGATCATCGAAGAACCCAGCATCGAGAAGACGCAGGAACTCATGGGCGCCGTAGACGTAGTAGTT
GCTACGGGTGGTATGGGCATGGTGAAGTCTGCATATTCTTCAGGAAAGCCTTCTTTCGGTGTTGGAGCC
GGTAACGTTCAGGTGATCGTGGATAGCAACATCGATTTCGAAGCTGCTGCAGAAAAAATCATCACCGGT
CGTGCTTTCGACAACGGTATCATCTGCTCAGGCGAACAGAGCATCATCTACAACGAGGCTGACAAGGAA
GCAGTTTTCACAGCATTCCGCAACCACGGTGCATATTTCTGTGACGAAGCCGAAGGAGATCGGGCTCGT
GCAGCTATCTTCGAAAATGGAGCCATCGCGAAAGATGTAGTAGGTCAGAGCGTTGCCTTCATTGCCAAG
AAAGCAAACATCAATATCCCCGAGGGTACCCGTATTCTCGTTGTTGAAGCTCGCGGCGTAGGAGCAGAA
GACGTTATCTGTAAGGAAAAGATGTGTCCCGTAATGTGCGCCCTCAGCTACAAGCACTTCGAAGAAGGT
GTAGAAATCGCACGTACGAACCTCGCCAACGAAGGTAACGGCCACACCTGTGCTATCCACTCCAACAAT
CAGGCACACATCATCCTCGCAGGATCAGAGCTGACGGTATCTCGTATCGTAGTGAATGCTCCGAGTGCC
ACTACAGCAGGCGGTCACATCCAAAACGGTCTTGCCGTAACCAATACGCTCGGATGCGGATCATGGGGT
AATAACTCTATCTCCGAGAACTTCACTTACAAGCACCTCCTCAACATTTCACGCATCGCACCGTTGAATTC
AAGCATTCACATCCCCGATGACAAAGAAATCTGGGAACTCTAA

FIG. 18B

MEIKEMVSLARKAQKEYQATHNQEAVDNICRAAAKVIYENAAILAREAVDETGMGVYEHKVAKNQGKSKG
VWYNLHNKKSIGILNIDERTGMIEIAKPIGVVGAVTPTTNPIVTPMSNIIFALKTCNAIIIAPHPRSKKCSAHAVR
LIKEAIAPFNVPEGMVQIIEEPSIEKTQELMGAVDVVVATGGMGMVKSAYSSGKPSFGVGAGNVQVIVDSNI
DFEAAAEKIITGRAFDNGIICSGEQSIIYNEADKEAVFTAFRNHGAYFCDEAEGDRARAAIFENGAIAKDVVGQ
SVAFIAKKANINIPEGTRILVVEARGVGAEDVICKEKMCPVMCALSYKHFEEGVEIARTNLANEGNGHTCAIHS
NNQAHIILAGSELTVSRIVVNAPSATTAGGHIQNGLAVTNTLGCGSWGNNSISENFTYKHLLNISRIAPLNSSI
HIPDDKEIWEL

FIG. 19A

ATGCAACTTTTCAAACTCAAGAGTGTAACACATCACTTTGACACTTTTGCAGAATTTGCCAAGGAATTCTG
TCTTGGAGAACGCGACTTGGTAATTACCAACGAGTTCATCTATGAACCGTATATGAAGGCATGCCAGCTC
CCCTGCCATTTTGTTATGCAGGAGAAATATGGGCAAGGCGAGCCTTCTGACGAAATGATGAATAACATC
TTGGCAGACATCCGTAATATCCAGTTCGACCGCGTAATCGGTATCGGAGGAGGTACGGTTATTGACATC
TCTAAACTTTTCGTTCTGAAAGGATTAAATGATGTACTCGATGCATTCGACCGCAAAATACCTCTTATCAA
AGAGAAAGAACTGATCATTGTGCCCACAACATGCGGAACGGGTAGCGAGGTGACGAACATTTCTATCG
CAGAAATCAAAAGCCGTCACACCAAAATGGGATTGGCTGACGATGCCATTGTTGCAGACCATGCCATCA
TCATACCTGAACTTCTGAAGAGCTTGCCTTTCCACTTCTACGCATGCAGTGCAATCGATGCTCTTATCCAT
GCCATCGAGTCATACGTATCTCCTAAAGCCAGTCCATATTCTCGTCTGTTCAGTGAGGCGGCTTGGGACA
TTATCCTGGAAGTATTCAAGAAAATCGCCGAACACGGCCCTGAATACCGCTTCGAAAAGCTGGGAGAAA
TGATCATGGCCAGCAACTATGCCGGTATAGCCTTCGGAAATGCAGGAGTAGGAGCCGTCCACGCACTAT
CCTACCCGTTGGGAGGCAACTATCACGTGCCGCATGGAGAAGCAAACTATCAGTTCTTCACAGAGGTAT
TCAAAGTATACCAAAAGAAGAATCCTTTCGGCTATATAGTCGAACTCAACTGGAAGCTCTCCAAGATACT
GAACTGCCAGCCCGAATACGTATATCCGAAGCTGGATGAACTTCTCGGATGCCTTCTTACCAAGAAACCT
TTGCACGAATACGGCATGAAGGACGAAGAGGTAAGAGGCTTTGCGGAATCAGTGCTTAAGACACAGCA
AAGATTGCTCGCCAACAACTACGTAGAGCTTACTGTAGATGAGATCGAAGGTATCTACAGAAGACTCTA
CTAA

FIG. 19B

MQLFKLKSVTHHFDTFAEFAKEFCLGERDLVITNEFIYEPYMKACQLPCHFVMQEKYGQGEPSDEMMNNIL
ADIRNIQFDRVIGIGGGTVIDISKLFVLKGLNDVLDAFDRKIPLIKEKELIIVPTTCGTGSEVTNISIAEIKSRHTKM
GLADDAIVADHAIIIPELLKSLPFHFYACSAIDALIHAIESYVSPKASPYSRLFSEAAWDIILEVFKKIAEHGPEYRFE
KLGEMIMASNYAGIAFGNAGVGAVHALSYPLGGNYHVPHGEANYQFFTEVFKVYQKKNPFGYIVELNWKLS
KILNCQPEYVYPKLDELLGCLLTKKPLHEYGMKDEEVRGFAESVLKTQQRLLANNYVELTVDEIEGIYRRLY

FIG. 20A

ATGAAAGACGTATTAGCGGAATATGCCTCCCGAATTGTTTCGGCCGAAGAAGCCGTAAAACATATCAAA
AATGGAGAACGGGTAGCTTTGTCACATGCTGCCGGAGTTCCTCAGAGTTGTGTTGATGCACTGGTACAA
CAGGCCGACCTTTTCCAGAATGTCGAAATTTATCACATGCTTTGTCTCGGCGAAGGAAAATATATGGCAC
CTGAAATGGCCCCTCACTTCCGACACATAACCAATTTTGTAGGTGGTAATTCTCGTAAAGCAGTTGAGGA
AAATAGAGCCGACTTCATTCCGGTATTCTTTTATGAAGTGCCATCAATGATTCGCAAAGACATCCTTCACA
TAGATGTCGCCATCGTTCAGCTTTCAATGCCTGATGAGAATGGTTACTGTAGTTTTGGAGTATCTTGCGA
TTATAGCAAACCGGCAGCAGAAAGCGCTCATTTAGTTATAGGGGAAATCAACCGTCAAATGCCATATGT
ACATGGCGACAACTTGATTCACATATCGAAGTTGGATTACATCGTGATGGCAGACTACCCTATCTATTCT
CTTGCAAAGCCCAAAATCGGAGAAGTAGAAGAAGCTATCGGGCGTAATTGTGCCGAGCTTATTGAAGA
TGGTGCCACACTCCAACTCGGTATCGGCGCGATTCCTGATGCAGCCCTGTTATTCCTCAAGGACAAAAAA
GATCTGGGGATCCATACCGAGATGTTCTCCGATGGTGTTGTCGAATTAGTTCGCAGTGGAGTAATTACA
GGAAAGAAAAAGACACTTCACCCCGGAAAGATGGTCGCAACCTTCTTAATGGGAAGCGAAGACGTATA
TCATTTCATCGACAAAAATCCCGATGTAGAACTTTATCCGGTAGATTACGTCAATGATCCGCGAGTAATC
GCTCAAAATGATAATATGGTCAGCATCAATAGCTGTATCGAAATCGATCTTATGGGACAAGTCGTGTCC
GAATGTATAGGAAGCAAGCAATTCAGCGGAACCGGCGGTCAAGTAGATTATGTTCGTGGAGCAGCATG
GTCTAAAAACGGCAAAAGCATCATGGCAATTCCCTCAACAGCCAAAAACGGTACTGCATCTCGAATTGT
ACCTATAATTGCAGAGGGAGCTGCTGTAACAACCCTCCGCAACGAAGTCGATTACGTTGTAACCGAATA
CGGTATAGCACAACTCAAAGGAAAGAGTTTGCGCCAGCGAGCAGAAGCTCTTATTGCCATAGCCCACCC
GGATTTCAGAGAGGAACTAACGAAACATCTCCGCAAACGTTTCGGATAA

FIG. 20B

MKDVLAEYASRIVSAEEAVKHIKNGERVALSHAAGVPQSCVDALVQQADLFQNVEIYHMLCLGEGKYMAPE
MAPHFRHITNFVGGNSRKAVEENRADFIPVFFYEVPSMIRKDILHIDVAIVQLSMPDENGYCSFGVSCDYSKP
AAESAHLVIGEINRQMPYVHGDNLIHISKLDYIVMADYPIYSLAKPKIGEVEEAIGRNCAELIEDGATLQLGIGAI
PDAALLFLKDKKDLGIHTEMFSDGVVELVRSGVITGKKKTLHPGKMVATFLMGSEDVYHFIDKNPDVELYPV
DYVNDPRVIAQNDNMVSINSCIEIDLMGQVVSECIGSKQFSGTGGQVDYVRGAAWSKNGKSIMAIPSTAKN
GTASRIVPIIAEGAAVTTLRNEVDYVVTEYGIAQLKGKSLRQRAEALIAIAHPDFREELTKHLRKRFG

FIG. 21A
ATGATTAAGAGTTTTAATGAAATTATCATGAAGGTAAAGAGCAAAGAAATGAAAAAAGTTGCTGT
TGCTGTAGCACAAGACGAGCCAGTACTTGAAGCAGTAAGAGATGCTAAGAAAAATGGTATTGCAG
ATGCTATTCTTGTTGGAGACCATGACGAAATCGTGTCAATCGCGCTTAAAATAGGAATGGATGTA
AATGATTTTGAAATAGTAAACGAGCCTAACGTTAAGAAAGCTGCTTTAAAGGCAGTAGAGCTTGT
ATCAACTGGAAAAGCTGATATGGTAATGAAGGGACTTGTAAATACAGCAACTTTCTTAAGATCTG
TATTAAACAAAGAAGTTGGACTTAGAACAGGAAAAACTATGTCTCACGTTGCAGTATTTGAAACT
GAGAAATTTGATAGACTATTATTTTTAACAGATGTTGCTTTCAATACTTATCCTGAATTAAAGGA
AAAAATTGATATAGTAAACAATTCAGTTAAGGTTGCACATGCAATAGGAATTGAAAATCCAAAGG
TTGCTCCAATTTGTGCAGTTGAGGTTATAAACCCTAAAATGCCATCAACACTTGATGCAGCAATG
CTTTCAAAAATGAGTGACAGAGGACAAATTAAAGGTTGTGTAGTTGACGGACCTTTAGCACTTGA
TATAGCTTTATCAGAAGAAGCAGCACATCATAAGGGAGTAACAGGAGAAGTTGCTGGAAAAGCTG
ATATCTTCTTAATGCCAAACATAGAAACAGGAAATGTAATGTATAAGACTTTAACATATACAACT
GATTCAAAAAATGGAGGAATCTTAGTTGGAACTTCTGCACCAGTTGTTTTAACTTCAAGAGCTGA
CAGCCATGAAACAAAAATGAACTCTATAGCACTTGCAGCTTTAGTTGCAGGCAATAAATAA

FIG. 21B
MIKSFNEIIMKVKSKEMKKVAVAVAQDEPVLEAVRDAKKNGIADAILVGDHDEIVSIALKIGMDV
NDFEIVNEPNVKKAALKAVELVSTGKADMVMKGLVNTATFLRSVLNKEVGLRTGKTMSHVAVFET
EKFDRLLFLTDVAPNTYPELKEKIDIVNNSVKVAHAIGIENPKVAPICAVEVINPKMPSTLDAAM
LSKMSDRGQIKGCVVDGPLALDIALSEEAAHHKGVTGEVAGKADIFLMPNIETGNVMYKTLTYTT
DSKNGGILVGTSAPVVLTSRADSHETKMNSIALAALVAGNK

FIG. 22A

ATGTATAGATTACTAATAATCAATCCTGGCTCGACCTCAACTAAAATTGGTATTTATGACGATGA
AAAAGAGATATTTGAGAAGACTTTAAGACATTCAGCTGAAGAGATAGAAAAATATAACACTATAT
TTGATCAATTTCAATTCAGAAAGAATGTAATTTTAGATGCGTTAAAAGAAGCAAACATAGAAGTA
AGTTCTTTAAATGCTGTAGTTGGAAGAGGCGGACTCTTAAAGCCAATAGTAAGTGGAACTTATGC
AGTAAATCAAAAAATGCTTGAAGACCTTAAAGTAGGAGTTCAAGGTCAGCATGCGTCAAATCTTG
GTGGAATTATTGCAAATGAAATAGCAAAAGAAATAAATGTTCCAGCATACATAGTTGATCCAGTT
GTTGTGGATGAGCTTGATGAAGTTTCAAGAATATCAGGAATGGCTGACATTCCAAGAAAAGTAT
ATTCCATGCATTAAATCAAAAAGCAGTTGCTAGAAGATATGCAAAAGAAGTTGGAAAAAAATACG
AAGATCTTAATTTAATCGTAGTCCACATGGGTGGAGGTACTTCAGTAGGTACTCATAAAGATGGT
AGAGTAATAGAAGTTAATAATACACTTGATGGAGAAGGTCCATTCTCACCAGAAAGAAGTGGTGG
AGTTCCAATAGGAGATCTTGTAAGATTGTGCTTCAGCAACAAATATACTTATGAAGAAGTAATGA
AAAAGATAAACGGCAAAGGCGGAGTTGTTAGTTACTTAAATACTATCGATTTTAAGGCTGTAGTT
GATAAAGCTCTTGAAGGAGATAAGAAATGTGCACTTATATATGAAGCTTTCACATTCCAGGTAGC
AAAAGAGATAGGAAAATGTTCAACCGTTTTAAAAGGAAATGTAGATGCAATAATCTTAACAGGCG
GAATTGCGTACAACGAGCATGTATGTAATGCCATAGAGGATAGAGTAAAATTCATAGCACCTGTA
GTTAGATATGGTGGAGAAGATGAACTTCTTGCACTTGCAGAAGGTGGACTTAGAGTTTTAAGAGG
AGAAGAAAAAGCTAAGGAATACAAATAA

FIG. 22B

MYRLLIINPGSTSTKIGIYDDEKEIFEKTLRHSAEEIEKYNTIPDQFQFRKNVILDALKEANIEV
SSLNAVVGRGGLLKPIVSGTYAVNQKMLEDLKVGVQGQHASNLGGIIANEIAKEINVPAYIVDPV
VVDELDEVSRISGMADIPRKSIFHALNQKAVARRYAKEVGKKYEDLNLIVVHMGGGTSVGTHKDG
RVIEVNNTLDGEGPFSPERSGGVPIGDLVRLCFSNKYTYEEVMKKINGKGGVVSYLNTIDFKAVV
DKALEGDKKCALIYEAFTFQVAKEIGKCSTVLKGNVDAIILTGGIAYNEHVCNAIEDRVKFIAPV
VRYGGEDELLALAEGGLRVLRGEEKAKEYK

FIG. 23A

ATGATTAAGAGTTTTAATGAAATTATCATGAAGGTAAAGAGCAAAGAAATGAAAAAAGTTGCTGT
TGCTGTAGCACAAGACGAGCCAGTACTTGAAGCAGTACGCGATGCTAAGAAAAATGGTATTGCAG
ATGCTATTCTTGTTGGCGACCATGACGAAATCGTGTCAATCGCGCTTAAAATAGGCATGGATGTA
AATGATTTTGAAATAGTAAACGAGCCTAACGTTAAGAAAGCTGCTTTAAAGGCAGTAGAGCTGGT
ATCAACTGGAAAAGCTGATATGGTAATGAAGGGACTTGTAAATACAGCAACTTTCTTACGCTCTG
TATTAAACAAAGAAGTTGGACTGAGAACAGGAAAAACTATGTCTCACGTTGCAGTATTTGAAACT
GAGAAATTTGATCGTCTGTTATTTTTAACAGATGTTGCTTTCAATACTTATCCTGAATTAAAGGA
AAAAATTGATATCGTAAACAATTCAGTTAAGGTTGCACATGCAATAGGTATTGAAAATCCAAAGG
TTGCTCCAATTTGTGCAGTTGAGGTTATAAACCCTAAAATGCCATCAACACTTGATGCAGCAATG
CTTTCAAAAATGAGTGACAGAGGACAAATTAAAGGTTGTGTAGTTGACGGACCGTTAGCACTTGA
TATCGCTTTATCAGAAGAAGCAGCACATCATAAGGGCGTAACAGGAGAAGTTGCTGGAAAAGCTG
ATATCTTCTTAATGCCAAACATTGAAACAGGAAATGTAATGTATAAGACTTTAACATATACAACT
GATAGCAAAAATGGCGGAATCTTAGTTGGAACTTCTGCACCAGTTGTTTTAACTTCACGCGCTGA
CAGCCATGAAACAAAAATGAACTCTATTGCACTTGCAGCTTTAGTTGCAGGCAATAAATAA

FIG. 23B

ATGATTAAGAGTTTTAATGAAATTATCATGAAGGTAAAGAGCAAAGAAATGAAAAAAGTTGCTGT
TGCTGTAGCACAAGACGAGCCAGTACTTGAAGCAGTACGCGATGCTAAGAAAAATGGTATTGCCG
ATGCTATTCTGGTTGGCGACCATGACGAAATCGTGTCTATCGCGCTGAAAATAGGCATGGATGTA
AATGATTTTGAAATTGTTAACGAGCCTAACGTTAAGAAAGCTGCGTTAAAGGCAGTAGAGCTGGT
ATCAACTGGAAAAGCTGATATGGTAATGAAGGGACTGGTAAATACCGCAACTTTCTTACGCTCTG
TATTAAACAAAGAAGTTGGTCTGCGTACAGGAAAAACCATGTCTCACGTTGCAGTATTTGAAACT
GAGAAATTTGATCGTCTGTTATTTTTAACAGATGTTGCTTTCAATACTTATCCTGAATTAAAGGA
AAAAATTGATATCGTTAACAATAGCGTTAAGGTTGCACATGCCATTGGTATTGAAAATCCAAAGG
TTGCTCCAATTTGTGCAGTTGAGGTTATTAACCCGAAAATGCCATCAACACTTGATGCAGCAATG
CTTTCAAAAATGAGTGACCGCGGACAAATTAAAGGTTGTGTAGTTGACGGACCGCTGGCACTTGA
TATCGCTTTATCAGAAGAAGCAGCACATCATAAAGGCGTAACAGGAGAAGTTGCTGGAAAAGCTG
ATATCTTCTTAATGCCAAACATTGAAACAGGAAATGTAATGTATAAGACGTTAACCTATACCACT
GATAGCAAAAATGGCGGCATCCTGGTTGGAACTTCTGCACCAGTTGTTTTAACTTCACGCGCTGA
CAGCCATGAAACAAAAATGAACTCTATTGCACTGGCAGCGCTGGTTGCAGGCAATAAATAA

FIG. 23C
ATGATTAAGAGTTTTAATGAAATTATCATGAAGGTAAAGAGCAAAGAAATGAAAAAAGTTGCTGT
TGCTGTTGCACAAGACGAGCCGGTACTGGAAGCGGTACGCGATGCTAAGAAAAATGGTATTGCCG
ATGCTATTCTGGTTGGCGACCATGACGAAATCGTCTCTATCGCGCTGAAAATTGGCATGGATGTT
AATGATTTTGAAATTGTTAACGAGCCTAACGTTAAGAAAGCTGCGCTGAAGGCGGTAGAGCTGGT
TTCCACCGGAAAAGCTGATATGGTAATGAAAGGGCTGGTGAATACCGCAACTTTCTTACGCAGCG
TACTGAACAAAGAAGTTGGTCTGCGTACCGGAAAAACCATGAGTCACGTTGCGGTATTTGAAACT
GAGAAATTTGATCGTCTGCTGTTTCTGACCGATGTTGCTTTCAATACTTATCCTGAATTAAAAGA
AAAAATTGATATCGTTAACAATAGCGTTAAGGTTGCGCATGCCATTGGTATTGAAAATCCAAAGG
TTGCTCCAATTTGTGCAGTTGAGGTTATTAACCCGAAAATGCCATCAACACTTGATGCCGCAATG
CTTAGCAAAATGAGTGACCGCGGACAAATTAAAGGTTGTGTGGTTGACGGCCCGCTGGCACTGGA
TATCGCGTTAAGCGAAGAAGCGGCACATCATAAAGGCGTAACCGGCGAAGTTGCTGGAAAAGCTG
ATATCTTCCTGATGCCAAACATTGAAACAGGCAATGTAATGTATAAAACGTTAACCTATACCACT
GATAGCAAAAATGGCGGCATCCTGGTTGGAACTTCTGCACCAGTTGTTTTAACCTCACGCGCTGA
CAGCCATGAAACCAAAATGAACAGCATTGCACTGGCAGCGCTGGTTGCAGGCAATAAATAA

FIG. 23D
ATGATTAAAAGTTTTAACGAAATTATCATGAAAGTGAAAAGCAAAGAGATGAAAAAAGTGGCGGT
TGCGGTTGCGCAGGATGAACCGGTGCTGGAAGCGGTGCGCGATGCCAAAAAAAACGGTATTGCCG
ATGCCATTCTGGTGGGCGATCACGATGAAATTGTCTCTATTGCGCTGAAAATTGGCATGGATGTT
AACGATTTTGAAATTGTTAATGAACCGAACGTGAAAAAAGCGGCGCTGAAAGCGGTTGAACTGGT
TTCCACCGGTAAAGCCGATATGGTGATGAAAGGGCTGGTGAATACCGCAACCTTCCTGCGCAGCG
TGCTGAATAAAGAAGTGGGTCTGCGTACCGGTAAACCATGAGTCATGTTGCGGTGTTTGAAACC
GAAAAATTTGACCGTCTGCTGTTTCTGACCGATGTTGCGTTTAATACCTATCCGGAACTGAAAGA
GAAAATTGATATCGTTAATAACAGCGTGAAAGTGGCGCATGCCATTGGTATTGAAAACCCGAAAG
TGGCGCCGATTTGCGCGGTTGAAGTGATTAACCCGAAAATGCCGTCAACGCTGGATGCCGCGATG
CTCAGCAAAATGAGCGATCGCGGTCAAATCAAAGGCTGTGTGGTTGATGGCCCGCTGGCGCTGGA
TATCGCGCTTAGCGAAGAAGCGGCGCATCATAAAGGCGTGACCGGCGAAGTGGCCGGTAAAGCCG
ATATTTTCCTGATGCCGAATATTGAAACCGGCAACGTGATGTATAAAACGCTGACCTATACCACC
GACAGCAAAAACGGCGGCATTCTGGTGGGTACCAGCGCGCCGGTGGTGCTGACCTCGCGCGCCGA
CAGCCATGAAACCAAAATGAACAGCATTGCGCTGGCGGCGCTGGTGGCCGGTAATAAATAA

FIG. 24A

ATGTATCGTTACTGATTATCAATCCTGGCTCGACCTCAACTAAAATTGGTATTTATGACGATGA
AAAAGAGATATTTGAGAAGACTTTACGTCATTCAGCTGAAGAGATAGAAAAATATAACACTATAT
TTGATCAATTTCAGTTCAGAAAGAATGTAATTCTCGATGCGTTAAAAGAAGCAAACATTGAAGTA
AGTTCTTTAAATGCTGTAGTTGGACGCGGCGGACTGTTAAAGCCAATAGTAAGTGGAACTTATGC
AGTAAATCAAAAAATGCTTGAAGACCTTAAAGTAGGCGTTCAAGGTCAGCATGCGTCAAATCTTG
GTGGAATTATTGCAAATGAAATAGCAAAAGAAATAAATGTTCCAGCATACATCGTTGATCCAGTT
GTTGTGGATGAGCTTGATGAAGTTTCACGTATATCAGGAATGGCTGACATTCCACGTAAAAGTAT
ATTCCATGCATTAAATCAAAAAGCAGTTGCTAGACGCTATGCAAAAGAAGTTGGAAAAAAATACG
AAGATCTTAATTTAATCGTGGTCCACATGGGTGGCGGTACTTCAGTAGGTACTCATAAAGATGGT
AGAGTAATTGAAGTTAATAATACACTTGATGGAGAAGGTCCATTCTCACCAGAAAGAAGTGGTGG
CGTTCCAATAGGCGATCTTGTACGTTTGTGCTTCAGCAACAAATATACTTATGAAGAAGTAATGA
AAAAGATAAACGGCAAAGGCGGCGTTGTTAGTTACTTAAATACTATCGATTTTAAGGCTGTAGTT
GATAAAGCTCTTGAAGGCGATAAGAAATGTGCACTTATATATGAAGCTTTCACATTCCAGGTAGC
AAAAGAGATAGGAAAATGTTCAACCGTTTTAAAAGGAAATGTAGATGCAATAATCTTAACAGGCG
GAATTGCGTACAACGAGCATGTATGTAATGCCATAGAGGATAGAGTAAAATTCATTGCACCTGTA
GTTCGTTATGGTGGAGAAGATGAACTTCTTGCACTTGCAGAAGGTGGACTGCGCGTTTTACGCGG
AGAAGAAAAAGCTAAGGAATACAAATAA

FIG. 24B

ATGTATCGTTACTGATTATCAATCCTGGCTCGACCTCAACTAAAATTGGTATTTATGACGATGA
AAAAGAGATATTTGAGAAGACGTTACGTCATTCAGCTGAAGAGATTGAAAAATATAACACTATAT
TTGATCAATTTCAGTTCCGCAAGAATGTGATTCTCGATGCGTTAAAAGAAGCAAACATTGAAGTC
AGTTCTTTAAATGCTGTAGTTGGACGCGGCGGACTGTTAAAGCCAATTGTCAGTGGAACTTATGC
AGTAAATCAAAAAATGCTTGAAGACCTTAAAGTGGGCGTTCAAGGTCAGCATGCCAGCAATCTTG
GTGGCATTATTGCCAATGAAATCGCAAAAGAAATCAATGTTCCAGCATACATCGTTGATCCGGTT
GTTGTGGATGAGCTTGATGAAGTTAGCCGTATAAGCGGAATGGCTGACATTCCACGTAAAAGTAT
ATTCCATGCATTAAATCAAAAAGCAGTTGCTCGTCGCTATGCAAAAGAAGTTGGTAAAAAATACG
AAGATCTTAATTTAATCGTGGTCCACATGGGTGGCGGTACTTCAGTAGGTACTCATAAAGATGGT
CGCGTGATTGAAGTTAATAATACACTTGATGGCGAAGGTCCATTCTCACCAGAACGTAGTGGTGG
CGTTCCAATTGGCGATCTGGTACGTTTGTGCTTCAGCAACAAATATACTTATGAAGAAGTGATGA
AAAAGATAAACGGCAAAGGCGGCGTTGTTAGTTACCTGAATACTATCGATTTTAAGGCTGTAGTT
GATAAAGCGCTTGAAGGCGATAAGAAATGTGCACTGATTTATGAAGCTTTCACCTTCCAGGTAGC
AAAAGAGATTGGTAAATGTTCAACCGTTTTAAAAGGAAATGTGATGCCATTATCTTAACAGGCG
GCATTGCTTACAACGAGCATGTATGTAATGCCATTGAGGATCGCGTAAAATTCATTGCACCTGTA
GTTCGTTATGGTGGCGAAGATGAACTGCTGGCACTGGCAGAAGGTGGACTGCGCGTTTTACGCGG
CGAAGAAAAAGCGAAGGAATACAAATAA

FIG. 24C
ATGTATCGTCTGCTGATTATCAATCCTGGCTCGACCTCAACTAAAATTGGTATTTATGACGATGA
AAAAGAGATATTTGAGAAAACGTTACGTCATAGCGCTGAAGAGATTGAAAAATATAACACTATTT
TTGATCAATTTCAGTTCCGCAAGAATGTGATTCTCGATGCGCTGAAAGAAGCAAACATTGAAGTC
AGTTCGCTGAATGCGGTAGTTGGTCGCGGCGGTCTGCTGAAGCCAATTGTCAGCGGCACTTATGC
GGTAAATCAAAAAATGCTGGAAGACCTGAAAGTGGGCGTTCAGGGGCAGCATGCCAGCAATCTTG
GTGGCATTATTGCCAATGAAATCGCCAAAGAAATCAATGTTCCGGCATACATCGTTGATCCGGTT
GTTGTGGATGAGCTGGATGAAGTTAGCCGTATCAGCGGAATGGCTGACATTCCACGTAAAAGTAT
TTTCCATGCACTGAATCAAAAAGCGGTTGCGCGTCGCTATGCAAAAGAAGTTGGTAAAAAATACG
AAGATCTTAATCTGATCGTGGTGCATATGGGTGGCGGTACTAGCGTCGGTACTCATAAAGATGGT
CGCGTGATTGAAGTTAATAATACACTTGATGGCGAAGGTCCATTCTCACCAGAACGTAGCGGTGG
CGTTCCAATTGGCGATCTGGTACGTTTGTGCTTCAGCAACAAATATACCTATGAAGAAGTGATGA
AAAAGATAAACGGCAAAGGCGGCGTTGTAGTTACCTGAATACTATCGATTTTAAGGCGGTAGTT
GATAAAGCGCTGGAAGGCGATAAGAAATGTGCACTGATTTATGAAGCGTTCACCTTCCAGGTGGC
AAAAGAGATTGGTAAATGTTCAACCGTTCTGAAAGGCAATGTTGATGCCATTATCCTGACCGGCG
GCATTGCTTACAACGAGCATGTTTGTAATGCCATTGAGGATCGCGTAAAATTCATTGCACCTGTG
GTTCGTTATGGTGGCGAAGATGAACTGCTGGCACTGGCAGAAGGTGGTCTGCGCGTTTTACGCGG
CGAAGAAAAAGCGAAAGAATACAAATAA

FIG. 24D
ATGTATCGTCTGCTGATTATCAACCCGGGCAGCACCTCAACCAAAATTGGTATTTACGACGATGA
AAAAGAGATTTTTGAAAAAACGCTGCGTCACAGCGCAGAAGAGATTGAAAAATACAACACCATTT
TCGATCAGTTCCAGTTCCGCAAAAAACGTGATTCTCGATGCGCTGAAAGAAGCCAATATTGAAGTC
TCCTCGCTGAATGCGGTGGTCGGTCGCGGCGGTCTGCTGAAACCGATTGTCAGCGGCACTTATGC
GGTTAATCAGAAAATGCTGGAAGATCTGAAAGTGGGCGTGCAGGGGCAGCATGCCAGCAATCTCG
GCGGCATTATCGCCAATGAAATCGCCAAAGAGATCAACGTGCCGGCTTATATCGTCGATCCGGTG
GTGGTTGATGAACTGGATGAAGTCAGCCGTATCAGCGGCATGGCGGATATTCCGCGTAAAAGCAT
TTTCCATGCGCTGAATCAGAAAGCGGTTGCGCGTCGCTATGCCAAAGAAGTGGGTAAAAAATATG
AAGATCTCAATCTGATTGTGGTGCATATGGGCGGCGGCACCAGCGTCGGTACGCATAAAGATGGT
CGCGTGATTGAAGTGAATAACACGCTGGATGGCGAAGGGCCGTTCTCGCCGGAACGTAGCGGCGG
CGTGCCGATTGGCGATCTGGTGCGTCTGTGTTTCAGCAATAAATACACCTACGAAGAAGTGATGA
AAAAAATCAACGGCAAAGGCGGCGTGGTTAGCTATCTGAATACCATCGATTTTAAAGCGGTGGTT
GATAAAGCGCTGGAAGGCGATAAAAAATGCGCGCTGATTTATGAAGCGTTTACCTTCCAGGTGGC
GAAAGAGATTGGTAAATGTTCAACCGTGCTGAAAGGCAACGTTGATGCCATTATTCTGACCGGCG
GCATTGCTTATAACGAACATGTTTGTAATGCCATTGAAGATCGCGTGAAATTTATTGCGCCGGTG
GTGCGTTACGGCGGCGAAGATGAACTGCTGGCGCTGGCGGAAGGCGGTCTGCGCGTGCTGCGCGG
CGAAGAAAAAGCGAAAGAGTACAAATAA

FIG. 27A

ATGAATAAAGACACACTAATACCTACAACTAAAGATTTAAAAGTAAAAACAAATGGTGAAAACAT
TAATTTAAAGAACTACAAGGATAATTCTTCATGTTTCGGAGTATTCGAAAATGTTGAAAATGCTA
TAAGCAGCGCTGTACACGCACAAAAGATATTATCCCTTCATTATACAAAAGAGCAAAGAGAAAAA
ATCATAACTGAGATAAGAAAGGCCGCATTACAAAATAAAGAGGTCTTGGCTACAATGATTCTAGA
AGAAACACATATGGGAAGATATGAGGATAAAATATTAAAACATGAATTGGTAGCTAAATATACTC
CTGGTACAGAAGATTTAACTACTACTGCTTGGTCAGGTGATAATGGTCTTACAGTTGTAGAAATG
TCTCCATATGGTGTTATAGGTGCAATAACTCCTTCTACGAATCCAACTGAAACTGTAATATGTAA
TAGCATAGGCATGATAGCTGCTGGAAATGCTGTAGTATTTAACGGACACCCATGCGCTAAAAAAT
GTGTTGCCTTTGCTGTTGAAATGATAAATAAGGCAATTATTTCATGTGGCGGTCCTGAAAATCTA
GTAACAACTATAAAAAATCCAACTATGGAGTCTCTAGATGCAATTATTAAGCATCCTTCAATAAA
ACTTCTTTGCGGAACTGGGGGTCCAGGAATGGTAAAAACCCTCTTAAATTCTGGTAAGAAAGCTA
TAGGTGCTGGTGCTGGAAATCCACCAGTTATTGTAGATGATACTGCTGATATAGAAAAGGCTGGT
AGGAGCATCATTGAAGGCTGTTCTTTTGATAATAATTTACCTTGTATTGCAGAAAAAGAAGTATT
TGTTTTTGAGAATGTTGCAGATGATTTAATATCTAACATGCTAAAAAATAATGCTGTAATTATAA
ATGAAGATCAAGTATCAAAATTAATAGATTTAGTATTACAAAAAAATAATGAAACTCAAGAATAC
TTTATAAACAAAAAATGGGTAGGAAAAGATGCAAAATTATTCTTAGATGAAATAGATGTTGAGTC
TCCTTCAAATGTTAAATGCATAATCTGCGAAGTAAATGCAAATCATCCATTTGTTATGACAGAAC
TCATGATGCCAATATTGCCAATTGTAAGAGTTAAAGATATAGATGAAGCTATTAAATATGCAAAG
ATAGCAGAACAAAATAGAAAACATAGTGCCTATATTTATTCTAAAAATATAGACAACCTAAATAG
ATTTGAAAGAGAAATAGATACTACTATTTTTGTAAAGAATGCTAAATCTTTTGCTGGTGTTGGTT
ATGAAGCAGAAGGATTTACAACTTTCACTATTGCTGGATCTACTGGTGAGGGAATAACCTCTGCA
AGGAATTTTACAAGACAAAGAAGATGTGTACTTGCCGGCTAA

FIG. 27B

MNKDTLIPTTKDLKVKTNGENINLKNYKDNSSCFGVFENVENAISSAVHAQKILSLHYTKEQREK
IITEIRKAALQNKEVLATMILEETHMGRYEDKILKHELVAKYTPGTEDLPTTAWSGDNGLTVVEM
SPYGVIGAITPSTNPTETVICNSIGMIAAGNAVVFNGHPCAKKCVAPAVEMINKAIISCGGPENL
VTTIKNPTMESLDAIIKHPSIKLLCGTGGPGMVKTLLNSGKKAIGAGAGNPPVIVDDTADIEKAG
RSIIEGCSFDNNLPCIAEKEVFVFENVADDLISNMLKNNAVIINEDQVSKLIDLVLQKNNETQEY
FINKKWVGKDAKLFLDEIDVESPSNVKCIICEVNANHPFVMTELMMPILPIVRVKDIDEAIKYAK
IAEQNRKHSAYIYSKNIDNLNRFEREIDTTIFVKNAKSFAGVGYEAEGFTTPTIAGSTGEGITSA
RNFTRQRRCVLAG

FIG. 28A

```
ATGAATAAAGACACACTAATACCTACAACTAAAGATTTAAAAGTAAAAACAAATGGTGAAAACAT
TAATTTAAAGAACTACAAGGATAATTCTTCATGTTTCGGCGTATTCGAAAATGTTGAAAATGCTA
TAAGCAGCGCTGTACACGCACAAAAGATATTATCCCTTCATTATACAAAAGAGCAACGTGAAAAA
ATCATAACTGAGATAAGAAAGGCCGCATTACAAAATAAAGAGGTCTTGGCTACAATGATTCTGGA
AGAAACACATATGGGACGTTATGAGGATAAAATATTAAAACATGAATTGGTAGCTAAATATACTC
CTGGTACAGAAGATTTAACTACTACTGCCTGGTCAGGTGATAATGGTCTGACAGTTGTAGAAATG
TCTCCATATGGTGTTATTGGTGCAATAACTCCTTCTACGAATCCAACTGAAACTGTAATATGTAA
TAGCATAGGCATGATTGCTGCTGGAAATGCTGTAGTATTTAACGGACACCCATGCGCTAAAAAAT
GTGTTGCCTTTGCTGTTGAAATGATAAATAAGGCAATTATTTCATGTGGCGGTCCTGAAAATCTG
GTAACAACTATAAAAAATCCAACCATGGAGTCTCTGGATGCAATTATTAAGCATCCTTCAATAAA
ACTTCTTTGCGGAACTGGGGGTCCAGGAATGGTAAAAACCCTGTTAAATTCTGGTAAGAAAGCTA
TAGGTGCTGGTGCTGGAAATCCACCAGTTATTGTCGATGATACTGCTGATATAGAAAAGGCTGGT
CGTAGCATCATTGAAGGCTGTTCTTTTGATAATAATTTACCTTGTATTGCAGAAAAAGAAGTATT
TGTTTTTGAGAATGTTGCAGATGATTTAATATCTAACATGCTAAAAAATAATGCTGTAATTATAA
ATGAAGATCAAGTATCAAAATTAATCGATTTAGTATTACAAAAAAATAATGAAACTCAAGAATAC
TTTATAAACAAAAAATGGGTAGGAAAAGATGCAAAATTATTCCTCGATGAAATAGATGTTGAGTC
TCCTTCAAATGTTAAATGCATAATCTGCGAAGTAAATGCAAATCATCCATTTGTTATGACAGAAC
TGATGATGCCAATATTGCCAATTGTACGCGTTAAAGATATCGATGAAGCTATTAAATATGCAAAG
ATAGCAGAACAAAATAGAAAACATAGTGCCTATATTTATTCTAAAAATATCGACAACCTGAATCG
CTTTGAACGTGAAATAGATACTACTATTTTTGTAAAGAATGCTAAATCTTTTGCTGGTGTTGGTT
ATGAAGCAGAAGGATTTACAACTTTCACTATTGCTGGATCTACTGGTGAGGGAATAACCTCTGCA
CGTAATTTTACACGCCAACGTCGCTGTGTACTTGCCGGCTAA
```

FIG. 28B

```
ATGAATAAAGACACACTGATCCCTACAACTAAAGATTTAAAAGTAAAAACAAATGGTGAAAACAT
TAATTTAAAGAACTACAAAGATAATAGCAGTTGTTTCGGCGTATTCGAAAATGTTGAAAATGCTA
TCAGCAGCGCTGTACACGCACAAAAGATATTATCGCTGCATTATACAAAAGAGCAACGTGAAAAA
ATCATCACTGAGATACGTAAGGCCGCATTACAAAATAAAGAGGTGCTGGCTACAATGATTCTGGA
AGAAACACATATGGGACGTTATGAGGATAAAATATTAAAACATGAACTGGTAGCTAAATATACTC
CTGGTACAGAAGATTTAACTACTACTGCCTGGAGCGGTGATAATGGTCTGACAGTTGTAGAAATG
TCTCCATATGGTGTTATTGGTGCAATAACTCCTTCTACCAATCCAACTGAAACTGTAATTTGTAA
TAGCATTGGCATGATTGCTGCTGGAAATGCTGTAGTATTTAACGGACACCCATGCGCTAAAAAAT
GTGTTGCCTTTGCTGTTGAAATGATCAATAAGGCAATTATTAGCTGTGGCGGTCCGGAAAATCTG
GTAACAACTATAAAAAATCCAACCATGGAGTCTCTGGATGCCATTATTAAGCATCCTTCAATAAA
ACTGCTTTGCGGAACTGGCGGTCCAGGAATGGTAAAAACCCTGTTAAATTCTGGTAAGAAAGCTA
TTGGTGCTGGTGCTGGAAATCCACCAGTTATTGTCGATGATACTGCTGATATTGAAAAGGCTGGT
CGTAGCATCATTGAAGGCTGTTCTTTTGATAATAATTTACCTTGTATTGCAGAAAAAGAAGTATT
TGTTTTTGAGAATGTTGCAGATGATTTAATATCTAACATGCTGAAAAATAATGCTGTAATTATCA
ATGAAGATCAGGTATCAAAATTAATCGATTTAGTATTACAAAAAAATAATGAAACTCAAGAATAC
TTTATCAACAAAAAATGGGTAGGTAAAGATGCAAAATTATTCCTCGATGAAATCGATGTTGAGTC
TCCTTCAAATGTTAAATGCATTATCTGCGAAGTGAATGCCAATCATCC
```

FIG. 28B continued
ATTTGTTATGACAGAACTGATGATGCCAATATTGCCAATTGTGCGCGTTAAAGATATCGATGAAG
CTATTAAATATGCAAAGATTGCAGAACAAAATAGAAAACATAGTGCCTATATTTATAGCAAAAAT
ATCGACAACCTGAATCGCTTTGAACGTGAAATCGATACTACTATTTTTGTAAAGAATGCTAAATC
TTTTGCTGGTGTTGGTTATGAAGCAGAAGGATTTACCACTTTCACTATTGCTGGATCTACTGGTG
AGGGCATAACCTCTGCACGTAATTTTACCCGCCAACGTCGCTGTGTACTGGCCGGCTAA

FIG. 28C
ATGAATAAAGACACGCTGATCCCGACAACTAAAGATCTGAAAGTAAAAACCAATGGTGAAAACAT
TAATCTGAAGAACTACAAAGATAATAGCAGTTGTTTCGGCGTATTCGAAAATGTTGAAAATGCTA
TCAGCAGCGCGGTACACGCACAAAAGATACTCTCGCTGCATTATACCAAAGAGCAACGTGAAAAA
ATCATCACTGAGATCCGTAAGGCCGCATTACAAAATAAAGAGGTGCTGGCAACAATGATTCTGGA
AGAAACACATATGGGACGTTATGAGGATAAAATACTGAAACATGAACTGGTGGCGAAATATACGC
CTGGTACTGAAGATTTAACCACCACTGCCTGGAGCGGTGATAATGGTCTGACCGTTGTGGAAATG
TCGCCTTATGGTGTTATTGGTGCAATTACGCCTTCAACCAATCCAACTGAAACGGTAATTTGTAA
TAGCATTGGCATGATTGCTGCTGGAAATGCGGTAGTATTTAACGGTCACCCCTCGCTAAAAAAT
GTGTTGCCTTTGCTGTTGAAATGATCAATAAAGCGATTATTAGCTGTGGCGGTCCGGAAAATCTG
GTAACCACTATAAAAATCCAACCATGGAGTCGCTGGATGCCATTATTAAGCATCCTTCAATCAA
ACTGCTGTGCGGCACTGGCGGTCCAGGAATGGTGAAAACCCTGCTGAATAGCGGTAAGAAAGCGA
TTGGTGCTGGTGCTGGAAATCCACCAGTTATTGTCGATGATACTGCTGATATTGAAAAGCGGGT
CGTAGCATCATTGAAGGCTGTTCTTTTGATAATAATTTACCTTGTATTGCAGAAAAAGAAGTATT
TGTTTTTGAGAATGTTGCCGATGATCTGATCTCTAACATGCTGAAAAATAATGCGGTGATTATCA
ATGAAGATCAGGTTAGCAAACTGATCGATCTGGTATTACAAAAAAATAATGAAACTCAAGAATAC
TTTATCAACAAAAAATGGGTAGGTAAAGATGCAAAACTGTTCCTCGATGAAATCGATGTTGAGTC
GCCTTCAAATGTTAAATGCATTATCTGCGAAGTGAATGCCAATCATCCATTTGTGATGACCGAAC
TGATGATGCCAATTTTGCCGATTGTGCGCGTTAAAGATATCGATGAAGCGATTAAATATGCAAAG
ATTGCAGAACAAAATCGTAAACATAGTGCCTATATTTATAGCAAAAATATCGACAACCTGAATCG
CTTTGAACGTGAAATCGATACCACTATTTTTGTGAAGAATGCTAAATCTTTTGCTGGTGTTGGTT
ATGAAGCAGAAGGTTTTACCACTTTCACTATTGCTGGAAGCACCGGTGAAGGCATTACCTCTGCA
CGTAATTTTACCCGCCAACGTCGCTGTGTACTGGCCGGCTAA

FIG. 28D
ATGAATAAAGATACGCTGATCCCGACCACCAAAGATCTGAAAGTGAAAACCAACGGCGAAAATAT
CAACCTGAAAAACTATAAAGATAACAGCAGTTGCTTTGGCGTGTTTGAAAACGTTGAAAACGCCA
TCTCCAGCGCGGTGCATGCGCAAAAAATTCTCTCGCTGCATTACACCAAAGAGCAGCGTGAAAAA
ATTATCACCGAAATCCGTAAAGCGGCGCTGCAAAACAAAGAAGTGCTGGCAACCATGATCCTGGA
AGAAACGCATATGGGGCGTTATGAAGATAAAATTCTGAAACATGAACTGGTGGCGAAATACACGC
CGGGCACTGAAGATCTGACCACCACCGCCTGGAGCGGCGATAACGGCCTGACCGTGGTGGAGATG
TCGCCTTATGGCGTGATTGGCGCGATTACGCCGTCAACCAACCCGACCGAAACGGTGATTTGTAA
CAGCATTGGCATGATTGCCGCGGGTAATGCGGTGGTGTTTAACGGTCATCCCTGCGCGAAAAAAT
GTGTGGCGTTTGCCGTTGAGATGATCAACAAAGCGATTATCAGCTGCGGCGGCCCGGAAAATCTG
GTGACCACCATCAAAAATCCGACCATGGAATCGCTGGATGCCATTATCAAACATCCTTCCATCAA
ACTGCTGTGCGGCACCGGCGGCCCGGGCATGGTGAAAACGCTGCTGAACAGCGGTAAAAAGCGA
TTGGCGCGGGCGCGGGTAACCCGCCGGTGATTGTCGATGACACCGCCGATATT

FIG. 28D continued

GAAAAAGCGGGGCGTAGCATTATTGAAGGCTGTTCTTTTGATAACAACCTGCCCTGCATTGCCGA
AAAAGAAGTGTTTGTCTTTGAAAACGTCGCCGATGATCTGATCAGCAATATGCTGAAAAACAACG
CGGTGATTATCAATGAAGATCAGGTTAGCAAACTGATCGATCTGGTGCTGCAAAAAAACAACGAA
ACGCAGGAATATTTTATCAACAAAAAATGGGTTGGTAAAGATGCCAAACTGTTTCTCGATGAAAT
CGATGTTGAATCGCCGTCTAACGTGAAATGTATTATCTGCGAAGTGAACGCCAACCATCCGTTTG
TGATGACCGAACTGATGATGCCGATTCTGCCGATTGTGCGCGTGAAAGATATCGATGAAGCGATT
AAATATGCCAAAATTGCCGAACAAAACCGTAAACACAGCGCCTATATTTACAGCAAAAATATCGA
TAACCTGAACCGCTTTGAACGTGAAATCGATACCACCATTTTTGTGAAAAATGCCAAAAGTTTTG
CCGGCGTTGGTTATGAAGCGGAAGGTTTTACCACCTTTACCATTGCCGGTAGCACCGGCGAAGGC
ATTACCAGCGCCCGTAATTTTACCCGCCAGCGTCGCTGCGTGCTGGCGGGCTAA

FIG. 31A

ATGAAAGCTGCAGTAGTAGAGCAATTTAAGGAACCATTAAAAATTAAAGAAGTGGAAAAGCCATC
TATTTCATATGGCGAAGTATTAGTCCGCATTAAAGCATGCGGTGTATGCCATACGGACTTGCACG
CCGCTCATGGCGATTGGCCAGTAAAACCAAAACTTCCTTTAATCCCTGGCCATGAAGGAGTCGGA
ATTGTTGAAGAAGTCGGTCCGGGGGTAACCCATTTAAAAGTGGGAGACCGCGTTGGAATTCCTTG
GTTATATTCTGCGTGCGGCCATTGCGAATATTGTTTAAGCGGACAAGAAGCATTATGTGAACATC
AACAAAACGCCGGCTACTCAGTCGACGGGGGTTATGCAGAATATTGCAGAGCTGCGCCAGATTAT
GTGGTGAAAATTCCTGACAACTTATCGTTTGAAGAAGCTGCTCCTATTTTCTGCGCCGGAGTTAC
TACTTATAAAGCGTTAAAAGTCACAGGTACAAAACCGGGAGAATGGGTAGCGATCTATGGCATCG
GCGGCCTTGGACATGTTGCCGTCCAGTATGCGAAAGCGATGGGGCTTCATGTTGTTGCAGTGGAT
ATCGGCGATGAGAAACTGGAACTTGCAAAAGAGCTTGGCGCCGATCTTGTTGTAAATCCTGCAAA
AGAAAATGCGGCCCAATTTATGAAAGAGAAAGTCGGCGGAGTACACGCGGCTGTTGTGACAGCTG
TATCTAAACCTGCTTTTCAATCTGCGTACAATTCTATCCGCAGAGGCGGCACGTGCGTGCTTGTC
GGATTACCGCCGGAAGAAATGCCTATTCCAATCTTTGATACGGTATTAAACGGAATTAAAATTAT
CGGTTCCATTGTCGGCACGCGGAAAGACTTGCAAGAAGCGCTTCAGTTCGCTGCAGAAGGTAAAG
TAAAAACCATTATTGAAGTGCAACCTCTTGAAAAAATTAACGAAGTATTTGACAGAATGCTAAAA
GGAGAAATTAACGGACGGGTTGTTTTAACGTTAGAAAATAATAATTAA

FIG. 31B

MKAAVVEQFKEPLKIKEVEKPSISYGEVLVRIKACGVCHTDLHAAHGDWPVKPKLPLIPGHEGVG
IVEEVGPGVTHLKVGDRVGIPWLYSACGHCEYCLSGQEALCEHQQNAGYSVDGGYAEYCRAAPDY
VVKIPDNLSFEEAAPIFCAGVTTYKALKVTGTKPGEWVAIYGIGGLGHVAVQYAKAMGLHVVAVD
IGDEKLELAKELGADLVVNPAKENAAQFMKEKVGGVHAAVVTAVSKPAFQSAYNSIRRGGTCVLV
GLPPEEMPIPIPDTVLNGIKIIGSIVGTRKDLQEALQPAAEGKVKTIIEVQPLEKINEVFDRMLK
GEINGRVVLTLENNN

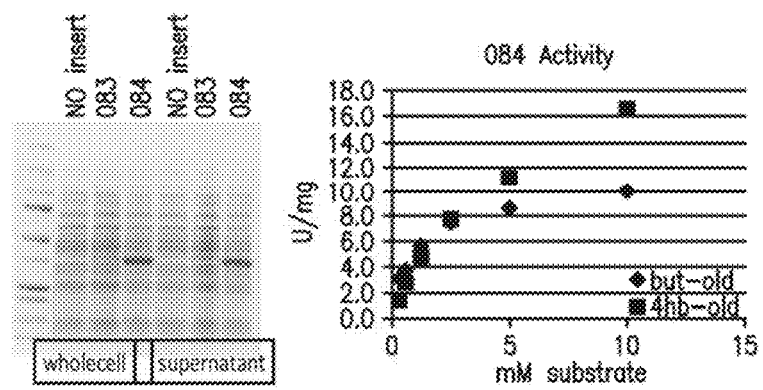
FIG. 32A  FIG. 32B
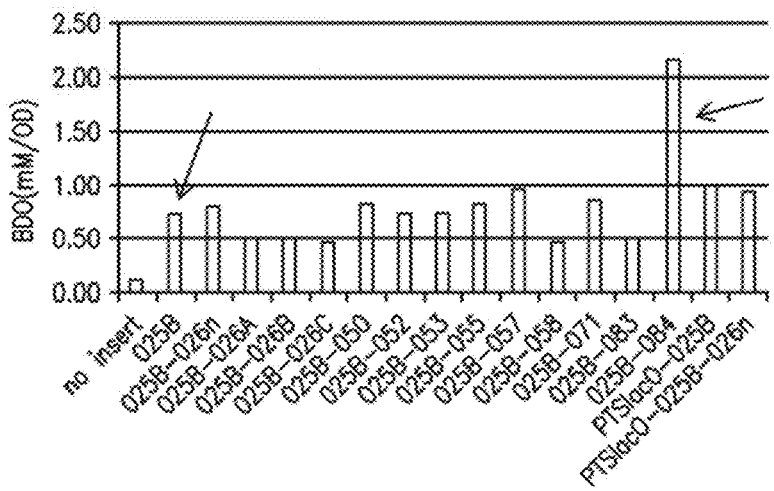
FIG. 33
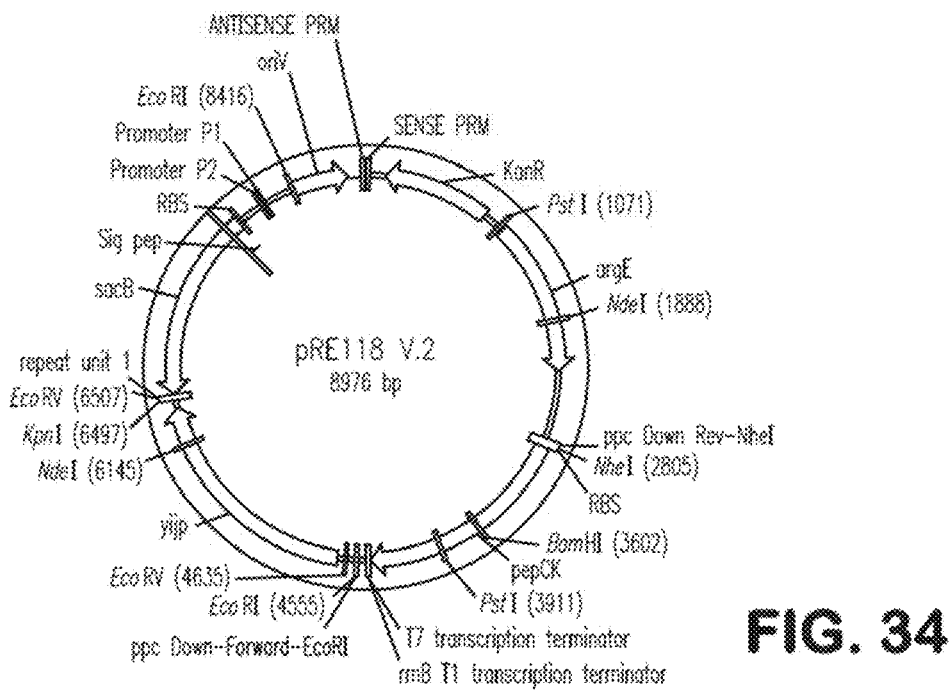
FIG. 34 aTGGCTATCGAAATCAAAGTACCGGACATCGGGGCTGATGAAGTTGAAATCACCGAGATCCTGGTCAAA
GTGGGCGACAAAGTTGAAGCCGAACAGTCGCTGATCACCGTAGAAGGCGACAAAGCCTCTATGGAAGT
TCCGTCTCCGCAGGCGGGTATCGTTAAAGAGATCAAAGTCTCTGTTGGCGATAAAACCCAGACCGGCGC
ACTGATTATGATTTTCGATTCCGCCGACGGTGCAGCAGACGCTGCACCTGCTCAGGCAGAAGAGAAGAA
AGAAGCAGCTCCGGCAGCAGCACCAGCGGCTGCGGCGGCAAAAGACGTTAACGTTCCGGATATCGGCA
GCGACGAAGTTGAAGTGACCGAAATCCTGGTGAAAGTTGGCGATAAAGTTGAAGCTGAACAGTCGCTG
ATCACCGTAGAAGGCGACAAGGCTTCTATGGAAGTTCCGGCTCCGTTTGCTGGCACCGTGAAAGAGATC
AAAGTGAACGTGGGTGACAAAGTGTCTACCGGCTCGCTGATTATGGTCTTCGAAGTCGCGGGTGAAGC
AGGCGCGGCAGCTCCGGCCGCTAAACAGGAAGCAGCTCCGGCAGCGGCCCCTGCACCAGCGGCTGGC
GTGAAAGAAGTTAACGTTCCGGATATCGGCGGTGACGAAGTTGAAGTGACTGAAGTGATGGTGAAAGT
GGGCGACAAAGTTGCCGCTGAACAGTCACTGATCACCGTAGAAGGCGACAAAGCTTCTATGGAAGTTCC
GGCGCCGTTTGCAGGCGTCGTGAAGGAACTGAAAGTCAACGTTGGCGATAAAGTGAAAACTGGCTCGC
TGATTATGATCTTCGAAGTTGAAGGCGCAGCGCCTGCGGCAGCTCCTGCGAAACAGGAAGCGGCAGCG
CCGGCACCGGCAGCAAAAGCTGAAGCCCCGGCAGCAGCACCAGCTGCGAAAGCGGAAGGCAAATCTG
AATTTGCTGAAAACGACGCTTATGTTCACGCGACTCCGCTGATCCGCCGTCTGGCACGCGAGTTTGGTGT
TAACCTTGCGAAAGTGAAGGGCACTGGCCGTAAAGGTCGTATCCTGCGCGAAGACGTTCAGGCTTACGT
GAAAGAAGCTATCAAACGTGCAGAAGCAGCTCCGGCAGCGACTGGCGGTGGTATCCCTGGCATGCTGC
CGTGGCCGAAGGTGGACTTCAGCAAGTTTGGTGAAATCGAAGAAGTGGAACTGGGCCGCATCCAGAAA
ATCTCTGGTGCGAACCTGAGCCGTAACTGGGTAATGATCCCGCATGTTACTCACTTCGACAAAACCGATA
TCACCGAGTTGGAAGCGTTCCGTAAACAGCAGAACGAAGAAGCGGCGAAACGTAAGCTGGATGTGAAG
ATCACCCCGGTTGTCTTCATCATGAAAGCCGTTGCTGCAGCTCTTGAGCAGATGCCTCGCTTCAATAGTTC
GCTGTCGGAAGACGGTCAGCGTCTGACCCTGAAGAAATACATCAACATCGGTGTGGCGGTGGATACCC
CGAACGGTCTGGTTGTTCCGGTATTCAAAGACGTCAACAAGAAAGGCATCATCGAGCTGTCTCGCGAGC
TGATGACTATTTCTAAGAAAGCGCGTGACGGTAAGCTGACTGCGGGCGAAATGCAGGGCGGTTGCTTC
ACCATCTCCAGCATCGGCGGCCTGGGTACTACCCACTTCGCGCCGATTGTGAACGCGCCGGAAGTGGCT
ATCCTCGGCGTTTCCAAGTCCGCGATGGAGCCGGTGTGGAATGGTAAAGAGTTCGTGCCGCGTCTGATG
CTGCCGATTTCTCTCTCCTTCGACCACGCGTGATCGACGGTGCTGATGGTGCCCGTTTCATTACCATCAT
TAACAACACGCTGTCTGACATTCGCCGTCTGGTGATGTAAGTAAAAGAGCCGGCCCAACGGCCGGCTTT
TTTCTGGTAATCTCATGAATGTATTGAGGTTATTAGCGAATAGACAAATCGGTTGCCGTTTGTTGTTTAAA
AATTGTTAACAATTTTGTAAAATACCGACGGATAGAACGACCCGGTGGTGGTTAGGGTATTACTTCACAT
ACCCTATGGATTTCTGGGTGCAGCAAGGTAGCAAGCGCCAGAATCCCCAGGAGCTTACATAAGTAAGTG
ACTGGGGTGAGGGCGTGAAGCTAACGCCGCTGCGGCCTGAAAGACGACGGGTATGACCGCCGGAGAT
AAATATATAGAGGTCATGATGAGTACTGAAATCAAAACTCAGGTCGTGGTACTTGGGGCAGGCCCCGCA
GGTTACTCCGCTGCCTTCCGTTGCGCTGATTTAGGTCTGGAAACCGTAATCGTAGAACGTTACAACACCC
TTGGCGGTGTTTGTCTGAACGTGGGTTGTATCCCTTCTAAAGCGCTGCTGCACGTGGCAAAAGTTATCGA
AGAAGCGAAAGCGCTGGCCGAACACGGCATCGTTTTCGGCGAACCGAAAACTGACATTGACAAGATCC
GCACCTGGAAAGAAAAAGTCATCACTCAGCTGACCGGTGGTCTGGCTGGCATGGCCAAAGGTCGTAAA
GTGAAGGTGGTTAACGGTCTGGGTAAATTTACCGGCGCTAACACCCTGGAAGTGGAAGGCGAAAACGG
CAAAACCGTGATCAACTTCGACAACGCCATCATCGCGGCGGGTTCCCGTCCGATTCAGCTGCCGTTTATC
CCGCATGAAGATCCGCGCGTATGGACTCCACCGACGCGCTGGAACTGAAATCTGTACCGAAACGCATG
CTGGTGATGGGCGGCGGTATCATCGGTCTGGAAATGGGTACCGTATACCATGCGCTGGGTTCAGAGATT
GACGTGGTGGAAATGTTCGACCAGGTTATCCCGGCTGCCGACAAAGACGTGGTGAAAGTCTTCACCAAA
CGCATCAGCAAGAAATTTAACCTGATGCTGGAAGCCAAAGTGACTGCCGTTGAAGCGAAAGAAGACGG

FIG. 35

TATTTACGTTTCCATGGAAGGTAAAAAAGCACCGGCGGAAGCGCAGCGTTACGACGCAGTGCTGGTCG
CTATCGGCCGCGTACCGAATGGTAAAAACCTCGATGCAGGTAAAGCTGGCGTGGAAGTTGACGATCGC
GGCTTCATCCGCGTTGACAAACAAATGCGCACCAACGTGCCGCACATCTTTGCTATCGGCGATATCGTCG
GTCAGCCGATGCTGGCGCACAAAGGTGTCCATGAAGGCCACGTTGCCGCAGAAGTTATCTCCGGTCTGA
AACACTACTTCGATCCGAAAGTGATCCCATCCATCGCCTACACTAAACCAGAAGTGGCATGGGTCGGTCT
GACCGAGAAAGAAGCGAAAGAGAAAGGCATCAGCTACGAAACCGCCACCTTCCCGTGGGCTGCTTCCG
GCCGTGCTATCGCTTCTGACTGCGCAGATGGTATGACCAAACTGATCTTCGACAAAGAGACCCACCGTG
TTATCGGCGGCGCGATTGTCGGCACCAACGGCGGCGAGCTGCTGGGTGAGATCGGCCTGGCTATCGAG
ATGGGCTGTGACGCTGAAGACATCGCCCTGACCATCCACGCTCACCCGACTCTGCACGAGTCCGTTGGC
CTGGCGGCGGAAGTGTTCGAAGGCAGCATCACCGACCTGCCAAACGCCAAAGCGAAGAAAAAGTAACT
TTTTCTTTCAGGAAAAAAGCATAAGCGGCTCCGGGAGCCGCTTTTTTTATGCCTGATGTTTAGAACTATG
TCACTGTTCATAAACCGCTACACCTCATACATACTTTAAGGGCGAATTCTGCAGATATCCATCACACTGGC
GGCCGCTCGAGCATGCATCTAGCACATCCGGCAATTAAAAAAGCGGCTAACCACGCCGCTTTTTTTACGT
CTGCAATTTACCTTTCCAGTCTTCTTGCTCCACGTTCAGAGAGACGTTCGCATACTGCTGACCGTTGCTCG
TTATTCAGCCTGACAGTATGGTTACTGTCGTTTAGACGTTGTGGCGGCTCTCCTGAACTTTCTCCCGAA
AAACCTGACGTTGTTCAGGTGATGCCGATTGAACACGCTGGCGGGCGTTATCACGTTGCTGTTGATTCA
GTGGGCGCTGCTGTACTTTTTCCTT

FIG. 35 continued

```
                                                                    Section 1
              (1)  1         10        20        30        40       52
   EC-lpdA   (1)  MMSTEIKTQVVVLGAGPAGYSAAFRCADLGLETVIVERYNTLGGVCLNVGCI
KP-lpdA mutated (1) MMSTEIKTQVVVLGAGPAGYSAAFRCADLGLETVIVERYSTLGGVCLNVGCI
                                                                    Section 2
              (53) 53       60        70        80        90       104
   EC-lpdA   (53) PSKALLHVAKVIEEAKALAEHGIVFGEPKTDIDKIRTWKEKVINQLTGGLAG
KP-lpdA mutated (53) PSKALLHVAKVIEEAKALAEHGIVFGEPKTDIDKIRTWKEKVIEQLTGGLAG
                                                                    Section 3
              (105) 105    110       120       130       140       156
   EC-lpdA   (105) MAKGRKVKVVNGLGKFTGANTLEVEGENGKTVINFDNAIIAAGSRPIQLPFI
KP-lpdA mutated (105) MAKGRKVKVVNGLGKFTGANTLEVEGENGKTVINFDNAIIAAGSRPIQLPFI
                                                                    Section 4
              (157) 157    170       180       190               208
   EC-lpdA   (157) PHEDPRIWDSTDALELKEVPERLLVMGGGIIGLEMGTVYHALGSQIDVVEMF
KP-lpdA mutated (157) PHEDPRVWDSTDALELKSVPKRMLVMGGGIIGLEMGTVYHALGSEIDVVEMF
                                                                    Section 5
              (209) 209    220       230       240       250       260
   EC-lpdA   (209) DQVIPAADKDIVKVFTKRISKKFNLMLETKVTAVEAKEDGIYVTMEGKKAPA
KP-lpdA mutated (209) DQVIPAADKDVVKVFTKRISKKFNLMLEAKVTAVEAKEDGIYVSMEGKKAPA
                                                                    Section 6
              (261) 261    270       280       290       300       312
   EC-lpdA   (261) EPQRYDAVLVAIGRVPNGKNLDAGKAGVEVDDRGFIRVDKQLRTNVPHIFAI
KP-lpdA mutated (261) EAQRYDAVLVAIGRVPNGKNLDAGKAGVEVDDRGFIRVDKQMRTNVPHIFAI
                                                                    Section 7
              (313) 313    320       330       340       350       364
   EC-lpdA   (313) GDIVGQPMLAHKGVHEGHVAAEVIAGKKHYFDPKVIPSIAYTEPEVAWVGLT
KP-lpdA mutated (313) GDIVGQPMLAHKGVHEGHVAAEVISGLKHYFDPKVIPSIAYTKPEVAWVGLT
                                                                    Section 8
              (365) 365    370       380       390       400       416
   EC-lpdA   (365) EKEAKEKGISYETATFPWAASGRAIASDCADGMTKLIFDKESHRVIGGAIVG
KP-lpdA mutated (365) EKEAKEKGISYETATFPWAASGRAIASDCADGMTKLIFDKETHRVIGGAIVG
                                                                    Section 9
              (417) 417    430       440       450       468
   EC-lpdA   (417) TNGGELLGEIGLAIEMGCDAEDIALTIHAHPTLHESVGLAAEVFEGSITDLP
KP-lpdA mutated (417) TNGGELLGEIGLAIEMGCDAEDIALTIHAHPTLHESVGLAAEVFEGSITDLP (469) 469    476
   EC-lpdA   (469) NPKAKKK-
KP-lpdA mutated (469) NAKAKKK-
```

FIG. 36

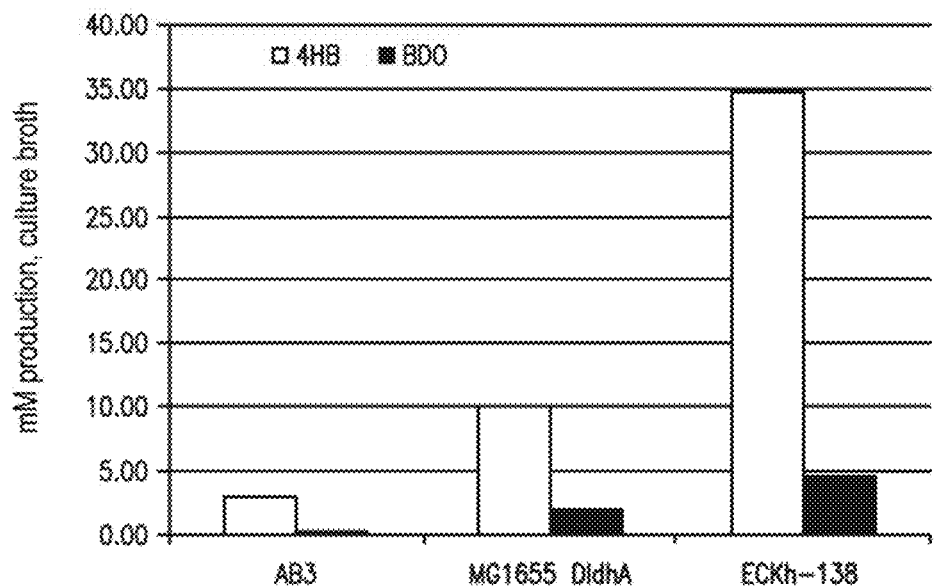

FIG. 37

*ataataatacatatgaaccatgcgagttacgggcctat*aagccaggcgagata<u>atg</u>atctatatcaatttctcatctataatgctttgttagtatctcgtcgccgacttaataaagagagagtta*gtgtgaaagctgacaaccctttgatcttttacttcctgctgcaatggccaaagtggccgaagaggcgggtgtctataaagcaacgaaacatccgcttaagactttctatctggcgattaccgccggtgttttcatctcaatcgcattcaccactggcacaggcaca*GAAGGTAGGTGTTAC*atgtcagaacgtttacacaatgacgtggatcctattattat*

FIG. 38

```
AAGAGGTAAAAGAATAATGGCTATCGAAATCAAAGTACCGGACATCGGGGCTGATGAAGTTGAAATCA
CCGAGATCCTGGTCAAAGTGGGCGACAAAGTTGAAGCCGAACAGTCGCTGATCACCGTAGAAGGCGAC
AAAGCCTCTATGGAAGTTCCGTCTCCGCAGGCGGGTATCGTTAAAGAGATCAAAGTCTCTGTTGGCGAT
AAAACCCAGACCGGCGCACTGATTATGATTTTCGATTCCGCCGACGGTGCAGCAGACGCTGCACCTGCT
CAGGCAGAAGAGAAGAAAGAAGCAGCTCCGGCAGCAGCACCAGCGGCTGCGGCGGCAAAAGACGTTA
ACGTTCCGGATATCGGCAGCGACGAAGTTGAAGTGACCGAAATCCTGGTGAAAGTTGGCGATAAAGTT
GAAGCTGAACAGTCGCTGATCACCGTAGAAGGCGACAAGGCTTCTATGGAAGTTCCGGCTCCGTTTGCT
GGCACCGTGAAAGAGATCAAAGTGAACGTGGGTGACAAAGTGTCTACCGGCTCGCTGATTATGGTCTTC
GAAGTCGCGGGTGAAGCAGGCGCGGCAGCTCCGGCCGCTAAACAGGAAGCAGCTCCGGCAGCGGCCC
CTGCACCAGCGGCTGGCGTGAAAGAAGTTAACGTTCCGGATATCGGCGGTGACGAAGTTGAAGTGACT
GAAGTGATGGTGAAAGTGGGCGACAAAGTTGCCGCTGAACAGTCACTGATCACCGTAGAAGGCGACAA
AGCTTCTATGGAAGTTCCGGCGCCGTTTGCAGGCGTCGTGAAGGAACTGAAAGTCAACGTTGGCGATAA
AGTGAAAACTGGCTCGCTGATTATGATCTTCGAAGTTGAAGGCGCAGCGCCTGCGGCAGCTCCTGCGAA
ACAGGAAGCGGCAGCGCCGGCACCGGCAGCAAAAGCTGAAGCCCCGGCAGCAGCACCAGCTGCGAAA
GCGGAAGGCAAATCTGAATTTGCTGAAAACGACGCTTATGTTCACGCGACTCCGCTGATCCGCCGTCTG
GCACGCGAGTTTGGTGTTAACCTTGCGAAAGTGAAGGGCACTGGCCGTAAAGGTCGTATCCTGCGCGA
AGACGTTCAGGCTTACGTGAAAGAAGCTATCAAACGTGCAGAAGCAGCTCCGGCAGCGACTGGCGGTG
GTATCCCTGGCATGCTGCCGTGGCCGAAGGTGGACTTCAGCAAGTTTGGTGAAATCGAAGAAGTGGAA
CTGGGCCGCATCCAGAAAATCTCTGGTGCGAACCTGAGCCGTAACTGGGTAATGATCCCGCATGTTACT
CACTTCGACAAAACCGATATCACCGAGTTGGAAGCGTTCCGTAAACAGCAGAACGAAGAAGCGGCGAA
ACGTAAGCTGGATGTGAAGATCACCCCGGTTGTCTTCATCATGAAAGCCGTTGCTGCAGCTCTTGAGCA
GATGCCTCGCTTCAATAGTTCGCTGTCGGAAGACGGTCAGCGTCTGACCCTGAAGAAATACATCAACAT
CGGTGTGGCGGTGGATACCCCGAACGGTCTGGTTGTTCCGGTATTCAAAGACGTCAACAAGAAAGGCA
TCATCGAGCTGTCTCGCGAGCTGATGACTATTTCTAAGAAAGCGCGTGACGGTAAGCTGACTGCGGGCG
AAATGCAGGGCGGTTGCTTCACCATCTCCAGCATCGGCGGCCTGGGTACTACCCACTTCGCGCCGATTGT
GAACGCGCCGGAAGTGGCTATCCTCGGCGTTTCCAAGTCCGCGATGGAGCCGGTGTGGAATGGTAAAG
AGTTCGTGCCGCGTCTGATGCTGCCGATTTCTCTCTCCTTCGACCACCGCGTGATCGACGGTGCTGATGG
TGCCCGTTTCATTACCATCATTAACAACACGCTGTCTGACATTCGCCGTCTGGTGATGTAAGTAAAAGAG
CCGGCCCAACGGCCGGCTTTTTTCTGGTAATCTCATGAATGTATTGAGGTTATTAGCGAATAGACAAATC
GGTTGCCGTTTGTTAAGCCAGGCGAGATATGATCTATATCAATTTCTCATCTATAATGCTTTGTTAGTATC
TCGTCGCCGACTTAATAAAGAGAGAGTTAGTCTTCTATATCACAGCAAGAAGGTAGGTGTTACATGATG
AGTACTGAAATCAAAACTCAGGTCGTGGTACTTGGGGCAGGCCCCGCAGGTTACTCTGCAGCCTTCCGT
TGCGCTGATTTAGGTCTGGAAACCGTCATCGTAGAACGTTACAGCACCCTCGGTGGTGTTTGTCTGAACG
TGGGTTGTATCCCTTCTAAAGCGCTGCTGCACGTGGCAAAAGTTATCGAAGAAGCGAAAGCGCTGGCCG
AACACGGCATCGTTTTCGGCGAACCGAAAACTGACATTGACAAGATCCGCACCTGGAAAGAAAAAGTCA
TCACTCAGCTGACCGGTGGTCTGGCTGGCATGGCCAAAGGTCGTAAAGTGAAGGTGGTTAACGGTCTG
GGTAAATTTACCGGCGCTAACACCCTGGAAGTGGAAGGCGAAAACGGCAAAACCGTGATCAACTTCGA
CAACGCCATCATCGCGGCGGGTTCCCGTCCGATTCAGCTGCCGTTTATCCCGCATGAAGATCCGCGCGTA
TGGGACTCCACCGACGCGCTGGAACTGAAATCTGTACCGAAACGCATGCTGGTGATGGGCGGCGGTAT
CATCGGTCTGGAAATGGGTACCGTATACCATGCGCTGGGTTCAGAGATTGACGTGGTGGAAATGTTCGA
CCAGGTTATCCCGGCTGCCGACAAAGACGTGGTGAAAGTCTTCACCAAACGCATCAGCAAGAAATTTAA
CCTGATGCTGGAAGCCAAAGTGACTGCCGTTGAAGCGAAAGAAGACGGTATTTACGTTTCCATGGAAG
GTAAAAAGCACCGGCGGAAGCGCAGCGTTACGACGCAGTGCTGGTCGCTATCGGCCGCGTACCGAAT
GGTAAAAACCTCGATGCAGGTAAAGCTGGCGTGGAAGTTGACGATCGCGGCTTCATCCGCGTTGACAA
```

FIG. 39

```
ACAAATGCGCACCAACGTGCCGCACATCTTTGCTATCGGCGATATCGTCGGTCAGCCGATGCTGGCGCA
CAAAGGTGTCCATGAAGGCCACGTTGCCGCAGAAGTTATCTCCGGTCTGAAACACTACTTCGATCCGAA
AGTGATCCCATCCATCGCCTACACTAAACCAGAAGTGGCATGGGTCGGTCTGACCGAGAAAGAAGCGA
AAGAGAAAGGCATCAGCTACGAAACCGCCACCTTCCCGTGGGCTGCTTCCGGCCGTGCTATCGCTTCTG
ACTGCGCAGATGGTATGACCAAACTGATCTTCGACAAAGAGACCCACCGTGTTATCGGCGGCGCGATTG
TCGGCACCAACGGCGGCGAGCTGCTGGGTGAGATCGGCCTGGCTATCGAGATGGGCTGTGACGCTGAA
GACATCGCCCTGACCATCCACGCTCACCCGACTCTGCACGAGTCCGTTGGCCTGGCGGCGGAAGTGTTC
GAAGGCAGCATCACCGACCTGCCAAACGCCAAAGCGAAGAAAAAGTAACTTTTTCTTTCAGGAAAAAAG
CATAAGCGGCTCCGGGAGCCGCTTTTTTTATGCCTGATGTTTAGAACTATGTCACTGTTCATAAACCGCTA
CACCTCATACATACTTTAAGGGCGAATTCTGCAGATATCCATCACACTGGCGGCCGCTCGAGCATGCATC
TAGCACATCCGGCAATTAAAAAAGCGGCTAACCACGCCGCTTTTTTTACGTCTGCAATTTACCTTTCCAGT
CTTCTTGCTCCACGTTCAGAGAGACGTTCGCATACTGCTGACCGTTGCTCGTTATTCAGCCTGACAGTAT
GGTTACTGTCGTTTAGACGTTGTGGGCGGCTCTCCTGAACTTTCTCCCGAAAAACCTGACGTTGTTCAGG
TGATGCCGATTGAACACGCTGGCGGGCGTTATCACGTTGCTGTTGATTCAGTGGGCGCTGCTGTACTTTT
TCCTTAAACACCTGGCGCTGCTCTGGTGATGCGGACTGAATACGCTCACGCGCTGCGTCTCTTCGCTGCT
GGTTCTGCGGGTTAGTCTGCATTTTCTCGCGAACCGCCTGGCGCTGCTCAGGCGAGGCGGACTGAATGC
GCTCACGCGCTGCCTCTCTTCGCTGCTGGATCTTCGGGTTAGTCTGCATTCTCTCGCGAACTGCCTGGCG
CTGCTCAGGCGAGGCGGACTGATAACGCTGACGAGCGGCGTCCTTTTGTTGCTGGGTCAGTGGTTGGC
GACGGCTGAAGTCGTGGAAGTCGTCATAGCTCCCATAGTGTTCAGCTTCATTAAACCGCTGTGCCGCTGC
CTGACGTTGGGTACCTCGTGTAATGACTGGTGCGGCGTGTGTTCGTTGCTGAAACTGATTTGCTGCCGCC
TGACGCTGGCTGTCGCGCGTTGGGGCAGGTAATTGCGTGGCGCTCATTCCGCCGTTGACATCGGTTTGA
TGAAACCGCTTTGCCATATCCTGATCATGATAGGGCACACCATTACGGTAGTTTGGATTGTGCCGCCATG
CCATATTCTTATCAGTAAGATGCTCACCGGTGATACGGTTGAAATTGTTGACGTCGATATTGATGTTGTC
GCCGTTGTGTTGCCAGCCATTACCGTCACGATGACCGCCATCGTGGTGATGATAATCAT
```

```
TTATTTGGTGATATTGGTACCAATATCATGCAGCAAACGGTGCAACATTGCCGTGTCTCGTTGCTCTAAA
AGCCCCAGGCGTTGTTGTAACCAGTCGACCAGTTTTATGTCATCTGCCACTGCCAGAGTCGTCAGCAATG
TCATGGCTCGTTCGCGTAAAGCTTGCAGTTGATGTTGGTCTGCCGTTGCATCACTTTTCGCCGGTTGTTGT
ATTAATGTTGCTAATTGATAGCAATAGACCATCACCGCCTGCCCCAGATTGAGCGAAGGATAATCCGCCA
CCATCGGCACACCAGTAAGAACGTCAGCCAACGCTAACTCTTCGTTAGTCAACCCGGAATCTTCGCGACC
AAACACCAGCGCGGCATGGCTCATCCATGAAGATTTTCCTCTAACAGCGGCACCAGTTCAACTGGCGT
GGCGTAGTAATGATATTTCGCCCGACTGCGCGCAGTGGTGGCGACAGTGAAATCGACATCGTGTAACG
ATTCAGCCAATGTCGGGAAAACTTTAATATTATCAATAATATCACCAGATCCATGTGCGACCCAGCGGGT
GGCTGGCTCCAGGTGTGCCTGACTATCGACAATCCGCAGATCGCTAAACCCCATCGTTTTCATTGCCCGC
GCCGCTGCCCCAATATTTTCTGCTCTGGCGGGTGCGACCAGAATAATCGTTATACGCATATTGCCACTCTT
CTTGATCAAATAACCGCGAACCGGGTGATCACTGTCAACTTATTACGCGGTGCGAATTTACAAATTCTTA
ACGTAAGTCGCAGAAAAGCCCTTTACTTAGCTTAAAAAAGGCTAAACTATTTCCTGACTGTACTAACGG
TTGAGTTGTTAAAAAATGCTACATATCCTTCTGTTTACTTAGGATAATTTTATAAAAAATAAATCTCGACA
ATTGGATTCACCACGTTTATTAGTTGTATGATGCAACTAGTTGGATTATTAAAATAATGTGACGAAAGCT
AGCATTTAGATACGATGATTTCATCAAACTGTTAACGTGCTACAATTGAACTTGATATATGTCAACGAAG
CGTAGTTTTATTGGGTGTCCGGCCCCTCTTAGCCTGTTATGTTGCTGTTAAAATGGTTAGGATGACAGCC
GTTTTTGACACTGTCGGGTCCTGAGGGAAAGTACCCACGACCAAGCTAATGATGTTGTTGACGTTGATG
GAAAGTGCATCAAGAACGCAATTACGTACTTTAGTCATGTTACGCCGATCATGTTAATTTGCAGCATGCA
TCAGGCAGGTCAGGGACTTTTGTACTTCCTGTTTCGATTTAGTTGGCAATTTAGGTAGCAAACGAATTCA
TCGGCTTTACCACCGTCAAAAAAACGGCGCTTTTTAGCGCCGTTTTTATTTTTCAACCTTATTTCCAGATA
CGTAACTCATCGTCCGTTGTAACTTCTTTACTGGCTTTCATTTTCGGCAGTGAAAACGCATACCAGTCGAT
ATTACGGGTCACAAACATCATGCCGGCCAGCGCCACCACCAGCACACTGGTTCCCAACAACAGCGCGCT
ATCGGCAGAGTTGAGCAGTCCCCACATCACACCATCCAGCAACAACAGCGCGAGGGTAAACAACATGCT
GTTGCACCAACCTTTCAATACCGCTTGCAAATAAATACCGTTCATTATCGCCCCAATCAGACTGGCGATTA
TCCATGCCACGGTAAAACCGGTATGTTCAGAAAGCGCCAGCAAGAGCAAATAAAACATCACCAATGAAA
GCCCCACCAGCAAATATTGCATTGGGTGTAAACGTTGCGCGGTGAGCGTTTCAAAAACAAAGAACGCCA
TAAAAGTCAGTGCAATCAGCAGAATGGCGTACTTAGTCGCCCGGTCAGTTAATTGGTATTGATCGGCTG
GCGTCGTTACTGCGACGCTAAACGCCGGGAAGTTTTCCCAGCCGGTATCATTGCCTGAAGCAAAACGCT
CACCGAGATTATTAGCAAACCAGCTGCTTTGCCAGTGCGCCTGAAAACCTGACTCGCTAACTTCCCGTTT
GGCTGGTAGAAAATCACCTAAAAAACTGGGATGCGGCCAGTTGCTGGTTAAGGTCATTTCGCTATTACG
CCCGCCAGGCACCACAGAAAGATCGCCGGTACCGCTTAAATTCAGGGCCATATTCAGCTTCAGGTTCTG
CTTCCGCCAGTCCCCTTCAGGTAAAGGGATATGCACGCCCTGCCCGCCTTGCTCTAACCCGGTGCCGGGT
TCAATGGTCAGCGCCGTTCCGTTAACTTCAGGCGCTTTCACCACACCAATACCACGCGCATCCCCGACGC
TAATCACAATAAATGGCTTGCCTAAGGTGATATTTGGCGCGTTGAGTTCGCTAAGACGCGAAACATCGA
AATCGGCTTTTAACGTTAAATCACTGTGCCAGACCTGACCGGTATAAATCCCTATCTTGCGTTCTTCCACG
TTCTGATTGCCATCAACCATCAATGACTCAGGTAACCAAAAATGGATAAAACTTCGTTTCCGCTGCAGGG
TTTTAT
```

FIG. 42

```
AAGCCACAGCAGGATGCCCACTGCAACAAAGGTGATCACACCGGAAACGCGATGGAGAATGGACGCTA
TCGCCGTGATGGGGAACCGGATGGTCTGTAGGTCCAGATTAACAGGTCTTTGTTTTTTCACATTTCTTAT
CATGAATAACGCCCACATGCTGTTCTTATTATTCCCTGGGGACTACGGGCACAGAGGTTAACTTTCTGTT
ACCTGGAGACGTCGGGATTTCCTTCCTCCGGTCTGCTTGCGGGTCAGACAGCGTCCTTTCTATAACTGCG
CGTCATGCAAAACACTGCTTCCAGATGCGAAAACGACACGTTACAACGCTGGGTGGCTCGGGATTGCAG
GGTGTTCCGGAGACCTGGCGGCAGTATAGGCTGTTCACAAAATCATTACAATTAACCTACATATAGTTTG
TCGGGTTTTATCCTGAACAGTGATCCAGGTCACGATAACAACATTTATTTAATTTTTAATCATCTAATTTG
ACAATCATTCAACAAAGTTGTTACAAACATTACCAGGAAAAGCATATAATGCGTAAAAGTTATGAAGTC
GGTATTTCACCTAAGATTAACTTATGTAACAGTGTGGAAGTATTGACCAATTCATTCGGGACAGTTATTA
GTGGTAGACAAGTTTAATAATTCGGATTGCTAAGTACTTGATTCGCCATTTATTCGTCATCAATGGATCCT
TTACCTGCAAGCGCCCAGAGCTCTGTACCCAGGTTTTCCCCTCTTTCACAGAGCGGCGAGCCAAATAAAA
AACGGGTAAAGCCAGGTTGATGTGCGAAGGCAAATTTAAGTTCCGGCAGTCTTACGCAATAAGGCGCT
AAGGAGACCTTAAATGGCTGATACAAAAGCAAAACTCACCCTCAACGGGGATACAGCTGTTGAACTGGA
TGTGCTGAAAGGCACGCTGGGTCAAGATGTTATTGATATCCGTACTCTCGGTTCAAAAGGTGTGTTCACC
TTTGACCCAGGCTTCACTTCAACCGCATCCTGCGAATCTAAAATTACTTTTATTGATGGTGATGAAGGTAT
TTTGCTGCACCGCGGTTTCCCGATCGATCAGCTGGCGACCGATTCTAACTACCTGGAAGTTTGTTACATC
CTGCTGAATGGTGAAAAACCGACTCAGGAACAGTATGACGAATTTAAAACTACGGTGACCCGTCATACC
ATGATCCACGAGCAGATTACCCGTCTGTTCCATGCTTTCCGTCGCGACTCGCATCCAATGGCAGTCATGT
GTGGTATTACCGGCGCGCTGGCGGCGTTCTATCACGACTCGCTGGATGTTAACAATCCTCGTCACCGTGA
AATTGCCGCGTTCCTCCTGCTGTCGAAAATGCCGACCATGGCCGCGATGTGTTACAAGTATTCCATTGGT
CAGCCATTTGTTTACCCGCGCAACGATCTCTCCTACGCCGGTAACTTCCTGAATATGATGTTCTCCACGCC
GTGCGAACCGTATGAAGTTAATCCGATTCTGGAACGTGCTATGGACCGTATTCTGATCCTGCACGCTGAC
CATGAACAGAACGCCTCTACCTCCACCGTGCGTACCGCTGGCTCTTCGGGTGCGAACCCGTTTGCCTGTA
TCGCAGCAGGTATTGCTTCACTGTGGGACCTGCGCACGGCGGTGCTAACGAAGCGGCGCTGAAAATG
CTGGAAGAAATCAGCTCCGTTAAACACATTCCGGAATTTGTTCGTCGTGCGAAAGACAAAAATGATTCTT
TCCGCCTGATGGGCTTCGGTCACCGCGTGTACAAAAATTACGACCCGCGCGCCACCGTAATGCGTGAAA
CCTGCCATGAAGTGCTGAAAGAGCTGGGCACGAAGGATGACCTGCTGGAAGTGGCTATGGAGCTGGAA
AACATCGCGCTGAACGACCCGTACTTTATCGAGAAGAAACTGTACCCGAACGTCGATTTCTACTCTGGTA
TCATCCTGAAAGCGATGGGTATTCCGTCTTCCATGTTCACCGTCATTTTCGCAATGGCACGTACCGTTGG
CTGGATCGCCCACTGGAGCGAAATGCACAGTGACGGTATGAAGATTGCCCGTCCGCGTCAGCTGTATAC
AGGATATGAAAACGCGACTTTAAAAGCGATATCAAGCGTTAATGGTTGATTGCTAAGTTGTAAATATTT
TAACCCGCCGTTCATATGGCGGGTTGATTTTTATATGCCTAAACACAAAAAATTGTAAAATAAAATCCA
TTAACAGACCTATATAGATATTTAAAAGAATAGAACAGCTCAAATTATCAGCAACCCAATACTTTCAATT
AAAAACTTCATGGTAGTCGCATTTATAACCCTATGAAAATGACGTCTATCTATACCCCCTATATTTTATTC
ATCATACAACAAATTCATGATACCAATAATTTAGTTTTGCATTTAATAAAACTAACAATATTTTTAAGCAA
AACTAAAAACTAGCAATAATCAAATACGATATTCTGGCGTAGCTATACCCCTATTCTATATCCTTAAAGGA
CTCTGTTATGTTTAAAGGACAAAAAACATTGGCCGCACTGGCCGTATCTCTGCTGTTCACTGCACCTGTTT
ATGCTGCTGATGAAGGTTCTGGCGAAATTCACTTTAAGGGGGAGGTTATTGAAGCACCTTGTGAAATTC
ATCCAGAAGATATTGATAAAAACATAGATCTTGGACAAGTCACGACAACCCATATAAACCGGGAGCATC
ATAGCAATAAAGTGGCCGTCGACATTCGCTTGATCAACTGTGATCTGCCTGCTTCTGACAACGGTAGCG
GAATGCCGGTATCCAAAGTTGGCGTAACCTTCGATAGCACGGCTAAGACAACTGGTGCTACGCCTTTGT
TGAGCAACACCAGTGCAGGCGAAGCAACTGGGGTCGGTGTACGACTGATGGACAAAAATGACGGTAAC
ATCGTATTAGGTTCAGCCGCGCCAGATCTTGACCTGGATGCAAGCTCATCAGAACAGACGCTGAACTTTT
TCGCCTGGAT
```

FIG. 43

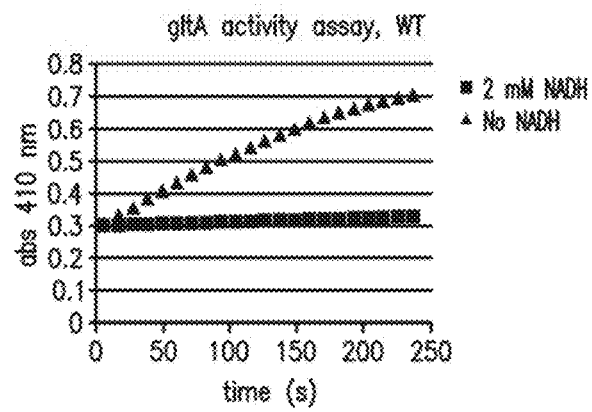
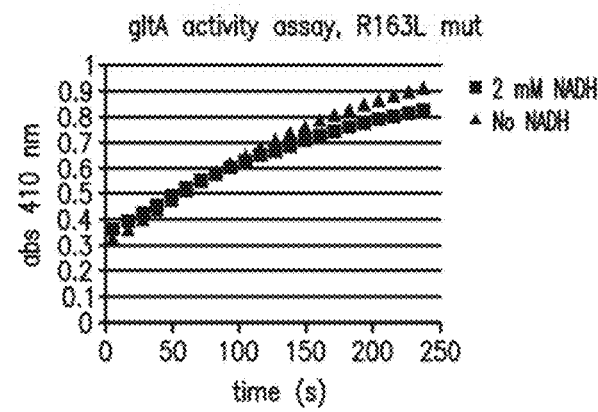
FIG. 44A  FIG. 44B
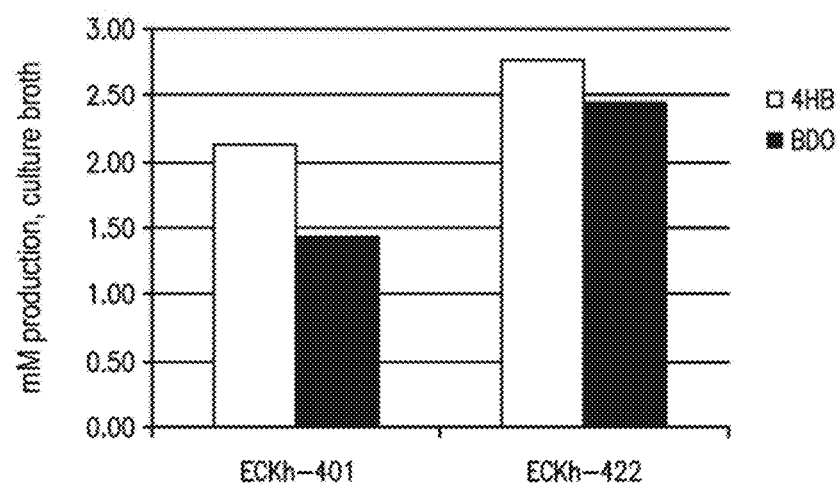
FIG. 45

```
CGCGATGTCGACGTCACGAAACTGAAAAAACCGCTCTACATTCTGGCGACTGCTGATGAAGAAACCAGT
ATGGCCGGAGCGCGTTATTTTGCCGAAACTACCGCCCTGCGCCCGGATTGCGCCATCATTGGCGAACCG
ACGTCACTACAACCGGTACGCGCACATAAAGGTCATATCTCTAACGCCATCCGTATTCAGGGCCAGTCG
GGGCACTCCAGCGATCCAGCACGCGGAGTTAACGCTATCGAACTAATGCACGACGCCATCGGGCATATT
TTGCAATTGCGCGATAACCTGAAAGAACGTTATCACTACGAAGCGTTTACCGTGCCATACCCTACGCTCA
ACCTCGGGCATATTCACGGTGGCGACGCTTCTAACCGTATTTGCGCTTGCTGTGAGTTGCATATGGATAT
TCGTCCGCTGCCTGGCATGACACTCAATGAACTTAATGGTTTGCTCAACGATGCATTGGCTCCGGTGAGC
GAACGCTGGCCGGGTCGTCTGACGGTCGACGAGCTGCATCCGCCGATCCCTGGCTATGAATGCCCACCG
AATCATCAACTGGTTGAAGTGGTTGAGAAATTGCTCGGAGCAAAAACCGAAGTGGTGAACTACTGTACC
GAAGCGCCGTTTATTCAAACGTTATGCCCGACGCTGGTGTTGGGGCCTGGCTCAATTAATCAGGCTCATC
AACCTGATGAATATCTGGAAACACGGTTTATCAAGCCCACCCGCGAACTGATAACCCAGGTAATTCACCA
TTTTTGCTGGCATTAAAACGTAGGCCGGATAAGGCGCTCGCGCCGCATCCGGCGCTGTTGCCAAACTCC
AGTGCCGCAATAATGTCGGATGCGATGCTTGCGCATCTTATCCGACCTACAGTGACTCAAACGATGCCCA
ACCGTAGGCCGGATAAGGCGCTCGCGCCGCATCCGGCACTGTTGCCAAACTCCAGTGCCGCAATAATGT
CGGATGCGATACTTGCGCATCTTATCCGACCGACAGTGACTCAAACGATGCCCAACTGTAGGCCGGATA
AGGCGCTCGCGCCGCATCCGGCACTGTTGCCAAACTCCAGTGCCGCAATAATGTCGGATGCGATACTTG
CGCATCTTATCCGACCTACACCTTTGGTGTTACTTGGGGCGATTTTTTAACATTTCCATAAGTTACGCTTAT
TTAAAGCGTCGTGAATTTAATGACGTAAATTCCTGCTATTTATTCGTTTGCTGAAGCGATTTCGCAGCATT
TGACGTCACCGCTTTTACGTGGCTTTATAAAAGACGACGAAAAGCAAAGCCCGAGCATATTCGCGCCAA
TGCTAGCAAGAGGAGAAGTCGACATGACAGACTTAAATAAAGTGGTAAAAGAACTTGAAGCTCTTGGT
ATTTATGACGTAAAAGAAGTTGTTTACAATCCAAGCTACGAGCAATTGTTCGAAGAAGAAACTAAACCA
GGTTTAGAAGGCTTTGAAAAAGGTACTTTAACTACGACTGGTGCAGTGGCAGTAGATACAGGTATCTTC
ACAGGTCGTTCTCCAAAAGATAAATATATCGTGTTAGATGAAAAAACCAAAGATACTGTTTGGTGGACA
TCTGAAACAGCAAAAAACGACAACAAGCCAATGAACCAAGCTACATGGCAAAGCTTAAAAGACTTGGTA
ACCAACCAGCTTTCTCGTAAACGCTTATTTGTAGTTGATGGTTTCTGTGGTGCGAGCGAACACGACCGTA
TTGCAGTACGTATTGTCACTGAAGTAGCGTGGCAAGCACATTTTGTAAAAAATATGTTTATTCGCCCAAC
TGAAGAACAACTCAAAAATTTTGAACCAGATTTCGTTGTAATGAATGGTTCTAAAGTAACCAATCCAAAC
TGGAAAGAACAAGGTTTAAATTCAGAAAACTTTGTTGCTTTCAACTTGACTGAACGCATTCAATTAATCG
GTGGTACTTGGTACGGCGGTGAAATGAAAAAGGTATGTTCTCAATCATGAACTACTTCCTACCACTTAA
AGGTGTTGGTGCAATGCACTGCTCAGCTAACGTTGGTAAAGATGGCGATGTAGCAATCTTCTTCGGCTT
ATCTGGCACAGGTAAAACAACCCTTTCAACGGATCCAAAACGTGAATTAATCGGTGACGATGAACACGG
CTGGGATGATGTGGGTATCTTTAACTTTGAAGGTGGTTGCTATGCGAAAACCATTCACCTTTCAGAAGAA
AATGAACCAGATATTTACCGCGCTATCCGTCGCGACGCATTATTAGAAACGTGGTTGTTCGTGCAGATG
GTTCTGTTGATTTCGATGATGGTTCAAAAACAGAAAATACTCGCGTGTCTTACCCAATTTATCACATTGAT
AACATTGTAAAACCAGTTTCTCGTGCAGGTCACGCAACTAAAGTGATTTTCTTAACTGCAGATGCATTTG
GCGTATTACCACCAGTATCTAAATTGACACCAGAACAAACTAAATACTACTTCTTATCTGGTTTCACAGCA
AAATTAGCAGGTACTGAACGTGGTATTACTGAACCAACTCCAACTTTCTCAGCATGTTTCGGTGCTGCGT
TCTTAACCCTTCACCCAACTCAATATGCAGAAGTGTTAGTAAAACGTATGCAAGCAGTGGGTGCTGAAG
CTTACTTAGTAAATACTGGTTGGAATGGCACAGGCAAACGTATCTCAATCAAAGATACTCGCGGAATCAT
TGATGCAATCTTAGATGGCTCAATTGAAAAAGCTGAAATGGGCGAATTACCAATCTTTAACTTAGCCATT
CCTAAAGCATTACCAGGTGTAGATTCTGCAATCTTAGATCCTCGCGATACTTACGCAGATAAAGCACAAT
GGCAATCAAAAGCTGAAGACTTAGCAGGTCGTTTTGTGAAAAACTTTGTTAAATATGCAACTAACGAAG
AAGGCAAAGCTTTAATTGCAGCTGGTCCTAAAGCTTAATCTAGAAAGCTTCCTAGAGGCATCAAATAAA
ACGAAAGGCTCAGTCGAAAGACTGGGCCTTTCGTTTTATCTGTTGTTTGTCGGTGAACGCTCTCCTGAGT
```

FIG. 48

```
AGGACGAATTCACTTCTGTTCTAACACCCTCGTTTTCAATATATTTCTGTCTGCATTTTATTCAAATTCTGA
ATATACCTTCAGATATCCTTAAGGAATTGTCGTTACATTCGGCGATATTTTTTCAAGACAGGTTCTTACTA
TGCATTCCACAGAAGTCCAGGCTAAACCTCTTTTTAGCTGGAAAGCCCTGGGTTGGGCACTGCTCTACTT
TTGGTTTTTCTCTACTCTGCTACAGGCCATTATTTACATCAGTGGTTATAGTGGCACTAACGGCATTCGCG
ACTCGCTGTTATTCAGTTCGCTGTGGTTGATCCCGGTATTCCTCTTTCCGAAGCGGATTAAAATTATTGCC
GCAGTAATCGGCGTGGTGCTATGGGCGGCCTCTCTGGCGGCGCTGTGCTACTACGTCATCTACGGTCAG
GAGTTCTCGCAGAGCGTTCTGTTTGTGATGTTCGAAACCAACACCAACGAAGCCAGCGAGTATTTAAGC
CAGTATTTCAGCCTGAAAATTGTGCTTATCGCGCTGGCCTATACGGCGGTGGCAGTTCTGCTGTGGACAC
GCCTGCGCCCGGTCTATATTCCAAAGCCGTGGCGTTATGTTGTCTCTTTTGCCCTGCTTTATGGCTTGATT
CTGCATCCGATCGCCATGAATACGTTTATCAAAAACAAGCCGTTTGAGAAAACGTTGGATAACCTGGCCT
CGCGTATGGAGCCTGCCGCACCGTGGCAATTCCTGACCGGCTATTATCAGTATCGTCAGCAACTAAACTC
GCTAACAAAGTTACTGAATGAAAATAATGCCTTGCCGCCACTGGCTAATTTCAAAGATGAATCGGGTAA
CGAACCGCGCACTTTAGTGCTGGTGATTGGCGAGTCGACCCAGCGCGGACGCATGAGTCTGTACGGTTA
TCCGCGTGAAACCACGCCGGAGCTGGATGCGCTGCATAAAACCGATCCGAATCTGACCGTGTTTAATAA
CGTAGTTACGTCTCGTCCGTACACCATTGAAATCCTGCAACAGGCGCTGACCTTTGCCAATGAAAAGAAC
CCGGATCTGTATCTGACGCAGCCGTCGCTGATGAACATGATGAAACAGGCGGGTTATAAAACCTTC
```

FIG. 48 (cont'd)

```
AATAGGCGTATCACGAGGCCCTTTCGTCTTCACCTCGAGAATTGTGAGCGGATAACAATTGACATTGTGA
GCGGATAACAAGATACTGAGCACATCAGCAGGACGCACTGACCGAATTCAATTAAGCTAGCAAGAGGA
GAAGTCGAGATGAACTTACATGAATATCAGGCAAAACAACTTTTTGCCCGCTATGGCTTACCAGCACCG
GTGGGTTATGCCTGTACTACTCCGCGCAAGCAGAAGAAGCCGCTTCAAAAATCGGTGCCGGTCCGTGG
GTAGTGAAATGTCAGGTTCACGCTGGTGGCCGCGGTAAAGCGGGCGGTGTGAAAGTTGTAAACAGCAA
AGAAGACATCCGTGCTTTTGCAGAAAACTGGCTGGGCAAGCGTCTGGTAACGTATCAAACAGATGCCAA
TGGCCAACCGGTTAACCAGATTCTGGTTGAAGCAGCGACCGATATCGCTAAAGAGCTGTATCTCGGTGC
CGTTGTTGACCGTAGTTCCCGTCGTGTGGTCTTTATGGCCTCCACCGAAGGCGGCGTGGAAATCGAAAA
AGTGGCGGAAGAAACTCCGCACCTGATCCATAAAGTTGCGCTTGATCCGCTGACTGGCCCGATGCCGTA
TCAGGGACGCGAGCTGGCGTTCAAACTGGGTCTGGAAGGTAAACTGGTTCAGCAGTTCACCAAAATCTT
CATGGGCCTGGCGACCATTTTCCTGGAGCGCGACCTGGCGTTGATCGAAATCAACCCGCTGGTCATCAC
CAAACAGGGCGATCTGATTTGCCTCGACGGCAAACTGGGCGCTGACGGCAACGCACTGTTCCGCCAGCC
TGATCTGCGCGAAATGCGTGACCAGTCGCAGGAAGATCCGCGTGAAGCACAGGCTGCACAGTGGGAAC
TGAACTACGTTGCGCTGGACGGTAACATCGGTTGTATGGTTAACGGCGCAGGTCTGGCGATGGGTACG
ATGGACATCGTTAAACTGCACGGCGGCGAACCGGCTAACTTCCTTGACGTTGGCGGCGGCGCAACCAAA
GAACGTGTAACCGAAGCGTTCAAAATCATCCTCTCTGACGACAAAGTGAAAGCCGTTCTGGTTAACATCT
TCGGCGGTATCGTTCGTTGCGACCTGATCGCTGACGGTATCATCGGCGCGGTAGCAGAAGTGGGTGTTA
ACGTACCGGTCGTGGTACGTCTGGAAGGTAACAACGCCGAACTCGGCGCGAAGAAACTGGCTGACAGC
GGCCTGAATATTATTGCAGCAAAAGGTCTGACGGATGCAGCTCAGCAGGTTGTTGCCGCAGTGGAGGG
GAAATAATGTCCATTTTAATCGATAAAAACACCAAGGTTATCTGCCAGGGCTTTACCGGTAGCCAGGGG
ACTTTCCACTCAGAACAGGCCATTGCATACGGCACTAAAATGGTTGGCGGCGTAACCCCAGGTAAAGGC
GGCACCACCCACCTCGGCCTGCCGGTGTTCAACACCGTGCGTGAAGCCGTTGCTGCCACTGGCGCTACC
GCTTCTGTTATCTACGTACCAGCACCGTTCTGCAAAGACTCCATTCTGGAAGCCATCGACGCAGGCATCA
AACTGATTATCACCATCACTGAAGGCATCCCGACGCTGGATATGCTGACCGTGAAAGTGAAGCTGGATG
AAGCAGGCGTTCGTATGATCGGCCCGAACTGCCCAGGCGTTATCACTCCGGGTGAATGCAAAATCGGTA
TCCAGCCTGGTCACATTCACAAACCGGGTAAAGTGGGTATCGTTTCCCGTTCCGGTACACTGACCTATGA
AGCGGTTAAACAGACCACGGATTACGGTTTCGGTCAGTCGACCTGTGTCGGTATCGGCGGTGACCCGAT
CCCGGGCTCTAACTTTATCGACATTCTCGAAATGTTCGAAAAAGATCCGCAGACCGAAGCGATCGTGAT
GATCGGTGAGATCGGCGGTAGCGCTGAAGAAGAAGCAGCTGCGTACATCAAAGAGCACGTTACCAAGC
CAGTTGTGGGTTACATCGCTGGTGTGACTGCGCCGAAAGGCAAACGTATGGGCCACGCGGGTGCCATC
ATTGCCGGTGGGAAAGGGACTGCGGATGAGAAATTCGCTGCTCTGGAAGCCGCAGGCGTGAAAACCGT
TCGCAGCCTGGCGGATATCGGTGAAGCACTGAAAACTGTTCTGAAATAATCTAGCAAGAGGAGAAGTC
GACATGGAAATCAAAGAAATGGTGAGCCTTGCACGCAAGGCTCAGAAGGAGTATCAAGCTACCCATAA
CCAAGAAGCAGTTGACAACATTTGCCGAGCTGCAGCAAAAGTTATTTATGAAAATGCAGCTATTCTGGC
TCGCGAAGCAGTAGACGAAACCGGCATGGGCGTTTACGAACACAAAGTGGCCAAGAATCAAGGCAAAT
CCAAAGGTGTTTGGTACAACCTCCACAATAAAAAATCGATTGGTATCCTCAATATAGACGAGCGTACCG
GTATGATCGAGATTGCAAAGCCTATCGGAGTTGTAGGAGCCGTAACGCCGACGACCAACCCGATCGTTA
CTCCGATGAGCAATATCATCTTTGCTCTTAAGACCTGCAATGCCATCATTATTGCCCCCCACCCCAGATCC
AAAAAATGCTCTGCACACGCAGTTCGTCTGATCAAAGAAGCTATCGCTCCGTTCAACGTACCGGAAGGT
ATGGTTCAGATCATCGAAGAACCCAGCATCGAGAAGACGCAGGAACTCATGGGCGCCGTAGACGTAGT
AGTTGCTACGGGTGGTATGGGCATGGTGAAGTCTGCATATTCTTCAGGAAAGCCTTCTTTCGGTGTTGG
AGCCGGTAACGTTCAGGTGATCGTGGATAGCAACATCGATTTCGAAGCTGCTGCAGAAAAAATCATCAC
```

FIG. 52

```
CGGTCGTGCTTTCGACAACGGTATCATCTGCTCAGGCGAACAGAGCATCATCTACAACGAGGCTGACAA
GGAAGCAGTTTTCACAGCATTCCGCAACCACGGTGCATATTTCTGTGACGAAGCCGAAGGAGATCGGGC
TCGTGCAGCTATCTTCGAAAATGGAGCCATCGCGAAAGATGTAGTAGGTCAGAGCGTTGCCTTCATTGC
CAAGAAAGCAAACATCAATATCCCCGAGGGTACCCGTATTCTCGTTGTTGAAGCTCGCGGCGTAGGAGC
AGAAGACGTTATCTGTAAGGAAAAGATGTGTCCCGTAATGTGCGCCCTCAGCTACAAGCACTTCGAAGA
AGGTGTAGAAATCGCACGTACGAACCTCGCCAACGAAGGTAACGGCCACACCTGTGCTATCCACTCCAA
CAATCAGGCACACATCATCCTCGCAGGATCAGAGCTGACGGTATCTCGTATCGTAGTGAATGCTCCGAG
TGCCACTACAGCAGGCGGTCACATCCAAAACGGTCTTGCCGTAACCAATACGCTCGGATGCGGATCATG
GGGTAATAACTCTATCTCCGAGAACTTCACTTACAAGCACCTCCTCAACATTTCACGCATCGCACCGTTGA
ATTCAAGCATTCACATCCCCGATGACAAAGAAATCTGGGAACTCTAATCTAGCAAGAGGAGAAGTCGAC
ATGCAACTTTTCAAACTCAAGAGTGTAACACATCACTTTGACACTTTTGCAGAATTTGCCAAGGAATTCTG
TCTTGGAGAACGCGACTTGGTAATTACCAACGAGTTCATCTATGAACCGTATATGAAGGCATGCCAGCTC
CCCTGCCATTTTGTTATGCAGGAGAAATATGGGCAAGGCGAGCCTTCTGACGAAATGATGAATAACATC
TTGGCAGACATCCGTAATATCCAGTTCGACCGCGTAATCGGTATCGGAGGAGGTACGGTTATTGACATC
TCTAAACTTTTCGTTCTGAAAGGATTAAATGATGTACTCGATGCATTCGACCGCAAAATACCTCTTATCAA
AGAGAAAGAACTGATCATTGTGCCCACAACATGCGGAACGGGTAGCGAGGTGACGAACATTTCTATCG
CAGAAATCAAAAGCCGTCACACCAAAATGGGATTGGCTGACGATGCCATTGTTGCAGACCATGCCATCA
TCATACCTGAACTTCTGAAGAGCTTGCCTTTCCACTTCTACGCATGCAGTGCAATCGATGCTCTTATCCAT
GCCATCGAGTCATACGTATCTCCTAAAGCCAGTCCATATTCTCGTCTGTTCAGTGAGGCGGCTTGGGACA
TTATCCTGGAAGTATTCAAGAAAATCGCCGAACACGGCCCTGAATACCGCTTCGAAAAGCTGGGAGAAA
TGATCATGGCCAGCAACTATGCCGGTATAGCCTTCGGAAATGCAGGAGTAGGAGCCGTCCACGCACTAT
CCTACCCGTTGGGAGGCAACTATCACGTGCCGCATGGAGAAGCAAACTATCAGTTCTTCACAGAGGTAT
TCAAAGTATACCAAAAGAAGAATCCTTTCGGCTATATAGTCGAACTCAACTGGAAGCTCTCCAAGATACT
GAACTGCCAGCCCGAATACGTATATCCGAAGCTGGATGAACTTCTCGGATGCCTTCTTACCAAGAAACCT
TTGCACGAATACGGCATGAAGGACGAAGAGGTAAGAGGCTTTGCGGAATCAGTGCTTAAGACACAGCA
AAGATTGCTCGCCAACAACTACGTAGAGCTTACTGTAGATGAGATCGAAGGTATCTACAGAAGACTCTA
CTAATCTAGAAAGCTTCCTAGAGGCATCAAATAAAACGAAAGGCTCAGTCGAAAGACTGGGCCTTTCGT
TTTATCTGTTGTTTGTCGGTGAACGCTCTCCTGAGTAGGACAAATCCGCCGCCCTAGACCTAGGCGTTCG
GCTGCGACACGTCTTGAGCGATTGTGTAGGCTGGAGCTGCTTCGAAGTTCCTATACTTTCTAGAGAATAG
GAACTTCGGAATAGGAACTAAGGAGGATATTCATATGGACCATGGCTAATTCCCAT
```

FIG. 52 (cont'd)

```
TCGAGAAATTTATCAAAAAGAGTGTTGACTTGTGAGCGGATAACAATGATACTTAGATTCAATTGTGAG
CGGATAACAATTTCACACAGAATTCAATTAAGCTAGCAAGAGGAGAAGTCGACATGGCCAACATAAGTT
CACCATTCGGGCAAAACGAATGGCTGGTTGAAGAGATGTACCGCAAGTTCCGCGACGACCCCTCCTCGG
TCGATCCCAGCTGGCACGAGTTCCTGGTTGACTACAGCCCCGAACCCACCTCCCAACCAGCTGCCGAACC
AACCCGGGTTACCTCGCCACTCGTTGCCGAGCGGGCCGCTGCGGCCGCCCCGCAGGCACCCCCAAGCC
GGCCGACACCGCGGCCGCGGGCAACGGCGTGGTCGCCGCACTGGCCGCCAAAACTGCCGTTCCCCGC
CAGCCGAAGGTGACGAGGTAGCGGTGCTGCGCGGCGCCGCCGCGGCCGTCGTCAAGAACATGTCCGC
GTCGTTGGAGGTGCCGACGGCGACCAGCGTCCGGGCGGTCCCGGCCAAGCTACTGATCGACAACCGGA
TCGTCATCAACAACCAGTTGAAGCGGACCCGCGGCGGCAAGATCTCGTTCACGCATTTGCTGGGCTACG
CCCTGGTGCAGGCGGTGAAGAAATTCCCGAACATGAACCGGCACTACACCGAAGTCGACGGCAAGCCC
ACCGCGGTCACGCCGGCGCACACCAATCTCGGCCTGGCGATCGACCTGCAAGGCAAGGACGGGAAGCG
TTCCCTGGTGGTGGCCGGCATCAAGCGGTGCGAGACCATGCGATTCGCGCAGTTCGTCACGGCCTACGA
AGACATCGTACGCCGGGCCCGCGACGGCAAGCTGACCACTGAAGACTTTGCCGGCGTGACGATTTCGCT
GACCAATCCCGGAACCATCGGCACCGTGCATTCGGTGCCGCGGCTGATGCCCGGCCAGGGCGCCATCAT
CGGCGTGGGCGCCATGGAATACCCCGCCGAGTTTCAAGGCGCCAGCGAGGAACGCATCGCCGAGCTGG
GCATCGGCAAATTGATCACTTTGACCTCCACCTACGACCACCGCATCATCCAGGGCGCGGAATCGGGCG
ACTTCCTGCGCACCATCCACGAGTTGCTGCTCTCGGATGGCTTCTGGGACGAGGTCTTCCGCGAACTGAG
CATCCCATATCTGCCGGTGCGCTGGAGCACCGACAACCCCGACTCGATCGTCGACAAGAACGCTCGCGT
CATGAACTTGATCGCGGCCTACCGCAACCGCGGCCATCTGATGGCCGATACCGACCCGCTGCGGTTGGA
CAAAGCTCGGTTCCGCAGTCACCCCGACCTCGAAGTGCTGACCCACGGCCTGACGCTGTGGGATCTCGA
TCGGGTGTTCAAGGTCGACGGCTTTGCCGGTGCGCAGTACAAGAAACTGCGCGACGTGCTGGGCTTGCT
GCGCGATGCCTACTGCCGCCACATCGGCGTGGAGTACGCCCATATCCTCGACCCCGAACAAAAGGAGTG
GCTCGAACAACGGGTCGAGACCAAGCACGTCAAACCCACTGTGGCCCAACAGAAATACATCCTCAGCAA
GCTCAACGCCGCCGAGGCCTTTGAAACGTTCCTACAGACCAAGTACGTCGGCCAGAAGCGGTTCTCGCT
GGAAGGCGCCGAAAGCGTGATCCCGATGATGGACGCGGCGATCGACCAGTGCGCTGAGCACGGCCTC
GACGAGGTGGTCATCGGGATGCCGCACCGGGGCCGGCTCAACGTGCTGGCCAACATCGTCGGCAAGCC
GTACTCGCAGATCTTCACCGAGTTCGAGGGCAACCTGAATCCGTCGCAGGCGCACGGCTCCGGTGACGT
CAAGTACCACCTGGGCGCCACCGGGCTGTACCTGCAGATGTTCGGCGACAACGACATTCAGGTGTCGCT
GACCGCCAACCCGTCGCATCTGGAGGCCGTCGACCCGGTGCTGGAGGGATTGGTGCGGGCCAAGCAGG
ATCTGCTCGACCACGGAAGCATCGACAGCGACGGCCAACGGGCGTTCTCGGTGGTGCCGCTGATGTTGC
ATGGCGATGCCGCGTTCGCCGGTCAGGGTGTGGTCGCCGAGACGCTGAACCTGGCGAATCTGCCGGGC
TACCGCGTCGGCGGCACCATCCACATCATCGTCAACAACCAGATCGGCTTCACCACCGCGCCCGAGTATT
CCAGGTCCAGCGAGTACTGCACCGACGTCGCAAAGATGATCGGGGCACCGATCTTTCACGTCAACGGCG
ACGACCCGGAGGCGTGTGTCTGGGTGGCGCGGTTGGCGGTGGACTTCCGACAACGGTTCAAGAAGGAC
GTCGTCATCGACATGCTGTGCTACCGCCGCCGCGGGCACAACGAGGGTGACGACCCGTCGATGACCAA
CCCCTACATGTACGACGTCGTCGACACCAAGCGCGGGCCCGCAAAAGCTACACCGAAGCCCTGATCGG
ACGTGGCGACATCTCGATGAAGGAGGCCGAGGACGCGCTGCGCGACTACCAGGGCCAGCTGGAACGG
GTGTTCAACGAAGTGCGCGAGCTGGAGAAGCACGGTGTGCAGCCGAGCGAGTCGGTCGAGTCCGACC
AGATGATTCCCGCGGGGCTGGCCACTGCGGTGGACAAGTCGCTGCTGGCCCGGATCGGCGATGCGTTC
CTCGCCTTGCCGAACGGCTTCACCGCGCACCCGCGAGTCCAACCGGTGCTGGAGAAGCGCCGGGAGAT
GGCCTATGAAGGCAAGATCGACTGGGCCTTTGGCGAGCTGCTGGCGCTGGGCTCGCTGGTGGCCGAAG
GCAAGCTGGTGCGCTTGTCGGGGCAGGACAGCCGCCGCGGCACCTTCTCCCAGCGGCATTCGGTTCTCA
TCGACCGCCACACTGGCGAGGAGTTCACACCACTGCAGCTGCTGGCGACCAACTCCGACGGCAGCCCGA
CCGGCGGAAAGTTCCTGGTCTACGACTCGCCACTGTCGGAGTACGCCGCCGTCGGCTTCGAGTACGGCT
ACACTGTGGGCAATCCGGACGCCGTGGTGCTCTGGGAGGCGCAGTTCGGCGACTTCGTCAACGGCGCA
```

FIG. 53

```
CAGTCGATCATCGACGAGTTCATCAGCTCCGGTGAGGCCAAGTGGGGCCAATTGTCCAACGTCGTGCTG
CTGTTACCGCACGGGCACGAGGGGCAGGGACCCGACCACACTTCTGCCCGGATCGAACGCTTCTTGCAG
TTGTGGGCGGAAGGTTCGATGACCATCGCGATGCCGTCGACTCCGTCGAACTACTTCCACCTGCTACGCC
GGCATGCCCTGGACGGCATCCAACGCCCGCTGATCGTGTTCACGCCCAAGTCGATGTTGCGTCACAAGG
CCGCCGTCAGCGAAATCAAGGACTTCACCGAGATCAAGTTCCGCTCAGTGCTGGAGGAACCCACCTATG
AGGACGGCATCGGAGACCGCAACAAGGTCAGCCGGATCCTGCTGACCAGTGGCAAGCTGTATTACGAG
CTGGCCGCCCGCAAGGCCAAGGACAACCGCAATGACCTCGCGATCGTGCGGCTTGAACAGCTCGCCCC
GCTGCCCAGGCGTCGACTGCGTGAAACGCTGGACCGCTACGAGAACGTCAAGGAGTTCTTCTGGGTCCA
AGAGGAACCGGCCAACCAGGGTGCGTGGCCGCGATTCGGGCTCGAACTACCCGAGCTGCTGCCTGACA
AGTTGGCCGGGATCAAGCGAATCTCGCGCCGGGCGATGTCAGCCCCGTCGTCAGGCTCGTCGAAGGTG
CACGCCGTCGAACAGCAGGAGATCCTCGACGAGGCGTTCGGCTAATCTAGCAAGAGGAGAAGTCGACA
TGAAGTTATTAAAATTGGCACCTGATGTTTATAAATTTGATACTGCAGAGGAGTTTATGAAATACTTTAA
GGTTGGAAAAGGTGACTTTATACTTACTAATGAATTTTTATATAAACCTTTCCTTGAGAAATTCAATGATG
GTGCAGATGCTGTATTTCAGGAGAAATATGGACTCGGTGAACCTTCTGATGAAATGATAAACAATATAA
TTAAGGATATTGGAGATAAACAATATAATAGAATTATTGCTGTAGGGGGAGGATCTGTAATAGATATAG
CCAAAATCCTCAGTCTTAAGTATACTGATGATTCATTGGATTTGTTTGAGGGAAAAGTACCTCTTGTAAA
AAACAAAGAATTAATTATAGTTCCAACTACATGTGGAACAGGTTCAGAAGTTACAAATGTATCAGTTGCA
GAATTAAAGAGAAGACATACTAAAAAAGGAATTGCTTCAGACGAATTATATGCAACTTATGCAGTACTT
GTACCAGAATTTATAAAAGGACTTCCATATAAGTTTTTTGTAACCAGCTCCGTAGATGCCTTAATACATGC
AACAGAAGCTTATGTATCTCCAAATGCAAATCCTTATACTGATATGTTTAGTGTAAAAGCTATGGAGTTA
ATTTTAAATGGATACATGCAAATGGTAGAGAAAGGAAATGATTACAGAGTTGAAATAATTGAGGATTTT
GTTATAGGCAGCAATTATGCAGGTATAGCTTTTGGAAATGCAGGAGTGGGAGCGGTTCACGCACTCTCA
TATCCAATAGGCGGAAATTATCATGTGCCTCATGGAGAAGCAAATTATCTGTTTTTTACAGAAATATTTA
AAACTTATTATGAGAAAAATCCAAATGGCAAGATTAAAGATGTAAATAAACTATTAGCAGGCATACTAA
AATGTGATGAAAGTGAAGCTTATGACAGTTTATCACAACTTTTAGATAAATTATTGTCAAGAAAACCATT
AAGAGAATATGGAATGAAAGAGGAAGAAATTGAAACTTTTGCTGATTCAGTAATAGAAGGACAGCAGA
GACTGTTGGTAAACAATTATGAACCTTTTTCAAGAGAAGACATAGTAAACACATATAAAAAGTTATATTA
ATCTAGAAAGCTTCCTAGAGGCATCAAATAAAACGAAAGGCTCAGTCGAAAGACTGGGCCTTTCGTTTT
ATCTGTTGTTTGTCGGTGAACGCTCTCCTGAGTAGGACAAATCCGCCGCCCTAGACCTA
```

```
4601  TTGCTTGGG ATTGTGCTGC TTTGAAGGCC GACTGGAGA CTCTTGGAC ACCAGGCTA GTAGACGTT TTCTTGGAA TTGGTAAT TGTGCCGTG
      AACGAACCC TAACACGACG AAATTGCGG CTGACCTAT CAGGAACTGG TGGTTCCGAT GGTCTGTCA ANGAGCGTT AAAGCCGTA ACAAGGGAC
                                                cac8
```

```
4701  AGTTGCTAT TTGGCATTTT CTTCTTGAGT AAAAAGCGG AGCAAATGT TATGAAAGG CCTGTACCTT CACCAATGTA CAGTAAACT TTTTGGGTT
      TCAAGGATA AAGATAAAA GAAGAACTCA TTTTTTGGCC TCGTTTACA ATAGTTTAC GGACAATGAA GTGGTATAGT CACATTTGA AAAAGGCAA
4801  GTGTGATA GCTGTATC GTCAAGGG AAATAATA TAGTAAATC CTTAGGCGTG CTAAATATCG GCGATATAA ACGCTCGTTT GGTGTCGTGG
      CACAGCTAT CGAGATAAG GGATGGCC TTTATTAT ATGATTTAC CAATGGGAC GATTATTAGG GGATAGCTT TGGGAGTAA GTACAAGCC
4901  TGAGTGGCT CAAATTACT TGAGTTGAC GGTGGCCTGA TTTCGGAC ATTGATTGCA TTCATTTGGAC TGTCCCGAT ATACGGTCC TGGAATGCA
      ATGTGAGGA GTTAAGATGA AGTCAGGGG CGACAGGACT AAGGTCGG TAACGAGG AAGTAGTAG AGAGGGCA TGTGCCGG AGCTTAAGT
5001  TGAAGGATG CATTGGGAG TGAGTATGG AGTGGGCCA TATTGTCA CCGAAGATG AGTTTTGAA TATTAAGCA GTGACTTTC ACTGAGA
      ATTCTTAC GTAAGGCTC ACTGCATGC TGACTGCGT ATAAGCAGT GGCTTCTAC TCAAACTCT ATAATTCCGT CGACTGAAG TGACTGT
                                                              _____
                                                                                   ANTISENSE_PRM
```

MICROORGANISMS FOR THE PRODUCTION OF 1,4- BUTANEDIOL AND RELATED METHODS

This application is a continuation of application Ser. No. 15/148,759, filed May 6, 2016, now U.S. Pat. No. 10,273,508, which is a continuation of application Ser. No. 13/361,799, filed Jan. 30, 2012, now U.S. Pat. No. 9,434,964, which is a continuation of application Ser. No. 12/794,700, filed Jun. 4, 2010, now U.S. Pat. No. 8,129,169, which claims the benefit of priority of U.S. provisional application No. 61/184,311, filed Jun. 4, 2009, the entire contents of each of which is incorporated herein by reference.

BACKGROUND OF THE INVENTION

Incorporated herein by reference is the Sequence Listing being concurrently submitted via EFS-Web as an ASCII text file named 12956-475-999_SeqList.TXT, created Mar. 6, 2019, and being 150,422 bytes in size.

This invention relates generally to in silico design of organisms and engineering of organisms, more particularly to organisms having 1,4-butanediol biosynthesis capability.

The compound 4-hydroxybutanoic acid (4-hydroxybutanoate, 4-hydroxybutyrate, 4-HB) is a 4-carbon carboxylic acid that has industrial potential as a building block for various commodity and specialty chemicals. In particular, 4-HB has the potential to serve as a new entry point into the 1,4-butanediol family of chemicals, which includes solvents, resins, polymer precursors, and specialty chemicals. 1,4-Butanediol (BDO) is a polymer intermediate and industrial solvent with a global market of about 3 billion lb/year. BDO is currently produced from petrochemical precursors, primarily acetylene, maleic anhydride, and propylene oxide.

For example, acetylene is reacted with 2 molecules of formaldehyde in the Reppe synthesis reaction (Kroschwitz and Grant, *Encyclopedia of Chem. Tech.*, John Wiley and Sons, Inc., New York (1999)), followed by catalytic hydrogenation to form 1,4-butanediol. It has been estimated that 90% of the acetylene produced in the U.S. is consumed for butanediol production. Alternatively, it can be formed by esterification and catalytic hydrogenation of maleic anhydride, which is derived from butane. Downstream, butanediol can be further transformed; for example, by oxidation to γ-butyrolactone, which can be further converted to pyrrolidone and N-methyl-pyrrolidone, or hydrogenolysis to tetrahydrofuran. These compounds have varied uses as polymer intermediates, solvents, and additives, and have a combined market of nearly 2 billion lb/year.

It is desirable to develop a method for production of these chemicals by alternative means that not only substitute renewable for petroleum-based feedstocks, and also use less energy- and capital-intensive processes. The Department of Energy has proposed 1,4-diacids, and particularly succinic acid, as key biologically-produced intermediates for the manufacture of the butanediol family of products (DOE Report, "Top Value-Added Chemicals from Biomass", 2004). However, succinic acid is costly to isolate and purify and requires high temperatures and pressures for catalytic reduction to butanediol.

Thus, there exists a need for alternative means for effectively producing commercial quantities of 1,4-butanediol and its chemical precursors. The present invention satisfies this need and provides related advantages as well.

SUMMARY OF INVENTION

The invention provides non-naturally occurring microbial organisms containing a 1,4-butanediol (BDO) pathway comprising at least one exogenous nucleic acid encoding a BDO pathway enzyme expressed in a sufficient amount to produce BDO and further optimized for expression of BDO. The invention additionally provides methods of using such microbial organisms to produce BDO.

BRIEF DESCRIPTION OF THE DRAWINGS

(FIG. 3A) 4-HB concentration in culture broth; (FIG. 3B) succinate concentration in culture broth; (FIG. 3C) culture OD, measured at 600 nm. Clusters of bars represent the 24 hour, 48 hour, and 72 hour (if measured) timepoints. The codes along the x-axis indicate the strain/plasmid combination used. The first index refers to the host strain: 1, MG1655 lacI$^Q$; 2, MG1655 ΔgabD lacI$^Q$; 3, MG1655 ΔgabD ΔaldA lacI$^Q$. The second index refers to the plasmid combination used: 1, pZE13-0004-0035 and pZA33-0036; 2, pZE13-0004-0035 and pZA33-0010n; 3, pZE13-0004-0008 and pZA33-0036; 4, pZE13-0004-0008 and pZA33-0010n; 5, Control vectors pZE13 and pZA33.

FIGS. 6A and 6B, mass 116 characteristic fragment of derivatized BDO, containing 2 carbon atoms; FIGS. 6C and 6D, mass 177 characteristic fragment of derivatized BDO, containing 1 carbon atom; FIGS. 6E and 6F, mass 117 characteristic fragment of derivatized 4-HB, containing 2 carbon atoms; FIGS. 6G and 6H, mass 233 characteristic fragment of derivatized 4-HB, containing 4 carbon atoms.

FIG. 8A shows BDO pathways from succinyl-CoA. FIG. 8B shows BDO pathways from alpha-ketoglutarate.

FIGS. 9A-9C show exemplary BDO pathways. FIGS. 9A and 9B show pathways from 4-aminobutyrate. FIG. 9C shows a pathway from acetoactyl-CoA to 4-aminobutyrate.

FIG. 11 shows exemplary BDO pathways from glutamate.

FIG. 12 shows exemplary BDO pathways from acetoacetyl-CoA.

FIGS. 14A-14C show the nucleotide and amino acid sequences of E. coli succinyl-CoA synthetase. FIG. 14A shows the nucleotide sequence (SEQ ID NO:45) of the E. coli sucCD operon. FIG. 14B (SEQ ID NO:46) and 14C (SEQ ID NO:47) show the amino acid sequences of the succinyl-CoA synthetase subunits encoded by the sucCD operon.

FIGS. 15A and 15B show the nucleotide and amino acid sequences of Mycobacterium bovis alpha-ketoglutarate decarboxylase. FIG. 15A shows the nucleotide sequence (SEQ ID NO:48) of Mycobacterium bovis sucA gene. FIG. 15B shows the amino acid sequence (SEQ ID NO:49) of M. bovis alpha-ketoglutarate decarboxylase.

FIG. 18 A shows the nucleotide sequence (SEQ ID NO:50) of CoA-dependent succinate semialdehyde dehydrogenase (sucD) from Porphyromonas gingivalis, and FIG. 18B shows the encoded amino acid sequence (SEQ ID NO:51).

FIG. 19A shows the nucleotide sequence (SEQ ID NO:52) of 4-hydroxybutyrate dehydrogenase (4hbd) from Porphymonas gingivalis, and FIG. 19B shows the encoded amino acid sequence (SEQ ID NO:53).

FIG. 20A shows the nucleotide sequence (SEQ ID NO:54) of 4-hydroxybutyrate CoA transferase (cat2) from Porphyromonas gingivalis, and FIG. 20B shows the encoded amino acid sequence (SEQ ID NO:55).

FIG. 21A shows the nucleotide sequence (SEQ ID NO:56) of phosphotransbutyrylase (ptb) from Clostridium acetobutylicum, and FIG. 21B shows the encoded amino acid sequence (SEQ ID NO:57).

FIG. 22A shows the nucleotide sequence (SEQ ID NO:58) of butyrate kinase (buk1) from Clostridium acetobutylicum, and FIG. 22B shows the encoded amino acid sequence (SEQ ID NO:59).

FIGS. 23A-23D show alternative nucleotide sequences for C. acetobutylicum 020 (phosphtransbutyrylase) with altered codons for more prevalent E. coli codons relative to the C. acetobutylicum native sequence. FIGS. 23A-23D (020A-020D, SEQ ID NOS:60-63, respectively) contain sequences with increasing numbers of rare E. coli codons replaced by more prevalent codons (A<B<C<D).

FIGS. 24A-24D show alternative nucleotide sequences for C. acetobuytlicum 021 (butyrate kinase) with altered codons for more prevalent E. coli codons relative to the C. acetobutylicum native sequence. FIGS. 24A-24D (021A-021B, SEQ ID NOS:64-67, respectively) contain sequences with increasing numbers of rare E. coli codons replaced by more prevalent codons (A<B<C<D).

FIG. 25A shows sodium dodecyl sulfate polyacrylamide gel electrophoresis (SDS-PAGE) stained for proteins with Coomassie blue; lane 1, control vector with no insert; lane 2, expression of C. acetobutylicum native sequences in E. coli; lane 3, expression of 020B-021B codon optimized PTB-BK; lane 4, expression of 020C-021C codon optimized PTB-BK. The positions of BK and PTB are shown. FIG. 25B shows the BK and PTB activities of native C. acetobutylicum sequence (2021n) compared to codon optimized 020B-021B (2021B) and 020C-021C (2021C).

FIG. 27A shows the nucleotide sequence (SEQ ID NO:68) of the native Clostridium biejerinckii ald gene (025n), and FIG. 27B shows the encoded amino acid sequence (SEQ ID NO:69).

FIGS. 28A-28D show alternative gene sequences for the Clostridium beijerinckii ald gene (025A-025D, SEQ ID NOS:70-73, respectively), in which increasing numbers of rare codons are replaced by more prevalent codons (A<B<C<D).

FIG. 30 shows BDO production in strains containing the native C. beijerinckii ald gene (025n) or variants with optimized codons for expression in E. coli (025A-025D). FIG. 30B shows production of ethanol and BDO in strains expressing the C. acetobutylicum AdhE2 enzyme (002C) compared to the codon optimized variant 025B. The third set shows expression of P. gingivalis sucD (035). In all cases, P. gingivalis Cat2 (034) is also expressed.

FIG. 31A shows the nucleotide sequence (SEQ ID NO:74) of the adh1 gene from Geobacillus thermoglucosidasius, and FIG. 31B shows the encoded amino acid sequence (SEQ ID NO:75).

FIG. 32A shows the expression of the Geobacillus thermoglucosidasius adh1 gene in E. coli. Either whole cell lysates or supernatants were analyzed by SDS-PAGE and stained with Coomassie blue for plasmid with no insert, plasmid with 083 (Geotrichum capitatum N-benzyl-3-pyrrolidinol dehydrogenase) and plasmid with 084 (Geobacillus thermoglucosidasius adh1) inserts. FIG. 32B shows the activity of 084 with butyraldehyde (diamonds) or 4-hydroxybutyraldehyde (squares) as substrates.

FIG. 33 shows the production of BDO in various strains: plasmid with no insert; 025B, 025B-026n; 025B-026A; 025B-026B; 025B-026C; 025B-050; 025B-052; 025B-053; 025B-055; 025B-057; 025B-058; 025B-071; 025B-083; 025B-084; PTSlacO-025B; PTSlacO-025B-026n.

FIG. 34 shows a plasmid map for the vector pRE119-V2.

FIG. 35 shows the sequence (SEQ ID NO:76) of the ECKh-138 region encompassing the aceF and lpdA genes. The K. pneumonia lpdA gene is underlined, and the codon changed in the Glu354Lys mutant shaded.

FIG. 36 shows the protein sequence comparison of the native E. coli lpdA (SEQ ID NO:77) and the mutant K. pneumonia lpdA (SEQ ID NO:78).

FIG. 37 shows 4-hydroxybutyrate (left bars) and BDO (right bars) production in the strains AB3, MG1655 ΔldhA and ECKh-138. All strains expressed E. coli sucCD, P. gingivalis sucD, P. gingivalis 4hbd on the medium copy plasmid pZA33, and P. gingivalis Cat2, C. acetobutylicum AdhE2 on the high copy plasmid pZE13.

FIG. 38 shows the nucleotide sequence (SEQ ID NO:79) of the 5' end of the aceE gene fused to the pflB-p6 promoter and ribosome binding site (RBS). The 5' italicized sequence shows the start of the aroP gene, which is transcribed in the opposite direction from the pdh operon. The 3' italicized sequence shows the start of the aceE gene. In upper case: pflB RBS. Underlined: FNR binding site. In bold: pflB-p6 promoter sequence.

FIG. 39 shows the nucleotide sequence (SEQ ID NO:80) in the aceF-lpdA region in the strain ECKh-456.

FIG. 41B shows the sequence (nucleotide sequence, SEQ ID NO:81, and coded amino acid sequence, SEQ ID NO:82) of the PCR product of the amplification of chloramphenicol resistance gene (CAT) flanked by FRT sites and homology regions from the mdh gene from the plasmid pKD3.

FIG. 42 shows the sequence (SEQ ID NO:83) of the arcA deleted region in strain ECKh-401.

FIG. 43 shows the sequence (SEQ ID NO:84) of the region encompassing a mutated gltA gene of strain ECKh-422.

FIGS. 44A and 44B show the citrate synthase activity of wild type gltA gene product (FIG. 44A) and the R163L mutant (FIG. 44B). The assay was performed in the absence (diamonds) or presence of 0.4 mM NADH (squares).

FIG. 45 shows the 4-hydroxybutyrate (left bars) and BDO (right bars) production in strains ECKh-401 and ECKh-422, both expressing genes for the complete BDO pathway on plasmids.

FIG. 48 shows the sequence (SEQ ID NO:85) of the region following replacement of PEP carboxylase (ppc) by H. influenzae phosphoenolpyruvate carboxykinase (pepck). The pepck coding region is underlined.

FIG. 52 shows the nucleotide sequence (SEQ ID NO:86) of the genomic DNA of strain ECKh-426 in the region of insertion of a polycistronic DNA fragment containing a promoter, sucCD gene, sucD gene, 4hbd gene and a terminator sequence.

FIG. 53 shows the nucleotide sequence (SEQ ID NO:87) of the chromosomal region of strain ECKh-432 in the region of insertion of a polycistronic sequence containing a promoter, sucA gene, C. kluyveri 4hbd gene and a terminator sequence.

FIG. 55 shows a PCR product (SEQ ID NO:88) containing the non-phosphotransferase (non-PTS) sucrose utilization genes flanked by regions of homology to the rrnC region.

DETAILED DESCRIPTION OF THE INVENTION

Figure 1:
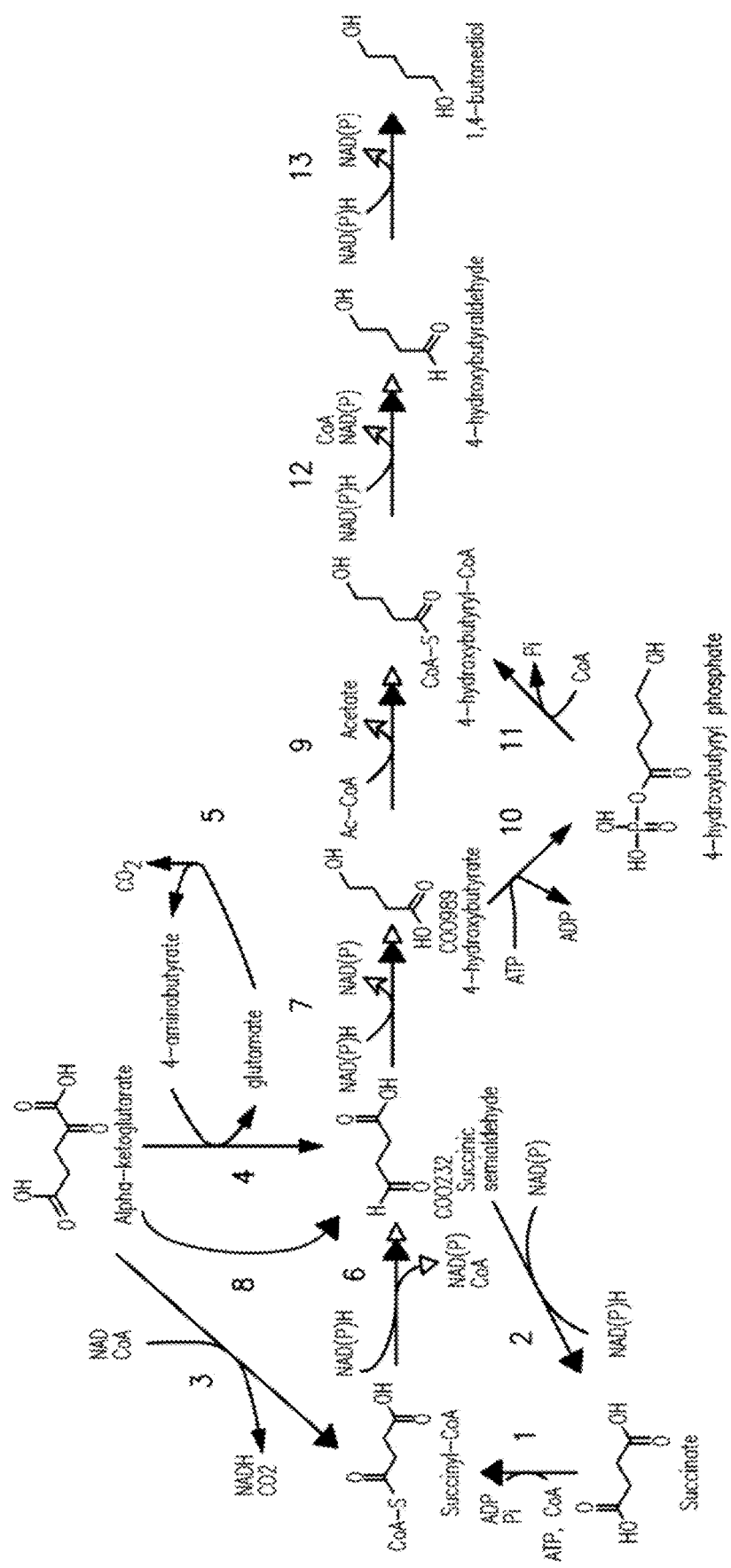
FIG. 1 is a schematic diagram showing biochemical pathways to 4-hydroxybutyurate (4-HB) and to 1,4-butanediol production. The first 5 steps are endogenous to *E. coli*, while the remainder can be expressed heterologously. Enzymes catalyzing the biosynthetic reactions are: (1) succinyl-CoA synthetase; (2) CoA-independent succinic semialdehyde dehydrogenase; (3) α-ketoglutarate dehydrogenase; (4) glutamate:succinate semialdehyde transaminase; (5) glutamate decarboxylase; (6) CoA-dependent succinic semialdehyde dehydrogenase; (7) 4-hydroxybutanoate dehydrogenase; (8) α-ketoglutarate decarboxylase; (9) 4-hydroxybutyryl CoA:acetyl-CoA transferase; (10) butyrate kinase; (11) phosphotransbutyrylase; (12) aldehyde dehydrogenase; (13) alcohol dehydrogenase.

The present invention is directed to the design and production of cells and organisms having biosynthetic production capabilities for 4-hydroxybutanoic acid (4-14B), γ-butyrolactone and 1,4-butanediol (BDO). The invention, in particular, relates to the design of microbial organisms capable of producing BDO by introducing one or more nucleic acids encoding a BDO pathway enzyme.

In one embodiment, the invention utilizes in silico stoichiometric models of Escherichia coli metabolism that identify metabolic designs for biosynthetic production of 4-hydroxybutanoic acid (4-HB) and 1,4-butanediol (BDO). The results described herein indicate that metabolic pathways can be designed and recombinantly engineered to achieve the biosynthesis of 4-HB and downstream products such as 1,4-butanediol in Escherichia coli and other cells or organisms. Biosynthetic production of 4-HB, for example, for the in silico designs can be confirmed by construction of strains having the designed metabolic genotype. These metabolically engineered cells or organisms also can be subjected to adaptive evolution to further augment 4-HB biosynthesis, including under conditions approaching theoretical maximum growth.

In certain embodiments, the 4-HB biosynthesis characteristics of the designed strains make them genetically stable and particularly useful in continuous bioprocesses. Separate strain design strategies were identified with incorporation of different non-native or heterologous reaction capabilities into *E. coli* or other host organisms leading to 4-HB and 1,4-butanediol producing metabolic pathways from either CoA-independent succinic semialdehyde dehydrogenase, succinyl-CoA synthetase and CoA-dependent succinic semialdehyde dehydrogenase, or glutamate:succinic semialdehyde transaminase. In silico metabolic designs were identified that resulted in the biosynthesis of 4-HB in both *E. coli* and yeast species from each of these metabolic pathways. The 1,4-butanediol intermediate γ-butyrolactone can be generated in culture by spontaneous cyclization under conditions at pH<7.5, particularly under acidic conditions, such as below pH 5.5, for example, pH<7, pH<6.5, pH<6, and particularly at pH<5.5 or lower.

Strains identified via the computational component of the platform can be put into actual production by genetically engineering any of the predicted metabolic alterations which lead to the biosynthetic production of 4-HB, 1,4-butanediol or other intermediate and/or downstream products. In yet a further embodiment, strains exhibiting biosynthetic production of these compounds can be further subjected to adaptive evolution to further augment product biosynthesis. The levels of product biosynthesis yield following adaptive evolution also can be predicted by the computational component of the system.

In other specific embodiments, microbial organisms were constructed to express a 4-HB biosynthetic pathway encoding the enzymatic steps from succinate to 4-HB and to 4-HB-CoA. Co-expression of succinate coenzyme A transferase, CoA-dependent succinic semialdehyde dehydrogenase, NAD-dependent 4-hydroxybutyrate dehydrogenase and 4-hydroxybutyrate coenzyme A transferase in a host microbial organism resulted in significant production of 4-HB compared to host microbial organisms lacking a 4-HB biosynthetic pathway. In a further specific embodiment, 4-HB-producing microbial organisms were generated that utilized α-ketoglutarate as a substrate by introducing nucleic acids encoding α-ketoglutarate decarboxylase and NAD-dependent 4-hydroxybutyrate dehydrogenase.

In another specific embodiment, microbial organisms containing a 1,4-butanediol (BDO) biosynthetic pathway were constructed that biosynthesized BDO when cultured in the presence of 4-HB. The BDO biosynthetic pathway consisted of a nucleic acid encoding either a multifunctional aldehyde/alcohol dehydrogenase or nucleic acids encoding an aldehyde dehydrogenawse and an alcohol dehydrogenase. To support growth on 4-HB substrates, these BDO-producing microbial organisms also expressed 4-hydroxybutyrate CoA transferase or 4-butyrate kinase in conjunction with phosphotranshydroxybutyrlase. In yet a further specific embodiment, microbial organisms were generated that synthesized BDO through exogenous expression of nucleic acids encoding a functional 4-HB biosynthetic pathway and a functional BDO biosynthetic pathway. The 4-HB biosynthetic pathway consisted of succinate coenzyme A transferase, CoA-dependent succinic semialdehyde dehydrogenase, NAD-dependent 4-hydroxybutyrate dehydrogenase and 4-hydroxybutyrate coenzyme A transferase. The BDO pathway consisted of a multifunctional aldehyde/alcohol dehydrogenase. Further described herein are additional pathways for production of BDO (see FIGS. 8-13).

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modification include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a biosynthetic pathway for a BDO family of compounds.

A metabolic modification refers to a biochemical reaction that is altered from its naturally occurring state. Therefore, non-naturally occurring microorganisms having genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "4-hydroxybutanoic acid" is intended to mean a 4-hydroxy derivative of butyric acid having the chemical formula $C_4H_8O_3$ and a molecular mass of 104.11 g/mol (126.09 g/mol for its sodium salt). The chemical compound 4-hydroxybutanoic acid also is known in the art as 4-HB, 4-hydroxybutyrate, gamma-hydroxybutyric acid or GHB. The term as it is used herein is intended to include any of the compound's various salt forms and include, for example, 4-hydroxybutanoate and 4-hydroxybutyrate. Specific examples of salt forms for 4-HB include sodium 4-HB and potassium 4-HB. Therefore, the terms 4-hydroxybutanoic acid, 4-HB, 4-hydroxybutyrate, 4-hydroxybutanoate, gamma-hydroxybutyric acid and GHB as well as other art recognized names are used synonymously herein.

As used herein, the term "monomeric" when used in reference to 4-HB is intended to mean 4-HB in a non-polymeric or underivatized form. Specific examples of polymeric 4-HB include poly-4-hydroxybutanoic acid and copolymers of, for example, 4-HB and 3-HB. A specific example of a derivatized form of 4-HB is 4-HB-CoA. Other polymeric 4-HB forms and other derivatized forms of 4-HB also are known in the art.

As used herein, the term "γ-butyrolactone" is intended to mean a lactone having the chemical formula $C_4H_6O_2$ and a molecular mass of 86.089 g/mol. The chemical compound γ-butyrolactone also is know in the art as GBL, butyrolactone, 1,4-lactone, 4-butyrolactone, 4-hydroxybutyric acid lactone, and gamma-hydroxybutyric acid lactone. The term as it is used herein is intended to include any of the compound's various salt forms.

As used herein, the term "1,4-butanediol" is intended to mean an alcohol derivative of the alkane butane, carrying two hydroxyl groups which has the chemical formula $C_4H_{10}O_2$ and a molecular mass of 90.12 g/mol. The chemical compound 1,4-butanediol also is known in the art as BDO and is a chemical intermediate or precursor for a family of compounds referred to herein as BDO family of compounds.

As used herein, the term "tetrahydrofuran" is intended to mean a heterocyclic organic compound corresponding to the fully hydrogenated analog of the aromatic compound furan which has the chemical formula $C_4H_8O$ and a molecular mass of 72.11 g/mol. The chemical compound tetrahydrofuran also is known in the art as THF, tetrahydrofuran, 1,4-epoxybutane, butylene oxide, cyclotetramethylene oxide, oxacyclopentane, diethylene oxide, oxolane, furanidine, hydrofuran, tetra-methylene oxide. The term as it is used herein is intended to include any of the compound's various salt forms.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein are described with reference to a suitable source organism such as E. coli, yeast, or other organisms disclosed herein and their corresponding metabolic reactions or a suitable source organism for desired genetic material such as genes encoding enzymes for their corresponding metabolic reactions. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the growth-coupled production of a biochemical product, those skilled in the art will understand that the orthologous gene harboring the metabolic activity to be disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene compared to a gene encoding the function sought to be substituted. Therefore, a nonorthologous gene includes, for example, a paralog or an unrelated gene.

Therefore, in identifying and constructing the non-naturally occurring microbial organisms of the invention having 4-HB, GBL and/or BDO biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

Disclosed herein are non-naturally occurring microbial biocatalyst or microbial organisms including a microbial organism having a 4-hydroxybutanoic acid (4-HB) biosynthetic pathway that includes at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, glutamate:succinic semialdehyde transaminase, alpha-ketoglutarate decarboxylase, or glutamate decarboxylase, wherein the exogenous nucleic acid is expressed in sufficient amounts to produce monomeric 4-hydroxybutanoic acid (4-HB). 4-hydroxybutanoate dehydrogenase is also referred to as 4-hydroxybutyrate dehydrogenase or 4-HB dehydrogenase. Succinyl-CoA synthetase is also referred to as succinyl-CoA synthase or succinyl-CoA ligase.

Also disclosed herein is a non-naturally occurring microbial biocatalyst or microbial organism including a microbial organism having a 4-hydroxybutanoic acid (4-HB) biosynthetic pathway having at least one exogenous nucleic acid encoding 4-hydroxybutanoate dehydrogenase, succinyl-CoA synthetase, CoA-dependent succinic semialdehyde dehydrogenase, or α-ketoglutarate decarboxylase, wherein the exogenous nucleic acid is expressed in sufficient amounts to produce monomeric 4-hydroxybutanoic acid (4-HB).

The non-naturally occurring microbial biocatalysts or microbial organisms can include microbial organisms that employ combinations of metabolic reactions for biosynthetically producing the compounds of the invention. The biosynthesized compounds can be produced intracellularly and/or secreted into the culture medium. Exemplary compounds produced by the non-naturally occurring microorganisms include, for example, 4-hydroxybutanoic acid, 1,4-butanediol and γ-butyrolactone.

In one embodiment, a non-naturally occurring microbial organism is engineered to produce 4-HB. This compound is one useful entry point into the 1,4-butanediol family of compounds. The biochemical reactions for formation of 4-HB from succinate, from succinate through succinyl-CoA or from α-ketoglutarate are shown in steps 1-8 of FIG. 1.

It is understood that any combination of appropriate enzymes of a BDO pathway can be used so long as conversion from a starting component to the BDO product is achieved. Thus, it is understood that any of the metabolic pathways disclosed herein can be utilized and that it is well understood to those skilled in the art how to select appropriate enzymes to achieve a desired pathway, as disclosed herein.

In another embodiment, disclosed herein is a non-naturally occurring microbial organism, comprising a microbial organism having a 1,4-butanediol (BDO) pathway comprising at least one exogenous nucleic acid encoding a BDO pathway enzyme expressed in a sufficient amount to produce BDO, the BDO pathway comprising 4-aminobutyrate CoA transferase, 4-aminobutyryl-CoA hydrolase, 4-aminobutyrate-CoA ligase, 4-aminobutyryl-CoA oxidoreductase (deaminating), 4-aminobutyryl-CoA transaminase, or 4-hydroxybutyryl-CoA dehydrogenase (see Example VII Table 17). The BDO pathway further can comprise 4-hydroxybutyryl-CoA reductase (alcohol forming), 4-hydroxybutyryl-CoA reductase, or 1,4-butanediol dehydrogenase.

It is understood by those skilled in the art that various combinations of the pathways can be utilized, as disclosed herein. For example, in a non-naturally occurring microbial organism, the nucleic acids can encode 4-aminobutyrate CoA transferase, 4-aminobutyryl-CoA hydrolase, or 4-aminobutyrate-CoA ligase; 4-aminobutyryl-CoA oxidoreductase (deaminating) or 4-aminobutyryl-CoA transaminase; and 4-hydroxybutyryl-CoA dehydrogenase. Other exemplary combinations are specifically describe below and further can be found in FIGS. 8-13. For example, the BDO pathway can further comprise 4-hydroxybutyryl-CoA reductase (alcohol forming), 4-hydroxybutyryl-CoA reductase, or 1,4-butanediol dehydrogenase.

Additionally disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising 4-aminobutyrate CoA transferase, 4-aminobutyryl-CoA hydrolase, 4-aminobutyrate-CoA ligase, 4-aminobutyryl-CoA reductase (alcohol forming), 4-aminobutyryl-CoA reductase, 4-aminobutan-1-ol dehydrogenase, 4-aminobutan-1-ol oxidoreductase (deaminating) or 4-aminobutan-1-ol transaminase (see Example VII and Table 18), and can further comprise 1,4-butanediol dehydrogenase. For example, the exogenous nucleic acids can encode 4-aminobutyrate CoA transferase, 4-aminobutyryl-CoA hydrolase, or 4-aminobutyrate-CoA ligase; 4-aminobutyryl-CoA reductase (alcohol forming); and 4-aminobutan-1-ol oxidoreductase (deaminating) or 4-aminobutan-1-ol transaminase. In addition, the nucleic acids can encode. 4-aminobutyrate CoA transferase, 4-aminobutyryl-CoA hydrolase, or 4-aminobutyrate-CoA ligase; 4-aminobutyryl-CoA reductase; 4-aminobutan-1-ol dehydrogenase; and 4-aminobutan-1-ol oxidoreductase (deaminating) or 4-aminobutan-1-ol transaminase.

Also disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising 4-aminobutyrate kinase, 4-aminobutyraldehyde dehydrogenase (phosphorylating), 4-aminobutan-1-ol dehydrogenase, 4-aminobutan-1-ol oxidoreductase (deaminating), 4-aminobutan-1-ol transaminase, [(4-aminobutanolyl)oxy]phosphonic acid oxidoreductase (deaminating), [(4-aminobutanolyl)oxy]phosphonic acid transaminase, 4-hydroxybutyryl-phosphate dehydrogenase, or 4-hydroxybutyraldehyde dehydrogenase (phosphorylating) (see Example VII and Table 19). For example, the exogenous nucleic acids can encode 4-aminobutyrate kinase; 4-aminobutyraldehyde dehydrogenase (phosphorylating); 4-aminobutan-1-ol dehydrogenase; and 4-aminobutan-1-ol oxidoreductase (deaminating) or 4-aminobutan-1-ol transaminase. Alternatively, the exogenous nucleic acids can encode 4-aminobutyrate kinase; [(4-aminobutanolyl)oxy]phosphonic acid oxidoreductase (deaminating) or [(4-aminobutanolyl)oxy]phosphonic acid transaminase; 4-hydroxybutyryl-phosphate dehydrogenase; and 4-hydroxybutyraldehyde dehydrogenase (phosphorylating).

Additionally disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising alpha-ketoglutarate 5-kinase, 2,5-dioxopentanoic semialdehyde dehydrogenase (phosphorylating), 2,5-dioxopentanoic acid reductase, alpha-ketoglutarate CoA transferase, alpha-ketoglutaryl-CoA hydrolase, alpha-ketoglutaryl-CoA ligase, alpha-ketoglutaryl-CoA reductase, 5-hydroxy-2-oxopentanoic acid dehydrogenase, alpha-ketoglutaryl-CoA reductase (alcohol forming), 5-hydroxy-2-oxopentanoic acid decarboxylase, or 5-hydroxy-2-oxopentanoic acid dehydrogenase (decarboxylation) (see Example VIII and Table 20). The BDO pathway can further comprise 4-hydroxybutyryl-CoA reductase (alcohol forming), 4-hydroxybutyryl-CoA reductase, or 1,4-butanediol dehydrogenase. For example, the exogenous nucleic acids can encode alpha-ketoglutarate 5-kinase; 2,5-dioxopentanoic semialdehyde dehydrogenase (phosphorylating); 2,5-dioxopentanoic acid reductase; and 5-hydroxy-2-oxopentanoic acid decarboxylase. Alternatively, the exogenous nucleic acids can encode alpha-ketoglutarate 5-kinase; 2,5-dioxopentanoic semialdehyde dehydrogenase (phosphorylating); 2,5-dioxopentanoic acid reductase; and 5-hydroxy-2-oxopentanoic acid dehydrogenase (decarboxylation). Alternatively, the exogenous nucleic acids can encode alpha-ketoglutarate CoA transferase, alpha-ketoglutaryl-CoA hydrolase, or alpha-ketoglutaryl-CoA ligase; alpha-ketoglutaryl-CoA reductase, 5-hydroxy-2-oxopentanoic acid dehydrogenase; and 5-hydroxy-2-oxopentanoic acid decarboxylase. In another embodiment, the exogenous nucleic acids can encode alpha-ketoglutarate CoA transferase, alpha-ketoglutaryl-CoA hydrolase, or alpha-ketoglutaryl-CoA ligase; alpha-ketoglutaryl-CoA reductase, 5-hydroxy-2-oxopentanoic acid dehydrogenase, and 5-hydroxy-2-oxopentanoic acid dehydrogenase (decarboxylation). Alternatively, the exogenous nucleic acids can encode alpha-ketoglutarate CoA transferase, alpha-ketoglutaryl-CoA hydrolase, or alpha-ketoglutaryl-CoA ligase; alpha-ketoglutaryl-CoA reductase (alcohol forming); and 5-hydroxy-2-oxopentanoic acid decarboxylase. In yet another embodiment, the exogenous nucleic acids can encode alpha-ketoglutarate CoA transferase, alpha-ketoglutaryl-CoA hydrolase, or alpha-ketoglutaryl-CoA ligase; alpha-ketoglutaryl-CoA reductase (alcohol forming); and 5-hydroxy-2-oxopentanoic acid dehydrogenase (decarboxylation).

Further disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising glutamate CoA transferase, glutamyl-CoA hydrolase, glutamyl-CoA ligase, glutamate 5-kinase, glutamate-5-semialdehyde dehydrogenase (phosphorylating), glutamyl-CoA reductase, glutamate-5-semialdehyde reductase, glutamyl-CoA reductase (alcohol forming), 2-amino-5-hydroxypentanoic acid oxidoreductase (deaminating), 2-amino-5-hydroxypentanoic acid transaminase, 5-hydroxy-2-oxopentanoic acid decarboxylase, 5-hydroxy-2-oxopentanoic acid dehydrogenase (decarboxylation) (see Example IX and Table 21). For example, the exogenous nucleic acids can encode glutamate CoA transferase, glutamyl-CoA hydrolase, or glutamyl-CoA ligase; glutamyl-CoA reductase; glutamate-5-semialdehyde reductase; 2-amino-5-hydroxypentanoic acid oxidoreductase (deaminating) or 2-amino-5-hydroxypentanoic acid transaminase; and 5-hydroxy-2-oxopentanoic acid decarboxylase or 5-hydroxy-2-oxopentanoic acid dehydrogenase (decarboxylation). Alternatively, the exogenous nucleic acids can encode glutamate 5-kinase; glutamate-5-semialdehyde dehydrogenase (phosphorylating); glutamate-5-semialdehyde reductase; 2-amino-5-hydroxypentanoic acid oxidoreductase (deaminating) or 2-amino-5-hydroxypentanoic acid transaminase; and 5-hydroxy-2-oxopentanoic acid decarboxylase or 5-hydroxy-2-oxopentanoic acid dehydrogenase (decarboxylation). In still another embodiment, the exogenous nucleic acids can encode glutamate CoA transferase, glutamyl-CoA hydrolase, or glutamyl-CoA ligase; glutamyl-CoA reductase (alcohol forming); 2-amino-5-hydroxypentanoic acid oxidoreductase (deaminating) or 2-amino-5-hydroxypentanoic acid transaminase; and 5-hydroxy-2-oxopentanoic acid decarboxylase or 5-hydroxy-2-oxopentanoic acid dehydrogenase (decarboxylation). In yet another embodiment, the exogenous nucleic acids can encode glutamate 5-kinase; glutamate-5-semialdehyde dehydrogenase (phosphorylating); 2-amino-5-hydroxypentanoic acid oxidoreductase (deaminating) or 2-amino-5-hydroxypentanoic acid transaminase; and 5-hydroxy-2-oxopentanoic acid decarboxylase or 5-hydroxy-2-oxopentanoic acid dehydrogenase (decarboxylation).

Also disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising 3-hydroxybutyryl-CoA dehydrogenase, 3-hydroxybutyryl-CoA dehydratase, vinylacetyl-CoA Δ-isomerase, or 4-hydroxybutyryl-CoA dehydratase (see Example X and Table 22). For example, the exogenous nucleic acids can encode 3-hydroxybutyryl-CoA dehydrogenase; 3-hydroxybutyryl-CoA dehydratase; vinylacetyl-CoA Δ-isomerase; and 4-hydroxybutyryl-CoA dehydratase.

Further disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising homoserine deaminase, homoserine CoA transferase, homoserine-CoA hydrolase, homoserine-CoA ligase, homoserine-CoA deaminase, 4-hydroxybut-2-enoyl-CoA transferase, 4-hydroxybut-2-enoyl-CoA hydrolase, 4-hydroxybut-2-enoyl-CoA ligase, 4-hydroxybut-2-enoate reductase, 4-hydroxybutyryl-CoA transferase, 4-hydroxybutyryl-CoA hydrolase, 4-hydroxybutyryl-CoA ligase, or 4-hydroxybut-2-enoyl-CoA reductase (see Example XI and Table 23). For example, the exogenous nucleic acids can encode homoserine deaminase; 4-hydroxybut-2-enoyl-CoA transferase, 4-hydroxybut-2-enoyl-CoA hydrolase, 4-hydroxybut-2-enoyl-CoA ligase; 4-hydroxybut-2-enoyl-CoA reductase. Alternatively, the exogenous nucleic acids can encode homoserine CoA transferase, homoserine-CoA hydrolase, or homoserine-CoA ligase; homoserine-CoA deaminase; and 4-hydroxybut-2-enoyl-CoA reductase. In a further embodiment, the exogenous nucleic acids can encode homoserine deaminase; 4-hydroxybut-2-enoate reductase; and 4-hydroxybutyryl-CoA transferase, 4-hydroxybutyryl-CoA hydrolase, or 4-hydroxybutyryl-CoA ligase. Alternatively, the exogenous nucleic acids can encode homoserine CoA transferase, homoserine-CoA hydrolase, or homoserine-CoA ligase; homoserine-CoA deaminase; and 4-hydroxybut-2-enoyl-CoA reductase.

Further disclosed herein is a non-naturally occurring microbial organism, comprising a microbial organism having a BDO pathway comprising at least one exogenous nucleic acid encoding a BDO pathway enzyme expressed in a sufficient amount to produce BOD, the BDO pathway comprising succinyl-CoA reductase (alcohol forming), 4-hydroxybutyryl-CoA hydrolase, 4-hydroxybutyryl-CoA ligase, 4-hydroxybutanal dehydrogenase (phosphorylating) (see Table 15). Such a BDO pathway can further comprise succinyl-CoA reductase, 4-hydroxybutyrate dehydrogenase, 4-hydroxybutyryl-CoA transferase, 4-hydroxybutyrate kinase, phosphotrans-4-hydroxybutyrylase, 4-hydroxybutyryl-CoA reductase, 4-hydroxybutyryl-CoA reductase (alcohol forming), or 1,4-butanediol dehydrogenase.

Additionally disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising glutamate dehydrogenase, 4-aminobutyrate oxidoreductase (deaminating), 4-aminobutyrate transaminase, glutamate decarboxylase, 4-hydroxybutyryl-CoA hydrolase, 4-hydroxybutyryl-CoA ligase, 4-hydroxybutanal dehydrogenase (phosphorylating)(see Table 16). Such a BDO pathway can further comprise alpha-ketoglutarate decarboxylase, 4-hydroxybutyrate dehydrogenase, 4-hydroxybutyryl-CoA transferase, 4-hydroxybutyrate kinase, phosphotrans-4-hydroxybutyrylase, 4-hydroxybutyryl-CoA reductase, 4-hydroxybutyryl-CoA reductase (alcohol forming), or 1,4-butanediol dehydrogenase.

The pathways described above are merely exemplary. One skilled in the art can readily select appropriate pathways from those disclosed herein to obtain a suitable BDO pathway or other metabolic pathway, as desired.

The invention provides genetically modified organisms that allow improved production of a desired product such as BDO by increasing the product or decreasing undesirable byproducts. As disclosed herein, the invention provides a non-naturally occurring microbial organism, comprising a microbial organism having a 1,4-butanediol (BDO) pathway comprising at least one exogenous nucleic acid encoding a BDO pathway enzyme expressed in a sufficient amount to produce BDO. In one embodiment, the microbial organism is genetically modified to express exogenous succinyl-CoA synthetase (see Example XII). For example, the succinyl-CoA synthetase can be encoded by an *Escherichia coli* sucCD genes.

In another embodiment, the microbial organism is genetically modified to express exogenous alpha-ketoglutarate decarboxylase (see Example XIII). For example, the alpha-ketoglutarate decarboxylase can be encoded by the *Mycobacterium bovis* sucA gene. In still another embodiment, the microbial organism is genetically modified to express exogenous succinate semialdehyde dehydrogenase and 4-hydroxybutyrate dehydrogenase and optionally 4-hydroxybutyryl-CoA/acetyl-CoA transferase (see Example XIII). For example, the succinate semialdehyde dehydrogenase (CoA-dependent), 4-hydroxybutyrate dehydrogenase and 4-hydroxybutyryl-CoA/acetyl-CoA transferase can be encoded by *Porphyromonas gingivalis* W83 genes. In an additional embodiment, the microbial organism is genetically modified to express exogenous butyrate kinase and phosphotransbutyrylase (see Example XIII). For example, the butyrate kinase and phosphotransbutyrylase can be encoded by *Clostridium acetobutilicum* buk1 and ptb genes.

In yet another embodiment, the microbial organism is genetically modified to express exogenous 4-hydroxybutyryl-CoA reductase (see Example XIII). For example, the 4-hydroxybutyryl-CoA reductase can be encoded by *Clostridium beijerinckii* ald gene. Additionally, in an embodiment of the invention, the microbial organism is genetically modified to express exogenous 4-hydroxybutanal reductase (see Example XIII). For example, the 4-hydroxybutanal reductase can be encoded by *Geobacillus thermoglucosidasius* adh1 gene. In another embodiment, the microbial organism is genetically modified to express exogenous pyruvate dehydrogenase subunits (see Example XIV). For example, the exogenous pyruvate dehydrogenase can be NADH insensitive. The pyruvate dehydrogenase subunit can be encoded by the *Klebsiella pneumonia* lpdA gene. In a particular embodiment, the pyruvate dehydrogenase subunit genes of the microbial organism can be under the control of a pyruvate formate lyase promoter.

In still another embodiment, the microbial organism is genetically modified to disrupt a gene encoding an aerobic respiratory control regulatory system (see Example XV). For example, the disruption can be of the arcA gene. Such an organism can further comprise disruption of a gene encoding malate dehydrogenase. In a further embodiment, the microbial organism is genetically modified to express an exogenous NADH insensitive citrate synthase (see Example XV). For example, the NADH insensitive citrate synthase can be encoded by gltA, such as an R163L mutant of gltA. In still another embodiment, the microbial organism is genetically modified to express exogenous phosphoenolpyruvate carboxykinase (see Example XVI). For example, the phosphoenolpyruvate carboxykinase can be encoded by an *Haemophilus* influenza phosphoenolpyruvate carboxykinase gene.

It is understood that any of a number of genetic modifications, as disclosed herein, can be used alone or in various combinations of one or more of the genetic modifications disclosed herein to increase the production of BDO in a BDO producing microbial organism. In a particular embodiment, the microbial organism can be genetically modified to incorporate any and up to all of the genetic modifications that lead to increased production of BDO. In a particular embodiment, the microbial organism containing a BDO pathway can be genetically modified to express exogenous succinyl-CoA synthetase; to express exogenous alpha-ketoglutarate decarboxylase; to express exogenous succinate semialdehyde dehydrogenase and 4-hydroxybutyrate dehydrogenase and optionally 4-hydroxybutyryl-CoA/acetyl-CoA transferase; to express exogenous butyrate kinase and phosphotransbutyrylase; to express exogenous 4-hydroxybutyryl-CoA reductase; and to express exogenous 4-hydroxybutanal reductase; to express exogenous pyruvate dehydrogenase; to disrupt a gene encoding an aerobic respiratory control regulatory system; to express an exogenous NADH insensitive citrate synthase; and to express exogenous phosphoenolpyruvate carboxykinase. Such strains for improved production are described in Examples XII-XIX. It is thus understood that, in addition to the modifications described above, such strains can additionally include other modifications disclosed herein. Such modifications include, but are not limited to, deletion of endogenous lactate dehydrogenase (ldhA), alcohol dehydrogenase (adhE), and/or pyruvate formate lyase (pflB)(see Examples XII-XIX and Table 28).

Additionally provided is a microbial organism in which one or more genes encoding the exogenously expressed enzymes are integrated into the fimD locus of the host organism (see Example XVII). For example, one or more genes encoding a BDO pathway enzyme can be integrated into the fimD locus for increased production of BDO. Further provided is a microbial organism expressing a non-phosphotransferase sucrose uptake system that increases production of BDO.

Although the genetically modified microbial organisms disclosed herein are exemplified with microbial organisms containing particular BDO pathway enzymes, it is understood that such modifications can be incorporated into any microbial organism having a BDO pathway suitable for enhanced production in the presence of the genetic modifications. The microbial organisms of the invention can thus have any of the BDO pathways disclosed herein. For example, the BDO pathway can comprise 4-hydroxybutanoate dehydrogenase, succinyl-CoA synthetase, CoA-dependent succinic semialdehyde dehydrogenase, 4-hydroxybutyrate:CoA transferase, 4-butyrate kinase, phosphotransbutyrylase, alpha-ketoglutarate decarboxylase, aldehyde dehydrogenase, alcohol dehydrogenase or an aldehyde/alcohol dehydrogenase (see FIG. 1). Alternatively, the BDO pathway can comprise 4-aminobutyrate CoA transferase, 4-aminobutyryl-CoA hydrolase, 4-aminobutyrate-CoA ligase, 4-aminobutyryl-CoA oxidoreductase (deaminating), 4-aminobutyryl-CoA transaminase, or 4-hydroxybutyryl-CoA dehydrogenase (see Table 17). Such a BDO pathway can further comprise 4-hydroxybutyryl-CoA reductase (alcohol forming), 4-hydroxybutyryl-CoA reductase, or 1,4-butanediol dehydrogenase Additionally, the BDO pathway can comprise 4-aminobutyrate CoA transferase, 4-aminobutyryl-CoA hydrolase, 4-aminobutyrate-CoA ligase, 4-aminobutyryl-CoA reductase (alcohol forming), 4-aminobutyryl-CoA reductase, 4-aminobutan-1-ol dehydrogenase, 4-aminobutan-1-ol oxidoreductase (deaminating) or 4-aminobutan-1-ol transaminase (see Table 18). Also, the BDO pathway can comprise 4-aminobutyrate kinase, 4-aminobutyraldehyde dehydrogenase (phosphorylating), 4-aminobutan-1-ol dehydrogenase, 4-aminobutan-1-ol oxidoreductase (deaminating), 4-aminobutan-1-ol transaminase, [(4-aminobutanolyl)oxy]phosphonic acid oxidoreductase (deaminating), [(4-aminobutanolyl)oxy]phosphonic acid transaminase, 4-hydroxybutyryl-phosphate dehydrogenase, or 4-hydroxybutyraldehyde dehydrogenase (phosphorylating) (see Table 19). Such a pathway can further comprise 1,4-butanediol dehydrogenase.

The BDO pathway can also comprise alpha-ketoglutarate 5-kinase, 2,5-dioxopentanoic semialdehyde dehydrogenase (phosphorylating), 2,5-dioxopentanoic acid reductase, alpha-ketoglutarate CoA transferase, alpha-ketoglutaryl-CoA hydrolase, alpha-ketoglutaryl-CoA ligase, alpha-ketoglutaryl-CoA reductase, 5-hydroxy-2-oxopentanoic acid dehydrogenase, alpha-ketoglutaryl-CoA reductase (alcohol forming), 5-hydroxy-2-oxopentanoic acid decarboxylase, or 5-hydroxy-2-oxopentanoic acid dehydrogenase (decarboxylation)(see Table 20). Such a BDO pathway can further comprise 4-hydroxybutyryl-CoA reductase (alcohol forming), 4-hydroxybutyryl-CoA reductase, or 1,4-butanediol dehydrogenase. Additionally, the BDO pathway can comprise glutamate CoA transferase, glutamyl-CoA hydrolase, glutamyl-CoA ligase, glutamate 5-kinase, glutamate-5-semialdehyde dehydrogenase (phosphorylating), glutamyl-CoA reductase, glutamate-5-semialdehyde reductase, glutamyl-CoA reductase (alcohol forming), 2-amino-5- hydroxypentanoic acid oxidoreductase (deaminating), 2-amino-5-hydroxypentanoic acid transaminase, 5-hydroxy-2-oxopentanoic acid decarboxylase, 5-hydroxy-2-oxopentanoic acid dehydrogenase (decarboxylation)(see Table 21). Such a BDO pathway can further comprise 4-hydroxybutyryl-CoA reductase (alcohol forming), 4-hydroxybutyryl-CoA reductase, or 1,4-butanediol dehydrogenase.

Additionally, the BDO pathway can comprise 3-hydroxybutyryl-CoA dehydrogenase, 3-hydroxybutyryl-CoA dehydratase, vinylacetyl-CoA Δ-isomerase, or 4-hydroxybutyryl-CoA dehydratase (see Table 22). Also, the BDO pathway can comprise homoserine deaminase, homoserine CoA transferase, homoserine-CoA hydrolase, homoserine-CoA ligase, homoserine-CoA deaminase, 4-hydroxybut-2-enoyl-CoA transferase, 4-hydroxybut-2-enoyl-CoA hydrolase, 4-hydroxybut-2-enoyl-CoA ligase, 4-hydroxybut-2-enoate reductase, 4-hydroxybutyryl-CoA transferase, 4-hydroxybutyryl-CoA hydrolase, 4-hydroxybutyryl-CoA ligase, or 4-hydroxybut-2-enoyl-CoA reductase (see Table 23). Such a BDO pathway can further comprise 4-hydroxybutyryl-CoA reductase (alcohol forming), 4-hydroxybutyryl-CoA reductase, or 1,4-butanediol dehydrogenase.

The BDO pathway can additionally comprise succinyl-CoA reductase (alcohol forming), 4-hydroxybutyryl-CoA hydrolase, 4-hydroxybutyryl-CoA ligase, or 4-hydroxybutanal dehydrogenase (phosphorylating) (see Table 15). Such a pathway can further comprise succinyl-CoA reductase, 4-hydroxybutyrate dehydrogenase, 4-hydroxybutyryl-CoA transferase, 4-hydroxybutyrate kinase, phosphotrans-4-hydroxybutyrylase, 4-hydroxybutyryl-CoA reductase, 4-hydroxybutyryl-CoA reductase (alcohol forming), or 1,4-butanediol dehydrogenase. Also, the BDO pathway can comprise glutamate dehydrogenase, 4-aminobutyrate oxidoreductase (deaminating), 4-aminobutyrate transaminase, glutamate decarboxylase, 4-hydroxybutyryl-CoA hydrolase, 4-hydroxybutyryl-CoA ligase, or 4-hydroxybutanal dehydrogenase (phosphorylating)(see Table 16). Such a BDO pathway can further comprise alpha-ketoglutarate decarboxylase, 4-hydroxybutyrate dehydrogenase, 4-hydroxybutyryl-CoA transferase, 4-hydroxybutyrate kinase, phosphotrans-4-hydroxybutyrylase, 4-hydroxybutyryl-CoA reductase, 4-hydroxybutyryl-CoA reductase (alcohol forming), or 1,4-butanediol dehydrogenase.

The invention is described herein with general reference to the metabolic reaction, reactant or product thereof, or with specific reference to one or more nucleic acids or genes encoding an enzyme associated with or catalyzing the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constitutes also references the gene or genes encoding the enzymes that catalyze the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes as well as the reactants and products of the reaction.

The production of 4-HB via biosynthetic modes using the microbial organisms of the invention is particularly useful because it can produce monomeric 4-HB. The non-naturally occurring microbial organisms of the invention and their biosynthesis of 4-HB and BDO family compounds also is particularly useful because the 4-HB product can be (1) secreted; (2) can be devoid of any derivatizations such as Coenzyme A; (3) avoids thermodynamic changes during biosynthesis; (4) allows direct biosynthesis of BDO, and (5) allows for the spontaneous chemical conversion of 4-HB to γ-butyrolactone (GBL) in acidic pH medium. This latter characteristic also is particularly useful for efficient chemical synthesis or biosynthesis of BDO family compounds such as 1,4-butanediol and/or tetrahydrofuran (THF), for example.

Microbial organisms generally lack the capacity to synthesize 4-HB and therefore any of the compounds disclosed herein to be within the 1,4-butanediol family of compounds or known by those in the art to be within the 1,4-butanediol family of compounds. Moreover, organisms having all of the requisite metabolic enzymatic capabilities are not known to produce 4-HB from the enzymes described and biochemical pathways exemplified herein. Rather, with the possible exception of a few anaerobic microorganisms described further below, the microorganisms having the enzymatic capability use 4-HB as a substrate to produce, for example, succinate. In contrast, the non-naturally occurring microbial organisms of the invention can generate 4-HB or BDO as a product. As described above, the biosynthesis of 4-HB in its monomeric form is not only particularly useful in chemical synthesis of BDO family of compounds, it also allows for the further biosynthesis of BDO family compounds and avoids altogether chemical synthesis procedures.

The non-naturally occurring microbial organisms of the invention that can produce 4-HB or BDO are produced by ensuring that a host microbial organism includes functional capabilities for the complete biochemical synthesis of at least one 4-HB or BDO biosynthetic pathway of the invention. Ensuring at least one requisite 4-HB or BDO biosynthetic pathway confers 4-HB biosynthesis capability onto the host microbial organism.

Five 4-HB biosynthetic pathways are exemplified herein and shown for purposes of illustration in FIG. 1. Additional 4-HB and BDO pathways are described in FIGS. 8-13. One 4-HB biosynthetic pathway includes the biosynthesis of 4-HB from succinate (the succinate pathway). The enzymes participating in this 4-HB pathway include CoA-independent succinic semialdehyde dehydrogenase and 4-hydroxybutanoate dehydrogenase. In this pathway, CoA-independent succinic semialdehyde dehydrogenase catalyzes the reverse reaction to the arrow shown in FIG. 1. Another 4-HB biosynthetic pathway includes the biosynthesis from succinate through succinyl-CoA (the succinyl-CoA pathway). The enzymes participating in this 4-HB pathway include succinyl-CoA synthetase, CoA-dependent succinic semialdehyde dehydrogenase and 4-hydroxybutanoate dehydrogenase. Three other 4-HB biosynthetic pathways include the biosynthesis of 4-HB from α-ketoglutarate (the α-ketoglutarate pathways). Hence, a third 4-HB biosynthetic pathway is the biosynthesis of succinic semialdehyde through glutamate:succinic semialdehyde transaminase, glutamate decarboxylase and 4-hydroxybutanoate dehydrogenase. A fourth 4-HB biosynthetic pathway also includes the biosynthesis of 4-HB from α-ketoglutarate, but utilizes α-ketoglutarate decarboxylase to catalyze succinic semialdehyde synthesis. 4-hydroxybutanoate dehydrogenase catalyzes the conversion of succinic semialdehyde to 4-HB. A fifth 4-HB biosynthetic pathway includes the biosynthesis from α-ketoglutarate through succinyl-CoA and utilizes α-ketoglutarate dehydrogenase to produce succinyl-CoA, which funnels into the succinyl-CoA pathway described above. Each of these 4-HB biosynthetic pathways, their substrates, reactants and products are described further below in the Examples. As described herein, 4-HB can further be biosynthetically converted to BDO by inclusion of appropriate enzymes to produce BDO (see Example). Thus, it is understood that a 4-HB pathway can be used with enzymes for converting 4-HB to BDO to generate a BDO pathway.

The non-naturally occurring microbial organisms of the invention can be produced by introducing expressible nucleic acids encoding one or more of the enzymes participating in one or more 4-HB or BDO biosynthetic pathways. Depending on the host microbial organism chosen for biosynthesis, nucleic acids for some or all of a particular 4-HB or BDO biosynthetic pathway can be expressed. For example, if a chosen host is deficient in one or more enzymes in a desired biosynthetic pathway, for example, the succinate to 4-HB pathway, then expressible nucleic acids for the deficient enzyme(s), for example, both CoA-independent succinic semialdehyde dehydrogenase and 4-hydroxybutanoate dehydrogenase in this example, are introduced into the host for subsequent exogenous expression. Alternatively, if the chosen host exhibits endogenous expression of some pathway enzymes, but is deficient in others, then an encoding nucleic acid is needed for the deficient enzyme(s) to achieve 4-HB or BDO biosynthesis. For example, if the chosen host exhibits endogenous CoA-independent succinic semialdehyde dehydrogenase, but is deficient in 4-hydroxybutanoate dehydrogenase, then an encoding nucleic acid is needed for this enzyme to achieve 4-HB biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as 4-HB or BDO.

In like fashion, where 4-HB biosynthesis is selected to occur through the succinate to succinyl-CoA pathway (the succinyl-CoA pathway), encoding nucleic acids for host deficiencies in the enzymes succinyl-CoA synthetase, CoA-dependent succinic semialdehyde dehydrogenase and/or 4-hydroxybutanoate dehydrogenase are to be exogenously expressed in the recipient host. Selection of 4-HB biosynthesis through the α-ketoglutarate to succinic semialdehyde pathway (the α-ketoglutarate pathway) can utilize exogenous expression for host deficiencies in one or more of the enzymes for glutamate:succinic semialdehyde transaminase, glutamate decarboxylase and/or 4-hydroxybutanoate dehydrogenase, or α-ketoglutarate decarboxylase and 4-hydroxybutanoate dehydrogenase. One skilled in the art can readily determine pathway enzymes for production of 4-HB or BDO, as disclosed herein.

Depending on the 4-HB or BDO biosynthetic pathway constituents of a selected host microbial organism, the non-naturally occurring microbial organisms of the invention will include at least one exogenously expressed 4-HB or BDO pathway-encoding nucleic acid and up to all encoding nucleic acids for one or more 4-HB or BDO biosynthetic pathways. For example, 4-HB or BDO biosynthesis can be established in a host deficient in a pathway enzyme or protein through exogenous expression of the corresponding encoding nucleic acid. In a host deficient in all enzymes or proteins of a 4-HB or BDO pathway, exogenous expression of all enzyme or proteins in the pathway can be included, although it is understood that all enzymes or proteins of a pathway can be expressed even if the host contains at least one of the pathway enzymes or proteins. For example, 4-HB biosynthesis can be established from all five pathways in a host deficient in 4-hydroxybutanoate dehydrogenase through exogenous expression of a 4-hydroxybutanoate dehydrogenase encoding nucleic acid. In contrast, 4-HB biosynthesis can be established from all five pathways in a host deficient in all eight enzymes through exogenous expression of all eight of CoA-independent succinic semialdehyde dehydrogenase, succinyl-CoA synthetase, CoA-dependent succinic semialdehyde dehydrogenase, glutamate:succinic semialdehyde transaminase, glutamate decarboxylase, α-ketoglutarate decarboxylase, α-ketoglutarate dehydrogenase and 4-hydroxybutanoate dehydrogenase.

Given the teachings and guidance provided herein, those skilled in the art will understand that the number of encoding nucleic acids to introduce in an expressible form will, at least, parallel the 4-HB or BDO pathway deficiencies of the selected host microbial organism. Therefore, a non-naturally occurring microbial organism of the invention can have one, two, three, four, five, six, seven, eight or up to all nucleic acids encoding the enzymes disclosed herein constituting one or more 4-HB or BDO biosynthetic pathways. In some embodiments, the non-naturally occurring microbial organisms also can include other genetic modifications that facilitate or optimize 4-HB or BDO biosynthesis or that confer other useful functions onto the host microbial organism. One such other functionality can include, for example, augmentation of the synthesis of one or more of the 4-HB pathway precursors such as succinate, succinyl-CoA, α-ketoglutarate, 4-aminobutyrate, glutamate, acetoacetyl-CoA, and/or homoserine.

Generally, a host microbial organism is selected such that it produces the precursor of a 4-HB or BDOpathway, either as a naturally produced molecule or as an engineered product that either provides de novo production of a desired precursor or increased production of a precursor naturally produced by the host microbial organism. For example, succinyl-CoA, α-ketoglutarate, 4-aminobutyrate, glutamate, acetoacetyl-CoA, and homoserine are produced naturally in a host organism such as E. coli. A host organism can be engineered to increase production of a precursor, as disclosed herein. In addition, a microbial organism that has been engineered to produce a desired precursor can be used as a host organism and further engineered to express enzymes or proteins of a 4-HB or BDO pathway.

In some embodiments, a non-naturally occurring microbial organism of the invention is generated from a host that contains the enzymatic capability to synthesize 4-HB or BDO. In this specific embodiment it can be useful to increase the synthesis or accumulation of a 4-HB or BDO pathway product to, for example, drive 4-HB or BDO pathway reactions toward 4-HB or BDO production. Increased synthesis or accumulation can be accomplished by, for example, overexpression of nucleic acids encoding one or more of the 4-HB or BDO pathway enzymes disclosed herein. Over expression of the 4-HB or BDO pathway enzyme or enzymes can occur, for example, through exogenous expression of the endogenous gene or genes, or through exogenous expression of the heterologous gene or genes. Therefore, naturally occurring organisms can be readily generated to be non-naturally 4-HB or BDO producing microbial organisms of the invention through overexpression of one, two, three, four, five, six and so forth up to all nucleic acids encoding 4-HB or BDO biosynthetic pathway enzymes. In addition, a non-naturally occurring organism can be generated by mutagenesis of an endogenous gene that results in an increase in activity of an enzyme in the 4-HB or BDO biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism (see Examples).

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

Sources of encoding nucleic acids for a 4-HB or BDO pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisiae, Saccharomyces kluyveri, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pediococcus pentosaceus, Zymomonas mobilis, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum* marine gamma proteobacterium, butyrate-producing bacterium, and others disclosed herein (see Examples). For example, microbial organisms having 4-HB or BDO biosynthetic production are exemplified herein with reference to *E. coli* and yeast hosts. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite 4-HB or BDO biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of 4-HB or BDO and other compounds of the invention described herein with reference to a particular organism such as *E. coli* or yeast can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative 4-HB or BDO biosynthetic pathway exists in an unrelated species, 4-HB or BDO biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual genes usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize 4-HB, such as monomeric 4-HB, or BDO.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escheri-* chia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens, and Pseudomonas putida. Exemplary yeasts or fungi include species selected from Saccharomyces cerevisiae, Schizosaccharomyces pombe, Kluyveromyces lactis, Kluyveromyces marxianus, Aspergillus terreus, Aspergillus niger and Pichia pastoris. E. coli is a particularly useful host organisms since it is a well characterized microbial organism suitable for genetic engineering. Other particularly useful host organisms include yeast such as Saccharomyces cerevisiae.

Methods for constructing and testing the expression levels of a non-naturally occurring 4-HB- or BDO-producing host can be performed, for example, by recombinant and detection methods well known in the art. Such methods can be found described in, for example, Sambrook et al., *Molecular Cloning: A Laboratory Manual, Third Ed.*, Cold Spring Harbor Laboratory, New York (2001); Ausubel et al., *Current Protocols in Molecular Biology*, John Wiley and Sons, Baltimore, Md. (1999). 4-HB and GBL can be separated by, for example, HPLC using a Spherisorb 5 ODS1 column and a mobile phase of 70% 10 mM phosphate buffer (pH=7) and 30% methanol, and detected using a UV detector at 215 nm (Hennessy et al. 2004, J. Forensic Sci. 46(6):1-9). BDO is detected by gas chromatography or by HPLC and refractive index detector using an Aminex HPX-87H column and a mobile phase of 0.5 mM sulfuric acid (Gonzalez-Pajuelo et al., *Met. Eng.* 7:329-336 (2005)).

Exogenous nucleic acid sequences involved in a pathway for production of 4-HB or BDO can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to harbor one or more 4-HB biosynthetic pathway and/or one or more BDO biosynthetic encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The non-naturally occurring microbial organisms of the invention are constructed using methods well known in the art as exemplified herein to exogenously express at least one nucleic acid encoding a 4-HB or BDO pathway enzyme in sufficient amounts to produce 4-HB, such as monomeric 4-HB, or BDO. It is understood that the microbial organisms of the invention are cultured under conditions sufficient to produce 4-HB or BDO. Exemplary levels of expression for 4-HB enzymes in each pathway are described further below in the Examples. Following the teachings and guidance provided herein, the non-naturally occurring microbial organisms of the invention can achieve biosynthesis of 4-HB, such as monomeric 4-HB, or BDO resulting in intracellular concentrations between about 0.1-200 mM or more, for example, 0.1-25 mM or more. Generally, the intracellular concentration of 4-HB, such as monomeric 4-HB, or BDO is between about 3-150 mM or more, particularly about 5-125 mM or more, and more particularly between about 8-100 mM, for example, about 3-20 mM, particularly between about 5-15 mM and more particularly between about 8-12 mM, including about 10 mM, 20 mM, 50 MM, 80 mM or more. Intracellular concentrations between and above each of these exemplary ranges also can be achieved from the non-naturally occurring microbial organisms of the invention. In particular embodiments, the microbial organisms of the invention, particularly strains such as those disclosed herein (see Examples XII-XIX and Table 28), can provide improved production of a desired product such as BDO by increasing the production of BDO and/or decreasing undesirable byproducts. Such production levels include, but are not limited to, those disclosed herein and including from about 1 gram to about 25 grams per liter, for example about 2, 3, 4, 5, 6, 7, 8, 9, 10, 11, 12, 13, 14, 15, 16, 17, 18, 19, 20, 21, 22, 23, 24, or even higher amounts of product per liter.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application Ser. No. 11/891,602, filed Aug. 10, 2007. Any of these conditions can be employed with the non-naturally occurring microbial organisms as well as other anaerobic conditions well known in the art. Under such anaerobic conditions, the 4-HB or BDO producers can synthesize 4-HB or BDO at intracellular concentrations of 5-10 mM or more as well as all other concentrations exemplified herein. It is understood that, even though the above description refers to intracellular concentrations, 4-HB or BDO producing microbial organisms can produce 4-HB or BDO intracellularly and/or secrete the product into the culture medium.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of 4-HB or BDO includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The invention also provides a non-naturally occurring microbial biocatalyst including a microbial organism having 4-hydroxybutanoic acid (4-HB) and 1,4-butanediol (BDO) biosynthetic pathways that include at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, 4-hydroxybutyrate:CoA transferase, glutamate:succinic semialdehyde transaminase, glutamate decarboxylase, CoA-independent aldehyde dehydrogenase, CoA-dependent aldehyde dehydrogenase or alcohol dehydrogenase, wherein the exogenous nucleic acid is expressed in sufficient amounts to produce 1,4-butanediol (BDO). 4-Hydroxybutyrate:CoA transferase also is known as 4-hydroxybutyryl CoA:acetyl-CoA transferase. Additional 4-HB or BDO pathway enzymes are also disclosed herein (see Examples and FIGS. 8-13).

The invention further provides non-naturally occurring microbial biocatalyst including a microbial organism having 4-hydroxybutanoic acid (4-HB) and 1,4-butanediol (BDO) biosynthetic pathways, the pathways include at least one exogenous nucleic acid encoding 4-hydroxybutanoate dehydrogenase, succinyl-CoA synthetase, CoA-dependent succinic semialdehyde dehydrogenase, 4-hydroxybutyrate:CoA transferase, 4-butyrate kinase, phosphotransbutyrylase, α-ketoglutarate decarboxylase, aldehyde dehydrogenase, alcohol dehydrogenase or an aldehyde/alcohol dehydrogenase, wherein the exogenous nucleic acid is expressed in sufficient amounts to produce 1,4-butanediol (BDO).

Non-naturally occurring microbial organisms also can be generated which biosynthesize BDO. As with the 4-HB producing microbial organisms of the invention, the BDO producing microbial organisms also can produce intracellularly or secret the BDO into the culture medium. Following the teachings and guidance provided previously for the construction of microbial organisms that synthesize 4-HB, additional BDO pathways can be incorporated into the 4-HB producing microbial organisms to generate organisms that also synthesize BDO and other BDO family compounds. The chemical synthesis of BDO and its downstream products are known. The non-naturally occurring microbial organisms of the invention capable of BDO biosynthesis circumvent these chemical synthesis using 4-HB as an entry point as illustrated in FIG. 1. As described further below, the 4-HB producers also can be used to chemically convert 4-HB to GBL and then to BDO or THF, for example. Alternatively, the 4-HB producers can be further modified to include biosynthetic capabilities for conversion of 4-HB and/or GBL to BDO.

The additional BDO pathways to introduce into 4-HB producers include, for example, the exogenous expression in a host deficient background or the overexpression of one or more of the enzymes exemplified in FIG. 1 as steps 9-13. One such pathway includes, for example, the enzyme activities necessary to carryout the reactions shown as steps 9, 12 and 13 in FIG. 1, where the aldehyde and alcohol dehydrogenases can be separate enzymes or a multifunctional enzyme having both aldehyde and alcohol dehydrogenase activity. Another such pathway includes, for example, the enzyme activities necessary to carry out the reactions shown as steps 10, 11, 12 and 13 in FIG. 1, also where the aldehyde and alcohol dehydrogenases can be separate enzymes or a multifunctional enzyme having both aldehyde and alcohol dehydrogenase activity. Accordingly, the additional BDO pathways to introduce into 4-HB producers include, for example, the exogenous expression in a host deficient background or the overexpression of one or more of a 4-hydroxybutyrate:CoA transferase, butyrate kinase, phosphotransbutyrylase, CoA-independent aldehyde dehydrogenase, CoA-dependent aldehyde dehydrogenase or an alcohol dehydrogenase. In the absence of endogenous acyl-CoA synthetase capable of modifying 4-HB, the non-naturally occurring BDO producing microbial organisms can further include an exogenous acyl-CoA synthetase selective for 4-HB, or the combination of multiple enzymes that have as a net reaction conversion of 4-HB into 4-HB-CoA. As exemplified further below in the Examples, butyrate kinase and phosphotransbutyrylase exhibit BDO pathway activity and catalyze the conversions illustrated in FIG. 1 with a 4-HB substrate. Therefore, these enzymes also can be referred to herein as 4-hydroxybutyrate kinase and phosphotranshydroxybutyrylase respectively.

Exemplary alcohol and aldehyde dehydrogenases that can be used for these in vivo conversions from 4-HB to BDO are listed below in Table 1.

TABLE 1

Alcohol and Aldehyde Dehydrogenases for Conversion of 4-HB to BDO.

| ALCOHOL DEHYDROGENASES | |
|---|---|
| ec:1.1.1.1 | alcohol dehydrogenase |
| ec:1.1.1.2 | alcohol dehydrogenase (NADP+) |

TABLE 1-continued

Alcohol and Aldehyde Dehydrogenases for Conversion of 4-HB to BDO.

| EC number | Enzyme name |
|---|---|
| ec:1.1.1.4 | (R,R)-butanediol dehydrogenase |
| ec:1.1.1.5 | acetoin dehydrogenase |
| ec:1.1.1.6 | glycerol dehydrogenase |
| ec:1.1.1.7 | propanediol-phosphate dehydrogenase |
| ec:1.1.1.8 | glycerol-3-phosphate dehydrogenase (NAD+) |
| ec:1.1.1.11 | D-arabinitol 4-dehydrogenase |
| ec:1.1.1.12 | L-arabinitol 4-dehydrogenase |
| ec:1.1.1.13 | L-arabinitol 2-dehydrogenase |
| ec:1.1.1.14 | L-iditol 2-dehydrogenase |
| ec:1.1.1.15 | D-iditol 2-dehydrogenase |
| ec:1.1.1.16 | galactitol 2-dehydrogenase |
| ec:1.1.1.17 | mannitol-1-phosphate 5-dehydrogenase |
| ec:1.1.1.18 | inositol 2-dehydrogenase |
| ec:1.1.1.21 | aldehyde reductase |
| ec:1.1.1.23 | histidinol dehydrogenase |
| ec:1.1.1.26 | glyoxylate reductase |
| ec:1.1.1.27 | L-lactate dehydrogenase |
| ec:1.1.1.28 | D-lactate dehydrogenase |
| ec:1.1.1.29 | glycerate dehydrogenase |
| ec:1.1.1.30 | 3-hydroxybutyrate dehydrogenase |
| ec:1.1.1.31 | 3-hydroxyisobutyrate dehydrogenase |
| ec:1.1.1.35 | 3-hydroxyacyl-CoA dehydrogenase |
| ec:1.1.1.36 | acetoacetyl-CoA reductase |
| ec:1.1.1.37 | malate dehydrogenase |
| ec:1.1.1.38 | malate dehydrogenase (oxaloacetate-decarboxylating) |
| ec:1.1.1.39 | malate dehydrogenase (decarboxylating) |
| ec:1.1.1.40 | malate dehydrogenase (oxaloacetate-decarboxylating) (NADP+) |
| ec:1.1.1.41 | isocitrate dehydrogenase (NAD+) |
| ec:1.1.1.42 | isocitrate dehydrogenase (NADP+) |
| ec:1.1.1.54 | allyl-alcohol dehydrogenase |
| ec:1.1.1.55 | lactaldehyde reductase (NADPH) |
| ec:1.1.1.56 | ribitol 2-dehydrogenase |
| ec:1.1.1.59 | 3-hydroxypropionate dehydrogenase |
| ec:1.1.1.60 | 2-hydroxy-3-oxopropionate reductase |
| ec:1.1.1.61 | 4-hydroxybutyrate dehydrogenase |
| ec:1.1.1.66 | omega-hydroxydecanoate dehydrogenase |
| ec:1.1.1.67 | mannitol 2-dehydrogenase |
| ec:1.1.1.71 | alcohol dehydrogenase [NAD(P)+] |
| ec:1.1.1.72 | glycerol dehydrogenase (NADP+) |
| ec:1.1.1.73 | octanol dehydrogenase |
| ec:1.1.1.75 | (R)-aminopropanol dehydrogenase |
| ec:1.1.1.76 | (S,S)-butanediol dehydrogenase |
| ec:1.1.1.77 | lactaldehyde reductase |
| ec:1.1.1.78 | methylglyoxal reductase (NADH-dependent) |
| ec:1.1.1.79 | glyoxylate reductase (NADP+) |
| ec:1.1.1.80 | isopropanol dehydrogenase (NADP+) |
| ec:1.1.1.81 | hydroxypyruvate reductase |
| ec:1.1.1.82 | malate dehydrogenase (NADP+) |
| ec:1.1.1.83 | D-malate dehydrogenase (decarboxylating) |
| ec:1.1.1.84 | dimethylmalate dehydrogenase |
| ec:1.1.1.85 | 3-isopropylmalate dehydrogenase |
| ec:1.1.1.86 | ketol-acid reductoisomerase |
| ec:1.1.1.87 | homoisocitrate dehydrogenase |
| ec:1.1.1.88 | hydroxymethylglutaryl-CoA reductase |
| ec:1.1.1.90 | aryl-alcohol dehydrogenase |
| ec:1.1.1.91 | aryl-alcohol dehydrogenase (NADP+) |
| ec:1.1.1.92 | oxaloglycolate reductase (decarboxylating) |
| ec:1.1.1.94 | glycerol-3-phosphate dehydrogenase [NAD(P)+] |
| ec:1.1.1.95 | phosphoglycerate dehydrogenase |
| ec:1.1.1.97 | 3-hydroxybenzyl-alcohol dehydrogenase |
| ec:1.1.1.101 | acylglycerone-phosphate reductase |
| ec:1.1.1.103 | L-threonine 3-dehydrogenase |
| ec:1.1.1.104 | 4-oxoproline reductase |
| ec:1.1.1.105 | retinol dehydrogenase |
| ec:1.1.1.110 | indolelactate dehydrogenase |
| ec:1.1.1.112 | indanol dehydrogenase |
| ec:1.1.1.113 | L-xylose 1-dehydrogenase |
| ec:1.1.1.129 | L-threonate 3-dehydrogenase |
| ec:1.1.1.137 | ribitol-5-phosphate 2-dehydrogenase |
| ec:1.1.1.138 | mannitol 2-dehydrogenase (NADP+) |
| ec:1.1.1.140 | sorbitol-6-phosphate 2-dehydrogenase |
| ec:1.1.1.142 | D-pinitol dehydrogenase |
| ec:1.1.1.143 | sequoyitol dehydrogenase |
| ec:1.1.1.144 | perillyl-alcohol dehydrogenase |
| ec:1.1.1.156 | glycerol 2-dehydrogenase (NADP+) |
| ec:1.1.1.157 | 3-hydroxybutyryl-CoA dehydrogenase |
| ec:1.1.1.163 | cyclopentanol dehydrogenase |
| ec:1.1.1.164 | hexadecanol dehydrogenase |
| ec:1.1.1.165 | 2-alkyn-1-ol dehydrogenase |
| ec:1.1.1.166 | hydroxycyclohexanecarboxylate dehydrogenase |
| ec:1.1.1.167 | hydroxymalonate dehydrogenase |
| ec:1.1.1.174 | cyclohexane-1,2-diol dehydrogenase |
| ec:1.1.1.177 | glycerol-3-phosphate 1-dehydrogenase (NADP+) |
| ec:1.1.1.178 | 3-hydroxy-2-methylbutyryl-CoA dehydrogenase |
| ec:1.1.1.185 | L-glycol dehydrogenase |
| ec:1.1.1.190 | indole-3-acetaldehyde reductase (NADH) |
| ec:1.1.1.191 | indole-3-acetaldehyde reductase (NADPH) |
| ec:1.1.1.192 | long-chain-alcohol dehydrogenase |
| ec:1.1.1.194 | coniferyl-alcohol dehydrogenase |
| ec:1.1.1.195 | cinnamyl-alcohol dehydrogenase |
| ec:1.1.1.198 | (+)-borneol dehydrogenase |
| ec:1.1.1.202 | 1,3-propanediol dehydrogenase |
| ec:1.1.1.207 | (−)-menthol dehydrogenase |
| ec:1.1.1.208 | (+)-neomenthol dehydrogenase |
| ec:1.1.1.216 | farnesol dehydrogenase |
| ec:1.1.1.217 | benzyl-2-methyl-hydroxybutyrate dehydrogenase |
| ec:1.1.1.222 | (R)-4-hydroxyphenyllactate dehydrogenase |
| ec:1.1.1.223 | isopiperitenol dehydrogenase |
| ec:1.1.1.226 | 4-hydroxycyclohexanecarboxylate dehydrogenase |
| ec:1.1.1.229 | diethyl 2-methyl-3-oxosuccinate reductase |
| ec:1.1.1.237 | hydroxyphenylpyruvate reductase |
| ec:1.1.1.244 | methanol dehydrogenase |
| ec:1.1.1.245 | cyclohexanol dehydrogenase |
| ec:1.1.1.250 | D-arabinitol 2-dehydrogenase |
| ec:1.1.1.251 | galactitol 1-phosphate 5-dehydrogenase |
| ec:1.1.1.255 | mannitol dehydrogenase |
| ec:1.1.1.256 | fluoren-9-ol dehydrogenase |
| ec:1.1.1.257 | 4-(hydroxymethyl)benzenesulfonate dehydrogenase |
| ec:1.1.1.258 | 6-hydroxyhexanoate dehydrogenase |
| ec:1.1.1.259 | 3-hydroxypimeloyl-CoA dehydrogenase |
| ec:1.1.1.261 | glycerol-1-phosphate dehydrogenase [NAD(P)+] |
| ec:1.1.1.265 | 3-methylbutanal reductase |
| ec:1.1.1.283 | methylglyoxal reductase (NADPH-dependent) |
| ec:1.1.1.286 | isocitrate-homoisocitrate dehydrogenase |

TABLE 1-continued

Alcohol and Aldehyde Dehydrogenases for Conversion of 4-HB to BDO.

| | |
|---|---|
| ec:1.1.1.287 | D-arabinitol dehydrogenase (NADP+) |
| | butanol dehydrogenase |
| ALDEHYDE DEHYDROGENASES | |
| ec:1.2.1.2 | formate dehydrogenase |
| ec:1.2.1.3 | aldehyde dehydrogenase (NAD+) |
| ec:1.2.1.4 | aldehyde dehydrogenase (NADP+) |
| ec:1.2.1.5 | aldehyde dehydrogenase [NAD(P)+] |
| ec:1.2.1.7 | benzaldehyde dehydrogenase (NADP+) |
| ec:1.2.1.8 | betaine-aldehyde dehydrogenase |
| ec:1.2.1.9 | glyceraldehyde-3-phosphate dehydrogenase (NADP+) |
| ec:1.2.1.10 | acetaldehyde dehydrogenase (acetylating) |
| ec:1.2.1.11 | aspartate-semialdehyde dehydrogenase |
| ec:1.2.1.12 | glyceraldehyde-3-phosphate dehydrogenase (phosphorylating) |
| ec:1.2.1.13 | glyceraldehyde-3-phosphate dehydrogenase (NADP+) (phosphorylating) |
| ec:1.2.1.15 | malonate-semialdehyde dehydrogenase |
| ec:1.2.1.16 | succinate-semialdehyde dehydrogenase [NAD(P)+] |
| ec:1.2.1.17 | glyoxylate dehydrogenase (acylating) |
| ec:1.2.1.18 | malonate-semialdehyde dehydrogenase (acetylating) |
| ec:1.2.1.19 | aminobutyraldehyde dehydrogenase |
| ec:1.2.1.20 | glutarate-semialdehyde dehydrogenase |
| ec:1.2.1.21 | glycolaldehyde dehydrogenase |
| ec:1.2.1.22 | lactaldehyde dehydrogenase |
| ec:1.2.1.23 | 2-oxoaldehyde dehydrogenase (NAD+) |
| ec:1.2.1.24 | succinate-semialdehyde dehydrogenase |
| ec:1.2.1.25 | 2-oxoisovalerate dehydrogenase (acylating) |
| ec:1.2.1.26 | 2,5-dioxovalerate dehydrogenase |
| ec:1.2.1.27 | methylmalonate-semialdehyde dehydrogenase (acylating) |
| ec:1.2.1.28 | benzaldehyde dehydrogenase (NAD+) |
| ec:1.2.1.29 | aryl-aldehyde dehydrogenase |
| ec:1.2.1.30 | aryl-aldehyde dehydrogenase (NADP+) |
| ec:1.2.1.31 | L-aminoadipate-semialdehyde dehydrogenase |
| ec:1.2.1.32 | aminomuconate-semialdehyde dehydrogenase |
| ec:1.2.1.36 | retinal dehydrogenase |
| ec:1.2.1.39 | phenylacetaldehyde dehydrogenase |
| ec:1.2.1.41 | glutamate-5-semialdehyde dehydrogenase |
| ec:1.2.1.42 | hexadecanal dehydrogenase (acylating) |
| ec:1.2.1.43 | formate dehydrogenase (NADP+) |
| ec:1.2.1.45 | 4-carboxy-2-hydroxymuconate-6-semialdehyde dehydrogenase |
| ec:1.2.1.46 | formaldehyde dehydrogenase |
| ec:1.2.1.47 | 4-trimethylammoniobutyraldehyde dehydrogenase |
| ec:1.2.1.48 | long-chain-aldehyde dehydrogenase |
| ec:1.2.1.49 | 2-oxoaldehyde dehydrogenase (NADP+) |
| ec:1.2.1.51 | pyruvate dehydrogenase (NADP+) |
| ec:1.2.1.52 | oxoglutarate dehydrogenase (NADP+) |
| ec:1.2.1.53 | 4-hydroxyphenylacetaldehyde dehydrogenase |
| ec:1.2.1.57 | butanal dehydrogenase |
| ec:1.2.1.58 | phenylglyoxylate dehydrogenase (acylating) |
| ec:1.2.1.59 | glyceraldehyde-3-phosphate dehydrogenase (NAD(P)+) (phosphorylating) |
| ec:1.2.1.62 | 4-formylbenzenesulfonate dehydrogenase |
| ec:1.2.1.63 | 6-oxohexanoate dehydrogenase |
| ec:1.2.1.64 | 4-hydroxybenzaldehyde dehydrogenase |
| ec:1.2.1.65 | salicylaldehyde dehydrogenase |
| ec:1.2.1.66 | mycothiol-dependent formaldehyde dehydrogenase |
| ec:1.2.1.67 | vanillin dehydrogenase |
| ec:1.2.1.68 | coniferyl-aldehyde dehydrogenase |
| ec:1.2.1.69 | fluoroacetaldehyde dehydrogenase |
| ec:1.2.1.71 | succinylglutamate-semialdehyde dehydrogenase |

Other exemplary enzymes and pathways are disclosed herein (see Examples). Furthermore, it is understood that enzymes can be utilized for carry out reactions for which the substrate is not the natural substrate. While the activity for the non-natural substrate may be lower than the natural substrate, it is understood that such enzymes can be utilized, either as naturally occurring or modified using the directed evolution or adaptive evolution, as disclosed herein (see also Examples).

BDO production through any of the pathways disclosed herein are based, in part, on the identification of the appropriate enzymes for conversion of precursors to BDO. A number of specific enzymes for several of the reaction steps have been identified. For those transformations where enzymes specific to the reaction precursors have not been identified, enzyme candidates have been identified that are best suited for catalyzing the reaction steps. Enzymes have been shown to operate on a broad range of substrates, as discussed below. In addition, advances in the field of protein engineering also make it feasible to alter enzymes to act efficiently on substrates, even if not a natural substrate. Described below are several examples of broad-specificity enzymes from diverse classes suitable for a BDO pathway as well as methods that have been used for evolving enzymes to act on non-natural substrates.

A key class of enzymes in BDO pathways is the oxidoreductases that interconvert ketones or aldehydes to alcohols (1.1.1). Numerous exemplary enzymes in this class can operate on a wide range of substrates. An alcohol dehydrogenase (1.1.1.1) purified from the soil bacterium *Brevibacterium* sp KU 1309 (Hirano et al., *J. Biosc. Bioeng.* 100: 318-322 (2005)) was shown to operate on a plethora of aliphatic as well as aromatic alcohols with high activities. Table 2 shows the activity of the enzyme and its $K_m$ on different alcohols. The enzyme is reversible and has very high activity on several aldehydes also (Table 3).

TABLE 2

Relative activities of an alcohol dehydrogenase from *Brevibacterium* sp KU to oxidize various alcohols.

| Substrate | Relative Activity (0%) | $K_m$ (mM) |
|---|---|---|
| 2-Phenylethanol | 100* | 0.025 |
| (S)-2-Phenylpropanol | 156 | 0.157 |
| (R)-2-Phenylpropanol | 63 | 0.020 |
| Bynzyl alcohol | 199 | 0.012 |

TABLE 2-continued

Relative activities of an alcohol dehydrogenase
from Brevibacterium sp KU to oxidize various alcohols.

| Substrate | Relative Activity (0%) | $K_m$ (mM) |
|---|---|---|
| 3-Phenylpropanol | 135 | 0.033 |
| Ethanol | 76 | |
| 1-Butanol | 111 | |
| 1-Octanol | 101 | |
| 1-Dodecanol | 68 | |
| 1-Phenylethanol | 46 | |
| 2-Propanol | 54 | |

*The activity of 2-phenylethanol, corresponding to 19.2 U/mg, was taken as 100%.

TABLE 3

Relative activities of an alcohol dehydrogenase
from Brevibacterium sp KU 1309 to
reduce various carbonyl compounds.

| Substrate | Relative Activity (%) | $K_m$ (mM) |
|---|---|---|
| Phenylacetaldehyde | 100 | 0.261 |
| 2-Phenylpropionaldehyde | 188 | 0.864 |
| 1-Octylaldehyde | 87 | |
| Acetophenone | 0 | |

Lactate dehydrogenase (1.1.1.27) from *Ralstonia eutropha* is another enzyme that has been demonstrated to have high activities on several 2-oxoacids such as 2-oxobutyrate, 2-oxopentanoate and 2-oxoglutarate (a C5 compound analogous to 2-oxoadipate) (Steinbuchel and Schlegel, *Eur. J. Biochem.* 130:329-334 (1983)). Column 2 in Table 4 demonstrates the activities of ldhA from *R. eutropha* (formerly *A. eutrophus*) on different substrates (Steinbuchel and Schlegel, supra, 1983).

TABLE 4

The in vitro activity of *R. eutropha* ldhA (Steinbuchel and Schlegel, supra, 1983) on different substrates and compared with that on pyruvate.

| | Activity (%) of | | |
|---|---|---|---|
| Substrate | L(+)-lactate dehydrogenase from *A. eutrophus* | L(+)-lactate dehydrogenase from rabbit muscle | D(−)-lactate dehydrogenase from *L. leichmanii* |
| Glyoxylate | 8.7 | 23.9 | 5.0 |
| Pyruvate | 100.0 | 100.0 | 100.0 |
| 2-Oxobutyrate | 107.0 | 18.6 | 1.1 |
| 2-Oxovalerate | 125.0 | 0.7 | 0.0 |
| 3-Methyl-2-oxobutyrate | 28.5 | 0.0 | 0.0 |
| 3-Methyl-2-oxovalerate | 5.3 | 0.0 | 0.0 |
| 4-Methyl-2-oxopentanoate | 39.0 | 1.4 | 1.1 |
| Oxaloacetate | 0.0 | 33.1 | 23.1 |
| 2-Oxoglutarate | 79.6 | 0.0 | 0.0 |
| 3-Fluoropyruvate | 33.6 | 74.3 | 40.0 |

Oxidoreductases that can convert 2-oxoacids to their acyl-CoA counterparts (1.2.1) have been shown to accept multiple substrates as well. For example, branched-chain 2-keto-acid dehydrogenase complex (BCKAD), also known as 2-oxoisovalerate dehydrogenase (1.2.1.25), participates in branched-chain amino acid degradation pathways, converting 2-keto acids derivatives of valine, leucine and isoleucine to their acyl-CoA derivatives and $CO_2$. In some organisms including *Rattus norvegicus* (Paxton et al., *Biochem. J.* 234:295-303 (1986)) and *Saccharomyces cerevisiae* (Sinclair et al., *Biochem. Mol Biol. Int.* 32:911-922 (1993)), this complex has been shown to have a broad substrate range that includes linear oxo-acids such as 2-oxobutanoate and alpha-ketoglutarate, in addition to the branched-chain amino acid precursors.

Members of yet another class of enzymes, namely aminotransferases (2.6.1), have been reported to act on multiple substrates. Aspartate aminotransferase (aspAT) from *Pyrococcus fursious* has been identified, expressed in *E. coli* and the recombinant protein characterized to demonstrate that the enzyme has the highest activities towards aspartate and alpha-ketoglutarate but lower, yet significant activities towards alanine, glutamate and the aromatic amino acids (Ward et al., *Archaea* 133-141 (2002)). In another instance, an aminotransferase identified from *Leishmania mexicana* and expressed in *E. coli* (Vernal et al., *FEMS Microbiol. Lett.* 229:217-222 (2003)) was reported to have a broad substrate specificity towards tyrosine (activity considered 100% on tyrosine), phenylalanine (90%), tryptophan (85%), aspartate (30%), leucine (25%) and methionine (25%), respectively (Vernal et al., *Mol. Biochem. Parasitol* 96:83-92 (1998)). Similar broad specificity has been reported for a tyrosine aminotransferase from *Trypanosoma cruzi*, even though both of these enzymes have a sequence homology of only 6%. The latter enzyme can accept leucine, methionine as well as tyrosine, phenylalanine, tryptophan and alanine as efficient amino donors (Nowicki et al., *Biochim. Biophys. Acta* 1546: 268-281 (2001)).

CoA transferases (2.8.3) have been demonstrated to have the ability to act on more than one substrate. Specifically, a CoA transferase was purified from *Clostridium acetobutylicum* and was reported to have the highest activities on acetate, propionate, and butyrate. It also had significant activities with valerate, isobutyrate, and crotonate (Wiesenborn et al., *Appl. Environ. Microbiol.* 55:323-329 (1989)). In another study, the *E. coli* enzyme acyl-CoA:acetate-CoA transferase, also known as acetate-CoA transferase (EC 2.8.3.8), has been shown to transfer the CoA moiety to acetate from a variety of branched and linear acyl-CoA substrates, including isobutyrate (Matthies and Schink, *App. Environm. Microbiol.* 58:1435-1439 (1992)), valerate (Vanderwinkel et al., *Biochem. Biophys. Res Commun.* 33:902-908 (1968b)) and butanoate (Vanderwinkel et al., *Biochem. Biophys. Res Commun.* 33:902-908(1968a)).

Other enzyme classes additionally support broad substrate specificity for enzymes. Some isomerases (5.3.3) have also been proven to operate on multiple substrates. For example, L-rhamnose isomerase from *Pseudomonas stutzeri* catalyzes the isomerization between various aldoalses and ketoses (Yoshida et al., *J. Mol. Biol.* 365:1505-1516 (2007)). These include isomerization between L-rhamnose and L-rhamnulose, L-mannose and L-fructose, L-xylose and L-xylulose, D-ribose and D-ribulose, and D-allose and D-psicose.

In yet another class of enzymes, the phosphotransferases (2.7.1), the homoserine kinase (2.7.1.39) from *E. coli* that converts L-homoserine to L-homoserine phosphate, was found to phosphorylate numerous homoserine analogs. In these substrates, the carboxyl functional group at the R-position had been replaced by an ester or by a hydroxymethyl group (Huo and Viola, *Biochemistry* 35:16180-16185 (1996)). Table 5 demonstrates the broad substrate specificity of this kinase.

TABLE 5

The substrate specificity of homoserine kinase.

| Substrate | $k_{cat}$ | % $k_{cat}$ | $K_m$ (mM) | $k_{cat}/K_m$ |
|---|---|---|---|---|
| L-homoserine | 18.3 ± 0.1 | 100 | 0.14 ± 0.04 | 184 ± 17 |
| D-homoserine | 8.3 ± 1.1 | 32 | 31.8 ± 7.2 | 0.26 ± 0.03 |
| L-aspartate β-semialdehyde | 2.1 ± 0.1 | 8.2 | 0.28 ± 0.02 | 7.5 ± 0.3 |
| L-2-amino-1,4-butanediol | 2.0 ± 0.5 | 7.9 | 11.6 ± 6.5 | 0.17 ± 0.06 |
| L-2-amino-5-hydroxyvalerate | 2.5 ± 0.4 | 9.9 | 1.1 ± 0.5 | 2.3 ± 0.3 |
| L-homoserine methyl ester | 14.7 ± 2.6 | 80 | 4.9 ± 2.0 | 3.0 ± 0.6 |
| L-homoserine ethyl ester | 13.6 ± 0.8 | 74 | 1.9 ± 0.5 | 7.2 ± 1.7 |
| L-homoserine isopropyl ester | 13.6 ± 1.4 | 74 | 1.2 ± 0.5 | 11.3 ± 1.1 |
| L-homoserine n-propyl ester | 14.0 ± 0.4 | 76 | 3.5 ± 0.4 | 4.0 ± 1.2 |
| L-homoserine isobutyl ester | 16.4 ± 0.8 | 84 | 6.9 ± 1.1 | 2.4 ± 0.3 |
| L-homserine n-butyl ester | 29.1 ± 1.2 | 160 | 5.8 ± 0.8 | 5.0 ± 0.5 |

Another class of enzymes useful in BDO pathways is the acid-thiol ligases (6.2.1). Like enzymes in other classes, certain enzymes in this class have been determined to have broad substrate specificity. For example, acyl CoA ligase from *Pseudomonas putida* has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., *Appl. Environ. Microbiol.* 59:1149-1154 (1993)). A related enzyme, malonyl CoA synthetase (6.3.4.9) from *Rhizobium trifolii* could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., *J. Am. Chem. Soc.* 123:5822-5823 (2001)). Similarly, decarboxylases (4.1.1) have also been found with broad substrate ranges. Pyruvate decarboxylase (PDC), also termed keto-acid decarboxylase, is a key enzyme in alcoholic fermentation, catalyzing the decarboxylation of pyruvate to acetaldehyde. The enzyme isolated from *Saccharomyces cerevisiae* has a broad substrate range for aliphatic 2-keto acids including 2-ketobutyrate, 2-ketovalerate, and 2-phenylpyruvate (Li and Jordan, *Biochemistry* 38:10004-10012 (1999)). Similarly, benzoylformate decarboxylase has a broad substrate range and has been the target of enzyme engineering studies. The enzyme from *Pseudomonas putida* has been extensively studied and crystal structures of this enzyme are available (Polovnikova et al., *Biochemistry* 42:1820-1830 (2003); Hasson et al., *Biochemistry* 37:9918-9930 (1998)). Branched chain alpha-ketoacid decarboxylase (BCKA) has been shown to act on a variety of compounds varying in chain length from 3 to 6 carbons (Oku and Kaneda, *J. Biol. Chem.* 263:18386-18396 (1998); Smit et al., *Appl. Environ. Microbiol.* 71:303-311 (2005b)). The enzyme in *Lactococcus lactis* has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., *Appl. Environ. Microbiol.* 71:303-311 (2005a)).

Interestingly, enzymes known to have one dominant activity have also been reported to catalyze a very different function. For example, the cofactor-dependent phosphoglycerate mutase (5.4.2.1) from *Bacillus stearothermophilus* and *Bacillus subtilis* is known to function as a phosphatase as well (Rigden et al., *Protein Sci.* 10:1835-1846 (2001)). The enzyme from *B. stearothermophilus* is known to have activity on several substrates, including 3-phosphoglycerate, alpha-napthylphosphate, p-nitrophenylphosphate, AMP, fructose-6-phosphate, ribose-5-phosphate and CMP.

In contrast to these examples where the enzymes naturally have broad substrate specificities, numerous enzymes have been modified using directed evolution to broaden their specificity towards their non-natural substrates. Alternatively, the substrate preference of an enzyme has also been changed using directed evolution. Therefore, it is feasible to engineer a given enzyme for efficient function on a natural, for example, improved efficiency, or a non-natural substrate, for example, increased efficiency. For example, it has been reported that the enantioselectivity of a lipase from *Pseudomonas aeruginosa* was improved significantly (Reetz et al., *Agnew. Chem. Int. Ed Engl.* 36:2830-2832 (1997)). This enzyme hydrolyzed p-nitrophenyl 2-methyldecanoate with only 2% enantiomeric excess (ee) in favor of the (S)-acid. However, after four successive rounds of error-prone mutagenesis and screening, a variant was produced that catalyzed the requisite reaction with 81% ee (Reetz et al., *Agnew. Chem. Int. Ed Engl.* 36:2830-2832 (1997)).

Directed evolution methods have been used to modify an enzyme to function on an array of non-natural substrates. The substrate specificity of the lipase in *P. aeruginosa* was broadened by randomization of amino acid residues near the active site. This allowed for the acceptance of alpha-substituted carboxylic acid esters by this enzyme (Reetz et al., *Agnew. Chem. Int. Ed Engl.* 44:4192-4196 (2005)). In another successful modification of an enzyme, DNA shuffling was employed to create an *Escherichia coli* aminotransferase that accepted β-branched substrates, which were poorly accepted by the wild-type enzyme (Yano et al., *Proc. Nat. Acad. Sci. U.S.A.* 95:5511-5515 (1998)). Specifically, at the end of four rounds of shuffling, the activity of aspartate aminotransferase for valine and 2-oxovaline increased by up to five orders of magnitude, while decreasing the activity towards the natural substrate, aspartate, by up to 30-fold. Recently, an algorithm was used to design a retro-aldolase that could be used to catalyze the carbon-carbon bond cleavage in a non-natural and non-biological substrate, 4-hydroxy-4-(6-methoxy-2-naphthyl)-2-butanone (Jiang et al., *Science* 319:1387-1391 (2008)). These algorithms used different combinations of four different catalytic motifs to design new enzyme, and 20 of the selected designs for experimental characterization had four-fold improved rates over the uncatalyzed reaction (Jiang et al., *Science* 319: 1387-1391 (2008)). Thus, not only are these engineering approaches capable of expanding the array of substrates on which an enzyme can act, but they allow the design and construction of very efficient enzymes. For example, a method of DNA shuffling (random chimeragenesis on transient templates or RACHITT) was reported to lead to an engineered monooxygenase that had an improved rate of desulfurization on complex substrates as well as 20-fold faster conversion of a non-natural substrate (Coco et al., *Nat. Biotechnol.* 19:354-359 (2001)). Similarly, the specific activity of a sluggish mutant triosephosphate isomerase enzyme was improved up to 19-fold from 1.3 fold (Hermes et al., *Proc. Nat. Acad. Sci. U.S.A.* 87:696-700 1990)). This enhancement in specific activity was accomplished by using random mutagenesis over the whole length of the protein and the improvement could be traced back to mutations in six amino acid residues.

The effectiveness of protein engineering approaches to alter the substrate specificity of an enzyme for a desired substrate has also been demonstrated in several studies. Isopropylmalate dehydrogenase from *Thermus thermophilus* was modified by changing residues close to the active site so that it could now act on malate and D-lactate as substrates (Fujita et al., *Biosci. Biotechnol. Biochem.* 65:2695-2700 (2001)). In this study as well as in others, it was pointed out that one or a few residues could be modified to alter the substrate specificity. For example, the dihydroflavonol 4-reductase for which a single amino acid was changed in the presumed substrate-binding region could preferentially reduce dihydrokaempferol (Johnson et al., *Plant. J.* 25:325-333 (2001)). The substrate specificity of a very specific isocitrate dehydrogenase from *Escherichia coli* was changed form isocitrate to isopropylmalate by changing one residue in the active site (Doyle et al., *Biochemistry* 40:4234-4241 (2001)). Similarly, the cofactor specificity of a $NAD^+$-dependent 1,5-hydroxyprostaglandin dehydrogenase was altered to $NADP^+$ by changing a few residues near the N-terminal end (Cho et al., *Arch. Biochem. Biophys.* 419:139-146 (2003)). Sequence analysis and molecular modeling analysis were used to identify the key residues for modification, which were further studied by site-directed mutagenesis.

Numerous examples exist spanning diverse classes of enzymes where the function of enzyme was changed to favor one non-natural substrate over the natural substrate of the enzyme. A fucosidase was evolved from a galactosidase in *E. coli* by DNA shuffling and screening (Zhang et al., *Proc. Natl Acad. Sci. U.S.A.* 94:4504-4509 (1997)). Similarly, aspartate aminotransferase from *E. coli* was converted into a tyrosine aminotransferase using homology modeling and site-directed mutagenesis (Onuffer and Kirsch, *Protein Sci.*, 4:1750-1757 (1995)). Site-directed mutagenesis of two residues in the active site of benzoylformate decarboxylase from *P. putida* reportedly altered the affinity ($K_m$) towards natural and non-natural substrates (Siegert et al., *Protein Eng Des Sel* 18:345-357 (2005)). Cytochrome c peroxidase (CCP) from *Saccharomyces cerevisiae* was subjected to directed molecular evolution to generate mutants with increased activity against the classical peroxidase substrate guaiacol, thus changing the substrate specificity of CCP from the protein cytochrome c to a small organic molecule. After three rounds of DNA shuffling and screening, mutants were isolated which possessed a 300-fold increased activity against guaiacol and up to 1000-fold increased specificity for this substrate relative to that for the natural substrate (Iffland et al., *Biochemistry* 39:10790-10798 (2000)).

In some cases, enzymes with different substrate preferences than either of the parent enzymes have been obtained. For example, biphenyl-dioxygenase-mediated degradation of polychlorinated biphenyls was improved by shuffling genes from two bacteria, *Pseudomonas pseudoalcaligens* and *Burkholderia cepacia* (Kumamaru et al., *Nat. Biotechnol.* 16:663-666 (1998)). The resulting chimeric biphenyl oxygenases showed different substrate preferences than both the parental enzymes and enhanced the degradation activity towards related biphenyl compounds and single aromatic ring hydrocarbons such as toluene and benzene which were originally poor substrates for the enzyme.

In addition to changing enzyme specificity, it is also possible to enhance the activities on substrates for which the enzymes naturally have low activities. One study demonstrated that amino acid racemase from *P. putida* that had broad substrate specificity (on lysine, arginine, alanine, serine, methionine, cysteine, leucine and histidine among others) but low activity towards tryptophan could be improved significantly by random mutagenesis (Kino et al., *Appl. Microbiol. Biotechnol.* 73:1299-1305 (2007)). Similarly, the active site of the bovine BCKAD was engineered to favor alternate substrate acetyl-CoA (Meng and Chuang, *Biochemistry* 33:12879-12885 (1994)). An interesting aspect of these approaches is that even if random methods have been applied to generate these mutated enzymes with efficacious activities, the exact mutations or structural changes that confer the improvement in activity can be identified. For example, in the aforementioned study, the mutations that facilitated improved activity on tryptophan was traced back to two different positions.

Directed evolution has also been used to express proteins that are difficult to express. For example, by subjecting horseradish peroxidase to random mutagenesis and gene recombination, mutants were identified that had more than 14-fold higher activity than the wild type (Lin et al., *Biotechnol. Prog.* 15:467-471 (1999)).

Another example of directed evolution shows the extensive modifications to which an enzyme can be subjected to achieve a range of desired functions. The enzyme lactate dehydrogenase from *Bacillus stearothermophilus* was subjected to site-directed mutagenesis, and three amino acid substitutions were made at sites that were believed to determine the specificity towards different hydroxyacids (Clarke et al., *Biochem. Biophys. Res. Commun.* 148:15-23 (1987)). After these mutations, the specificity for oxaloacetate over pyruvate was increased to 500 in contrast to the wild type enzyme that had a catalytic specificity for pyruvate over oxaloacetate of 1000. This enzyme was further engineered using site-directed mutagenesis to have activity towards branched-chain substituted pyruvates (Wilks et al., *Biochemistry* 29:8587-8591 (1990)). Specifically, the enzyme had a 55-fold improvement in $K_{cat}$ for alpha-ketoisocaproate. Three structural modifications were made in the same enzyme to change its substrate specificity from lactate to malate. The enzyme was highly active and specific towards malate (Wilks et al., *Science* 242:1541-1544 (1988)). The same enzyme from *B. stearothermophilus* was subsequently engineered to have high catalytic activity towards alpha-keto acids with positively charged side chains, such as those containing ammonium groups (Hogan et al., *Biochemistry* 34:4225-4230 (1995)). Mutants with acidic amino acids introduced at position 102 of the enzyme favored binding of such side chain ammonium groups. The results obtained proved that the mutants showed up to 25-fold improvements in $k_{cat}/K_m$ values for omega-amino-alpha-keto acid substrates. Interestingly, this enzyme was also structurally modified to function as a phenyllactate dehydrogenase instead of a lactate dehydrogenase (Wilks et al., *Biochemistry* 31:7802-7806 1992). Restriction sites were introduced into the gene for the enzyme which allowed a region of the gene to be excised. This region coded for a mobile surface loop of the polypeptide (residues 98-110) which normally seals the active site from bulk solvent and is a major determinant of substrate specificity. The variable length and sequence loops were inserted so that hydroxyacid dehydrogenases with altered substrate specificities were generated. With one longer loop construction, activity with pyruvate was reduced one-million-fold but activity with phenylpyruvate was largely unaltered. A switch in specificity ($k_{cat}/K_m$) of 390,000-fold was achieved. The 1700:1 selectivity of this enzyme for phenylpyruvate over pyruvate is that required in a phenyllactate dehydrogenase. The studies described above indicate that various approaches of enzyme engineering can be used to obtain enzymes for the BDO pathways as disclosed herein.

As disclosed herein, biosynthetic pathways to 1,4-butanediol from a number of central metabolic intermediates are can be utilized, including acetyl-CoA, succinyl-CoA, alpha-ketoglutarate, glutamate, 4-aminobutyrate, and homoserine. Acetyl-CoA, succinyl-CoA and alpha-ketoglutarate are common intermediates of the tricarboxylic acid (TCA) cycle, a series of reactions that is present in its entirety in nearly all living cells that utilize oxygen for cellular respiration and is present in truncated forms in a number of anaerobic organisms. Glutamate is an amino acid that is derived from alpha-ketoglutarate via glutamate dehydrogenase or any of a number of transamination reactions (see FIG. 8B). 4-aminobutyrate can be formed by the decarboxylation of glutamate (see FIG. 8B) or from acetoacetyl-CoA via the pathway disclosed in FIG. 9C. Acetoacetyl-CoA is derived from the condensation of two acetyl-CoA molecules by way of the enzyme, acetyl-coenzyme A acetyltransferase, or equivalently, acetoacetyl-coenzyme A thiolase. Homoserine is an intermediate in threonine and methionine metabolism, formed from oxaloacetate via aspartate. The conversion of oxaloacetate to homoserine requires one NADH, two NADPH, and one ATP.

Pathways other than those exemplified above also can be employed to generate the biosynthesis of BDO in non-naturally occurring microbial organisms. In one embodiment, biosynthesis can be achieved using a L-homoserine to BDO pathway (see FIG. 13). This pathway has a molar yield of 0.90 mol/mol glucose, which appears restricted by the availability of reducing equivalents. A second pathway synthesizes BDO from acetoacetyl-CoA and is capable of achieving the maximum theoretical yield of 1.091 mol/mol glucose (see FIG. 9). Implementation of either pathway can be achieved by introduction of two exogenous enzymes into a host organism such as *E. coli*, and both pathways can additionally complement BDO production via succinyl-CoA. Pathway enzymes, thermodynamics, theoretical yields and overall feasibility are described further below.

Figure 2:
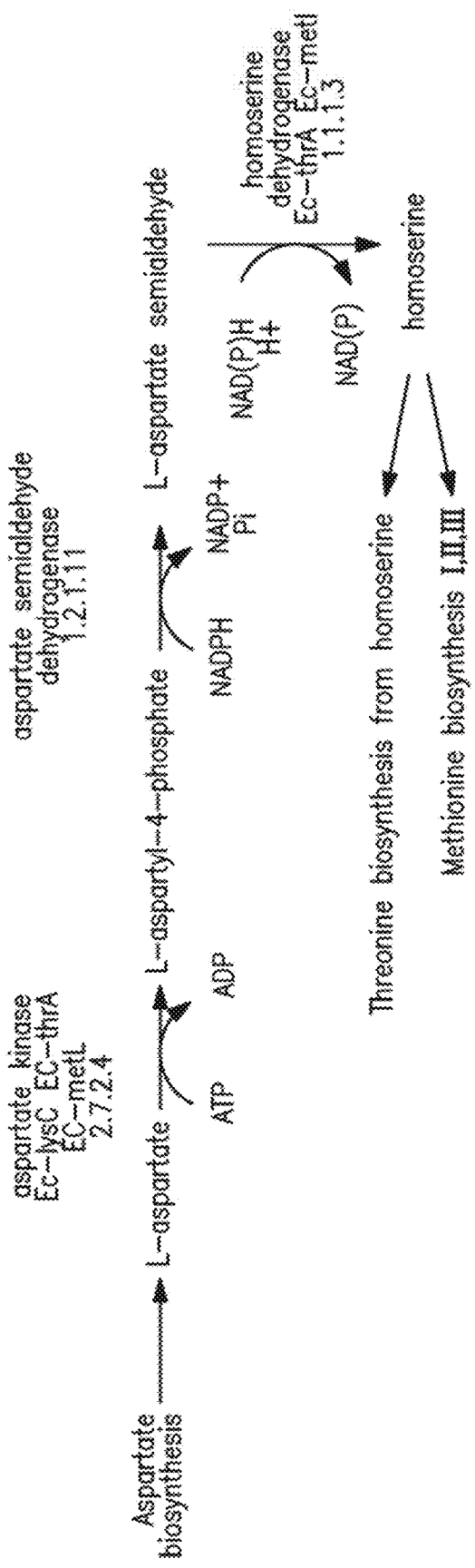
FIG. 2 is a schematic diagram showing homoserine biosynthesis in *E. coli*.

A homoserine pathway also can be engineered to generate BDO-producing microbial organisms. Homoserine is an intermediate in threonine and methionine metabolism, formed from oxaloacetate via aspartate. The conversion of oxaloacetate to homoserine requires one NADH, two NADPH, and one ATP (FIG. 2). Once formed, homoserine feeds into biosynthetic pathways for both threonine and methionine. In most organisms, high levels of threonine or methionine feedback to repress the homoserine biosynthesis pathway (Caspi et al., *Nucleic Acids Res.* 34:D511-D516 (1990)).

The transformation of homoserine to 4-hydroxybutyrate (4-HB) can be accomplished in two enzymatic steps as described herein. The first step of this pathway is deamination of homoserine by a putative ammonia lyase. In step 2, the product alkene, 4-hydroxybut-2-enoate is reduced to 4-HB by a putative reductase at the cost of one NADH. 4-HB can then be converted to BDO.

Enzymes available for catalyzing the above transformations are disclosed herein. For example, the ammonia lyase in step 1 of the pathway closely resembles the chemistry of aspartate ammonia-lyase (aspartase). Aspartase is a widespread enzyme in microorganisms, and has been characterized extensively (Viola, R. E., *Mol. Biol.* 74:295-341 (2008)). The crystal structure of the *E. coli* aspartase has been solved (Shi et al., *Biochemistry* 36:9136-9144 (1997)), so it is therefore possible to directly engineer mutations in the enzyme's active site that would alter its substrate specificity to include homoserine. The oxidoreductase in step 2 has chemistry similar to several well-characterized enzymes including fumarate reductase in the *E. coli* TCA cycle. Since the thermodynamics of this reaction are highly favorable, an endogenous reductase with broad substrate specificity will likely be able to reduce 4-hydroxybut-2-enoate. The yield of this pathway under anaerobic conditions is 0.9 mol BDO per mol glucose.

The succinyl-CoA pathway was found to have a higher yield due to the fact that it is more energetically efficient. The conversion of one oxaloacetate molecule to BDO via the homoserine pathway will require the expenditure of 2 ATP equivalents. Because the conversion of glucose to two oxaloacetate molecules can generate a maximum of 3 ATP molecules assuming PEP carboxykinase to be reversible, the overall conversion of glucose to BDO via homoserine has a negative energetic yield. As expected, if it is assumed that energy can be generated via respiration, the maximum yield of the homoserine pathway increases to 1.05 mol/mol glucose which is 96% of the succinyl-CoA pathway yield. The succinyl-CoA pathway can channel some of the carbon flux through pyruvate dehydrogenase and the oxidative branch of the TCA cycle to generate both reducing equivalents and succinyl-CoA without an energetic expenditure. Thus, it does not encounter the same energetic difficulties as the homoserine pathway because not all of the flux is channeled through oxaloacetate to succinyl-CoA to BDO. Overall, the homoserine pathway demonstrates a high-yielding route to BDO.

An acetoacetate pathway also can be engineered to generate BDO-producing microbial organisms. Acetoacetate can be formed from acetyl-CoA by enzymes involved in fatty acid metabolism, including acetyl-CoA acetyltransferase and acetoacetyl-CoA transferase. Biosynthetic routes through acetoacetate are also particularly useful in microbial organisms that can metabolize single carbon compounds such as carbon monoxide, carbon dioxide or methanol to form acetyl-CoA.

Figure 8A:
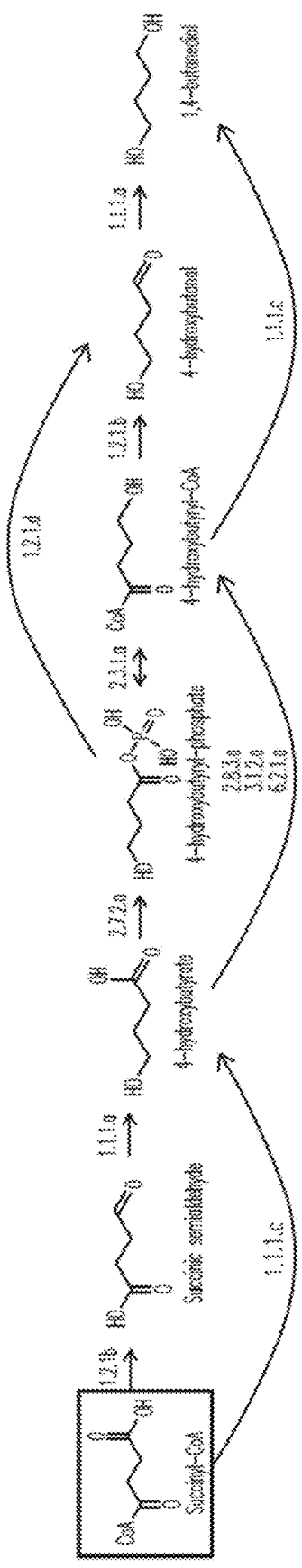
FIGS. 8A and 8B show exemplary 1,4-butanediol (BDO) pathways.
Figure 8B:
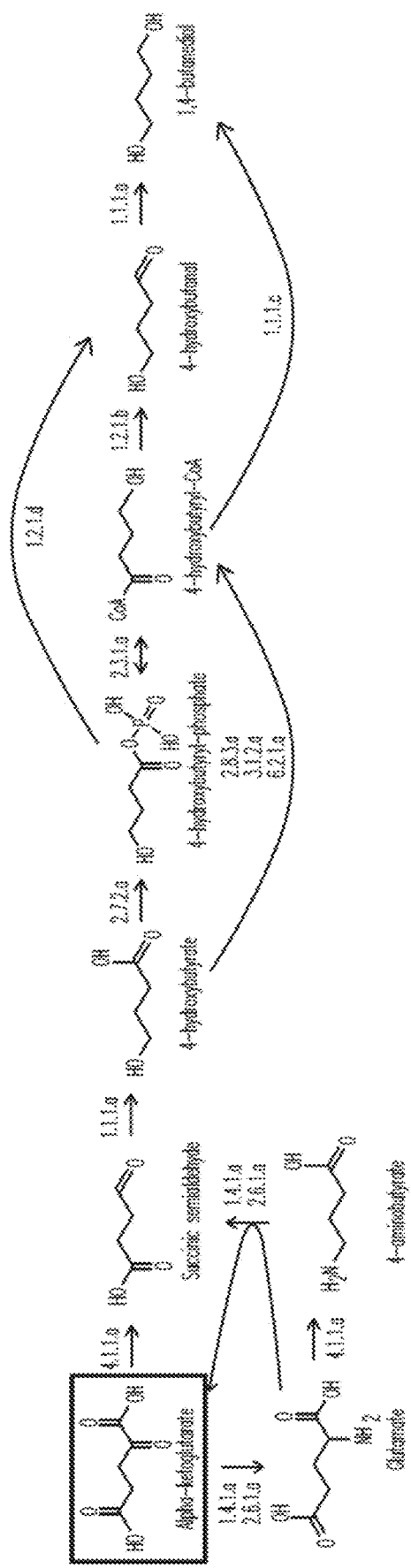

A three step route from acetoacetyl-CoA to 4-aminobutyrate (see FIG. 9C) can be used to synthesize BDO through acetoacetyl-CoA. 4-Aminobutyrate can be converted to succinic semialdehyde as shown in FIG. 8B. Succinic semialdehyde, which is one reduction step removed from succinyl-CoA or one decarboxylation step removed from α-ketoglutarate, can be converted to BDO following three reductions steps (FIG. 1). Briefly, step 1 of this pathway involves the conversion of acetoacetyl-CoA to acetoacetate by, for example, the *E. coli* acetoacetyl-CoA transferase encoded by the atoA and atoD genes (Hanai et al., *Appl. Environ. Microbiol.* 73: 7814-7818 (2007)). Step 2 of the acetoacetyl-CoA biopathway entails conversion of acetoacetate to 3-aminobutanoate by an ω-aminotransferase. The ω-amino acid:pyruvate aminotransferase (ω-APT) from *Alcaligens denitrificans* was overexpressed in *E. coli* and shown to have a high activity toward 3-aminobutanoate in vitro (Yun et al., *Appl. Environ. Microbiol.* 70:2529-2534 (2004)).

In step 2, a putative aminomutase shifts the amine group from the 3- to the 4-position of the carbon backbone. An aminomutase performing this function on 3-aminobutanoate has not been characterized, but an enzyme from *Clostridium sticklandii* has a very similar mechanism. The enzyme, D-lysine-5,6-aminomutase, is involved in lysine biosynthesis.

The synthetic route to BDO from acetoacetyl-CoA passes through 4-aminobutanoate, a metabolite in *E. coli* that's normally formed from decarboxylation of glutamate. Once formed, 4-aminobutanoate can be converted to succinic semialdehyde by 4-aminobutanoate transaminase (2.6.1.19), an enzyme which has been biochemically characterized.

One consideration for selecting candidate enzymes in this pathway is the stereoselectivity of the enzymes involved in steps 2 and 3. The ω-ABT in *Alcaligens denitrificans* is specific to the L-stereoisomer of 3-aminobutanoate, while D-lysine-5,6-aminomutase likely requires the D-stereoisomer. If enzymes with complementary stereoselectivity are not initially found or engineered, a third enzyme can be added to the pathway with racemase activity that can convert L-3-aminobutanoate to D-3-aminobutanoate. While amino acid racemases are widespread, whether these enzymes can function on ω-amino acids is not known.

The maximum theoretical molar yield of this pathway under anaerobic conditions is 1.091 mol/mol glucose. In order to generate flux from acetoacetyl-CoA to BDO it was necessary to assume that acetyl-CoA:acetoacetyl-CoA transferase is reversible. The function of this enzyme in *E. coli* is to metabolize short-chain fatty acids by first converting them into thioesters.

While the operation of acetyl-CoA:acetoacetyl-CoA transferase in the acetate-consuming direction has not been demonstrated experimentally in *E. coli*, studies on similar enzymes in other organisms support the assumption that this reaction is reversible. The enzyme butyryl-CoA:acetate:CoA transferase in gut microbes *Roseburia* sp. and *F. prasnitzii* operates in the acetate utilizing direction to produce butyrate (Duncan et al., *Appl. Environ. Microbiol* 68:5186-5190 (2002)). Another very similar enzyme, acetyl:succinate CoA-transferase in *Trypanosoma brucei*, also operates in the acetate utilizing direction. This reaction has a $\Delta_{rxn}G$ close to equilibrium, so high concentrations of acetate can likely drive the reaction in the direction of interest. At the maximum theoretical BDO production rate of 1.09 mol/mol glucose simulations predict that *E. coli* can generate 1.098 mol ATP per mol glucose with no fermentation byproducts. This ATP yield should be sufficient for cell growth, maintenance, and production. The acetoacetyl-CoA biopathway is a high-yielding route to BDO from acetyl-CoA.

Therefore, in addition to any of the various modifications exemplified previously for establishing 4-HB biosynthesis in a selected host, the BDO producing microbial organisms can include any of the previous combinations and permutations of 4-HB pathway metabolic modifications as well as any combination of expression for CoA-independent aldehyde dehydrogenase, CoA-dependent aldehyde dehydrogenase or an alcohol dehydrogenase or other enzymes disclosed herein to generate biosynthetic pathways for GBL and/or BDO. Therefore, the BDO producers of the invention can have exogenous expression of, for example, one, two, three, four, five, six, seven, eight, nine, or up to all enzymes corresponding to any of the 4-HB pathway and/or any of the BDO pathway enzymes disclosed herein.

Design and construction of the genetically modified microbial organisms is carried out using methods well known in the art to achieve sufficient amounts of expression to produce BDO. In particular, the non-naturally occurring microbial organisms of the invention can achieve biosynthesis of BDO resulting in intracellular concentrations between about 0.1-200 mM or more, such as about 0.1-25 mM or more, as discussed above. For example, the intracellular concentration of BDO is between about 3-20 mM, particularly between about 5-15 mM and more particularly between about 8-12 mM, including about 10 mM or more. Intracellular concentrations between and above each of these exemplary ranges also can be achieved from the non-naturally occurring microbial organisms of the invention. As with the 4-HB producers, the BDO producers also can be sustained, cultured or fermented under anaerobic conditions.

The invention further provides a method for the production of 4-HB. The method includes culturing a non-naturally occurring microbial organism having a 4-hydroxybutanoic acid (4-HB) biosynthetic pathway comprising at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, glutamate:succinic semialdehyde transaminase, α-ketoglutarate decarboxylase, or glutamate decarboxylase under substantially anaerobic conditions for a sufficient period of time to produce monomeric 4-hydroxybutanoic acid (4-HB). The method can additionally include chemical conversion of 4-HB to GBL and to BDO or THF, for example.

Additionally provided is a method for the production of 4-HB. The method includes culturing a non-naturally occurring microbial organism having a 4-hydroxybutanoic acid (4-HB) biosynthetic pathway including at least one exogenous nucleic acid encoding 4-hydroxybutanoate dehydrogenase, succinyl-CoA synthetase, CoA-dependent succinic semialdehyde dehydrogenase or α-ketoglutarate decarboxylase under substantially anaerobic conditions for a sufficient period of time to produce monomeric 4-hydroxybutanoic acid (4-HB). The 4-HB product can be secreted into the culture medium.

Further provided is a method for the production of BDO. The method includes culturing a non-naturally occurring microbial biocatalyst or microbial organism, comprising a microbial organism having 4-hydroxybutanoic acid (4-HB) and 1,4-butanediol (BDO) biosynthetic pathways, the pathways including at least one exogenous nucleic acid encoding 4-hydroxybutanoate dehydrogenase, succinyl-CoA synthetase, CoA-dependent succinic semialdehyde dehydrogenase, 4-hydroxybutyrate:CoA transferase, 4-hydroxybutyrate kinase, phosphotranshydroxybutyrylase, α-ketoglutarate decarboxylase, aldehyde dehydrogenase, alcohol dehydrogenase or an aldehyde/alcohol dehydrogenase for a sufficient period of time to produce 1,4-butanediol (BDO). The BDO product can be secreted into the culture medium.

Additionally provided are methods for producing BDO by culturing a non-naturally occurring microbial organism having a BDO pathway of the invention. The BDO pathway can comprise at least one exogenous nucleic acid encoding a BDO pathway enzyme expressed in a sufficient amount to produce BDO, under conditions and for a sufficient period of time to produce BDO, the BDO pathway comprising 4-aminobutyrate CoA transferase, 4-aminobutyryl-CoA hydrolase, 4-aminobutyrate-CoA ligase, 4-aminobutyryl-CoA oxidoreductase (deaminating), 4-aminobutyryl-CoA transaminase, or 4-hydroxybutyryl-CoA dehydrogenase (see Example VII and Table 17).

Alternatively, the BDO pathway can compare at least one exogenous nucleic acid encoding a BDO pathway enzyme expressed in a sufficient amount to produce BDO, under conditions and for a sufficient period of time to produce BDO, the BDO pathway comprising 4-aminobutyrate CoA transferase, 4-aminobutyryl-CoA hydrolase, 4-aminobutyrate-CoA ligase, 4-aminobutyryl-CoA reductase (alcohol forming), 4-aminobutyryl-CoA reductase, 4-aminobutan-1-ol dehydrogenase, 4-aminobutan-1-ol oxidoreductase (deaminating) or 4-aminobutan-1-ol transaminase (see Example VII and Table 18).

In addition, the invention provides a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising 4-aminobutyrate kinase, 4-aminobutyraldehyde dehydrogenase (phosphorylating), 4-aminobutan-1-ol dehydrogenase, 4-aminobutan-1-ol oxidoreductase (deaminating), 4-aminobutan-1-ol transaminase, [(4-aminobutanolyl)oxy]phosphonic acid oxidoreductase (deaminating), [(4-aminobutanolyl)oxy]phosphonic acid transaminase, 4-hydroxybutyryl-phosphate dehydrogenase, or 4-hydroxybutyraldehyde dehydrogenase (phosphorylating) (see Example VII and Table 19).

The invention further provides a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising alpha-ketoglutarate 5-kinase, 2,5-dioxopentanoic semialdehyde dehydrogenase (phosphorylating), 2,5-dioxopentanoic acid reductase, alpha-ketoglutarate CoA transferase, alpha-ketoglutaryl-CoA hydrolase, alpha-ketoglutaryl-CoA ligase, alpha-ketoglutaryl-CoA reductase, 5-hydroxy-2-oxopentanoic acid dehydrogenase, alpha-ketoglutaryl-CoA reductase (alcohol forming), 5-hydroxy-2-oxopentanoic acid decarboxylase, or 5-hydroxy-2-oxopentanoic acid dehydrogenase (decarboxylation)(see Example VIII and Table 20).

The invention additionally provides a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising glutamate CoA transferase, glutamyl-CoA hydrolase, glutamyl-CoA ligase, glutamate 5-kinase, glutamate-5-semialdehyde dehydrogenase (phosphorylating), glutamyl-CoA reductase, glutamate-5-semialdehyde reductase, glutamyl-CoA reductase (alcohol forming), 2-amino-5-hydroxypentanoic acid oxidoreductase (deaminating), 2-amino-5-hydroxypentanoic acid transaminase, 5-hydroxy-2-oxopentanoic acid decarboxylase, 5-hydroxy-2-oxopentanoic acid dehydrogenase (decarboxylation)(see Example IX and Table 21).

The invention additionally includes a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising 3-hydroxybutyryl-CoA dehydrogenase, 3-hydroxybutyryl-CoA dehydratase, vinylacetyl-CoA Δ-isomerase, or 4-hydroxybutyryl-CoA dehydratase (see Example X and Table 22).

Also provided is a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising homoserine deaminase, homoserine CoA transferase, homoserine-CoA hydrolase, homoserine-CoA ligase, homoserine-CoA deaminase, 4-hydroxybut-2-enoyl-CoA transferase, 4-hydroxybut-2-enoyl-CoA hydrolase, 4-hydroxybut-2-enoyl-CoA ligase, 4-hydroxybut-2-enoate reductase, 4-hydroxybutyryl-CoA transferase, 4-hydroxybutyryl-CoA hydrolase, 4-hydroxybutyryl-CoA ligase, or 4-hydroxybut-2-enoyl-CoA reductase (see Example XI and Table 23).

The invention additionally provides a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising succinyl-CoA reductase (alcohol forming), 4-hydroxybutyryl-CoA hydrolase, 4-hydroxybutyryl-CoA ligase, 4-hydroxybutanal dehydrogenase (phosphorylating). Such a BDO pathway can further comprise succinyl-CoA reductase, 4-hydroxybutyrate dehydrogenase, 4-hydroxybutyryl-CoA transferase, 4-hydroxybutyrate kinase, phosphotrans-4-hydroxybutyrylase, 4-hydroxybutyryl-CoA reductase, 4-hydroxybutyryl-CoA reductase (alcohol forming), or 1,4-butanediol dehydrogenase.

Also provided is a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising glutamate dehydrogenase, 4-aminobutyrate oxidoreductase (deaminating), 4-aminobutyrate transaminase, glutamate decarboxylase, 4-hydroxybutyryl-CoA hydrolase, 4-hydroxybutyryl-CoA ligase, 4-hydroxybutanal dehydrogenase (phosphorylating).

The invention additionally provides methods of producing a desired product using the genetically modified organisms disclosed herein that allow improved production of a desired product such as BDO by increasing the product or decreasing undesirable byproducts. Thus, the invention provides a method for producing 1,4-butanediol (BDO), comprising culturing the non-naturally occurring microbial organisms disclosed herein under conditions and for a sufficient period of time to produce BDO. In one embodiment, the invention provides a method of producing BDO using a non-naturally occurring microbial organism, comprising a microbial organism having a 1,4-butanediol (BDO) pathway comprising at least one exogenous nucleic acid encoding a BDO pathway enzyme expressed in a sufficient amount to produce BDO. In one embodiment, the microbial organism is genetically modified to express exogenous succinyl-CoA synthetase (see Example XII). For example, the succinyl-CoA synthetase can be encoded by an *Escherichia coli* sucCD genes.

In another embodiment, the microbial organism is genetically modified to express exogenous alpha-ketoglutarate decarboxylase (see Example XIII). For example, the alpha-ketoglutarate decarboxylase can be encoded by the *Mycobacterium bovis* sucA gene. In still another embodiment, the microbial organism is genetically modified to express exogenous succinate semialdehyde dehydrogenase and 4-hydroxybutyrate dehydrogenase and optionally 4-hydroxybutyryl-CoA/acetyl-CoA transferase (see Example XIII). For example, the succinate semialdehyde dehydrogenase (CoA-dependent), 4-hydroxybutyrate dehydrogenase and 4-hydroxybutyryl-CoA/acetyl-CoA transferase can be encoded by *Porphyromonas gingivalis* W83 genes. In an additional embodiment, the microbial organism is genetically modified to express exogenous butyrate kinase and phosphotransbutyrylase (see Example XIII). For example, the butyrate kinase and phosphotransbutyrylase can be encoded by *Clostridium acetobutilicum* buk1 and ptb genes.

In yet another embodiment, the microbial organism is genetically modified to express exogenous 4-hydroxybutyryl-CoA reductase (see Example XIII). For example, the 4-hydroxybutyryl-CoA reductase can be encoded by *Clostridium beijerinckii* ald gene. Additionally, in an embodiment of the invention, the microbial organism is genetically modified to express exogenous 4-hydroxybutanal reductase (see Example XIII). For example, the 4-hydroxybutanal reductase can be encoded by *Geobacillus thermoglucosidasius* adh1 gene. In another embodiment, the microbial organism is genetically modified to express exogenous pyruvate dehydrogenase subunits (see Example XIV). For example, the exogenous pyruvate dehydrogenase can be NADH insensitive. The pyruvate dehydrogenase subunit can be encoded by the *Klebsiella pneumonia* lpdA gene. In a particular embodiment, the pyruvate dehydrogenase subunit genes of the microbial organism can be under the control of a pyruvate formate lyase promoter.

In still another embodiment, the microbial organism is genetically modified to disrupt a gene encoding an aerobic respiratory control regulatory system (see Example XV). For example, the disruption can be of the arcA gene. Such an organism can further comprise disruption of a gene encoding malate dehydrogenase. In a further embodiment, the microbial organism is genetically modified to express an exogenous NADH insensitive citrate synthase (see Example XV). For example, the NADH insensitive citrate synthase can be encoded by gltA, such as an R163L mutant of gltA. In still another embodiment, the microbial organism is genetically modified to express exogenous phosphoenolpyruvate carboxykinase (see Example XVI). For example, the phosphoenolpyruvate carboxykinase can be encoded by an *Haemophilus* influenza phosphoenolpyruvate carboxykinase gene. It is understood that strains exemplified herein for improved production of BDO can similarly be used, with appropriate modifications, to produce other desired products, for example, 4-hydroxybutyrate or other desired products disclosed herein.

It is understood that, in methods of the invention, any of the one or more exogenous nucleic acids can be introduced into a microbial organism to produce a non-naturally occurring microbial organism of the invention. The nucleic acids can be introduced so as to confer, for example, a 4-HB, BDO, THF or GBL biosynthetic pathway onto the microbial organism. Alternatively, encoding nucleic acids can be introduced to produce an intermediate microbial organism having the biosynthetic capability to catalyze some of the required reactions to confer 4-HB, BDO, THF or GBL biosynthetic capability. For example, a non-naturally occurring microbial organism having a 4-HB biosynthetic pathway can comprise at least two exogenous nucleic acids encoding desired enzymes, such as the combination of 4-hydroxybutanoate dehydrogenase and α-ketoglutarate decarboxylase; 4-hydroxybutanoate dehydrogenase and CoA-independent succinic semialdehyde dehydrogenase; 4-hydroxybutanoate dehydrogenase and CoA-dependent succinic semialdehyde dehydrogenase; CoA-dependent succinic semialdehyde dehydrogenase and succinyl-CoA synthetase; succinyl-CoA synthetase and glutamate decarboxylase, and the like. Thus, it is understood that any combination of two or more enzymes of a biosynthetic pathway can be included in a non-naturally occurring microbial organism of the invention. Similarly, it is understood that any combination of three or more enzymes of a biosynthetic pathway can be included in a non-naturally occurring microbial organism of the invention, for example, 4-hydroxybutanoate dehydrogenase, α-ketoglutarate decarboxylase and CoA-dependent succinic semialdehyde dehydrogenase; CoA-independent succinic semialdehyde dehydrogenase and succinyl-CoA synthetase; 4-hydroxybutanoate dehydrogenase, CoA-dependent succinic semialdehyde dehydrogenase and glutamate:succinic semialdehyde transaminase, and so forth, as desired, so long as the combination of enzymes of the desired biosynthetic pathway results in production of the corresponding desired product.

Similarly, for example, with respect to any one or more exogenous nucleic acids introduced to confer BDO production, a non-naturally occurring microbial organism having a BDO biosynthetic pathway can comprise at least two exogenous nucleic acids encoding desired enzymes, such as the combination of 4-hydroxybutanoate dehydrogenase and α-ketoglutarate decarboxylase; 4-hydroxybutanoate dehydrogenase and 4-hydroxybutyryl CoA:acetyl-CoA transferase; 4-hydroxybutanoate dehydrogenase and butyrate kinase; 4-hydroxybutanoate dehydrogenase and phosphotransbutyrylase; 4-hydroxybutyryl CoA:acetyl-CoA transferase and aldehyde dehydrogenase; 4-hydroxybutyryl CoA:acetyl-CoA transferase and alcohol dehydrogenase; 4-hydroxybutyryl CoA:acetyl-CoA transferase and an aldehyde/alcohol dehydrogenase, 4-aminobutyrate-CoA transferase and 4-aminobutyryl-CoA transaminase; 4-aminobutyrate kinase and 4-aminobutan-1-ol oxidoreductase (deaminating), and the like. Thus, it is understood that any combination of two or more enzymes of a biosynthetic pathway can be included in a non-naturally occurring microbial organism of the invention. Similarly, it is understood that any combination of three or more enzymes of a biosynthetic pathway can be included in a non-naturally occurring microbial organism of the invention, for example, 4-hydroxybutanoate dehydrogenase, α-ketoglutarate decarboxylase and 4-hydroxybutyryl CoA:acetyl-CoA transferase; 4-hydroxybutanoate dehydrogenase, butyrate kinase and phosphotransbutyrylase; 4-hydroxybutanoate dehydrogenase, 4-hydroxybutyryl CoA:acetyl-CoA transferase and aldehyde dehydrogenase; 4-hydroxybutyryl CoA:acetyl-CoA transferase, aldehyde dehydrogenase and alcohol dehydrogenase; butyrate kinase, phosphotransbutyrylase and an aldehyde/alcohol dehydrogenase; 4-aminobutyryl-CoA hydrolase, 4-aminobutyryl-CoA reductase and 4-aminobutan-1-ol transaminase; 3-hydroxybutyryl-CoA dehydrogenase, 3-hydroxybutyryl-CoA dehydratase and 4-hydroxybutyryl-CoA dehydratase, and the like. Similarly, any combination of four, five or more enzymes of a biosynthetic pathway as disclosed herein can be included in a non-naturally occurring microbial organism of the invention, as desired, so long as the combination of enzymes of the desired biosynthetic pathway results in production of the corresponding desired product.

Any of the non-naturally occurring microbial organisms described herein can be cultured to produce and/or secrete the biosynthetic products of the invention. For example, the 4-HB producers can be cultured for the biosynthetic production of 4-HB. The 4-HB can be isolated or be treated as described below to generate GBL, THF and/or BDO. Similarly, the BDO producers can be cultured for the biosynthetic production of BDO. The BDO can be isolated or subjected to further treatments for the chemical synthesis of BDO family compounds, as disclosed herein.

The growth medium can include, for example, any carbohydrate source which can supply a source of carbon to the non-naturally occurring microorganism. Such sources include, for example, sugars such as glucose, sucrose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, sucrose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of 4-HB or BDO and other compounds of the invention.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, 4-HB, BDO and any of the intermediates metabolites in the 4-HB pathway, the BDO pathway and/or the combined 4-HB and BDO pathways. All that is required is to engineer in one or more of the enzyme activities shown in FIG. 1 to achieve biosynthesis of the desired compound or intermediate including, for example, inclusion of some or all of the 4-HB and/or BDO biosynthetic pathways. Accordingly, the invention provides a non-naturally occurring microbial organism that secretes 4-HB when grown on a carbohydrate, secretes BDO when grown on a carbohydrate and/or secretes any of the intermediate metabolites shown in FIG. 1 when grown on a carbohydrate. The BDO producing microbial organisms of the invention can initiate synthesis from, for example, succinate, succinyl-CoA, α-ketogluterate, succinic semialdehyde, 4-HB, 4-hydroxybutyrylphosphate, 4-hydroxybutyryl-CoA (4-HB-CoA) and/or 4-hydroxybutyraldehyde.

In some embodiments, culture conditions include anaerobic or substantially anaerobic growth or maintenance conditions. Exemplary anaerobic conditions have been described previously and are well known in the art. Exemplary anaerobic conditions for fermentation processes are described below in the Examples. Any of these conditions can be employed with the non-naturally occurring microbial organisms as well as other anaerobic conditions well known in the art. Under such anaerobic conditions, the 4-HB and BDO producers can synthesize monomeric 4-HB and BDO, respectively, at intracellular concentrations of 5-10 mM or more as well as all other concentrations exemplified previously.

A number of downstream compounds also can be generated for the 4-HB and BDO producing non-naturally occurring microbial organisms of the invention. With respect to the 4-HB producing microbial organisms of the invention, monomeric 4-HB and GBL exist in equilibrium in the culture medium. The conversion of 4-HB to GBL can be efficiently accomplished by, for example, culturing the microbial organisms in acid pH medium. A pH less than or equal to 7.5, in particular at or below pH 5.5, spontaneously converts 4-HB to GBL.

The resultant GBL can be separated from 4-HB and other components in the culture using a variety of methods well known in the art. Such separation methods include, for example, the extraction procedures exemplified in the Examples as well as methods which include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art. Separated GBL can be further purified by, for example, distillation.

Another down stream compound that can be produced from the 4-HB producing non-naturally occurring microbial organisms of the invention includes, for example, BDO. This compound can be synthesized by, for example, chemical hydrogenation of GBL. Chemical hydrogenation reactions are well known in the art. One exemplary procedure includes the chemical reduction of 4-HB and/or GBL or a mixture of these two components deriving from the culture using a heterogeneous or homogeneous hydrogenation catalyst together with hydrogen, or a hydride-based reducing agent used stoichiometrically or catalytically, to produce 1,4-butanediol.

Other procedures well known in the art are equally applicable for the above chemical reaction and include, for example, WO No. 82/03854 (Bradley, et al.), which describes the hydrogenolysis of gamma-butyrolactone in the vapor phase over a copper oxide and zinc oxide catalyst. British Pat. No. 1,230,276, which describes the hydrogenation of gamma-butyrolactone using a copper oxide-chromium oxide catalyst. The hydrogenation is carried out in the liquid phase. Batch reactions also are exemplified having high total reactor pressures. Reactant and product partial pressures in the reactors are well above the respective dew points. British Pat. No. 1,314,126, which describes the hydrogenation of gamma-butyrolactone in the liquid phase over a nickel-cobalt-thorium oxide catalyst. Batch reactions are exemplified as having high total pressures and component partial pressures well above respective component dew points. British Pat. No. 1,344,557, which describes the hydrogenation of gamma-butyrolactone in the liquid phase over a copper oxide-chromium oxide catalyst. A vapor phase or vapor-containing mixed phase is indicated as suitable in some instances. A continuous flow tubular reactor is exemplified using high total reactor pressures. British Pat. No. 1,512,751, which describes the hydrogenation of gamma-butyrolactone to 1,4-butanediol in the liquid phase over a copper oxide-chromium oxide catalyst. Batch reactions are exemplified with high total reactor pressures and, where determinable, reactant and product partial pressures well above the respective dew points. U.S. Pat. No. 4,301,077, which describes the hydrogenation to 1,4-butanediol of gamma-butyrolactone over a Ru—Ni—Co—Zn catalyst. The reaction can be conducted in the liquid or gas phase or in a mixed liquid-gas phase. Exemplified are continuous flow liquid phase reactions at high total reactor pressures and relatively low reactor productivities. U.S. Pat. No. 4,048,196, which describes the production of 1,4-butanediol by the liquid phase hydrogenation of gamma-butyrolactone over a copper oxide-zinc oxide catalyst. Further exemplified is a continuous flow tubular reactor operating at high total reactor pressures and high reactant and product partial pressures. And U.S. Pat. No. 4,652,685, which describes the hydrogenation of lactones to glycols.

A further downstream compound that can be produced form the 4-HB producing microbial organisms of the invention includes, for example, THF. This compound can be synthesized by, for example, chemical hydrogenation of GBL. One exemplary procedure well known in the art applicable for the conversion of GBL to THF includes, for example, chemical reduction of 4-HB and/or GBL or a mixture of these two components deriving from the culture using a heterogeneous or homogeneous hydrogenation catalyst together with hydrogen, or a hydride-based reducing agent used stoichiometrically or catalytically, to produce tetrahydrofuran. Other procedures well know in the art are equally applicable for the above chemical reaction and include, for example, U.S. Pat. No. 6,686,310, which describes high surface area sol-gel route prepared hydrogenation catalysts. Processes for the reduction of maleic acid to tetrahydrofuran (THF) and 1,4-butanediol (BDO) and for the reduction of gamma butyrolactone to tetrahydrofuran and 1,4-butanediol also are described.

The culture conditions can include, for example, liquid culture procedures as well as fermentation and other large scale culture procedures. As described further below in the Examples, particularly useful yields of the biosynthetic products of the invention can be obtained under anaerobic or substantially anaerobic culture conditions.

Suitable purification and/or assays to test for the production of 4-HB or BDO can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme or protein activities from the exogenous DNA sequences can also be assayed using methods well known in the art.

The 4-HB or BDO product can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

The invention further provides a method of manufacturing 4-HB. The method includes fermenting a non-naturally occurring microbial organism having a 4-hydroxybutanoic acid (4-HB) biosynthetic pathway comprising at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, glutamate:succinic semialdehyde transaminase, a-ketoglutarate decarboxylase, or glutamate decarboxylase under substantially anaerobic conditions for a sufficient period of time to produce monomeric 4-hydroxybutanoic acid (4-HB), the process comprising fed-batch fermentation and batch separation; fed-batch fermentation and continuous separation, or continuous fermentation and continuous separation.

The culture and chemical hydrogenations described above also can be scaled up and grown continuously for manufacturing of 4-HB, GBL, BDO and/or THF. Exemplary growth procedures include, for example, fed-batch fermentation and batch separation; fed-batch fermentation and continuous separation, or continuous fermentation and continuous separation. All of these processes are well known in the art. Employing the 4-HB producers allows for simultaneous 4-HB biosynthesis and chemical conversion to GBL, BDO and/or THF by employing the above hydrogenation procedures simultaneous with continuous cultures methods such as fermentation. Other hydrogenation procedures also are well known in the art and can be equally applied to the methods of the invention.

Fermentation procedures are particularly useful for the biosynthetic production of commercial quantities of 4-HB and/or BDO. Generally, and as with non-continuous culture procedures, the continuous and/or near-continuous production of 4-HB or BDO will include culturing a non-naturally occurring 4-HB or BDO producing organism of the invention in sufficient nutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of 4-HB, BDO or other 4-HB derived products of the invention can be utilized in, for example, fed-batch fermentation and batch separation; fed-batch fermentation and continuous separation, or continuous fermentation and continuous separation. Examples of batch and continuous fermentation procedures well known in the art are exemplified further below in the Examples.

In addition, to the above fermentation procedures using the 4-HB or BDO producers of the invention for continuous production of substantial quantities of monomeric 4-HB and BDO, respectively, the 4-HB producers also can be, for example, simultaneously subjected to chemical synthesis procedures as described previously for the chemical conversion of monomeric 4-HB to, for example, GBL, BDO and/or THF. The BDO producers can similarly be, for example, simultaneously subjected to chemical synthesis procedures as described previously for the chemical conversion of BDO to, for example, THF, GBL, pyrrolidones and/or other BDO family compounds. In addition, the products of the 4-HB and BDO producers can be separated from the fermentation culture and sequentially subjected to chemical conversion, as disclosed herein.

Briefly, hydrogenation of GBL in the fermentation broth can be performed as described by Frost et al., *Biotechnology Progress* 18: 201-211 (2002). Another procedure for hydrogenation during fermentation include, for example, the methods described in, for example, U.S. Pat. No. 5,478,952. This method is further exemplified in the Examples below.

Therefore, the invention additionally provides a method of manufacturing γ-butyrolactone (GBL), tetrahydrofuran (THF) or 1,4-butanediol (BDO). The method includes fermenting a non-naturally occurring microbial organism having 4-hydroxybutanoic acid (4-HB) and/or 1,4-butanediol (BDO) biosynthetic pathways, the pathways comprise at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, 4-hydroxybutyrate:CoA transferase, glutamate:succinic semialdehyde transaminase, α-ketoglutarate decarboxylase, glutamate decarboxylase, 4-hydroxybutanoate kinase, phosphotransbutyrylase, CoA-independent 1,4-butanediol semialdehyde dehydrogenase, CoA-dependent 1,4-butanediol semialdehyde dehydrogenase, CoA-independent 1,4-butanediol alcohol dehydrogenase or CoA-dependent 1,4-butanediol alcohol dehydrogenase, under substantially anaerobic conditions for a sufficient period of time to produce 1,4-butanediol (BDO), GBL or THF, the fermenting comprising fed-batch fermentation and batch separation; fed-batch fermentation and continuous separation, or continuous fermentation and continuous separation.

In addition to the biosynthesis of 4-HB, BDO and other products of the invention as described herein, the non-naturally occurring microbial organisms and methods of the invention also can be utilized in various combinations with each other and with other microbial organisms and methods well known in the art to achieve product biosynthesis by other routes. For example, one alternative to produce BDO other than use of the 4-HB producers and chemical steps or other than use of the BDO producer directly is through addition of another microbial organism capable of converting 4-HB or a 4-HB product exemplified herein to BDO.

One such procedure includes, for example, the fermentation of a 4-HB producing microbial organism of the invention to produce 4-HB, as described above and below. The 4-HB can then be used as a substrate for a second microbial organism that converts 4-HB to, for example, BDO, GBL and/or THF. The 4-HB can be added directly to another culture of the second organism or the original culture of 4-HB producers can be depleted of these microbial organisms by, for example, cell separation, and then subsequent addition of the second organism to the fermentation broth can utilized to produce the final product without intermediate purification steps. One exemplary second organism having the capacity to biochemically utilize 4-HB as a substrate for conversion to BDO, for example, is *Clostridium acetobutylicum* (see, for example, Jewell et al., *Current Microbiology*, 13:215-19 (1986)).

In other embodiments, the non-naturally occurring microbial organisms and methods of the invention can be assembled in a wide variety of subpathways to achieve biosynthesis of, for example, 4-HB and/or BDO as described. In these embodiments, biosynthetic pathways for a desired product of the invention can be segregated into different microbial organisms and the different microbial organisms can be co-cultured to produce the final product. In such a biosynthetic scheme, the product of one microbial organism is the substrate for a second microbial organism until the final product is synthesized. For example, the biosynthesis of BDO can be accomplished as described previously by constructing a microbial organism that contains biosynthetic pathways for conversion of one pathway intermediate to another pathway intermediate or the product, for example, a substrate such as endogenous succinate through 4-HB to the final product BDO. Alternatively, BDO also can be biosynthetically produced from microbial organisms through co-culture or co-fermentation using two organisms in the same vessel. A first microbial organism being a 4-HB producer with genes to produce 4-HB from succinic acid, and a second microbial organism being a BDO producer with genes to convert 4-HB to BDO.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce 4-HB, BDO, GBL and THF products of the invention.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of BDO.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/

00660, filed Jan. 10, 2002, and U.S. patent application Ser. No. 11/891,602, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of E. coli metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

The methods exemplified above and further illustrated in the Examples below enable the construction of cells and organisms that biosynthetically produce, including obligatory couple production of a target biochemical product to growth of the cell or organism engineered to harbor the identified genetic alterations. In this regard, metabolic alterations have been identified that result in the biosynthesis of 4-HB and 1,4-butanediol. Microorganism strains constructed with the identified metabolic alterations produce elevated levels of 4-HB or BDO compared to unmodified microbial organisms. These strains can be beneficially used for the commercial production of 4-HB, BDO, THF and GBL, for example, in continuous fermentation process without being subjected to the negative selective pressures.

Therefore, the computational methods described herein enable the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

It is understood that modifications which do not substantially affect the activity of the various embodiments of this invention are also included within the definition of the invention provided herein. Accordingly, the following examples are intended to illustrate but not limit the present invention.

Any of the non-naturally occurring microbial organisms described herein can be cultured to produce and/or secrete the biosynthetic products of the invention. For example, the BDO producers can be cultured for the biosynthetic production of BDO.

For the production of BDO, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in U.S. publication 2009/0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

In addition to renewable feedstocks such as those exemplified above, the BDO producing microbial organisms of the invention also can be modified for growth on syngas as its source of carbon. In this specific embodiment, one or more proteins or enzymes are expressed in the BDO producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, Acetogenesis, pp. 3-60 Chapman and Hall, New York, (1994)). This can be summarized by the following equation:

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a BDO pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, BDO and any of the intermediate metabolites in the BDO pathway. All that is required is to engineer in one or more of the required enzyme or protein activities to achieve biosynthesis of the desired compound or intermediate including, for example, inclusion of some or all of the BDO biosynthetic pathways. Accordingly, the invention provides a non-naturally occurring microbial organism that produces and/or secretes BDO when grown on a carbohydrate or other carbon source and produces and/or secretes any of the intermediate metabolites shown in the BDO pathway when grown on a carbohydrate or other carbon source. The BDO producing microbial organisms of the invention can initiate synthesis from an intermediate in a BDO pathway, as disclosed herein.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of BDO.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. patent application Ser. No. 11/891,602, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

It is understood that modifications which do not substantially affect the activity of the various embodiments of this invention are also provided within the definition of the invention provided herein. Accordingly, the following examples are intended to illustrate but not limit the present invention.

Example I

Biosynthesis of 4-Hydroxybutanoic Acid

This example describes exemplary biochemical pathways for 4-HB production.

Previous reports of 4-HB synthesis in microbes have focused on this compound as an intermediate in production of the biodegradable plastic poly-hydroxyalkanoate (PHA) (U.S. Pat. No. 6,117,658). The use of 4-HB/3-HB copolymers over poly-3-hydroxybutyrate polymer (PHB) can result in plastic that is less brittle (Saito and Doi, *Intl. J. Biol. Macromol.* 16:99-104 (1994)). The production of monomeric 4-HB described herein is a fundamentally distinct process for several reasons: (1) the product is secreted, as opposed to PHA which is produced intracellularly and remains in the cell; (2) for organisms that produce hydroxybutanoate polymers, free 4-HB is not produced, but rather the Coenzyme A derivative is used by the polyhydroxyalkanoate synthase; (3) in the case of the polymer, formation of the granular product changes thermodynamics; and (4) extracellular pH is not an issue for production of the polymer, whereas it will affect whether 4-HB is present in the free acid or conjugate base state, and also the equilibrium between 4-HB and GBL.

4-HB can be produced in two enzymatic reduction steps from succinate, a central metabolite of the TCA cycle, with succinic semialdehyde as the intermediate (FIG. 1). The first of these enzymes, succinic semialdehyde dehydrogenase, is native to many organisms including *E. coli*, in which both NADH- and NADPH-dependent enzymes have been found (Donnelly and Cooper, *Eur. J. Biochem.* 113:555-561 (1981); Donnelly and Cooper, *J. Bacteriol.* 145:1425-1427 (1981); Marek and Henson, *J. Bacteriol.* 170:991-994 (1988)). There is also evidence supporting succinic semialdehyde dehydrogenase activity in *S. cerevisiae* (Ramos et al., *Eur. J. Biochem.* 149:401-404 (1985)), and a putative gene has been identified by sequence homology. However, most reports indicate that this enzyme proceeds in the direction of succinate synthesis, as shown in FIG. 1 (Donnelly and Cooper, supra; Lutke-Eversloh and Steinbuchel, *FEMS Microbiol. Lett.* 181:63-71 (1999)), participating in the degradation pathway of 4-HB and gamma-aminobutyrate. Succinic semialdehyde also is natively produced by certain microbial organisms such as *E. coli* through the TCA cycle intermediate α-ketogluterate via the action of two enzymes: glutamate:succinic semialdehyde transaminase and glutamate decarboxylase. An alternative pathway, used by the obligate anaerobe *Clostridium kluyveri* to degrade succinate, activates succinate to succinyl-CoA, then converts succinyl-CoA to succinic semialdehyde using an alternative succinic semialdehyde dehydrogenase which is known to function in this direction (Sohling and Gottschalk, *Eur. J. Biochem.* 212:121-127 (1993)). However, this route has the energetic cost of ATP required to convert succinate to succinyl-CoA.

The second enzyme of the pathway, 4-hydroxybutanoate dehydrogenase, is not native to *E. coli* or yeast but is found in various bacteria such as *C. kluyveri* and *Ralstonia eutropha* (Lutke-Eversloh and Steinbuchel, supra; Sohling and Gottschalk, *J. Bacteriol.* 178:871-880 (1996); Valentin et al., *Eur. J. Biochem.* 227:43-60 (1995); Wolff and Kenealy, *Protein Expr. Purif.* 6:206-212 (1995)). These enzymes are known to be NADH-dependent, though NADPH-dependent forms also exist. An additional pathway to 4-HB from alpha-ketoglutarate was demonstrated in *E. coli* resulting in the accumulation of poly(4-hydroxybutyric acid) (Song et al., *Wei Sheng Wu Xue. Bao.* 45:382-386 (2005)). The recombinant strain required the overexpression of three heterologous genes, PHA synthase (*R. eutropha*), 4-hydroxybutyrate dehydrogenase (*R. eutropha*) and 4-hydroxybutyrate:CoA transferase (*C. kluyveri*), along with two native *E. coli* genes: glutamate:succinic semialdehyde transaminase and glutamate decarboxylase. Steps 4 and 5 in FIG. 1 can alternatively be carried out by an alpha-ketoglutarate decarboxylase such as the one identified in *Euglena gracilis* (Shigeoka et al., *Biochem. J.* 282(Pt2):319-323 (1992); Shigeoka and Nakano, *Arch. Biochem. Biophys.* 288:22-28 (1991); Shigeoka and Nakano, *Biochem J.* 292(Pt 2):463-467 (1993)). However, this enzyme has not previously been applied to impact the production of 4-HB or related polymers in any organism.

The microbial production capabilities of 4-hydroxybutyrate were explored in two microbes, *Escherichia coli* and *Saccharomyces cerevisiae*, using in silico metabolic models of each organism. Potential pathways to 4-HB proceed via a succinate, succinyl-CoA, or alpha-ketoglutarate intermediate as shown in FIG. 1.

A first step in the 4-HB production pathway from succinate involves the conversion of succinate to succinic semialdehyde via an NADH- or NADPH-dependant succinic semialdehyde dehydrogenase. In *E. coli*, gabD is an NADP-dependant succinic semialdehyde dehydrogenase and is part of a gene cluster involved in 4-aminobutyrate uptake and degradation (Niegemann et al., *Arch. Microbiol.* 160:454-460 (1993); Schneider et al., *J. Bacteriol.* 184:6976-6986 (2002)). sad is believed to encode the enzyme for NAD-dependant succinic semialdehyde dehydrogenase activity (Marek and Henson, supra). *S. cerevisiae* contains only the NADPH-dependant succinic semialdehyde dehydrogenase, putatively assigned to UGA2, which localizes to the cytosol (Huh et al., *Nature* 425:686-691 (2003)). The maximum yield calculations assuming the succinate pathway to 4-HB in both *E. coli* and *S. cerevisiae* require only the assumption that a non-native 4-HB dehydrogenase has been added to their metabolic networks.

The pathway from succinyl-CoA to 4-hydroxybutyrate was described in U.S. Pat. No. 6,117,658 as part of a process for making polyhydroxyalkanoates comprising 4-hydroxybutyrate monomer units. *Clostridium kluyveri* is one example organism known to possess CoA-dependant succinic semialdehyde dehydrogenase activity (Sohling and Gottschalk, supra; Sohling and Gottschalk, supra). In this study, it is assumed that this enzyme, from *C. kluyveri* or another organism, is expressed in *E. coli* or *S. cerevisiae* along with a non-native or heterologous 4-HB dehydrogenase to complete the pathway from succinyl-CoA to 4-HB. The pathway from alpha-ketoglutarate to 4-HB was demonstrated in *E. coli* resulting in the accumulation of poly(4-hydroxybutyric acid) to 30% of dry cell weight (Song et al., supra). As *E. coli* and *S. cerevisiae* natively or endogenously possess both glutamate:succinic semialdehyde transaminase and glutamate decarboxylase (Coleman et al., *J Biol. Chem.* 276:244-250 (2001)), the pathway from AKG to 4-HB can be completed in both organisms by assuming only that a non-native 4-HB dehydrogenase is present.

Example II

Biosynthesis of 1,4-Butanediol from Succinate and Alpha-Ketoglutarate

This example illustrates the construction and biosynthetic production of 4-HB and BDO from microbial organisms. Pathways for 4-HB and BDO are disclosed herein.

There are several alternative enzymes that can be utilized in the pathway described above. The native or endogenous enzyme for conversion of succinate to succinyl-CoA (Step 1 in FIG. 1) can be replaced by a CoA transferase such as that encoded by the cat1 gene *C. kluyveri* (Sohling and Gottschalk, *Eur. J Biochem.* 212:121-127 (1993)), which functions in a similar manner to Step 9. However, the production of acetate by this enzyme may not be optimal, as it might be secreted rather than being converted back to acetyl-CoA. In this respect, it also can be beneficial to eliminate acetate formation in Step 9. As one alternative to this CoA transferase, a mechanism can be employed in which the 4-HB is first phosphorylated by ATP and then converted to the CoA derivative, similar to the acetate kinase/phosphotransacetylase pathway in *E. coli* for the conversion of acetate to acetyl-CoA. The net cost of this route is one ATP, which is the same as is required to regenerate acetyl-CoA from acetate. The enzymes phosphotransbutyrylase (ptb) and butyrate kinase (bk) are known to carry out these steps on the non-hydroxylated molecules for butyrate production in *C. acetobutylicum* (Cary et al., *Appl Environ Microbiol* 56:1576-1583 (1990); Valentine, R. C. and R. S. Wolfe, *J Biol Chem.* 235:1948-1952 (1960)). These enzymes are reversible, allowing synthesis to proceed in the direction of 4-HB.

BDO also can be produced via α-ketoglutarate in addition to or instead of through succinate. A described previously, and exemplified further below, one pathway to accomplish product biosynthesis is with the production of succinic semialdehyde via α-ketoglutarate using the endogenous enzymes (FIG. 1, Steps 4-5). An alternative is to use an α-ketoglutarate decarboxylase that can perform this conversion in one step (FIG. 1, Step 8; Tian et al., *Proc Natl Acad Sci U.S.A* 102:10670-10675 (2005)).

For the construction of different strains of BDO-producing microbial organisms, a list of applicable genes was assembled for corroboration. Briefly, one or more genes within the 4-HB and/or BDO biosynthetic pathways were identified for each step of the complete BDO-producing pathway shown in FIG. 1, using available literature resources, the NCBI genetic database, and homology searches. The genes cloned and assessed in this study are presented below in in Table 6, along with the appropriate references and URL citations to the polypeptide sequence. As discussed further below, some genes were synthesized for codon optimization while others were cloned via PCR from the genomic DNA of the native or wild-type organism. For some genes both approaches were used, and in this case the native genes are indicated by an "n" suffix to the gene identification number when used in an experiment. Note that only the DNA sequences differ; the proteins are identical.

TABLE 6

Genes expressed in host BDO-producing microbial organisms.

| Gene ID number | Reaction number (FIG. 1) | Gene name | Source organism | Enzyme name | Link to protein sequence | Reference |
|---|---|---|---|---|---|---|
| 0001 | 9 | Cat2 | Clostridium kluyveri DSM 555 | 4-hydroxybutyrate coenzyme A transferase | ncbi.nlm.nih.gov/entrez/viewer.fcgi?db=nuccore&id=1228100 | 1 |
| 0002 | 12/13 | adhE | Clostridium acetobutylicum ATCC 824 | Aldehyde/alcohol dehydrogenase | ncbi.nlm.nih.gov/entrez/viewer.fcgi?db=protein&val=15004739 | 2 |
| 0003 | 12/13 | adhE2 | Clostridium acetobutylicum ATCC 824 | Aldehyde/alcohol dehydrogenase | ncbi.nlm.nih.gov/entrez/viewer.fcgi?val=NP_149325.1 | 2 |
| 0004 | 1 | Cat1 | Clostridium kluyveri DSM 555 | Succinate coenzyme A transferase | ncbi.nlm.nih.gov/entrez/viewer.fcgi?db=nuccore&id=1228100 | 1 |
| 0008 | 6 | sucD | Clostridium kluyveri DSM 555 | Succinic semialdehyde dehydrogenase (CoA-dependent) | ncbi.nlm.nih.gov/entrez/viewer.fcgi?db=nuccore&id=1228100 | 1 |
| 0009 | 7 | 4-HBd | Ralstonia eutropha H16 | 4-hydroxybutyrate dehydrogenase (NAD-dependent) | ncbi.nlm.nih.gov/entrez/viewer.fcgi?val=YP_726053.1 | 2 |
| 0010 | 7 | 4-HBd | Clostridium kluyveri DSM 555 | 4-hydroxybutyrate dehydrogenase (NAD-dependent) | ncbi.nlm.nih.gov/entrez/viewer.fcgi?db=nuccore&id=1228100 | 1 |
| 0011 | 12/13 | adhE | E. coli | Aldehyde/alcohol dehydrogenase | shigen.nig.ac.jp/ecoli/pec/genes.List.DetailAction.do?fromListFlag=true&featureType=1&orfId=1219 | 2 |
| 0012 | 12/13 | yqhD | E. coli | Aldehyde/alcohol dehydrogenase | shigen.nig.ac.jp/ecoli/pec/genes.List.DetailAction.do | 2 |
| 0013 | 13 | bdhB | Clostridium acetobutylicum ATCC 824 | Butanol dehydrogenase II | ncbi.nlm.nih.gov/entrez/viewer.fcgi?val=NP_349891.1 | 2 |
| 0020 | 11 | ptb | Clostridium acetobutylicum ATCC 824 | Phosphotransbutyrylase | ncbi.nlm.nih.gov/entrez/viewer.fcgi?db=protein&id=15896327 | 2 |
| 0021 | 10 | buk1 | Clostridium acetobutylicum ATCC 824 | Butyrate kinase I | ncbi.nlm.nih.gov/entrez/viewer.fcgi?db=protein&id=20137334 | 2 |
| 0022 | 10 | buk2 | Clostridium acetobutylicum ATCC 824 | Butyrate kinase II | ncbi.nlm.nih.gov/entrez/viewer.fcgi?db=protein&id=20137415 | 2 |
| 0023 | 13 | adhEm | isolated from metalibrary of anaerobic sewage digester microbial consortia | Alcohol dehydrogenase | | (37d) |

TABLE 6-continued

Genes expressed in host BDO-producing microbial organisms.

| Gene ID number | Reaction number (FIG. 1) | Gene name | Source organism | Enzyme name | Link to protein sequence | Reference |
|---|---|---|---|---|---|---|
| 0024 | 13 | adhE | Clostridium thermocellum | Alcohol dehydrogenase | genome.jp/dbget-bin/www_bget?cth:Cthe_0423 | (31)d} |
| 0025 | 13 | ald | Clostridium beijerinckii | Coenzyme A-acylating aldehyde dehydrogenase | ncbi.nlm.nih.gov/entrez/viewer.fcgi?db=protein&id=49036681 | |
| 0026 | 13 | bdhA | Clostridium acetobutylicum ATCC 824 | Butanol dehydrogenase | ncbi.nlm.nih.gov/entrez/viewer.fcgi?val=NP_349892.1 | 2 |
| 0027 | 12 | bld | Clostridium saccharoperbutylacetonicum | Butyraldehyde dehydrogenase | ncbi.nlm.nih.gov/entrez/viewer.fcgi?db=protein&id=31075383 | 4 |
| 0028 | 13 | bdh | Clostridium saccharoperbutylacetonicum | Butanol dehydrogenase | ncbi.nlm.nih.gov/entrez/viewer.fcgi?db=protein&id=124221917 | 4 |
| 0029 | 12/13 | adhE | Clostridium tetani | Aldehyde/alcohol dehydrogenase | genome.jp/dbget-bin/www_bget?ctc:CTC01366 | |
| 0030 | 12/13 | adhE | Clostridium perfringens | Aldehyde/alcohol dehydrogenase | ncbi.nlm.nih.gov/entrez/viewer.fcgi?val=NP_977400.1 | |
| 0031 | 12/13 | adhE | Clostridium difficile | Aldehyde/alcohol dehydrogenase | genome.jp/dbget-bin/www_bget?cdf:CD2966 | |
| 0032 | 8 | sucA | Mycobacterium bovis BCG, Pasteur | α-ketoglutarate decarboxylase | ncbi.nlm.nih.gov/entrez/viewer.fcgi?db=protein&val=6249316 | 5 |
| 0033 | 9 | cat2 | Clostridium aminobutyricum | 4-hydroxybutyrate coenzyme A transferase | ncbi.nlm.nih.gov/entrez/viewer.fcgi?db=protein&val=6249316 | |
| 0034 | 9 | cat2 | Porphyromonas gingivalis W83 | 4-hydroxybutyrate coenzyme A transferase | ncbi.nlm.nih.gov/entrez/viewer.fcgi?db=protein&val=34541558 | |
| 0035 | 6 | sucD | Porphyromonas gingivalis W83 | Succinic semialdehyde dehydrogenase (CoA-dependent) | ncbi.nlm.nih.gov/entrez/viewer.fcgi?val=NP_904963.1 | |
| 0036 | 7 | 4-HBd | Porphyromonas gingivalis W83 | NAD-dependent 4-hydroxybutyrate dehydrogenase | ncbi.nlm.nih.gov/entrez/viewer.fcgi?val=NP_904964.1 | |
| 0037 | 7 | gbd | Uncultured bacterium | 4-hydroxybutyrate dehydrogenase | ncbi.nlm.nih.gov/entrez/viewer.fcgi?db=nuccore&id=5916168 | 6 |
| 0038 | 1 | sucCD | E. coli | Succinyl-CoA synthetase | shigen.nig.ac.jp/ecoli/pec/genes.List.DetailAction.do | |

[1] Sohling and Gottschalk, Eur. J. Biochem. 212: 121-127 (1993); Sohling and Gottschalk, J. Bacteriol. 178: 871-880 (1996)
[2] Nolling et al., J. Bacteriol. 183: 4823-4838 (2001)
[3] Pohlmann et al., Nat. Biotechnol. 24: 1257-1262 (2006)
[4] Kosaka et al., Biosci. Biotechnol. Biochem. 71: 58-68 (2007)
[5] Brosch et al., Proc. Natl. Acad. Sci. U.S.A. 104: 5596-5601 (2007)
[6] Henne et al., Appl. Environ. Microbiol. 65: 3901-3907 (1999)

Expression Vector Construction for BDO Pathway.

Vector backbones and some strains were obtained from Dr. Rolf Lutz of Expressys (expressys.de/). The vectors and strains are based on the pZ Expression System developed by Dr. Rolf Lutz and Prof. Hermann Bujard (Lutz, R. and H. Bujard, *Nucleic Acids Res* 25:1203-1210 (1997)). Vectors obtained were pZE13luc, pZA33luc, pZS*13luc and pZE22luc and contained the luciferase gene as a stuffer fragment. To replace the luciferase stuffer fragment with a lacZ-alpha fragment flanked by appropriate restriction enzyme sites, the luciferase stuffer fragment was first removed from each vector by digestion with EcoRI and XbaI. The lacZ-alpha fragment was PCR amplified from pUC19 with the following primers:

```
lacZalpha-RI
                                           (SEQ ID NO: 1)
5'GACGAATTCGCTAGCAAGAGGAGAAGTCGACATGTCCAATTCACTG
GCCGTCGTTTTAC3' lacZalpha 3'BB
                                           (SEQ ID NO: 2)
5'-GACCCTAGGAAGCTTTCTAGAGTCGACCTATGCGGCATCAGAGCA
GA-3'.
```

This generated a fragment with a 5' end of EcoRI site, NheI site, a Ribosomal Binding Site, a SalI site and the start codon. On the 3' end of the fragment contained the stop codon, XbaI, HindIII, and AvrII sites. The PCR product was digested with EcoRI and AvrII and ligated into the base vectors digested with EcoRI and XbaI (XbaI and AvrII have compatible ends and generate a non-site). Because NheI and XbaI restriction enzyme sites generate compatible ends that can be ligated together (but generate a NheI/XbaI non-site that is not digested by either enzyme), the genes cloned into the vectors could be "Biobricked" together (openwetware-.org/wiki/Synthetic Biology:BioBricks). Briefly, this method enables joining an unlimited number of genes into the vector using the same 2 restriction sites (as long as the sites do not appear internal to the genes), because the sites between the genes are destroyed after each addition.

All vectors have the pZ designation followed by letters and numbers indication the origin of replication, antibiotic resistance marker and promoter/regulatory unit. The origin of replication is the second letter and is denoted by E for ColE1, A for p15A and S for pSC101-based origins. The first number represents the antibiotic resistance marker (1 for Ampicillin, 2 for Kanamycin, 3 for Chloramphenicol, 4 for Spectinomycin and 5 for Tetracycline). The final number defines the promoter that regulated the gene of interest (1 for $P_{LtetO-1}$, 2 for $P_{LlacO-1}$, 3 for $P_{A1lacO-1}$, and 4 for $P_{lac/ara-1}$). The MCS and the gene of interest follows immediately after. For the work discussed here we employed two base vectors, pZA33 and pZE13, modified for the biobricks insertions as discussed above. Once the gene(s) of interest have been cloned into them, resulting plasmids are indicated using the four digit gene codes given in Table 6; e.g., pZA33-XXXX-YYYY-....

Host Strain Construction.

The parent strain in all studies described here is *E. coli* K-12 strain MG1655. Markerless deletion strains in adhE, gabD, and aldA were constructed under service contract by a third party using the redET method (Datsenko, K. A. and B. L. Wanner, *Proc Natl Acad Sci U.S.A* 97:6640-6645 (2000)). Subsequent strains were constructed via bacteriophage P1 mediated transduction (Miller, J. Experiments in Molecular Genetics, Cold Spring Harbor Laboratories, New York (1973)). Strain C600Z1 (laci$^q$, PN25-tetR, Sp$^R$, lacY1, leuB6, mcrB+, supE44, thi-1, thr-1, tonA21) was obtained from Expressys and was used as a source of a lacI$^q$ allele for P1 transduction. Bacteriophage P1vir was grown on the C600Z1 *E. coli* strain, which has the spectinomycin resistance gene linked to the lacI$^q$. The P1 lysate grown on C600Z1 was used to infect MG1655 with selection for spectinomycin resistance. The spectinomycin resistant colonies were then screened for the linked lacI$^q$ by determining the ability of the transductants to repress expression of a gene linked to a $P_{A1laeO-1}$ promoter. The resulting strain was designated MG1655 lacI$^q$. A similar procedure was used to introduce lacI$^Q$ into the deletion strains.

Production of 4-HB from Succinate.

For construction of a 4-HB producer from succinate, genes encoding steps from succinate to 4-HB and 4-HB-CoA (1, 6, 7, and 9 in FIG. 1) were assembled onto the pZA33 and pZE13 vectors as described below. Various combinations of genes were assessed, as well as constructs bearing incomplete pathways as controls (Tables 7 and 8). The plasmids were then transformed into host strains containing lacI$^Q$, which allow inducible expression by addition of isopropyl β-D-1-thiogalactopyranoside (IPTG). Both wild-type and hosts with deletions in genes encoding the native succinic semialdehyde dehydrogenase (step 2 in FIG. 1) were tested.

Activity of the heterologous enzymes were first tested in in vitro assays, using strain MG1655 lacI$^Q$ as the host for the plasmid constructs containing the pathway genes. Cells were grown aerobically in LB media (Difco) containing the appropriate antibiotics for each construct, and induced by addition of IPTG at 1 mM when the optical density (OD600) reached approximately 0.5. Cells were harvested after 6 hours, and enzyme assays conducted as discussed below.

In Vitro Enzyme Assays.

To obtain crude extracts for activity assays, cells were harvested by centrifugation at 4,500 rpm (Beckman-Coulter, Allegera X-15R) for 10 min. The pellets were resuspended in 0.3 mL BugBuster (Novagen) reagent with benzonase and lysozyme, and lysis proceeded for 15 minutes at room temperature with gentle shaking. Cell-free lysate was obtained by centrifugation at 14,000 rpm (Eppendorf centrifuge 5402) for 30 min at 4° C. Cell protein in the sample was determined using the method of Bradford et al., *Anal. Biochem.* 72:248-254 (1976), and specific enzyme assays conducted as described below. Activities are reported in Units/mg protein, where a unit of activity is defined as the amount of enzyme required to convert 1 μmol of substrate in 1 min. at room temperature. In general, reported values are averages of at least 3 replicate assays.

Succinyl-CoA transferase (Cat1) activity was determined by monitoring the formation of acetyl-CoA from succinyl-CoA and acetate, following a previously described procedure Sohling and Gottschalk, *J. Bacteriol.* 178:871-880 (1996). Succinyl-CoA synthetase (SucCD) activity was determined by following the formation of succinyl-CoA from succinate and CoA in the presence of ATP. The experiment followed a procedure described by Cha and Parks, *J. Biol. Chem.* 239:1961-1967 (1964). CoA-dependent succinate semialdehyde dehydrogenase (SucD) activity was determined by following the conversion of NAD to NADH at 340 nm in the presence of succinate semialdehyde and CoA (Sohling and Gottschalk, *Eur. J. Biochem.* 212: 121-127 (1993)). 4-HB dehydrogenase (4-HBd) enzyme activity was determined by monitoring the oxidation of NADH to NAD at 340 nm in the presence of succinate semialdehyde. The experiment followed a published procedure Gerhardt et al. *Arch. Microbiol.* 174:189-199 (2000). 4-HB CoA transferase (Cat2) activity was determined using a modified procedure from Scherf and Buckel, *Appl. Environ. Microbiol.* 57:2699-2702 (1991). The formation of 4-HB-CoA or butyryl-CoA formation from acetyl-CoA and 4-HB or butyrate was determined using HPLC.

Alcohol (ADH) and aldehyde (ALD) dehydrogenase was assayed in the reductive direction using a procedure adapted from several literature sources (Durre et al., *FEMS Microbiol. Rev.* 17:251-262 (1995); Palosaari and Rogers, *J. Bacteriol.* 170:2971-2976 (1988) and Welch et al., *Arch. Biochem. Biophys.* 273:309-318 (1989). The oxidation of NADH is followed by reading absorbance at 340 nM every four seconds for a total of 240 seconds at room temperature. The reductive assays were performed in 100 mM MOPS (adjusted to pH 7.5 with KOH), 0.4 mM NADH, and from 1 to 50 µl of cell extract. The reaction is started by adding the following reagents: 100 µl of 100 mM acetaldehyde or butyraldehyde for ADH, or 100 µl of 1 mM acetyl-CoA or butyryl-CoA for ALD. The Spectrophotometer is quickly blanked and then the kinetic read is started. The resulting slope of the reduction in absorbance at 340 nM per minute, along with the molar extinction coefficient of NAD(P)H at 340 nM (6000) and the protein concentration of the extract, can be used to determine the specific activity.

The enzyme activity of PTB is measured in the direction of butyryl-CoA to butyryl-phosphate as described in Cary et al. *J. Bacteriol.* 170:4613-4618 (1988). It provides inorganic phosphate for the conversion, and follows the increase in free CoA with the reagent 5,5'-dithiobis-(2-nitrobenzoic acid), or DTNB. DTNB rapidly reacts with thiol groups such as free CoA to release the yellow-colored 2-nitro-5-mercaptobenzoic acid (TNB), which absorbs at 412 nm with a molar extinction coefficient of 14,140 M cm$^{-1}$. The assay buffer contained 150 mM potassium phosphate at pH 7.4, 0.1 mM DTNB, and 0.2 mM butyryl-CoA, and the reaction was started by addition of 2 to 50 µL cell extract. The enzyme activity of BK is measured in the direction of butyrate to butyryl-phosphate formation at the expense of ATP. The procedure is similar to the assay for acetate kinase previously described Rose et al., *J. Biol. Chem.* 211:737-756 (1954). However we have found another acetate kinase enzyme assay protocol provided by Sigma to be more useful and sensitive. This assay links conversion of ATP to ADP by acetate kinase to the linked conversion of ADP and phosphoenol pyruvate (PEP) to ATP and pyruvate by pyruvate kinase, followed by the conversion of pyruvate and NADH to lactate and NAD+ by lactate dehydrogenase. Substituting butyrate for acetate is the only major modification to enable the assay to follow BK enzyme activity. The assay mixture contained 80 mM triethanolamine buffer at pH 7.6, 200 mM sodium butyrate, 10 mM MgCl2, 0.1 mM NADH, 6.6 mM ATP, 1.8 mM phosphoenolpyruvate. Pyruvate kinase, lactate dehydrogenase, and myokinase were added according to the manufacturer's instructions. The reaction was started by adding 2 to 50 µL cell extract, and the reaction was monitored based on the decrease in absorbance at 340 nm indicating NADH oxidation.

Analysis of CoA Derivatives by HPLC.

An HPLC based assay was developed to monitor enzymatic reactions involving coenzyme A (CoA) transfer. The developed method enabled enzyme activity characterization by quantitative determination of CoA, acetyl CoA (AcCoA), butyryl CoA (BuCoA) and 4-hydroxybutyrate CoA (4-HB-CoA) present in in-vitro reaction mixtures. Sensitivity down to low µM was achieved, as well as excellent resolution of all the CoA derivatives of interest.

Chemical and sample preparation was performed as follows. Briefly, CoA, AcCoA, BuCoA and all other chemicals, were obtained from Sigma-Aldrich. The solvents, methanol and acetonitrile, were of HPLC grade. Standard calibration curves exhibited excellent linearity in the 0.01-1 mg/mL concentration range. Enzymatic reaction mixtures contained 100 mM Tris HCl buffer (pH 7), aliquots were taken at different time points, quenched with formic acid (0.04% final concentration) and directly analyzed by HPLC.

HPLC analysis was performed using an Agilent 1100 HPLC system equipped with a binary pump, degasser, thermostated autosampler and column compartment, and diode array detector (DAD), was used for the analysis. A reversed phase column, Kromasil 100 Sum C18, 4.6×150 mm (Peeke Scientific), was employed. 25 mM potassium phosphate (pH 7) and methanol or acetonitrile, were used as aqueous and organic solvents at 1 mL/min flow rate. Two methods were developed: a short one with a faster gradient for the analysis of well-resolved CoA, AcCoA and BuCoA, and a longer method for distinguishing between closely eluting AcCoA and 4-HBCoA. Short method employed acetonitrile gradient (0 min-5%, 6 min-30%, 6.5 min-5%, 10 min-5%) and resulted in the retention times 2.7, 4.1 and 5.5 min for CoA, AcCoA and BuCoA, respectively. In the long method methanol was used with the following linear gradient: 0 min-5%, 20 min-35%, 20.5 min-5%, 25 min-5%. The retention times for CoA, AcCoA, 4-HBCoA and BuCoA were 5.8, 8.4, 9.2 and 16.0 min, respectively. The injection volume was 5 µL, column temperature 30° C., and UV absorbance was monitored at 260 nm.

The results demonstrated activity of each of the four pathway steps (Table 7), though activity is clearly dependent on the gene source, position of the gene in the vector, and the context of other genes with which it is expressed. For example, gene 0035 encodes a succinic semialdehyde dehydrogenase that is more active than that encoded by 0008, and 0036 and 0010n are more active 4-HB dehydrogenase genes than 0009. There also seems to be better 4-HB dehydrogenase activity when there is another gene preceding it on the same operon.

TABLE 7

In vitro enzyme activities in cell extracts from MG1655 lacI$^Q$ containing the plasmids expressing genes in the 4-HB-CoA pathway. Activities are reported in Units/mg protein, where a unit of activity is defined as the amount of enzyme required to convert 1 µmol of substrate in 1 min. at room temperature.

| Sample # | pZE13 (a) | pZA33 (b) | OD600 | Cell Prot (c) | Cat1 | SucD | 4HBd | Cat2 |
|---|---|---|---|---|---|---|---|---|
| 1 | cat1 (0004) | | 2.71 | 6.43 | 1.232 | | | 0.00 |
| 2 | cat1 (0004)-sucD (0035) | | 2.03 | 5.00 | 0.761 | 2.57 | | |
| 3 | cat1 (0004)-sucD (0008) | | 1.04 | 3.01 | 0.783 | 0.01 | | |

TABLE 7-continued

In vitro enzyme activities in cell extracts from MG1655 lacI$^Q$ containing the plasmids expressing genes in the 4-HB-CoA pathway. Activities are reported in Units/mg protein, where a unit of activity is defined as the amount of enzyme required to convert 1 μmol of substrate in 1 min. at room temperature.

| Sample # | pZE13 (a) | pZA33 (b) | OD600 | Cell Prot (c) | Cat1 | SucD | 4HBd | Cat2 |
|---|---|---|---|---|---|---|---|---|
| 4 | sucD (0035) | | 2.31 | 6.94 | | 2.32 | | |
| 5 | sucD (0008) | | 1.10 | 4.16 | | 0.05 | | |
| 6 | | 4hbd (0009) | 2.81 | 7.94 | 0.003 | | 0.25 | |
| 7 | | 4hbd (0036) | 2.63 | 7.84 | | | 3.31 | |
| 8 | | 4hbd (0010n) | 2.00 | 5.08 | | | 2.57 | |
| 9 | cat1 (0004)-sucD (0035) | 4hbd (0009) | 2.07 | 5.04 | 0.600 | 1.85 | 0.01 | |
| 10 | cat1 (0004)-sucD (0035) | 4hbd (0036) | 2.08 | 5.40 | 0.694 | 1.73 | 0.41 | |
| 11 | cat1 (0004)-sucD (0035) | 4hbd (0010n) | 2.44 | 4.73 | 0.679 | 2.28 | 0.37 | |
| 12 | cat1 (0004)-sucD (0008) | 4hbd (0009) | 1.08 | 3.99 | 0.572 | −0.01 | 0.02 | |
| 13 | cat1 (0004)-sucD (0008) | 4hbd (0036) | 0.77 | 2.60 | 0.898 | −0.01 | 0.04 | |
| 14 | cat1 (0004)-sucD (0008) | 4hbd (0010n) | 0.63 | 2.47 | 0.776 | 0.00 | 0.00 | |
| 15 | | cat2 (0034) | 2.56 | 7.86 | | | | 1.283 |
| 16 | | cat2 (0034)-4hbd (0036) | 3.13 | 8.04 | | | 24.86 | 0.993 |
| 17 | | cat2 (0034)-4hbd (0010n) | 2.38 | 7.03 | | | 7.45 | 0.675 |
| 18 | | 4hbd (0036)-cat2 (0034) | 2.69 | 8.26 | | | 2.15 | 7.490 |
| 19 | | 4hbd (0010n)-cat2 (0034) | 2.44 | 6.59 | | | 0.59 | 4.101 |

(a) Genes expressed from Plac on pZE13, a high-copy plasmid with colE1 origin and ampicillin resistance. Gene identification numbers are as given in Table 6
(b) Genes expressed from Plac on pZA33, a medium-copy plasmid with pACYC origin and chloramphenicol resistance.
(c) Cell protein given as mg protein per mL extract.

Recombinant strains containing genes in the 4-HB pathway were then evaluated for the ability to produce 4-HB in vivo from central metabolic intermediates. Cells were grown anaerobically in LB medium to OD600 of approximately 0.4, then induced with 1 mM IPTG. One hour later, sodium succinate was added to 10 mM, and samples taken for analysis following an additional 24 and 48 hours. 4-HB in the culture broth was analyzed by GC-MS as described below. The results indicate that the recombinant strain can produce over 2 mM 4-HB after 24 hours, compared to essentially zero in the control strain (Table 8).

cluster was cloned onto pZE13 along with candidate genes for the remaining steps to 4-HB to create pZE13-0038-0035-0036.

Production of 4-HB from Glucose.

Although the above experiments demonstrate a functional pathway to 4-HB from a central metabolic intermediate (succinate), an industrial process would require the production of chemicals from low-cost carbohydrate feedstocks such as glucose or sucrose. Thus, the next set of experiments was aimed to determine whether endogenous succinate produced by the cells during growth on glucose could fuel the 4-HB pathway. Cells were grown anaerobically in M9 minimal medium (6.78 g/L Na$_2$HPO$_4$, 3.0 g/L KH$_2$PO$_4$, 0.5

TABLE 8

Production of 4-HB from succinate in *E. coli* strains harboring plasmids expressing various combinations of 4-HB pathway genes.

| Sample | | | | 24 Hours | | | 48 Hours | | |
|---|---|---|---|---|---|---|---|---|---|
| # | Host Strain | pZE13 | pZA33 | OD600 | 4HB, μM | 4HB norm. (a) | OD600 | 4HB, μM | 4HB norm. (a) |
| 1 | MG1655 lacIq | cat1 (0004)-sucD (0035) | 4hbd (0009) | 0.47 | 487 | 1036 | 1.04 | 1780 | 1711 |
| 2 | MG1655 lacIq | cat1 (0004)-sucD (0035) | 4hbd (0027) | 0.41 | 111 | 270 | 0.99 | 214 | 217 |
| 3 | MG1655 lacIq | cat1 (0004)-sucD (0035) | 4hbd (0036) | 0.47 | 863 | 1835 | 0.48 | 2152 | 4484 |
| 4 | MG1655 lacIq | cat1 (0004)-sucD (0035) | 4hbd (0010n) | 0.46 | 956 | 2078 | 0.49 | 2221 | 4533 |
| 5 | MG1655 lacIq | cat1 (0004)-sucD (0008) | 4hbd (0009) | 0.38 | 493 | 1296 | 0.37 | 1338 | 3616 |
| 6 | MG1655 lacIq | cat1 (0004)-sucD (0008) | 4hbd (0027) | 0.32 | 26 | 81 | 0.27 | 87 | 323 |
| 7 | MG1655 lacIq | cat1 (0004)-sucD (0008) | 4hbd (0036) | 0.24 | 506 | 2108 | 0.31 | 1448 | 4672 |
| 8 | MG1655 lacIq | cat1 (0004)-sucD (0008) | 4hbd (0010n) | 0.24 | 78 | 324 | 0.56 | 233 | 416 |
| 9 | MG1655 lacIq gabD | cat1 (0004)-sucD (0035) | 4hbd (0009) | 0.53 | 656 | 1237 | 1.03 | 1643 | 1595 |
| 10 | MG1655 lacIq gabD | cat1 (0004)-sucD (0035) | 4hbd (0027) | 0.44 | 92 | 209 | 0.98 | 214 | 218 |
| 11 | MG1655 lacIq gabD | cat1 (0004)-sucD (0035) | 4hbd (0036) | 0.51 | 1072 | 2102 | 0.97 | 2358 | 2431 |
| 12 | MG1655 lacIq gabD | cat1 (0004)-sucD (0035) | 4hbd (0010n) | 0.51 | 981 | 1924 | 0.97 | 2121 | 2186 |
| 13 | MG1655 lacIq gabD | cat1 (0004)-sucD (0008) | 4hbd (0009) | 0.35 | 407 | 1162 | 0.77 | 1178 | 1530 |
| 14 | MG1655 lacIq gabD | cat1 (0004)-sucD (0008) | 4hbd (0027) | 0.51 | 19 | 36 | 1.07 | 50 | 47 |
| 15 | MG1655 lacIq gabD | cat1 (0004)-sucD (0008) | 4hbd (0036) | 0.35 | 584 | 1669 | 0.78 | 1350 | 1731 |
| 16 | MG1655 lacIq gabD | cat1 (0004)-sucD (0008) | 4hbd (0010n) | 0.32 | 74 | 232 | 0.82 | 232 | 283 |
| 17 | MG1655 lacIq | vector only | vector only | 0.8 | 1 | 2 | 1.44 | 3 | 2 |
| 18 | MG1655 lacIq gabD | vector only | vector only | 0.89 | 1 | 2 | 1.41 | 7 | 5 |

(a) Normalized 4-HB concentration, μM/OD600 units

Figure 3A:
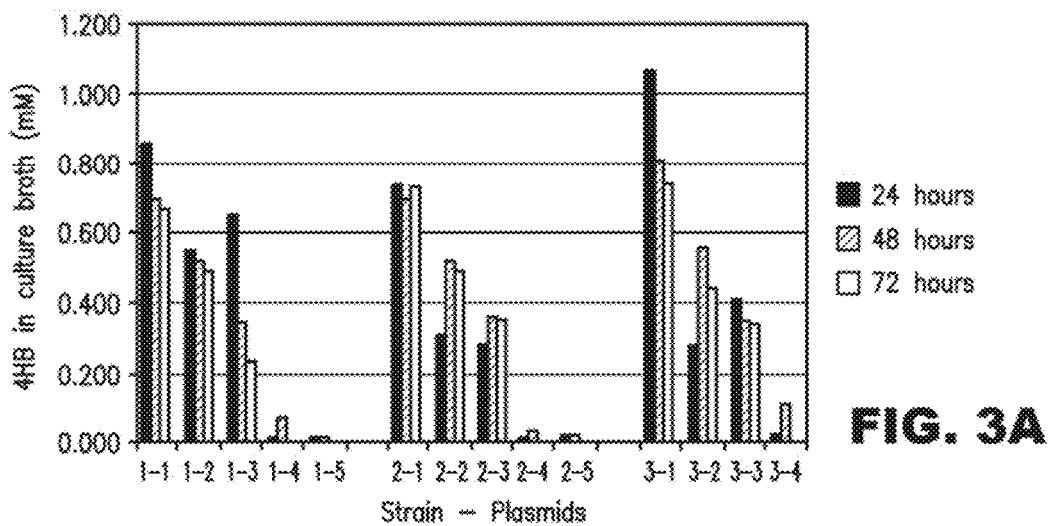
FIGS. 3A-3C show the production of 4-HB in glucose minimal medium using *E. coli* strains harboring plasmids expressing various combinations of 4-HB pathway genes.
Figure 3B:
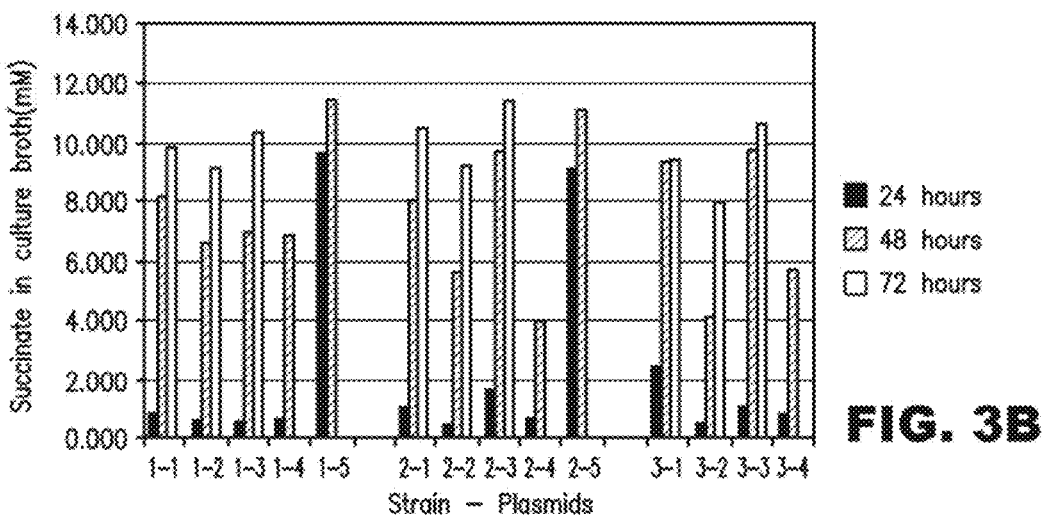
Figure 3C:
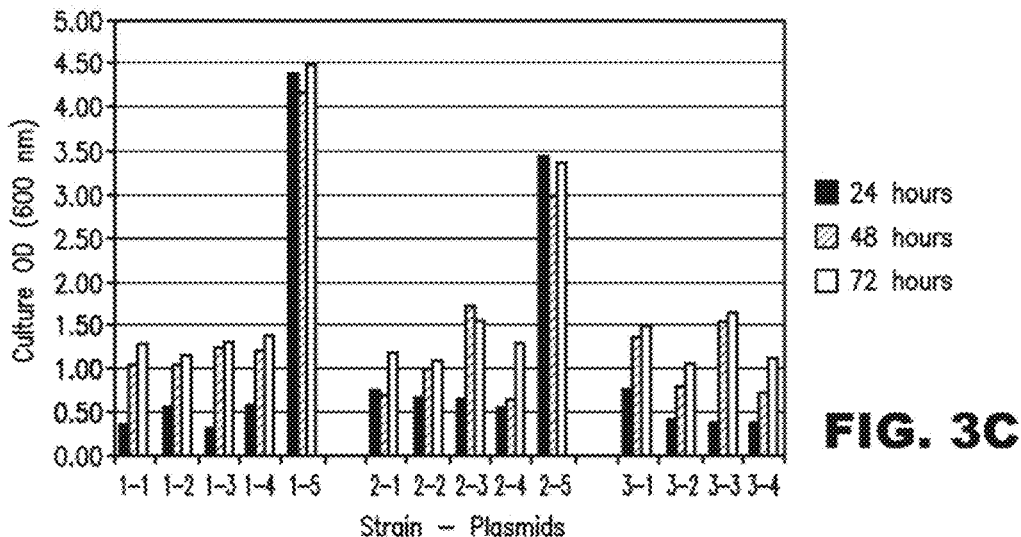

An alternate to using a CoA transferase (cat1) to produce succinyl-CoA from succinate is to use the native *E. coli* sucCD genes, encoding succinyl-CoA synthetase. This gene g/L NaCl, 1.0 g/L NH$_4$Cl, 1 mM MgSO$_4$, 0.1 mM CaCl$_2$) supplemented with 20 g/L glucose, 100 mM 3-(N-morpholino)propanesulfonic acid (MOPS) to improve the buffering capacity, 10 µg/mL thiamine, and the appropriate antibiotics. 0.25 mM IPTG was added when OD600 reached approximately 0.2, and samples taken for 4-HB analysis every 24 hours following induction. In all cases 4-HB plateaued after 24 hours, with a maximum of about 1 mM in the best strains (FIG. 3a), while the succinate concentration continued to rise (FIG. 3b). This indicates that the supply of succinate to the pathway is likely not limiting, and that the bottleneck may be in the activity of the enzymes themselves or in NADH availability. 0035 and 0036 are clearly the best gene candidates for CoA-dependent succinic semialdehyde dehydrogenase and 4-HB dehydrogenase, respectively. The elimination of one or both of the genes encoding known (gabD) or putative (aldA) native succinic semialdehyde dehydrogenases had little effect on performance. Finally, it should be noted that the cells grew to a much lower OD in the 4-HB-producing strains than in the controls (FIG. 3c).

Figure 4:
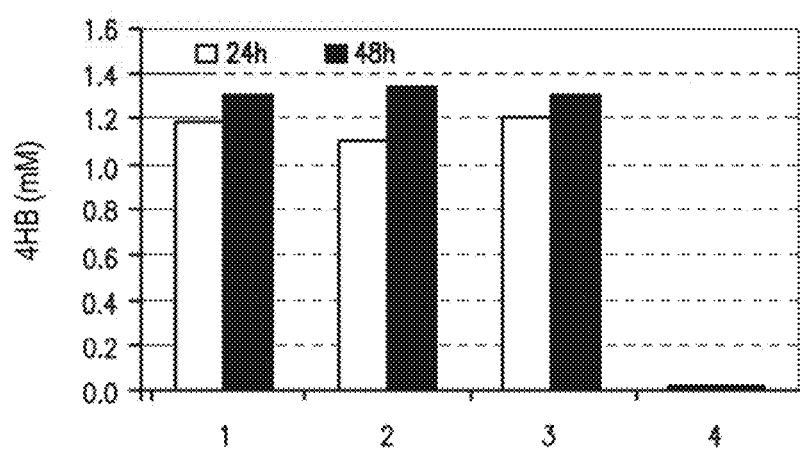
FIG. 4 shows the production of 4-HB from glucose in *E. coli* strains expressing α-ketoglutarate decarboxylase from *Mycobacterium tuberculosis*. Strains 1-3 contain pZE13-0032 and pZA33-0036. Strain 4 expresses only the empty vectors pZE13 and pZA33. Host strains are as follows: 1 and 4, MG1655 lacI$^Q$; 2, MG1655 ΔgabD lacI$^Q$; 3, MG1655 ΔgabD ΔaldA lacI$^Q$. The bars refer to concentration at 24 and 48 hours.

An alternate pathway for the production of 4-HB from glucose is via α-ketoglutarate. We explored the use of an α-ketoglutarate decarboxylase from *Mycobacterium tuberculosis* Tian et al., *Proc. Natl. Acad. Sci. USA* 102:10670-10675 (2005) to produce succinic semialdehyde directly from α-ketoglutarate (step 8 in FIG. 1). To demonstrate that this gene (0032) was functional in vivo, we expressed it on pZE13 in the same host as 4-HB dehydrogenase (gene 0036) on pZA33. This strain was capable of producing over 1.0 mM 4-HB within 24 hours following induction with 1 mM IPTG (FIG. 4). Since this strain does not express a CoA-dependent succinic semialdehyde dehydrogenase, the possibility of succinic semialdehyde production via succinyl-CoA is eliminated. It is also possible that the native genes responsible for producing succinic semialdehyde could function in this pathway (steps 4 and 5 in FIG. 1); however, the amount of 4-HB produced when the pZE13-0032 plasmid was left out of the host is the negligible.

Production of BDO from 4-HB.

The production of BDO from 4-HB required two reduction steps, catalyzed by dehydrogenases. Alcohol and aldehyde dehydrogenases (ADH and ALD, respectively) are NAD+/H and/or NADP+/H-dependent enzymes that together can reduce a carboxylic acid group on a molecule to an alcohol group, or in reverse, can perform the oxidation of an alcohol to a carboxylic acid. This biotransformation has been demonstrated in wild-type *Clostridium acetobutylicum* (Jewell et al., *Current Microbiology*, 13:215-19 (1986)), but neither the enzymes responsible nor the genes responsible were identified. In addition, it is not known whether activation to 4-HB-CoA is first required (step 9 in FIG. 1), or if the aldehyde dehydrogenase (step 12) can act directly on 4-HB. We developed a list of candidate enzymes from *C. acetobutylicum* and related organisms based on known activity with the non-hydroxylated analogues to 4-HB and pathway intermediates, or by similarity to these characterized genes (Table 6). Since some of the candidates are multifunctional dehydrogenases, they could potentially catalyze both the NAD(P)H-dependent reduction of the acid (or CoA-derivative) to the aldehyde, and of the aldehyde to the alcohol. Before beginning work with these genes in *E. coli*, we first validated the result referenced above using *C. acetobutylicum* ATCC 824. Cells were grown in Schaedler broth (Accumedia, Lansing, Mich.) supplemented with 10 mM 4-HB, in an anaerobic atmosphere of 10% $CO_2$, 10% $H_2$, and 80% $N_2$ at 30° C. Periodic culture samples were taken, centrifuged, and the broth analyzed for BDO by GC-MS as described below. BDO concentrations of 0.1 mM, 0.9 mM, and 1.5 mM were detected after 1 day, 2 days, and 7 days incubation, respectively. No BDO was detected in culture grown without 4-HB addition. To demonstrate that the BDO produced was derived from glucose, we grew the best BDO producing strain MG1655 lacI$^Q$ pZE13-0004-0035-0002 pZA33-0034-0036 in M9 minimal medium supplemented with 4 g/L uniformly labeled $^{13}$C-glucose. Cells were induced at OD of 0.67 with 1 mM IPTG, and a sample taken after 24 hours. Analysis of the culture supernatant was performed by mass spectrometry.

Gene candidates for the 4-HB to BDO conversion pathway were next tested for activity when expressed in the *E. coli* host MG1655 lacI$^Q$. Recombinant strains containing each gene candidate expressed on pZA33 were grown in the presence of 0.25 mM IPTG for four hours at 37° C. to fully induce expression of the enzyme. Four hours after induction, cells were harvested and assayed for ADH and ALD activity as described above. Since 4-HB-CoA and 4-hydroxybutyraldehyde are not available commercially, assays were performed using the non-hydroxylated substrates (Table 9). The ratio in activity between 4-carbon and 2-carbon substrates for *C. acetobutylicum* adhE2 (0002) and *E. coli* adhE (0011) were similar to those previously reported in the literature a Atsumi et al., *Biochim. Biophys. Acta.* 1207:1-11 (1994).

TABLE 9

In vitro enzyme activities in cell extracts from MG1655 lacI$^Q$ containing pZA33 expressing gene candidates for aldehyde and alcohol dehydrogenases. Activities are expressed in µmol min$^{-1}$ mg cell protein$^{-1}$.

| | Aldehyde dehydrogenase | | Alcohol dehydrogenase | |
| --- | --- | --- | --- | --- |
| | Substrate | | | |
| Gene | Butyryl-CoA | Acetyl-CoA | Butyraldehyde | Acetaldehyde |
| 0002 | 0.0076 | 0.0046 | 0.0264 | 0.0247 |
| 0003n | 0.0060 | 0.0072 | 0.0080 | 0.0075 |
| 0011 | 0.0069 | 0.0095 | 0.0265 | 0.0093 |
| 0013 | N.D. | N.D. | 0.0130 | 0.0142 |
| 0023 | 0.0089 | 0.0137 | 0.0178 | 0.0235 |
| 0025 | 0 | 0.0001 | N.D. | N.D. |
| 0026 | 0 | 0.0005 | 0.0024 | 0.0008 |

N.D., not determined.

Figure 5:
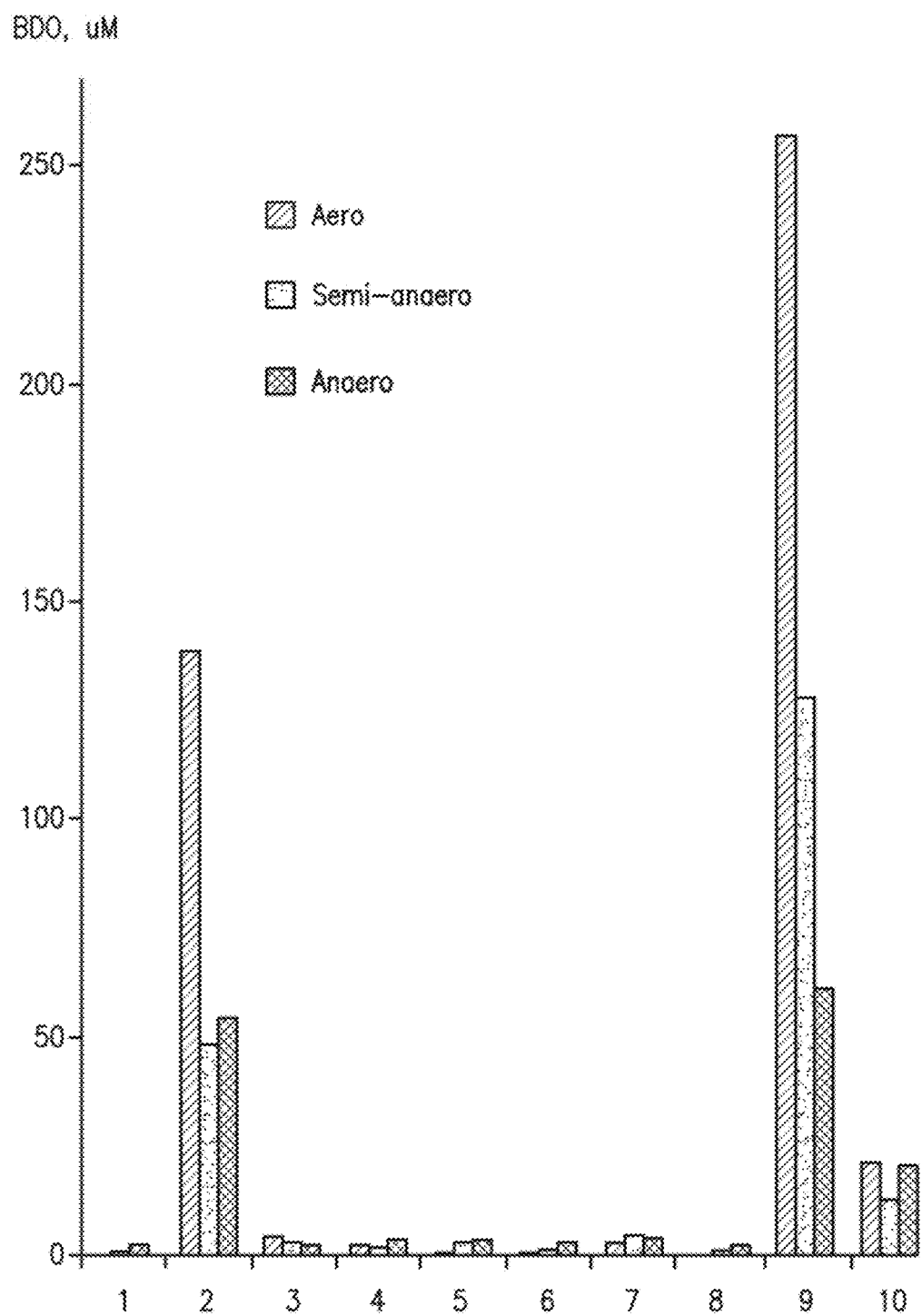
FIG. 5 shows the production of BDO from 10 mM 4-HB in recombinant *E. coli* strains. Numbered positions correspond to experiments with MG1655 lacI$^Q$ containing pZA33-0024, expressing cat2 from *P. gingivalis*, and the following genes expressed on pZE13: 1, none (control); 2, 0002; 3, 0003; 4, 0003n; 5, 0011; 6, 0013; 7, 0023; 8, 0025; 9, 0008n; 10, 0035. Gene numbers are defined in Table 6. For each position, the bars refer to aerobic, microaerobic, and anaerobic conditions, respectively. Microaerobic conditions were created by sealing the culture tubes but not evacuating them.
Figure 6A:
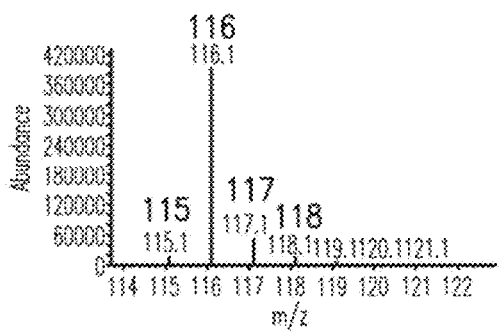
FIGS. 6A-6H show the mass spectrum of 4-HB and BDO produced by MG1655 lacI$^Q$ pZE13-0004-0035-0002 pZA33-0034-0036 grown in M9 minimal medium supplemented with 4 g/L unlabeled glucose (FIGS. 6A, 6C, 6E and 6G) uniformly labeled $^{13}$C-glucose (FIGS. 6B, 6D, 6F and 6H).
Figure 6B:
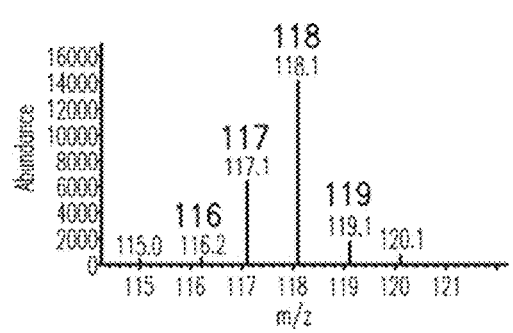
Figure 6C:
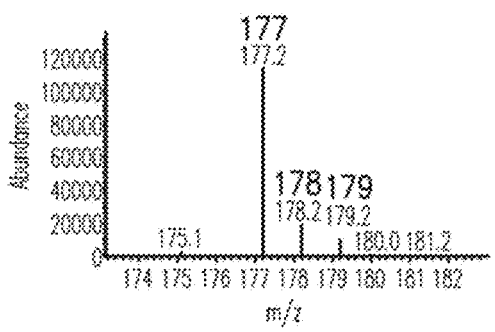
Figure 6D:
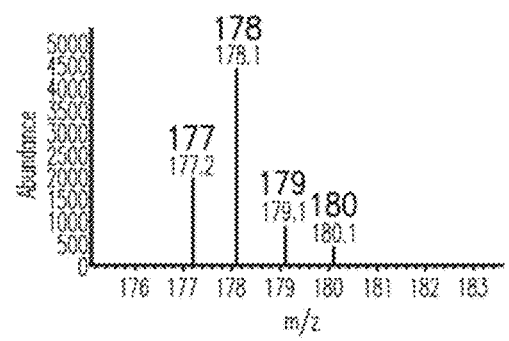
Figure 6E:
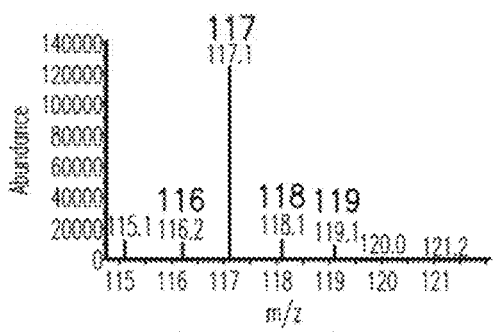
Figure 6F:
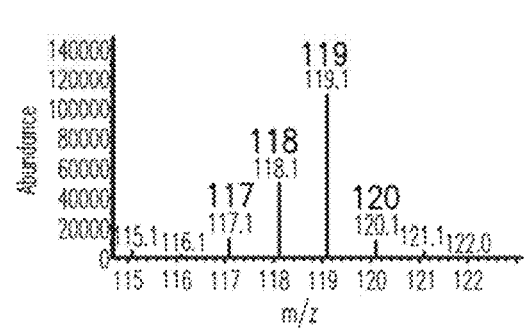
Figure 6G:
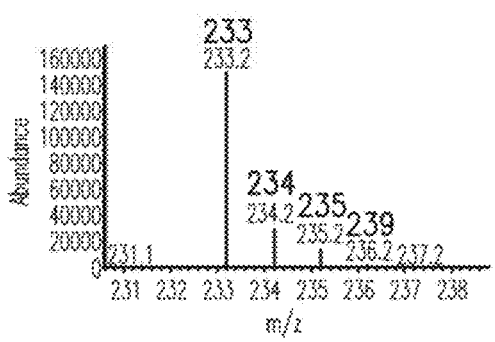
Figure 6H:
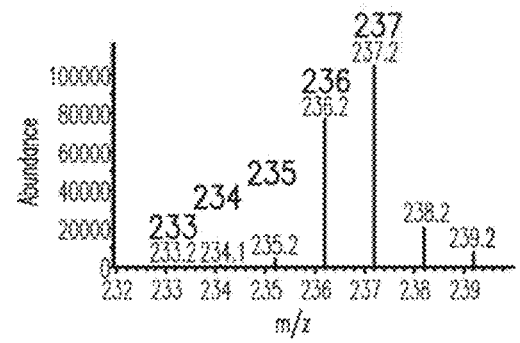

For the BDO production experiments, cat2 from *Porphyromonas gingivalis* W83 (gene 0034) was included on pZA33 for the conversion of 4-HB to 4-HB-CoA, while the candidate dehydrogenase genes were expressed on pZE13. The host strain was MG1655 lacI$^Q$. Along with the alcohol and aldehyde dehydrogenase candidates, we also tested the ability of CoA-dependent succinic semialdehyde dehydrogenases (sucD) to function in this step, due to the similarity of the substrates. Cells were grown to an OD of about 0.5 in LB medium supplemented with 10 mM 4-HB, induced with 1 mM IPTG, and culture broth samples taken after 24 hours and analyzed for BDO as described below. The best BDO production occurred using adhE2 from *C. acetobutylicum*, sucD from *C. kluyveri*, or sucD from *P. gingivalis* (FIG. 5). Interestingly, the absolute amount of BDO produced was higher under aerobic conditions; however, this is primarily due to the lower cell density achieved in anaerobic cultures. When normalized to cell OD, the BDO production per unit biomass is higher in anaerobic conditions (Table 10).

TABLE 10

Absolute and normalized BDO concentrations from cultures of cells expressing adhE2 from C. acetobutylicum, sucD from C. kluyveri, or sucD from P. gingivalis (data from experiments 2, 9, and 10 in FIG. 3), as well as the negative control (experiment 1).

| Gene expressed | Conditions | BDO (µM) | OD (600 nm) | BDO/OD |
|---|---|---|---|---|
| none | Aerobic | 0 | 13.4 | 0 |
| none | Microaerobic | 0.5 | 6.7 | 0.09 |
| none | Anaerobic | 2.2 | 1.26 | 1.75 |
| 0002 | Aerobic | 138.3 | 9.12 | 15.2 |
| 0002 | Microaerobic | 48.2 | 5.52 | 8.73 |
| 0002 | Anaerobic | 54.7 | 1.35 | 40.5 |
| 0008n | Aerobic | 255.8 | 5.37 | 47.6 |
| 0008n | Microaerobic | 127.9 | 3.05 | 41.9 |
| 0008n | Anaerobic | 60.8 | 0.62 | 98.1 |
| 0035 | Aerobic | 21.3 | 14.0 | 1.52 |
| 0035 | Microaerobic | 13.1 | 4.14 | 3.16 |
| 0035 | Anaerobic | 21.3 | 1.06 | 20.1 |

As discussed above, it may be advantageous to use a route for converting 4-HB to 4-HB-CoA that does not generate acetate as a byproduct. To this aim, we tested the use of phosphotransbutyrylase (ptb) and butyrate kinase (bk) from C. acetobutylicum to carry out this conversion via steps 10 and 11 in FIG. 1. The native ptb/bk operon from C. acetobutylicum (genes 0020 and 0021) was cloned and expressed in pZA33. Extracts from cells containing the resulting construct were taken and assayed for the two enzyme activities as described herein. The specific activity of BK was approximately 65 U/mg, while the specific activity of PTB was approximately 5 U/mg. One unit (U) of activity is defined as conversion of 1 µM substrate in 1 minute at room temperature. Finally, the construct was tested for participation in the conversion of 4-HB to BDO. Host strains were transformed with the pZA33-0020-0021 construct described and pZE13-0002, and compared to use of cat2 in BDO production using the aerobic procedure used above in FIG. 5. The BK/PTB strain produced 1 mM BDO, compared to 2 mM when using cat2 (Table 11). Interestingly, the results were dependent on whether the host strain contained a deletion in the native adhE gene.

TABLE 11

Absolute and normalized BDO concentrations from cultures of cells expressing adhE2 from C. acetobutylicum in pZE13 along with either cat2 from P. gingivalis (0034) or the PTB/BK genes from C. acetobutylicum on pZA33. Host strains were either MG1655 lacI$^Q$ or MG1655 ΔadhE lacI$^Q$.

| Genes | Host Strain | BDO (µM) | OD (600 nm) | BDO/OD |
|---|---|---|---|---|
| 0034 | MG1655 lacI$^Q$ | 0.827 | 19.9 | 0.042 |
| 0020 + 0021 | MG1655 lacI$^Q$ | 0.007 | 9.8 | 0.0007 |
| 0034 | MG1655 ΔadhE lacI$^Q$ | 2.084 | 12.5 | 0.166 |
| 0020 + 0021 | MG1655 ΔadhE lacI$^Q$ | 0.975 | 18.8 | 0.052 |

Production of BDO from Glucose.

The final step of pathway corroboration is to express both the 4-HB and BDO segments of the pathway in E. coli and demonstrate production of BDO in glucose minimal medium. New plasmids were constructed so that all the required genes fit on two plasmids. In general, cat1, adhE, and sucD genes were expressed from pZE13, and cat2 and 4-HBd were expressed from pZA33. Various combinations of gene source and gene order were tested in the MG1655 lacI$^Q$ background. Cells were grown anaerobically in M9 minimal medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) supplemented with 20 g/L glucose, 100 mM 3-(N-morpholino)propanesulfonic acid (MOPS) to improve the buffering capacity, 10 µg/mL thiamine, and the appropriate antibiotics. 0.25 mM IPTG was added approximately 15 hours following inoculation, and culture supernatant samples taken for BDO, 4-HB, and succinate analysis 24 and 48 hours following induction. The production of BDO appeared to show a dependency on gene order (Table 12). The highest BDO production, over 0.5 mM, was obtained with cat2 expressed first, followed by 4-HBd on pZA33, and cat1 followed by P. gingivalis sucD on pZE13. The addition of C. acetobutylicum adhE2 in the last position on pZE13 resulted in slight improvement. 4-HB and succinate were also produced at higher concentrations.

TABLE 12

Production of BDO, 4-HB, and succinate in recombinant E. coli strains expressing combinations of BDO pathway genes, grown in minimal medium supplemented with 20 g/L glucose. Concentrations are given in mM.

| Sample | pZE13 | pZA33 | Induction OD | 24 Hours | | | | 48 Hours | | | |
|---|---|---|---|---|---|---|---|---|---|---|---|
| | | | | OD600 nm | Su | 4HB | BDO | OD600 nm | Su | 4HB | BDO |
| 1 | cat1 (0004)-sucD (0035) | 4hbd (0036)-cat2 (0034) | 0.92 | 1.29 | 5.44 | 1.37 | 0.240 | 1.24 | 6.42 | 1.49 | 0.280 |
| 2 | cat1 (0004)-sucD (0008N) | 4hbd (0036)-cat2 (0034) | 0.36 | 1.11 | 6.90 | 1.24 | 0.011 | 1.06 | 7.63 | 1.33 | 0.011 |

TABLE 12-continued

Production of BDO, 4-HB, and succinate in recombinant E. coli strains expressing combinations of BDO pathway genes, grown in minimal medium supplemented with 20 g/L glucose. Concentrations are given in mM.

| | | | Induction | 24 Hours | | | | 48 Hours | | | |
|---|---|---|---|---|---|---|---|---|---|---|---|
| Sample | pZE13 | pZA33 | OD | OD600 nm | Su | 4HB | BDO | OD600 nm | Su | 4HB | BDO |
| 3 | adhE (0002)-cat1 (0004)-sucD (0035) | 4hbd (0036)-cat2 (0034) | 0.20 | 0.44 | 0.34 | 1.84 | 0.050 | 0.60 | 1.93 | 2.67 | 0.119 |
| 4 | cat1 (0004)-sucD (0035)-adhE (0002) | 4hbd (0036)-cat2 (0034) | 1.31 | 1.90 | 9.02 | 0.73 | 0.073 | 1.95 | 9.73 | 0.82 | 0.077 |
| 5 | adhE (0002)-cat1 (0004)-sucD (0008N) | 4hbd (0036)-cat2 (0034) | 0.17 | 0.45 | 1.04 | 1.04 | 0.008 | 0.94 | 7.13 | 1.02 | 0.017 |
| 6 | cat1 (0004)-sucD (0008N)-adhE (0002) | 4hbd (0036)-cat2 (0034) | 1.30 | 1.77 | 10.47 | 0.25 | 0.004 | 1.80 | 11.49 | 0.28 | 0.003 |
| 7 | cat1 (0004)-sucD (0035) | cat2 (0034)-4hbd (0036) | 1.09 | 1.29 | 5.63 | 2.15 | 0.461 | 1.38 | 6.66 | 2.30 | 0.520 |
| 8 | cat1 (0004)-sucD (0008N) | cat2 (0034)-4hbd (0036) | 1.81 | 2.01 | 11.28 | 0.02 | 0.000 | 2.24 | 11.13 | 0.02 | 0.000 |
| 9 | adhE (0002)-cat1 (0004)-sucD (0035) | cat2 (0034)-4hbd (0036) | 0.24 | 1.99 | 2.02 | 2.32 | 0.106 | 0.89 | 4.85 | 2.41 | 0.186 |
| 10 | cat1 (0004)-sucD (0035)-adhE (0002) | cat2 (0034)-4hbd (0036) | 0.98 | 1.17 | 5.30 | 2.08 | 0.569 | 1.33 | 6.15 | 2.14 | 0.640 |
| 11 | adhE (0002)-cat1 (0004)-sucD (0008N) | cat2 (0034)-4hbd (0036) | 0.20 | 0.53 | 1.38 | 2.30 | 0.019 | 0.91 | 8.10 | 1.49 | 0.034 |
| 12 | cat1 (0004)-sucD (0008N)-adhE (0002) | cat2 (0034)-4hbd (0036) | 2.14 | 2.73 | 12.07 | 0.16 | 0.000 | 3.10 | 11.79 | 0.17 | 0.002 |
| 13 | vector only | vector only | 2.11 | 2.62 | 9.03 | 0.01 | 0.000 | 3.00 | 12.05 | 0.01 | 0.000 |

Analysis of BDO, 4-HB and Succinate by GCMS.

BDO, 4-HB and succinate in fermentation and cell culture samples were derivatized by silylation and quantitatively analyzed by GCMS using methods adapted from literature reports ((Simonov et al., J. Anal Chem. 59:965-971 (2004)). The developed method demonstrated good sensitivity down to 1 µM, linearity up to at least 25 mM, as well as excellent selectivity and reproducibility.

Sample preparation was performed as follows: 100 µL filtered (0.2 µm or 0.45 µm syringe filters) samples, e.g. fermentation broth, cell culture or standard solutions, were dried down in a Speed Vac Concentrator (Savant SVC-100H) for approximately 1 hour at ambient temperature, followed by the addition of 20 µL 10 mM cyclohexanol solution, as an internal standard, in dimethylformamide. The mixtures were vortexed and sonicated in a water bath (Branson 3510) for 15 min to ensure homogeneity. 100 µL silylation derivatization reagent, N,O-bis(trimethylsilyl)tri-flouro-acetimide (BSTFA) with 1% trimethylchlorosilane, was added, and the mixture was incubated at 70° C. for 30 min. The derivatized samples were centrifuged for 5 min, and the clear solutions were directly injected into GCMS. All the chemicals and reagents were from Sigma-Aldrich, with the exception of BDO which was purchased from J. T. Baker.

GCMS was performed on an Agilent gas chromatograph 6890N, interfaced to a mass-selective detector (MSD) 5973N operated in electron impact ionization (EI) mode has been used for the analysis. A DB-5MS capillary column (J&W Scientific, Agilent Technologies), 30 m×0.25 mm i.d.×0.25 µm film thickness, was used. The GC was operated in a split injection mode introducing 1 µL of sample at 20:1 split ratio. The injection port temperature was 250° C. Helium was used as a carrier gas, and the flow rate was maintained at 1.0 mL/min. A temperature gradient program was optimized to ensure good resolution of the analytes of interest and minimum matrix interference. The oven was initially held at 80° C. for 1 min, then ramped to 120° C. at 2° C./min, followed by fast ramping to 320° C. at 100° C./min and final hold for 6 min at 320° C. The MS interface transfer line was maintained at 280° C. The data were acquired using 'lowmass' MS tune settings and 30-400 m/z mass-range scan. The total analysis time was 29 min including 3 min solvent delay. The retention times corresponded to 5.2, 10.5, 14.0 and 18.2 min for BSTFA-derivatized cyclohexanol, BDO, 4-HB and succinate, respectively. For quantitative analysis, the following specific mass fragments were selected (extracted ion chromatograms): m/z 157 for internal standard cyclohexanol, 116 for BDO, and 147 for both 4-HB and succinate. Standard calibration curves were constructed using analyte solutions in the corresponding cell culture or fermentation medium to match sample matrix as close as possible. GCMS data were processed using Environmental Data Analysis ChemStation software (Agilent Technologies).

The results indicated that most of the 4-HB and BDO produced were labeled with $^{13}C$ (FIG. 6, right-hand sides). Mass spectra from a parallel culture grown in unlabeled glucose are shown for comparison (FIG. 6, left-hand sides). Note that the peaks seen are for fragments of the derivatized molecule containing different numbers of carbon atoms from the metabolite. The derivatization reagent also contributes some carbon and silicon atoms that naturally-occurring label distribution, so the results are not strictly quantitative.

Production of BDO from 4-HB Using Alternate Pathways.

The various alternate pathways were also tested for BDO production. This includes use of the native E. coli SucCD enzyme to convert succinate to succinyl-CoA (Table 13, rows 2-3), use of α-ketoglutarate decarboxylase in the α-ketoglutarate pathway (Table 13, row 4), and use of PTB/BK as an alternate means to generate the CoA-derivative of 4HB (Table 13, row 1). Strains were constructed containing plasmids expressing the genes indicated in Table 13, which encompass these variants. The results show that in all cases, production of 4-HB and BDO occurred (Table 13).

TABLE 13

Production of BDO, 4-HB, and succinate in recombinant *E. coli* strains genes for different BDO pathway variants, grown anaerobically in minimal medium supplemented with 20 g/L glucose, and harvested 24 hours after induction with 0.1 mM IPTG. Concentrations are given in mM.

| Genes on pZE13 | Genes on pZA33 | Succinate | 4-HB | BDO |
| --- | --- | --- | --- | --- |
| 0002 + 0004 + 0035 | 0020n – 0021n – 0036 | 0.336 | 2.91 | 0.230 |
| 0038 + 0035 | 0034 – 0036 | 0.814 | 2.81 | 0.126 |
| 0038 + 0035 | 0036 – 0034 | 0.741 | 2.57 | 0.114 |
| 0035 + 0032 | 0034 – 0036 | 5.01 | 0.538 | 0.154 |

Example III

Biosynthesis of 4-Hydroxybutanoic Acid, γ-Butyrolactone and 1,4-Butanediol

This Example describes the biosynthetic production of 4-hydroxybutanoic acid, γ-butyrolactone and 1,4-butanediol using fermentation and other bioprocesses.

Figure 7:
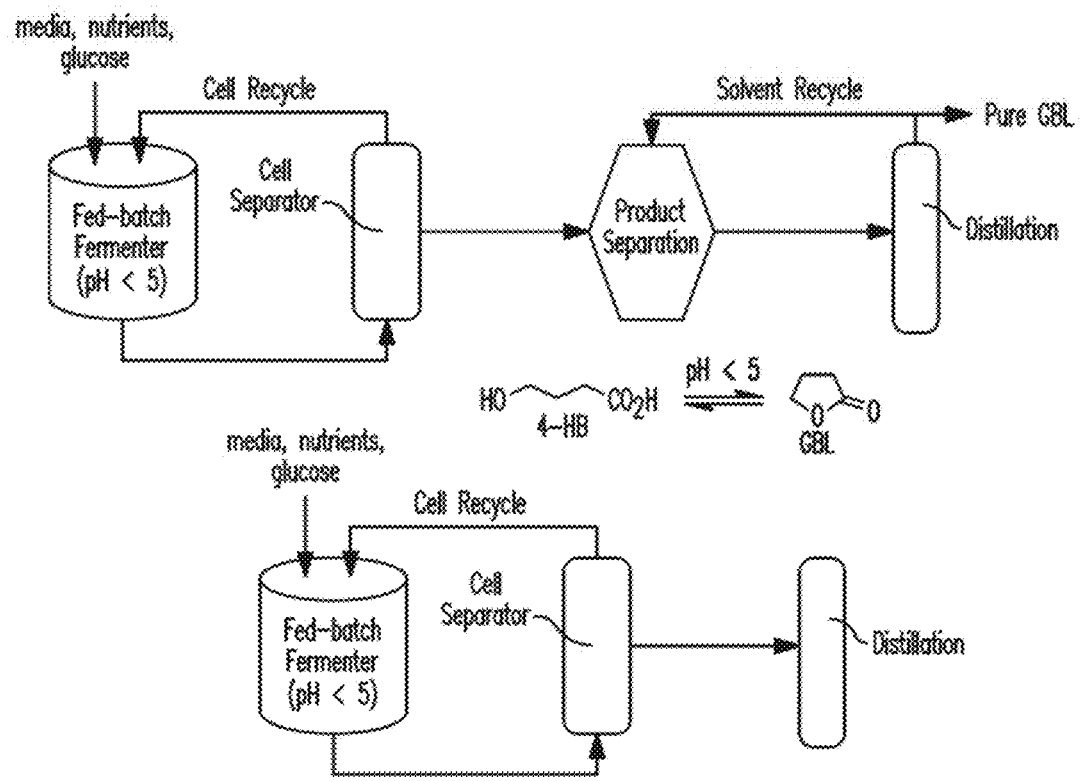
FIG. 7 is a schematic process flow diagram of bioprocesses for the production of γ-butyrolactone. The upper panel illustrates fed-batch fermentation with batch separation and the lower panel illustrates fed-batch fermentation with continuous separation.

Methods for the integration of the 4-HB fermentation step into a complete process for the production of purified GBL, 1,4-butanediol (BDO) and tetrahydrofuran (THF) are described below. Since 4-HB and GBL are in equilibrium, the fermentation broth will contain both compounds. At low pH this equilibrium is shifted to favor GBL. Therefore, the fermentation can operate at pH 7.5 or less, generally pH 5.5 or less. After removal of biomass, the product stream enters into a separation step in which GBL is removed and the remaining stream enriched in 4-HB is recycled. Finally, GBL is distilled to remove any impurities. The process operates in one of three ways: 1) fed-batch fermentation and batch separation; 2) fed-batch fermentation and continuous separation; 3) continuous fermentation and continuous separation. The first two of these modes are shown schematically in FIG. 7. The integrated fermentation procedures described below also are used for the BDO producing cells of the invention for biosynthesis of BDO and subsequent BDO family products.

Fermentation Protocol to Produce 4-HB/GBL (Batch):

The production organism is grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until 4-HB reaches a concentration of between 20-200 g/L, with the cell density being between 5 and 10 g/L. The pH is not controlled, and will typically decrease to pH 3-6 by the end of the run. Upon completion of the cultivation period, the fermenter contents are passed through a cell separation unit (e.g., centrifuge) to remove cells and cell debris, and the fermentation broth is transferred to a product separations unit. Isolation of 4-HB and/or GBL would take place by standard separations procedures employed in the art to separate organic products from dilute aqueous solutions, such as liquid-liquid extraction using a water immiscible organic solvent (e.g., toluene) to provide an organic solution of 4-HB/GBL. The resulting solution is then subjected to standard distillation methods to remove and recycle the organic solvent and to provide GBL (boiling point 204-205° C.) which is isolated as a purified liquid.

Fermentation Protocol to Produce 4-HB/GBL (Fully Continuous):

The production organism is first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The 4-HB concentration in the bioreactor remains constant at 30-40 g/L, and the cell density remains constant between 3-5 g/L. Temperature is maintained at 30 degrees C., and the pH is maintained at 4.5 using concentrated NaOH and HCl, as required. The bioreactor is operated continuously for one month, with samples taken every day to assure consistency of 4-HB concentration. In continuous mode, fermenter contents are constantly removed as new feed medium is supplied. The exit stream, containing cells, medium, and products 4-HB and/or GBL, is then subjected to a continuous product separations procedure, with or without removing cells and cell debris, and would take place by standard continuous separations methods employed in the art to separate organic products from dilute aqueous solutions, such as continuous liquid-liquid extraction using a water immiscible organic solvent (e.g., toluene) to provide an organic solution of 4-HB/GBL. The resulting solution is subsequently subjected to standard continuous distillation methods to remove and recycle the organic solvent and to provide GBL (boiling point 204-205° C.) which is isolated as a purified liquid.

GBL Reduction Protocol:

Once GBL is isolated and purified as described above, it will then be subjected to reduction protocols such as those well known in the art (references cited) to produce 1,4-butanediol or tetrahydrofuran (THF) or a mixture thereof. Heterogeneous or homogeneous hydrogenation catalysts combined with GBL under hydrogen pressure are well known to provide the products 1,4-butanediol or tetrahydrofuran (THF) or a mixture thereof. It is important to note that the 4-HB/GBL product mixture that is separated from the fermentation broth, as described above, may be subjected directly, prior to GBL isolation and purification, to these same reduction protocols to provide the products 1,4-butanediol or tetrahydrofuran or a mixture thereof. The resulting products, 1,4-butanediol and THF are then isolated and purified by procedures well known in the art.

Fermentation and Hydrogenation Protocol to Produce BDO or THF Directly (Batch):

Cells are grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until 4-HB reaches a concentration of between 20-200 g/L, with the cell density being between 5 and 10 g/L. The pH is not controlled, and will typically decrease to pH 3-6 by the end of the run. Upon completion of the cultivation period, the fermenter contents are passed through a cell separation unit (e.g., centrifuge) to remove cells and cell debris, and the fermentation broth is transferred to a reduction unit (e.g., hydrogenation vessel), where the mixture 4-HB/GBL is directly reduced to either 1,4-butanediol or THF or a mixture thereof. Following completion of the reduction procedure, the reactor contents are transferred to a product separations unit. Isolation of 1,4-butanediol and/or THF would take place by standard separations procedures employed in the art to separate organic products from dilute aqueous solutions, such as liquid-liquid extraction using a water immiscible organic solvent (e.g., toluene) to provide an organic solution of 1,4-butanediol and/or THF. The resulting solution is then subjected to standard distillation methods to remove and recycle the organic solvent and to provide 1,4-butanediol and/or THF which are isolated as a purified liquids.

Fermentation and Hydrogenation Protocol to Produce BDO or THF Directly (Fully Continuous):

The cells are first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The 4-HB concentration in the bioreactor remains constant at 30-40 g/L, and the cell density remains constant between 3-5 g/L. Temperature is maintained at 30 degrees C., and the pH is maintained at 4.5 using concentrated NaOH and HCl, as required. The bioreactor is operated continuously for one month, with samples taken every day to assure consistency of 4-HB concentration. In continuous mode, fermenter contents are constantly removed as new feed medium is supplied. The exit stream, containing cells, medium, and products 4-HB and/or GBL, is then passed through a cell separation unit (e.g., centrifuge) to remove cells and cell debris, and the fermentation broth is transferred to a continuous reduction unit (e.g., hydrogenation vessel), where the mixture 4-HB/GBL is directly reduced to either 1,4-butanediol or THF or a mixture thereof. Following completion of the reduction procedure, the reactor contents are transferred to a continuous product separations unit. Isolation of 1,4-butanediol and/or THF would take place by standard continuous separations procedures employed in the art to separate organic products from dilute aqueous solutions, such as liquid-liquid extraction using a water immiscible organic solvent (e.g., toluene) to provide an organic solution of 1,4-butanediol and/or THF. The resulting solution is then subjected to standard continuous distillation methods to remove and recycle the organic solvent and to provide 1,4-butanediol and/or THF which are isolated as a purified liquids.

Fermentation Protocol to Produce BDO Directly (Batch):

The production organism is grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until BDO reaches a concentration of between 20-200 g/L, with the cell density generally being between 5 and 10 g/L. Upon completion of the cultivation period, the fermenter contents are passed through a cell separation unit (e.g., centrifuge) to remove cells and cell debris, and the fermentation broth is transferred to a product separations unit. Isolation of BDO would take place by standard separations procedures employed in the art to separate organic products from dilute aqueous solutions, such as liquid-liquid extraction using a water immiscible organic solvent (e.g., toluene) to provide an organic solution of BDO. The resulting solution is then subjected to standard distillation methods to remove and recycle the organic solvent and to provide BDO (boiling point 228-229° C.) which is isolated as a purified liquid.

Fermentation Protocol to Produce BDO Directly (Fully Continuous):

The production organism is first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The BDO concentration in the bioreactor remains constant at 30-40 g/L, and the cell density remains constant between 3-5 g/L. Temperature is maintained at 30 degrees C., and the pH is maintained at 4.5 using concentrated NaOH and HCl, as required. The bioreactor is operated continuously for one month, with samples taken every day to assure consistency of BDO concentration. In continuous mode, fermenter contents are constantly removed as new feed medium is supplied. The exit stream, containing cells, medium, and the product BDO, is then subjected to a continuous product separations procedure, with or without removing cells and cell debris, and would take place by standard continuous separations methods employed in the art to separate organic products from dilute aqueous solutions, such as continuous liquid-liquid extraction using a water immiscible organic solvent (e.g., toluene) to provide an organic solution of BDO. The resulting solution is subsequently subjected to standard continuous distillation methods to remove and recycle the organic solvent and to provide BDO (boiling point 228-229° C.) which is isolated as a purified liquid (mpt 20° C.).

Example IV

Exemplary BDO Pathways

This example describes exemplary enzymes and corresponding genes for 1,4-butandiol (BDO) synthetic pathways.

Exemplary BDO synthetic pathways are shown in FIGS. 8-13. The pathways depicted in FIGS. 8-13 are from common central metabolic intermediates to 1,4-butanediol. All transformations depicted in FIGS. 8-13 fall into the 18 general categories of transformations shown in Table 14. Below is described a number of biochemically characterized candidate genes in each category. Specifically listed are genes that can be applied to catalyze the appropriate transformations in FIGS. 9-13 when cloned and expressed in a host organism. The top three exemplary genes for each of the key steps in FIGS. 9-13 are provided in Tables 15-23 (see below). Exemplary genes were provided for the pathways depicted in FIG. 8 are described herein.

TABLE 14

Enzyme types required to convert common central metabolic intermediates into 1,4-butanediol. The first three digits of each label correspond to the first three Enzyme Commission number digits which denote the general type of transformation independent of substrate specificity.

| Label | Function |
| --- | --- |
| 1.1.1.a | Oxidoreductase (ketone to hydroxyl or aldehyde to alcohol) |
| 1.1.1.c | Oxidoreductase (2 step, acyl-CoA to alcohol) |
| 1.2.1.b | Oxidoreductase (acyl-CoA to aldehyde) |
| 1.2.1.c | Oxidoreductase (2-oxo acid to acyl-CoA, decarboxylation) |
| 1.2.1.d | Oxidoreductase (phosphorylating/dephosphorylating) |
| 1.3.1.a | Oxidoreductase operating on CH—CH donors |
| 1.4.1.a | Oxidoreductase operating on amino acids |
| 2.3.1.a | Acyltransferase (transferring phosphate group) |
| 2.6.1.a | Aminotransferase |
| 2.7.2.a | Phosphotransferase, carboxyl group acceptor |
| 2.8.3.a | Coenzyme-A transferase |
| 3.1.2.a | Thiolester hydrolase (CoA specific) |
| 4.1.1.a | Carboxy-lyase |
| 4.2.1.a | Hydro-lyase |
| 4.3.1.a | Ammonia-lyase |
| 5.3.3.a | Isomerase |
| 5.4.3.a | Aminomutase |
| 6.2.1.a | Acid-thiol ligase |

1.1.1.a—Oxidoreductase (Aldehyde to Alcohol or Ketone to Hydroxyl)

Aldehyde to alcohol. Exemplary genes encoding enzymes that catalyze the conversion of an aldehyde to alcohol, that is, alcohol dehydrogenase or equivalently aldehyde reductase, include alrA encoding a medium-chain alcohol dehydrogenase for C2-C14 (Tani et al. *Appl. Environ. Microbiol.* 66:5231-5235 (2000)), ADH2 from *Saccharomyces cerevisiae* (Atsumi et al. *Nature* 451:86-89 (2008)), yqhD from *E. coli* which has preference for molecules longer than C(3) (Sulzenbacher et al. *Journal of Molecular Biology* 342:489-502 (2004)), and bdh I and bdh II from *C. acetobutylicum* which converts butyryaldehyde into butanol (Walter et al. *Journal of Bacteriology* 174:7149-7158 (1992)). The protein sequences for each of these exemplary gene products, if available, can be found using the following GenBank accession numbers:

| alrA | BAB12273.1 | *Acinetobacter* sp. Strain M-1 |
| ADH2 | NP_014032.1 | *Saccharymyces cerevisiae* |
| yqhD | NP_417484.1 | *Escherichia coli* |
| bdh I | NP_349892.1 | *Clostridium acetobutylicum* |
| bdh II | NP_349891.1 | *Clostridium acetobutylicum* |

Enzymes exhibiting 4-hydroxybutyrate dehydrogenase activity (EC 1.1.1.61) also fall into this category. Such enzymes have been characterized in *Ralstonia eutropha* (Bravo et al. *J. Forensic Sci.* 49:379-387 (2004), *Clostridium kluyveri* (Wolff et al. *Protein Expr. Purif.* 6:206-212 (1995)) and *Arabidopsis thaliana* (Breitkreuz et al. *J. Biol. Chem.* 278:41552-41556 (2003)).

| 4hbd | YP_726053.1 | *Ralstonia eutropha* H16 |
| 4hbd | L21902.1 | *Clostridium kluyveri* DSM 555 |
| 4hbd | Q94B07 | *Arabidopsis thaliana* |

Another exemplary enzyme is 3-hydroxyisobutyrate dehydrogenase which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al. *J Mol Biol* 352:905-17 (2005)). The reversibility of the human 3-hydroxyisobutyrate dehydrogenase was demonstrated using isotopically-labeled substrate (Manning et al. *Biochem J* 231:481-484 (1985)). Additional genes encoding this enzyme include 3hidh in *Homo sapiens* (Hawes et al. *Methods Enzymol.* 324:218-228 (2000)) and *Oryctolagus cuniculus* (Chowdhury et al. *Biosci. Biotechnol Biochem.* 60:2043-2047 (1996); Hawes et al. *Methods Enzymol.* 324:218-228 (2000)), mmsb in *Pseudomonas aeruginosa*, and dhat in *Pseudomonas putida* (Aberhart et al. *J Chem. Soc. [Perkin 1]* 6:1404-1406 (1979); Chowdhury et al. *Biosci. Biotechnol Biochem.* 67:438-441 (2003); Chowdhury et al. *Biosci. Biotechnol Biochem.* 60:2043-2047 (1996)).

| P84067 | P84067 | *Thermus thermophilus* |
| mmsb | P28811.1 | *Pseudomonas aeruginosa* |
| dhat | Q59477.1 | *Pseudomonas putida* |
| 3hidh | P31937.2 | *Homo sapiens* |
| 3hidh | P32185.1 | *Oryctolagus cuniculus* |

Several 3-hydroxyisobutyrate dehydrogenase enzymes have also been shown to convert malonic semialdehyde to 3-hydroxyproprionic acid (3-HP). Three gene candidates exhibiting this activity are mmsB from *Pseudomonas aeruginosa* PAO1(62), mmsB from *Pseudomonas putida* KT2440 (Liao et al., US Publication 2005/0221466) and mmsB from *Pseudomonas putida* E23 (Chowdhury et al., *Biosci. Biotechnol. Biochem.* 60:2043-2047 (1996)). An enzyme with 3-hydroxybutyrate dehydrogenase activity in *Alcaligenes faecalis* M3A has also been identified (Gokam et al., U.S. Pat. No. 7,393,676; Liao et al., US Publication No. 2005/0221466). Additional gene candidates from other organisms including *Rhodobacter spaeroides* can be inferred by sequence similarity.

| mmsB | AAA25892.1 | *Pseudomonas aeruginosa* |
| mmsB | NP_252259.1 | *Pseudomonas aeruginosa* PAO1 |
| mmsB | NP_746775.1 | *Pseudomonas putida* KT2440 |
| mmsB | JC7926 | *Pseudomonas putida* E23 |
| orfB1 | AAL26884 | *Rhodobacter spaeroides* |

The conversion of malonic semialdehyde to 3-HP can also be accomplished by two other enzymes: NADH-dependent 3-hydroxypropionate dehydrogenase and NADPH-dependent malonate semialdehyde reductase. An NADH-dependent 3-hydroxypropionate dehydrogenase is thought to participate in beta-alanine biosynthesis pathways from propionate in bacteria and plants (Rathinasabapathi, B. *Journal of Plant Pathology* 159:671-674 (2002); Stadtman, E. R. *J. Am. Chem. Soc.* 77:5765-5766 (1955)). This enzyme has not been associated with a gene in any organism to date. NADPH-dependent malonate semialdehyde reductase catalyzes the reverse reaction in autotrophic $CO_2$-fixing bacteria. Although the enzyme activity has been detected in *Metallosphaera sedula*, the identity of the gene is not known (Alber et al. *J. Bacteriol.* 188:8551-8559 (2006)).

Ketone to Hydroxyl.

There exist several exemplary alcohol dehydrogenases that convert a ketone to a hydroxyl functional group. Two such enzymes from *E. coli* are encoded by malate dehydrogenase (mdh) and lactate dehydrogenase (ldhA). In addition, lactate dehydrogenase from *Ralstonia eutropha* has been shown to demonstrate high activities on substrates of various chain lengths such as lactate, 2-oxobutyrate, 2-oxopentanoate and 2-oxoglutarate (Steinbuchel, A. and H. G. Schlegel *Eur. J. Biochem.* 130:329-334 (1983)). Conversion of alpha-ketoadipate into alpha-hydroxyadipate can be catalyzed by 2-ketoadipate reductase, an enzyme reported to be found in rat and in human placenta (Suda et al. *Arch. Biochem. Biophys.* 176:610-620 (1976); Suda et al. *Biochem. Biophys. Res. Commun.* 77:586-591 (1977)). An additional candidate for this step is the mitochondrial 3-hydroxybutyrate dehydrogenase (bdh) from the human heart which has been cloned and characterized (Marks et al. *J. Biol. Chem.* 267:15459-15463 (1992)). This enzyme is a dehydrogenase that operates on a 3-hydroxyacid. Another exemplary alcohol dehydrogenase converts acetone to isopropanol as was shown in *C. beijerinckii* (Ismaiel et al. *J. Bacteriol.* 175: 5097-5105 (1993)) and *T. brockii* (Lamed et al. *Biochem. J.* 195:183-190 (1981); Peretz and Burstein *Biochemistry* 28:6549-6555 (1989)).

| mdh | AAC76268.1 | *Escherichia coli* |
|---|---|---|
| ldhA | NP_415898.1 | *Escherichia coli* |
| ldh | YP_725182.1 | *Ralstonia eutropha* |
| bdh | AAA58352.1 | *Homo sapiens* |
| adh | AAA23199.2 | *Clostridium beijerinckii* NRRL B593 |
| adh | P14941.1 | *Thermoanaerobacter brockii* HTD4 |

Exemplary 3-hydroxyacyl dehydrogenases which convert acetoacetyl-CoA to 3-hydroxybutyryl-CoA include hbd from *C. acetobutylicum* (Boynton et al. *Journal of Bacteriology* 178:3015-3024 (1996)), hbd from *C. beijerinckii* (Colby et al. *Appl Environ. Microbiol* 58:3297-3302 (1992)), and a number of similar enzymes from *Metallosphaera sedula* (Berg et al. Archaea. Science. 318:1782-1786 (2007)).

| hbd | NP_349314.1 | *Clostridium acetobutylicum* |
|---|---|---|
| hbd | AAN114586.1 | *Clostridium beijerinckii* |
| Msed_1423 | YP_001191505 | *Metallosphaera sedula* |
| Msed_0399 | YP_001190500 | *Metallosphaera sedula* |
| Msed_0389 | YP_001190490 | *Metallosphaera sedula* |
| Msed_1993 | YP_001192057 | *Metallosphaera sedula* |

1.1.1.c—Oxidoredutase (2 Step, Acyl-CoA to Alcohol)

Exemplary 2-step oxidoreductases that convert an acyl-CoA to alcohol include those that transform substrates such as acetyl-CoA to ethanol (for example, adhE from *E. coli* (Kessler et al. *FEBS. Lett.* 281:59-63 (1991)) and butyryl-CoA to butanol (for example, adhE2 from *C. acetobutylicum* (Fontaine et al. *J. Bacteriol.* 184:821-830 (2002)). In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al. *J. Gen. Appl. Microbiol.* 18:43-55 (1972); Koo et al. Biotechnol Lett. 27:505-510 (2005)).

| adhE | NP_415757.1 | *Escherichia coli* |
|---|---|---|
| adhE2 | AAK09379.1 | *Clostridium acetobutylicum* |
| adhE | AAV66076.1 | *Leuconostoc mesenteroides* |

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J. Bacteriol.* 184:2404-2410 (2002); Strauss and Fuchs, *Eur. J. Biochem.* 215:633-643 (1993)). This enzyme, with a mass of 300 kDa, is highly substrate-specific and shows little sequence similarity to other known oxidoreductases (Hugler et al., *J. Bacteriol.* 184:2404-2410 (2002)). No enzymes in other organisms have been shown to catalyze this specific reaction; however there is bioinformatic evidence that other organisms may have similar pathways (Klatt et al., *Environ. Microbiol.* 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity.

| mcr | AAS20429.1 | *Chloroflexus aurantiacus* |
|---|---|---|
| Rcas_2929 | YP_001433009.1 | *Roseiflexus castenholzii* |
| NAP1_02720 | ZP_01039179.1 | *Erythrobacter* sp. NAP1 |
| MGP2080_00535 | ZP_1626393.1 | marine gamma proteobacterium HTCC2080 |

Longer chain acyl-CoA molecules can be reduced by enzymes such as the jojoba (*Simmondsia chinensis*) FAR which encodes an alcohol-forming fatty acyl-CoA reductase. Its overexpression in *E. coli* resulted in FAR activity and the accumulation of fatty alcohol (Metz et al. *Plant Physiology* 122:635-644) 2000)).

| FAR | AAD38039.1 | *Simmondsia chinensis* |
|---|---|---|

1.2.1.b—Oxidoreductase (Acyl-CoA to Aldehyde)

Several acyl-CoA dehydrogenases are capable of reducing an acyl-CoA to its corresponding aldehyde. Exemplary genes that encode such enzymes include the *Acinetobacter calcoaceticus* acr1 encoding a fatty acyl-CoA reductase (Reiser and Somerville, *J. Bacteriology* 179:2969-2975 (1997)), the *Acinetobacter* sp. M-1 fatty acyl-CoA reductase (Ishige et al. *Appl. Environ. Microbiol.* 68:1192-1195 (2002)), and a CoA- and NADP-dependent succinate semialdehyde dehydrogenase encoded by the sucD gene in *Clostridium kluyveri* (Sohling and Gottschalk *J Bacteriol* 178:871-80 (1996); Sohling and Gottschalk *J Bacteriol.* 178:871-880 (1996)). SucD of *P. gingivalis* is another succinate semialdehyde dehydrogenase (Takahashi et al. *J. Bacteriol.* 182:4704-4710 (2000)). The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski et al. *J Bacteriol.* 175:377-385 (1993)).

| acr1 | YP_047869.1 | *Acinetobacter calcoaceticus* |
|---|---|---|
| acr1 | AAC45217 | *Acinetobacter baylyi* |
| acr1 | BAB85476.1 | *Acinetobacter* sp. Strain M-1 |
| sucD | P38947.1 | *Clostridium kluyveri* |
| sucD | NP_904963.1 | *Porphyromonas gingivalis* |
| bphG | BAA03892.1 | *Pseudomonas* sp |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al. *Science* 318:1782-1786 (2007); Thauer, R. K. *Science* 318:1732-1733 (2007)). The enzyme utilizes NADPH as a cofactor and has been characterized in Metallosphaera and *Sulfolobus* spp (Alber et al. *J. Bacteriol.* 188:8551-8559 (2006); Hugler et al. *J. Bacteriol.* 184:2404-2410 (2002)). The enzyme is encoded by Msed_0709 in *Metallosphaera sedula* (Alber et al. *J. Bacteriol.* 188:8551-8559 (2006); Berg et al. *Science* 318:1782-1786 (2007)). A gene encoding a malonyl-CoA reductase from *Sulfolobus tokodaii* was cloned and heterologously expressed in *E. coli* (Alber et al. *J. Bacteriol.* 188:8551-8559 (2006)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*.

| | | |
|---|---|---|
| Msed_0709 | YP_001190808.1 | *Metallosphaera sedula* |
| mcr | NP_378167.1 | *Sulfolobus tokodaii* |
| asd-2 | NP_343563.1 | *Sulfolobus solfataricus* |
| Sad_2370 | YP_256941.1 | *Sulfolobus acidocaldarius* |

1.2.1.c—Oxidoreductase (2-Oxo Acid to Acyl-CoA, Decarboxylation)

Enzymes in this family include 1) branched-chain 2-keto-acid dehydrogenase, 2) alpha-ketoglutarate dehydrogenase, and 3) the pyruvate dehydrogenase multienzyme complex (PDHC). These enzymes are multi-enzyme complexes that catalyze a series of partial reactions which result in acylating oxidative decarboxylation of 2-keto-acids. Each of the 2-keto-acid dehydrogenase complexes occupies key positions in intermediary metabolism, and enzyme activity is typically tightly regulated (Fries et al. *Biochemistry* 42:6996-7002 (2003)). The enzymes share a complex but common structure composed of multiple copies of three catalytic components: alpha-ketoacid decarboxylase (E1), dihydrolipoamide acyltransferase (E2) and dihydrolipoamide dehydrogenase (E3). The E3 component is shared among all 2-keto-acid dehydrogenase complexes in an organism, while the E1 and E2 components are encoded by different genes. The enzyme components are present in numerous copies in the complex and utilize multiple cofactors to catalyze a directed sequence of reactions via substrate channeling. The overall size of these dehydrogenase complexes is very large, with molecular masses between 4 and 10 million Da (that is, larger than a ribosome).

Activity of enzymes in the 2-keto-acid dehydrogenase family is normally low or limited under anaerobic conditions in *E. coli*. Increased production of NADH (or NADPH) could lead to a redox-imbalance, and NADH itself serves as an inhibitor to enzyme function. Engineering efforts have increased the anaerobic activity of the *E. coli* pyruvate dehydrogenase complex (Kim et al. *Appl. Environ. Microbiol.* 73:1766-1771 (2007); Kim et al. *J. Bacteriol.* 190: 3851-3858) 2008); Zhou et al. *Biotechnol. Lett.* 30:335-342 (2008)). For example, the inhibitory effect of NADH can be overcome by engineering an H322Y mutation in the E3 component (Kim et al. *J. Bacteriol.* 190:3851-3858 (2008)). Structural studies of individual components and how they work together in complex provide insight into the catalytic mechanisms and architecture of enzymes in this family (Aevarsson et al. *Nat. Struct. Biol.* 6:785-792 (1999); Zhou et al. *Proc. Natl. Acad. Sci. U.S.A.* 98:14802-14807 (2001)). The substrate specificity of the dehydrogenase complexes varies in different organisms, but generally branched-chain keto-acid dehydrogenases have the broadest substrate range.

Alpha-ketoglutarate dehydrogenase (AKGD) converts alpha-ketoglutarate to succinyl-CoA and is the primary site of control of metabolic flux through the TCA cycle (Hansford, R. G. *Curr. Top. Bioenerg.* 10:217-278 (1980)). Encoded by genes sucA, sucB and lpd in *E. coli*, AKGD gene expression is downregulated under anaerobic conditions and during growth on glucose (Park et al. *Mol. Microbiol.* 15:473-482 (1995)). Although the substrate range of AKGD is narrow, structural studies of the catalytic core of the E2 component pinpoint specific residues responsible for substrate specificity (Knapp et al. *J. Mol. Biol.* 280:655-668 (1998)). The *Bacillus subtilis* AKGD, encoded by odhAB (E1 and E2) and pdhD (E3, shared domain), is regulated at the transcriptional level and is dependent on the carbon source and growth phase of the organism (Resnekov et al. *Mol. Gen. Genet.* 234:285-296 (1992)). In yeast, the LPD1 gene encoding the E3 component is regulated at the transcriptional level by glucose (Roy and Dawes *J. Gen. Microbiol.* 133:925-933 (1987)). The E1 component, encoded by KGD1, is also regulated by glucose and activated by the products of HAP2 and HAP3 (Repetto and Tzagoloff *Mol. Cell Biol.* 9:2695-2705 (1989)). The AKGD enzyme complex, inhibited by products NADH and succinyl-CoA, is well-studied in mammalian systems, as impaired function of has been linked to several neurological diseases (Tretter and dam-Vizi *Philos. Trans. R. Soc. Lond B Biol. Sci.* 360:2335-2345 (2005)).

| | | |
|---|---|---|
| sucA | NP_415254.1 | *Escherichia coli* str. K12 substr. MG1655 |
| sucB | NP_415255.1 | *Escherichia coli* str. K12 substr. MG1655 |
| lpd | NP_414658.1 | *Escherichia coli* str. K12 substr. MG1655 |
| odhA | P23129.2 | *Bacillus subtilis* |
| odhB | P16263.1 | *Bacillus subtilis* |
| pdhD | P21880.1 | *Bacillus subtilis* |
| KGD1 | NP_012141.1 | *Saccharomyces cerevisiae* |
| KGD2 | NP_010432.1 | *Saccharomyces cerevisiae* |
| LPD1 | NP_116635.1 | *Saccharomyces cerevisiae* |

Branched-chain 2-keto-acid dehydrogenase complex (BCKAD), also known as 2-oxoisovalerate dehydrogenase, participates in branched-chain amino acid degradation pathways, converting 2-keto acids derivatives of valine, leucine and isoleucine to their acyl-CoA derivatives and $CO_2$. The complex has been studied in many organisms including *Bacillus subtilis* (Wang et al. *Eur. J. Biochem.* 213:1091-1099 (1993)), *Rattus norvegicus* (Namba et al. *J. Biol. Chem.* 244:4437-4447 (1969)) and *Pseudomonas putida* (Sokatch *J. Bacteriol.* 148:647-652 (1981)). In *Bacillus subtilis* the enzyme is encoded by genes pdhD (E3 component), bfmBB (E2 component), bfmBAA and bfmBAB (E1 component) (Wang et al. *Eur. J. Biochem.* 213:1091-1099 (1993)). In mammals, the complex is regulated by phosphorylation by specific phosphatases and protein kinases. The complex has been studied in rat hepatocites (Chicco et al. *J. Biol. Chem.* 269:19427-19434 (1994)) and is encoded by genes Bckdha (E1 alpha), Bckdhb (E1 beta), Dbt (E2), and Dld (E3). The E1 and E3 components of the *Pseudomonas putida* BCKAD complex have been crystallized (Aevarsson et al. *Nat. Struct. Biol.* 6:785-792 (1999); Mattevi *Science* 255:1544-1550 (1992)) and the enzyme complex has been studied (Sokatch et al. *J. Bacteriol.* 148:647-652 (1981)). Transcription of the *P. putida* BCKAD genes is activated by the gene product of bkdR (Hester et al. *Eur. J. Biochem.* 233:828-836 (1995)). In some organisms including *Rattus norvegicus* (Paxton et al. *Biochem. J.* 234:295-303 (1986)) and *Saccharomyces cerevisiae* (Sinclair et al. *Biochem. Mol. Biol. Int.* 31:911-922 (1993)), this complex has been shown to have a broad substrate range that includes linear oxo-acids such as 2-oxobutanoate and alpha-ketoglutarate, in addition to the branched-chain amino acid precursors. The active site of the bovine BCKAD was engineered to favor alternate substrate acetyl-CoA (Meng and Chuang, *Biochemistry* 33:12879-12885 (1994)).

| | | |
|---|---|---|
| bfmBB | NP_390283.1 | *Bacillus subtilis* |
| bfmBAA | NP_390285.1 | *Bacillus subtilis* |
| bfmBAB | NP_390284.1 | *Bacillus subtilis* |
| pdhD | P21880.1 | *Bacillus subtilis* |
| lpdV | P09063.1 | *Pseudomonas putida* |
| bkdB | P09062.1 | *Pseudomonas putida* |
| bkdA1 | NP_746515.1 | *Pseudomonas putida* |
| bkdA2 | NP_746516.1 | *Pseudomonas putida* |
| Bckdha | NP_036914.1 | *Rattus norvegicus* |
| Bckdhb | NP_062140.1 | *Rattus norvegicus* |
| Dbt | NP_445764.1 | *Rattus norvegicus* |
| Dld | NP_955417.1 | *Rattus norvegicus* |

The pyruvate dehydrogenase complex, catalyzing the conversion of pyruvate to acetyl-CoA, has also been extensively studied. In the *E. coli* enzyme, specific residues in the E1 component are responsible for substrate specificity (Bisswanger, H. *J Biol Chem*. 256:815-822 (1981); Bremer, *J. Eur. J Biochem*. 8:535-540 (1969); Gong et al. *J Biol Chem*. 275:13645-13653 (2000)). As mentioned previously, enzyme engineering efforts have improved the *E. coli* PDH enzyme activity under anaerobic conditions (Kim et al. *Appl. Environ. Microbiol.* 73:1766-1771 (2007); Kim *J. Bacteriol.* 190:3851-3858 (2008); Zhou et al. *Biotechnol. Lett.* 30:335-342 (2008)). In contrast to the *E. coli* PDH, the *B. subtilis* complex is active and required for growth under anaerobic conditions (Nakano *J. Bacteriol.* 179:6749-6755 (1997)). The *Klebsiella pneumoniae* PDH, characterized during growth on glycerol, is also active under anaerobic conditions (Menzel et al. *J. Biotechnol.* 56:135-142 (1997)). Crystal structures of the enzyme complex from bovine kidney (Zhou et al. *Proc. Natl. Acad. Sci. U.S.A.* 98:14802-14807 (2001)) and the E2 catalytic domain from *Azotobacter vinelandii* are available (Mattevi et al. *Science* 255:1544-1550 (1992)). Some mammalian PDH enzymes complexes can react on alternate substrates such as 2-oxobutanoate, although comparative kinetics of *Rattus norvegicus* PDH and BCKAD indicate that BCKAD has higher activity on 2-oxobutanoate as a substrate (Paxton et al. *Biochem. J.* 234:295-303 (1986)).

| | | |
|---|---|---|
| aceE | NP_414656.1 | *Escherichia coli* str. K12 substr. MG 1655 |
| aceF | NP_414657.1 | *Escherichia coli* str. K12 substr. MG 1655 |
| lpd | NP_414658.1 | *Escherichia coli* str. K12 substr. MG 1655 |
| pdhA | P21881.1 | *Bacillus subtilis* |
| pdhB | P21882.1 | *Bacillus subtilis* |
| pdhC | P21883.2 | *Bacillus subtilis* |
| pdhD | P21880.1 | *Bacillus subtilis* |
| aceE | YP_001333808.1 | *Klebsiella pneumonia* MGH78578 |
| aceF | YP_001333809.1 | *Klebsiella pneumonia* MGH78578 |
| lpdA | YP_001333810.1 | *Klebsiella pneumonia* MGH78578 |
| Pdha1 | NP_001004072.2 | *Rattus norvegicus* |
| Pdha2 | NP_446446.1 | *Rattus norvegicus* |
| Dlat | NP_112287.1 | *Rattus norvegicus* |
| Dld | NP_955417.1 | *Rattus norvegicus* |

As an alternative to the large multienzyme 2-keto-acid dehydrogenase complexes described above, some anaerobic organisms utilize enzymes in the 2-ketoacid oxidoreductase family (OFOR) to catalyze acylating oxidative decarboxylation of 2-keto-acids. Unlike the dehydrogenase complexes, these enzymes contain iron-sulfur clusters, utilize different cofactors, and use ferredoxin or flavodixin as electron acceptors in lieu of NAD(P)H. While most enzymes in this family are specific to pyruvate as a substrate (POR) some 2-ketoacid:ferredoxin oxidoreductases have been shown to accept a broad range of 2-ketoacids as substrates including alpha-ketoglutarate and 2-oxobutanoate (Fukuda and Wakagi *Biochim. Biophys. Acta* 1597:74-80 (2002); Zhang et al. *J. Biochem.* 120:587-599 (1996)). One such enzyme is the OFOR from the thermoacidophilic archaeon *Sulfolobus tokodaii* 7, which contains an alpha and beta subunit encoded by gene ST2300 (Fukuda and Wakagi *Biochim. Biophys. Acta* 1597:74-80 (2002); Zhang et al. *J. Biochem.* 120:587-599 (1996)). A plasmid-based expression system has been developed for efficiently expressing this protein in *E. coli* (Fukuda et al. *Eur. J. Biochem.* 268:5639-5646 (2001)) and residues involved in substrate specificity were determined (Fukuda and Wakagi *Biochim. Biophys. Acta* 1597:74-80 (2002)). Two OFORs from *Aeropyrum pernix* str. K1 have also been recently cloned into *E. coli*, characterized, and found to react with a broad range of 2-oxoacids (Nishizawa et al. *FEBS Lett.* 579:2319-2322 (2005)). The gene sequences of these OFOR candidates are available, although they do not have GenBank identifiers assigned to date. There is bioinformatic evidence that similar enzymes are present in all archaea, some anaerobic bacteria and amitochondrial eukarya (Fukuda and Wakagi *Biochim. Biophys. Acta* 1597:74-80 (2005)). This class of enzyme is also interesting from an energetic standpoint, as reduced ferredoxin could be used to generate NADH by ferredoxin-NAD reductase (Petitdemange et al. *Biochim. Biophys. Acta* 421:334-337 (1976)). Also, since most of the enzymes are designed to operate under anaerobic conditions, less enzyme engineering may be required relative to enzymes in the 2-keto-acid dehydrogenase complex family for activity in an anaerobic environment.

| | | |
|---|---|---|
| ST2300 | NP_378302.1 | *Sulfolobus tokodaii* 7 |

1.2.1.d—Oxidoreductase (Phosphorylating/Dephosphorylating)

Exemplary enzymes in this class include glyceraldehyde 3-phosphate dehydrogenase which converts glyceraldehyde-3-phosphate into D-glycerate 1,3-bisphosphate (for example, *E. coli* gapA (Branlant and Branlant *Eur. J. Biochem.* 150:61-66(1985)), aspartate-semialdehyde dehydrogenase which converts L-aspartate-4-semialdehyde into L-4-aspartyl-phosphate (for example, *E. coli* asd (Biellmann et al. *Eur. J. Biochem.* 104:53-58 (1980)), N-acetyl-gamma-glutamyl-phosphate reductase which converts N-acetyl-L-glutamate-5-semialdehyde into N-acetyl-L-glutamyl-5-phosphate (for example, *E. coli* argC (Parsot et al. *Gene* 68:275-283 (1988)), and glutamate-5-semialdehyde dehydrogenase which converts L-glutamate-5-semialdehyde into L-glutamyl-5-phospate (for example, *E. coli* proA (Smith et al. *J. Bacteriol.* 157:545-551 (1984)).

| | | |
|---|---|---|
| gapA | P0A9B2.2 | *Escherichia coli* |
| asd | NP_417891.1 | *Escherichia coli* |
| argC | NP_418393.1 | *Escherichia coli* |
| proA | NP_414778.1 | *Escherichia coli* |

1.3.1.a—Oxidoreductase Operating on CH—CH Donors

An exemplary enoyl-CoA reductase is the gene product of bcd from *C. acetobutylicum* (Atsumi et al. *Metab Eng* (2007); Boynton et al. *Journal of Bacteriology* 178:3015-

3024 (1996), which naturally catalyzes the reduction of crotonyl-CoA to butyryl-CoA. Activity of this enzyme can be enhanced by expressing bcd in conjunction with expression of the *C. acetobutylicum* etfAB genes, which encode an electron transfer flavoprotein. An additional candidate for the enoyl-CoA reductase step is the mitochondrial enoyl-CoA reductase from *E. gracilis* (Hoffmeister et al. *Journal of Biological Chemistry* 280:4329-4338 (2005)). A construct derived from this sequence following the removal of its mitochondrial targeting leader sequence was cloned in *E. coli* resulting in an active enzyme (Hoffmeister et al., supra, (2005)). This approach is well known to those skilled in the art of expressing eukaryotic genes, particularly those with leader sequences that may target the gene product to a specific intracellular compartment, in prokaryotic organisms. A close homolog of this gene, TDE0597, from the prokaryote *Treponema denticola* represents a third enoyl-CoA reductase which has been cloned and expressed in *E. coli* (Tucci and Martin *FEBS Letters* 581:1561-1566 (2007)).

| bcd | NP_349317.1 | *Clostridium acetobutylicum* |
|---|---|---|
| etfA | NP_349315.1 | *Clostridium acetobutylicum* |
| etfB | NP_349316.1 | *Clostridium acetobutylicum* |
| TER | Q5EU90.1 | *Euglena gracilis* |
| TDE0597 | NP_971211.1 | *Treponema denticola* |

Exemplary 2-enoate reductase (EC 1.3.1.31) enzymes are known to catalyze the NADH-dependent reduction of a wide variety of α, β-unsaturated carboxylic acids and aldehydes (Rohdich et al. *J. Biol. Chem.* 276:5779-5787 (2001)). 2-Enoate reductase is encoded by enr in several species of Clostridia (Giesel and Simon *Arch Microbiol.* 135(1): p. 51-57 (2001) including *C. tyrobutyricum*, and *C. thermoaceticum* (now called *Moorella thermoaceticum*) (Rohdich et al., supra, (2001)). In the recently published genome sequence of *C. kluyveri*, 9 coding sequences for enoate reductases have been reported, out of which one has been characterized (Seedorf et al. *Proc Natl Acad Sci U.S.A* 105(6):2128-33 (2008)). The enr genes from both *C. tyrobutyricum* and *C. thermoaceticum* have been cloned and sequenced and show 59% identity to each other. The former gene is also found to have approximately 75% similarity to the characterized gene in *C. kluyveri* (Giesel and Simon *Arch Microbiol* 135(1):51-57 (1983)). It has been reported based on these sequence results that enr is very similar to the dienoyl CoA reductase in *E. coli* (fadH) (163 Rohdich et al., supra (2001)). The *C. thermoaceticum* enr gene has also been expressed in an enzymatically active form in *E. coli* (163 Rohdich et al., supra (2001)).

| fadH | NP_417552.1 | *Escherichia coli* |
|---|---|---|
| enr | ACA54153.1 | *Clostridium botulinum* A3 str |
| enr | CAA71086.1 | *Clostridium tyrobutyricum* |
| enr | CAA76083.1 | *Clostridium kluyveri* |
| enr | YP_430895.1 | *Moorella thermoacetica* |

1.4.1.a—Oxidoreductase Operating on Amino Acids

Most oxidoreductases operating on amino acids catalyze the oxidative deamination of alpha-amino acids with NAD+ or NADP+ as acceptor. Exemplary oxidoreductases operating on amino acids include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (Korber et al. *J. Mol. Biol.* 234:1270-3024 1273 (1993); McPherson and Wootton *Nucleic. Acids Res.* 11:5257-5266 (1983)), gdh from *Thermotoga maritima* (Kort et al. *Extremophiles* 1:52-60 (1997); Lebbink, et al. *J. Mol. Biol.* 280:287-296 (1998)); Lebbink et al. *J. Mol. Biol.* 289:357-369 (1999)), and gdhA1 from *Halobacterium salinarum* (Ingoldsby et al. *Gene* 349:237-244 (2005)) catalyze the reversible interconversion of glutamate to 2-oxoglutarate and ammonia, while favoring NADP(H), NAD(H), or both, respectively. The ldh gene of *Bacillus cereus* encodes the LeuDH protein that has a wide of range of substrates including leucine, isoleucine, valine, and 2-aminobutanoate (Ansorge and Kula *Biotechnol Bioeng.* 68:557-562 (2000); Stoyan et al. *J. Biotechnol* 54:77-80 (1997)). The nadXgene from *Thermotoga* maritime encoding for the aspartate dehydrogenase is involved in the biosynthesis of NAD (Yang et al. *J. Biol. Chem.* 278:8804-8808 (2003)).

| gdhA | P00370 | *Escherichia coli* |
|---|---|---|
| gdh | P96110.4 | *Thermotoga maritima* |
| gdhA1 | NP_279651.1 | *Halobacterium salinarum* |
| ldh | P0A393 | *Bacillus cereus* |
| nadX | NP_229443.1 | *Thermotoga maritima* |

The lysine 6-dehydrogenase (deaminating), encoded by lysDH gene, catalyze the oxidative deamination of the ε-amino group of L-lysine to form 2-aminoadipate-6-semialdehyde, which in turn nonenzymatically cyclizes to form Δ1-piperideine-6-carboxylate (Misono and Nagasaki *J. Bacteriol.* 150:398-401 (1982)). The lysDH gene from *Geobacillus stearothermophilus* encodes a thermophilic NAD-dependent lysine 6-dehydrogenase (Heydari et al. *Appl Environ. Microbiol* 70:937-942 (2004)). In addition, the lysDH gene from *Aeropyrum pernix* K1 is identified through homology from genome projects.

| lysDH | AB052732 | *Geobacillus stearothermophilus* |
|---|---|---|
| lysDH | NP_147035.1 | *Aeropyrum pernix* K1 |
| ldh | P0A393 | *Bacillus cereus* |

2.3.1.a—Acyltransferase (Transferring Phosphate Group)

Exemplary phosphate transferring acyltransferases include phosphotransacetylase, encoded by pta, and phosphotransbutyrylase, encoded by ptb. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Similarly, the ptb gene from *C. acetobutylicum* encodes an enzyme that can convert butyryl-CoA into butyryl-phosphate (Walter et al. *Gene* 134(1): p. 107-11 (1993)); Huang et al. *J Mol Microbiol Biotechnol* 2(1): p. 33-38 (2000). Additional ptb genes can be found in butyrate-producing bacterium L2-50 (Louis et al. *J. Bacteriol.* 186: 2099-2106 (2004)) and *Bacillus megaterium* (Vazquez et al. *Curr. Microbiol* 42:345-349 (2001)).

| pta | NP_416800.1 | *Escherichia coli* |
|---|---|---|
| ptb | NP_349676 | *Clostridium acetobutylicum* |
| ptb | AAR19757.1 | butyrate-producing bacterium L2-50 |
| ptb | CAC07932.1 | *Bacillus megaterium* |

2.6.1.a—Aminotransferase

Aspartate aminotransferase transfers an amino group from aspartate to alpha-ketoglutarate, forming glutamate and oxaloacetate. This conversion is catalyzed by, for example, the gene products of aspC from *Escherichia coli* (Yagi et al. *FEBS Lett.* 100:81-84 (1979); Yagi et al. *Methods Enzymol.* 113:83-89 (1985)), AAT2 from *Saccharomyces cerevisiae* (Yagi et al. *J Biochem.* 92:35-43 (1982)) and ASPS from *Arabidopsis thaliana* (48, 108, 225 48. de la et al. *Plant J* 46:414-425 (2006); Kwok and Hanson *J Exp. Bot.* 55:595-604 (2004); Wilkie and Warren *Protein Expr. Purif.* 12:381-389 (1998)). Valine aminotransferase catalyzes the conversion of valine and pyruvate to 2-ketoisovalerate and alanine. The *E. coli* gene, avtA, encodes one such enzyme (Whalen and Berg *J. Bacteriol.* 150:739-746 (1982)). This gene product also catalyzes the amination of α-ketobutyrate to generate α-aminobutyrate, although the amine donor in this reaction has not been identified (Whalen and Berg *J. Bacteriol.* 158:571-574 (1984)). The gene product of the *E. coli* serC catalyzes two reactions, phosphoserine aminotransferase and phosphohydroxythreonine aminotransferase (Lam and Winkler *J. Bacteriol.* 172:6518-6528 (1990)), and activity on non-phosphorylated substrates could not be detected (Drewke et al. *FEBS. Lett.* 390:179-182 (1996)).

| aspC | NP_415448.1 | *Escherichia coli* |
|---|---|---|
| AAT2 | P23542.3 | *Saccharomyces cerevisiae* |
| ASp5 | P46248.2 | *Arabidopsis thaliana* |
| avtA | YP_026231.1 | *Escherichia coli* |
| serC | NP_415427.1 | *Escherichia coli* |

Cargill has developed a beta-alanine/alpha-ketoglutarate aminotransferase for producing 3-HP from beta-alanine via malonyl-semialdehyde (PCT/US2007/076252 (Jessen et al)). The gene product of SkPYD4 in *Saccharomyces kluyveri* was also shown to preferentially use beta-alanine as the amino group donor (Andersen et al. *FEBS. J.* 274:1804-1817 (2007)). SkUGA1 encodes a homologue of *Saccharomyces cerevisiae* GABA aminotransferase, UGA1 (Ramos et al. *Eur. J. Biochem.* 149:401-404 (1985)), whereas SkPYD4 encodes an enzyme involved in both β-alanine and GABA transamination (Andersen et al. *FEBS. J.* 274:1804-1817 (2007)). 3-Amino-2-methylpropionate transaminase catalyzes the transformation from methylmalonate semialdehyde to 3-amino-2-methylpropionate. The enzyme has been characterized in *Rattus norvegicus* and *Sus scrofa* and is encoded by Abat (Kakimoto et al. *Biochim. Biophys. Acta* 156:374-380 (1968); Tamaki et al. *Methods Enzymol.* 324: 376-389 (2000)). Enzyme candidates in other organisms with high sequence homology to 3-amino-2-methylpropionate transaminase include Gta-1 in *C. elegans* and gabT in *Bacillus subtilus*. Additionally, one of the native GABA aminotransferases in *E. coli*, encoded by gene gabT, has been shown to have broad substrate specificity (Liu et al. *Biochemistry* 43:10896-10905 (2004); Schulz et al. *Appl Environ Microbiol* 56:1-6 (1990)). The gene product of puuE catalyzes the other 4-aminobutyrate transaminase in *E. coli* (Kurihara et al. *J. Biol. Chem.* 280:4602-4608 (2005).).

| SkyPYD4 | ABF58893.1 | *Saccharomyces kluyveri* |
|---|---|---|
| SkUGA1 | ABF58894.1 | *Saccharomyces kluyveri* |
| UGA1 | NP_011533.1 | *Saccharomyces cerevisiae* |
| Abat | P50554.3 | *Rattus norvegicus* |
| Abat | P80147.2 | *Sus scrofa* |
| Gta-1 | Q21217.1 | *Caenorhabditis elegans* |
| gabT | P94427.1 | *Bacillus subtilus* |
| gabT | P22256.1 | *Escherichia coli* K12 |
| puuE | NP_415818.1 | *Escherichia coli* K12 |

The X-ray crystal structures of *E. coli* 4-aminobutyrate transaminase unbound and bound to the inhibitor were reported (Liu et al. *Biochemistry* 43:10896-10905 (2004)). The substrates binding and substrate specificities were studied and suggested. The roles of active site residues were studied by site-directed mutagenesis and X-ray crystallography (Liu et al. *Biochemistry* 44:2982-2992 (2005)). Based on the structural information, attempt was made to engineer *E. coli* 4-aminobutyrate transaminase with novel enzymatic activity. These studies provide a base for evolving transaminase activity for BDO pathways.

2.7.2.a—Phosphotransferase, Carboxyl Group Acceptor

Exemplary kinases include the *E. coli* acetate kinase, encoded by ackA (Skarstedt and Silverstein *J. Biol. Chem.* 251:6775-6783 (1976)), the *C. acetobutylicum* butyrate kinases, encoded by buk1 and buk2 (Walter et al. *Gene* 134(1):107-111 (1993) (Huang et al. *J Mol Microbiol Biotechnol* 2(1):33-38 (2000)], and the *E. coli* gamma-glutamyl kinase, encoded by proB (Smith et al. *J. Bacteriol.* 157:545-551 (1984)). These enzymes phosphorylate acetate, butyrate, and glutamate, respectively. The ackA gene product from *E. coli* also phosphorylates propionate (Hesslinger et al. *Mol. Microbiol* 27:477-492 (1998)).

| ackA | NP_416799.1 | *Escherichia coli* |
|---|---|---|
| buk1 | NP_349675 | *Clostridium acetobutylicum* |
| buk2 | Q97111 | *Clostridium acetobutylicum* |
| proB | NP_414777.1 | *Escherichia coli* |

2.8.3.a—Coenzyme-A Transferase

In the CoA-transferase family, *E. coli* enzyme acyl-CoA: acetate-CoA transferase, also known as acetate-CoA transferase (EC 2.8.3.8), has been shown to transfer the CoA moiety to acetate from a variety of branched and linear acyl-CoA substrates, including isobutyrate (Matthies and Schink *Appl Environ Microbiol* 58:1435-1439 (1992)), valerate (Vanderwinkel et al. *Biochem. Biophys. Res Commun.* 33:902-908 (1968)) and butanoate (Vanderwinkel, supra (1968)). This enzyme is encoded by atoA (alpha subunit) and atoD (beta subunit) in *E. coli* sp. K12 (Korolev et al. *Acta Crystallogr. D Biol Crystallogr.* 58:2116-2121 (2002); Vanderwinkel, supra (1968)) and actA and cg0592 in *Corynebacterium glutamicum* ATCC 13032 (Duncan et al. *Appl Environ Microbiol* 68:5186-5190 (2002)). Additional genes found by sequence homology include atoD and atoA in *Escherichia coli* UT 189.

| atoA | P76459.1 | *Escherichia coli* K12 |
|---|---|---|
| atoD | P76458.1 | *Escherichia coli* K12 |
| actA | YP_226809.1 | *Corynebacterium glutamicum* ATCC 13032 |
| cg0592 | YP_224801.1 | *Corynebacterium glutamicum* ATCC 13032 |
| atoA | ABE07971.1 | *Escherichia coli* UT 189 |
| atoD | ABE07970.1 | *Escherichia coli* UT 189 |

Similar transformations are catalyzed by the gene products of cat1, cat2, and cat3 of *Clostridium kluyveri* which have been shown to exhibit succinyl-CoA, 4-hydroxybutyryl-CoA, and butyryl-CoA acetyltransferase activity, respectively (Seedorf et al. *Proc Natl Acad Sci U.S.A.* 105(6):2128-2133 (2008); Sohling and Gottschalk *J Bacteriol* 178(3):871-880 (1996)].

| | | |
|---|---|---|
| cat1 | P38946.1 | Clostridium kluyveri |
| cat2 | P38942.2 | Clostridium kluyveri |
| cat3 | EDK35586.1 | Clostridium kluyveri |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack and Buckel *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al. *Eur. J. Biochem.* 118:315-321 (1981)). The enzyme has been cloned and expressed in *E. coli* (Mac et al. *Eur. J. Biochem.* 226:41-51 (1994)).

| | | |
|---|---|---|
| gctA | CAA57199.1 | Acidaminococcus fermentans |
| gctB | CAA57200.1 | Acidaminococcus fermentans |

3.1.2.a—Thiolester Hydrolase (CoA Specific)

In the CoA hydrolase family, the enzyme 3-hydroxyisobutyryl-CoA hydrolase is specific for 3-HIBCoA and has been described to efficiently catalyze the desired transformation during valine degradation (Shimomura et al. *J Biol Chem* 269:14248-14253 (1994)). Genes encoding this enzyme include hibch of *Rattus norvegicus* (Shimomura et al., supra (1994); Shimomura et al. *Methods Enzymol.* 324:229-240 (2000) and *Homo sapiens* (Shimomura et al., supra, 2000). Candidate genes by sequence homology include hibch of *Saccharomyces cerevisiae* and BC 2292 of *Bacillus cereus*.

| | | |
|---|---|---|
| hibch | Q5XIE6.2 | Rattus norvegicus |
| hibch | Q6NVY1.2 | Homo sapiens |
| hibch | P28817.2 | Saccharomyces cerevisiae |
| BC_2292 | Q81DR3 | Bacillus cereus |

The conversion of adipyl-CoA to adipate can be carried out by an acyl-CoA hydrolase or equivalently a thioesterase. The top *E. coli* gene candidate is tesB (Naggert et al. *J Biol Chem.* 266(17):11044-11050 (1991)] which shows high similarity to the human acot8 which is a dicarboxylic acid acetyltransferase with activity on adipyl-CoA (Westin et al. *J Biol Chem* 280(46): 38125-38132 (2005). This activity has also been characterized in the rat liver (Deana, *Biochem Int.* 26(4): p. 767-773 (1992)).

| | | |
|---|---|---|
| tesB | NP_414986 | Escherichia coli |
| acot8 | CAA15502 | Homo sapiens |
| acot8 | NP_570112 | Rattus norvegicus |

Other potential *E. coli* thiolester hydrolases include the gene products of tesA (Bonner and Bloch, *J Biol Chem.* 247(10):3123-3133 (1972)), ybgC (Kuznetsova et al., *FEMS Microbiol Rev.* 29(2):263-279 (2005); Zhuang et al., *FEBS Lett.* 516(1-3):161-163 (2002)) paaI (Song et al., *J Biol Chem.* 281(16):11028-11038 (2006)), and ybdB (Leduc et al., *J Bacteriol.* 189(19):7112-7126 (2007)).

| | | |
|---|---|---|
| tesA | NP_415027 | Escherichia coli |
| ybgC | NP_415264 | Escherichia coli |
| paaI | NP_415914 | Escherichia coli |
| ybdB | NP_415129 | Escherichia coli |

Several eukaryotic acetyl-CoA hydrolases (EC 3.1.2.1) have broad substrate specificity. The enzyme from *Rattus norvegicus* brain (Robinson et al. *Biochem. Biophys. Res. Commun.* 71:959-965 (1976)) can react with butyryl-CoA, hexanoyl-CoA and malonyl-CoA.

| | | |
|---|---|---|
| acot12 | NP_570103.1 | Rattus norvegicus |

4.1.1.a—Carboxy-lyase

An exemplary carboxy-lyase is acetolactate decarboxylase which participates in citrate catabolism and branched-chain amino acid biosynthesis, converting 2-acetolactate to acetoin. In *Lactococcus lactis* the enzyme is composed of six subunits, encoded by gene aldB, and is activated by valine, leucine and isoleucine (Goupil et al. *Appl. Environ. Microbiol.* 62:2636-2640 (1996); Goupil-Feuillerat et al. *J. Bacteriol.* 182:5399-5408 (2000)). This enzyme has been overexpressed and characterized in *E. coli* (Phalip et al. *FEBS Lett.* 351:95-99 (1994)). In other organisms the enzyme is a dimer, encoded by aldC in *Streptococcus thermophilus* (Monnet et al. *Lett. Appl. Microbiol.* 36:399-405 (2003)), aldB in *Bacillus brevis* (Diderichsen et al. *J. Bacteriol.* 172:4315-4321 (1990); Najmudin et al. *Acta Crystallogr. D. Biol. Crystallogr.* 59:1073-1075 (2003)) and budA from *Enterobacter aerogenes* (Diderichsen et al. *J. Bacteriol.* 172:4315-4321 (1990)). The enzyme from *Bacillus brevis* was cloned and overexpressed in *Bacillus subtilis* and characterized crystallographically (Najmudin et al. *Acta Crystallogr. D. Biol. Crystallogr* 59:1073-1075 (2003)). Additionally, the enzyme from *Leuconostoc lactis* has been purified and characterized but the gene has not been isolated (O'Sullivan et al. *FEMS Microbiol. Lett.* 194:245-249 (2001)).

| | | |
|---|---|---|
| aldB | NP_267384.1 | Lactococcus lactis |
| aldC | Q8L208 | Streptococcus thermophilus |
| aldB | P23616.1 | Bacillus brevis |
| budA | P05361.1 | Enterobacter aerogenes |

Aconitate decarboxylase catalyzes the final step in itaconate biosynthesis in a strain of *Candida* and also in the filamentous fungus *Aspergillus terreus* (Bonnarme et al. *J Bacteriol.* 177:3573-3578 (1995); Willke and Vorlop *Appl Microbiol Biotechnol* 56:289-295 (2001)). Although itaconate is a compound of biotechnological interest, the aconitate decarboxylase gene or protein sequence has not been reported to date.

4-oxalocronate decarboxylase has been isolated from numerous organisms and characterized. Genes encoding this enzyme include dmpH and dmpE in *Pseudomonas* sp. (strain 600) (Shingler et al. *J Bacteriol.* 174:711-724 (1992)), xylII and xylIII from *Pseudomonas putida* (Kato and Asano *Arch. Microbiol* 168:457-463 (1997); Lian and Whitman *J. Am. Chem. Soc.* 116:10403-10411 (1994); Stanley et al. *Biochemistry* 39:3514 (2000)) and Reut_B5691 and Reut_B5692 from *Ralstonia eutropha JMP*134 (Hughes et al. *J Bacteriol.* 158:79-83 (1984)). The genes encoding the enzyme from *Pseudomonas* sp. (strain 600) have been cloned and expressed in *E. coli* (Shingler et al. *J Bacteriol.* 174:711-724 (1992)).

| | | |
|---|---|---|
| dmpH | CAA43228.1 | *Pseudomonas* sp. CF600 |
| dmpE | CAA43225.1 | *Pseudomonas* sp. CF600 |
| xylII | YP_709328.1 | *Pseudomonas putida* |
| xylIII | YP_709353.1 | *Pseudomonas putida* |
| Reut_B5691 | YP_299880.1 | *Ralstonia eutropha* JMP134 |
| Reut_B5692 | YP_299881.1 | *Ralstonia eutropha* JMP134 |

An additional class of decarboxylases has been characterized that catalyze the conversion of cinnamate (phenylacrylate) and substituted cinnamate derivatives to the corresponding styrene derivatives. These enzymes are common in a variety of organisms and specific genes encoding these enzymes that have been cloned and expressed in *E. coli* are: pad 1 from *Saccharomyces cerevisae* (Clausen et al. *Gene* 142:107-112 (1994)), pdc from *Lactobacillus plantarum* (Barthelmebs et al. *Appl Environ Microbiol* 67:1063-1069 (2001); Qi et al. *Metab Eng* 9:268-276 (2007); Rodriguez et al. *J. Agric. Food Chem.* 56:3068-3072 (2008)), pofK (pad) from *Klebsiella oxytoca* (Hashidoko et al. *Biosci. Biotech. Biochem.* 58:217-218 (1994); Uchiyama et al. *Biosci. Biotechnol. Biochem.* 72:116-123 (2008)), *Pedicoccus pentosaceus* (Barthelmebs et al. *Appl Environ Microbiol* 67:1063-1069 (2001)), and padC from *Bacillus subtilis* and *Bacillus pumilus* (Lingen et al. *Protein Eng* 15:585-593 (2002)). A ferulic acid decarboxylase from *Pseudomonas fluorescens* also has been purified and characterized (Huang et al. *J. Bacteriol.* 176:5912-5918 (1994)). Importantly, this class of enzymes have been shown to be stable and do not require either exogenous or internally bound co-factors, thus making these enzymes ideally suitable for biotransformations (Sariaslani, *Annu. Rev. Microbiol.* 61:51-69 (2007)).

| | | |
|---|---|---|
| pad1 | AB368798 | *Saccharomyces cerevisae* |
| pdc | U63827 | *Lactobacillus plantarum* |
| pofK (pad) | AB330293 | *Klebsiella oxytoca* |
| padC | AF017117 | *Bacillus subtilis* |
| pad | AJ276891 | *Pedicoccus pentosaceus* |
| pad | AJ278683 | *Bacillus pumilus* |

Additional decarboxylase enzymes can form succinic semialdehyde from alpha-ketoglutarate. These include the alpha-ketoglutarate decarboxylase enzymes from *Euglena gracilis* (Shigeoka et al. *Biochem. J.* 282(Pt 2):319-323 (1992); Shigeoka and Nakano *Arch. Biochem. Biophys.* 288:22-28 (1991); Shigeoka and Nakano *Biochem. J.* 292 (Pt 2):463-467 (1993)), whose corresponding gene sequence has yet to be determined, and from *Mycobacterium tuberculosis* (Tian et al. *Proc Natl Acad Sci U.S.A.* 102:10670-10675 (2005)). In addition, glutamate decarboxylase enzymes can convert glutamate into 4-aminobutyrate such as the products of the *E. coli* gadA and gadB genes (De Biase et al. *Protein. Expr. Purif.* 8:430-438 (1993)).

| | | |
|---|---|---|
| kgd | O50463.4 | *Mycobacterium tuberculosis* |
| gadA | NP_417974 | *Escherichia coli* |
| gadB | NP_416010 | *Escherichia coli* |

Keto-Acid Decarboxylases

Pyruvate decarboxylase (PDC, EC 4.1.1.1), also termed keto-acid decarboxylase, is a key enzyme in alcoholic fermentation, catalyzing the decarboxylation of pyruvate to acetaldehyde. This enzyme has a broad substrate range for aliphatic 2-keto acids including 2-ketobutyrate, 2-ketovalerate, 3-hydroxypyruvate and 2-phenylpyruvate (Berg et al. *Science* 318:1782-1786 (2007)). The PDC from *Zymomonas mobilus*, encoded by pdc, has been a subject of directed engineering studies that altered the affinity for different substrates (Siegert et al. *Protein Eng Des Sel* 18:345-357 (2005)). The PDC from *Saccharomyces cerevisiae* has also been extensively studied, engineered for altered activity, and functionally expressed in *E. coli* (Killenberg-Jabs et al. *Eur. J. Biochem.* 268:1698-1704 (2001); Li and Jordan *Biochemistry* 38:10004-10012 (1999); ter Schure et al. *Appl. Environ. Microbiol.* 64:1303-1307 (1998)). The crystal structure of this enzyme is available (Killenberg-Jabs *Eur. J. Biochem.* 268:1698-1704 (2001)). Other well-characterized PDC candidates include the enzymes from *Acetobacter pasteurians* (Chandra et al. *Arch. Microbiol.* 176:443-451 (2001)) and *Kluyveromyces lactis* (Krieger et al. *Eur. J. Biochem.* 269: 3256-3263 (2002)).

| Gene | GenBank ID | Organism |
|---|---|---|
| pdc | P06672.1 | *Zymomonas mobilus* |
| pdc1 | P06169 | *Saccharomyces cerevisiae* |
| pdc | Q8L388 | *Acetobacter pasteurians* |
| pdc1 | Q12629 | *Kluyveromyces lactis* |

Like PDC, benzoylformate decarboxylase (EC 4.1.1.7) has a broad substrate range and has been the target of enzyme engineering studies. The enzyme from *Pseudomonas putida* has been extensively studied and crystal structures of this enzyme are available (Hasson et al. *Biochemistry* 37:9918-9930 (1998); Polovnikova et al. *Biochemistry* 42:1820-1830 (2003)). Site-directed mutagenesis of two residues in the active site of the *Pseudomonas putida* enzyme altered the affinity (Km) of naturally and non-naturally occurring substrates (Siegert *Protein Eng Des Sel* 18:345-357 (2005)). The properties of this enzyme have been further modified by directed engineering (Lingen et al. *Protein Eng* 15:585-593 (2002)); Lingen *Chembiochem* 4:721-726 (2003)). The enzyme from *Pseudomonas aeruginosa*, encoded by mdlC, has also been characterized experimentally (Barrowman et al. *FEMS Microbiology Letters* 34:57-60 (1986)). Additional gene candidates from *Pseudomonas stutzeri*, *Pseudomonas fluorescens* and other organisms can be inferred by sequence homology or identified using a growth selection system developed in *Pseudomonas putida* (Henning et al. *Appl. Environ. Microbiol.* 72:7510-7517 (2006)).

| | | |
|---|---|---|
| mdlC | P20906.2 | *Pseudomonas putida* |
| mdlC | Q9HUR2.1 | *Pseudomonas aeruginosa* |
| dpgB | ABN80423.1 | *Pseudomonas stutzeri* |
| ilvB-1 | YP_260581.1 | *Pseudomonas fluorescens* |

4.2.1.a—Hydro-lyase

The 2-(hydroxymethyl)glutarate dehydratase of *Eubacterium barkeri* is an exemplary hydro-lyase. This enzyme has been studied in the context of nicotinate catabolism and is encoded by hmd (Alhapel et al. *Proc Natl Acad Sci USA* 103:12341-12346 (2006)). Similar enzymes with high sequence homology are found in *Bacteroides capillosus*, *Anaerotruncus colihominis*, and *Natranaerobius thermophilius*.

| | | |
|---|---|---|
| hmd | ABC88407.1 | *Eubacterium barkeri* |
| BACCAP_02294 | ZP_02036683.1 | *Bacteroides capillosus* ATCC 29799 |

| ANACOL_02527 | ZP_02443222.1 | *Anaerotruncus colihominis* DSM 17241 |
| NtherDRAFT_2368 | ZP_02852366.1 | *Natranaerobius thermophilus* JW/NM-WN-LF |

A second exemplary hydro-lyase is fumarate hydratase, an enzyme catalyzing the dehydration of malate to fumarate. A wealth of structural information is available for this enzyme and researchers have successfully engineered the enzyme to alter activity, inhibition and localization (Weaver, T. *Acta Crystallogr. D Biol Crystallogr.* 61:1395-1401 (2005)). Additional fumarate hydratases include those encoded by fumC from *Escherichia coli* (Estevez et al. *Protein Sci.* 11:1552-1557 (2002); Hong and Lee *Biotechnol. Bioprocess Eng.* 9:252-255 (2004); Rose and Weaver *Proc Natl Acad Sci USA* 101:3393-3397 (2004)), *Campylobacter jejuni* (Smith et al. *Int. J Biochem. Cell Biol* 31:961-975 (1999)) and *Thermus thermophilus* (Mizobata et al. *Arch. Biochem. Biophys.* 355:49-55 (1998)), and fumH from *Rattus norvegicus* (Kobayashi et al. *J Biochem.* 89:1923-1931(1981)). Similar enzymes with high sequence homology include fum1 from *Arabidopsis thaliana* and fumC from *Corynebacterium glutamicum*.

| fumC | P05042.1 | *Escherichia coli* K12 |
| fumC | O69294.1 | *Campylobacter jejuni* |
| fumC | P84127 | *Thermus thermophilus* |
| fumH | P14408.1 | *Rattus norvegicus* |
| fum1 | P93033.2 | *Arabidopsis thaliana* |
| fumC | Q8NRN8.1 | *Corynebacterium glutamicum* |

Citramalate hydrolyase, also called 2-methylmalate dehydratase, converts 2-methylmalate to mesaconate. 2-Methylmalate dehydratase activity was detected in *Clostridium tetanomorphum, Morganella morganii, Citrobacter amalonaticus* in the context of the glutamate degradation VI pathway (Kato and Asano *Arch. Microbiol* 168:457-463 (1997)); however the genes encoding this enzyme have not been sequenced to date.

The gene product of crt from *C. acetobutylicum* catalyzes the dehydration of 3-hydroxybutyryl-CoA to crotonyl-CoA (Atsumi et al. *Metab Eng.;* 29 (2007)); Boynton et al. *Journal of Bacteriology* 178:3015-3024 (1996)). The enoyl-CoA hydratases, phaA and phaB, of *P. putida* are believed to carry out the hydroxylation of double bonds during phenylacetate catabolism; (Olivera et al. *Proc Natl Acad Sci USA* 95(11):6419-6424 (1998)). The paaA and paaB from *P. fluorescens* catalyze analogous transformations (14 Olivera et al., supra, 1998). Lastly, a number of *Escherichia coli* genes have been shown to demonstrate enoyl-CoA hydratase functionality including maoC (Park and Lee *J Bacteriol* 185(18):5391-5397 (2003)), paaF (Park and Lee *Biotechnol Bioeng.* 86(6):681-686 (2004a)); Park and Lee *Appl Biochem Biotechnol.* 113-116: 335-346 (2004b)); Ismail et al. *Eur J Biochem* 270(14):p. 3047-3054 (2003), and paaG (Park and Lee, supra, 2004; Park and Lee supra, 2004b; Ismail et al., supra, 2003).

| maoC | NP_415905.1 | *Escherichia coli* |
| paaF | NP_415911.1 | *Escherichia coli* |
| paaG | NP_415912.1 | *Escherichia coli* |
| crt | NP_349318.1 | *Clostridium acetobutylicum* |
| paaA | NP_745427.1 | *Pseudomonas putida* |
| paaB | NP_745426.1 | *Pseudomonas putida* |

| phaA | ABF82233.1 | *Pseudomonas fluorescens* |
| phaB | ABF82234.1 | *Pseudomonas fluorescens* |

The *E. coli* genes fadA and fadB encode a multienzyme complex that exhibits ketoacyl-CoA thiolase, 3-hydroxyacyl-CoA dehydrogenase, and enoyl-CoA hydratase activities (Yang et al. *Biochemistry* 30(27): p. 6788-6795 (1991); Yang et al. *J Biol Chem* 265(18): p. 10424-10429 (1990); Yang et al. *J Biol Chem* 266(24): p. 16255 (1991); Nakahigashi and Inokuchi *Nucleic Acids Res* 18(16): p. 4937 (1990)). The fadI and fadJ genes encode similar functions and are naturally expressed only anaerobically (Campbell et al. *Mol Microbiol* 47(3): p. 793-805 (2003). A method for producing poly[(R)-3-hydroxybutyrate] in *E. coli* that involves activating fadB (by knocking out a negative regulator, fadR) and co-expressing a non-native ketothiolase (phaA from *Ralstonia eutropha*) has been described previously (Sato et al. *J Biosci Bioeng* 103(1): 38-44 (2007)). This work clearly demonstrates that a β-oxidation enzyme, in particular the gene product of fadB which encodes both 3-hydroxyacyl-CoA dehydrogenase and enoyl-CoA hydratase activities, can function as part of a pathway to produce longer chain molecules from acetyl-CoA precursors.

| fadA | YP_026272.1 | *Escherichia coli* |
| fadB | NP_418288.1 | *Escherichia coli* |
| fadI | NP_416844.1 | *Escherichia coli* |
| fadJ | NP_416843.1 | *Escherichia coli* |
| fadR | NP_415705.1 | *Escherichia coli* |

4.3.1.a—Ammonia-lyase

Aspartase (EC 4.3.1.1), catalyzing the deamination of aspartate to fumarate, is a widespread enzyme in microorganisms, and has been characterized extensively (Viola, R. E. *Adv. Enzymol. Relat Areas Mol. Biol* 74:295-341 (2000)). The crystal structure of the *E. coli* aspartase, encoded by aspA, has been solved (Shi et al. *Biochemistry* 36:9136-9144 (1997)). The *E. coli* enzyme has also been shown to react with alternate substrates aspartatephenylmethylester, asparagine, benzyl-aspartate and malate (Ma et al. *Ann N.Y. Acad Sci* 672:60-65 (1992)). In a separate study, directed evolution was been employed on this enzyme to alter substrate specificity (Asano et al. *Biomol. Eng* 22:95-101 (2005)). Enzymes with aspartase functionality have also been characterized in *Haemophilus influenzae* (Sjostrom et al. *Biochim. Biophys. Acta* 1324:182-190 (1997)), *Pseudomonas fluorescens* (Takagi et al. *J. Biochem.* 96:545-552 (1984)), *Bacillus subtilus* (Sjostrom et al. *Biochim. Biophys. Acta* 1324:182-190 (1997)) and *Serratia marcescens* (Takagi and Kisumi *J Bacteriol.* 161:1-6 (1985)).

| aspA | NP_418562 | *Escherichia coli* K12 subsp. MG1655 |
| aspA | P44324.1 | *Haemophilus influenzae* |
| aspA | P07346.1 | *Pseudomonas fluorescens* |
| ansB | P26899.1 | *Bacillus subtilus* |
| aspA | P33109.1 | *Serratia marcescens* |

3-methylaspartase (EC 4.3.1.2), also known as beta-methylaspartase or 3-methylaspartate ammonia-lyase, catalyzes the deamination of threo-3-methylasparatate to mesaconate. The 3-methylaspartase from *Clostridium tetanomorphum* has been cloned, functionally expressed in *E. coli*, and crystallized (Asuncion et al. *Acta Crystallogr. D Biol Crystallogr.* 57:731-733 (2001); Asuncion et al. *J Biol Chem.*

277:8306-8311 (2002); Botting et al. *Biochemistry* 27:2953-2955 (1988); Goda et al. *Biochemistry* 31:10747-10756 (1992). In *Citrobacter amalonaticus*, this enzyme is encoded by BAA28709 (Kato and Asano *Arch. Microbiol* 168:457-463 (1997)). 3-Methylaspartase has also been crystallized from *E. coli* YG1002 (Asano and Kato *FEMS Microbiol Lett.* 118:255-258 (1994)) although the protein sequence is not listed in public databases such as GenBank. Sequence homology can be used to identify additional candidate genes, including CTC_02563 in *C. tetani* and ECs0761 in *Escherichia coli* O157:H7.

| MAL | AAB24070.1 | *Clostridium tetanomorphum* |
|---|---|---|
| BAA28709 | BAA28709.1 | *Citrobacter amalonaticus* |
| CTC_02563 | NIP_783085.1 | *Clostridium tetani* |
| ECs0761 | BAB34184.1 | *Escherichia coli* O157:H7 str. Sakai |

Ammonia-lyase enzyme candidates that form enoyl-CoA products include beta-alanyl-CoA ammonia-lyase (EC 4.3.1.6), which deaminates beta-alanyl-CoA, and 3-aminobutyryl-CoA ammonia-lyase (EC 4.3.1.14). Two beta-alanyl-CoA ammonia lyases have been identified and characterized in *Clostridium propionicum* (Herrmann et al. *FEBS J.* 272:813-821 (2005)). No other beta-alanyl-CoA ammonia lyases have been studied to date, but gene candidates can be identified by sequence similarity. One such candidate is MXAN_4385 in *Myxococcus xanthus*.

| acl2 | CAG29275.1 | *Clostridium propionicum* |
|---|---|---|
| acl1 | CAG29274.1 | *Clostridium propionicum* |
| MXAN_4385 | YP_632558.1 | *Myxococcus xanthus* |

5.3.3.a—Isomerase

The 4-hydroxybutyryl-CoA dehydratases from both *Clostridium aminobutyrium* and *C. kluyveri* catalyze the reversible conversion of 4-hydroxybutyryl-CoA to crotonyl-CoA and posses an intrinsic vinylacetyl-CoA Δ-isomerase activity (Scherf and Buckel *Eur. J Biochem.* 215:421-429 (1993); Scherf et al. *Arch. Microbiol* 161:239-245 (1994)). Both native enzymes were purified and characterized, including the N-terminal amino acid sequences (Scherf and Buckel, supra, 1993; Scherf et al., supra, 1994). The abfD genes from *C. aminobutyrium* and *C. kluyveri* match exactly with these N-terminal amino acid sequences, thus are encoding the 4-hydroxybutyryl-CoA dehydratases/vinylacetyl-CoA Δ-isomerase. In addition, the abfD gene from *Porphyromonas gingivalis* ATCC 33277 is identified through homology from genome projects.

| abfD | YP_001396399.1 | *Clostridium kluyveri* DSM 555 |
|---|---|---|
| abfD | P55792 | *Clostridium aminobutyricum* |
| abfD | YP_001928843 | *Porphyromonas gingivalis* ATCC 33277 |

5.4.3.a—Aminomutase

Lysine 2,3-aminomutase (EC 5.4.3.2) is an exemplary aminomutase that converts lysine to (3S)-3,6-diaminohexanoate, shifting an amine group from the 2- to the 3-position. The enzyme is found in bacteria that ferment lysine to acetate and butyrate, including as *Fusobacterium nuleatum* (kamA) (Barker et al. *J. Bacteriol.* 152:201-207 (1982)) and *Clostridium subterminale* (kamA) (Chirpich et al. *J. Biol. Chem.* 245:1778-1789 (1970)). The enzyme from *Clostridium subterminale* has been crystallized (Lepore et al. *Proc. Natl. Acad. Sci. U.S.A* 102:13819-13824 (2005)).

An enzyme encoding this function is also encoded by yodO in *Bacillus subtilus* (Chen et al. *Biochem. J.* 348 Pt 3:539-549 (2000)). The enzyme utilizes pyridoxal 5'-phosphate as a cofactor, requires activation by S-Adenosylmethoionine, and is stereoselective, reacting with the only with L-lysine. The enzyme has not been shown to react with alternate substrates.

| yodO | O34676.1 | *Bacillus subtilus* |
|---|---|---|
| kamA | Q9XBQ8.1 | *Clostridium subterminale* |
| kamA | Q8RHX4 | *Fusobacterium nuleatum* subsp. *nuleatum* |

A second aminomutase, beta-lysine 5,6-aminomutase (EC 5.4.3.3), catalyzes the next step of lysine fermentation to acetate and butyrate, which transforms (3S)-3,6-diaminohexanoate to (3S,5S)-3,5-diaminohexanoate, shifting a terminal amine group from the 6- to the 5-position. This enzyme also catalyzes the conversion of lysine to 2,5-diaminohexanoate and is also called lysine-5,6-aminomutase (EC 5.4.3.4). The enzyme has been crystallized in *Clostridium sticklandii* (kamD, kamE) (Berkovitch et al. *Proc. Natl. Acad. Sci. U.S.A* 101:15870-15875 (2004)). The enzyme from *Porphyromonas gingivalis* has also been characterized (Tang et al. *Biochemistry* 41:8767-8776 (2002)).

| kamD | AAC79717.1 | *Clostridium sticklandii* |
|---|---|---|
| kamE | AAC79718.1 | *Clostridium sticklandii* |
| kamD | NC_002950.2 | *Porphyromonas gingivalis* W83 |
| kamE | NC_002950.2 | *Porphyromonas gingivalis* W83 |

Ornithine 4,5-aminomutase (EC 5.4.3.5) converts D-ornithine to 2,4-diaminopentanoate, also shifting a terminal amine to the adjacent carbon. The enzyme from *Clostridium sticklandii* is encoded by two genes, oraE and oraS, and has been cloned, sequenced and expressed in *E. coli* (Chen et al. *J. Biol. Chem.* 276:44744-44750 (2001)). This enzyme has not been characterized in other organisms to date.

| oraE | AAK72502 | *Clostridium sticklandii* |
|---|---|---|
| oraS | AAK72501 | *Clostridium sticklandii* |

Tyrosine 2,3-aminomutase (EC 5.4.3.6) participates in tyrosine biosynthesis, reversibly converting tyrosine to 3-amino-3-(4-hydroxyphenyl)propanoate by shifting an amine from the 2- to the 3-position. In *Streptomyces globisporus* the enzyme has also been shown to react with tyrosine derivatives (Christenson et al. *Biochemistry* 42:12708-12718 (2003)). Sequence information is not available.

Leucine 2,3-aminomutase (EC 5.4.3.7) converts L-leucine to beta-leucine during leucine degradation and biosynthesis. An assay for leucine 2,3-aminomutase detected activity in many organisms (Poston, J. M. *Methods Enzymol.* 166:130-135 (1988)) but genes encoding the enzyme have not been identified to date.

Cargill has developed a novel 2,3-aminomutase enzyme to convert L-alanine to β-alanine, thus creating a pathway from pyruvate to 3-HP in four biochemical steps (Liao et al., U.S. Publication No. 2005-0221466).

6.2.1.a—Acid-Thiol Ligase

An exemplary acid-thiol ligase is the gene products of sucCD of *E. coli* which together catalyze the formation of succinyl-CoA from succinate with the concammant consumption of one ATP, a reaction which is reversible in vivo (Buck et al. *Biochemistry* 24(22): p. 6245-6252 (1985)). Additional exemplary CoA-ligases include the rat dicarboxylate-CoA ligase for which the sequence is yet uncharacterized (Vamecq et al. *Biochem J.* 230(3): p. 683-693 (1985)), either of the two characterized phenylacetate-CoA ligases from *P. chrysogenum* (Lamas-Maceiras et al. *Biochem J* 395(1):147-155 (2006); Wang et al. *Biochem Biophys Res Commun,* 360(2):453-458 (2007)), the phenylacetate-CoA ligase from *Pseudomonas putida* (Martinez-Blanco et al. *J Biol Chem.* 265(12):7084-7090 (1990)), and the 6-carboxyhexanoate-CoA ligase from *Bacillus subtilis* (Bower et al. *J Bacteriol* 178(14):4122-4130 (1996)).

| | | |
|---|---|---|
| sucC | NP_415256.1 | *Escherichia coli* |
| sucD | AAC73823.1 | *Escherichia coli* |
| phl | CAJ15517.1 | *Penicillium chrysogenum* |
| phlB | ABS19624.1 | *Penicillium chrysogenum* |
| paaF | AAC24333.2 | *Pseudomonas putida* |
| bioW | NP_390902.2 | *Bacillus subtilis* |

Example V

Exemplary BDO Pathway from Succinyl-CoA

This example describes exemplary BDO pathways from succinyl-CoA.

BDO pathways from succinyl-CoA are described herein and have been described previously (see U.S. application Ser. No. 12/049,256, filed Mar. 14, 2008, and PCT application serial No. US08/57168, filed Mar. 14, 2008, each of which is incorporated herein by reference). Additional pathways are shown in FIG. 8A. Enzymes of such exemplary BDO pathways are listed in Table 15, along with exemplary genes encoding these enzymes.

Briefly, succinyl-CoA can be converted to succinic semialdehyde by succinyl-CoA reductase (or succinate semialdehyde dehydrogenase) (EC 1.2.1.b). Succinate semialdehyde can be converted to 4-hydroxybutyrate by 4-hydroxybutyrate dehydrogenase (EC 1.1.1.a), as previously described. Alternatively, succinyl-CoA can be converted to 4-hydroxybutyrate by succinyl-CoA reductase (alcohol forming) (EC 1.1.1.c). 4-Hydroxybutyrate can be converted to 4-hydroxybutyryl-CoA by 4-hydroxybutyryl-CoA transferase (EC 2.8.3.a), as previously described, or by 4-hydroxybutyryl-CoA hydrolase (EC 3.1.2.a) or 4-hydroxybutyryl-CoA ligase (or 4-hydroxybutyryl-CoA synthetase) (EC 6.2.1.a). Alternatively, 4-hydroxybutyrate can be converted to 4-hydroxybutyryl-phosphate by 4-hydroxybutyrate kinase (EC 2.7.2.a), as previously described. 4-Hydroxybutyryl-phosphate can be converted to 4-hydroxybutyryl-CoA by phosphotrans-4-hydroxybutyrylase (EC 2.3.1.a), as previously described. Alternatively, 4-hydroxybutyryl-phosphate can be converted to 4-hydroxybutanal by 4-hydroxybutanal dehydrogenase (phosphorylating) (EC 1.2.1.d). 4-Hydroxybutyryl-CoA can be converted to 4-hydroxybutanal by 4-hydroxybutyryl-CoA reductase (or 4-hydroxybutanal dehydrogenase) (EC 1.2.1.b). Alternatively, 4-hydroxybutyryl-CoA can be converted to 1,4-butanediol by 4-hydroxybutyryl-CoA reductase (alcohol forming) (EC 1.1.1.c). 4-Hydroxybutanal can be converted to 1,4-butanediol by 1,4-butanediol dehydrogenase (EC 1.1.1.a), as previously described.

TABLE 15

BDO pathway from succinyl-CoA.

| FIG. | EC class | Desired substrate | Desired product | Enzyme name | Gene name | GenBank ID (if available) | Organism | Known Substrates |
|---|---|---|---|---|---|---|---|---|
| 8A | 1.2.1.b | succinyl-CoA | succinic semialdehyde | succinyl-CoA reductase (or succinate semialdehyde dehydrogenase) | sucD | P38947.1 | *Clostridium kluyveri* | succinyl-CoA |
| | | | | | sucD | NP_904963.1 | *Porphyromonas gingivalis* | succinyl-CoA |
| | | | | | Msed_0709 | YP_001190808.1 | *Metallosphaera sedula* | malonyl-CoA |
| 8A | 1.1.1.a | succinate semialdehyde | 4-hydroxybutyrate | 4-hydroxybutyrate dehydrogenase | 4hbd | YP_726053.1 | *Ralstonia eutropha* H16 | 4-hydroxybutyrate |
| | | | | | 4hbd | L21902.1 | *Clostridium kluyveri* DSM 555 | 4-hydroxybutyrate |
| | | | | | 4hbd | Q94B07 | *Arabidopsis thaliana* | 4-hydroxybutyrate |
| 8A | 1.1.1.c | succinyl-CoA | 4-hydroxybutyrate | succinyl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |
| 8A | 2.8.3.a | 4-hydroxybutyrate | 4-hydroxybutyryl-CoA | 4-hydroxybutyryl-CoA transferase | cat1, cat2, cat3 | P38946.1, P38942.2, EDK35586.1 | *Clostridium kluyveri* | succinate, 4-hydroxybutyrate, butyrate |
| | | | | | gctA, gctB | CAA57199.1, CAA57200.1 | *Acidaminococcus fermentans* | glutarate |
| | | | | | atoA, atoD | P76459.1, P76458.1 | *Escherichia coli* | butanoate |

TABLE 15-continued

BDO pathway from succinyl-CoA.

| FIG. | EC class | Desired substrate | Desired product | Enzyme name | Gene name | GenBank ID (if available) | Organism | Known Substrates |
|---|---|---|---|---|---|---|---|---|
| 8A | 3.1.2.a | 4-hydroxybutyrate | 4-hydroxybutyryl-CoA | 4-hydroxybutyryl-CoA hydrolase | tesB | NP_414986 | *Escherichia coli* | adipyl-CoA |
| | | | | | acot12 | NP_570103.1 | *Rattus norvegicus* | butyryl-CoA |
| | | | | | hibch | Q6NVY1.2 | *Homo sapiens* | 3-hydroxypropanoyl-CoA |
| 8A | 6.2.1.a | 4-hydroxybutyrate | 4-hydroxybutyryl-CoA | 4-hydroxybutyryl-CoA ligase (or 4-hydroxybutyryl-CoA synthetase) | sucCD | NP_415256.1, AAC73823.1 | *Escherichia coli* | succinate |
| | | | | | phl | CAJ15517.1 | *Penicillium chrysogenum* | phenylacetate |
| | | | | | bioW | NP_390902.2 | *Bacillus subtilis* | 6-carboxyhexanoate |
| 8A | 2.7.2.a | 4-hydroxybutyrate | 4-hydroxybutyryl-phosphate | 4-hydroxybutyrate kinase | ackA | NP_416799.1 | *Escherichia coli* | acetate, propionate |
| | | | | | buk1 | NP_349675 | *Clostridium acetobutylicum* | butyrate |
| | | | | | buk2 | Q97II1 | *Clostridium acetobutylicum* | butyrate |
| 8A | 2.3.1.a | 4-hydroxybutyryl-phosphate | 4-hydroxybutyryl-CoA | phosphotrans-4-hydroxybutyrylase | ptb | NP_349676 | *Clostridium acetobutylicum* | butyryl-phosphate |
| | | | | | ptb | AAR19757.1 | butyrate-producing bacterium L2-50 | butyryl-phosphate |
| | | | | | ptb | CAC07932.1 | *Bacillus megaterium* | butyryl-phosphate |
| 8A | 1.2.1.d | 4-hydroxybutyryl-phosphate | 4-hydroxybutanal | 4-hydroxybutanal dehydrogenase (phosphorylating) | asd | NP_417891.1 | *Escherichia coli* | L-4-aspartyl-phosphate |
| | | | | | proA | NP_414778.1 | *Escherichia coli* | L-glutamyl-5-phospate |
| | | | | | gapA | P0A9B2.2 | *Escherichia coli* | Glyceraldehyde-3-phosphate |
| 8A | 1.2.1.b | 4-hydroxybutyryl-CoA | 4-hydroxybutanal | 4-hydroxybutyryl-CoA reductase (or 4-hydroxybutanal dehydrogenase) | sucD | P38947.1 | *Clostridium kluyveri* | succinyl-CoA |
| | | | | | sucD | NP_904963.1 | *Porphyromonas gingivalis* | succinyl-CoA |
| | | | | | Msed_0709 | YP_001190808.1 | *Metallosphaera sedula* | malonyl-CoA |
| 8A | 1.1.1.c | 4-hydroxybutyryl-CoA | 1,4-butanediol | 4-hydroxybutyryl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |
| 8A | 1.1.1.a | 4-hydroxybutanal | 1,4-butanediol | 1,4-butanediol dehydrogenase | ADH2 | NP_014032.1 | *Saccharymyces cerevisiae* | general |
| | | | | | yqhD | NP_417484.1 | *Escherichia coli* | >C3 |
| | | | | | 4hbd | L21902.1 | *Clostridium kluyveri* DSM 555 | Succinate semialdehyde |

Example VI

Additional Exemplary BDO Pathways from Alpha-Ketoglutarate

This example describes exemplary BDO pathways from alpha-ketoglutarate.

BDO pathways from succinyl-CoA are described herein and have been described previously (see U.S. application Ser. No. 12/049,256, filed Mar. 14, 2008, and PCT application serial No. US08/57168, filed Mar. 14, 2008, each of which is incorporated herein by reference). Additional pathways are shown in FIG. 8B. Enzymes of such exemplary BDO pathways are listed in Table 16, along with exemplary genes encoding these enzymes.

Briefly, alpha-ketoglutarate can be converted to succinic semialdehyde by alpha-ketoglutarate decarboxylase (EC 4.1.1.a), as previously described. Alternatively, alpha-ketoglutarate can be converted to glutamate by glutamate dehydrogenase (EC 1.4.1.a). 4-Aminobutyrate can be converted to succinic semialdehyde by 4-aminobutyrate oxidoreductase (deaminating) (EC 1.4.1.a) or 4-aminobutyrate transaminase (EC 2.6.1.a). Glutamate can be converted to 4-aminobutyrate by glutamate decarboxylase (EC 4.1.1.a).

Succinate semialdehyde can be converted to 4-hydroxybutyrate by 4-hydroxybutyrate dehydrogenase (EC 1.1.1.a), as previously described. 4-Hydroxybutyrate can be converted to 4-hydroxybutyryl-CoA by 4-hydroxybutyryl-CoA transferase (EC 2.8.3.a), as previously described, or by 4-hydroxybutyryl-CoA hydrolase (EC 3.1.2.a), or 4-hydroxybutyryl-CoA ligase (or 4-hydroxybutyryl-CoA synthetase) (EC 6.2.1.a). 4-Hydroxybutyrate can be converted to 4-hydroxybutyryl-phosphate by 4-hydroxybutyrate kinase (EC 2.7.2.a). 4-Hydroxybutyryl-phosphate can be converted to 4-hydroxybutyryl-CoA by phosphotrans-4-hydroxybutyrylase (EC 2.3.1.a), as previously described. Alternatively, 4-hydroxybutyryl-phosphate can be converted to 4-hydroxybutanal by 4-hydroxybutanal dehydrogenase (phosphorylating) (EC 1.2.1.d). 4-Hydroxybutyryl-CoA can be converted to 4-hydroxybutanal by 4-hydroxybutyryl-CoA reductase (or 4-hydroxybutanal dehydrogenase) (EC 1.2.1.b), as previously described. 4-Hydroxybutyryl-CoA can be converted to 1,4-butanediol by 4-hydroxybutyryl-CoA reductase (alcohol forming) (EC 1.1.1.c). 4-Hydroxybutanal can be converted to 1,4-butanediol by 1,4-butanediol dehydrogenase (EC 1.1.1.a), as previously described.

TABLE 16

BDO pathway from alpha-ketoglutarate.

| FIG. | EC class | Desired substrate | Desired product | Enzyme name | Gene name | GenBank ID (if available) | Organism | Known Substrates |
|---|---|---|---|---|---|---|---|---|
| 8B | 4.1.1.a | alpha-ketoglutarate | succinic semialdehyde | alpha-ketoglutarate decarboxylase | kgd | O50463.4 | Mycobacterium tuberculosis | alpha-ketoglutarate |
|  |  |  |  |  | gadA | NP_417974 | Escherichia coli | glutamate |
|  |  |  |  |  | gadB | NP_416010 | Escherichia coli | glutamate |
| 8B | 1.4.1.a | alpha-ketoglutarate | glutamate | glutamate dehydrogenase | gdhA | P00370 | Escherichia coli | glutamate |
|  |  |  |  |  | gdh | P96110.4 | Thermotoga maritima | glutamate |
|  |  |  |  |  | gdhA1 | NP_279651.1 | Halobacterium salinarum | glutamate |
| 8B | 1.4.1.a | 4-aminobutyrate | succinic semialdehyde | 4-aminobutyrate oxidoreductase (deaminating) | lysDH | AB052732 | Geobacillus stearothermophilus | lysine |
|  |  |  |  |  | lysDH | NP_147035.1 | Aeropyrum pernix K1 | lysine |
|  |  |  |  |  | ldh | P0A393 | Bacillus cereus | leucine, isoleucine, valine, 2-aminobutanoate |
| 8B | 2.6.1.a | 4-aminobutyrate | succinic semialdehyde | 4-aminobutyrate transaminase | gabT | P22256.1 | Escherichia coli | 4-aminobutyrate |
|  |  |  |  |  | puuE | NP_415818.1 | Escherichia coli | 4-aminobutyryate |
|  |  |  |  |  | UGA1 | NP_011533.1 | Saccharomyces cerevisiae | 4-aminobutyryate |
| 8B | 4.1.1.a | glutamate | 4-aminobutyrate | glutamate decarboxylase | gadA | NP_417974 | Escherichia coli | glutamate |
|  |  |  |  |  | gadB | NP_416010 | Escherichia coli | glutamate |
|  |  |  |  |  | kgd | O50463.4 | Mycobacterium tuberculosis | alpha-ketoglutarate |
| 8B | 1.1.1.a | succinate semialdehyde | 4-hydroxybutyrate | 4-hydroxybutyrate dehydrogenase | 4hbd | YP_726053.1 | Ralstonia eutropha H16 | 4-hydroxybutyrate |
|  |  |  |  |  | 4hbd | L21902.1 | Clostridium kluyveri DSM 555 | 4-hydroxybutyrate |
|  |  |  |  |  | 4hbd | Q94B07 | Arabidopsis thaliana | 4-hydroxybutyrate |
| 8B | 2.8.3.a | 4-hydroxybutyrate | 4-hydroxybutyryl-CoA | 4-hydroxybutyryl-CoA transferase | cat1, cat2, cat3 | P38946.1, P38942.2, EDK35586.1 | Clostridium kluyveri | succinate, 4-hydroxybutyrate, butyrate |
|  |  |  |  |  | gctA, gctB | CAA57199.1, CAA57200.1 | Acidaminococcus fermentans | glutarate |
|  |  |  |  |  | atoA, atoD | P76459.1, P76458.1 | Escherichia coli | butanoate |
| 8B | 3.1.2.a | 4-hydroxybutyrate | 4-hydroxybutyryl-CoA | 4-hydroxybutyryl-CoA hydrolase | tesB | NP_414986 | Escherichia coli | adipyl-CoA |
|  |  |  |  |  | acot12 | NP_570103.1 | Rattus norvegicus | butyryl-CoA |
|  |  |  |  |  | hibch | Q6NVY1.2 | Homo sapiens | 3-hydroxy-propanoyl-CoA |
| 8B | 6.2.1.a | 4-hydroxybutyrate | 4-hydroxybutyryl-CoA | 4-hydroxybutyryl-CoA ligase (or 4-hydroxybutyryl-CoA synthetase) | sucCD | NP_415256.1, AAC73823.1 | Escherichia coli | succinate |
|  |  |  |  |  | phl | CAJ15517.1 | Penicillium chrysogenum | phenylacetate |
|  |  |  |  |  | bioW | NP_390902.2 | Bacillus subtilis | 6-carboxyhexanoate |

TABLE 16-continued

BDO pathway from alpha-ketoglutarate.

| FIG. | EC class | Desired substrate | Desired product | Enzyme name | Gene name | GenBank ID (if available) | Organism | Known Substrates |
|---|---|---|---|---|---|---|---|---|
| 8B | 2.7.2.a | 4-hydroxybutyrate | 4-hydroxybutyryl-phosphate | 4-hydroxybutyrate kinase | ackA | NP_416799.1 | *Escherichia coli* | acetate, propionate |
| | | | | | buk1 | NP_349675 | *Clostridium acetobutylicum* | butyrate |
| | | | | | buk2 | Q97II1 | *Clostridium acetobutylicum* | butyrate |
| 8B | 2.3.1.a | 4-hydroxybutyryl-phosphate | 4-hydroxybutyryl-CoA | phosphotrans-4-hydroxybutyrylase | ptb | NP_349676 | *Clostridium acetobutylicum* | butyryl-phosphate |
| | | | | | ptb | AAR19757.1 | butyrate-producing bacterium L2-50 | butyryl-phosphate |
| | | | | | ptb | CAC07932.1 | *Bacillus megaterium* | butyryl-phosphate |
| 8B | 1.2.1.d | 4-hydroxybutyryl-phosphate | 4-hydroxybutanal | 4-hydroxybutanal dehydrogenase (phosphorylating) | asd | NP_417891.1 | *Escherichia coli* | L-4-aspartyl-phosphate |
| | | | | | proA | NP_414778.1 | *Escherichia coli* | L-glutamyl-5-phospate |
| | | | | | gapA | P0A9B2.2 | *Escherichia coli* | Glyceraldehyde-3-phosphate |
| 8B | 1.2.1.b | 4-hydroxybutyryl-CoA | 4-hydroxybutanal | 4-hydroxybutyryl-CoA reductase (or 4-hydroxybutanal dehydrogenase) | sucD | P38947.1 | *Clostridium kluyveri* | succinyl-CoA |
| | | | | | sucD | NP_904963.1 | *Porphyromonas gingivalis* | succinyl-CoA |
| | | | | | Msed_0709 | YP_001190808.1 | *Metallosphaera sedula* | malonyl-CoA |
| 8B | 1.1.1.c | 4-hydroxybutyryl-CoA | 1,4-butanediol | 4-hydroxybutyryl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |
| 8B | 1.1.1.a | 4-hydroxybutanal | 1,4-butanediol | 1,4-butanediol dehydrogenase | ADH2 | NP_014032.1 | *Saccharymyces cerevisiae* | general |
| | | | | | yqhD | NP_417484.1 | *Escherichia coli* | >C3 |
| | | | | | 4hbd | L21902.1 | *Clostridium kluyveri* DSM 555 | Succinate semialdehyde |

Example VII

BDO Pathways from 4-Aminobutyrate

This example describes exemplary BDO pathways from 4-aminobutyrate.

Figure 9A:
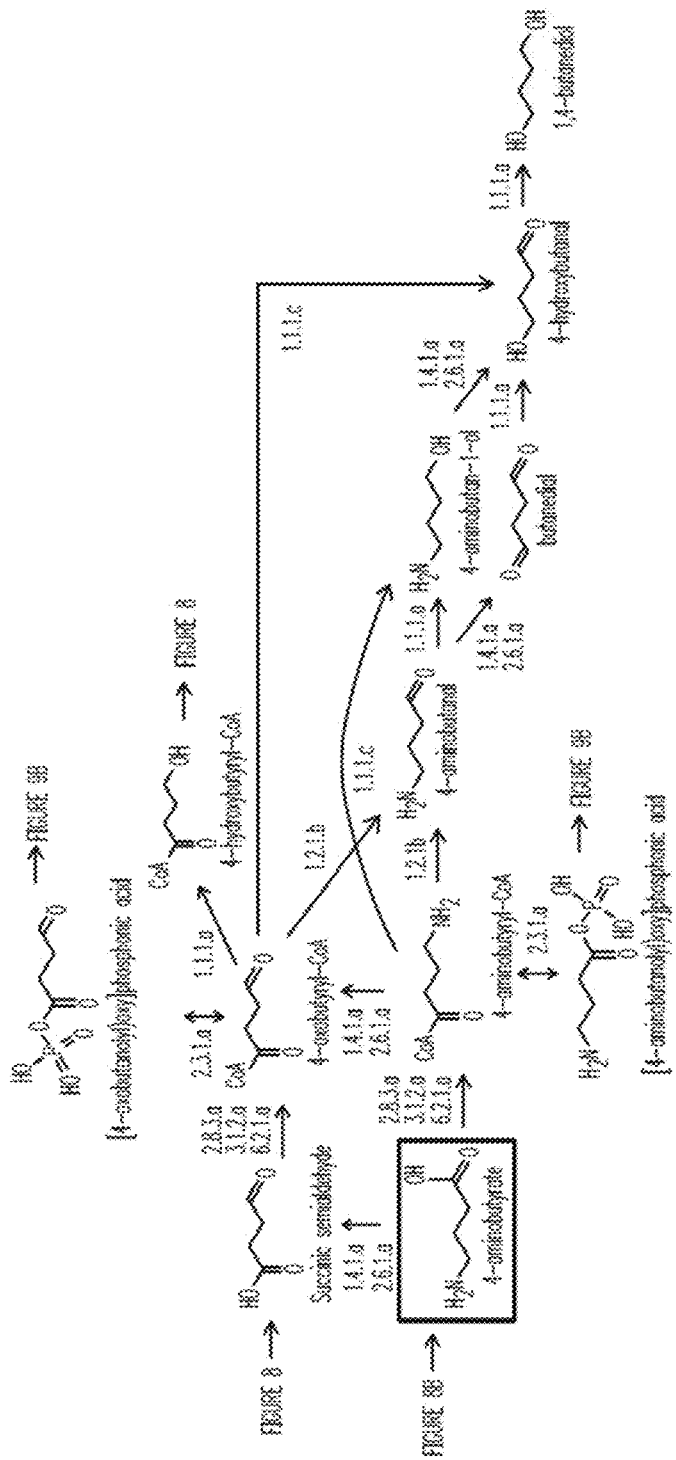

FIG. 9A depicts exemplary BDO pathways in which 4-aminobutyrate is converted to BDO. Enzymes of such an exemplary BDO pathway are listed in Table 17, along with exemplary genes encoding these enzymes.

Briefly, 4-aminobutyrate can be converted to 4-aminobutyryl-CoA by 4-aminobutyrate CoA transferase (EC 2.8.3.a), 4-aminobutyryl-CoA hydrolase (EC 3.1.2.a), or 4-aminobutyrate-CoA ligase (or 4-aminobutyryl-CoA synthetase) (EC 6.2.1.a). 4-aminobutyryl-CoA can be converted to 4-oxobutyryl-CoA by 4-aminobutyryl-CoA oxidoreductase (deaminating) (EC 1.4.1.a) or 4-aminobutyryl-CoA transaminase (EC 2.6.1.a). 4-oxobutyryl-CoA can be converted to 4-hydroxybutyryl-CoA by 4-hydroxybutyryl-CoA dehydrogenase (EC 1.1.1.a). 4-hydroxybutyryl-CoA can be converted to 1,4-butanediol by 4-hydroxybutyryl-CoA reductase (alcohol forming) (EC 1.1.1.c). Alternatively, 4-hydroxybutyryl-CoA can be converted to 4-hydroxybutanal by 4-hydroxybutyryl-CoA reductase (or 4-hydroxybutanal dehydrogenase) (EC 1.2.1.b). 4-hydroxybutanal can be converted to 1,4-butanediol by 1,4-butanediol dehydrogenase (EC 1.1.1.a).

TABLE 17

BDO pathway from 4-aminobutyrate.

| FIG. | EC class | Desired substrate | Desired product | Enzyme name | Gene name |
|---|---|---|---|---|---|
| 9A | 2.8.3.a | 4-aminobutyrate | 4-aminobutyryl-CoA | 4-aminobutyrate CoA transferase | cat1, cat2, cat3 |
| | | | | | gctA, gctB |
| | | | | | atoA, atoD |

TABLE 17-continued

| | | | BDO pathway from 4-aminobutyrate. | | |
|---|---|---|---|---|---|
| 9A | 3.1.2.a | 4-aminobutyrate | 4-aminobutyryl-CoA | 4-aminobutyryl-CoA hydrolase | tesB |
| | | | | | acot12 |
| | | | | | hibch |
| 9A | 6.2.1.a | 4-aminobutyrate | 4-aminobutyryl-CoA | 4-aminobutyrate-CoA ligase (or 4-aminobutyryl-CoA synthetase) | sucCD |
| | | | | | phl |
| | | | | | bioW |
| 9A | 1.4.1.a | 4-aminobutyryl-CoA | 4-oxobutyryl-CoA | 4-aminobutyryl-CoA oxidoreductase (deaminating) | lysDH |
| | | | | | lysDH |
| | | | | | ldh |
| 9A | 2.6.1.a | 4-aminobutyryl-CoA | 4-oxobutyryl-CoA | 4-aminobutyryl-CoA transaminase | gabT |
| | | | | | abat |
| | | | | | SkyPYD4 |
| 9A | 1.1.1.a | 4-oxobutyryl-CoA | 4-hydroxybutyryl-CoA | 4-hydroxybutyryl-CoA dehydrogenase | ADH2 |
| | | | | | yqhD |
| | | | | | 4hbd |
| 8 | 1.1.1.c | 4-hydroxybutyryl-CoA | 1,4-butanediol | 4-hydroxybutyryl-CoA reductase (alcohol forming) | adhE2 |
| | | | | | mcr |
| | | | | | FAR |
| 8 | 1.2.1.b | 4-hydroxybutyryl-CoA | 4-hydroxybutanal | 4-hydroxybutyryl-CoA reductase (or 4-hydroxybutanal dehydrogenase) | sucD |
| | | | | | sucD |
| | | | | | Msed_0709 |
| 8 | 1.1.1.a | 4-hydroxybutanal | 1,4-butanediol | 1,4-butanediol dehydrogenase | ADH2 |
| | | | | | yqhD |
| | | | | | 4hbd |

| FIG. | EC class | GenBank ID (if available) | Organism | Known Substrates |
|---|---|---|---|---|
| 9A | 2.8.3.a | P38946.1, P38942.2, EDK35586.1 | *Clostridium kluyveri* | succinate, 4-hydroxybutyrate, butyrate |
| | | CAA57199.1, CAA57200.1 | *Acidaminococcus fermentans* | glutarate |
| | | P76459.1, P76458.1 | *Escherichia coli* | butanoate |
| 9A | 3.1.2.a | NP_414986 | *Escherichia coli* | adipyl-CoA |
| | | NP_570103.1 | *Rattus norvegicus* | butyryl-CoA |
| | | Q6NVY1.2 | *Homo sapiens* | 3-hydroxypropanoyl-CoA |
| 9A | 6.2.1.a | NP_415256.1, AAC73823.1 | *Escherichia coli* | succinate |
| | | CAJ15517.1 | *Penicillium chrysogenum* | phenylacetate |
| | | NP_390902.2 | *Bacillus subtilis* | 6-carboxyhexanoate |
| 9A | 1.4.1.a | AB052732 | *Geobacillus stearothermophilus* | lysine |
| | | NP_147035.1 | *Aeropyrum pernix* K1 | lysine |
| | | P0A393 | *Bacillus cereus* | leucine, isoleucine, valine, 2-aminobutanoate |
| 9A | 2.6.1.a | P22256.1 | *Escherichia coli* | 4-aminobutyryate |
| | | P50554.3 | *Rattus norvegicus* | 3-amino-2-methylpropionate |
| | | ABF58893.1 | *Saccharomyces kluyveri* | beta-alanine |
| 9A | 1.1.1.a | NP_014032.1 | *Saccharymoyces cerevisiae* | general |
| | | NP_417484.1 | *Escherichia coli* | >C3 |
| | | L21902.1 | *Clostridium kluyveri* DSM 555 | Succinate semialdehyde |

TABLE 17-continued

| | | | BDO pathway from 4-aminobutyrate. | |
|---|---|---|---|---|
| 8 | 1.1.1.c | AAK09379.1 | *Clostridium acetobutylicum* | butanoyl-CoA |
| | | AAS20429.1 | *Chloroflexus aurantiacus* | malonyl-CoA |
| | | AAD38039.1 | *Simmondsia chinensis* | long chain acyl-CoA |
| 8 | 1.2.1.b | P38947.1 | *Clostridium kluyveri* | Succinyl-CoA |
| | | NP_904963.1 | *Porphyromonas gingivalis* | Succinyl-CoA |
| | | YP_001190808.1 | *Metallosphaera sedula* | Malonyl-CoA |
| 8 | 1.1.1.a | NP_014032.1 | *Saccharymyces cerevisiae* | general |
| | | NP_417484.1 | *Escherichia coli* | >C3 |
| | | L21902.1 | *Clostridium kluyveri* DSM 555 | Succinate semialdehyde |

Enzymes for another exemplary BDO pathway converting 4-aminobutyrate to BDO is shown in FIG. 9A. Enzymes of such an exemplary BDO pathway are listed in Table 18, along with exemplary genes encoding these enzymes.

Briefly, 4-aminobutyrate can be converted to 4-aminobutyryl-CoA by 4-aminobutyrate CoA transferase (EC 2.8.3.a), 4-aminobutyryl-CoA hydrolase (EC 3.1.2.a) or 4-aminobutyrate-CoA ligase (or 4-aminobutyryl-CoA synthetase) (EC 6.2.1.a). 4-aminobutyryl-CoA can be converted to 4-aminobutan-1-ol by 4-aminobutyryl-CoA reductase (alcohol forming) (EC 1.1.1.c). Alternatively, 4-aminobutyryl-CoA can be converted to 4-aminobutanal by 4-aminobutyryl-CoA reductase (or 4-aminobutanal dehydrogenase) (EC 1.2.1.b), and 4-aminobutanal converted to 4-aminobutan-1-ol by 4-aminobutan-1-ol dehydrogenase (EC 1.1.1.a). 4-aminobutan-1-ol can be converted to 4-hydroxybutanal by 4-aminobutan-1-ol oxidoreductase (deaminating) (EC 1.4.1.a) or 4-aminobutan-1-ol transaminase (EC 2.6.1.a). 4-hydroxybutanal can be converted to 1,4-butanediol by 1,4-butanediol dehydrogenase (EC 1.1.1.a).

TABLE 18

| | | | BDO pathway from 4-aminobutyrate. | | | | |
|---|---|---|---|---|---|---|---|
| FIG. | EC class | Desired substrate | Desired product | Enzyme name | Gene name | GenBank ID (if available) | Organism | Known Substrate |
| 9A | 2.8.3.a | 4-aminobutyrate | 4-aminobutyryl-CoA | 4-aminobutyrate CoA transferase | cat1, cat2, cat3 | P38946.1, P38942.2, EDK35586.1 | *Clostridium kluyveri* | succinate, 4-hydroxybutyrate, butyrate |
| | | | | | gctA, gctB | CAA57199.1, CAA57200.1 | *Acidaminococcus fermentans* | glutarate |
| | | | | | atoA, atoD | P76459.1, P76458.1 | *Escherichia coli* | butanoate |
| 9A | 3.1.2.a | 4-aminobutyrate | 4-aminobutyryl-CoA | 4-aminobutyryl-CoA hydrolase | tesB | NP_414986 | *Escherichia coli* | adipyl-CoA |
| | | | | | acot12 | NP_570103.1 | *Rattus norvegicus* | butyryl-CoA |
| | | | | | hibch | Q6NVY1.2 | *Homo sapiens* | 3-hydroxypropanoyl-CoA |
| 9A | 6.2.1.a | 4-aminobutyrate | 4-aminobutyryl-CoA | 4-aminobutyrate-CoA ligase (or 4-aminobutyryl-CoA synthetase) | sucCD | NP_415256.1, AAC73823.1 | *Escherichia coli* | succinate |
| | | | | | phl | CAJ15517.1 | *Penicillium chrysogenum* | phenylacetate |
| | | | | | bioW | NP_390902.2 | *Bacillus subtilis* | 6-carboxyhexanoate |
| 9A | 1.1.1.c | 4-aminobutyryl-CoA | 4-aminobutan-1-ol | 4-aminobutyryl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |
| 9A | 1.2.1.b | 4-aminobutyryl-CoA | 4-aminobutanal | 4-aminobutyryl-CoA reductase (or 4-aminobutanal dehydrogenase) | sucD | P38947.1 | *Clostridium kluyveri* | Succinyl-CoA |
| | | | | | sucD | NP_904963.1 | *Porphyromonas gingivalis* | Succinyl-CoA |
| | | | | | Msed_0709 | YP_001190808.1 | *Metallosphaera sedula* | Malonyl-CoA |

TABLE 18-continued

BDO pathway from 4-aminobutyrate.

| FIG. | EC class | Desired substrate | Desired product | Enzyme name | Gene name | GenBank ID (if available) | Organism | Known Substrate |
|---|---|---|---|---|---|---|---|---|
| 9A | 1.1.1.a | 4-aminobutanal | 4-aminobutan-1-ol | 4-aminobutan-1-ol dehydrogenase | ADH2 | NP_014032.1 | Saccharymyces cerevisiae | general |
|  |  |  |  |  | yqhD | NP_417484.1 | Escherichia coli | >C3 |
|  |  |  |  |  | 4hbd | L21902.1 | Clostridium kluyveri DSM 555 | Succinate semialdehyde |
| 9A | 1.4.1.a | 4-aminobutan-1-ol | 4-hydroxybutanal | 4-aminobutan-1-ol oxidoreductase (deaminating) | lysDH | AB052732 | Geobacillus stearothermophilus | lysine |
|  |  |  |  |  | lysDH | NP_147035.1 | Aeropyrum pernix K1 | lysine |
|  |  |  |  |  | ldh | P0A393 | Bacillus cereus | leucine, isoleucine, valine, 2-aminobutanoate |
| 9A | 2.6.1.a | 4-aminobutan-1-ol | 4-hydroxybutanal | 4-aminobutan-1-ol transaminase | gabT | P22256.1 | Escherichia coli | 4-aminobutyryate |
|  |  |  |  |  | abat | P50554.3 | Rattus norvegicus | 3-amino-2-methylpropionate |
|  |  |  |  |  | SkyPYD4 | ABF58893.1 | Saccharomyces kluyveri | beta-alanine |
| 9A | 1.1.1.a | 4-hydroxybutanal | 1,4-butanediol | 1,4-butanediol dehydrogenase | ADH2 | NP_014032.1 | Saccharymyces cerevisiae | general |
|  |  |  |  |  | yqhD | NP_417484.1 | Escherichia coli | >C3 |
|  |  |  |  |  | 4hbd | L21902.1 | Clostridium kluyveri DSM 555 | Succinate semialdehyde |

FIG. 9B depicts exemplary BDO pathway in which 4-aminobutyrate is converted to BDO. Enzymes of such an exemplary BDO pathway are listed in Table 19, along with exemplary genes encoding these enzymes.

Briefly, 4-aminobutyrate can be converted to [(4-aminobutanolyl)oxy] phosphonic acid by 4-aminobutyrate kinase (EC 2.7.2.a). [(4-aminobutanolyl)oxy] phosphonic acid can be converted to 4-aminobutanal by 4-aminobutyraldehyde dehydrogenase (phosphorylating) (EC 1.2.1.d). 4-aminobutanal can be converted to 4-aminobutan-1-ol by 4-aminobutan-1-ol dehydrogenase (EC 1.1.1.a). 4-aminobutan-1-ol can be converted to 4-hydroxybutanal by 4-aminobutan-1-ol oxidoreductase (deaminating) (EC 1.4.1.a) or 4-aminobutan-1-ol transaminase (EC 2.6.1.a). Alternatively, [(4-aminobutanolyl)oxy] phosphonic acid can be converted to [(4-oxobutanolyl)oxy] phosphonic acid by [(4-aminobutanolyl)oxy]phosphonic acid oxidoreductase (deaminating) (EC 1.4.1.a) or [(4-aminobutanolyl)oxy]phosphonic acid transaminase (EC 2.6.1.a). [(4-oxobutanolyl)oxy] phosphonic acid can be converted to 4-hydroxybutyryl-phosphate by 4-hydroxybutyryl-phosphate dehydrogenase (EC 1.1.1.a). 4-hydroxybutyryl-phosphate can be converted to 4-hydroxybutanal by 4-hydroxybutyraldehyde dehydrogenase (phosphorylating) (EC 1.2.1.d). 4-hydroxybutanal can be converted to 1,4-butanediol by 1,4-butanediol dehydrogenase (EC 1.1.1.a).

TABLE 19

BDO pathway from 4-aminobutyrate.

| FIG. | EC class | Desired substrate | Desired product | Enzyme name | Gene name |
|---|---|---|---|---|---|
| 9B | 2.7.2.a | 4-aminobutyrate | [(4-aminobutanolyl)oxy] phosphonic acid | 4-aminobutyrate kinase | ackA |
|  |  |  |  |  | buk1 |
|  |  |  |  |  | proB |
| 9B | 1.2.1.d | [(4-aminobutanolyl)oxy] phosphonic acid | 4-aminobutanal | 4-aminobutyraldehyde dehydrogenase (phosphorylating) | asd |
|  |  |  |  |  | proA |
|  |  |  |  |  | gapA |
| 9B | 1.1.1.a | 4-aminobutanal | 4-aminobutan-1-ol | 4-aminobutan-1-ol dehydrogenase | ADH2 |
|  |  |  |  |  | yqhD |
|  |  |  |  |  | 4hbd |
| 9B | 1.4.1.a | 4-aminobutan-1-ol | 4-hydroxybutanal | 4-aminobutan-1-ol oxidoreductase (deaminating) | lysDH |
|  |  |  |  |  | lysDH |
|  |  |  |  |  | ldh |

TABLE 19-continued

| | | | | | |
|---|---|---|---|---|---|
| \multicolumn{6}{l}{BDO pathway from 4-aminobutyrate.} |
| 9B | 2.6.1.a | 4-aminobutan-1-ol | 4-hydroxybutanal | 4-aminobutan-1-ol transaminase | gabT |
| | | | | | abat |
| | | | | | SkyPYD4 |
| 9B | 1.4.1.a | [(4-aminobutanolyl)oxy] phosphonic acid | [(4-oxobutanolyl)oxy] phosphonic acid | [(4-aminobutanolyl)oxy]phosphonic acid oxidoreductase (deaminating) | lysDH |
| | | | | | lysDH |
| | | | | | ldh |
| 9B | 2.6.1.a | [(4-aminobutanolyl)oxy] phosphonic acid | [(4-oxobutanolyl)oxy] phosphonic acid | [(4-aminobutanolyl)oxy]phosphonic acid transaminase | gabT |
| | | | | | SkyPYD4 |
| | | | | | serC |
| 9B | 1.1.1.a | [(4-oxobutanolyl)oxy] phosphonic acid | 4-hydroxybutyryl-phosphate | 4-hydroxybutyryl-phosphate dehydrogenase | ADH2 |
| | | | | | yqhD |
| | | | | | 4hbd |
| 9B | 1.2.1.d | 4-hydroxybutyryl-phosphate | 4-hydroxybutanal | 4-hydroxybutyraldehyde dehydrogenase (phosphorylating) | asd |
| | | | | | proA |
| | | | | | gapA |
| 9B | 1.1.1.a | 4-hydroxybutanal | 1,4-butanediol | 1,4-butanediol dehydrogenase | ADH2 |
| | | | | | yqhD |
| | | | | | 4hbd |

| FIG. | EC class | GenBank ID (if available) | Organism | Known Substrate |
|---|---|---|---|---|
| 9B | 2.7.2.a | NP_416799.1 | Escherichia coli | acetate, propionate |
| | | NP_349675 | Clostridium acetobutylicum | butyrate |
| | | NP_414777.1 | Escherichia coli | glutamate |
| 9B | 1.2.1.d | NP_417891.1 | Escherichia coli | L-4-aspartyl-phosphate |
| | | NP_414778.1 | Escherichia coli | L-glutamyl-5-phospate |
| | | P0A9B2.2 | Escherichia coli | Glyceraldehyde-3-phosphate |
| 9B | 1.1.1.a | NP_014032.1 | Saccharymyces cerevisiae | general |
| | | NP_417484.1 | Escherichia coli | >C3 |
| | | L21902.1 | Clostridium kluyveri DSM 555 | Succinate semialdehyde |
| 9B | 1.4.1.a | AB052732 | Geobacillus stearothermophilus | lysine |
| | | NP_147035.1 | Aeropyrum pernix K1 | lysine |
| | | P0A393 | Bacillus cereus | leucine, isoleucine, valine, 2-aminobutanoate |
| 9B | 2.6.1.a | P22256.1 | Escherichia coli | 4-aminobutyryate |
| | | P50554.3 | Rattus norvegicus | 3-amino-2-methylpropionate |
| | | ABF58893.1 | Saccharomyces kluyveri | beta-alanine |
| 9B | 1.4.1.a | AB052732 | Geobacillus stearothermophilus | lysine |
| | | NP_147035.1 | Aeropyrum pernix K1 | lysine |
| | | P0A393 | Bacillus cereus | leucine, isoleucine, valine, 2-aminobutanoate |
| 9B | 2.6.1.a | P22256.1 | Escherichia coli | 4-aminobutyryate |
| | | ABF58893.1 | Saccharomyces kluyveri | beta-alanine |
| | | NP_415427.1 | Escherichia coli | phosphoserine, phosphohydroxythreonine |

TABLE 19-continued

| | | | BDO pathway from 4-aminobutyrate. | |
|---|---|---|---|---|
| 9B | 1.1.1.a | NP_014032.1 | *Saccharymyces cerevisiae* | general |
| | | NP_417484.1 | *Escherichia coli* | >C3 |
| | | L21902.1 | *Clostridium kluyveri* DSM 555 | Succinate semialdehyde |
| 9B | 1.2.1.d | NP_417891.1 | *Escherichia coli* | L-4-aspartyl-phosphate |
| | | NP_414778.1 | *Escherichia coli* | L-glutamyl-5-phospate |
| | | P0A9B2.2 | *Escherichia coli* | Glyceraldehyde-3-phosphate |
| 9B | 1.1.1.a | NP_014032.1 | *Saccharymyces cerevisiae* | general |
| | | NP_417484.1 | *Escherichia coli* | >C3 |
| | | L21902.1 | *Clostridium kluyveri* DSM 555 | Succinate semialdehyde |

FIG. 9C shows an exemplary pathway through acetoacetate.

Example VIII

Exemplary BDO Pathways from Alpha-Ketoglutarate

This example describes exemplary BDO pathways from alpha-ketoglutarate.

Figure 10:
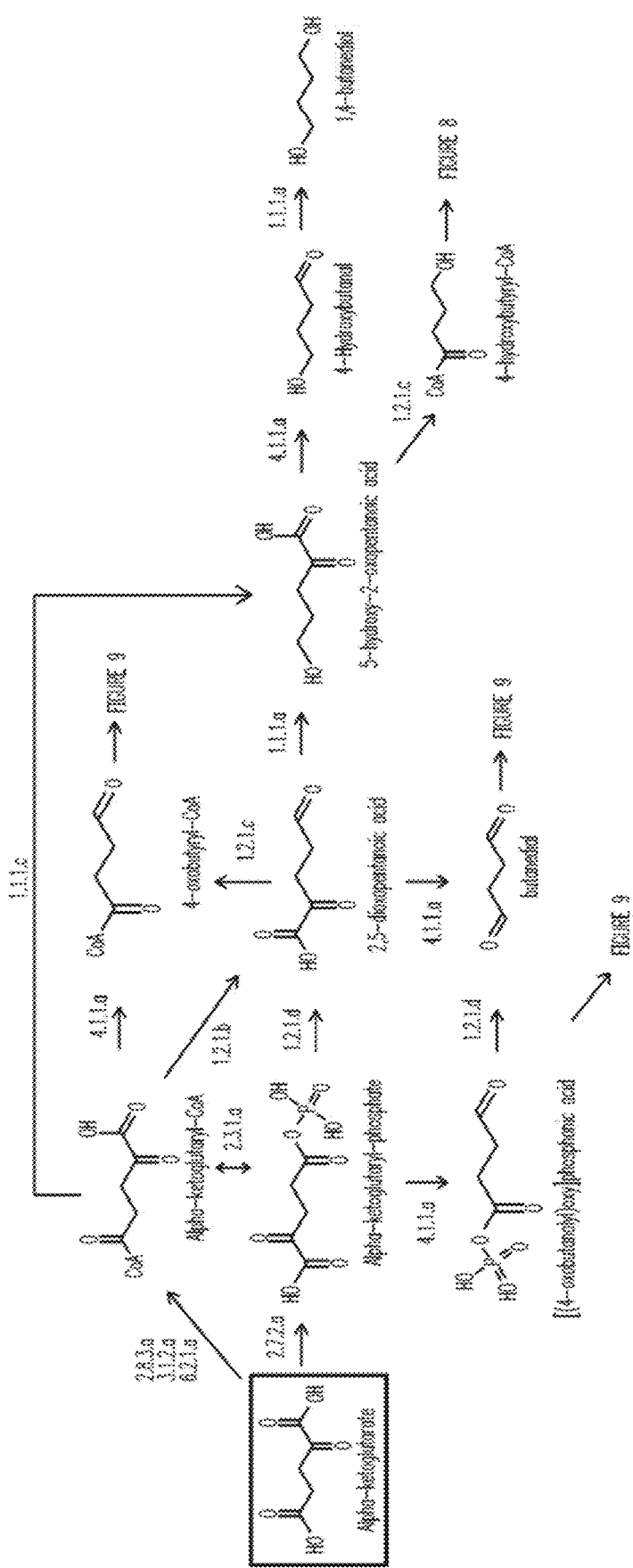
FIG. 10 shows exemplary BDO pathways from alpha-ketoglutarate.

FIG. 10 depicts exemplary BDO pathways in which alpha-ketoglutarate is converted to BDO. Enzymes of such an exemplary BDO pathway are listed in Table 20, along with exemplary genes encoding these enzymes.

Briefly, alpha-ketoglutarate can be converted to alpha-ketoglutaryl-phosphate by alpha-ketoglutarate 5-kinase (EC 2.7.2.a). Alpha-ketoglutaryl-phosphate can be converted to 2,5-dioxopentanoic acid by 2,5-dioxopentanoic semialdehyde dehydrogenase (phosphorylating) (EC 1.2.1.d). 2,5-dioxopentanoic acid can be converted to 5-hydroxy-2-oxopentanoic acid by 2,5-dioxopentanoic acid reductase (EC 1.1.1.a). Alternatively, alpha-ketoglutarate can be converted to alpha-ketoglutaryl-CoA by alpha-ketoglutarate CoA transferase (EC 2.8.3.a), alpha-ketoglutaryl-CoA hydrolase (EC 3.1.2.a) or alpha-ketoglutaryl-CoA ligase (or alpha-ketoglutaryl-CoA synthetase) (EC 6.2.1.a). Alpha-ketoglutaryl-CoA can be converted to 2,5-dioxopentanoic acid by alpha-ketoglutaryl-CoA reductase (or 2,5-dioxopentanoic acid dehydrogenase) (EC 1.2.1.b). 2,5-Dioxopentanoic acid can be converted to 5-hydroxy-2-oxopentanoic acid by 5-hydroxy-2-oxopentanoic acid dehydrogenase. Alternatively, alpha-ketoglutaryl-CoA can be converted to 5-hydroxy-2-oxopentanoic acid by alpha-ketoglutaryl-CoA reductase (alcohol forming) (EC 1.1.1.c). 5-hydroxy-2-oxopentanoic acid can be converted to 4-hydroxybutanal by 5-hydroxy-2-oxopentanoic acid decarboxylase (EC 4.1.1.a). 4-hydroxybutanal can be converted to 1,4-butanediol by 1,4-butanediol dehydrogenase (EC 1.1.1.a). 5-hydroxy-2-oxopentanoic acid can be converted to 4-hydroxybutyryl-CoA by 5-hydroxy-2-oxopentanoic acid dehydrogenase (decarboxylation) (EC 1.2.1.c).

TABLE 20

| | | | BDO pathway from alpha-ketoglutarate. | | |
|---|---|---|---|---|---|
| FIG. | EC class | Desired substrate | Desired product | Enzyme name | Gene name | GenBank ID (if available) |
| 10 | 2.7.2.a | alpha-ketoglutarate | alpha-ketoglutaryl-phosphate | alpha-ketoglutarate 5-kinase | ackA | NP_416799.1 |
| | | | | | buk1 | NP_349675 |
| | | | | | proB | NP_414777.1 |
| 10 | 1.2.1.d | alpha-ketoglutaryl-phosphate | 2,5-dioxopentanoic acid | 2,5-dioxopentanoic semialdehyde dehydrogenase (phosphorylating) | proA | NP_414778.1 |
| | | | | | asd | NP_417891.1 |
| | | | | | gapA | P0A9B2.2 |
| 10 | 1.1.1.a | 2,5-dioxopentanoic acid | 5-hydroxy-2-oxopentanoic acid | 2,5-dioxopentanoic acid reductase | ADH2 | NP_014032.1 |
| | | | | | yqhD | NP_417484.1 |
| | | | | | 4hbd | L21902.1 |
| 10 | 2.8.3.a | alpha-ketoglutarate | alpha-ketoglutaryl-CoA | alpha-ketoglutarate CoA transferase | cat1, cat2, cat3 | P38946.1, P38942.2, EDK35586.1 |
| | | | | | gctA, gctB | CAA57199.1, CAA57200.1 |
| | | | | | atoA, atoD | P76459.1, P76458.1 |

TABLE 20-continued

BDO pathway from alpha-ketoglutarate.

| | | | | | | |
|---|---|---|---|---|---|---|
| 10 | 3.1.2.a | alpha-ketoglutarate | alpha-ketoglutaryl-CoA | alpha-ketoglutaryl-CoA hydrolase | tesB | NP_414986 |
| | | | | | acot12 | NP_570103.1 |
| | | | | | hibch | Q6NVY1.2 |
| 10 | 6.2.1.a | alpha-ketoglutarate | alpha-ketoglutaryl-CoA | alpha-ketoglutaryl-CoA ligase (or alpha-ketoglutaryl-CoA synthetase) | sucCD | NP_415256.1, AAC73823.1 |
| | | | | | phl | CAJ15517.1 |
| | | | | | bioW | NP_390902.2 |
| 10 | 1.2.1.b | alpha-ketoglutaryl-CoA | 2,5-dioxopentanoic acid | alpha-ketoglutaryl-CoA reductase (or 2,5-dioxopentanoic acid dehydrogenase) | sucD | P38947.1 |
| | | | | | Msed_0709 | YP_001190808.1 |
| | | | | | bphG | BAA03892.1 |
| 10 | 1.1.1.a | 2,5-dioxopentanoic acid | 5-hydroxy-2-oxopentanoic acid | 5-hydroxy-2-oxopentanoic acid dehydrogenase | ADH2 | NP_014032.1 |
| | | | | | yqhD | NP_417484.1 |
| | | | | | 4hbd | L21902.1 |
| 10 | 1.1.1.c | alpha-ketoglutaryl-CoA | 5-hydroxy-2-oxopentanoic acid | alpha-ketoglutaryl-CoA reductase (alcohol forming) | adhE2 | AAK09379.1 |
| | | | | | mcr | AAS20429.1 |
| | | | | | FAR | AAD38039.1 |
| 10 | 4.1.1.a | 5-hydroxy-2-oxopentanoic acid | 4-hydroxybutanal | 5-hydroxy-2-oxopentanoic acid decarboxylase | pdc | P06672.1 |
| | | | | | mdlC | P20906.2 |
| | | | | | pdc1 | P06169 |
| 10 | 1.1.1.a | 4-hydroxybutanal | 1,4-butanediol | 1,4-butanediol dehydrogenase | ADH2 | NP_014032.1 |
| | | | | | yqhD | NP_417484.1 |
| | | | | | 4hbd | L21902.1 |
| 10 | 1.2.1.c | 5-hydroxy-2-oxopentanoic acid | 4-hydroxybutyryl-CoA | 5-hydroxy-2-oxopentanoic acid dehydrogenase (decarboxylation) | sucA, sucB, lpd | NP_415254.1, NP_415255.1, NP_414658.1 |
| | | | | | bfmBB, bfmBAA, bfmBAB, bfmBAB, pdhD | NP_390283.1, NP_390285.1, NP_390284.1, P21880.1 |
| | | | | | Bckdha, Bckdhb, Dbt, Dld | NP_036914.1, NP_062140.1, NP_445764.1, NP_955417.1 |

| FIG. | EC class | Organism | Known Substrate |
|---|---|---|---|
| 10 | 2.7.2.a | Escherichia coli | acetate, propionate |
| | | Clostridium acetobutylicum | butyrate |
| | | Escherichia coli | glutamate |
| 10 | 1.2.1.d | Escherichia coli | L-glutamyl-5-phospate |
| | | Escherichia coli | L-4-aspartyl-phosphate |
| | | Escherichia coli | Glyceraldehyde-3-phosphate |
| 10 | 1.1.1.a | Saccharymyces cerevisiae | general |
| | | Escherichia coli | >C3 |
| | | Clostridium kluyveri DSM 555 | Succinate semialdehyde |
| 10 | 2.8.3.a | Clostridium kluyveri | succinate, 4-hydroxybutyrate, butyrate |
| | | Acidaminococcus fermentans | glutarate |
| | | Escherichia coli | butanoate |

TABLE 20-continued

BDO pathway from alpha-ketoglutarate.

| | | | |
|---|---|---|---|
| 10 | 3.1.2.a | *Escherichia coli*<br>*Rattus norvegicus*<br>*Homo sapiens* | adipyl-CoA<br>butyryl-CoA<br>3-hydroxypropanoyl-CoA |
| 10 | 6.2.1.a | *Escherichia coli*<br>*Penicillium chrysogenum*<br>*Bacillus subtilis* | succinate<br>phenylacetate<br>6-carboxyhexanoate |
| 10 | 1.2.1.b | *Clostridium kluyveri*<br>*Metallosphaera sedula*<br>*Pseudomonas* sp | Succinyl-CoA<br>Malonyl-CoA<br>Acetaldehyde,<br>Propionaldehyde,<br>Butyraldehyde,<br>Isobutyraldehyde and<br>Formaldehyde |
| 10 | 1.1.1.a | *Saccharymyces cerevisiae*<br>*Escherichia coli*<br>*Clostridium kluyveri* DSM 555 | general<br>>C3<br>Succinate semialdehyde |
| 10 | 1.1.1.c | *Clostridium acetobutylicum*<br>*Chloroflexus aurantiacus*<br>*Simmondsia chinensis* | butanoyl-CoA<br>malonyl-CoA<br>long chain acyl-CoA |
| 10 | 4.1.1.a | *Zymomonas mobilus*<br>*Pseudomonas putida*<br>*Saccharomyces cerevisiae* | 2-oxopentanoic acid<br>2-oxopentanoic acid<br>pyruvate |
| 10 | 1.1.1.a | *Saccharymyces cerevisiae*<br>*Escherichia coli*<br>*Clostridium kluyveri* DSM 555 | general<br>>C3<br>Succinate semialdehyde |
| 10 | 1.2.1.c | *Escherichia coli*<br>*Bacillus subtilis*<br><br>*Rattus norvegicus* | Alpha-ketoglutarate<br>2-keto acids derivatives of valine, leucine and isoleucine<br>2-keto acids derivatives of valine, leucine and isoleucine |

Example IX

Exemplary BDO Pathways from Glutamate

This example describes exemplary BDO pathways from glutamate.

FIG. 11 depicts exemplary BDO pathways in which glutamate is converted to BDO. Enzymes of such an exemplary BDO pathway are listed in Table 21, along with exemplary genes encoding these enzymes.

Briefly, glutamate can be converted to glutamyl-CoA by glutamate CoA transferase (EC 2.8.3.a), glutamyl-CoA hydrolase (EC 3.1.2.a) or glutamyl-CoA ligase (or glutamyl-CoA synthetase) (EC 6.2.1.a). Alternatively, glutamate can be converted to glutamate-5-phosphate by glutamate 5-kinase (EC 2.7.2.a). Glutamate-5-phosphate can be converted to glutamate-5-semialdehyde by glutamate-5-semialdehyde dehydrogenase (phosphorylating) (EC 1.2.1.d). Glutamyl-CoA can be converted to glutamate-5-semialdehyde by glutamyl-CoA reductase (or glutamate-5-semialdehyde dehydrogenase) (EC 1.2.1.b). Glutamate-5-semialdehyde can be converted to 2-amino-5-hydroxypentanoic acid by glutamate-5-semialdehyde reductase (EC 1.1.1.a). Alternatively, glutamyl-CoA can be converted to 2-amino-5-hydroxypentanoic acid by glutamyl-CoA reductase (alcohol forming) (EC 1.1.1.c). 2-Amino-5-hydroxypentanoic acid can be converted to 5-hydroxy-2-oxopentanoic acid by 2-amino-5-hydroxypentanoic acid oxidoreductase (deaminating) (EC 1.4.1.a) or 2-amino-5-hydroxypentanoic acid transaminase (EC 2.6.1.a). 5-Hydroxy-2-oxopentanoic acid can be converted to 4-hydroxybutanal by 5-hydroxy-2-oxopentanoic acid decarboxylase (EC 4.1.1.a). 4-Hydroxybutanal can be converted to 1,4-butanediol by 1,4-butanediol dehydrogenase (EC 1.1.1.a). Alternatively, 5-hydroxy-2-oxopentanoic acid can be converted to 4-hydroxybutyryl-CoA by 5-hydroxy-2-oxopentanoic acid dehydrogenase (decarboxylation) (EC 1.2.1.c).

TABLE 21

BDO pathway from glutamate.

| FIG. | EC class | Desired substrate | Desired product | Enzyme name | Gene name |
|---|---|---|---|---|---|
| 11 | 2.8.3.a | glutamate | glutamyl-CoA | glutamate CoA transferase | cat1, cat2, cat3<br><br>gctA, gctB<br>atoA, atoD |
| 11 | 3.1.2.a | glutamate | glutamyl-CoA | glutamyl-CoA hydrolase | tesB<br><br>acot12<br>hibch |

TABLE 21-continued

| | | | | | |
|---|---|---|---|---|---|
| | | | BDO pathway from glutamate. | | |
| 11 | 6.2.1.a | glutamate | glutamyl-CoA | glutamyl-CoA ligase (or glutamyl-CoA synthetase) | sucCD |
| | | | | | phl |
| | | | | | bioW |
| 11 | 2.7.2.a | glutamate | glutamate-5-phosphate | glutamate 5-kinase | ackA |
| | | | | | buk1 |
| | | | | | proB |
| 11 | 1.2.1.d | glutamate-5-phosphate | glutamate-5-semialdehyde | glutamate-5-semialdehyde dehydrogenase (phosphorylating) | proA |
| | | | | | asd |
| | | | | | gapA |
| 11 | 1.2.1.b | glutamyl-CoA | glutamate-5-semialdehyde | glutamyl-CoA reductase (or glutamate-5-semialdehyde dehydrogenase) | sucD |
| | | | | | Msed_0709 |
| | | | | | bphG |
| 11 | 1.1.1.a | glutamate-5-semialdehyde | 2-amino-5-hydroxypentanoic acid | glutamate-5-semialdehyde reductase | ADH2 |
| | | | | | yqhD |
| | | | | | 4hbd |
| 11 | 1.1.1.c | glutamyl-CoA | 2-amino-5-hydroxypentanoic acid | glutamyl-CoA reductase (alcohol forming) | adhE2 |
| | | | | | mcr |
| | | | | | FAR |
| 11 | 1.4.1.a | 2-amino-5-hydroxypentanoic acid | 5-hydroxy-2-oxopentanoic acid | 2-amino-5-hydroxypentanoic acid oxidoreductase (deaminating) | gdhA |
| | | | | | ldh |
| | | | | | nadX |
| 11 | 2.6.1.a | 2-amino-5-hydroxypentanoic acid | 5-hydroxy-2-oxopentanoic acid | 2-amino-5-hydroxypentanoic acid transaminase | aspC |
| | | | | | AAT2 |
| | | | | | avtA |
| 11 | 4.1.1.a | 5-hydroxy-2-oxopentanoic acid | 4-hydroxybutanal | 5-hydroxy-2-oxopentanoic acid decarboxylase | pdc |
| | | | | | mdlC |
| | | | | | pdc1 |
| 11 | 1.1.1.a | 4-hydroxybutanal | 1,4-butanediol | 1,4-butanediol dehydrogenase | ADH2 |
| | | | | | yqhD |
| | | | | | 4hbd |
| 11 | 1.2.1.c | 5-hydroxy-2-oxopentanoic acid | 4-hydroxybutyryl-CoA | 5-hydroxy-2-oxopentanoic acid dehydrogenase (decarboxylation) | sucA, sucB, lpd |
| | | | | | bfmBB, bfmBAA, bfmBAB, bfmBAB, pdhD Bckdha, Bckdhb, Dbt, Dld |

| FIG. | EC class | GenBank ID (if available) | Organism | Known Substrate |
|---|---|---|---|---|
| 11 | 2.8.3.a | P38946.1, P38942.2, EDK35586.1 | *Clostridium kluyveri* | succinate, 4-hydroxybutyrate, butyrate |
| | | CAA57199.1, CAA57200.1 | *Acidaminococcus fermentans* | glutarate |
| | | P76459.1, P76458.1 | *Escherichia coli* | butanoate |
| 11 | 3.1.2.a | NP_414986 | *Escherichia coli* | adipyl-CoA |
| | | NP_570103.1 | *Rattus norvegicus* | butyryl-CoA |
| | | Q6NVY1.2 | *Homo sapiens* | 3-hydroxypropanoyl-CoA |

TABLE 21-continued

| | | | | |
|---|---|---|---|---|
| | | BDO pathway from glutamate. | | |
| 11 | 6.2.1.a | NP_415256.1, AAC73823.1 | *Escherichia coli* | succinate |
| | | CAJ15517.1 | *Penicillium chrysogenum* | phenylacetate |
| | | NP_390902.2 | *Bacillus subtilis* | 6-carboxyhexanoate |
| 11 | 2.7.2.a | NP_416799.1 | *Escherichia coli* | acetate, propionate |
| | | NP_349675 | *Clostridium acetobutylicum* | butyrate |
| | | NP_414777.1 | *Escherichia coli* | glutamate |
| 11 | 1.2.1.d | NP_414778.1 | *Escherichia coli* | L-glutamyl-5-phospate |
| | | NP_417891.1 | *Escherichia coli* | L-4-aspartyl-phosphate |
| | | P0A9B2.2 | *Escherichia coli* | Glyceraldehyde-3-phosphate |
| 11 | 1.2.1.b | P38947.1 | *Clostridium kluyveri* | Succinyl-CoA |
| | | YP_001190808.1 | *Metallosphaera sedula* | Malonyl-CoA |
| | | BAA03892.1 | *Pseudomonas* sp | Acetaldehyde, Propionaldehyde, Butyraldehyde, Isobutyraldehyde and Formaldehyde |
| 11 | 1.1.1.a | NP_014032.1 | *Saccharymyces cerevisiae* | general |
| | | NP_417484.1 | *Escherichia coli* | >C3 |
| | | L21902.1 | *Clostridium kluyveri* DSM 555 | Succinate semialdehyde |
| 11 | 1.1.1.c | AAK09379.1 | *Clostridium acetobutylicum* | butanoyl-CoA |
| | | AAS20429.1 | *Chloroflexus aurantiacus* | malonyl-CoA |
| | | AAD38039.1 | *Simmondsia chinensis* | long chain acyl-CoA |
| 11 | 1.4.1.a | P00370 | *Escherichia coli* | glutamate |
| | | P0A393 | *Bacillus cereus* | leucine, isoleucine, valine, 2-aminobutanoate |
| | | NP_229443.1 | *Thermotoga maritima* | aspartate |
| 11 | 2.6.1.a | NP_415448.1 | *Escherichia coli* | aspartate |
| | | P23542.3 | *Saccharomyces cerevisiae* | aspartate |
| | | YP_026231.1 | *Escherichia coli* | valine, alpha-aminobutyrate |
| 11 | 4.1.1.a | P06672.1 | *Zymomonas mobilus* | 2-oxopentanoic acid |
| | | P20906.2 | *Pseudomonas putida* | 2-oxopentanoic acid |
| | | P06169 | *Saccharomyces cerevisiae* | pyruvate |
| 11 | 1.1.1.a | NP_014032.1 | *Saccharymyces cerevisiae* | general |
| | | NP_417484.1 | *Escherichia coli* | >C3 |
| | | L21902.1 | *Clostridium kluyveri* DSM 555 | Succinate semialdehyde |
| 11 | 1.2.1.c | NP_415254.1, NP_415255.1, NP_414658.1 | *Escherichia coli* | Alpha-ketoglutarate |
| | | NP_390283.1, NP_390285.1, NP_390284.1, P21880.1 | *Bacillus subtilis* | 2-keto acids derivatives of valine, leucine and isoleucine |
| | | NP_036914.1, NP_062140.1, NP_445764.1, NP_955417.1 | *Rattus norvegicus* | 2-keto acids derivatives of valine, leucine and isoleucine |

Example X

Exemplary BDO from Acetoacetyl-CoA

This example describes an exemplary BDO pathway from acetoacetyl-CoA.

FIG. 12 depicts exemplary BDO pathways in which acetoacetyl-CoA is converted to BDO. Enzymes of such an exemplary BDO pathway are listed in Table 22, along with exemplary genes encoding these enzymes.

Briefly, acetoacetyl-CoA can be converted to 3-hydroxybutyryl-CoA by 3-hydroxybutyryl-CoA dehydrogenase (EC 1.1.1.a). 3-Hydroxybutyryl-CoA can be converted to crotonoyl-CoA by 3-hydroxybutyryl-CoA dehydratase (EC 4.2.1.a). Crotonoyl-CoA can be converted to vinylacetyl-CoA by vinylacetyl-CoA Δ-isomerase (EC 5.3.3.3). Vinylacetyl-CoA can be converted to 4-hydroxybutyryl-CoA by 4-hydroxybutyryl-CoA dehydratase (EC 4.2.1.a). 4-Hydroxybutyryl-CoA can be converted to 1,4-butanediol by 4-hydroxybutyryl-CoA reductase (alcohol forming) (EC 1.1.1.c). Alternatively, 4-hydroxybutyryl-CoA can be converted to 4-hydroxybutanal by 4-hydroxybutyryl-CoA reductase (or 4-hydroxybutanal dehydrogenase) (EC 1.2.1.b). 4-Hydroxybutanal can be converted to 1,4-butanediol by 1,4-butanediol dehydrogenase (EC 1.1.1.a).

Briefly, homoserine can be converted to 4-hydroxybut-2-enoate by homoserine deaminase (EC 4.3.1.a). Alternatively, homoserine can be converted to homoserine-CoA by homoserine CoA transferase (EC 2.8.3.a), homoserine-CoA hydrolase (EC 3.1.2.a) or homoserine-CoA ligase (or homoserine-CoA synthetase) (EC 6.2.1.a). Homoserine-CoA can be converted to 4-hydroxybut-2-enoyl-CoA by homoserine-CoA deaminase (EC 4.3.1.a). 4-Hydroxybut-2-enoate can be

TABLE 22

BDO pathway from acetoacetyl-CoA.

| FIG. | EC class | Desired substrate | Desired product | Enzyme name | Gene name | GenBank ID (if available) | Organism | Known Substrate |
|---|---|---|---|---|---|---|---|---|
| 12 | 1.1.1.a | acetoacetyl-CoA | 3-hydroxybutyryl-CoA | 3-hydroxybutyryl-CoA dehydrogenase | hbd | NP_349314.1 | Clostridium acetobutylicum | 3-hydroxybutyryl-CoA |
| | | | | | hbd | AAM14586.1 | Clostridium beijerinckii | 3-hydroxybutyryl-CoA |
| | | | | | Msed_1423 | YP_001191505 | Metallosphaera sedula | presumed 3-hydroxybutyryl-CoA |
| 12 | 4.2.1.a | 3-hydroxybutyryl-CoA | crotonoyl-CoA | 3-hydroxybutyryl-CoA dehydratase | crt | NP_349318.1 | Clostridium acetobutylicum | 3-hydroxybutyryl-CoA |
| | | | | | maoC | NP_415905.1 | Escherichia coli | 3-hydroxybutyryl-CoA |
| | | | | | paaF | NP_415911.1 | Escherichia coli | 3-hydroxyadipyl-CoA |
| 12 | 5.3.3.3 | crotonoyl-CoA | vinylacetyl-CoA | vinylacetyl-CoA Δ-isomerase | abfD | YP_001396399.1 | Clostridium kluyveri DSM 555 | 4-hydroxybutyryl-CoA |
| | | | | | abfD | P55792 | Clostridium aminobutyricum | 4-hydroxybutyryl-CoA |
| | | | | | abfD | YP_001928843 | Porphyromonas gingivalis ATCC 33277 | 4-hydroxybutyryl-CoA |
| 12 | 4.2.1.a | vinylacetyl-CoA | 4-hydroxybutyryl-CoA | 4-hydroxybutyryl-CoA dehydratase | abfD | YP_001396399.1 | Clostridium kluyveri DSM 555 | 4-hydroxybutyryl-CoA |
| | | | | | abfD | P55792 | Clostridium aminobutyricum | 4-hydroxybutyryl-CoA |
| | | | | | abfD | YP_001928843 | Porphyromonas gingivalis ATCC 33277 | 4-hydroxybutyryl-CoA |
| 12 | 1.1.1.c | 4-hydroxybutyryl-CoA | 1,4-butanediol | 4-hydroxybutyryl-CoA reductase (alcohol forming) | adhE2 | AAK09379.1 | Clostridium acetobutylicum | butanoyl-CoA |
| | | | | | mcr | AAS20429.1 | Chloroflexus aurantiacus | malonyl-CoA |
| | | | | | FAR | AAD38039.1 | Simmondsia chinensis | long chain acyl-CoA |
| 12 | 1.2.1.b | 4-hydroxybutyryl-CoA | 4-hydroxybutanal | 4-hydroxybutyryl-CoA reductase (or 4-hydroxybutanal dehydrogenase) | sucD | P38947.1 | Clostridium kluyveri | Succinyl-CoA |
| | | | | | sucD | NP_904963.1 | Porphyromonas gingivalis | Succinyl-CoA |
| | | | | | Msed_0709 | YP_001190808.1 | Metallosphaera sedula | Malonyl-CoA |
| 12 | 1.1.1.a | 4-hydroxybutanal | 1,4-butanediol | 1,4-butanediol dehydrogenase | ADH2 | NP_014032.1 | Saccharomyces cerevisiae | general |
| | | | | | yqhD | NP_417484.1 | Escherichia coli | >C3 |
| | | | | | 4hbd | L21902.1 | Clostridium kluyveri DSM 555 | Succinate semialdehyde |

Example XI

Exemplary BDO Pathway from Homoserine

This example describes an exemplary BDO pathway from homoserine.

Figure 13:
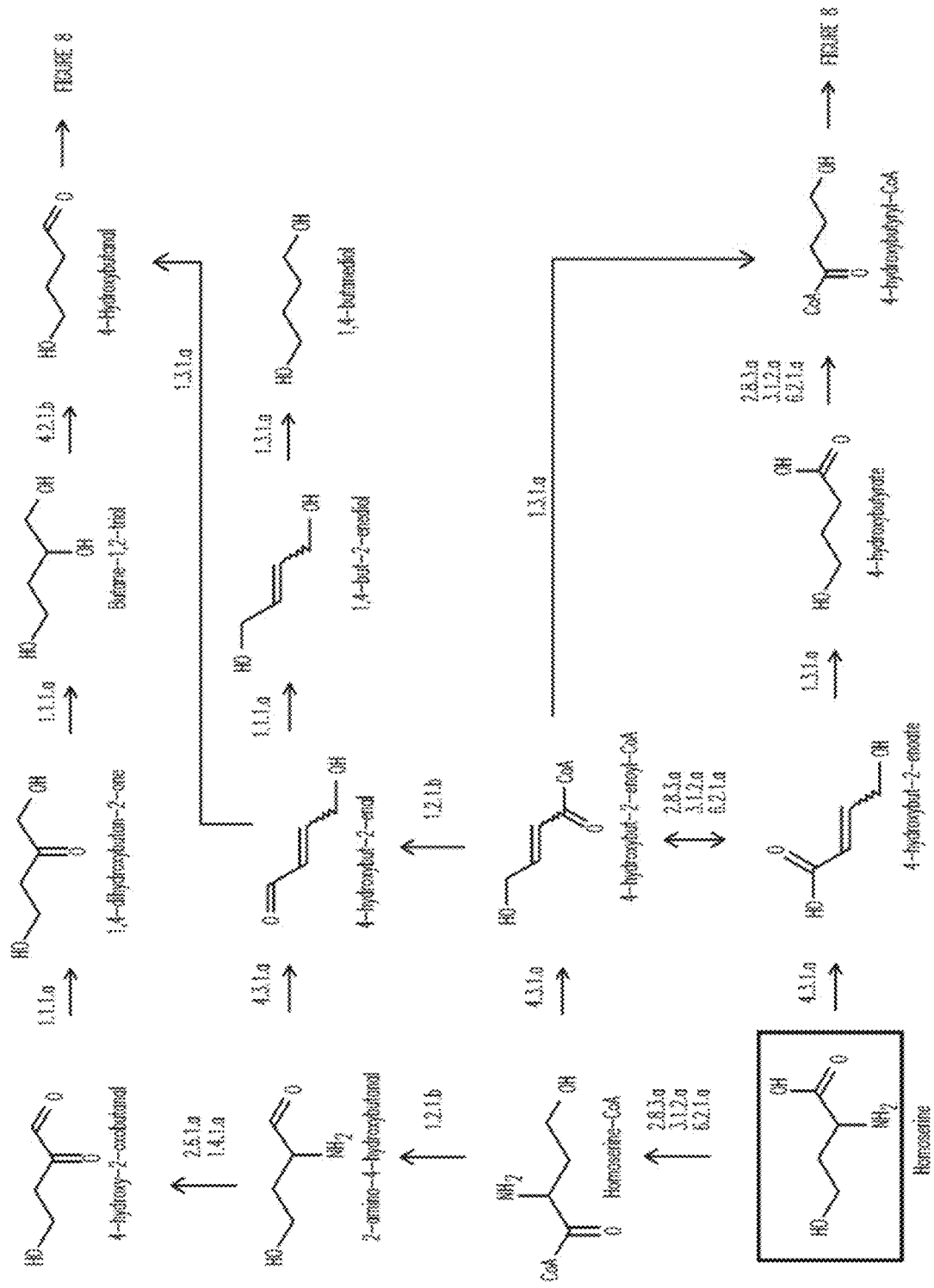
FIG. 13 shows exemplary BDO pathways from homoserine.

FIG. 13 depicts exemplary BDO pathways in which homoserine is converted to BDO. Enzymes of such an exemplary BDO pathway are listed in Table 23, along with exemplary genes encoding these enzymes.

converted to 4-hydroxybut-2-enoyl-CoA by 4-hydroxybut-2-enoyl-CoA transferase (EC 2.8.3.a), 4-hydroxybut-2-enoyl-CoA hydrolase (EC 3.1.2.a), or 4-hydroxybut-2-enoyl-CoA ligase (or 4-hydroxybut-2-enoyl-CoA synthetase) (EC 6.2.1.a). Alternatively, 4-hydroxybut-2-enoate can be converted to 4-hydroxybutyrate by 4-hydroxybut-2-enoate reductase (EC 1.3.1.a). 4-Hydroxybutyrate can be converted to 4-hydroxybutyryl-coA by 4-hydroxybutyryl-CoA transferase (EC 2.8.3.a), 4-hydroxybutyryl-CoA hydrolase (EC 3.1.2.a), or 4-hydroxybutyryl-CoA ligase (or 4-hy droxybutyryl-CoA synthetase) (EC 6.2.1.a). 4-Hydroxybut-2-enoyl-CoA can be converted to 4-hydroxybutyryl-CoA by 4-hydroxybut-2-enoyl-CoA reductase (EC 1.3.1.a). 4-Hydroxybutyryl-CoA can be converted to 1,4-butanediol by 4-hydroxybutyryl-CoA reductase (alcohol forming) (EC 1.1.1.c). Alternatively, 4-hydroxybutyryl-CoA can be converted to 4-hydroxybutanal by 4-hydroxybutyryl-CoA reductase (or 4-hydroxybutanal dehydrogenase) (EC 1.2.1.b). 4-Hydroxybutanal can be converted to 1,4-butanediol by 1,4-butanediol dehydrogenase (EC 1.1.1.a).

TABLE 23

BDO pathway from homoserine.

| FIG. | EC class | Desired substrate | Desired product | Enzyme name | Gene name |
|---|---|---|---|---|---|
| 13 | 4.3.1.a | homoserine | 4-hydroxybut-2-enoate | homoserine deaminase | aspA |
| 13 | 2.8.3.a | homoserine | homoserine-CoA | homoserine CoA transferase | aspA aspA cat1, cat2, cat3 gctA, gctB atoA, atoD |
| 13 | 3.1.2.a | homoserine | homoserine-CoA | homoserine-CoA hydrolase | tesB acot12 hibch |
| 13 | 6.2.1.a | homoserine | homoserine-CoA | homoserine-CoA ligase (or homoserine-CoA synthetase) | sucCD phl bioW |
| 13 | 4.3.1.a | homoserine-CoA | 4-hydroxybut-2-enoyl-CoA | homoserine-CoA deaminase | acl1 acl2 MXAN_4385 |
| 13 | 2.8.3.a | 4-hydroxybut-2-enoate | 4-hydroxybut-2-enoyl-CoA | 4-hydroxybut-2-enoyl-CoA transferase | cat1, cat2, cat3 gctA, gctB atoA, atoD |
| 13 | 3.1.2.a | 4-hydroxybut-2-enoate | 4-hydroxybut-2-enoyl-CoA | 4-hydroxybut-2-enoyl-CoA hydrolase | tesB acot12 hibch |
| 13 | 6.2.1.a | 4-hydroxybut-2-enoate | 4-hydroxybut-2-enoyl-CoA | 4-hydroxybut-2-enoyl-CoA ligase (or 4-hydroxybut-2-enoyl-CoA synthetase) | sucCD phl bioW |
| 13 | 1.3.1.a | 4-hydroxybut-2-enoate | 4-hydroxybutyrate | 4-hydroxybut-2-enoate reductase | enr |
| 13 | 2.8.3.a | 4-hydroxybutyrate | 4-hydroxybutyryl-coA | 4-hydroxybutyryl-CoA transferase | enr enr cat1, cat2, cat3 gctA, gctB atoA, atoD |
| 13 | 3.1.2.a | 4-hydroxybutyrate | 4-hydroxybutyryl-coA | 4-hydroxybutyryl-CoA hydrolase | tesB acot12 hibch |
| 13 | 6.2.1.a | 4-hydroxybutyrate | 4-hydroxybutyryl-coA | 4-hydroxybutyryl-CoA ligase (or 4-hydroxybutyryl-CoA synthetase) | sucCD phl bioW |
| 13 | 1.3.1.a | 4-hydroxybut-2-enoyl-CoA | 4-hydroxybutyryl-CoA | 4-hydroxybut-2-enoyl-CoA reductase | bcd, etfA, etfB TER TDE0597 |
| 8 | 1.1.1.c | 4-hydroxybutyryl-CoA | 1,4-butanediol | 4-hydroxybutyryl-CoA reductase (alcohol forming) | adhE2 mcr FAR |

TABLE 23-continued

BDO pathway from homoserine.

| | | | | | |
|---|---|---|---|---|---|
| 8 | 1.2.1.b | 4-hydroxybutyryl-CoA | 4-hydroxybutanal | 4-hydroxybutyryl-CoA reductase (or 4-hydroxybutanal dehydrogenase) | sucD |
| | | | | | sucD |
| | | | | | Msed_0709 |
| 8 | 1.1.1.a | 4-hydroxybutanal | 1,4-butanediol | 1,4-butanediol dehydrogenase | ADH2 |
| | | | | | yqhD |
| | | | | | 4hbd |

| FIG. | EC class | GenBank ID (if available) | Organism | Known Substrate |
|---|---|---|---|---|
| 13 | 4.3.1.a | NP_418562 | *Escherichia coli* | aspartate |
| | | P44324.1 | *Haemophilus influenzae* | aspartate |
| | | P07346 | *Pseudomonas fluorescens* | aspartate |
| 13 | 2.8.3.a | P38946.1, P38942.2, EDK35586.1 | *Clostridium kluyveri* | succinate, 4-hydroxybutyrate, butyrate |
| | | CAA57199.1, CAA57200.1 | *Acidaminococcus fermentans* | glutarate |
| | | P76459.1, P76458.1 | *Escherichia coli* | butanoate |
| 13 | 3.1.2.a | NP_414986 | *Escherichia coli* | adipyl-CoA |
| | | NP_570103.1 | *Rattus norvegicus* | butyryl-CoA |
| | | Q6NVY1.2 | *Homo sapiens* | 3-hydroxypropanoyl-CoA |
| 13 | 6.2.1.a | NP_415256.1, AAC73823.1 | *Escherichia coli* | succinate |
| | | CAJ15517.1 | *Penicillium chrysogenum* | phenylacetate |
| | | NP_390902.2 | *Bacillus subtilis* | 6-carboxyhexanoate |
| 13 | 4.3.1.a | CAG29274.1 | *Clostridium propionicum* | beta-alanyl-CoA |
| | | CAG29275.1 | *Clostridium propionicum* | beta-alanyl-CoA |
| | | YP_632558.1 | *Myxococcus xanthus* | beta-alanyl-CoA |
| 13 | 2.8.3.a | P38946.1, P38942.2, EDK35586.1 | *Clostridium kluyveri* | succinate, 4-hydroxybutyrate, butyrate |
| | | CAA57199.1, CAA57200.1 | *Acidaminococcus fermentans* | glutarate |
| | | P76459.1, P76458.1 | *Escherichia coli* | butanoate |
| 13 | 3.1.2.a | NP_414986 | *Escherichia coli* | adipyl-CoA |
| | | NP_570103.1 | *Rattus norvegicus* | butyryl-CoA |
| | | Q6NVY1.2 | *Homo sapiens* | 3-hydroxypropanoyl-CoA |
| 13 | 6.2.1.a | NP_415256.1, AAC73823.1 | *Escherichia coli* | succinate |
| | | CAJ15517.1 | *Penicillium chrysogenum* | phenylacetate |
| | | NP_390902.2 | *Bacillus subtilis* | 6-carboxyhexanoate |
| 13 | 1.3.1.a | CAA71086.1 | *Clostridium tyrobutyricum* | |
| | | CAA76083.1 | *Clostridium kluyveri* | |
| | | YP_430895.1 | *Moorella thermoacetica* | |
| 13 | 2.8.3.a | P38946.1, P38942.2, EDK35586.1 | *Clostridium kluyveri* | succinate, 4-hydroxybutyrate, butyrate |
| | | CAA57199.1, CAA57200.1 | *Acidaminococcus fermentans* | glutarate |
| | | P76459.1, P76458.1 | *Escherichia coli* | butanoate |
| 13 | 3.1.2.a | NP_414986 | *Escherichia coli* | adipyl-CoA |
| | | NP_570103.1 | *Rattus norvegicus* | butyryl-CoA |
| | | Q6NVY1.2 | *Homo sapiens* | 3-hydroxypropanoyl-CoA |

TABLE 23-continued

BDO pathway from homoserine.

| | | | | |
|---|---|---|---|---|
| 13 | 6.2.1.a | NP_415256.1, AAC73823.1 | *Escherichia coli* | succinate |
| | | CAJ15517.1 | *Penicillium chrysogenum* | phenylacetate |
| | | NP_390902.2 | *Bacillus subtilis* | 6-carboxyhexanoate |
| 13 | 1.3.1.a | NP_349317.1, NP_349315.1, NP_349316.1 | *Clostridium acetobutylicum* | |
| | | Q5EU90.1 | *Euglena gracilis* | |
| | | NP_971211.1 | *Treponema denticola* | |
| 8 | 1.1.1.c | AAK09379.1 | *Clostridium acetobutylicum* | butanoyl-CoA |
| | | AAS20429.1 | *Chloroflexus aurantiacus* | malonyl-CoA |
| | | AAD38039.1 | *Simmondsia chinensis* | long chain acyl-CoA |
| 8 | 1.2.1.b | P38947.1 | *Clostridium kluyveri* | Succinyl-CoA |
| | | NP_904963.1 | *Porphyromonas gingivalis* | Succinyl-CoA |
| | | YP_001190808.1 | *Metallosphaera sedula* | Malonyl-CoA |
| 8 | 1.1.1.a | NP_014032.1 | *Saccharymyces cerevisiae* | general |
| | | NP_417484.1 | *Escherichia coli* | >C3 |
| | | L21902.1 | *Clostridium kluyveri* DSM 555 | Succinate semialdehyde |

Example XII

BDO Producing Strains Expressing Succinyl-CoA Synthetase

This example describes increased production of BDO in BDO producing strains expressing succinyl-CoA synthetase.

As discussed above, succinate can be a precursor for production of BDO by conversion to succinyl-CoA (see also WO2008/115840, WO 2009/023493, U.S. publication 2009/0047719, U.S. publication 2009/0075351). Therefore, the host strain was genetically modified to overexpress the *E. coli* sucCD genes, which encode succinyl-CoA synthetase. The nucleotide sequence of the *E. coli* sucCD operon is shown in FIG. 14A, and the amino acid sequences for the encoded succinyl-CoA synthetase subunits are shown in FIGS. 14B and 14C. Briefly, the *E. coli* sucCD genes were cloned by PCR from *E. coli* chromosomal DNA and introduced into multicopy plasmids pZS*13, pZA13, and pZE33 behind the PA1lacO-1 promoter (Lutz and Bujard, *Nucleic Acids Res.* 25:1203-1210 (1997)) using standard molecular biology procedures.

The *E. coli* sucCD genes, which encode the succinyl-CoA synthetase, were overexpressed. The results showed that introducing into the strains sucCD to express succinyl-CoA synthetase improved BDO production in various strains compared to either native levels of expression or expression of cat1, which is a succinyl-CoA/acetyl-CoA transferase. Thus, BDO production was improved by overexpressing the native *E. coli* sucCD genes encoding succinyl-CoA synthetase.

Example XIII

Expression of Heterologous Genes Encoding BDO Pathway Enzymes

This example describes the expression of various non-native pathway enzymes to provide improved production of BDO.

Alpha-Ketoglutarate Decarboxylase.

The *Mycobacterium bovis* sucA gene encoding alpha-ketoglutarate decarboxylase was expressed in host strains. Overexpression of *M. bovis* sucA improved BDO production (see also WO2008/115840, WO 2009/023493, U.S. publication 2009/0047719, U.S. publication 2009/0075351). The nucleotide and amino acid sequences of *M. bovis* sucA and the encoded alpha-ketoglutarate decarboxylase are shown in FIG. 15.

To construct the *M. bovis* sucA expressing strains, fragments of the sucA gene encoding the alpha-ketoglutarate decarboxylase were amplified from the genomic DNA of *Mycobacterium bovis* BCG (ATCC 19015; American Type Culture Collection, Manassas Va.) using primers shown below. The full-length gene was assembled by ligation reaction of the four amplified DNA fragments, and cloned into expression vectors pZS*13 and pZE23 behind the $P_{A1lacO-1}$ promoter (Lutz and Bujard, *Nucleic Acids Res.* 25:1203-1210 (1997)). The nucleotide sequence of the assembled gene was verified by DNA sequencing.

```
Primers for fragment 1:
                                        (SEQ ID NO: 3)
5'-ATGTACCGCAAGTTCCGC-3'

(SEQ ID NO: 4)
5'-CAATTTGCCGATGCCCAG-3'

Primers for fragment 2:
                                        (SEQ ID NO: 5)
5'-GCTGACCACTGAAGACTTTG-3'

(SEQ ID NO: 6)
5'-GATCAGGGCTTCGGTGTAG-3'

Primers for fragment 3:
                                        (SEQ ID NO: 7)
5'-TTGGTGCGGGCCAAGCAGGATCTGCTC-3'

(SEQ ID NO: 8)
5'-TCAGCCGAACGCCTCGTCGAGGATCTCCTG-3'
```

-continued

Primers for fragment 4:
(SEQ ID NO: 9)
5'-TGGCCAACATAAGTTCACCATTCGGGCAAAAC-3'

(SEQ ID NO: 10)
5'-TCTCTTCAACCAGCCATTCGTTTTGCCCG-3'

Figure 16:
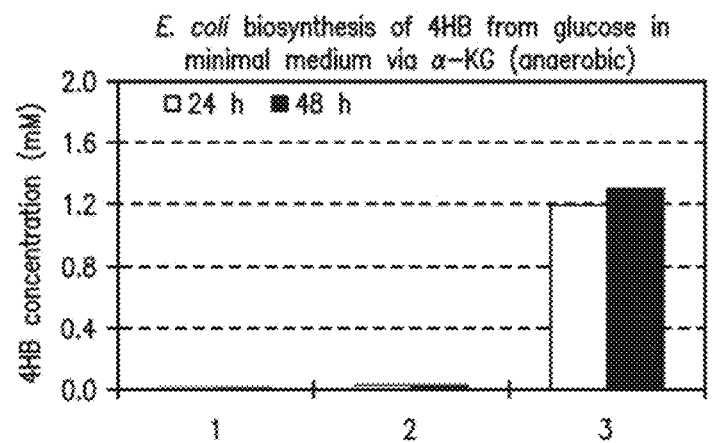
FIG. 16 shows biosynthesis in E. coli of 4-hydroxybutyrate from glucose in minimal medium via alpha-ketoglutarate under anaerobic (microaerobic) conditions. The host strain is ECKh-401. The experiments are labeled based on the upstream pathway genes present on the plasmid pZA33 as follows: 1) 4hbd-sucA; 2) sucCD-sucD-4hbd; 3) sucCD-sucD-4hbd-sucA.

Functional expression of the alpha-ketoglutarate decarboxylase was demonstrated using both in vitro and in vivo assays. The SucA enzyme activity was measured by following a previously reported method (Tian et al., Proc. Natl. Acad. Sci. USA 102:10670-10675 (2005)). The reaction mixture contained 50 mM potassium phosphate buffer, pH 7.0, 0.2 mM thiamine pyrophosphate, 1 mM $MgCl_2$, 0.8 mM ferricyanide, 1 mM alpha-ketoglutarate and cell crude lysate. The enzyme activity was monitored by the reduction of ferricyanide at 430 nm. The in vivo function of the SucA enzyme was verified using E. coli whole-cell culture. Single colonies of E. coli MG1655 lacI$^q$ transformed with plasmids encoding the SucA enzyme and the 4-hydroxybutyrate dehydrogenase (4Hbd) was inoculated into 5 mL of LB medium containing appropriate antibiotics. The cells were cultured at 37° C. overnight aerobically. A 200 uL of this overnight culture was introduced into 8 mL of M9 minimal medium (6.78 g/L $Na_2HPO_4$, 3.0 g/L $KH_2PO_4$, 0.5 g/L NaCl, 1.0 g/L $NH_4Cl$, 1 mM $MgSO_4$, 0.1 mM $CaCl_2$) supplemented with 20 g/L glucose, 100 mM 3-(N-morpholino)propanesulfonic acid (MOPS) to improve the buffering capacity, 10 μg/mL thiamine, and the appropriate antibiotics. Microaerobic conditions were established by initially flushing capped anaerobic bottles with nitrogen for 5 minutes, then piercing the septum with a 23G needle following inoculation. The needle was kept in the bottle during growth to allow a small amount of air to enter the bottles. The protein expression was induced with 0.2 mM isopropyl β-D-1-thiogalactopyranoside (IPTG) when the culture reached mid-log growth phase. As controls, E. coli MG1655 lacI$^q$ strains transformed with only the plasmid encoding the 4-hydroxybutyrate dehydrogenase and only the empty vectors were cultured under the same condition (see Table 23). The accumulation of 4-hydroxybutyrate (4HB) in the culture medium was monitored using LCMS method. Only the E. coli strain expressing the Mycobacterium alpha-ketoglutarate decarboxylase produced significant amount of 4HB (see FIG. 16).

TABLE 24

Three strains containing various plasmid controls and encoding sucA and 4-hydroxybutyrate dehydrogenase.

|   | Host | pZE13 | pZA33 |
|---|------|-------|-------|
| 1 | MG1655 lacIq | vector | vector |
| 2 | MG1655 lacIq | vector | 4hbd |
| 3 | MG1655 lacIq | sucA | 4hbd |

Figure 17:
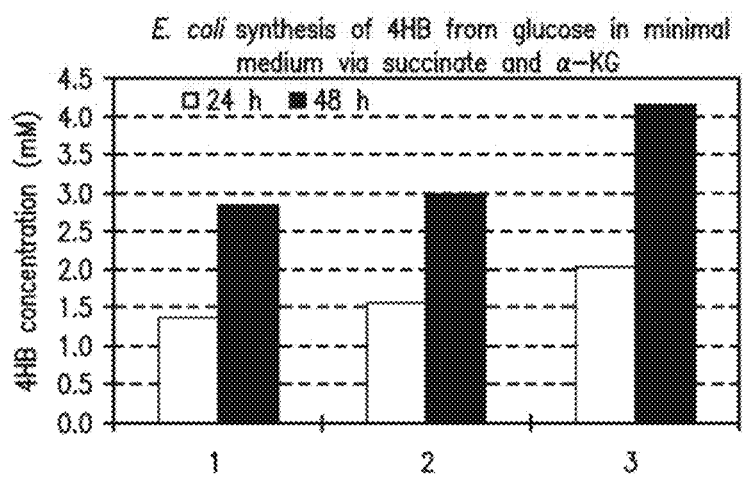
FIG. 17 shows biosynthesis in E. coli of 4-hydroxybutyrate from glucose in minimal medium via succinate and alpha-ketoglutarate. The host strain is wild-type MG1655. The experiments are labeled based on the genes present on the plasmids pZE13 and pZA33 as follows: 1) empty control vectors 2) empty pZE13, pZA33-4hbd; 3) pZE13-sucA, pZA33-4hbd.

A separate experiment demonstrated that the alpha-ketoglutarate decarboxylase pathway functions independently of the reductive TCA cycle. E. coli strain ECKh-401 (ΔadhE ΔldhA ΔpflB ΔlpdA::K.p.lpdA322 Δmdh ΔarcA) was used as the host strain (see Table 25). All the three constructs contained the gene encoding 4HB dehydrogenase (4Hbd). Construct 1 also contained the gene encoding the alpha-ketoglutarate decarboxylase (sucA). Construct 2 contained the genes encoding the succinyl-CoA synthetase (sucCD) and the CoA-dependent succinate semialdehyde dehydrogenase (sucD), which are required for the synthesis of 4HB via the reductive TCA cycle. Construct 3 contains all the genes from 1 and 2. The three E. coli strains were cultured under the same conditions as described above except the second culture was under the microaerobic condition. By expressing the SucA enzyme, construct 3 produced more 4HB than construct 2, which relies on the reductive TCA cycle for 4HB synthesis (see FIG. 17).

Further support for the contribution of alpha-ketoglutarate decarboxylase to production of 4HB and BDO was provided by flux analysis experiments. Cultures of ECKh-432, which contains both sucCD-sucD and sucA on the chromosome, were grown in M9 minimal medium containing a mixture of 1-13C-glucose (60%) and U-13C-glucose (40%). The biomass was harvested, the protein isolated and hydrolyzed to amino acids, and the label distribution of the amino acids analyzed by gas chromatography-mass spectrometry (GCMS) as described previously (Fischer and Sauer, Eur. J. Biochem. 270:880-891 (2003)). In addition, the label distribution of the secreted 4HB and BDO was analyzed by GCMS as described in WO2008115840 A2. This data was used to calculate the intracellular flux distribution using established methods (Suthers et al., Metab. Eng. 9:387-405 (2007)). The results indicated that between 56% and 84% of the alpha-ketoglutarate was channeled through alpha-ketoglutarate decarboxylase into the BDO pathway. The remainder was oxidized by alpha-ketoglutarate dehydrogenase, which then entered BDO via the succinyl-CoA route.

These results demonstrate 4-hydroxybutyrate producing strains that contain the sucA gene from Mycobacterium bovis BCG expressed on a plasmid. When the plasmid encoding this gene is not present, 4-hydroxybutyrate production is negligible when sucD (CoA-dependant succinate semialdehyde dehydrogenase) is not expressed. The M. bovis gene is a close homolog of the Mycobacterium tuberculosis gene whose enzyme product has been previously characterized (Tian et al., supra, 2005).

Succinate Semialdehyde Dehydrogenase (CoA-Dependent), 4-Hydroxybutyrate Dehydrogenase, and 4-Hydroxybutyryl-CoA/Acetyl-CoA Transferase.

The genes from Porphyromonas gingivalis W83 can be effective components of the pathway for 1,4-butanediol production (see also WO2008/115840, WO 2009/023493, U.S. publication 2009/0047719, U.S. publication 2009/0075351). The nucleotide sequence of CoA-dependent succinate semialdehyde dehydrogenase (sucD) from Porphyromonas gingivalis is shown in FIG. 18A, and the encoded amino acid sequence is shown in FIG. 18B. The nucleotide sequence of 4-hydroxybutyrate dehydrogenase (4hbd) from Porphymonas gingivalis is shown in FIG. 19A, and the encoded amino acid sequence is shown in FIG. 19B. The nucleotide sequence of 4-hydroxybutyrate CoA transferase (cat2) from Porphyromonas gingivalis is shown in FIG. 20A, and the encoded amino acid sequence is shown in FIG. 20B.

Briefly, the genes from Porphyromonas gingivalis W83 encoding succinate semialdehyde dehydrogenase (CoA-dependent) and 4-hydroxybutyrate dehydrogenase, and in some cases additionally 4-hydroxybutyryl-CoA/acetyl-CoA, were cloned by PCR from P. gingivalis chromosomal DNA and introduced into multicopy plasmids pZS*13, pZA13, and pZE33 behind the PA1lacO-1 promoter (Lutz and Bujard, Nucleic Acids Res. 25:1203-1210 (1997)) using standard molecular biology procedures. These plasmids were then introduced into host strains.

The Porphyromonas gingivalis W83 genes were introduced into production strains as described above. Some strains included only succinate semialdehyde dehydrogenase (CoA-dependant) and 4-hydroxybutyrate dehydrogenase without 4-hydroxybutyryl-CoA/acetyl-CoA transferase.

Butyrate Kinase and Phosphotransbutyrylase.

Butyrate kinase (BK) and phosphotransbutyrylase (PTB) enzymes can be utilized to produce 4-hydroxybutyryl-CoA (see also WO2008/115840, WO 2009/023493, U.S. publication 2009/0047719, U.S. publication 2009/0075351). In particular, the *Clostridium acetobutylicum* genes, buk1 and ptb, can be utilized as part of a functional BDO pathway.

Initial experiments involved the cloning and expression of the native *C. acetobutylicum* PTB (020) and BK (021) genes in *E. coli*. Where required, the start codon and stop codon for each gene were modified to "ATG" and "TAA," respectively, for more optimal expression in *E. coli*. The *C. acetobutylicum* gene sequences (020N and 021N) and their corresponding translated peptide sequences are shown in FIGS. 21 and 22.

The PTB and BK genes exist in *C. acetobutylicum* as an operon, with the PTB (020) gene expressed first. The two genes are connected by the sequence "atta aagttaagtg gaggaatgtt aac" (SEQ ID NO:11) that includes a re-initiation ribosomal binding site for the downstream BK (021) gene. The two genes in this context were fused to lac-controlled promoters in expression vectors for expression in *E. coli* (Lutz and Bujard, *Nucleic Acids Res.* 25:1203-1210 (1997)).

Expression of the two proteins from these vector constructs was found to be low in comparison with other exogenously expressed genes due to the high incidence of codons in the *C. acetobutylicum* genes that occur only rarely in *E. coli*. Therefore new 020 and 021 genes were predicted that changed rare codons for alternates that are more highly represented in *E. coli* gene sequences. This method of codon optimization followed algorithms described previously (Sivaraman et al., *Nucleic Acids Res.* 36:e16(2008)). This method predicts codon replacements in context with their frequency of occurrence when flanked by certain codons on either side. Alternative gene sequences for 020 (FIG. 23) and 021 (FIG. 24) were determined in which increasing numbers of rare codons were replaced by more prevalent codons (A<B<C<D) based on their incidence in the neighboring codon context. No changes in actual peptide sequence compared to the native 020 and 021 peptide sequences were introduced in these predicted sequences.

Figure 25A:
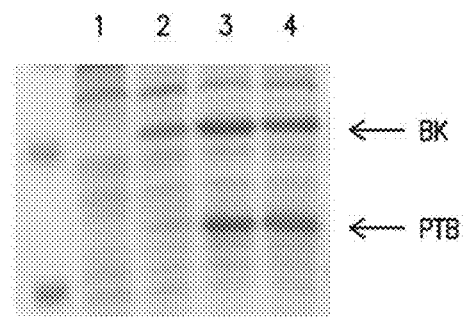
FIGS. 25A and 25B show improved expression of butyrate kinase (BK) and phosphotransbutyrylase (PTB) with optimized codons for expression in E. coli.
Figure 25B:
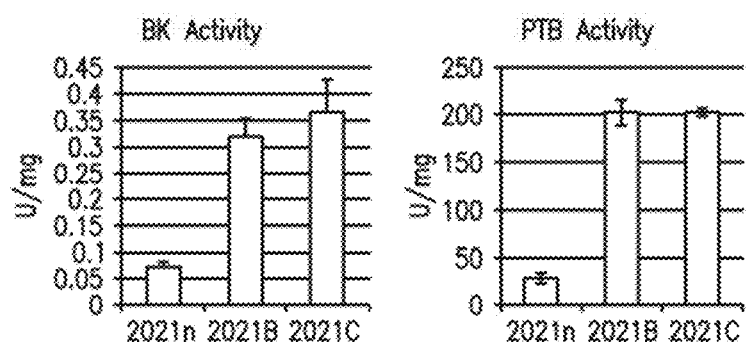

The improvement in expression of the BK and PTB proteins resulting from codon optimization is shown in FIG. 25A. Expression of the native gene sequences is shown in lane 2, while expression of the 020B-021B and 020C-021C is shown in lanes 3 and 4, respectively. Higher levels of protein expression in the codon-optimized operons 020B-021B (2021B) and 020C-021C (2021C) also resulted in increased activity compared to the native operon (2021n) in equivalently-expressed *E. coli* crude extracts (FIG. 25B).

Figure 26:
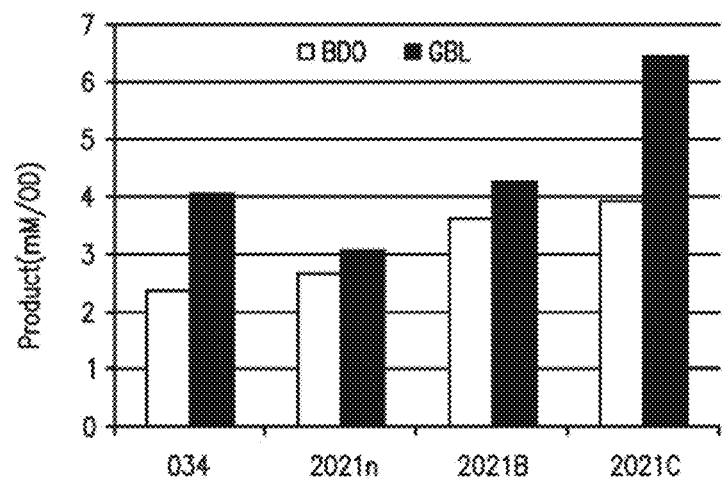
FIG. 26 shows production of BDO and gamma-butyrylactone (GBL) in various strains expressing BDO producing enzymes: Cat2 (034); 2021n; 2021B; 2021C.

The codon optimized operons were expressed on a plasmid in strain ECKh-432 (ΔadhE ΔldhA ΔpflB ΔlpdA:: K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd) along with the *C. acetobutylicum* aldehyde dehydrogenase to provide a complete BDO pathway. Cells were cultured in M9 minimal medium containing 20 g/L glucose, using a 23G needle to maintain microaerobic conditions as described above. The resulting conversion of glucose to the final product BDO was measured. Also measured was the accumulation of gamma-butyrylactone (GBL), which is a spontaneously rearranged molecule derived from 4Hb-CoA, the immediate product of the PTB-BK enzyme pair. FIG. 26 shows that expression of the native 2021n operon resulted in comparable BDO levels to an alternative enzyme function, Cat2 (034), that is capable of converting 4HB and free CoA to 4HB-CoA. GBL levels of 034 were significantly higher than 2021n, suggesting that the former enzyme has more activity than PTB-BK expressed from the native genes. However levels of both BDO and GBL were higher than either 034 or 2021n when the codon-optimized variants 2021B and 2021C were expressed, indicating that codon optimization of the genes for PTB and BK significantly increases their contributions to BDO synthesis in *E. coli*.

These results demonstrate that butyrate kinase (BK) and phosphotransbutyrylase (PTB) enzymes can be employed to convert 4-hydroxybutyrate to 4-hydroxybutyryl-CoA. This eliminates the need for a transferase enzyme such as 4-hydroxybutyryl-CoA/Acetyl-CoA transferase, which would generate one mole of acetate per mol of 4-hydroxybutyryl-CoA produced. The enzymes from *Clostridium acetobutylicum* are present in a number of engineered strains for BDO production.

4-hydroxybutyryl-CoA Reductase.

The *Clostridium beijerinckii* ald gene can be utilized as part of a functional BDO pathway (see also WO2008/115840, WO 2009/023493, U.S. publication 2009/0047719, U.S. publication 2009/0075351). The *Clostridium beijerinckii* ald can also be utilized to lower ethanol production in BDO producing strains. Additionally, a specific codon-optimized ald variant (GNM0025B) was found to improve BDO production.

Figure 29:
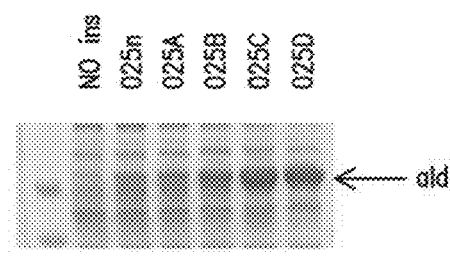
FIG. 29 shows expression of native C. beijerinckii ald gene and codon optimized variants; no ins (control with no insert), 025n, 025A, 025B, 025C, 025D.
Figure 30A:
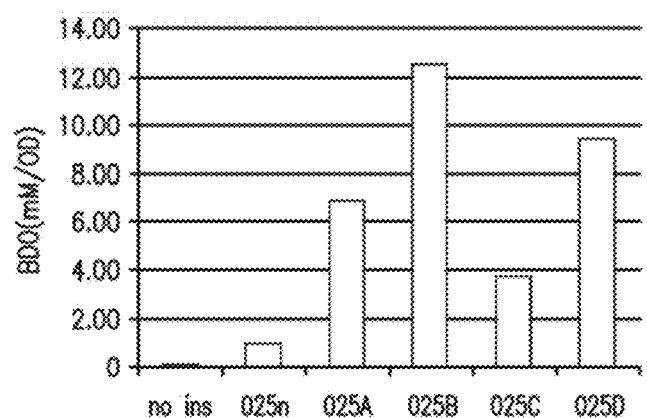
FIGS. 30A and 30B show BDO or BDO and ethanol production in various strains.

The native *C. beijerinckii* ald gene (025n) and the predicted protein sequence of the enzyme are shown in FIG. 27. As was seen for the *Clostridium acetobutylicum* PTB and BK genes, expression of the native *C. beijerinckii* ald gene was very low in *E. coli*. Therefore, four codon-optimized variants for this gene were predicted. FIGS. 28A-28D show alternative gene sequences for 025, in which increasing numbers of rare codons are replaced by more prevalent codons (A<B<C<D) based on their incidence in the neighboring codon context (25A, P=0.05; 25B, P=0.1; 25C, P=0.15; 25D, P=1). No changes in actual peptide sequence compared to the native 025 peptide sequence were introduced in these predictions. Codon optimization significantly increased expression of the *C. beijerinckii* ald (see FIG. 29), which resulted in significantly higher conversion of glucose to BDO in cells expressing the entire BDO pathway (FIG. 30A).

Figure 30B:
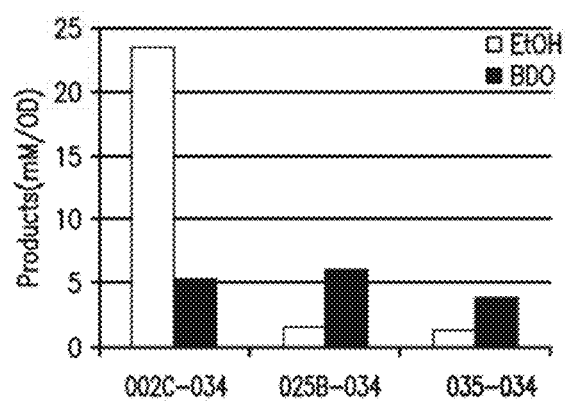

The native and codon-optimized genes were expressed on a plasmid along with *P. gingivalis* Cat2, in the host strain ECKh-432 (ΔadhE ΔldhA ΔpflB ΔlpdA::K.p.lpdA322 Δmdh ΔarcA gltAR163L ΔackA fimD:: *E. coli* sucCD, *P. gingivalis* sucD, *P. gingivalis* 4hbd fimD:: *M. bovis* sucA, *C. kluyveri* 4hbd), thus containing a complete BDO pathway. Cells were cultured microaerobically in M9 minimal medium containing 20 g/L glucose as described above. The relative production of BDO and ethanol by the *C. beijerinckii* Ald enzyme (expressed from codon-optimized variant gene 025B) was compared with the *C. acetobutylicum* AdhE2 enzyme (see FIG. 30B). The *C. acetobutylicum* AdhE2 enzyme (002C) produced nearly 4 times more ethanol than BDO. In comparison, the *C. beijerinckii* Ald (025B) (in conjunction with an endogenous ADH activity) produced equivalent amounts of BDO, yet the ratio of BDO to ethanol production was reversed for this enzyme compared to 002C. This suggests that the *C. beijerinckii* Ald is more specific for 4HB-CoA over acetyl-coA than the *C. acetobutylicum* AdhE2, and therefore the former is the preferred enzyme for inclusion in the BDO pathway.

The *Clostridium beijerinckii* ald gene (Toth et al., *Appl. Environ. Microbiol.* 65:4973-4980 (1999)) was tested as a candidate for catalyzing the conversion of 4-hydroxybutyryl-CoA to 4-hydroxybutanal. Over fifty aldehyde dehydrogenases were screened for their ability to catalyze the conversion of 4-hydroxybutyryl-CoA to 4-hydroxybutyraldehyde. The *C. beijerinckii* ald gene was chosen for implementation into BDO-producing strains due to the preference of this enzyme for 4-hydroxybutyryl-CoA as a substrate as opposed to acetyl-CoA. This is important because most other enzymes with aldehyde dehydrogenase functionality (for example, adhE2 from *C. acetobutylicum* (Fontaine et al., *J Bacteriol.* 184:821-830 (2002)) preferentially convert acetyl-CoA to acetaldehyde, which in turn is converted to ethanol. Utilization of the *C. beijerinckii* gene lowers the amount of ethanol produced as a byproduct in BDO-producing organisms. Also, a codon-optimized version of this gene expresses very well in *E. coli* (Sivaraman et al., *Nucleic Acids Res.* 36:e16 (2008)).

4-hydroxybutanal Reductase.

4-hydroxybutanal reductase activity of adh1 from *Geobacillus thermoglucosidasius* (M10EXG) was utilized. This led to improved BDO production by increasing 4-hydroxybutanal reductase activity over endogenous levels.

Multiple alcohol dehydrogenases were screened for their ability to catalyze the reduction of 4-hydroxybutanal to BDO. Most alcohol dehydrogenases with high activity on butyraldehyde exhibited far lower activity on 4-hydroxybutyraldehyde. One notable exception is the adh1 gene from *Geobacillus thermoglucosidasius* M10EXG (Jeon et al., *J. Biotechnol.* 135:127-133 (2008)) (GNM0084), which exhibits high activity on both 4-hydroxybutanal and butanal.

The native gene sequence and encoded protein sequence if the adh1 gene from *Geobacillus thermoglucosidasius* are shown in FIG. 31. The *G. thermoglucosidasius* ald1 gene was expressed in *E. coli*.

The Adh1 enzyme (084) expressed very well from its native gene in *E. coli* (see FIG. 32A). In ADH enzyme assays, the *E. coli* expressed enzyme showed very high reductive activity when butyraldehyde or 4HB-aldehyde were used as the substrates (see FIG. 32B). The Km values determined for these substrates were 1.2 mM and 4.0 mM, respectively. These activity values showed that the Adh1 enzyme was the most active on reduction of 4HB-aldehyde of all the candidates tested.

The 084 enzyme was tested for its ability to boost BDO production when coupled with the *C. beijerinckii* ald. The 084 gene was inserted behind the *C. beijerinckii* ald variant 025B gene to create a synthetic operon that results in coupled expression of both genes. Similar constructs linked 025B with other ADH candidate genes, and the effect of including each ADH with 025B on BDO production was tested. The host strain used was ECKh-459 (ΔadhE ldhA ΔpflB ΔlpdA::fnr-pflB6-K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd fimD:: *C. acetobutylicum* buk1, *C. acetobutylicum* ptb), which contains the remainder of the BDO pathway on the chromosome. The 084 ADH expressed in conjunction with 025B showed the highest amount of BDO (right arrow in FIG. 33) when compared with 025B only (left arrow in FIG. 33) and in conjunction with endogenous ADH functions. It also produced more BDO than did other ADH enzymes when paired with 025B, indicated as follows: 026A-C, codon-optimized variants of *Clostridium acetobutylicum* butanol dehydrogenase; 050, *Zymomonas mobilis* alcohol dehydrogenase I; 052, *Citrobacter freundii* 1,3-propanediol dehydrogenase; 053, *Lactobacillus brevis* 1,3-propanediol dehydrogenase; 057, *Bacteroides fragilis* lactaldehyde reductase; 058, *E. coli* 1,3-propanediol dehydrogenase; 071, *Bacillus subtilis* 168 alpha-ketoglutarate semialdehyde dehydrogenase. The constructs labeled "PT5lacO" are those in which the genes are driven by the PT5lacO promoter. In all other cases, the PA1lacO-1 promoter was used. This shows that inclusion of the 084 ADH in the BDO pathway increased BDO production.

Example XIV

BDO Producing Strains Expressing Pyruvate Dehydrogenase

This example describes the utilization of pyruvate dehydrogenase (PDH) to enhance BDO production. Heterologous expression of the *Klebsiella pneumonia* lpdA gene was used to enhance BDO production.

Computationally, the NADH-generating conversion of pyruvate to acetyl-CoA is required to reach the maximum theoretical yield of 1,4-butanediol (see also WO2008/115840, WO 2009/023493, U.S. publication 2009/0047719, U.S. publication 2009/0075351; WO 2008/018930; Kim et al., *Appl. Environ. Microbiol.* 73:1766-1771 (2007); Kim et al., *J. Bacteriol.* 190:3851-3858 (2008); Menzel et al., *J. Biotechnol.* 56:135-142 (1997)). Lack of PDH activity was shown to reduce the maximum anaerobic theoretical yield of BDO by 11% if phosphoenolpyruvate carboxykinase (PEPCK) activity cannot be attained and by 3% if PEPCK activity can be attained. More importantly, however, absence of PDH activity in the OptKnock strain #439, described in WO 2009/023493 and U.S. publication 2009/0047719, which has the knockout of ADHEr, ASPT, LDH_D, MDH and PFLi, would reduce the maximum anaerobic yield of BDO by 54% or by 43% if PEPCK activity is absent or present, respectively. In the presence of an external electron acceptor, lack of PDH activity would reduce the maximum yield of the knockout strain by 10% or by 3% assuming that PEPCK activity is absent or present, respectively.

PDH is one of the most complicated enzymes of central metabolism and is comprised of 24 copies of pyruvate decarboxylase (E1) and 12 molecules of dihydrolipoyl dehydrogenase (E3), which bind to the outside of the dihydrolipoyl transacetylase (E2) core. PDH is inhibited by high NADH/NAD, ATP/ADP, and Acetyl-CoA/CoA ratios. The enzyme naturally exhibits very low activity under oxygen-limited or anaerobic conditions in organisms such as *E. coli* due in large part to the NADH sensitivity of E3, encoded by lpdA. To this end, an NADH-insensitive version of the lpdA gene from *Klebsiella pneumonia* was cloned and expressed to increase the activity of PDH under conditions where the NADH/NAD ratio is expected to be high.

Replacement of the Native lpdA.

The pyruvate dehydrogenase operon of *Klebsiella pneumoniae* is between 78 and 95% identical at the nucleotide level to the equivalent operon of *E. coli*. It was shown previously that *K. pneumoniae* has the ability to grow anaerobically in presence of glycerol (Menzel et al., *J. Biotechnol.* 56:135-142 (1997); Menzel et al., *Biotechnol. Bioeng.* 60:617-626 (1998)). It has also been shown that two mutations in the lpdA gene of the operon of *E. coli* would increase its ability to grow anaerobically (Kim et al., *Appl. Environ. Microbiol.* 73:1766-1771 (2007); Kim et al., *J. Bacteriol.* 190:3851-3858 (2008)). The lpdA gene of *K. pneumonia* was amplified by PCR using genomic DNA (ATCC700721D) as template and the primers KP-lpdA-Bam (5'-acacgcggatccaacgtcccgg-3')(SEQ ID NO:12) and KP-lpdA-Nhe (5'-agcggctccgctagccgcttatg-3')(SEQ ID NO:13). The resulting fragment was cloned into the vector pCR-BluntII-TOPO (Invitrogen; Carlsbad Calif.), leading to plasmid pCR-KP-lpdA.

The chromosomal gene replacement was performed using a non-replicative plasmid and the sacB gene from *Bacillus subtilis* as a means of counterselection (Gay et al., *J. Bacteriol*. 153:1424-1431 (1983)). The vector used is pRE118 (ATCC87693) deleted of the oriT and IS sequences, which is 3.6 kb in size and carrying the kanamycin resistance gene. The sequence was confirmed, and the vector was called pRE118-V2 (see FIG. 34).

The *E. coli* fragments flanking the lpdA gene were amplified by PCR using the combination of primers: EC-aceF-Pst (5'-aagccgttgctgcagctcttgagc-3')(SEQ ID NO:14)+EC-aceF-Bam2 (5'-atctccggcggtcggatccgtcg-3')(SEQ ID NO:15) and EC-yacH-Nhe (5'-aaagcggctagccacgccgc-3')(SEQ ID NO:16)+EC-yacH-Kpn (5'-attacacgaggtacccaacg-3')(SEQ ID NO:17). A BamHI-XbaI fragment containing the lpdA gene of *K. pneumonia* was isolated from plasmid pCR-KP-lpdA and was then ligated to the above *E. coli* fragments digested with PstI+BamHI and NheI-KpnI respectively, and the pRE118-V2 plasmid digested with KpnI and PstI. The resulting plasmid (called pRE118-M2.1 lpdA yac) was subjected to Site Directed Mutagenesis (SDM) using the combination of primers KP-lpdA-HisTyr-F (5'-atgctggcgta-caaaggtgtcc-3')(SEQ ID NO:18) and (5'-ggacacctttgtacgccagcat-3')(SEQ ID NO:19) for the mutation of the His 322 residue to a Tyr residue or primers KP-lpdA-GluLys-F (5'-atcgcctacactaaaccagaagtgg-3')(SEQ ID NO:20) and KP-lpdA-GluLys-R (5'-ccacttctggtttagtgtaggc-gat-3')(SEQ ID NO:21) for the mutation of the residue Glu 354 to Lys residue. PCR was performed with the Polymerase Pfu Turbo (Stratagene; San Diego Calif.). The sequence of the entire fragment as well as the presence of only the desired mutations was verified. The resulting plasmid was introduced into electro competent cells of *E. coli* ΔadhE::Frt-ΔldhA::Frt by transformation. The first integration event in the chromosome was selected on LB agar plates containing Kanamycin (25 or 50 mg/L). Correct insertions were verified by PCR using 2 primers, one located outside the region of insertion and one in the kanamycin gene (5'-aggcagttccataggatggc-3')(SEQ ID NO:22). Clones with the correct insertion were selected for resolution. They were sub-cultured twice in plain liquid LB at the desired temperature and serial dilutions were plated on LB-no salt-sucrose 10% plates. Clones that grew on sucrose containing plates were screened for the loss of the kanamycin resistance gene on LB-low salt agar medium and the lpdA gene replacement was verified by PCR and sequencing of the encompassing region. Sequence of the insertion region was verified, and is as described below. One clone (named 4-4-P1) with mutation Glu354Lys was selected. This clone was then transduced with P1 lysate of *E. coli* ΔPflB::Frt leading to strain ECKh-138 (ΔadhE ΔldhA ΔpflB ΔlpdA::K.p.lpdA322).

The sequence of the ECKh-138 region encompassing the aceF and lpdA genes is shown in FIG. 35. The *K. pneumonia* lpdA gene is underlined, and the codon changed in the Glu354Lys mutant shaded. The protein sequence comparison of the native *E. coli* lpdA and the mutant *K. pneumonia* lpdA is shown in FIG. 36.

To evaluate the benefit of using *K. pneumoniae* lpdA in a BDO production strain, the host strains AB3 and ECKh-138 were transformed with plasmids expressing the entire BDO pathway from strong, inducible promoters. Specifically, *E. coli* sucCD, *P. gingivalis* sucD, *P. gingivalis* 4hbd were expressed on the medium copy plasmid pZA33, and *P. gingivalis* Cat2 and *C. acetobutylicum* AdhE2 were expressed on the high copy plasmid pZE13. These plasmids have been described in the literature (Lutz and H. Bujard, Nucleic Acids Res 25:1203-1210 (1997)), and their use for BDO pathway expression is described in Example XIII and WO2008/115840.

Cells were grown anaerobically at 37° C. in M9 minimal medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) supplemented with 20 g/L glucose, 100 mM 3-(N-morpholino)propanesulfonic acid (MOPS) to improve the buffering capacity, 10 µg/mL thiamine, and the appropriate antibiotics. Microaerobic conditions were established by initially flushing capped anaerobic bottles with nitrogen for 5 minutes, then piercing the septum with a 23G needle following inoculation. The needle was kept in the bottle during growth to allow a small amount of air to enter the bottles. 0.25 mM IPTG was added when OD600 reached approximately 0.2 to induce the pathway genes, and samples taken for analysis every 24 hours following induction. The culture supernatants were analyzed for BDO, 4HB, and other byproducts as described in Example II and in WO2008/115840. BDO and 4HB production in ECKh-138 was significantly higher after 48 hours than in AB3 or the host used in previous work, MG1655 ΔldhA (FIG. 37).

PDH Promoter Replacement.

It was previously shown that the replacement of the pdhR repressor by a transcriptional fusion containing the Fnr binding site, one of the pflB promoters, and its ribosome binding site (RBS), thus leading to expression of the aceEF-lpd operon by an anaerobic promoter, should increase pdh activity anaerobically (Zhou et al., *Biotechnol. Lett*. 30:335-342 (2008)). A fusion containing the Fnr binding site, the pflB-p6 promoter and an RBS binding site were constructed by overlapping PCR. Two fragments were amplified, one using the primers aceE-upstream-RC (5'-tgacatgtaacacc-taccttctgtgcctgtgccagtggttgctgtgatatagaag-3')(SEQ ID NO:23) and pflBp6-Up-Nde (5'-ataataatacatatgaac-catgcgagttacgggcctataagccaggcg-3')(SEQ ID NO:24) and the other using primers aceE-EcoRV-EC (5'-agtttttcgatatctg-catcagacaccggcacattgaaacgg-3')(SEQ ID NO:25) and aceE-upstream (5'-ctggcacaggcacagaaggtaggtgttacatgtcagaacgtt-tacacaatgacgtggatc-3')(SEQ ID NO:26). The tw fragments were assembled by overlapping PCR, and the final DNA fragment was digested with the restriction enzymes NdeI and BamHI. This fragment was subsequently introduced upstream of the aceE gene of the *E. coli* operon using pRE118-V2 as described above. The replacement was done in strains ECKh-138 and ECKh-422. The nucleotide sequence encompassing the 5' region of the aceE gene was verified and is shown in FIG. 37. FIG. 37 shows the nucleotide sequence of 5' end of the aceE gene fused to the pflB-p6 promoter and ribosome binding site (RBS). The 5' italicized sequence shows the start of the aroP gene, which is transcribed in the opposite direction from the pdh operon. The 3' italicized sequence shows the start of the aceE gene. In upper case: pflB RBS. Underlined: FNR binding site. In bold: pflB-p6 promoter sequence.

lpdA Promoter Replacement.

The promoter region containing the fnr binding site, the pflB-p6 promoter and the RBS of the pflB gene was amplified by PCR using chromosomal DNA template and primers aceF-pflBp6-fwd (5'-agacaaatcggttgccgtttgttaagccaggcgaga-tatgatctatatc-3')(SEQ ID NO:27) and lpdA-RB S-B-rev (5'-gagttttgatttcagtactcatcatgtaacacctaccttcttgctgtgatatag-3')

(SEQ ID NO:28). Plasmid 2-4a was amplified by PCR using primers B-RBS-lpdA fwd (5'-ctatatcacagcaagaaggtaggtgtta-catgatgagtactgaaatcaaaactc-3')(SEQ ID NO:29) and pflBp6-aceF-rev (5'-gatatagatcatatctcgcctggcttaacaaacggcaaccgat-ttgtct-3')(SEQ ID NO:30). The two resulting fragments were assembled using the BPS cloning kit (BPS Bioscience; San Diego Calif.). The resulting construct was sequenced verified and introduced into strain ECKh-439 using the pRE118-V2 method described above. The nucleotide sequence encompassing the aceF-lpdA region in the resulting strain ECKh-456 is shown in FIG. 39.

Figure 40:
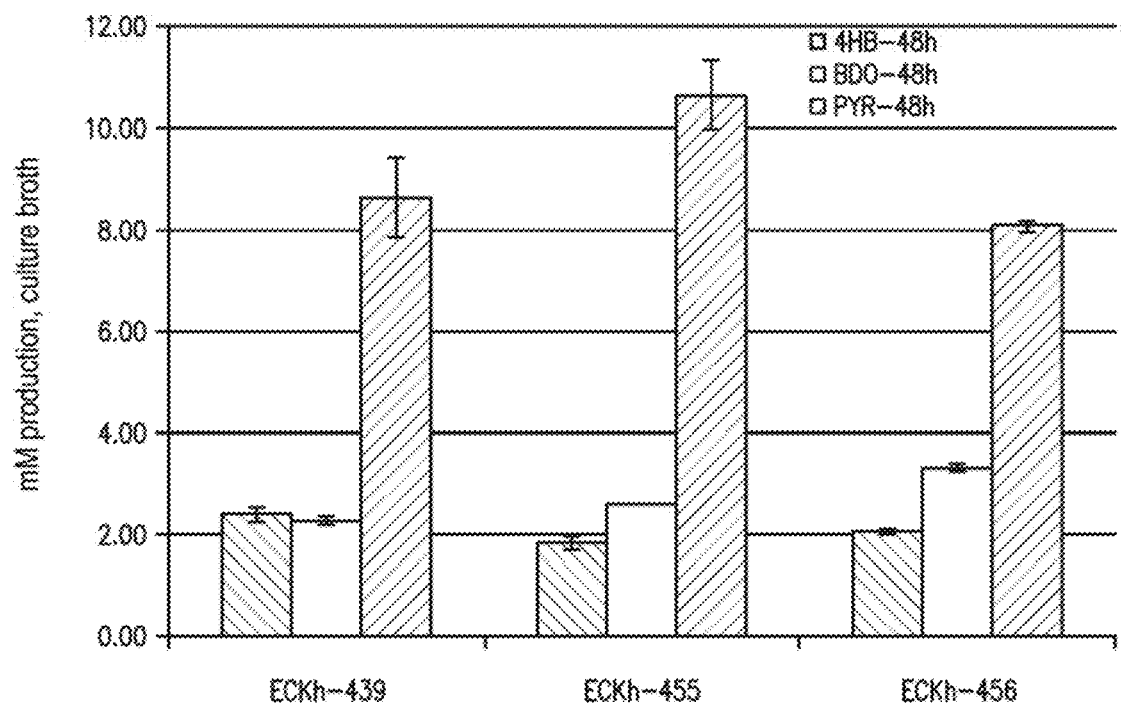
FIG. 40 shows the production of 4-hydroxybutyrate, BDO and pyruvate (left to right bars, respectively) for each of strains ECKh-439, ECKh-455 and ECKh-456.

The host strain ECKh-439 (ΔadhE ΔldhA ΔpflB ΔlpdA:: K.p.lpdA322 Δmdh ΔarcA gltAR163L ackA fimD:: *E. coli* sucCD, *P. gingivalis* sucD, *P. gingivalis* 4hbd fimD:: *M. bovis* sucA, *C. kluyveri* 4hbd), the construction of which is described below, and the pdhR and lpdA promoter replacement derivatives ECKh-455 and ECKh-456, were tested for BDO production. The strains were transformed with pZS*13 containing *P. gingivalis* Cat2 and *C. beijerinckii* Ald to provide a complete BDO pathway. Cells were cultured in M9 minimal medium supplemented with 20 g/L glucose as described above. 48 hours after induction with 0.2 mM IPTG, the concentrations of BDO, 4HB, and pyruvate were as shown in FIG. 40. The promoter replacement strains produce slightly more BDO than the isogenic parent.

These results demonstrated that expression of pyruvate dehydrogenase increased production of BDO in BDO producing strains.

Example XV

BDO Producing Strains Expressing Citrate Synthase and Aconitase

This example describes increasing activity of citrate synthase and aconitase to increase production of BDO. An R163L mutation into gltA was found to improve BDO production. Additionally, an arcA knockout was used to improve BDO production.

Computationally, it was determined that flux through citrate synthase (CS) and aconitase (ACONT) is required to reach the maximum theoretical yield of 1,4-butanediol (see also WO2008/115840, WO 2009/023493, U.S. publication 2009/0047719, U.S. publication 2009/0075351). Lack of CS or ACONT activity would reduce the maximum theoretical yield by 14% under anaerobic conditions. In the presence of an external electron acceptor, the maximum yield is reduced by 9% or by 6% without flux through CS or ACONT assuming the absence or presence of PEPCK activity, respectively. As with pyruvate dehydrogenase (PDH), the importance of CS and ACONT is greatly amplified in the knockout strain background in which ADHEr, ASPT, LDH_D, MDH and PFLi are knocked out (design #439)(see WO 2009/023493 and U.S. publication 2009/0047719, which is incorporated herein by reference).

The minimal OptKnock strain design described in WO 2009/023493 and U.S. publication 2009/0047719 had one additional deletion beyond ECKh-138, the mdh gene, encoding malate dehydrogenase. Deletion of this gene is intended to prevent flux to succinate via the reductive TCA cycle. The mdh deletion was performed using the λ red homologous recombination method (Datsenko and Wanner, *Proc. Natl. Acad. Sci. USA* 97:6640-6645 (2000)). The following oligonucleotides were used to PCR amplify the chloramphenicol resistance gene (CAT) flanked by FRT sites from pKD3:

```
                                        (SEQ ID NO: 31)
S-mdh-Kan 5' - TAT TGT GCA TAC AGA TGA ATT TTT

ATG CAA ACA GTC AGC CCT GAA GAA GGG TGT AGG CTG

GAG CTG CTT C - 3'

(SEQ ID NO: 32)
AS-mdh-Kan 5' - CAA AAA ACC GGA GTC TGT GCT CCG

GTT TTT TAT TAT CCG CTA ATC AAT TAC ATA TGA ATA

TCC TCC TTA G - 3'.
```

Figure 41A:
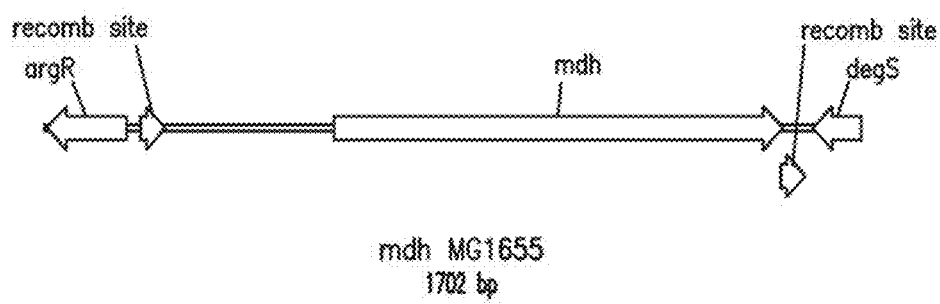
FIG. 41A shows a schematic of the recombination sites for deletion of the mdh gene.
Figure 41B:
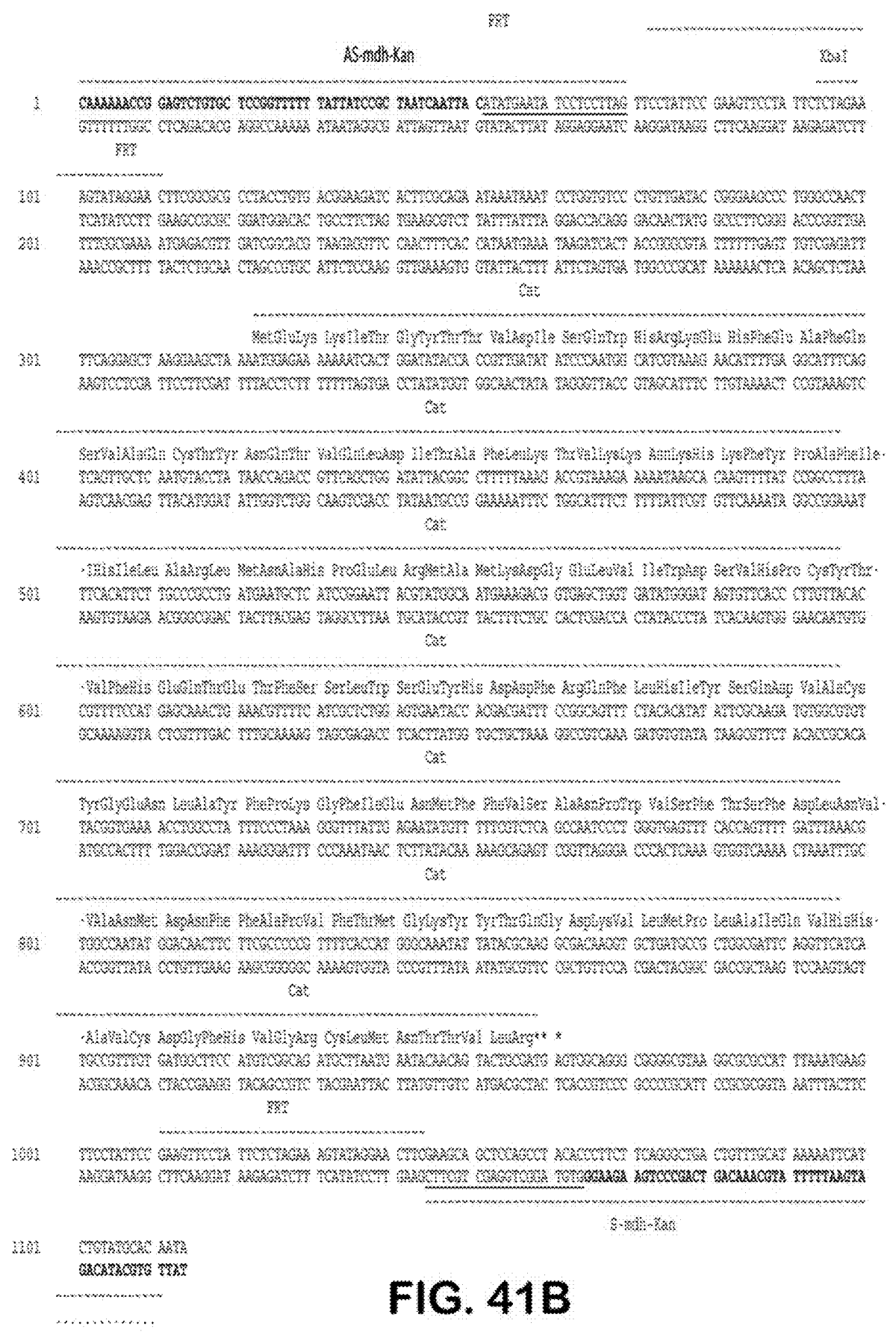

Underlined regions indicate homology to pKD3 plasmid and bold sequence refers to sequence homology upstream and downstream of the mdh ORF. After purification, the PCR product was electroporated into ECKh-138 electrocompetent cells that had been transformed with pRedET (tet) and prepared according to the manufacturer's instructions (gen-ebridges.com/gb/pdf/K001%20Q%20E%20BAC%20Modification%20Kit-version2.6-2007-screen.pdf). The PCR product was designed so that it integrated into the ECKh-138 genome at a region upstream of the mdh gene, as shown in FIG. 41.

Recombinants were selected for chloramphenicol resistance and streak purified. Loss of the mdh gene and insertion of CAT was verified by diagnostic PCR. To remove the CAT gene, a temperature sensitive plasmid pCP20 containing a FLP recombinase (Datsenko and Wanner, *Proc. Natl. Acad. Sci. USA* 97:6640-6645 (2000)) was transformed into the cell at 30° C. and selected for ampicillin resistance (AMP). Transformants were grown nonselectively at 42° C. overnight to thermally induce FLP synthesis and to cause lose of the plasmid. The culture was then streak purified, and individual colonies were tested for loss of all antibiotic resistances. The majority lost the FRT-flanked resistance gene and the FLP helper plasmid simultaneously. There was also a "FRT" scar leftover. The resulting strain was named ECKh-172.

CS and ACONT are not highly active or highly expressed under anaerobic conditions. To this end, the arcA gene, which encodes for a global regulator of the TCA cycle, was deleted. ArcA works during microaerobic conditions to induce the expression of gene products that allow the activity of central metabolism enzymes that are sensitive to low oxygen levels, aceE, pflB and adhE. It was shown that microaerobically, a deletion in arcA/arcB increases the specific activities of ldh, icd, gltA, mdh, and gdh genes (Salmon et al., *J. Biol. Chem.* 280:15084-15096 (2005); Shalel-Levanon et al., *Biotechnol. Bioeng.* 92(2):147-159 (2005). The upstream and downstream regions of the arcA gene of *E. coli* MG1655 were amplified by PCR using primers ArcA-up-EcoRI (5'-ataataatagaattcgtttgctacctaaattgc-caactaaatcgaaacagg-3')(SEQ ID NO:33) with ArcA-up-KpnI (5'-tattattatggtaccaatatcatgcagcaaacggtgcaacattgccg-3') (SEQ ID NO:34) and ArcA-down-EcoRI (5'-tgatctggaagaat-tcatcggctttaccaccgtcaaaaaaaacggcg-3')(SEQ ID NO:35) with ArcA-down-PstI (5'-ataaaaccctgcagcggaaacgaagttttatc-catttttggttacctg-3')(SEQ ID NO:36), respectively. These fragments were subsequently digested with the restriction enzymes EcoRI and KpnI (upstream fragment) and EcoRI and PstI (downstream). They were then ligated into the pRE118-V2 plasmid digested with PstI and KpnI, leading to plasmid pRE118-ΔarcA. The sequence of plasmid pRE118-ΔarcA was verified. pRE118-ΔarcA was introduced into electro-competent cells of *E. coli* strain ECKh-172 (ΔadhE ΔldhA ΔpflB ΔlpdA::K.p.lpdA322 Δmdh). After integration and resolution on LB-no salt-sucrose plates as described above, the deletion of the arcA gene in the chromosome of the resulting strain ECKh-401 was verified by sequencing and is shown in FIG. 42.

The gltA gene of *E. coli* encodes for a citrate synthase. It was previously shown that this gene is inhibited allosterically by NADH, and the amino acids involved in this inhibition have been identified (Pereira et al., *J. Biol. Chem.* 269(1):412-417 (1994); Stokell et al., *J. Biol. Chem.* 278 (37):35435-35443 (2003)). The gltA gene of *E. coli* MG1655 was amplified by PCR using primers gltA-up (5'-ggaagagaggctggtacccagaagccacagcagga-3')(SEQ ID NO:37) and gltA-PstI (5'-gtaatcactgcgtaagcgc-catgccccggcgttaattc-3')(SEQ ID NO:38). The amplified fragment was cloned into pRE118-V2 after digestion with KpnI and PstI. The resulting plasmid was called pRE118-gltA. This plasmid was then subjected to site directed mutagenesis (SDM) using primers R163L-f (5'-at-tgccgcgttcctcctgctgtcga-3')(SEQ ID NO:39) and R163L-r (5'-cgacagcaggaggaacgcggcaat-3')(SEQ ID NO:40) to change the residue Arg 163 to a Lys residue. The sequence of the entire fragment was verified by sequencing. A variation of the λ red homologous recombination method (Datsenko and Wanner, *Proc. Natl. Acad. Sci. USA* 97:6640-6645 (2000)) was used to replace the native gltA gene with the R163L mutant allele without leaving a Frt scar. The general recombination procedure is the same as used to make the mdh deletion described above. First, the strain ECKh-172 was made streptomycin resistant by introducing an rpsL null mutation using the λ red homologous recombination method. Next, a recombination was done to replace the entire wild-type gltA coding region in this strain with a cassette comprised of a kanamycin resistance gene (kanR) and a wild-type copy of the *E. coli* rpsL gene. When introduced into an *E. coli* strain harboring an rpsL null mutation, the cassette causes the cells to change from resistance to the drug streptomycin to streptomycin sensitivity. DNA fragments were then introduced that included each of the mutant versions of the gltA gene along with appropriate homologous ends, and resulting colony growth was tested in the presence of streptomycin. This selected for strains in which the kanR/rpsL cassette had been replaced by the mutant gltA gene. Insertion of the mutant gene in the correct locus was confirmed by PCR and DNA sequencing analyses. The resulting strain was called ECKh-422, and has the genotype ΔadhE ΔldhA ΔpflB ΔlpdA::K.p.lpdA322 Δmdh ΔarcA gltAR163L. The region encompassing the mutated gltA gene of strain ECKh-422 was verified by sequencing, as shown in FIG. 43.

Crude extracts of the strains ECKh-401 and the gltAR163L mutant ECKh-422 were then evaluated for citrate synthase activity. Cells were harvested by centrifugation at 4,500 rpm (Beckman-Coulter, Allegera X-15R; Fullerton Calif.) for 10 min. The pellets were resuspended in 0.3 mL BugBuster (Novagen/EMD; San Diego Calif.) reagent with benzonase and lysozyme, and lysis proceeded for 15 minutes at room temperature with gentle shaking. Cell-free lysate was obtained by centrifugation at 14,000 rpm (Eppendorf centrifuge 5402; Hamburg Germany) for 30 min at 4° C. Cell protein in the sample was determined using the method of Bradford (Bradford, *Anal. Biochem.* 72:248-254 (1976)).

Citrate synthase activity was determined by following the formation of free coenzyme A (HS-CoA), which is released from the reaction of acetyl-CoA with oxaloacetate. The free thiol group of HS-CoA reacts with 5,5'-dithiobis-(2-nitrobenzoic acid) (DTNB) to form 5-thio-2-nitrobenzoic acid (TNB). The concentration of TNB is then monitored spectrophotometrically by measuring the absorbance at 410 nm (maximum at 412 nm). The assay mixture contained 100 mM Tris/HCl buffer (pH 7.5), 20 mM acetyl-CoA, 10 mM DTNB, and 20 mM oxaloacetate. For the evaluation of NADH inhibition, 0.4 mM NADH was also added to the reaction. The assay was started by adding 5 microliters of the cell extract, and the rate of reaction was measured by following the absorbance change over time. A unit of specific activity is defined as the μmol of product converted per minute per mg protein.

FIG. 44 shows the citrate synthase activity of wild type gltA gene product and the R163L mutant. The assay was performed in the absence or presence of 0.4 mM NADH.

Strains ECKh-401 and ECKh-422 were transformed with plasmids expressing the entire BDO pathway. *E. coli* sucCD, *P. gingivalis* sucD, *P. gingivalis* 4hbd, and *M. bovis* sucA were expressed on the low copy plasmid pZS*13, and *P. gingivalis* Cat2 and *C. acetobutylicum* AdhE2 were expressed on the medium copy plasmid pZE23. Cultures of these strains were grown microaerobically in M9 minimal medium supplemented with 20 g/L glucose and the appropriate antibiotics as described above. The 4HB and BDO concentrations at 48 hours post-induction averaged from duplicate cultures are shown in FIG. 45. Both are higher in ECKh-422 than in ECKh-401, demonstrating that the enhanced citrate synthase activity due to the gltA mutation results in increased flux to the BDO pathway.

Figure 46:
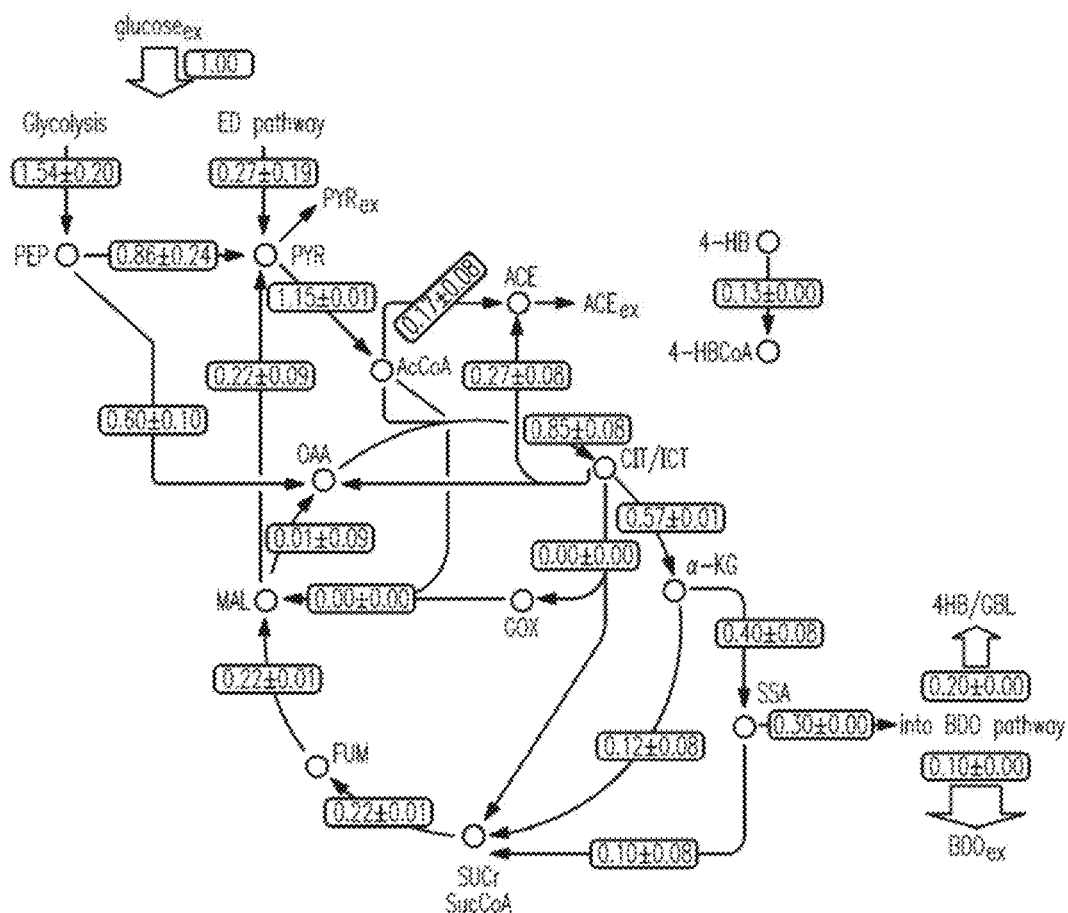
FIG. 46 shows central metabolic fluxes and associated 95% confidence intervals from metabolic labeling experiments. Values are molar fluxes normalized to a glucose uptake rate of 1 mmol/hr. The result indicates that carbon flux is routed through citrate synthase in the oxidative direction and that most of the carbon enters the BDO pathway rather than completing the TCA cycle.

The host strain modifications described in this section were intended to redirect carbon flux through the oxidative TCA cycle, which is consistent with the OptKnock strain design described in WO 2009/023493 and U.S. publication 2009/0047719. To demonstrate that flux was indeed routed through this pathway, $^{13}$C flux analysis was performed using the strain ECKh-432, which is a version of ECKh-422 in which the upstream pathway is integrated into the chromosome (as described in Example XVII). To complete the BDO pathway, *P. gingivalis* Cat2 and *C. beijerinckii* Ald were expressed from pZS*13. Four parallel cultures were grown in M9 minimal medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) containing 4 g/L total glucose of four different labeling ratios ($^{1-13}$C, only the first carbon atom in the glucose molecule is labeled with $^{13}$C; uniform-$^{13}$C, all carbon atoms are $^{13}$C):

1. 80 mol % unlabeled, 20 mol % uniform-$^{13}$C
2. 10 mol % unlabeled, 90 mol % uniform-$^{13}$C
3. 90 mol % $^{1-13}$C, 10 mol % uniform-$^{13}$C
4. 40 mol % $^{1-13}$C, 60 mol % uniform-$^{13}$C Parallel unlabeled cultures were grown in duplicate, from which frequent samples were taken to evaluate growth rate, glucose uptake rate, and product formation rates. In late exponential phase, the labeled cultures were harvested, the protein isolated and hydrolyzed to amino acids, and the label distribution of the amino acids analyzed by gas chromatography-mass spectrometry (GCMS) as described previously (Fischer and Sauer, *Eur. J. Biochem.* 270:880-891 (2003)). In addition, the label distribution of the secreted 4HB and BDO in the broth from the labeled cultures was analyzed by GCMS as described in WO2008115840. This data was collectively used to calculate the intracellular flux distribution using established methods (Suthers et al., *Metab. Eng.* 9:387-405 (2007)). The resulting central metabolic fluxes and associated 95% confidence intervals are shown in FIG. 46. Values are molar fluxes normalized to a glucose uptake rate of 1 mmol/hr. The result indicates that carbon flux is routed through citrate synthase in the oxidative direction, and that most of the carbon enters the BDO pathway rather than completing the TCA cycle. Furthermore, it confirms there is essentially no flux between malate and oxaloacetate due to the mdh deletion in this strain.

Figure 47A:
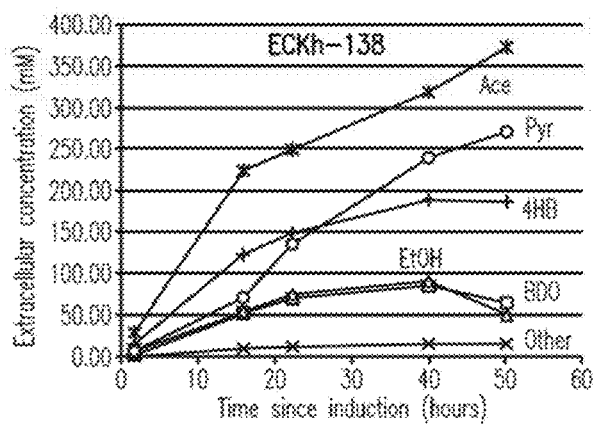
FIGS. 47A and 47B show extracellular product formation for strains ECKh-138 (FIG. 47A) and ECKh-422 (FIG. 47B), both expressing the entire BDO pathway on plasmids. The products measured were acetate (Ace), pyruvate (Pyr), 4-hydroxybutyrate (4HB), 1,4-butanediol (BDO), ethanol (EtOH), and other products, which include gamma-butyrolactone (GBL), succinate, and lactate.
Figure 47B:
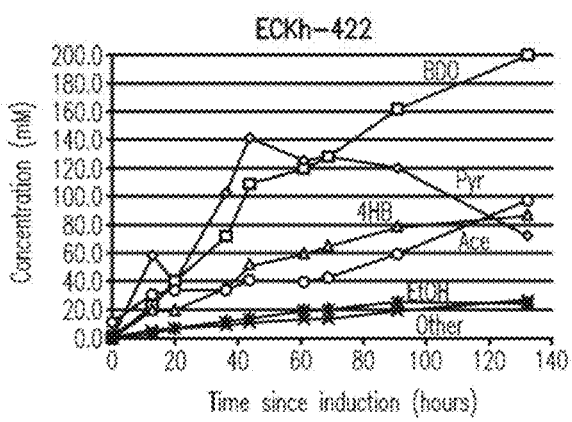

The advantage of using a knockout strain such as strains designed using OptKnock for BDO production (see WO 2009/023493 and U.S. publication 2009/0047719) can be observed by comparing typical fermentation profiles of ECKh-422 with that of the original strain ECKh-138, in which BDO is produced from succinate via the reductive TCA cycle (see FIG. 47). Fermentations were performed with 1 L initial culture volume in 2 L Biostat B+ bioreactors (Sartorius; Cedex France) using M9 minimal medium supplemented with 20 g/L glucose. The temperature was controlled at 37° C., and the pH was controlled at 7.0 using 2 M $NH_4OH$ or $Na_2CO_3$. Cells were grown aerobically to an OD600 of approximately 10, at which time the cultures were induced with 0.2 mM IPTG. One hour following induction, the air flow rate was reduced to 0.02 standard liters per minute for microaerobic conditions. The agitation rate was set at 700 rpm. Concentrated glucose was fed to maintain glucose concentration in the vessel between 0.5 and 10 g/L. Both strains were transformed with plasmids bearing the entire BDO pathway, as in the examples above. In ECKh-138, acetate, pyruvate, and 4HB dominate the fermentation, while with ECKh-422 BDO is the major product.

Example XVI

BDO Strains Expression Phosphoenolpyruvate Carboxykinase

This example describes the utilization of phosphoenolpyruvate carboxykinase (PEPCK) to enhance BDO production. The *Haemophilus* influenza PEPCK gene was used for heterologous expression.

Computationally, it was demonstrated that the ATP-generating conversion of oxaloacetate to phosphoenolpyruvate is required to reach the maximum theoretical yield of 1,4-butanediol (see also WO2008/115840, WO 2009/023493, U.S. publication 2009/0047719, U.S. publication 2009/0075351). Lack of PEPCK activity was shown to reduce the maximum theoretical yield of BDO by 12% assuming anaerobic conditions and by 3% assuming an external electron acceptor such as nitrate or oxygen is present.

In organisms such as *E. coli*, PEPCK operates in the gluconeogenic and ATP-consuming direction from oxaloacetate towards phosphoenolpyruvate. It has been hypothesized that kinetic limitations of PEPCK of *E. coli* prevent it from effectively catalyzing the formation of oxaloacetate from PEP. PEP carboxylase (PPC), which does not generate ATP but is required for efficient growth, is naturally utilized by *E. coli* to form oxaloacetate from phosphoenolpyruvate. Therefore, three non native PEPCK enzymes (Table 26) were tested for their ability to complement growth of a PPC mutant strain of *E. coli* in glucose minimal media.

TABLE 26

Sources of phosphoenolpyruvate carboxykinase sequences.

| PEPCK Source Strain | Accession Number, GenBank Reference Sequence |
|---|---|
| Haemophilus influenza | NC_000907.1 |
| Actinobacillus succinogenes | YP_001343536.1 |
| Mannheimia succiniciproducens | YP_089485.1 |

Growth complementation studies involved plasmid based expression of the candidate genes in Δppc mutant *E. coli* JW3978 obtained from the Keio collection (Baba et al., Molecular Systems Biology 2:2006.0008 (2006)). The genes were cloned behind the PA1lacO-1 promoter in the expression vectors pZA23 (medium copy) and pZE13 (high copy). These plasmids have been described previously (Lutz and Bujard, *Nucleic Acids Res.* 25:1203-1210 (1997)), and their use in expression BDO pathway genes has been described previously in WO2008115840.

Pre-cultures were grown aerobically in M9 minimal media with 4 g/L glucose. All pre-cultures were supplemented with aspartate (2 mM) to provide the Δppc mutants with a source for generating TCA cycle intermediates independent of PEPCK expression. M9 minimal media was also used in the test conditions with 4 g/L glucose, but no aspartate was added and IPTG was added to 0.5 mM. Table 27 shows the results of the growth complementation studies.

TABLE 27

Complementation of Δppc mutants with PEPCK from H. influenzae, A. succinogenes and M. succinoproducens when expressed from vectors pZA23 or pZE13.

| PEPCK Source Strain | Vector | Time (h) | $OD_{600}$ |
|---|---|---|---|
| H. influenzae | pZA23BB | 40 | 0.950 |
| Δppc Control | pZA23BB | 40 | 0.038 |
| A. succinogenes | pZA23BB | 40 | 0.055 |
| M. succinoproducens | pZA23BB | 40 | 0.214 |
| A. succinogenes | pZE13BB | 40 | 0.041 |
| M. succinoproducens | pZE13BB | 40 | 0.024 |
| Δppc Control | pZE13BB | 40 | 0.042 |

*Haemophilus* influenza PEPCK was found to complement growth in Δppc mutant *E. coli* best among the genes that were tested in the plasmid based screening. This gene was then integrated into the PPC locus of wild-type *E. coli* (MG1655) using the SacB counter selection method with pRE118-V2 discussed above (Gay et al., *J. Bacteriol.* 153: 1424-1431 (1983)). PEPCK was integrated retaining the *E. coli* native PPC promoter, but utilizing the non-native PEPCK terminator. The sequence of this region following replacement of ppc by *H. influenzae* pepck is shown in FIG. 48. The pepck coding region is underlined.

Figure 49:
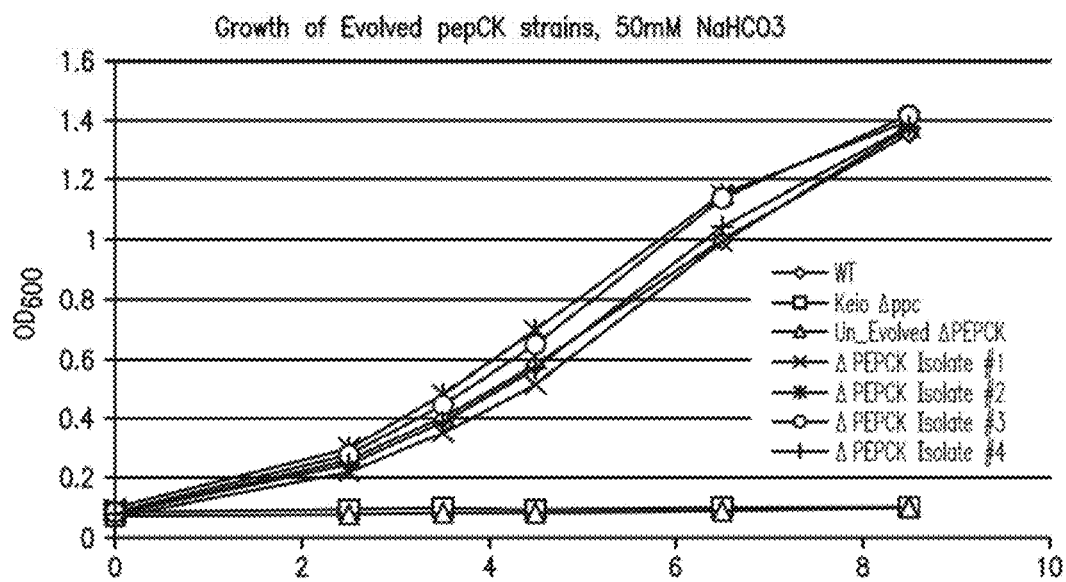
FIG. 49 shows growth of evolved pepCK strains grown in minimal medium containing 50 mM NaHCO$_3$.

Techniques for adaptive evolution were applied to improve the growth rate of the *E. coli* mutant (Δppc::H. inf pepCK). M9 minimal media with 4 g/L glucose and 50 mM sodium bicarbonate was used to culture and evolve this strain in an anaerobic environment. The high sodium bicarbonate concentration was used to drive the equilibrium of the PEPCK reaction toward oxaloacetate formation. To maintain exponential growth, the culture was diluted 2-fold whenever an OD600 of 0.5 was achieved. After about 100 generations over 3 weeks of adaptive evolution, anaerobic growth rates improved from about 8 h to that of wild type, about 2 h. Following evolution, individual colonies were isolated, and growth in anaerobic bottles was compared to that of the initial mutant and wild-type strain (see FIG. 49). M9 medium with 4 g/L glucose and 50 mM sodium bicarbonate was used.

The ppc/pepck gene replacement procedure described above was then repeated, this time using the BDO-producing strains ECKh-432 (ΔadhE ΔldhA ΔpflB ΔlpdA::K.p.lpdA322 Δmdh ΔarcA gltAR163L ΔackA fimD:: E. coli sucCD, P. gingivalis sucD, P. gingivalis 4hbd fimD:: M. bovis sucA, C. kluyveri 4hbd) and ECKh-439 as the hosts. These strains contain the TCA cycle enhancements discussed above as well as the upstream pathway integrated in the chromosome. ECKh-439 is a derivative of ECKh-432 that has the ackA gene deleted, which encodes acetate kinase. This deletion was performed using the sacB counterselection method described above.

Figure 50:
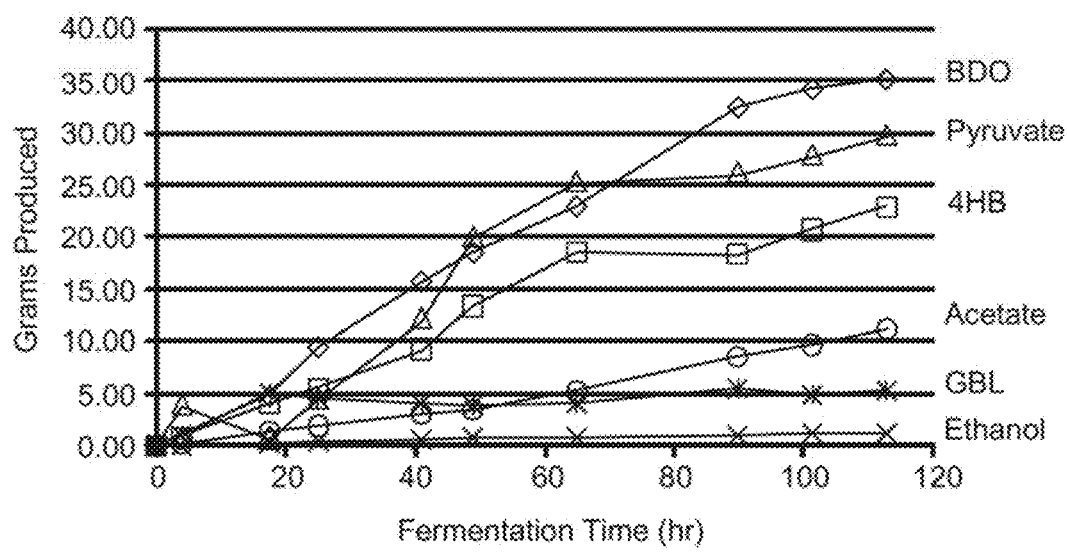
FIG. 50 shows product formation in strain ECKh-453 expressing P. gingivalis Cat2 and C. beijerinckii Ald on the plasmid pZS*13. The products measured were 1,4-butanediol (BDO), pyruvate, 4-hydroxybutyrate (4HB), acetate, γ-butyrolactone (GBL) and ethanol.

The Δppc::H. inf pepCK derivative of ECKh-439, called ECKh-453, was run in a fermentation. The downstream BDO pathway was supplied by pZS*13 containing P. gingivalis Cat2 and C. beijerinckii Ald. This was performed with 1 L initial culture volume in 2 L Biostat B+ bioreactors (Sartorius) using M9 minimal medium supplemented with 20 g/L glucose and 50 mM NaHCO$_3$. The temperature was controlled at 37° C., and the pH was controlled at 7.0 using 2 M NH$_4$OH or Na$_2$CO$_3$. Cells were grown aerobically to an OD600 of approximately 2, at which time the cultures were induced with 0.2 mM IPTG. One hour following induction, the air flow rate was reduced to 0.01 standard liters per minute for microaerobic conditions. The agitation rate was initially set at 700 rpm. The aeration rate was gradually increased throughout the fermentation as the culture density increased. Concentrated glucose solution was fed to maintain glucose concentration in the vessel between 0.5 and 10 g/L. The product profile is shown in FIG. 50. The observed phenotype, in which BDO and acetate are produced in approximately a one-to-one molar ratio, is highly similar to that predicted in WO 2009/023493 for design #439 (ADHEr, ASPT, LDH_D, MDH, PFLi). The deletion targeting the ASPT reaction was deemed unnecessary as the natural flux through aspartate ammonia-lyase is low.

Figure 51:
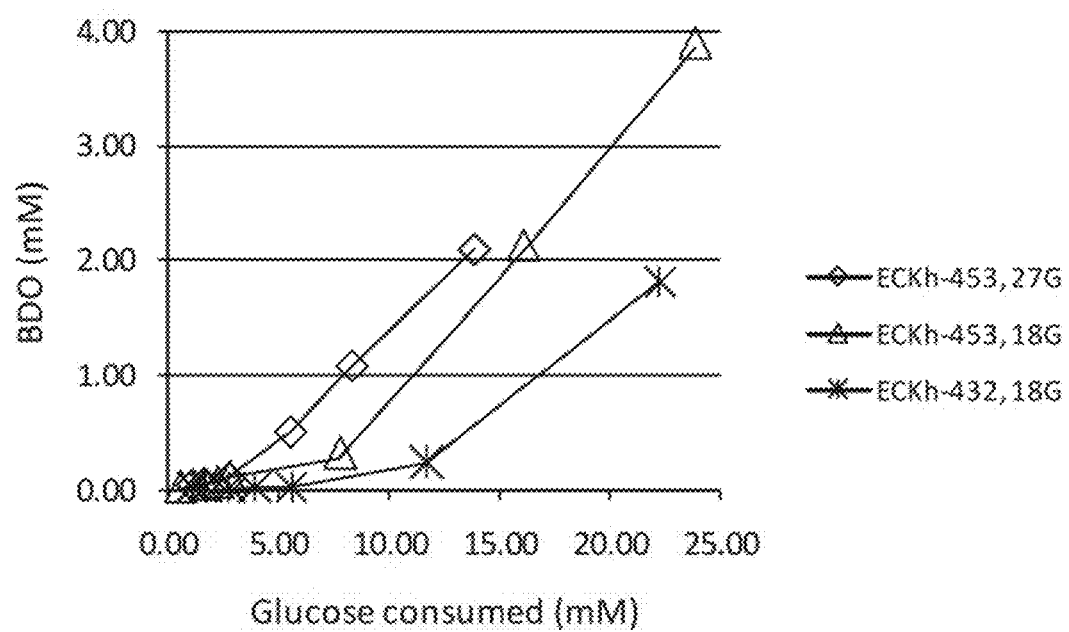
FIG. 51 shows BDO production of two strains, ECKh-453 and ECKh-432. Both contain the plasmid pZS*13 expressing P. gingivalis Cat2 and C. beijerinckii Ald. The cultures were grown under microaerobic conditions, with the vessels punctured with 27 or 18 gauge needles, as indicated.

A key feature of OptKnock strains is that production of the metabolite of interest is generally coupled to growth, and further, that, production should occur during exponential growth as well as in stationary phase. The growth coupling potential of ECKh-432 and ECKh-453 was evaluated by growth in microaerobic bottles with frequent sampling during the exponential phase. M9 medium containing 4 g/L glucose and either 10 mM NaHCO$_3$ (for ECKh-432) or 50 mM NaHCO$_3$ (for ECKh-453) was used, and 0.2 mM IPTG was included from inoculation. 18G needles were used for microaerobic growth of ECKh-432, while both 18G and 27G needles were tested for ECKh-453. The higher gauge needles result in less aeration. As shown in FIG. 51, ECKh-432 does not begin producing BDO until 5 g/L glucose has been consumed, corresponding to the onset of stationary phase. ECKh-453 produces BDO more evenly throughout the experiment. In addition, growth coupling improves as the aeration of the culture is reduced.

Example XVII

Integration of BDO Pathway Encoding Genes at Specific Integration Sites

This example describes integration of various BDO pathway genes into the fimD locus to provide more efficient expression and stability.

The entire upstream BDO pathway, leading to 4HB, has been integrated into the E. coli chromosome at the fimD locus. The succinate branch of the upstream pathway was integrated into the E. coli chromosome using the λ red homologous recombination method (Datsenko and Wanner, Proc. Natl. Acad. Sci. USA 97:6640-6645 (2000)). The recipient E. coli strain was ECKh-422 (ΔadhE ΔldhA ΔpflB ΔlpdA::K.p.lpdA322 Δmdh ΔarcA gltAR163L). A polycistronic DNA fragment containing a promoter, the sucCD gene, the sucD gene and the 4hbd gene and a terminator sequence was inserted into the AflIII site of the pKD3 plasmid. The following primers were used to amplify the operon together with the chloramphenicol marker from the plasmid. The underlined sequences are homologous to the target insertion site.

(SEQ ID NO: 41)
5'-<u>GTTTGCACGCTATAGCTGAGGTTGTTGTCTTCCAGCAACGTACC</u>
<u>GTATA</u>CAATAGGCGTATCACGAGGCCCTTTC-3'

(SEQ ID NO: 42)
5'-<u>GCTACAGCATGTCACACGATCTCAACGGTCGGATGACCAATCTG</u>
<u>GCTGGTATGGGAATTAGCCATGGTCC</u>-3'

Following DpnI treatment and DNA electrophoresis, the purified PCR product was used to transform E. coli strain harboring plasmid pKD46. The candidate strain was selected on plates containing chloramphenicol. Genomic DNA of the candidate strain was purified. The insertion sequence was amplified and confirmed by DNA sequencing. The chloramphenicol-resistant marker was removed from chromosome by flipase. The nucleotide sequence of the region after insertion and marker removal is shown in FIG. 52.

The alpha-ketoglutarate branch of the upstream pathway was integrated into the chromosome by homologous recombination. The plasmid used in this modification was derived from vector pRE118-V2, as referenced in Example XIV, which contains a kanamycin-resistant gene, a gene encoding the levansucrase (sacB) and a R6K conditional replication ori. The integration plasmid also contained a polycistronic sequence with a promoter, the sucA gene, the C. kluyveri 4hbd gene, and a terminator being inserted between two 1.5-kb DNA fragments that are homologous to the flanking regions of the target insertion site. The resulting plasmid was used to transform E. coli strain. The integration candidate was selected on plates containing kanamycin. The correct integration site was verified by PCR. To resolve the antibiotic marker from the chromosome, the cells were selected for growth on medium containing sucrose. The final strain was verified by PCR and DNA sequencing. The nucleotide sequence of the chromosomal region after insertion and marker removal is shown in FIG. 53.

Figure 54:
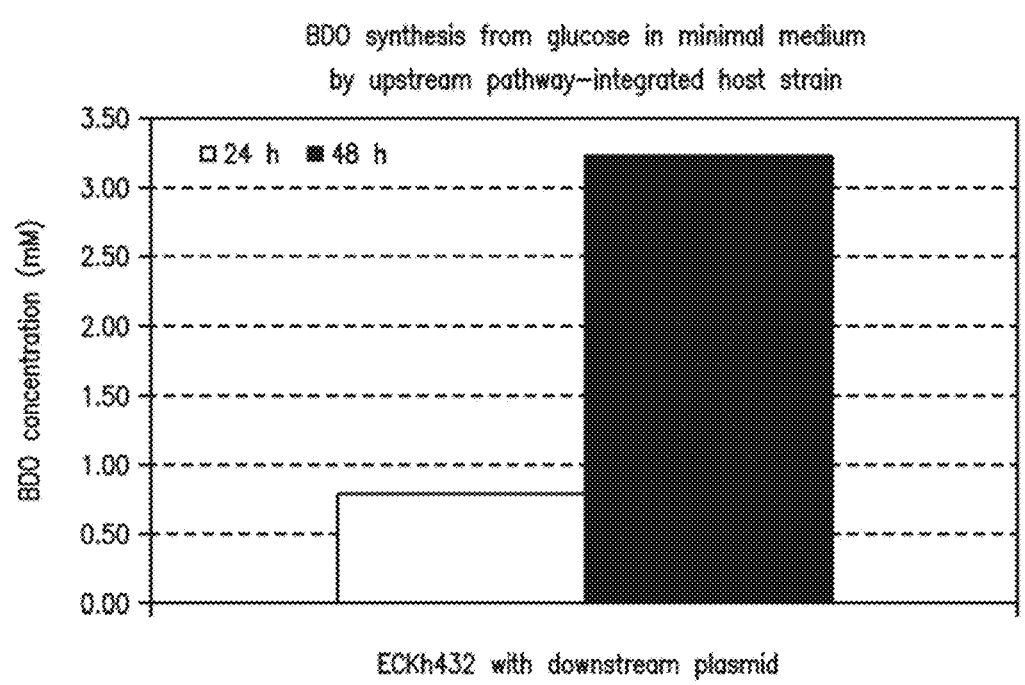
FIG. 54 shows BDO synthesis from glucose in minimal medium in the ECKh-432 strain having upstream BDO pathway encoding genes intergrated into the chromosome and containing a plasmid harboring downstream BDO pathway genes.

The resulting upstream pathway integration strain ECKh-432 was transformed with a plasmid harboring the downstream pathway genes. The construct was able to produce BDO from glucose in minimal medium (see FIG. 54).

Example XVIII

Use of a Non-Phosphotransferase Sucrose Uptake System to Reduce Pyruvate Byproduct Formation This example describes the utilization of a non-phosphotransferase (PTS) sucrose uptake system to reduce pyruvate as a byproduct in the conversion of sucrose to BDO.

Strains engineered for the utilization of sucrose via a phosphotransferase (PTS) system produce significant amounts of pyruvate as a byproduct. Therefore, the use of a non-PTS sucrose system can be used to decrease pyruvate formation because the import of sucrose would not be accompanied by the conversion of phosphoenolpyruvate (PEP) to pyruvate. This will increase the PEP pool and the flux to oxaloacetate through PPC or PEPCK.

Figure 55:
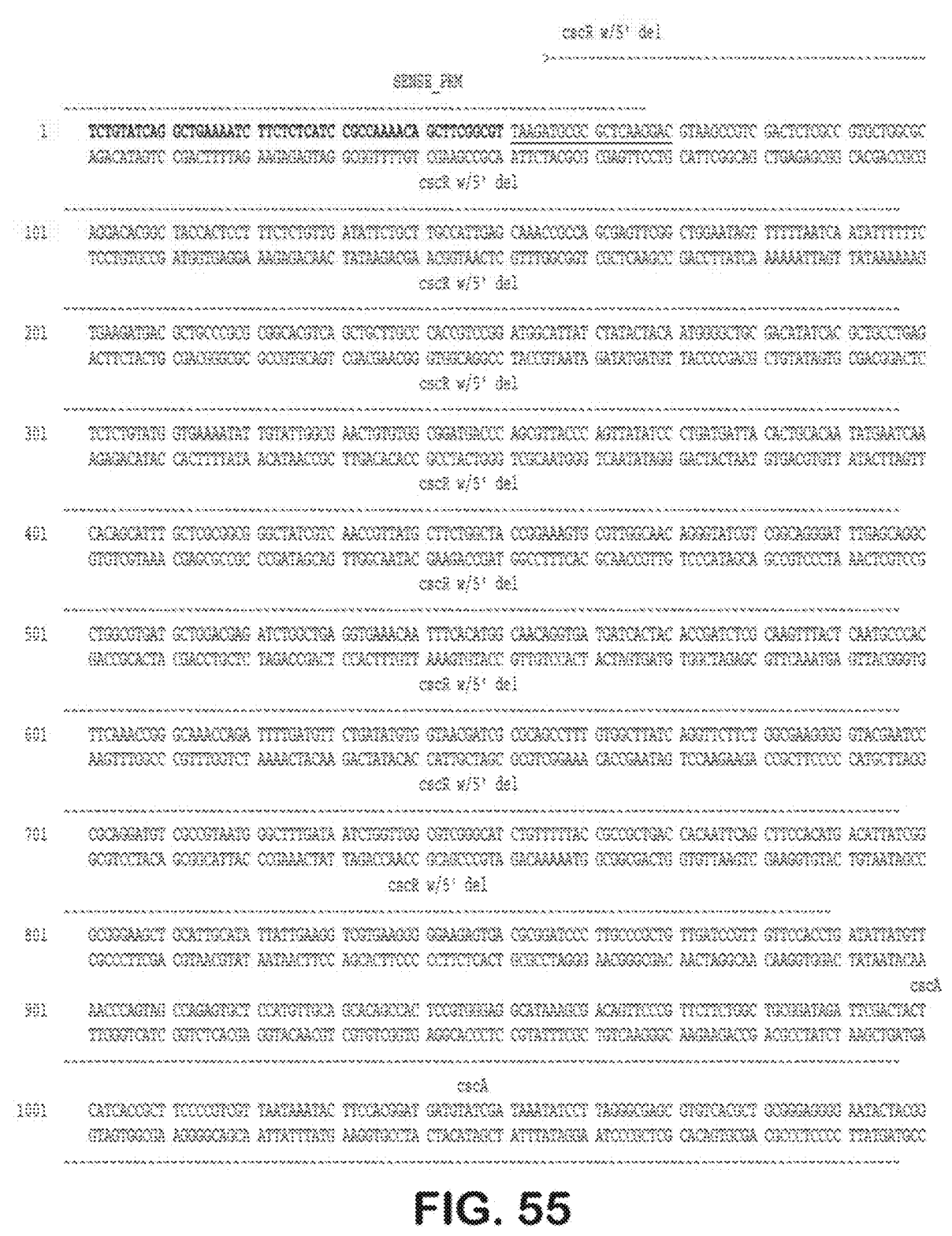
Figure 55:
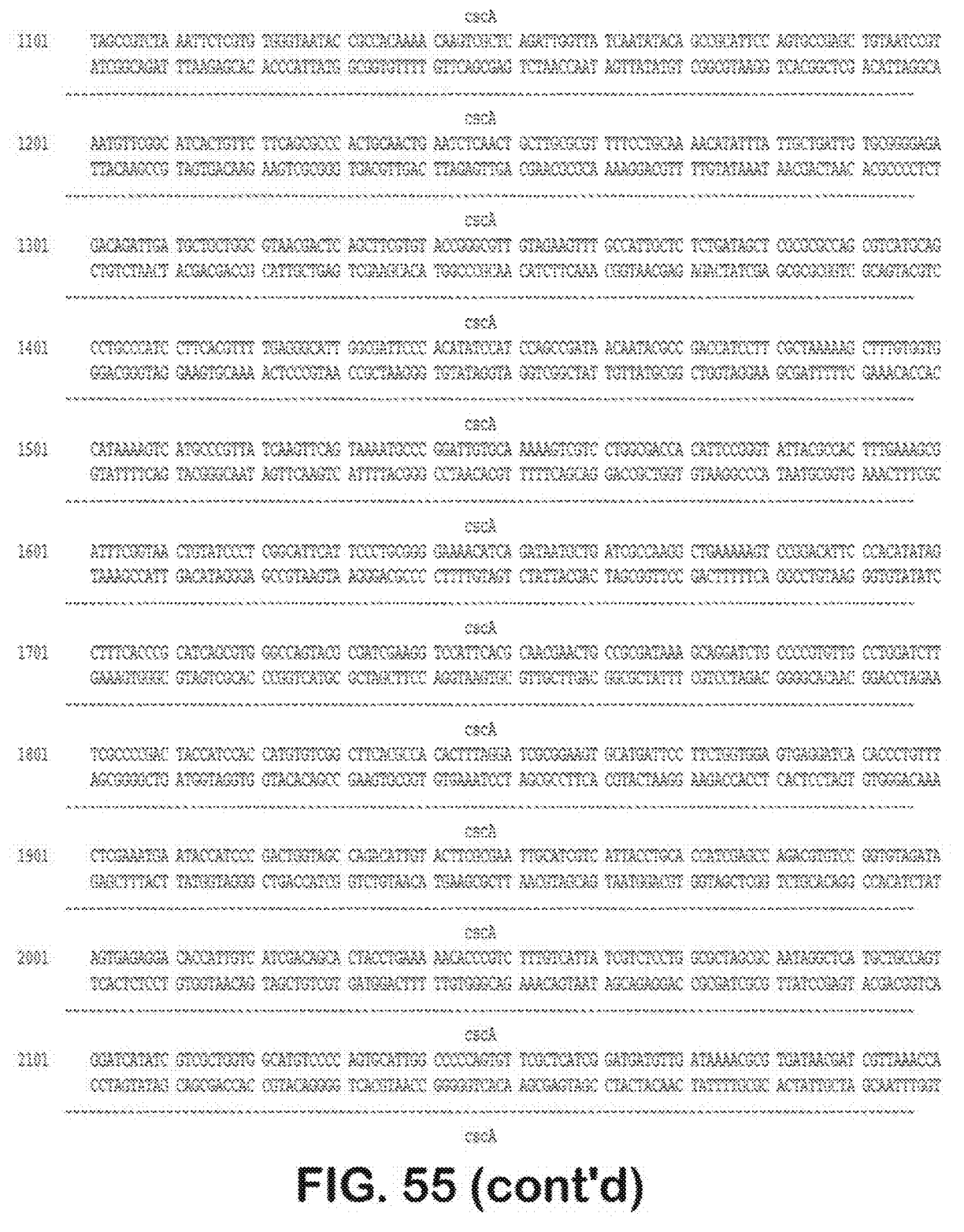
Figure 55:
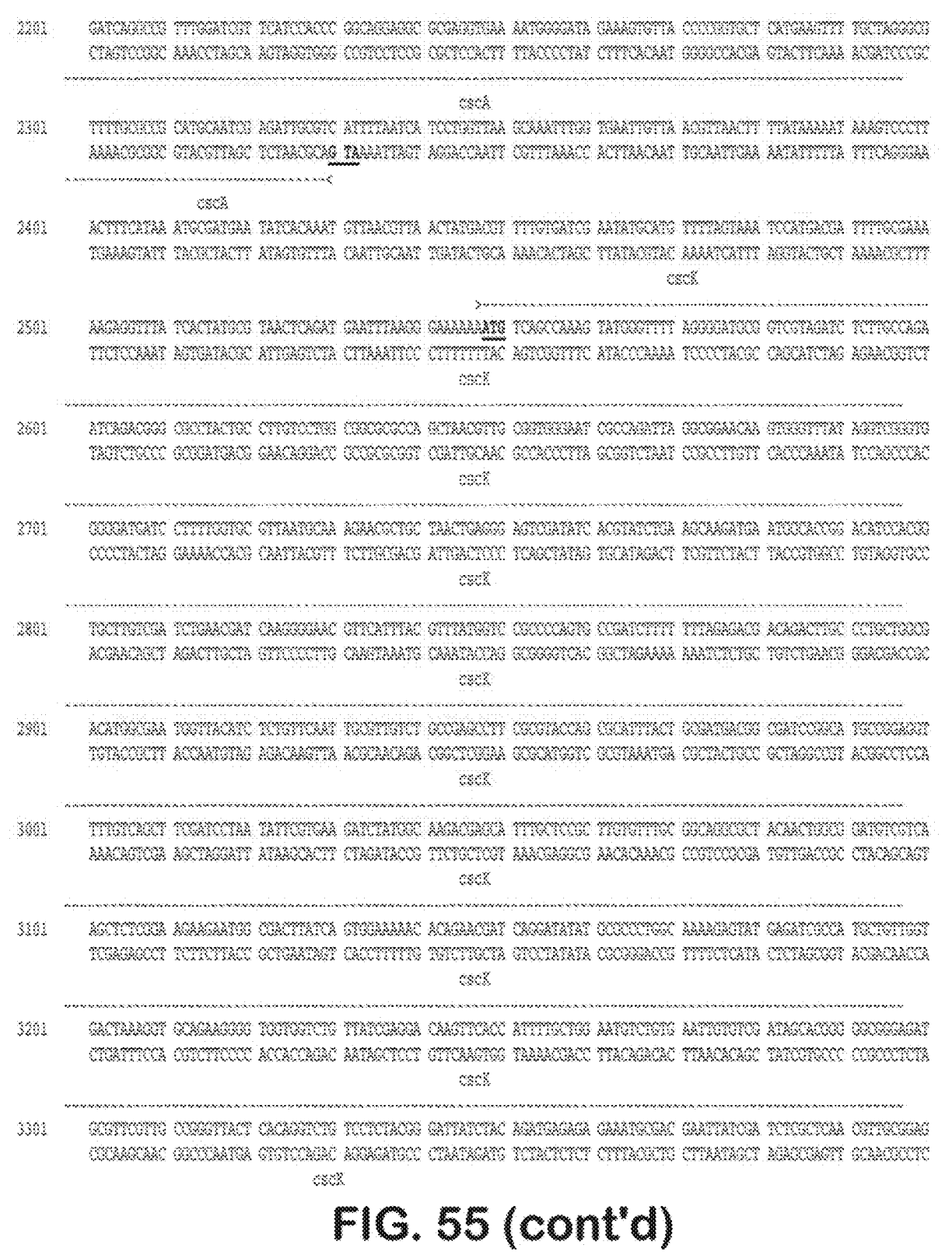
Figure 55:
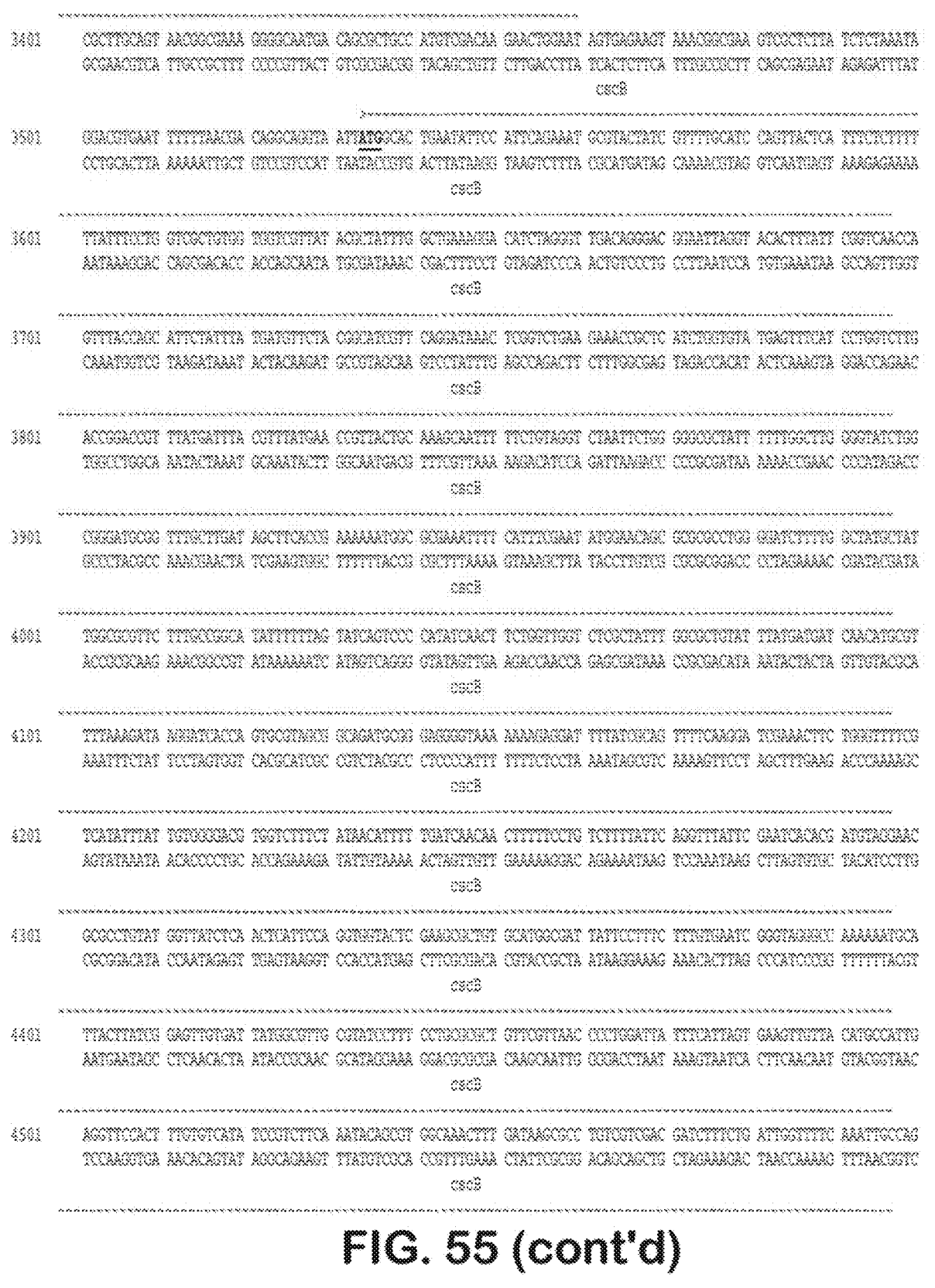

Insertion of a non-PTS sucrose operon into the rrnC region was performed. To generate a PCR product containing the non-PTS sucrose genes flanked by regions of homology to the rrnC region, two oligos were used to PCR amplify the csc genes from Mach1™ (Invitrogen, Carlsbad, Calif.). This strain is a descendent of W strain which is an E. coli strain known to be able to catabolize sucrose (Orencio-Trejo et al., Biotechnology Biofuels 1:8 (2008)). The sequence was derived from E. coli W strain KO11 (accession AY314757) (Shukla et al., Biotechnol. Lett. 26:689-693 (2004)) and includes genes encoding a sucrose permease (cscB), D-fructokinase (cscK), sucrose hydrolase (cscA), and a LacI-related sucrose-specific repressor (cscR). The first 53 amino acids of cscR was effectively removed by the placement of the AS primer. The sequences of the oligos were: rrnC 23S del S-CSC 5'-TGT GAG TGA AAG TCA CCT GCC TTA ATA TCT CAA AAC TCA TCT TCG GGT GA CGAAATATGGCGTGACTCGATAC-3' (SEQ ID NO:43) and rrnC 23S del AS-CSC 5'-TCT GTA TCA GGC TGA AAA TCT TCT CTC ATC CGC CAA AAC AGC TTC GGC GTTAAGATGCGCGCTCAAGGAC-3' (SEQ ID NO:44). Underlined regions indicate homology to the csc operon, and bold sequence refers to sequence homology upstream and downstream of the rrnC region. The sequence of the entire PCR product is shown in FIG. 55.

Figure 56:
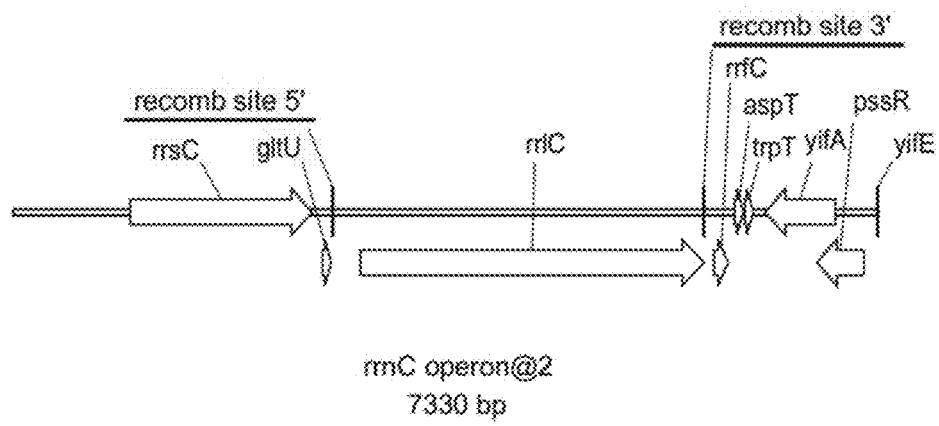
FIG. 56 shows a schematic diagram of the integrations site in the rrnC operon.

After purification, the PCR product was electroporated into MG1655 electrocompetent cells which had been transformed with pRedET (tet) and prepared according to manufacturer's instructions (genebridges.com/gb/pdf/K001%20Q%20E%20BAC%20Modification%20Kit-version2.6-2007-screen.pdf). The PCR product was designed so that it integrated into genome into the rrnC region of the chromosome. It effectively deleted 191 nucleotides upstream of rrlC (23S rRNA), all of the rrlC rRNA gene and 3 nucleotides downstream of rrlC and replaced it with the sucrose operon, as shown in FIG. 56.

Transformants were grown on M9 minimal salts medium with 0.4% sucrose and individual colonies tested for presence of the sucrose operon by diagnostic PCR. The entire rrnC::crcAKB region was transferred into the BDO host strain ECKh-432 by P1 transduction (Sambrook et al., Molecular Cloning: A Laboratory Manual, Third Ed., Cold Spring Harbor Laboratory, New York (2001), resulting in ECKh-463 (ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd rrnC::cscAKB). Recombinants were selected by growth on sucrose and verified by diagnostic PCR.

Figure 57:
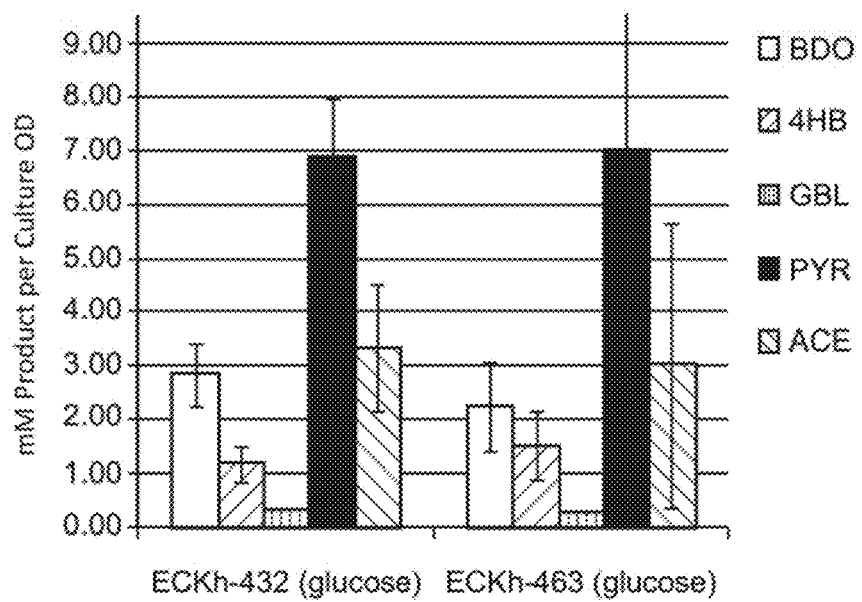
FIG. 57 shows average product concentration, normalized to culture OD600, after 48 hours of growth of strain ECKh-432 grown on glucose and strain ECKh-463 grown on sucrose. Both contain the plasmid pZS*13 expressing P. gingivalis Cat2 and C. beijerinckii Ald. The data is for 6 replicate cultures of each strain. The products measured were 1,4-butanediol (BDO), 4-hydroxybutyrate (4HB), γ-butyrolactone (GBL), pyruvate (PYR) and acetate (ACE) (left to right bars, respectively).

ECKh-463 was transformed with pZS*13 containing P. gingivalis Cat2 and C. beijerinckii Ald to provide a complete BDO pathway. Cells were cultured in M9 minimal medium (6.78 g/L $Na_2HPO_4$, 3.0 g/L $KH_2PO_4$, 0.5 g/L NaCl, 1.0 g/L $NH_4Cl$, 1 mM $MgSO_4$, 0.1 mM $CaCl_2$) supplemented with 10 g/L sucrose. 0.2 mM IPTG was present in the culture from the start. Anaerobic conditions were maintained using a bottle with 23G needle. As a control, ECKh-432 containing the same plasmid was cultured on the same medium, except with 10 g/L glucose instead of sucrose. FIG. 57 shows average product concentration, normalized to culture OD600, after 48 hours of growth. The data is for 6 replicate cultures of each strain. This demonstrates that BDO production from ECKh-463 on sucrose is similar to that of the parent strain on sucrose.

Example XIX

Summary of BDO Producing Strains

This example describes various BDO producing strains.
Table 28 summarizes various BDO producing strains disclosed above in Examples XII-XVIII.

TABLE 28

Summary of various BDO production strains.

| Strain # | Host Strain # | Host chromosome | Host Description | Plasmid-based |
|---|---|---|---|---|
| 1 | | ΔldhA | Single deletion derivative of E. coli MG1655 | E. coli sucCD, P. gingivalis sucD, P. gingivalis 4hbd, P. gingivalis Cat2, C. acetobutylicum AdhE2 |
| 2 | AB3 | ΔadhE ΔldhA ΔpflB | Succinate producing strain; derivative of E. coli MG1655 | E. coli sucCD, P. gingivalis sucD, P. gingivalis 4hbd, P. gingivalis Cat2, C. acetobutylicum AdhE2 |
| 3 | ECKh-138 | ΔadhE ΔldhA ΔpflB ΔlpdA::K.p.lpdA322 | Improvement of lpdA to increase pyruvate dehydrogenase flux | E. coli sucCD, P. gingivalis sucD, P. gingivalis 4hbd, P. gingivalis Cat2, C. acetobutylicum AdhE2 |
| 4 | ECKh-138 | ΔadhE ΔldhA ΔpflB ΔlpdA::K.p.lpdA322 | | E. coli sucCD, P. gingivalis sucD, P. gingivalis 4hbd, C. acetobutylicum buk1, C. acetobutylicum ptb, C. acetobutylicum AdhE2 |
| 5 | ECKh-401 | ΔadhE ΔldhA ΔpflB ΔlpdA::K.p.lpdA322 Δmdh ΔarcA | Deletions in mdh and arcA to direct flux through oxidative TCA cycle | E. coli sucCD, P. gingivalis sucD, P. gingivalis Cat2, C. acetobutylicum AdhE2 |

TABLE 28-continued

Summary of various BDO production strains.

| Strain # | Host Strain # | Host chromosome | Host Description | Plasmid-based |
|---|---|---|---|---|
| 6 | ECKh-401 | ΔadhE ΔldhA ΔpflB ΔlpdA::K.p.lpdA322 Δmdh ΔarcA | | M. bovis sucA, E. coli sucCD, P. gingivalis sucD, P. gingivalis 4hbd, P. gingivalis Cat2, C. acetobutylicum AdhE2 |
| 7 | ECKh-422 | ΔadhE ΔldhA ΔpflB ΔlpdA::K.p.lpdA322 Δmdh ΔarcA gltAR163L | Mutation in citrate synthase to improve anaerobic activity | E. coli sucCD, P. gingivalis sucD, P. gingivalis 4hbd, P. gingivalis Cat2, C. acetobutylicum AdhE2 |
| 8 | ECKh-422 | ΔadhE ΔldhA ΔpflB ΔlpdA::K.p.lpdA322 Δmdh ΔarcA gltAR163L | | M. bovis sucA, E. coli sucCD, P. gingivalis sucD, P. gingivalis 4hbd, P. gingivalis Cat2, C. acetobutylicum AdhE2 |
| 9 | ECKh-422 | ΔadhE ΔldhA ΔpflB ΔlpdA::K.p.lpdA322 Δmdh ΔarcA gltAR163L | | M. bovis sucA, E. coli sucCD, P. gingivalis sucD, P. gingivalis 4hbd, P. gingivalis Cat2, C. beijerinckii Ald |
| 10 | ECKh-426 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd | Succinate branch of upstream pathway integrated into ECKh-422 | P. gingivalis Cat2, C. beijerinckii Ald |
| 11 | ECKh-432 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd | Succinate and alpha-ketoglutarate upstream pathway branches integrated into ECKh-422 | P. gingivalis Cat2, C. beijerinckii Ald |
| 12 | ECKh-432 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd | | C. acetobutylicum buk1, C. acetobutylicum ptb, C. beijerinckii Ald |
| 13 | ECKh-439 | ΔadhE ΔldhA ΔpflB ΔlpdA::K.p.lpdA322 Δmdh ΔarcA gltAR163L ΔackA fimD:: E. coli sucCD, P. gingivalis sucD, P. gingivalis 4hbd fimD:: M. bovis sucA, C. kluyveri 4hbd | Acetate kinase deletion of ECKh-432 | P. gingivalis Cat2, C. beijerinckii Ald |
| 14 | ECKh-453 | ΔadhE ΔldhA ΔpflB ΔlpdA::K.p.lpdA322 Δmdh ΔarcA gltAR163L ΔackA Δppc::H.i.ppck fimD:: E. coli sucCD, P. gingivalis sucD, P. gingivalis 4hbd fimD:: M. bovis sucA, C. kluyveri 4hbd | Acetate kinase deletion and PPC/PEPCK replacement of ECKh-432 | P. gingivalis Cat2, C. beijerinckii Ald |
| 15 | ECKh-456 | ΔadhE ΔldhA ΔpflB ΔlpdA:fnr-pflB6-K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd | Replacement of lpdA promoter with anaerobic promoter in ECKh-432 | P. gingivalis Cat2, C. beijerinckii Ald |
| 16 | ECKh-455 | ΔadhE ΔldhA ΔpflB ΔlpdA:: K.p.lpdA322 ΔpdhR:: fnr-pflB6 Δmdh ΔarcA gltAR163L fimD:: E. coli sucCD, P. gingivalis sucD, P. gingivalis 4hbd fimD:: M. bovis sucA, C. kluyveri 4hbd | Replacement of pdhR and aceEF promoter with anaerobic promoter in ECKh-432 | P. gingivalis Cat2, C. beijerinckii Ald |
| 17 | ECKh-459 | ΔadhE ΔldhA ΔpflB ΔlpdA:: K.p.lpdA322 Δmdh ΔarcA gltAR163L fimD::E. coli sucCD, P. gingivalis sucD, P. gingivalis 4hbd fimD:: M. bovis sucA, C. kluyveri 4hbd fimD:: C. acetobutylicum buk1, C. acetobutylicum ptb | Integration of BK/PTB into ECKh-432 | C. beijerinckii Ald |

TABLE 28-continued

Summary of various BDO production strains.

| Host Strain # | Strain # | Host chromosome | Host Description | Plasmid-based |
|---|---|---|---|---|
| 18 | ECKh-459 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd fimD:: C. acetobutylicum buk1, C. acetobutylicum ptb | | C. beijerinckii Ald, G. thermoglucosidasius adh1 |
| 19 | ECKh-463 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd rrnC::cscAKB | Non-PTS sucrose genes inserted into ECKh-432 | P. gingivalis Cat2, C. beijerinckii Ald |
| 20 | ECKh-463 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd rrnC::cscAKB | | C. acetobutylicum buk1, C. acetobutylicum ptb, C. beijerinckii Ald |

The strains summarized in Table 28 are as follows. Strain 1: Single deletion derivative of E. coli MG1655, with deletion of endogenous ldhA; plasmid expression of E. coli sucCD, P. gingivalis sucD, P. gingivalis 4hbd, P. gingivalis Cat2, C. acetobutylicum AdhE2. Strain 2: Host strain AB3, a succinate producing strain, derivative of E. coli MG1655, with deletions of endogenous adhE ldhA pflB; plasmid expression of E. coli sucCD, P. gingivalis sucD, P. gingivalis 4hbd, P. gingivalis Cat2, C. acetobutylicum AdhE2.

Strain 3: Host strain ECKh-138, deletion of endogenous adhE, ldhA, pflB, deletion of endogenous lpdA and chromosomal insertion of Klebsiella pneumoniae lpdA with a Glu354Lys mutation at the lpdA locus; plasmid expression of E. coli sucCD, P. gingivalis sucD, P. gingivalis 4hbd, P. gingivalis Cat2, C. acetobutylicum AdhE2; strain provides improvement of lpdA to increase pyruvate dehydrogenase flux. Strain 4: Host strain ECKh-138, deletion of endogenous adhE, ldhA, pflB, and lpdA, chromosomal insertion of Klebsiella pneumoniae lpdA with a Glu354Lys mutation; plasmid expression E. coli sucCD, P. gingivalis sucD, P. gingivalis 4hbd, C. acetobutylicum buk1, C. acetobutylicum ptb, C. acetobutylicum AdhE2.

Strain 5: Host strain ECKh-401, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA; plasmid expression of E. coli sucCD, P. gingivalis sucD, P. gingivalis 4hbd, P. gingivalis Cat2, C. acetobutylicum AdhE2; strain has deletions in mdh and arcA to direct flux through oxidative TCA cycle. Strain 6: host strain ECKh-401, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA; plasmid expression of M. bovis sucA, E. coli sucCD, P. gingivalis sucD, P. gingivalis 4hbd, P. gingivalis Cat2, C. acetobutylicum AdhE2.

Strain 7: Host strain ECKh-422, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant; plasmid expression of E. coli sucCD, P. gingivalis sucD, P. gingivalis 4hbd, P. gingivalis Cat2, C. acetobutylicum AdhE2; strain has mutation in citrate synthase to improve anaerobic activity. Strain 8: strain ECKh-422, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant; plasmid expression of M. bovis sucA, E. coli sucCD, P. gingivalis sucD, P. gingivalis 4hbd, P. gingivalis Cat2, C. acetobutylicum AdhE2. Strain 9: host strain ECKh-422, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant; plasmid expression of M. bovis sucA, E. coli sucCD, P. gingivalis sucD, P. gingivalis 4hbd, P. gingivalis Cat2, C. beijerinckii Ald.

Strain 10: host strain ECKh-426, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant, chromosomal insertion at the fimD locus of E. coli sucCD, P. gingivalis sucD, P. gingivalis 4hbd; plasmid expression of P. gingivalis Cat2, C. beijerinckii Ald; strain has succinate branch of upstream pathway integrated into strain ECKh-422 at the fimD locus. Strain 11: host strain ECKh-432, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant, chromosomal insertion at the fimD locus of E. coli sucCD, P. gingivalis sucD, P. gingivalis 4hbd, chromosomal insertion at the fimD locus of M. bovis sucA, *C. kluyveri* 4hbd; plasmid expression of *P. gingivalis* Cat2, *C. beijerinckii* Ald; strain has succinate and alpha-ketoglutarate upstream pathway branches integrated into ECKh-422. Strain 12: host strain ECKh-432, deletion of endogenous adhE, ldhA, pflB, deletion of endogenous lpdA and chromosomal insertion of *Klebsiella pneumoniae lpdA with a Glu*354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd; plasmid expression of *C. acetobutylicum* buk1, *C. acetobutylicum* ptb, *C. beijerinckii* Ald.

Strain 13: host strain ECKh-439, deletion of endogenous adhE, ldhA, pflB, deletion of endogenous lpdA and chromosomal insertion of *Klebsiella pneumoniae lpdA with a Glu*354Lys mutation at the lpdA locus, deletion of endogenous mdh and arcA, chromosomal replacement of gltA with gltA Arg163Leu mutant, deletion of endogenous ackA, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd; plasmid expression of *P. gingivalis* Cat2, *C. beijerinckii* Ald; strain has acetate kinase deletion in strain ECKh-432. Strain 14: host strain ECKh-453, deletion of endogenous adhE, ldhA, pflB, deletion of endogenous lpdA and chromosomal insertion of *Klebsiella pneumoniae lpdA with a Glu*354Lys mutation at the lpdA locus, deletion of endogenous mdh and arcA, chromosomal replacement of gltA with gltA Arg163Leu mutant, deletion of endogenous ackA, deletion of endogenous ppc and insertion of *Haemophilus* influenza ppck at the ppc locus, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd; plasmid expression of *P. gingivalis* Cat2, *C. beijerinckii* Ald; strain has acetate kinase deletion and PPC/PEPCK replacement in strain ECKh-432.

Strain 15: host strain ECKh-456, deletion of endogenous adhE, ldhA, pflB, deletion of endogenous lpdA and chromosomal insertion of *Klebsiella pneumoniae lpdA with a Glu*354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, replacement of lpdA promoter with fnr binding site, pflB-p6 promoter and RBS of pflB; plasmid expression of *P. gingivalis* Cat2, *C. beijerinckii* Ald; strain has replacement of lpdA promoter with anaerobic promoter in strain ECKh-432. Strain 16: host strain ECKh-455, deletion of endogenous adhE, ldhA, pflB, deletion of endogenous lpdA and chromosomal insertion of *Klebsiella pneumoniae lpdA with a Glu*354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbdI, replacement of pdhR and aceEF promoter with fnr binding site, pflB-p6 promoter and RBS of pflB; plasmid expression of *P. gingivalis* Cat2, *C. beijerinckii* Ald; strain has replacement of pdhR and aceEF promoter with anaerobic promoter in ECKh-432.

Strain 17: host strain ECKh-459, deletion of endogenous adhE, ldhA, pflB, deletion of endogenous lpdA and chromosomal insertion of *Klebsiella pneumoniae lpdA with a Glu*354Lys mutation at the lpdA locus, deletion of endogenous mdh and arcA, chromosomal replacement of gltA with gltA Arg163Leu mutant, chromosomal insertion at the fimD locus of *E. coli* sucD, *P. gingivalis* sucD, *P. gingivalis* 4hbd, chromosomal insertion at the fimD locus of *M. bovis* sucA, *C. kluyveri* 4hbd, chromosomal insertion at the fimD locus of *C. acetobutylicum* buk1, *C. acetobutylicum* ptb; plasmid expression of *C. beijerinckii* Ald; strain has integration of BK/PTB into strain ECKh-432. Strain 18: host strain ECKh-459, deletion of endogenous adhE, ldhA, pflB, deletion of endogenous lpdA and chromosomal insertion of *Klebsiella pneumoniae lpdA with a Glu*354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, chromosomal insertion at the fimD locus of *C. acetobutylicum* buk1, *C. acetobutylicum* ptb; plasmid expression of *C. beijerinckii* Ald, *G. thermoglucosidasius* adh1.

Strain 19: host strain ECKh-463, deletion of endogenous adhE, ldhA, pflB, deletion of endogenous lpdA and chromosomal insertion of *Klebsiella pneumoniae lpdA with a Glu*354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, insertion at the rrnC locus of non-PTS sucrose operon genes sucrose permease (cscB), D-fructokinase (cscK), sucrose hydrolase (cscA), and a LacI-related sucrose-specific repressor (cscR); plasmid expression of *P. gingivalis* Cat2, *C. beijerinckii* Ald; strain has non-PTS sucrose genes inserted into strain ECKh-432. Strain 20: host strain ECKh-463 deletion of endogenous adhE, ldhA, pflB, deletion of endogenous lpdA and chromosomal insertion of *Klebsiella pneumoniae lpdA with a Glu*354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, insertion at the rrnC locus of non-PTS sucrose operon; plasmid expression of *C. acetobutylicum* buk1, *C. acetobutylicum* ptb, *C. beijerinckii* Ald.

In addition to the BDO producing strains disclosed herein, including those disclosed in Table 28, it is understood that additional modifications can be incorporated that further increase production of BDO and/or decrease undesirable byproducts. For example, a BDO producing strain, or a strain of Table 28, can incorporate additional knockouts to further increase the production of BDO or decrease an undesirable byproduct. Exemplary knockouts have been described previously (see U.S. publication 2009/0047719). Such knockout strains include, but are not limited to, ADHEr, NADH6; ADHEr, PPCK; ADHEr, SUCD4; ADHEr, ATPS4r; ADHEr, FUM; ADHEr, MDH; ADHEr, PFLi, PPCK; ADHEr, PFLi, SUCD4; ADHEr, ACKr, NADH6; ADHEr, NADH6, PFLi; ADHEr, ASPT, MDH; ADHEr, NADH6, PPCK; ADHEr, PPCK, THD2; ADHEr, ATPS4r, PPCK; ADHEr, MDH, THD2; ADHEr, FUM, PFLi; ADHEr, PPCK, SUCD4; ADHEr, GLCpts, PPCK; ADHEr, GLUDy, MDH; ADHEr, GLUDy, PPCK; ADHEr, FUM, PPCK; ADHEr, MDH, PPCK; ADHEr, FUM, GLUDy; ADHEr, FUM, HEX1; ADHEr, HEX1, PFLi; ADHEr, HEX1, THD2; ADHEr, FRD2, LDH_D, MDH; ADHEr, FRD2, LDH_D, ME2; ADHEr, MDH, PGL, THD2; ADHEr, G6PDHy, MDH, THD2; ADHEr, PFLi, PPCK, THD2; ADHEr, ACKr, AKGD, ATPS4r; ADHEr, GLCpts, PFLi, PPCK; ADHEr, ACKr, ATPS4r, SUCOAS; ADHEr, GLUDy, PFLi, PPCK; ADHEr, ME2, PFLi, SUCD4; ADHEr, GLUDy, PFLi, SUCD4; ADHEr, ATPS4r, LDH_D, SUCD4; ADHEr, FUM, HEX1, PFLi; ADHEr, MDH, NADH6, THD2; ADHEr, ATPS4r, MDH, NADH6; ADHEr, ATPS4r, FUM, NADH6; ADHEr, ASPT, MDH, NADH6; ADHEr, ASPT, MDH, THD2; ADHEr, ATPS4r, GLCpts, SUCD4; ADHEr, ATPS4r, GLUDy, MDH; ADHEr, ATPS4r, MDH, PPCK; ADHEr, ATPS4r, FUM, PPCK; ADHEr, ASPT, GLCpts, MDH; ADHEr, ASPT, GLUDy, MDH; ADHEr, ME2, SUCD4, THD2; ADHEr, FUM, PPCK, THD2; ADHEr, MDH, PPCK, THD2; ADHEr, GLUDy, MDH, THD2; ADHEr, HEX1, PFLi, THD2; ADHEr, ATPS4r, G6PDHy, MDH; ADHEr, ATPS4r, MDH, PGL; ADHEr, ACKr, FRD2, LDH_D; ADHEr, ACKr, LDH_D, SUCD4; ADHEr, ATPS4r, FUM, GLUDy; ADHEr, ATPS4r, FUM, HEX1; ADHEr, ATPS4r, MDH, THD2; ADHEr, ATPS4r, FRD2, LDH_D; ADHEr, ATPS4r, MDH, PGDH; ADHEr, GLCpts, PPCK, THD2; ADHEr, GLUDy, PPCK, THD2; ADHEr, FUM, HEX1, THD2; ADHEr, ATPS4r, ME2, THD2; ADHEr, FUM, ME2, THD2; ADHEr, GLCpts, GLUDy, PPCK; ADHEr, ME2, PGL, THD2; ADHEr, G6PDHy, ME2, THD2; ADHEr, ATPS4r, FRD2, LDH_D, ME2; ADHEr, ATPS4r, FRD2, LDH_D, MDH; ADHEr, ASPT, LDH_D, MDH, PFLi; ADHEr, ATPS4r, GLCpts, NADH6, PFLi; ADHEr, ATPS4r, MDH, NADH6, PGL; ADHEr, ATPS4r, G6PDHy, MDH, NADH6; ADHEr, ACKr, FUM, GLUDy, LDH_D; ADHEr, ACKr, GLUDy, LDH_D, SUCD4; ADHEr, ATPS4r, G6PDHy, MDH, THD2; ADHEr, ATPS4r, MDH, PGL, THD2; ADHEr, ASPT, G6PDHy, MDH, PYK; ADHEr, ASPT, MDH, PGL, PYK; ADHEr, ASPT, LDH_D, MDH, SUCOAS; ADHEr, ASPT, FUM, LDH_D, MDH; ADHEr, ASPT, LDH_D, MALS, MDH; ADHEr, ASPT, ICL, LDH_D, MDH; ADHEr, FRD2, GLUDy, LDH_D, PPCK; ADHEr, FRD2, LDH_D, PPCK, THD2; ADHEr, ACKr, ATPS4r, LDH_D, SUCD4; ADHEr, ACKr, ACS, PPC, PPCK; ADHEr, GLUDy, LDH_D, PPC, PPCK; ADHEr, LDH_D, PPC, PPCK, THD2; ADHEr, ASPT, ATPS4r, GLCpts, MDH; ADHEr, G6PDHy, MDH, NADH6, THD2; ADHEr, MDH, NADH6, PGL, THD2; ADHEr, ATPS4r, G6PDHy, GLCpts, MDH; ADHEr, ATPS4r, GLCpts, MDH, PGL; ADHEr, ACKr, LDH_D, MDH, SUCD4.

Table 29 shows the reactions of corresponding genes to be knocked out of a host organism such as *E. coli*. The corresponding metabolite corresponding to abbreviations in Table 29 are shown in Table 30.

TABLE 29

Corresponding genes to be knocked out to prevent a particular reaction from occurring in *E. coli*.

| Reaction Abbreviation | Reaction Stoichiometry* | Genes Encoding the Enzyme(s) Catalyzing Each Reaction& |
|---|---|---|
| ACKr | [c]: ac + atp <==> actp + adp | (b3115 or b2296 or b1849) |
| ACS | [c]: ac + atp + coa --> accoa + amp + ppi | b4069 |
| ACt6 | ac[p] + h[p] <==> ac[c] + h[c] | Non-gene associated |
| ADHEr | [c]: etoh + nad <==> acald + h + nadh | (b0356 or b1478 or b1241) |
|  | [c]: acald + coa + nad <==> accoa + h + nadh | (b1241 or b0351) |
| AKGD | [c]: akg + coa + nad --> co2 + nadh + succoa | (b0116 and b0726 and b0727) |
| ASNS2 | [c]: asp-L + atp + nh4 --> amp + asn-L + h + ppi | b3744 |
| ASPT | [c]: asp-L --> fum + nh4 | b4139 |
| ATPS4r | adp[c] + (4) h[p] + pi[c] <==> atp[c] + (3) h[c] + h2o[c] | (((b3736 and b3737 and b3738) and (b3731 and b3732 and b3733 and b3734 and b3735)) or ((b3736 and b3737 and b3738) and (b3731 and b3732 and b3733 and b3734 and b3735) and b3739)) |
| CBMK2 | [c]: atp + co2 + nh4 <==> adp + cbp +(2) h | (b0521 or b0323 or b2874) |
| EDA | [c]: 2ddg6p --> g3p + pyr | b1850 |
| ENO | [c]: 2pg <==> h2o + pep | b2779 |
| FBA | [c]: fdp <==> dhap + g3p | (b2097 or b2925 or b1773) |
| FBP | [c]: fdp + h2o --> f6p + pi | (b4232 or b3925) |
| FDH2 | for[p] + (2) h[c] + q8[c] --> co2[c] + h[p] + q8h2[c] | ((b3892 and b3893 and b3894) |
|  | for[p] + (2) h[c] + mqn8[c] --> co2[c] + h[p] + mql8[c] | or (b1474 and b1475 and b1476)) |
| FRD2 | [c]: fum + mql8 --> mqn8 + succ | (b4151 and b4152 and b4153 |
|  | [c]: 2dmmql8 + fum --> 2dmmq8 + succ | and b4154) |
| FTHFD | [c]: 10fthf + h2o --> for + h + thf | b1232 |
| FUM | [c]: fum + h2o <==> mal-L | (b1612 or b4122 or b1611) |
| G5SD | [c]: glu5p + h + nadph --> glu5sa + nadp + pi | b0243 |
| G6PDHy | [c]: g6p + nadp <==> 6pgl + h + nadph | b1852 |
| GLCpts | glc-D[p] + pep[c] --> g6p[c] + pyr[c] | ((b2417 and b1101 and b2415 and b2416) or (b1817 and b1818 and b1819 and b2415 and b2416) or (b2417 and b1621 and b2415 and b2416)) |
| GLU5K | [c]: atp + glu-L --> adp + glu5p | b0242 |
| GLUDy | [c]: glu-L + h2o + nadp <==> akg + h + nadph + nh4 | b1761 |
| GLYCL | [c]: gly + nad + thf --> co2 + mlthf + nadh + nh4 | (b2904 and b2903 and b2905 and b0116) |
| HEX1 | [c]: atp + glc-D --> adp + g6p + h | b2388 |
| ICL | [c]: icit --> glx + succ | b4015 |
| LDH_D | [c]: lac-D + nad <==> h + nadh + pyr | (b2133 or b1380) |
| MALS | [c]: accoa + glx + h2o --> coa + h + mal-L | (b4014 or b2976) |
| MDH | [c]: mal-L + nad <==> h + nadh + oaa | b3236 |

TABLE 29-continued

Corresponding genes to be knocked out to prevent a particular reaction from occurring in E. coli.

| Reaction Abbreviation | Reaction Stoichiometry* | Genes Encoding the Enzyme(s) Catalyzing Each Reaction& |
|---|---|---|
| ME2 | [c]: mal-L + nadp --> co2 + nadph + pyr | b2463 |
| MTHFC | [c]: h2o + methf <==> 10fthf + h | b0529 |
| NADH12 | [c]: h + mqn8 + nadh --> mql8 + nad<br>[c]: h + nadh + q8 --> nad + q8h2<br>[c]: 2dmmq8 + h + nadh --> 2dmmql8 + nad | b1109 |
| NADH6 | (4) h[c] + nadh[c] + q8[c] --> (3) h[p] + nad[c] + q8h2[c]<br>(4) h[c] + mqn8[c] + nadh[c] --> (3) h[p] + mql8[c] + nad[c]<br>2dmmq8[c] + (4) h[c] + nadh[c] --> 2dmmql8[c] + (3) h[p] + nad[c] | (b2276 and b2277 and b2278 and b2279 and b2280 and b2281 and b2282 and b2283 and b2284 and b2285 and b2286 and b2287 and b2288) |
| PFK | [c]: atp + f6p --> adp + fdp + h | (b3916 or b1723) |
| PFLi | [c]: coa + pyr --> accoa + for | (((b0902 and b0903 ) and b2579) or (b0902 and b0903) or (b0902 and b3114) or (b3951 and b3952)) |
| PGDH | [c]: 6pgc + nadp --> co2 + nadph + ru5p-D | b2029 |
| PGI | [c]: g6p <==> f6p | b4025 |
| PGL | [c]: 6pgl + h2o --> 6pgc + h | b0767 |
| PGM | [c]: 2pg <==> 3pg | (b3612 or b4395 or b0755 ) |
| PPC | [c]: co2 + h2o + pep -->h + oaa + pi | b3956 |
| PPCK | [c]: atp + oaa --> adp + co2 + pep | b3403 |
| PRO1z | [c]: fad + pro-L --> 1pyr5c + fadh2 + h | b1014 |
| PYK | [c]: adp + h + pep --> atp + pyr | b1854 or b1676) |
| PYRt2 | h[p] + pyr[p] <==> h[c] + pyr[c] | Non-gene associated |
| RPE | [c]: ru5p-D <==> xu5p-D | (b4301 or b3386) |
| SO4t2 | so4[e] <==> so4[p] | (b0241 or b0929 or b1377 or b2215) |
| SUCD4 | [c]: q8 + succ --> fum + q8h2 | (b0721 and b0722 and b0723 and b0724) |
| SUCOAS | [c]: atp + coa + succ <==> adp + pi + succoa | (b0728 and b0729) |
| SULabc | atp[c] + h2o[c] + so4[p] --> adp[c] + h[c] + pi[c] + so4[c] | ((b2422 and b2425 and b2424 and b2423) or (b0763 and b0764 and b0765) or (b2422 and b2424 and b2423 and b3917)) |
| TAL | [c]: g3p + s7p <==> e4p + f6p | (b2464 or b0008) |
| THD2 | (2) h[p] + nadh[c] + nadp[c] --> (2) h[c] + nad[c] + nadph[c] | (b1602 and b1603) |
| THD5 | [c]: nad + nadph --> nadh + nadp | (b3962 or (b1602 and b1603)) |
| TPI | [c]: dhap <==> g3p | b3919 |

TABLE 30

Metabolite names corresponding to abbreviations used in Table 29.

| Metabolite Abbreviation | Metabolite Name |
|---|---|
| 10fthf | 10-Formyltetrahydrofolate |
| 1pyr5c | 1-Pyrroline-5-carboxylate |
| 2ddg6p | 2-Dehydro-3-deoxy-D-gluconate 6-phosphate |
| 2dmmq8 | 2-Demethylmenaquinone 8 |
| 2dmmql8 | 2-Demethylmenaquinol 8 |
| 2pg | D-Glycerate 2-phosphate |
| 3pg | 3-Phospho-D-glycerate |
| 6pgc | 6-Phospho-D-gluconate |
| 6pgl | 6-phospho-D-glucono-1,5-lactone |
| ac | Acetate |
| acald | Acetaldehyde |
| accoa | Acetyl-CoA |
| actp | Acetyl phosphate |
| adp | ADP |
| akg | 2-Oxoglutarate |
| amp | AMP |
| asn-L | L-Asparagine |
| asp-L | L-Aspartate |
| atp | ATP |
| cbp | Carbamoyl phosphate |
| co2 | CO2 |
| coa | Coenzyme A |
| dhap | Dihydroxyacetone phosphate |
| e4p | D-Erythrose 4-phosphate |
| etoh | Ethanol |
| f6p | D-Fructose 6-phosphate |
| fad | Flavin adenine dinucleotide oxidized |
| fadh2 | Flavin adenine dinucleotide reduced |
| fdp | D-Fructose 1,6-bisphosphate |
| for | Formate |
| fum | Fumarate |
| g3p | Glyceraldehyde 3-phosphate |
| g6p | D-Glucose 6-phosphate |
| glc-D | D-Glucose |
| glu5p | L-Glutamate 5-phosphate |
| glu5sa | L-Glutamate 5-semialdehyde |
| glu-L | L-Glutamate |
| glx | Glyoxylate |
| gly | Glycine |
| h | H+ |
| h2o | H2O |
| icit | Isocitrate |
| lac-D | D-Lactate |
| mal-L | L-Malate |

TABLE 30-continued

Metabolite names corresponding to abbreviations used in Table 29.

| Metabolite Abbreviation | Metabolite Name |
|---|---|
| methf | 5,10-Methenyltetrahydrofolate |
| mlthf | 5,10-Methylenetetrahydrofolate |
| mql8 | Menaquinol 8 |
| mqn8 | Menaquinone 8 |
| nad | Nicotinamide adenine dinucleotide |
| nadh | Nicotinamide adenine dinucleotide - reduced |
| nadp | Nicotinamide adenine dinucleotide phosphate |
| nadph | Nicotinamide adenine dinucleotide phosphate - reduced |
| nh4 | Ammonium |
| oaa | Oxaloacetate |
| pep | Phosphoenolpyruvate |
| pi | Phosphate |
| ppi | Diphosphate |
| pro-L | L-Proline |
| pyr | Pyruvate |
| q8 | Ubiquinone-8 |
| q8h2 | Ubiquinol-8 |
| ru5p-D | D-Ribulose 5-phosphate |
| s7p | Sedoheptulose 7-phosphate |
| so4 | Sulfate |
| succ | Succinate |
| succoa | Succinyl-CoA |
| thf | 5,6,7,8-Tetrahydrofolate |
| xu5p-D | D-Xylulose 5-phosphate |

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring bacterial organism, comprising a bacterial organism having a 1,4-butanediol (BDO) pathway comprising at least one exogenous nucleic acid encoding a BDO pathway enzyme expressed in a sufficient amount to produce BDO, wherein said bacterial organism is genetically modified to express an exogenous succinyl-CoA synthetase; to express an exogenous alpha-ketoglutarate decarboxylase; to express an exogenous succinate semialdehyde dehydrogenase and a 4-hydroxybutyrate dehydrogenase and optionally a 4-hydroxybutyryl-CoA/acetyl-CoA transferase; to express an exogenous butyrate kinase and a phosphotransbutyrylase; to express an exogenous 4-hydroxybutyryl-CoA reductase; to express an exogenous 4-hydroxybutanal reductase; to express an exogenous pyruvate dehydrogenase; to disrupt a gene encoding an aerobic respiratory control regulatory system; to express an exogenous NADH insensitive citrate synthase; and to express an exogenous phosphoenolpyruvate carboxykinase.

2. The non-naturally occurring bacterial organism of claim 1, wherein said BDO pathway comprises 4-hydroxybutanoate dehydrogenase, succinyl-CoA synthetase, CoA-dependent succinic semialdehyde dehydrogenase, 4-hydroxybutyrate:CoA transferase, 4-butyrate kinase, phosphotransbutyrylase, alpha-ketoglutarate decarboxylase, aldehyde dehydrogenase, alcohol dehydrogenase or an aldehyde/alcohol dehydrogenase.

3. The non-naturally occurring bacterial organism of claim 1, wherein said BDO pathway comprises 4-aminobutyrate CoA transferase, 4-aminobutyryl-CoA hydrolase, 4-aminobutyrate-CoA ligase, 4-aminobutyryl-CoA oxidoreductase (deaminating), 4-aminobutyryl-CoA transaminase, or 4-hydroxybutyryl-CoA dehydrogenase.

4. The non-naturally occurring bacterial organism of claim 3, wherein said BDO pathway further comprises 4-hydroxybutyryl-CoA reductase (alcohol forming), 4-hydroxybutyryl-CoA reductase, or 1,4-butanediol dehydrogenase.

5. The non-naturally occurring bacterial organism of claim 1, wherein said BDO pathway comprises 4-aminobutyrate CoA transferase, 4-aminobutyryl-CoA hydrolase, 4-aminobutyrate-CoA ligase, 4-aminobutyryl-CoA reductase (alcohol forming), 4-aminobutyryl-CoA reductase, 4-aminobutan-1-ol dehydrogenase, 4-aminobutan-1-ol oxidoreductase (deaminating) or 4-aminobutan-1-ol transaminase.

6. The non-naturally occurring bacterial organism of claim 1, wherein said BDO pathway comprises 4-aminobutyrate kinase, 4-aminobutyraldehyde dehydrogenase (phosphorylating), 4-aminobutan-1-ol dehydrogenase, 4-aminobutan-1-ol oxidoreductase (deaminating), 4-aminobutan-1-ol transaminase, [(4-aminobutanolyl)oxy]phosphonic acid oxidoreductase (deaminating), [(4-aminobutanolyl)oxy] phosphonic acid transaminase, 4-hydroxybutyryl-phosphate dehydrogenase, or 4-hydroxybutyraldehyde dehydrogenase (phosphorylating).

7. The non-naturally occurring bacterial organism of claim 6, wherein said BDO pathway further comprises 1,4-butanediol dehydrogenase.

8. The non-naturally occurring bacterial organism of claim 1, wherein said BDO pathway comprises alpha-ketoglutarate 5-kinase, 2,5-dioxopentanoic semialdehyde dehydrogenase (phosphorylating), 2,5-dioxopentanoic acid reductase, alpha-ketoglutarate CoA transferase, alpha-ketoglutaryl-CoA hydrolase, alpha-ketoglutaryl-CoA ligase, alpha-ketoglutaryl-CoA reductase, 5-hydroxy-2-oxopentanoic acid dehydrogenase, alpha-ketoglutaryl-CoA reductase (alcohol forming), 5-hydroxy-2-oxopentanoic acid decarboxylase, or 5-hydroxy-2-oxopentanoic acid dehydrogenase (decarboxylation).

9. The non-naturally occurring bacterial organism of claim 8, wherein said BDO pathway further comprises 4-hydroxybutyryl-CoA reductase (alcohol forming), 4-hydroxybutyryl-CoA reductase, or 1,4-butanediol dehydrogenase.

10. The non-naturally occurring bacterial organism of claim 1, wherein said BDO pathway comprises glutamate CoA transferase, glutamyl-CoA hydrolase, glutamyl-CoA ligase, glutamate 5-kinase, glutamate-5-semialdehyde dehydrogenase (phosphorylating), glutamyl-CoA reductase, glutamate-5-semialdehyde reductase, glutamyl-CoA reductase (alcohol forming), 2-amino-5-hydroxypentanoic acid oxidoreductase (deaminating), 2-amino-5-hydroxypentanoic acid transaminase, 5-hydroxy-2-oxopentanoic acid decarboxylase, 5-hydroxy-2-oxopentanoic acid dehydrogenase (decarboxylation).

11. The non-naturally occurring bacterial organism of claim 10, wherein said BDO pathway further comprises 4-hydroxybutyryl-CoA reductase (alcohol forming), 4-hydroxybutyryl-CoA reductase, or 1,4-butanediol dehydrogenase.

12. The non-naturally occurring bacterial organism of claim 1, wherein said BDO pathway comprising 3-hydroxybutyryl-CoA dehydrogenase, 3-hydroxybutyryl-CoA dehydratase, vinylacetyl-CoA Δ-isomerase, or 4-hydroxybutyryl-CoA dehydratase.

13. The non-naturally occurring bacterial organism of claim 1, wherein said BDO pathway comprises homoserine deaminase, homoserine CoA transferase, homoserine-CoA hydrolase, homoserine-CoA ligase, homoserine-CoA deaminase, 4-hydroxybut-2-enoyl-CoA transferase, 4-hydroxybut-2-enoyl-CoA hydrolase, 4-hydroxybut-2-enoyl-CoA ligase, 4-hydroxybut-2-enoate reductase, 4-hydroxybutyryl-CoA transferase, 4-hydroxybutyryl-CoA hydrolase, 4-hydroxybutyryl-CoA ligase, or 4-hydroxybut-2-enoyl-CoA reductase.

14. The non-naturally occurring bacterial organism of claim 13, wherein said BDO pathway further comprises 4-hydroxybutyryl-CoA reductase (alcohol forming), 4-hydroxybutyryl-CoA reductase, or 1,4-butanediol dehydrogenase.

15. The non-naturally occurring bacterial organism of claim 1, wherein said BDO pathway comprises succinyl-CoA reductase (alcohol forming), 4-hydroxybutyryl-CoA hydrolase, 4-hydroxybutyryl-CoA ligase, or 4-hydroxybutanal dehydrogenase (phosphorylating).

16. The non-naturally occurring bacterial organism of claim 15, wherein said BDO pathway further comprises succinyl-CoA reductase, 4-hydroxybutyrate dehydrogenase, 4-hydroxybutyryl-CoA transferase, 4-hydroxybutyrate kinase, phosphotrans-4-hydroxybutyrylase, 4-hydroxybutyryl-CoA reductase, 4-hydroxybutyryl-CoA reductase (alcohol forming), or 1,4-butanediol dehydrogenase.

17. The non-naturally occurring bacterial organism of claim 1, wherein said BDO pathway comprises glutamate dehydrogenase, 4-aminobutyrate oxidoreductase (deaminating), 4-aminobutyrate transaminase, glutamate decarboxylase, 4-hydroxybutyryl-CoA hydrolase, 4-hydroxybutyryl-CoA ligase, or 4-hydroxybutanal dehydrogenase (phosphorylating).

18. The non-naturally occurring bacterial organism of claim 17, wherein said BDO pathway further comprises alpha-ketoglutarate decarboxylase, 4-hydroxybutyrate dehydrogenase, 4-hydroxybutyryl-CoA transferase, 4-hydroxybutyrate kinase, phosphotrans-4-hydroxybutyrylase, 4-hydroxybutyryl-CoA reductase, 4-hydroxybutyryl-CoA reductase (alcohol forming), or 1,4-butanediol dehydrogenase.

19. A non-naturally occurring bacterial organism, comprising a bacterial organism having a 1,4-butanediol (BDO) pathway comprising at least one exogenous nucleic acid encoding a BDO pathway enzyme expressed in a sufficient amount to produce BDO, wherein said bacterial organism is genetically modified and selected from the group consisting of:

a) a non-naturally occurring bacterial organism comprising deletion of endogenous adhE, IdhA, pflB, and lpdA genes; chromosomal insertion of a *Klebsiella pneumoniae* lpdA gene encoding a Glu354Lys mutation; and a vector comprising *E. coli* sucCD, *P. gingivalis* sucD, *P. gingivalis* 4hbd, *P. gingivalis* Cat2, and *C. acetobutylicum* adhE2 genes;

b) a non-naturally occurring bacterial organism comprising deletion of endogenous adhE, IdhA, pflB, and lpdA genes; chromosomal insertion of a *Klebsiella pneumoniae* lpdA gene encoding a Glu354Lys mutation; and a vector comprising *E. coli* sucCD, *P. gingivalis* sucD, *P. gingivalis* 4hbd, *C. acetobutylicum* buk1, *C. acetobutylicum* ptb, and *C. acetobutylicum* adhE2 genes;

c) a non-naturally occurring bacterial organism comprising deletion of endogenous adhE, IdhA, pflB, and lpdA genes; chromosomal insertion of a *Klebsiella pneumoniae* lpdA gene encoding a Glu354Lys mutation; deletion of endogenous mdh and arcA genes; and a vector comprising *E. coli* sucCD, *P. gingivalis* sucD, *P. gingivalis* 4hbd, *P. gingivalis* cat2, and *C. acetobutylicum* adhE2 genes;

d) a non-naturally occurring bacterial organism comprising deletion of endogenous adhE, IdhA, pflB, and lpdA genes; chromosomal insertion of a *Klebsiella pneumoniae* lpdA gene encoding a Glu354Lys mutation; deletion of endogenous mdh and arcA genes; and a vector comprising *M. bovis* sucA, *E. coli* sucCD, *P. gingivalis* sucD, *P. gingivalis* 4hbd, *P. gingivalis* cat2, and *C. acetobutylicum* adhE2 genes;

e) a non-naturally occurring bacterial organism comprising deletion of endogenous adhE, IdhA, pflB, and lpdA genes; chromosomal insertion of a *Klebsiella pneumoniae* lpdA gene encoding a Glu354Lys mutation; deletion of endogenous mdh and arcA genes; chromosomal replacement of an endogenous gltA gene with a gltA gene encoding a Arg163Leu mutation; and a vector comprising *E. coli* sucCD, *P. gingivalis* sucD, *P. gingivalis* 4hbd, *P. gingivalis* cat2, and *C. acetobutylicum* adhE2 genes;

f) a non-naturally occurring bacterial organism comprising deletion of endogenous adhE, IdhA, pflB, and lpdA genes; chromosomal insertion of a *Klebsiella pneumoniae* lpdA gene encoding a Glu354Lys mutation; deletion of endogenous mdh and arcA genes; chromosomal replacement of of an endogenous gltA gene with a gltA gene encoding a Arg163Leu mutation; and a vector comprising *M. bovis* sucA, *E. coli* sucCD, *P. gingivalis* sucD, *P. gingivalis* 4hbd, *P. gingivalis* cat2, and *C. acetobutylicum* adhE2 genes;

g) a non-naturally occurring bacterial organism comprising deletion of endogenous adhE, IdhA, pflB, and lpdA genes; chromosomal insertion of a *Klebsiella pneumoniae* lpdA gene encoding a Glu354Lys mutation; deletion of endogenous mdh and arcA genes; chromosomal replacement of of an endogenous gltA gene with a gltA gene encoding a Arg163Leu mutation; and a vector comprising *M. bovis* sucA, *E. coli* sucCD, *P. gingivalis* sucD, *P. gingivalis* 4hbd, *P. gingivalis* cat2, and *C. beijerinckii* ald genes;

h) a non-naturally occurring bacterial organism comprising deletion of endogenous adhE, IdhA, pflB, and lpdA genes; chromosomal insertion of a *Klebsiella pneumoniae* lpdA gene encoding a Glu354Lys mutation; deletion of endogenous mdh and arcA genes; chromosomal replacement of an endogenous gltA gene with a gltA gene encoding a Arg163Leu mutation; a chromosomal insertion at the fimD locus of *E. coli* sucCD, *P. gingivalis* sucD, *P. gingivalis* 4hbd genes, and a vector comprising *P. gingivalis* cat2, and *C. beijerinckii* ald genes;

i) a non-naturally occurring bacterial organism comprising deletion of endogenous adhE, IdhA, pflB, and IpdA genes; chromosomal insertion of a *Klebsiella pneumoniae* IpdA gene encoding a Glu354Lys mutation; deletion of endogenous mdh and arcA genes; chromosomal replacement of an endogenous gltA gene with a gltA gene encoding a Arg163Leu mutation; chromosomal insertion of *E. coli* sucCD, *P. gingivalis* sucD, *P. gingivalis* 4hbd, *M. bovis* sucA, and *C. kluyveri* 4hbd genes at the fimD locus of said non-naturally occurring bacterial organism; and a vector comprising *P. gingivalis* cat2, and *C. beijerinckii* ald genes;

j) a non-naturally occurring bacterial organism comprising deletion of endogenous adhE, IdhA, pflB, and IpdA genes; chromosomal insertion of a *Klebsiella pneumoniae* IpdA gene encoding a Glu354Lys mutation; deletion of endogenous mdh and arcA genes; chromosomal replacement of an endogenous gltA gene with a gltA gene encoding a Arg163Leu mutation; chromosomal insertion of *E. coli* sucCD, *P. gingivalis* sucD, *P. gingivalis* 4hbd, *M. bovis* sucA, and *C. kluyveri* 4hbd genes at the fimD locus of said non-naturally occurring bacterial organism; and a vector comprising *C. acetobutylicum* buk1, *C. acetobutylicum* ptb, *C. beijerinckii* ald genes;

k) a non-naturally occurring bacterial organism comprising deletion of endogenous adhE, IdhA, pflB, and IpdA genes; chromosomal insertion of a *Klebsiella pneumoniae* IpdA gene encoding a Glu354Lys mutation; deletion of endogenous mdh and arcA genes; chromosomal replacement of an endogenous gltA gene with a gltA gene encoding a Arg163Leu mutation; deletion of an endogenous ackA gene; chromosomal insertion of *E. coli* sucCD, *P. gingivalis* sucD, *P. gingivalis* 4hbd, *M. bovis* sucA, and *C. kluyveri* 4hbd genes at the fimD locus of said non-naturally occurring bacterial organism; and a vector comprising *P. gingivalis* cat2, and *C. beijerinckii* ald genes;

l) a non-naturally occurring bacterial organism comprising deletion of endogenous adhE, IdhA, pflB, and IpdA genes; chromosomal insertion of a *Klebsiella pneumoniae* IpdA gene encoding a Glu354Lys mutation; deletion of endogenous mdh and arcA genes; chromosomal replacement of an endogenous gltA gene with a gltA gene encoding a Arg163Leu mutation; deletion of an endogenous ackA gene; deletion of an endogenous ppc gene and insertion of an *Haemophilus influenza* ppck gene at the ppc locus; chromosomal insertion of *E. coli* sucCD, *P. gingivalis* sucD, *P. gingivalis* 4hbd, *M. bovis* sucA, and *C. kluyveri* 4hbd genes at the fimD locus of said non-naturally occurring bacterial organism; and a vector comprising *P. gingivalis* cat2, and *C. beijerinckii* ald genes;

m) a non-naturally occurring bacterial organism comprising deletion of endogenous adhE, IdhA, pflB, and IpdA genes; chromosomal insertion of a *Klebsiella pneumoniae* IpdA gene encoding a Glu354Lys mutation; deletion of endogenous mdh and arcA genes; chromosomal replacement of an endogenous gltA gene with a gltA gene encoding a Arg163Leu mutation; chromosomal insertion of *E. coli* sucCD, *P. gingivalis* sucD, *P. gingivalis* 4hbd, *M. bovis* sucA, and *C. kluyveri* 4hbd genes at the fimD locus of said non-naturally occurring bacterial organism; replacement of an IpdA promoter with a fnr binding site, pflB-p6 promoter and RBS of pflB gene; and a vector comprising *P. gingivalis* cat2, and *C. beijerinckii* ald genes;

n) a non-naturally occurring bacterial organism comprising deletion of endogenous adhE, IdhA, pflB, and IpdA genes; chromosomal insertion of a *Klebsiella pneumoniae* IpdA gene encoding a Glu354Lys mutation; deletion of endogenous mdh and arcA genes; chromosomal replacement of an endogenous gltA gene with a gltA gene encoding a Arg163Leu mutation; chromosomal insertion of *E. coli* sucCD, *P. gingivalis* sucD, *P. gingivalis* 4hbd, *M. bovis* sucA, and *C. kluyveri* 4hbdI genes at the fimD locus of said non-naturally occurring bacterial organism; replacement of pdhR and aceEF promoters with a fnr binding site, pflB-p6 promoter and RBS of pflB gene; and a vector comprising *P. gingivalis* cat2, and *C. beijerinckii* ald genes;

o) a non-naturally occurring bacterial organism comprising deletion of endogenous adhE, IdhA, pflB, and IpdA genes; chromosomal insertion of a *Klebsiella pneumoniae* IpdA gene encoding a Glu354Lys mutation; deletion of endogenous mdh and arcA genes; chromosomal replacement of an endogenous gltA gene with a gltA gene encoding a Arg163Leu mutation; chromosomal insertion of *E. coli* sucCD, *P. gingivalis* sucD, *P. gingivalis* 4hbd, *M. bovis* sucA, *C. kluyveri* 4hbd, *C. acetobutylicum* buk1, and *C. acetobutylicum* ptb genes at the fimD locus of said non-naturally occurring bacterial organism; and a vector comprising a *C. beijerinckii* ald gene;

p) a non-naturally occurring bacterial organism comprising deletion of endogenous adhE, IdhA, pflB, and IpdA genes; chromosomal insertion of a *Klebsiella pneumoniae* IpdA gene encoding a Glu354Lys mutation; deletion of endogenous mdh and arcA genes; chromosomal replacement of an endogenous gltA gene with a gltA gene encoding a Arg163Leu mutation; chromosomal insertion of *E. coli* sucCD, *P. gingivalis* sucD, *P. gingivalis* 4hbd, *M. bovis* sucA, *C. kluyveri* 4hbd, *C. acetobutylicum* buk1, and *C. acetobutylicum* ptb genes at the fimD locus of said non-naturally occurring bacterial organism; and a vector comprising *C. beijerinckii* ald and *G. thermoglucosidasius* adh1 genes;

q) a non-naturally occurring bacterial organism comprising deletion of endogenous adhE, IdhA, pflB, and IpdA genes; chromosomal insertion of a *Klebsiella pneumoniae* IpdA gene encoding a Glu354Lys mutation; deletion of endogenous mdh and arcA genes; chromosomal replacement of an endogenous gltA gene with a gltA gene encoding a Arg163Leu mutation; chromosomal insertion of *E. coli* sucCD, *P. gingivalis* sucD, *P. gingivalis* 4hbd, *M. bovis* sucA, and *C. kluyveri* 4hbdl genes at the fimD locus of said non-naturally occurring bacterial organism; insertion at the rrnC locus of non-PTS sucrose operon genes sucrose permease (cscB), D-fructokinase (cscK), sucrose hydrolase (cscA), and a LacI-related sucrose-specific repressor (cscR); and a vector comprising *P. gingivalis* cat2, and *C. beijerinckii* ald genes; and r) a non-naturally occurring bacterial organism comprising deletion of endogenous adhE, IdhA, pflB, and IpdA genes; chromosomal insertion of a *Klebsiella pneumoniae* IpdA gene encoding a Glu354Lys mutation; deletion of endogenous mdh and arcA genes; chromosomal replacement of an endogenous gltA gene with a gltA gene encoding a Arg163Leu mutation; chromosomal insertion of *E. coli* sucCD, *P. gingivalis* sucD, *P. gingivalis* 4hbd, *M. bovis* sucA, and *C. kluyveri* 4hbdl genes at the fimD locus of said non-naturally occurring bacterial organism; insertion at the rrnC locus of non- PTS sucrose operon genes; and a vector comprising *C. acetobutylicum* buk1, *C. acetobutylicum* ptb, and *C. beijerinckii* ald genes.

20. A method for producing 1,4-butanediol (BDO), comprising culturing the non-naturally occurring bacterial organism of claim 1 under conditions and for a sufficient period of time to produce BDO.

\* \* \* \* \*

SEQUENCE LISTING

```
<160> NUMBER OF SEQ ID NOS: 88

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacgaattcg ctagcaagag gagaagtcga catgtccaat tcactggccg tcgttttac      59

<210> SEQ ID NO 2
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaccctagga agctttctag agtcgaccta tgcggcatca gagcaga                   47

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgtaccgca agttccgc                                                   18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 4
caatttgccg atgcccag                                              18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctgaccact gaagactttg                                            20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatcagggct tcggtgtag                                             19

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttggtgcggg ccaagcagga tctgctc                                    27

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcagccgaac gcctcgtcga ggatctcctg                                 30

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tggccaacat aagttcacca ttcgggcaaa ac                              32

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
tctcttcaac cagccattcg ttttgcccg                                              29

<210> SEQ ID NO 11
<211> LENGTH: 27
<212> TYPE: DNA
<213> ORGANISM: Clostridium acetobutylicum

<400> SEQUENCE: 11
attaaagtta agtggaggaa tgttaac                                                27

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acacgcggat ccaacgtccc gg                                                     22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agcggctccg ctagccgctt atg                                                    23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aagccgttgc tgcagctctt gagc                                                   24

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atctccggcg gtcggatccg tcg                                                    23

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaagcggcta gccacgccgc                                                        20
```

```
<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
attacacgag gtacccaacg                                            20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atgctggcgt acaaaggtgt cc                                         22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggacaccttt gtacgccagc at                                         22

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atcgcctaca ctaaaccaga agtgg                                      25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccacttctgg tttagtgtag gcgat                                      25

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aggcagttcc ataggatggc                                            20

<210> SEQ ID NO 23
```

```
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgacatgtaa cacctacctt ctgtgcctgt gccagtggtt gctgtgatat agaag          55

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ataataatac atatgaacca tgcgagttac gggcctataa gccaggcg                 48

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agtttttcga tatctgcatc agacaccggc acattgaaac gg                       42

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctggcacagg cacagaaggt aggtgttaca tgtcagaacg tttacacaat gacgtggatc     60

<210> SEQ ID NO 27
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agacaaatcg gttgccgttt gttaagccag gcgagatatg atctatatc                49

<210> SEQ ID NO 28
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gagttttgat ttcagtactc atcatgtaac acctaccttc ttgctgtgat atag          54

<210> SEQ ID NO 29
<211> LENGTH: 54
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctatatcaca gcaagaaggt aggtgttaca tgatgagtac tgaaatcaaa actc            54

<210> SEQ ID NO 30
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gatatagatc atatctcgcc tggcttaaca aacggcaacc gatttgtct                  49

<210> SEQ ID NO 31
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tattgtgcat acagatgaat ttttatgcaa acagtcagcc ctgaagaagg gtgtaggctg      60
gagctgcttc                                                             70

<210> SEQ ID NO 32
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
caaaaaaccg gagtctgtgc tccggttttt tattatccgc taatcaatta catatgaata      60
tcctccttag                                                             70

<210> SEQ ID NO 33
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ataataatag aattcgtttg ctacctaaat tgccaactaa atcgaaacag g                51

<210> SEQ ID NO 34
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tattattatg gtaccaatat catgcagcaa acggtgcaac attgccg                    47
```

<210> SEQ ID NO 35
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgatctggaa gaattcatcg gctttaccac cgtcaaaaaa aacggcg         47

<210> SEQ ID NO 36
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ataaaaccct gcagcggaaa cgaagttttta tccattttttg gttacctg         48

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggaagagagg ctggtaccca gaagccacag cagga         35

<210> SEQ ID NO 38
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtaatcactg cgtaagcgcc atgccccggc gttaattc         38

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
attgccgcgt tcctcctgct gtcga         25

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cgacagcagg aggaacgcgg caat         24

<210> SEQ ID NO 41
<211> LENGTH: 75
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 41
gtttgcacgc tatagctgag gttgttgtct tccagcaacg taccgtatac aataggcgta    60
tcacgaggcc ctttc                                                     75

<210> SEQ ID NO 42
<211> LENGTH: 70
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 42
gctacagcat gtcacacgat ctcaacggtc ggatgaccaa tctggctggt atgggaatta    60
gccatggtcc                                                           70

<210> SEQ ID NO 43
<211> LENGTH: 73
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 43
tgtgagtgaa agtcacctgc cttaatatct caaaactcat cttcgggtga cgaaatatgg    60
cgtgactcga tac                                                       73

<210> SEQ ID NO 44
<211> LENGTH: 70
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 44
tctgtatcag gctgaaaatc ttctctcatc cgccaaaaca gcttcggcgt taagatgcgc    60
gctcaaggac                                                           70

<210> SEQ ID NO 45
<211> LENGTH: 2036
<212> TYPE: DNA
<213> ORGANISM: Escherichia coli

<400> SEQUENCE: 45
atgaacttac atgaatatca ggcaaaacaa ctttttgccc gctatggctt accagcaccg    60
gtgggttatg cctgtactac tccgcgcgaa gcagaagaag ccgcttcaaa aatcggtgcc   120
ggtccgtggg tagtgaaatg tcaggttcac gctggtggcc gcggtaaagc gggcggtgtg   180
aaagttgtaa acagcaaaga agacatccgt gcttttgcag aaaactggct gggcaagcgt   240
ctggtaacgt atcaaacaga tgccaatggc caaccggtta accagattct ggttgaagca   300
gcgaccgata tcgctaaaga gctgtatctc ggtgccgttg ttgaccgtag ttcccgtcgt   360

```
gtggtcttta tggcctccac cgaaggcggc gtggaaatcg aaaaagtggc ggaagaaact      420
ccgcacctga tccataaagt tgcgcttgat ccgctgactg ccccgatgcc gtatcaggga      480
cgcgagctgg cgttcaaact gggtctggaa ggtaaactgg ttcagcagtt caccaaaatc      540
ttcatgggcc tggcgaccat tttcctggag cgcgacctgg cgttgatcga aatcaacccg      600
ctggtcatca ccaaacaggg cgatctgatt tgcctcgacg caaactggg cgctgacggc       660
aacgcactgt tccgccagcc tgatctgcgc gaaatgcgtg accagtcgca ggaagatccg      720
cgtgaagcac aggctgcaca gtgggaactg aactacgttg cgctggacgg taacatcggt      780
tgtatggtta acggcgcagg tctggcgatg ggtacgatgg acatcgttaa actgcacggc      840
ggcgaaccgg ctaacttcct tgacgttggc ggcggcgcaa ccaaagaacg tgtaaccgaa      900
gcgttcaaaa tcatcctctc tgacgacaaa gtgaaagccg ttctggttaa catcttcggc      960
ggtatcgttc gttgcgacct gatcgctgac ggtatcatcg gcgcggtagc agaagtgggt     1020
gttaacgtac cggtcgtggt acgtctggaa ggtaacaacg ccgaactcgg cgcgaagaaa     1080
ctggctgaca gcggcctgaa tattattgca gcaaaaggtc tgacggatgc agctcagcag     1140
gttgttgccg cagtggaggg gaaataatgt ccatttttaat cgataaaaac accaaggtta     1200
tctgccaggg ctttaccggt agccaggga ctttccactc agaacaggcc attgcatacg      1260
gcactaaaat ggttggcggc gtaaccccag gtaaaggcgg caccacccac ctcggcctgc     1320
cggtgttcaa caccgtgcgt gaagccgttg ctgccactgg cgctaccgct tctgttatct     1380
acgtaccagc accgttctgc aaagactcca ttctggaagc catcgacgca ggcatcaaac     1440
tgattatcac catcactgaa ggcatcccga cgctggatat gctgaccgtg aaagtgaagc     1500
tggatgaagc aggcgttcgt atgatcggcc cgaactgccc aggcgttatc actccgggtg     1560
aatgcaaaat cggtatccag cctggtcaca ttcacaaacc gggtaaagtg gtatcgttt     1620
cccgttccgg tacactgacc tatgaagcgg ttaaacagac cacggattac ggtttcggtc     1680
agtcgacctg tgtcggtatc ggcggtgacc cgatcccggg ctctaacttt atcgacattc     1740
tcgaaatgtt cgaaaaagat ccgcagaccg aagcgatcgt gatgatcggt gagatcggcg     1800
gtagcgctga agaagaagca gctgcgtaca tcaaagagca cgttaccaag ccagttgtgg     1860
gttacatcgc tggtgtgact gcgccgaaag gcaaacgtat gggccacgcg ggtgccatca     1920
ttgccggtgg gaagggact gcggatgaga aattcgctgc tctggaagcc gcaggcgtga      1980
aaaccgttcg cagcctggcg gatatcggtg aagcactgaa aactgttctg aaataa         2036
```

<210> SEQ ID NO 46
<211> LENGTH: 388
<212> TYPE: PRT
<213> ORGANISM: Escherichia coli

<400> SEQUENCE: 46

Met Asn Leu His Glu Tyr Gln Ala Lys Gln Leu Phe Ala Arg Tyr Gly
1               5                   10                  15

Leu Pro Ala Pro Val Gly Tyr Ala Cys Thr Thr Pro Arg Glu Ala Glu
            20                  25                  30

Glu Ala Ala Ser Lys Ile Gly Ala Gly Pro Trp Val Val Lys Cys Gln
        35                  40                  45

Val His Ala Gly Gly Arg Gly Lys Ala Gly Gly Val Lys Val Val Asn
    50                  55                  60

Ser Lys Glu Asp Ile Arg Ala Phe Ala Glu Asn Trp Leu Gly Lys Arg
65                  70                  75                  80

Leu Val Thr Tyr Gln Thr Asp Ala Asn Gly Gln Pro Val Asn Gln Ile
                85                  90                  95

Leu Val Glu Ala Ala Thr Asp Ile Ala Lys Glu Leu Tyr Leu Gly Ala
            100                 105                 110

Val Val Asp Arg Ser Ser Arg Arg Val Val Phe Met Ala Ser Thr Glu
            115                 120                 125

Gly Gly Val Glu Ile Glu Lys Val Ala Glu Thr Pro His Leu Ile
            130                 135                 140

His Lys Val Ala Leu Asp Pro Leu Thr Gly Pro Met Pro Tyr Gln Gly
145                 150                 155                 160

Arg Glu Leu Ala Phe Lys Leu Gly Leu Glu Gly Lys Leu Val Gln Gln
                165                 170                 175

Phe Thr Lys Ile Phe Met Gly Leu Ala Thr Ile Phe Leu Glu Arg Asp
                180                 185                 190

Leu Ala Leu Ile Glu Ile Asn Pro Leu Val Ile Thr Lys Gln Gly Asp
            195                 200                 205

Leu Ile Cys Leu Asp Gly Lys Leu Gly Ala Asp Gly Asn Ala Leu Phe
            210                 215                 220

Arg Gln Pro Asp Leu Arg Glu Met Arg Asp Gln Ser Gln Glu Asp Pro
225                 230                 235                 240

Arg Glu Ala Gln Ala Ala Gln Trp Glu Leu Asn Tyr Val Ala Leu Asp
                245                 250                 255

Gly Asn Ile Gly Cys Met Val Asn Gly Ala Gly Leu Ala Met Gly Thr
                260                 265                 270

Met Asp Ile Val Lys Leu His Gly Gly Glu Pro Ala Asn Phe Leu Asp
            275                 280                 285

Val Gly Gly Gly Ala Thr Lys Glu Arg Val Thr Glu Ala Phe Lys Ile
            290                 295                 300

Ile Leu Ser Asp Asp Lys Val Lys Ala Val Leu Val Asn Ile Phe Gly
305                 310                 315                 320

Gly Ile Val Arg Cys Asp Leu Ile Ala Asp Gly Ile Ile Gly Ala Val
                325                 330                 335

Ala Glu Val Gly Val Asn Val Pro Val Val Val Arg Leu Glu Gly Asn
            340                 345                 350

Asn Ala Glu Leu Gly Ala Lys Lys Leu Ala Asp Ser Gly Leu Asn Ile
            355                 360                 365

Ile Ala Ala Lys Gly Leu Thr Asp Ala Ala Gln Gln Val Val Ala Ala
            370                 375                 380

Val Glu Gly Lys
385

<210> SEQ ID NO 47
<211> LENGTH: 289
<212> TYPE: PRT
<213> ORGANISM: Escherichia coli

<400> SEQUENCE: 47

Met Ser Ile Leu Ile Asp Lys Asn Thr Lys Val Ile Cys Gln Gly Phe
1               5                   10                  15

Thr Gly Ser Gln Gly Thr Phe His Ser Glu Gln Ala Ile Ala Tyr Gly
            20                  25                  30

Thr Lys Met Val Gly Gly Val Thr Pro Gly Lys Gly Gly Thr Thr His
            35                  40                  45

Leu Gly Leu Pro Val Phe Asn Thr Val Arg Glu Ala Val Ala Ala Thr
            50                  55                  60

-continued

```
Gly Ala Thr Ala Ser Val Ile Tyr Val Pro Ala Pro Phe Cys Lys Asp
65                  70                  75                  80

Ser Ile Leu Glu Ala Ile Asp Ala Gly Ile Lys Leu Ile Ile Thr Ile
                85                  90                  95

Thr Glu Gly Ile Pro Thr Leu Asp Met Leu Thr Val Lys Val Lys Leu
            100                 105                 110

Asp Glu Ala Gly Val Arg Met Ile Gly Pro Asn Cys Pro Gly Val Ile
        115                 120                 125

Thr Pro Gly Glu Cys Lys Ile Gly Ile Gln Pro Gly His Ile His Lys
    130                 135                 140

Pro Gly Lys Val Gly Ile Val Ser Arg Ser Gly Thr Leu Thr Tyr Glu
145                 150                 155                 160

Ala Val Lys Gln Thr Thr Asp Tyr Gly Phe Gly Gln Ser Thr Cys Val
                165                 170                 175

Gly Ile Gly Gly Asp Pro Ile Pro Gly Ser Asn Phe Ile Asp Ile Leu
            180                 185                 190

Glu Met Phe Glu Lys Asp Pro Gln Thr Glu Ala Ile Val Met Ile Gly
        195                 200                 205

Glu Ile Gly Gly Ser Ala Glu Glu Glu Ala Ala Ala Tyr Ile Lys Glu
    210                 215                 220

His Val Thr Lys Pro Val Val Gly Tyr Ile Ala Gly Val Thr Ala Pro
225                 230                 235                 240

Lys Gly Lys Arg Met Gly His Ala Gly Ala Ile Ile Ala Gly Gly Lys
                245                 250                 255

Gly Thr Ala Asp Glu Lys Phe Ala Ala Leu Glu Ala Ala Gly Val Lys
            260                 265                 270

Thr Val Arg Ser Leu Ala Asp Ile Gly Glu Ala Leu Lys Thr Val Leu
        275                 280                 285

Lys
```

<210> SEQ ID NO 48
<211> LENGTH: 3696
<212> TYPE: DNA
<213> ORGANISM: Mycobacterium bovis

<400> SEQUENCE: 48

```
atggccaaca taagttcacc attcgggcaa aacgaatggc tggttgaaga gatgtaccgc     60
aagttccgcg acgacccctc ctcggtcgat cccagctggc acgagttcct ggttgactac    120
agccccgaac ccacctccca accagctgcc gaaccaaccc gggttacctc gccactcgtt    180
gccgagcggg ccgctgcggc cgccccgcag gcaccccca agccggccga caccgcggcc    240
gcgggcaacg gcgtggtcgc cgcactggcc gccaaaactg ccgttccccc gccagccgaa    300
ggtgacgagg tagcggtgct gcgcggcgcc gccgcggccg tcgtcaagaa catgtccgcg    360
tcgttggagg tgccgacggc gaccagcgtc cgggcggtcc cggccaagct actgatcgac    420
aaccggatcg tcatcaacaa ccagttgaag cggacccgcg gcggcaagat ctcgttcacg    480
catttgctgg gctacgccct ggtgcaggcg gtgaagaaat tcccgaacat gaaccggcac    540
tacaccgaag tcgacggcaa gcccaccgcg gtcacgccgg cgcacaccaa tctcggcctg    600
gcgatcgacc tgcaaggcaa ggacgggaag cgttccctgg tggtggccgg catcaagcgg    660
tgcgagacca tgcgattcgc gcagttcgtc acggcctacg aagacatcgt acgccgggcc    720
cgcgacggca agctgaccac tgaagacttt gccggcgtga cgatttcgct gaccaatccc    780
```

```
ggaaccatcg gcaccgtgca ttcggtgccg cggctgatgc ccggccaggg cgccatcatc      840
ggcgtgggcg ccatggaata ccccgccgag tttcaaggcg ccagcgagga acgcatcgcc      900
gagctgggca tcggcaaatt gatcactttg acctccacct acgaccaccg catcatccag      960
ggcgcggaat cgggcgactt cctgcgcacc atccacgagt tgctgctctc ggatggcttc     1020
tgggacgagg tcttccgcga actgagcatc ccatatctgc cggtgcgctg gagcaccgac     1080
aaccccgact cgatcgtcga caagaacgct cgcgtcatga acttgatcgc ggcctaccgc     1140
aaccgcggcc atctgatggc cgataccgac ccgctgcggt tggacaaagc tcggttccgc     1200
agtcaccccg acctcgaagt gctgacccac ggcctgacgc tgtgggatct cgatcgggtg     1260
ttcaaggtcg acggctttgc cggtgcgcag tacaagaaac tgcgcgacgt gctgggcttg     1320
ctgcgcgatg cctactgccg ccacatcggc gtggagtacg cccatatcct cgaccccgaa     1380
caaaaggagt ggctcgaaca acgggtcgag accaagcacg tcaaacccac tgtgcccaa      1440
cagaaataca tcctcagcaa gctcaacgcc gccgaggcct ttgaaacgtt cctacagacc     1500
aagtacgtcg gccagaagcg gttctcgctg gaaggcgccg aaagcgtgat cccgatgatg     1560
gacgcggcga tcgaccagtg cgctgagcac ggcctcgacg aggtggtcat cgggatgccg     1620
caccggggcc ggctcaacgt gctggccaac atcgtcggca agccgtactc gcagatcttc     1680
accgagttcg agggcaacct gaatccgtcg caggcgcacg gctccggtga cgtcaagtac     1740
cacctgggcg ccaccgggct gtacctgcag atgttcggcg acaacgacat tcaggtgtcg     1800
ctgaccgcca acccgtcgca tctggaggcc gtcgacccgg tgctggaggg attggtgcgg     1860
gccaagcagg atctgctcga ccacggaagc atcgacagcg acggccaacg ggcgttctcg     1920
gtggtgccgc tgatgttgca tggcgatgcc gcgttcgccg gtcagggtgt ggtcgccgag     1980
acgctgaacc tggcgaatct gccgggctac cgcgtcggcg gcaccatcca catcatcgtc     2040
aacaaccaga tcggcttcac caccgcgccc gagtattcca ggtccagcga gtactgcacc     2100
gacgtcgcaa agatgatcgg ggcaccgatc tttcacgtca acggcgacga cccggaggcg     2160
tgtgtctggg tggcgcggtt ggcggtggac ttccgacaac ggttcaagaa ggacgtcgtc     2220
atcgacatgc tgtgctaccg ccgccgcggg cacaacgagg gtgacgaccc gtcgatgacc     2280
aaccccctaca tgtacgacgt cgtcgacacc aagcgcgggg cccgcaaaag ctacaccgaa     2340
gccctgatcg gacgtggcga catctcgatg aaggaggccg aggacgcgct gcgcgactac     2400
cagggccagc tggaacgggt gttcaacgaa gtgcgcgagc tggagaagca cggtgtgcag     2460
ccgagcgagt cggtcgagtc cgaccagatg attcccgcgg ggctggccac tgcggtggac     2520
aagtcgctgc tggcccggat cggcgatgcg ttcctcgcct tgccgaacgg cttcaccgcg     2580
cacccgcgag tccaaccggt gctggagaag cgccgggaga tggcctatga aggcaagatc     2640
gactgggcct ttggcgagct gctggcgctg ggctcgctgg tggccgaagg caagctggtg     2700
cgcttgtcgg ggcaggacag ccgccgcggc accttctccc agcggcattc ggttctcatc     2760
gaccgccaca ctgcgcgagga gttcacacca ctgcagctgc tggcgaccaa ctccgacggc     2820
agcccgaccg gcggaaagtt cctggtctac gactcgccac tgtcggagta cgccgccgtc     2880
ggcttcgagt acggctacac tgtgggcaat ccggacgccg tggtgctctg ggaggcgcag     2940
ttcggcgact tcgtcaacgg cgcacagtcg atcatcgacg agttcatcag ctccggtgag     3000
gccaagtggg gccaattgtc caacgtcgtg ctgctgttac cgcacgggca cgaggggcag     3060
ggaccccgacc acacttctgc ccggatcgaa cgcttcttgc agttgtgggc ggaaggttcg     3120
atgaccatcg cgatgccgtc gactccgtcg aactactccc acctgctacg ccggcatgcc     3180
```

```
ctggacggca tccaacgccc gctgatcgtg ttcacgccca agtcgatgtt gcgtcacaag   3240
gccgccgtca gcgaaatcaa ggacttcacc gagatcaagt tccgctcagt gctggaggaa   3300
cccacctatg aggacggcat cggagaccgc aacaaggtca gccggatcct gctgaccagt   3360
ggcaagctgt attacgagct ggccgcccgc aaggccaagg acaaccgcaa tgacctcgcg   3420
atcgtgcggc ttgaacagct cgccccgctg cccaggcgtc gactgcgtga aacgctggac   3480
cgctacgaga acgtcaagga gttcttctgg gtccaagagg aaccggccaa ccagggtgcg   3540
tggccgcgat tcgggctcga actacccgag ctgctgcctg acaagttggc cgggatcaag   3600
cgaatctcgc gccgggcgat gtcagccccg tcgtcaggct cgtcgaaggt gcacgccgtc   3660
gaacagcagg agatcctcga cgaggcgttc ggctaa                             3696
```

<210> SEQ ID NO 49
<211> LENGTH: 1231
<212> TYPE: PRT
<213> ORGANISM: Mycobacterium bovis

<400> SEQUENCE: 49

```
Met Ala Asn Ile Ser Ser Pro Phe Gly Gln Asn Glu Trp Leu Val Glu
1               5                   10                  15

Glu Met Tyr Arg Lys Phe Arg Asp Asp Pro Ser Ser Val Asp Pro Ser
            20                  25                  30

Trp His Glu Phe Leu Val Asp Tyr Ser Pro Glu Pro Thr Ser Gln Pro
        35                  40                  45

Ala Ala Glu Pro Thr Arg Val Thr Ser Pro Leu Val Ala Glu Arg Ala
    50                  55                  60

Ala Ala Ala Ala Pro Gln Ala Pro Pro Lys Pro Ala Asp Thr Ala Ala
65                  70                  75                  80

Ala Gly Asn Gly Val Val Ala Ala Leu Ala Ala Lys Thr Ala Val Pro
                85                  90                  95

Pro Pro Ala Glu Gly Asp Glu Val Ala Val Leu Arg Gly Ala Ala Ala
            100                 105                 110

Ala Val Val Lys Asn Met Ser Ala Ser Leu Glu Val Pro Thr Ala Thr
        115                 120                 125

Ser Val Arg Ala Val Pro Ala Lys Leu Leu Ile Asp Asn Arg Ile Val
    130                 135                 140

Ile Asn Asn Gln Leu Lys Arg Thr Arg Gly Gly Lys Ile Ser Phe Thr
145                 150                 155                 160

His Leu Leu Gly Tyr Ala Leu Val Gln Ala Val Lys Lys Phe Pro Asn
                165                 170                 175

Met Asn Arg His Tyr Thr Glu Val Asp Gly Lys Pro Thr Ala Val Thr
            180                 185                 190

Pro Ala His Thr Asn Leu Gly Leu Ala Ile Asp Leu Gln Gly Lys Asp
        195                 200                 205

Gly Lys Arg Ser Leu Val Val Ala Gly Ile Lys Arg Cys Glu Thr Met
    210                 215                 220

Arg Phe Ala Gln Phe Val Thr Ala Tyr Glu Asp Ile Val Arg Arg Ala
225                 230                 235                 240

Arg Asp Gly Lys Leu Thr Thr Glu Asp Phe Ala Gly Val Thr Ile Ser
                245                 250                 255

Leu Thr Asn Pro Gly Thr Ile Gly Thr Val His Ser Val Pro Arg Leu
            260                 265                 270

Met Pro Gly Gln Gly Ala Ile Ile Gly Val Gly Ala Met Glu Tyr Pro
```

```
                275                 280                 285
Ala Glu Phe Gln Gly Ala Ser Glu Glu Arg Ile Ala Glu Leu Gly Ile
        290                 295                 300
Gly Lys Leu Ile Thr Leu Thr Ser Thr Tyr Asp His Arg Ile Ile Gln
305                 310                 315                 320
Gly Ala Glu Ser Gly Asp Phe Leu Arg Thr Ile His Glu Leu Leu Leu
                325                 330                 335
Ser Asp Gly Phe Trp Asp Glu Val Phe Arg Glu Leu Ser Ile Pro Tyr
            340                 345                 350
Leu Pro Val Arg Trp Ser Thr Asp Asn Pro Asp Ser Ile Val Asp Lys
                355                 360                 365
Asn Ala Arg Val Met Asn Leu Ile Ala Ala Tyr Arg Asn Arg Gly His
            370                 375                 380
Leu Met Ala Asp Thr Asp Pro Leu Arg Leu Asp Lys Ala Arg Phe Arg
385                 390                 395                 400
Ser His Pro Asp Leu Glu Val Leu Thr His Gly Leu Thr Leu Trp Asp
                405                 410                 415
Leu Asp Arg Val Phe Lys Val Asp Gly Phe Ala Gly Ala Gln Tyr Lys
            420                 425                 430
Lys Leu Arg Asp Val Leu Gly Leu Leu Arg Asp Ala Tyr Cys Arg His
                435                 440                 445
Ile Gly Val Glu Tyr Ala His Ile Leu Asp Pro Glu Gln Lys Glu Trp
            450                 455                 460
Leu Glu Gln Arg Val Glu Thr Lys His Val Lys Pro Thr Val Ala Gln
465                 470                 475                 480
Gln Lys Tyr Ile Leu Ser Lys Leu Asn Ala Ala Glu Ala Phe Glu Thr
                485                 490                 495
Phe Leu Gln Thr Lys Tyr Val Gly Gln Lys Arg Phe Ser Leu Glu Gly
            500                 505                 510
Ala Glu Ser Val Ile Pro Met Met Asp Ala Ala Ile Asp Gln Cys Ala
                515                 520                 525
Glu His Gly Leu Asp Glu Val Val Ile Gly Met Pro His Arg Gly Arg
            530                 535                 540
Leu Asn Val Leu Ala Asn Ile Val Gly Lys Pro Tyr Ser Gln Ile Phe
545                 550                 555                 560
Thr Glu Phe Glu Gly Asn Leu Asn Pro Ser Gln Ala His Gly Ser Gly
                565                 570                 575
Asp Val Lys Tyr His Leu Gly Ala Thr Gly Leu Tyr Leu Gln Met Phe
            580                 585                 590
Gly Asp Asn Asp Ile Gln Val Ser Leu Thr Ala Asn Pro Ser His Leu
            595                 600                 605
Glu Ala Val Asp Pro Val Leu Glu Gly Leu Val Arg Ala Lys Gln Asp
            610                 615                 620
Leu Leu Asp His Gly Ser Ile Asp Ser Asp Gly Gln Arg Ala Phe Ser
625                 630                 635                 640
Val Val Pro Leu Met Leu His Gly Asp Ala Ala Phe Ala Gly Gln Gly
                645                 650                 655
Val Val Ala Glu Thr Leu Asn Leu Ala Asn Leu Pro Gly Tyr Arg Val
            660                 665                 670
Gly Gly Thr Ile His Ile Ile Val Asn Asn Gln Ile Gly Phe Thr Thr
            675                 680                 685
Ala Pro Glu Tyr Ser Arg Ser Ser Glu Tyr Cys Thr Asp Val Ala Lys
            690                 695                 700
```

```
Met Ile Gly Ala Pro Ile Phe His Val Asn Gly Asp Pro Glu Ala
705                 710                 715                 720

Cys Val Trp Val Ala Arg Leu Ala Val Asp Phe Arg Gln Arg Phe Lys
            725                 730                 735

Lys Asp Val Val Ile Asp Met Leu Cys Tyr Arg Arg Gly His Asn
            740                 745                 750

Glu Gly Asp Asp Pro Ser Met Thr Asn Pro Tyr Met Tyr Asp Val Val
            755                 760                 765

Asp Thr Lys Arg Gly Ala Arg Lys Ser Tyr Thr Glu Ala Leu Ile Gly
            770                 775                 780

Arg Gly Asp Ile Ser Met Lys Glu Ala Glu Asp Ala Leu Arg Asp Tyr
785                 790                 795                 800

Gln Gly Gln Leu Glu Arg Val Phe Asn Glu Val Arg Glu Leu Glu Lys
                805                 810                 815

His Gly Val Gln Pro Ser Glu Ser Val Glu Ser Asp Gln Met Ile Pro
                820                 825                 830

Ala Gly Leu Ala Thr Ala Val Asp Lys Ser Leu Leu Ala Arg Ile Gly
            835                 840                 845

Asp Ala Phe Leu Ala Leu Pro Asn Gly Phe Thr Ala His Pro Arg Val
850                 855                 860

Gln Pro Val Leu Glu Lys Arg Arg Glu Met Ala Tyr Glu Gly Lys Ile
865                 870                 875                 880

Asp Trp Ala Phe Gly Glu Leu Leu Ala Leu Gly Ser Leu Val Ala Glu
                885                 890                 895

Gly Lys Leu Val Arg Leu Ser Gly Gln Asp Ser Arg Arg Gly Thr Phe
            900                 905                 910

Ser Gln Arg His Ser Val Leu Ile Asp Arg His Thr Gly Glu Glu Phe
            915                 920                 925

Thr Pro Leu Gln Leu Leu Ala Thr Asn Ser Asp Gly Ser Pro Thr Gly
930                 935                 940

Gly Lys Phe Leu Val Tyr Asp Ser Pro Leu Ser Glu Tyr Ala Ala Val
945                 950                 955                 960

Gly Phe Glu Tyr Gly Tyr Thr Val Gly Asn Pro Asp Ala Val Val Leu
                965                 970                 975

Trp Glu Ala Gln Phe Gly Asp Phe Val Asn Gly Ala Gln Ser Ile Ile
                980                 985                 990

Asp Glu Phe Ile Ser Ser Gly Glu Ala Lys Trp Gly Gln Leu Ser Asn
            995                 1000                1005

Val Val Leu Leu Leu Pro His Gly His Glu Gly Gln Gly Pro Asp
            1010                1015                1020

His Thr Ser Ala Arg Ile Glu Arg Phe Leu Gln Leu Trp Ala Glu
            1025                1030                1035

Gly Ser Met Thr Ile Ala Met Pro Ser Thr Pro Ser Asn Tyr Phe
            1040                1045                1050

His Leu Leu Arg Arg His Ala Leu Asp Gly Ile Gln Arg Pro Leu
            1055                1060                1065

Ile Val Phe Thr Pro Lys Ser Met Leu Arg His Lys Ala Ala Val
            1070                1075                1080

Ser Glu Ile Lys Asp Phe Thr Glu Ile Lys Phe Arg Ser Val Leu
            1085                1090                1095

Glu Glu Pro Thr Tyr Glu Asp Gly Ile Gly Asp Arg Asn Lys Val
            1100                1105                1110
```

| Ser | Arg | Ile | Leu | Leu | Thr | Ser | Gly | Lys | Leu | Tyr | Tyr | Glu | Leu | Ala |
|---|---|---|---|---|---|---|---|---|---|---|---|---|---|---|
| 1115 | | | | | 1120 | | | | | 1125 | | | | |

| Ala | Arg | Lys | Ala | Lys | Asp | Asn | Arg | Asn | Asp | Leu | Ala | Ile | Val | Arg |
|---|---|---|---|---|---|---|---|---|---|---|---|---|---|---|
| 1130 | | | | | 1135 | | | | | 1140 | | | | |

| Leu | Glu | Gln | Leu | Ala | Pro | Leu | Pro | Arg | Arg | Leu | Arg | Glu | Thr |
|---|---|---|---|---|---|---|---|---|---|---|---|---|---|
| 1145 | | | | | 1150 | | | | | 1155 | | | | |

| Leu | Asp | Arg | Tyr | Glu | Asn | Val | Lys | Glu | Phe | Phe | Trp | Val | Gln | Glu |
|---|---|---|---|---|---|---|---|---|---|---|---|---|---|---|
| 1160 | | | | | 1165 | | | | | 1170 | | | | |

| Glu | Pro | Ala | Asn | Gln | Gly | Ala | Trp | Pro | Arg | Phe | Gly | Leu | Glu | Leu |
|---|---|---|---|---|---|---|---|---|---|---|---|---|---|---|
| 1175 | | | | | 1180 | | | | | 1185 | | | | |

| Pro | Glu | Leu | Leu | Pro | Asp | Lys | Leu | Ala | Gly | Ile | Lys | Arg | Ile | Ser |
|---|---|---|---|---|---|---|---|---|---|---|---|---|---|---|
| 1190 | | | | | 1195 | | | | | 1200 | | | | |

| Arg | Arg | Ala | Met | Ser | Ala | Pro | Ser | Ser | Gly | Ser | Ser | Lys | Val | His |
|---|---|---|---|---|---|---|---|---|---|---|---|---|---|---|
| 1205 | | | | | 1210 | | | | | 1215 | | | | |

| Ala | Val | Glu | Gln | Gln | Glu | Ile | Leu | Asp | Glu | Ala | Phe | Gly |
|---|---|---|---|---|---|---|---|---|---|---|---|---|
| 1220 | | | | | 1225 | | | | | 1230 | | |

<210> SEQ ID NO 50
<211> LENGTH: 1356
<212> TYPE: DNA
<213> ORGANISM: Porphyromonas gingivalis

<400> SEQUENCE: 50

```
atggaaatca aagaaatggt gagccttgca cgcaaggctc agaaggagta tcaagctacc      60
cataaccaag aagcagttga caacatttgc cgagctgcag caaaagttat ttatgaaaat     120
gcagctattc tggctcgcga agcagtagac gaaaccggca tgggcgttta cgaacacaaa     180
gtggccaaga tcaaggcaa atccaaaggt gtttggtaca acctccacaa taaaaaatcg     240
attggtatcc tcaatataga cgagcgtacc ggtatgatcg agattgcaaa gcctatcgga     300
gttgtaggag ccgtaacgcc gacgaccaac ccgatcgtta ctccgatgag caatatcatc     360
tttgctctta agacctgcaa tgccatcatt attgccccc accccagatc caaaaaatgc     420
tctgcacacg cagttcgtct gatcaaagaa gctatcgctc cgttcaacgt accggaaggt     480
atggttcaga tcatcgaaga acccagcatc gagaagacgc aggaactcat gggcgccgta     540
gacgtagtag ttgctacggg tggtatgggc atggtgaagt ctgcatattc ttcaggaaag     600
ccttctttcg tgttggagc cggtaacgtt caggtgatcg tggatagcaa catcgatttc     660
gaagctgctg cagaaaaaat catcaccggt cgtgctttcg acaacggtat catctgctca     720
ggcgaacaga gcatcatcta caacgaggct gacaaggaag cagtttcac agcattccgc     780 aaccacggtg catatttctg tgacgaagcc gaaggagatc gggctcgtgc agctatcttc     840
gaaaatggag ccatcgcgaa agatgtagta ggtcagagcg ttgccttcat tgccaagaaa     900
gcaaacatca atatccccga gggtacccgt attctcgttg ttgaagctcg cggcgtagga     960
gcagaagacg ttatctgtaa ggaaaagatg tgtcccgtaa tgtgcgccct cagctacaag    1020
cacttcgaag aaggtgtaga aatcgcacgt acgaacctcg ccaacgaagg taacggccac    1080
acctgtgcta tccactccaa caatcaggca cacatcatcc tcgcaggatc agagctgacg    1140
gtatctcgta tcgtagtgaa tgctccgagt gccactacag caggcggtca catccaaaac    1200
ggtcttgccg taaccaatac gctcggatgc ggatcatggg gtaataactc tatctccgag    1260
aacttcactt acaagcacct cctcaacatt tcacgcatcg caccgttgaa ttcaagcatt    1320
cacatccccg atgacaaaga aatctgggaa ctctaa                              1356
```

```
<210> SEQ ID NO 51
<211> LENGTH: 451
<212> TYPE: PRT
<213> ORGANISM: Porphyromonas gingivalis

<400> SEQUENCE: 51
```

| | | | | | | | | | | | | | | |
|---|---|---|---|---|---|---|---|---|---|---|---|---|---|---|
| Met | Glu | Ile | Lys | Glu | Met | Val | Ser | Leu | Ala | Arg | Lys | Ala | Gln | Lys | Glu |
| 1 | | | | 5 | | | | | 10 | | | | | 15 | |

| Tyr | Gln | Ala | Thr | His | Asn | Gln | Glu | Ala | Val | Asp | Asn | Ile | Cys | Arg | Ala |
| --- | --- | --- | --- | --- | --- | --- | --- | --- | --- | --- | --- | --- | --- | --- | --- |
| | | | 20 | | | | | 25 | | | | | 30 | | |

| Ala | Ala | Lys | Val | Ile | Tyr | Glu | Asn | Ala | Ala | Ile | Leu | Ala | Arg | Glu | Ala |
|---|---|---|---|---|---|---|---|---|---|---|---|---|---|---|---|
| | | 35 | | | | | 40 | | | | | 45 | | | |

| Val | Asp | Glu | Thr | Gly | Met | Gly | Val | Tyr | Glu | His | Lys | Val | Ala | Lys | Asn |
|---|---|---|---|---|---|---|---|---|---|---|---|---|---|---|---|
| | 50 | | | | | 55 | | | | | 60 | | | | |

| Gln | Gly | Lys | Ser | Lys | Gly | Val | Trp | Tyr | Asn | Leu | His | Asn | Lys | Lys | Ser |
|---|---|---|---|---|---|---|---|---|---|---|---|---|---|---|---|
| 65 | | | | | 70 | | | | | 75 | | | | | 80 |

| Ile | Gly | Ile | Leu | Asn | Ile | Asp | Glu | Arg | Thr | Gly | Met | Ile | Glu | Ile | Ala |
|---|---|---|---|---|---|---|---|---|---|---|---|---|---|---|---|
| | | | | 85 | | | | | 90 | | | | | 95 | |

| Lys | Pro | Ile | Gly | Val | Val | Gly | Ala | Val | Thr | Pro | Thr | Thr | Asn | Pro | Ile |
|---|---|---|---|---|---|---|---|---|---|---|---|---|---|---|---|
| | | | 100 | | | | | 105 | | | | | 110 | | |

| Val | Thr | Pro | Met | Ser | Asn | Ile | Ile | Phe | Ala | Leu | Lys | Thr | Cys | Asn | Ala |
|---|---|---|---|---|---|---|---|---|---|---|---|---|---|---|---|
| | | 115 | | | | | 120 | | | | | 125 | | | |

| Ile | Ile | Ile | Ala | Pro | His | Pro | Arg | Ser | Lys | Lys | Cys | Ser | Ala | His | Ala |
|---|---|---|---|---|---|---|---|---|---|---|---|---|---|---|---|
| 130 | | | | | 135 | | | | | 140 | | | | | |

| Val | Arg | Leu | Ile | Lys | Glu | Ala | Ile | Ala | Pro | Phe | Asn | Val | Pro | Glu | Gly |
|---|---|---|---|---|---|---|---|---|---|---|---|---|---|---|---|
| 145 | | | | | 150 | | | | | 155 | | | | | 160 |

| Met | Val | Gln | Ile | Ile | Glu | Glu | Pro | Ser | Ile | Glu | Lys | Thr | Gln | Glu | Leu |
|---|---|---|---|---|---|---|---|---|---|---|---|---|---|---|---|
| | | | | 165 | | | | | 170 | | | | | 175 | |

| Met | Gly | Ala | Val | Asp | Val | Val | Ala | Thr | Gly | Gly | Met | Gly | Met | Val |
|---|---|---|---|---|---|---|---|---|---|---|---|---|---|---|
| | | | 180 | | | | | 185 | | | | | 190 | |

| Lys | Ser | Ala | Tyr | Ser | Ser | Gly | Lys | Pro | Ser | Phe | Gly | Val | Gly | Ala | Gly |
|---|---|---|---|---|---|---|---|---|---|---|---|---|---|---|---|
| | | | 195 | | | | | 200 | | | | | 205 | | |

| Asn | Val | Gln | Val | Ile | Val | Asp | Ser | Asn | Ile | Asp | Phe | Glu | Ala | Ala | Ala |
|---|---|---|---|---|---|---|---|---|---|---|---|---|---|---|---|
| | 210 | | | | | 215 | | | | | 220 | | | | |

| Glu | Lys | Ile | Ile | Thr | Gly | Arg | Ala | Phe | Asp | Asn | Gly | Ile | Ile | Cys | Ser |
|---|---|---|---|---|---|---|---|---|---|---|---|---|---|---|---|
| 225 | | | | | 230 | | | | | 235 | | | | | 240 |

| Gly | Glu | Gln | Ser | Ile | Ile | Tyr | Asn | Glu | Ala | Asp | Lys | Glu | Ala | Val | Phe |
|---|---|---|---|---|---|---|---|---|---|---|---|---|---|---|---|
| | | | | 245 | | | | | 250 | | | | | 255 | |

| Thr | Ala | Phe | Arg | Asn | His | Gly | Ala | Tyr | Phe | Cys | Asp | Glu | Ala | Glu | Gly |
|---|---|---|---|---|---|---|---|---|---|---|---|---|---|---|---|
| | | | 260 | | | | | 265 | | | | | 270 | | |

| Asp | Arg | Ala | Arg | Ala | Ala | Ile | Phe | Glu | Asn | Gly | Ala | Ile | Ala | Lys | Asp |
|---|---|---|---|---|---|---|---|---|---|---|---|---|---|---|---|
| | | 275 | | | | | 280 | | | | | 285 | | | |

| Val | Val | Gly | Gln | Ser | Val | Ala | Phe | Ile | Ala | Lys | Lys | Ala | Asn | Ile | Asn |
|---|---|---|---|---|---|---|---|---|---|---|---|---|---|---|---|
| | 290 | | | | | 295 | | | | | 300 | | | | |

| Ile | Pro | Glu | Gly | Thr | Arg | Ile | Leu | Val | Val | Glu | Ala | Arg | Gly | Val | Gly |
|---|---|---|---|---|---|---|---|---|---|---|---|---|---|---|---|
| 305 | | | | | 310 | | | | | 315 | | | | | 320 |

| Ala | Glu | Asp | Val | Ile | Cys | Lys | Glu | Lys | Met | Cys | Pro | Val | Met | Cys | Ala |
|---|---|---|---|---|---|---|---|---|---|---|---|---|---|---|---|
| | | | | 325 | | | | | 330 | | | | | 335 | |

| Leu | Ser | Tyr | Lys | His | Phe | Glu | Glu | Gly | Val | Glu | Ile | Ala | Arg | Thr | Asn |
|---|---|---|---|---|---|---|---|---|---|---|---|---|---|---|---|
| | | | 340 | | | | | 345 | | | | | 350 | | |

| Leu | Ala | Asn | Glu | Gly | Asn | Gly | His | Thr | Cys | Ala | Ile | His | Ser | Asn | Asn |
|---|---|---|---|---|---|---|---|---|---|---|---|---|---|---|---|
| | | 355 | | | | | 360 | | | | | 365 | | | |

| Gln | Ala | His | Ile | Ile | Leu | Ala | Gly | Ser | Glu | Leu | Thr | Val | Ser | Arg | Ile |
|---|---|---|---|---|---|---|---|---|---|---|---|---|---|---|---|
| 370 | | | | | 375 | | | | | 380 | | | | | |

```
Val Val Asn Ala Pro Ser Ala Thr Thr Ala Gly Gly His Ile Gln Asn
385                 390                 395                 400

Gly Leu Ala Val Thr Asn Thr Leu Gly Cys Gly Ser Trp Gly Asn Asn
                405                 410                 415

Ser Ile Ser Glu Asn Phe Thr Tyr Lys His Leu Leu Asn Ile Ser Arg
            420                 425                 430

Ile Ala Pro Leu Asn Ser Ser Ile His Ile Pro Asp Asp Lys Glu Ile
        435                 440                 445

Trp Glu Leu
    450
```

<210> SEQ ID NO 52
<211> LENGTH: 1116
<212> TYPE: DNA
<213> ORGANISM: Porphyromonas gingivalis

<400> SEQUENCE: 52

```
atgcaacttt tcaaactcaa gagtgtaaca catcactttg acactttgc agaatttgcc      60
aaggaattct gtcttggaga acgcgacttg gtaattacca acgagttcat ctatgaaccg    120
tatatgaagg catgccagct cccctgccat tttgttatgc aggagaaata tgggcaaggc    180
gagccttctg acgaaatgat gaataacatc ttggcagaca tccgtaatat ccagttcgac    240
cgcgtaatcg gtatcggagg aggtacggtt attgacatct ctaaactttt cgttctgaaa    300
ggattaaatg atgtactcga tgcattcgac cgcaaaatac ctcttatcaa agagaaagaa    360
ctgatcattg tgcccacaac atgcggaacg ggtagcgagg tgacgaacat ttctatcgca    420
gaaatcaaaa gccgtcacac caaaatggga ttggctgacg atgccattgt tgcagaccat    480
gccatcatca tacctgaact tctgaagagc ttgcctttcc acttctacgc atgcagtgca    540
atcgatgctc ttatccatgc catcgagtca tacgtatctc taaagccag tccatattct     600
cgtctgttca gtgaggcggc ttgggacatt atcctggaag tattcaagaa atcgccgaa     660
cacggccctg aataccgctt cgaaaagctg ggagaaatga tcatggccag caactatgcc    720
ggtatagcct tcggaaatgc aggagtagga gccgtccacg cactatccta cccgttggga    780
ggcaactatc acgtgccgca tggagaagca aactatcagt tcttcacaga ggtattcaaa    840
gtataccaaa agaagaatcc tttcggctat atagtcgaac tcaactggaa gctctccaag    900
atactgaact gccagcccga atacgtatat ccgaagctgg atgaacttct cggatgcctt    960
cttaccaaga aacctttgca cgaatacggc atgaaggacg aagaggtaag aggctttgcg   1020
gaatcagtgc ttaagacaca gcaaagattg ctcgccaaca actacgtaga gcttactgta   1080
gatgagatcg aaggtatcta cagaagactc tactaa                             1116
```

<210> SEQ ID NO 53
<211> LENGTH: 371
<212> TYPE: PRT
<213> ORGANISM: Porphyromonas gingivalis

<400> SEQUENCE: 53

```
Met Gln Leu Phe Lys Leu Lys Ser Val Thr His His Phe Asp Thr Phe
1               5                   10                  15

Ala Glu Phe Ala Lys Glu Phe Cys Leu Gly Glu Arg Asp Leu Val Ile
                20                  25                  30

Thr Asn Glu Phe Ile Tyr Glu Pro Tyr Met Lys Ala Cys Gln Leu Pro
            35                  40                  45

Cys His Phe Val Met Gln Glu Lys Tyr Gly Gln Gly Glu Pro Ser Asp
```

```
                50                  55                  60
Glu Met Met Asn Asn Ile Leu Ala Asp Ile Arg Asn Ile Gln Phe Asp
 65                  70                  75                  80

Arg Val Ile Gly Ile Gly Gly Thr Val Ile Asp Ile Ser Lys Leu
                 85                  90                  95

Phe Val Leu Lys Gly Leu Asn Asp Val Leu Asp Ala Phe Asp Arg Lys
                100                 105                 110

Ile Pro Leu Ile Lys Glu Lys Glu Leu Ile Ile Val Pro Thr Thr Cys
                115                 120                 125

Gly Thr Gly Ser Glu Val Thr Asn Ile Ser Ile Ala Glu Ile Lys Ser
130                 135                 140

Arg His Thr Lys Met Gly Leu Ala Asp Asp Ala Ile Val Ala Asp His
145                 150                 155                 160

Ala Ile Ile Ile Pro Glu Leu Leu Lys Ser Leu Pro Phe His Phe Tyr
                165                 170                 175

Ala Cys Ser Ala Ile Asp Ala Leu Ile His Ala Ile Glu Ser Tyr Val
                180                 185                 190

Ser Pro Lys Ala Ser Pro Tyr Ser Arg Leu Phe Ser Glu Ala Ala Trp
                195                 200                 205

Asp Ile Ile Leu Glu Val Phe Lys Lys Ile Ala Glu His Gly Pro Glu
210                 215                 220

Tyr Arg Phe Glu Lys Leu Gly Glu Met Ile Met Ala Ser Asn Tyr Ala
225                 230                 235                 240

Gly Ile Ala Phe Gly Asn Ala Gly Val Gly Ala Val His Ala Leu Ser
                245                 250                 255

Tyr Pro Leu Gly Gly Asn Tyr His Val Pro His Gly Glu Ala Asn Tyr
                260                 265                 270

Gln Phe Phe Thr Glu Val Phe Lys Val Tyr Gln Lys Lys Asn Pro Phe
                275                 280                 285

Gly Tyr Ile Val Glu Leu Asn Trp Lys Leu Ser Lys Ile Leu Asn Cys
290                 295                 300

Gln Pro Glu Tyr Val Tyr Pro Lys Leu Asp Glu Leu Leu Gly Cys Leu
305                 310                 315                 320

Leu Thr Lys Lys Pro Leu His Glu Tyr Gly Met Lys Asp Glu Glu Val
                325                 330                 335

Arg Gly Phe Ala Glu Ser Val Leu Lys Thr Gln Gln Arg Leu Leu Ala
                340                 345                 350

Asn Asn Tyr Val Glu Leu Thr Val Asp Glu Ile Glu Gly Ile Tyr Arg
                355                 360                 365

Arg Leu Tyr
370

<210> SEQ ID NO 54
<211> LENGTH: 1296
<212> TYPE: DNA
<213> ORGANISM: Porphyromonas gingivalis

<400> SEQUENCE: 54
atgaaagacg tattagcgga atatgcctcc cgaattgttt cggccgaaga agccgtaaaa    60
catatcaaaa atggagaacg ggtagctttg tcacatgctg ccggagttcc tcagagttgt   120
gttgatgcac tggtacaaca ggccgaccct ttccagaatg tcgaaattta tcacatgctt   180
tgtctcggcg aaggaaaata tatggcacct gaaatggccc ctcacttccg acacataacc   240
aattttgtag gtggtaattc tcgtaaagca gttgaggaaa atagagccga cttcattccg   300
```

```
gtattctttt atgaagtgcc atcaatgatt cgcaaagaca tccttcacat agatgtcgcc    360
atcgttcagc tttcaatgcc tgatgagaat ggttactgta gttttggagt atcttgcgat    420
tatagcaaac cggcagcaga aagcgctcat ttagttatag gggaaatcaa ccgtcaaatg    480
ccatatgtac atggcgacaa cttgattcac atatcgaagt tggattacat cgtgatggca    540
gactacccta tctattctct tgcaaagccc aaaatcggag aagtagaaga agctatcggg    600
cgtaattgtg ccgagcttat tgaagatggt gccacactcc aactcggtat cggcgcgatt    660
cctgatgcag ccctgttatt cctcaaggac aaaaagatc tggggatcca taccgagatg    720
ttctccgatg gtgttgtcga attagttcgc agtggagtaa ttacaggaaa gaaaaagaca    780
cttcaccccg aaagatggt cgcaaccttc ttaatgggaa gcgaagacgt atatcatttc    840
atcgacaaaa atcccgatgt agaactttat ccggtagatt acgtcaatga tccgcgagta    900
atcgctcaaa atgataatat ggtcagcatc aatagctgta tcgaaatcga tcttatggga    960
caagtcgtgt ccgaatgtat aggaagcaag caattcagcg gaaccggcgg tcaagtagat   1020
tatgttcgtg gagcagcatg gtctaaaaac ggcaaaagca tcatggcaat tccctcaaca   1080
gccaaaaacg gtactgcatc tcgaattgta cctataattg cagagggagc tgctgtaaca   1140
accctccgca acgaagtcga ttacgttgta accgaatacg gtatagcaca actcaaagga   1200
aagagtttgc gccagcgagc agaagctctt attgccatag cccacccgga tttcagagag   1260
gaactaacga aacatctccg caaacgtttc ggataa                             1296

<210> SEQ ID NO 55
<211> LENGTH: 431
<212> TYPE: PRT
<213> ORGANISM: Porphyromonas gingivalis

<400> SEQUENCE: 55

Met Lys Asp Val Leu Ala Glu Tyr Ala Ser Arg Ile Val Ser Ala Glu
1               5                   10                  15

Glu Ala Val Lys His Ile Lys Asn Gly Glu Arg Val Ala Leu Ser His
                20                  25                  30

Ala Ala Gly Val Pro Gln Ser Cys Val Asp Ala Leu Val Gln Gln Ala
            35                  40                  45

Asp Leu Phe Gln Asn Val Glu Ile Tyr His Met Leu Cys Leu Gly Glu
        50                  55                  60

Gly Lys Tyr Met Ala Pro Glu Met Ala Pro His Phe Arg His Ile Thr
65                  70                  75                  80

Asn Phe Val Gly Gly Asn Ser Arg Lys Ala Val Glu Glu Asn Arg Ala
                85                  90                  95

Asp Phe Ile Pro Val Phe Phe Tyr Glu Val Pro Ser Met Ile Arg Lys
            100                 105                 110

Asp Ile Leu His Ile Asp Val Ala Ile Val Gln Leu Ser Met Pro Asp
        115                 120                 125

Glu Asn Gly Tyr Cys Ser Phe Gly Val Ser Cys Asp Tyr Ser Lys Pro
    130                 135                 140

Ala Ala Glu Ser Ala His Leu Val Ile Gly Glu Ile Asn Arg Gln Met
145                 150                 155                 160

Pro Tyr Val His Gly Asp Asn Leu Ile His Ile Ser Lys Leu Asp Tyr
                165                 170                 175

Ile Val Met Ala Asp Tyr Pro Ile Tyr Ser Leu Ala Lys Pro Lys Ile
            180                 185                 190
```

```
Gly Glu Val Glu Glu Ala Ile Gly Arg Asn Cys Ala Glu Leu Ile Glu
            195                 200                 205

Asp Gly Ala Thr Leu Gln Leu Gly Ile Gly Ala Ile Pro Asp Ala Ala
    210                 215                 220

Leu Leu Phe Leu Lys Asp Lys Asp Leu Gly Ile His Thr Glu Met
225                 230                 235                 240

Phe Ser Asp Gly Val Val Glu Leu Val Arg Ser Gly Val Ile Thr Gly
                245                 250                 255

Lys Lys Lys Thr Leu His Pro Gly Lys Met Val Ala Thr Phe Leu Met
                260                 265                 270

Gly Ser Glu Asp Val Tyr His Phe Ile Asp Lys Asn Pro Asp Val Glu
            275                 280                 285

Leu Tyr Pro Val Asp Tyr Val Asn Asp Pro Arg Val Ile Ala Gln Asn
    290                 295                 300

Asp Asn Met Val Ser Ile Asn Ser Cys Ile Glu Ile Asp Leu Met Gly
305                 310                 315                 320

Gln Val Val Ser Glu Cys Ile Gly Ser Lys Gln Phe Ser Gly Thr Gly
                325                 330                 335

Gly Gln Val Asp Tyr Val Arg Gly Ala Ala Trp Ser Lys Asn Gly Lys
            340                 345                 350

Ser Ile Met Ala Ile Pro Ser Thr Ala Lys Asn Gly Thr Ala Ser Arg
    355                 360                 365

Ile Val Pro Ile Ile Ala Glu Gly Ala Ala Val Thr Thr Leu Arg Asn
    370                 375                 380

Glu Val Asp Tyr Val Val Thr Glu Tyr Gly Ile Ala Gln Leu Lys Gly
385                 390                 395                 400

Lys Ser Leu Arg Gln Arg Ala Glu Ala Leu Ile Ala Ile Ala His Pro
                405                 410                 415

Asp Phe Arg Glu Glu Leu Thr Lys His Leu Arg Lys Arg Phe Gly
            420                 425                 430

<210> SEQ ID NO 56
<211> LENGTH: 906
<212> TYPE: DNA
<213> ORGANISM: Clostridium acetobutylicum

<400> SEQUENCE: 56
atgattaaga gttttaatga aattatcatg aaggtaaaga gcaaagaaat gaaaaagtt      60 gctgttgctg tagcacaaga cgagccagta cttgaagcag taagagatgc taagaaaaat    120
ggtattgcag atgctattct tgttggagac catgacgaaa tcgtgtcaat cgcgcttaaa    180
ataggaatgg atgtaaatga ttttgaaata gtaaacgagc taacgttaa gaaagctgct    240 ttaaaggcag tagagcttgt atcaactgga aaagctgata tggtaatgaa gggacttgta    300
aatacagcaa ctttcttaag atctgtatta aacaagaag ttggacttag aacaggaaaa    360
actatgtctc acgttgcagt atttgaaact gagaaatttg atagactatt atttttaaca    420
gatgttgctt tcaatactta tcctgaatta aaggaaaaaa ttgatatagt aaacaattca    480
gttaaggttg cacatgcaat aggaattgaa aatccaaagg ttgctccaat ttgtgcagtt    540
gaggttataa accctaaaat gccatcaaca cttgatgcag caatgctttc aaaaatgagt    600
gacagaggac aaattaaagg ttgtgtagtt gacggacctt agcacttga tatagcttta    660 tcagaagaag cagcacatca taagggagta acaggagaag ttgctggaaa agctgatatc    720
ttcttaatgc caaacataga aacaggaaat gtaatgtata agactttaac atatacaact    780
```

```
gattcaaaaa atggaggaat cttagttgga acttctgcac cagttgtttt aacttcaaga    840
gctgacagcc atgaaacaaa atgaactct atagcacttg cagctttagt tgcaggcaat    900
aaataa                                                              906
```

<210> SEQ ID NO 57
<211> LENGTH: 301
<212> TYPE: PRT
<213> ORGANISM: Clostridium acetobutylicum

<400> SEQUENCE: 57

```
Met Ile Lys Ser Phe Asn Glu Ile Ile Met Lys Val Lys Ser Lys Glu
1               5                   10                  15

Met Lys Lys Val Ala Val Ala Val Ala Gln Asp Glu Pro Val Leu Glu
            20                  25                  30

Ala Val Arg Asp Ala Lys Lys Asn Gly Ile Ala Asp Ala Ile Leu Val
        35                  40                  45

Gly Asp His Asp Glu Ile Val Ser Ile Ala Leu Lys Ile Gly Met Asp
    50                  55                  60

Val Asn Asp Phe Glu Ile Val Asn Glu Pro Asn Val Lys Lys Ala Ala
65                  70                  75                  80

Leu Lys Ala Val Glu Leu Val Ser Thr Gly Lys Ala Asp Met Val Met
                85                  90                  95

Lys Gly Leu Val Asn Thr Ala Thr Phe Leu Arg Ser Val Leu Asn Lys
            100                 105                 110

Glu Val Gly Leu Arg Thr Gly Lys Thr Met Ser His Val Ala Val Phe
        115                 120                 125

Glu Thr Glu Lys Phe Asp Arg Leu Leu Phe Leu Thr Asp Val Ala Phe
    130                 135                 140

Asn Thr Tyr Pro Glu Leu Lys Glu Lys Ile Asp Ile Val Asn Asn Ser
145                 150                 155                 160

Val Lys Val Ala His Ala Ile Gly Ile Glu Asn Pro Lys Val Ala Pro
                165                 170                 175

Ile Cys Ala Val Glu Val Ile Asn Pro Lys Met Pro Ser Thr Leu Asp
            180                 185                 190

Ala Ala Met Leu Ser Lys Met Ser Asp Arg Gly Gln Ile Lys Gly Cys
        195                 200                 205

Val Val Asp Gly Pro Leu Ala Leu Asp Ile Ala Leu Ser Glu Glu Ala
    210                 215                 220

Ala His His Lys Gly Val Thr Gly Glu Val Ala Gly Lys Ala Asp Ile
225                 230                 235                 240

Phe Leu Met Pro Asn Ile Glu Thr Gly Asn Val Met Tyr Lys Thr Leu
                245                 250                 255

Thr Tyr Thr Thr Asp Ser Lys Asn Gly Gly Ile Leu Val Gly Thr Ser
            260                 265                 270

Ala Pro Val Val Leu Thr Ser Arg Ala Asp Ser His Glu Thr Lys Met
        275                 280                 285

Asn Ser Ile Ala Leu Ala Ala Leu Val Ala Gly Asn Lys
    290                 295                 300
```

<210> SEQ ID NO 58
<211> LENGTH: 1068
<212> TYPE: DNA
<213> ORGANISM: Clostridium acetobutylicum

<400> SEQUENCE: 58

```
atgtatagat tactaataat caatcctggc tcgacctcaa ctaaaattgg tatttatgac    60
gatgaaaaag agatatttga gaagacttta agacattcag ctgaagagat agaaaaatat   120
aacactatat ttgatcaatt tcaattcaga aagaatgtaa ttttagatgc gttaaaagaa   180
gcaaacatag aagtaagttc tttaaatgct gtagttggaa gaggcggact cttaaagcca   240
atagtaagtg gaacttatgc agtaaatcaa aaaatgcttg aagaccttaa agtaggagtt   300
caaggtcagc atgcgtcaaa tcttggtgga attattgcaa atgaaatagc aaaagaaata   360
aatgttccag catacatagt tgatccagtt gttgtggatg agcttgatga agtttcaaga   420
atatcaggaa tggctgacat tccaagaaaa agtatattcc atgcattaaa tcaaaaagca   480
gttgctagaa gatatgcaaa agaagttgga aaaaaatacg aagatcttaa tttaatcgta   540
gtccacatgg gtggaggtac ttcagtaggt actcataaag atggtagagt aatagaagtt   600
aataatacac ttgatggaga aggtccattc tcaccagaaa gaagtggtgg agttccaata   660
ggagatcttg taagattgtg cttcagcaac aaatatactt atgaagaagt aatgaaaaag   720
ataaacggca aggcggagt tgttagttac ttaaatacta tcgattttaa ggctgtagtt   780
gataaagctc ttgaaggaga taagaaatgt gcacttatat atgaagcttt cacattccag   840
gtagcaaaag atataggaaa atgttcaacc gttttaaaag gaaatgtaga tgcaataatc   900
ttaacaggcg gaattgcgta caacgagcat gtatgtaatg ccatagagga tagagtaaaa   960
ttcatagcac ctgtagttag atatggtgga gaagatgaac ttcttgcact tgcagaaggt  1020
ggacttagag ttttaagagg agaagaaaaa gctaaggaat acaaataa               1068
```

<210> SEQ ID NO 59
<211> LENGTH: 355
<212> TYPE: PRT
<213> ORGANISM: Clostridium acetobutylicum

<400> SEQUENCE: 59

Met Tyr Arg Leu Leu Ile Ile Asn Pro Gly Ser Thr Ser Thr Lys Ile
1               5                   10                  15

Gly Ile Tyr Asp Asp Glu Lys Glu Ile Phe Glu Lys Thr Leu Arg His
            20                  25                  30

Ser Ala Glu Glu Ile Glu Lys Tyr Asn Thr Ile Phe Asp Gln Phe Gln
        35                  40                  45

Phe Arg Lys Asn Val Ile Leu Asp Ala Leu Lys Glu Ala Asn Ile Glu
    50                  55                  60

Val Ser Ser Leu Asn Ala Val Val Gly Arg Gly Gly Leu Leu Lys Pro
65                  70                  75                  80

Ile Val Ser Gly Thr Tyr Ala Val Asn Gln Lys Met Leu Glu Asp Leu
                85                  90                  95

Lys Val Gly Val Gln Gly Gln His Ala Ser Asn Leu Gly Gly Ile Ile
            100                 105                 110

Ala Asn Glu Ile Ala Lys Glu Ile Asn Val Pro Ala Tyr Ile Val Asp
        115                 120                 125

Pro Val Val Asp Glu Leu Asp Glu Val Ser Arg Ile Ser Gly Met
    130                 135                 140

Ala Asp Ile Pro Arg Lys Ser Ile Phe His Ala Leu Asn Gln Lys Ala
145                 150                 155                 160

Val Ala Arg Arg Tyr Ala Lys Glu Val Gly Lys Lys Tyr Glu Asp Leu
                165                 170                 175

Asn Leu Ile Val Val His Met Gly Gly Gly Thr Ser Val Gly Thr His
            180                 185                 190

```
Lys Asp Gly Arg Val Ile Glu Val Asn Asn Thr Leu Asp Gly Glu Gly
        195                 200                 205

Pro Phe Ser Pro Glu Arg Ser Gly Gly Val Pro Ile Gly Asp Leu Val
    210                 215                 220

Arg Leu Cys Phe Ser Asn Lys Tyr Thr Tyr Glu Glu Val Met Lys Lys
225                 230                 235                 240

Ile Asn Gly Lys Gly Val Val Ser Tyr Leu Asn Thr Ile Asp Phe
                245                 250                 255

Lys Ala Val Val Asp Lys Ala Leu Glu Gly Asp Lys Lys Cys Ala Leu
            260                 265                 270

Ile Tyr Glu Ala Phe Thr Phe Gln Val Ala Lys Glu Ile Gly Lys Cys
        275                 280                 285

Ser Thr Val Leu Lys Gly Asn Val Asp Ala Ile Glu Leu Thr Gly Gly
    290                 295                 300

Ile Ala Tyr Asn Glu His Val Cys Asn Ala Ile Glu Asp Arg Val Lys
305                 310                 315                 320

Phe Ile Ala Pro Val Val Arg Tyr Gly Gly Glu Asp Glu Leu Leu Ala
                325                 330                 335

Leu Ala Glu Gly Gly Leu Arg Val Leu Arg Gly Glu Gly Lys Ala Lys
            340                 345                 350

Glu Tyr Lys
        355

<210> SEQ ID NO 60
<211> LENGTH: 906
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
atgattaaga gttttaatga aattatcatg aaggtaaaga gcaaagaaat gaaaaaagtt      60
gctgttgctg tagcacaaga cgagccagta cttgaagcag tacgcgatgc taagaaaaat    120
ggtattgcag atgctattct tgttggcgac catgacgaaa tcgtgtcaat cgcgcttaaa    180
ataggcatgg atgtaaatga ttttgaaata gtaaacgagc taacgttaa gaaagctgct    240 ttaaaggcag tagagctggt atcaactgga aaagctgata tggtaatgaa gggacttgta    300
aatacagcaa ctttcttacg ctctgtatta aacaaagaag ttggactgag aacaggaaaa    360
actatgtctc acgttgcagt atttgaaact gagaaatttg atcgtctgtt atttttaaca    420
gatgttgctt tcaatactta tcctgaatta aaggaaaaaa ttgatatcgt aaacaattca    480
gttaaggttg cacatgcaat aggtattgaa atccaaaagg ttgctccaat ttgtgcagtt    540
gaggttataa accctaaaat gccatcaaca cttgatgcag caatgctttc aaaaatgagt    600
gacagaggac aaattaaagg ttgtgtagtt gacggaccgt tagcacttga tatcgcttta    660
tcagaagaag cagcacatca taagggcgta acaggagaag ttgctggaaa agctgatatc    720
ttcttaatgc aaacattga aacaggaaat gtaatgtata agactttaac atatacaact    780
gatagcaaaa atggcggaat cttagttgga acttctgcac cagttgtttt aacttcacgc    840
gctgacagcc atgaaacaaa aatgaactct attgcacttg cagctttagt tgcaggcaat    900
aaataa                                                                906

<210> SEQ ID NO 61
```

<211> LENGTH: 906
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 61

| | | | | | |
|---|---|---|---|---|---|
| atgattaaga | gttttaatga | aattatcatg | aaggtaaaga | gcaaagaaat gaaaaaagtt | 60 |
| gctgttgctg | tagcacaaga | cgagccagta | cttgaagcag | tacgcgatgc taagaaaaat | 120 |
| ggtattgccg | atgctattct | ggttggcgac | catgacgaaa | tcgtgtctat cgcgctgaaa | 180 |
| ataggcatgg | atgtaaatga | ttttgaaatt | gttaacgagc | taacgttaa gaaagctgcg | 240 |
| ttaaaggcag | tagagctggt | atcaactgga | aaagctgata | tggtaatgaa gggactggta | 300 |
| aataccgcaa | ctttcttacg | ctctgtatta | aacaaagaag | ttggtctgcg tacaggaaaa | 360 |
| accatgtctc | acgttgcagt | atttgaaact | gagaaatttg | atcgtctgtt atttttaaca | 420 |
| gatgttgctt | tcaatactta | tcctgaatta | aggaaaaaa | ttgatatcgt taacaatagc | 480 |
| gttaaggttg | cacatgccat | tggtattgaa | atccaaagg | ttgctccaat ttgtgcagtt | 540 |
| gaggttatta | acccgaaaat | gccatcaaca | cttgatgcag | caatgctttc aaaaatgagt | 600 |
| gaccgcggac | aaattaaagg | ttgtgtagtt | gacggaccgc | tggcacttga tatcgcttta | 660 |
| tcagaagaag | cagcacatca | taaaggcgta | acaggagaa | ttgctggaaa agctgatatc | 720 |
| ttcttaatgc | caaacattga | aacaggaaat | gtaatgtata | agacgttaac ctataccact | 780 |
| gatagcaaaa | atggcggcat | cctggttgga | acttctgcac | cagttgtttt aacttcacgc | 840 |
| gctgacagcc | atgaaacaaa | aatgaactct | attgcactgg | cagcgctggt tgcaggcaat | 900 |
| aaataa | | | | | 906 |

<210> SEQ ID NO 62
<211> LENGTH: 906
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 62

| | | | | | |
|---|---|---|---|---|---|
| atgattaaga | gttttaatga | aattatcatg | aaggtaaaga | gcaaagaaat gaaaaaagtt | 60 |
| gctgttgctg | ttgcacaaga | cgagccggta | ctggaagcgg | tacgcgatgc taagaaaaat | 120 |
| ggtattgccg | atgctattct | ggttggcgac | catgacgaaa | tcgtctctat cgcgctgaaa | 180 |
| attggcatgg | atgttaatga | ttttgaaatt | gttaacgagc | taacgttaa gaaagctgcg | 240 |
| ctgaaggcgg | tagagctggt | ttccaccgga | aaagctgata | tggtaatgaa agggctggtg | 300 |
| aataccgcaa | ctttcttacg | cagcgtactg | aacaaagaag | ttggtctgcg taccggaaaa | 360 |
| accatgagtc | acgttgcggt | atttgaaact | gagaaatttg | atcgtctgct gtttctgacc | 420 |
| gatgttgctt | tcaatactta | tcctgaatta | aagaaaaaa | ttgatatcgt taacaatagc | 480 |
| gttaaggttg | cgcatgccat | tggtattgaa | atccaaagg | ttgctccaat ttgtgcagtt | 540 |
| gaggttatta | acccgaaaat | gccatcaaca | cttgatgccg | caatgcttag caaaatgagt | 600 |
| gaccgcggac | aaattaaagg | ttgtgtggtt | gacggcccgc | tggcactgga tatcgcgtta | 660 |
| agcgaagaag | cggcacatca | taaaggcgta | accggcgaag | ttgctggaaa agctgatatc | 720 |
| ttcctgatgc | caaacattga | aacaggcaat | gtaatgtata | aaacgttaac ctataccact | 780 |
| gatagcaaaa | atggcggcat | cctggttgga | acttctgcac | cagttgtttt aacctcacgc | 840 |

```
gctgacagcc atgaaaccaa atgaacagc attgcactgg cagcgctggt tgcaggcaat      900
aaataa                                                                906
```

<210> SEQ ID NO 63
<211> LENGTH: 906
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
atgattaaaa gttttaacga aattatcatg aaagtgaaaa gcaaagagat gaaaaaagtg       60
gcggttgcgg ttgcgcagga tgaaccggtg ctggaagcgg tgcgcgatgc caaaaaaaac      120
ggtattgccg atgccattct ggtgggcgat cacgatgaaa ttgtctctat tgcgctgaaa      180
attggcatgg atgttaacga ttttgaaatt gttaatgaac cgaacgtgaa aaaagcggcg      240
ctgaaagcgg ttgaactggt ttccaccggt aaagccgata tggtgatgaa agggctggtg      300
aataccgcaa ccttcctgcg cagcgtgctg aataaagaag tgggtctgcg taccggtaaa      360
accatgagtc atgttgcggt gtttgaaacc gaaaaatttg accgtctgct gtttctgacc      420
gatgttgcgt ttaataccta tccggaactg aaagagaaaa ttgatatcgt taataacagc      480
gtgaaagtgg cgcatgccat tggtattgaa acccgaaaag tggcgccgat ttgcgcggtt      540
gaagtgatta acccgaaaat gccgtcaacg ctggatgccg cgatgctcag caaaatgagc      600
gatcgcggtc aaatcaaagg ctgtgtggtt gatggcccgc tggcgctgga tatcgcgctt      660
agcgaagaag cggcgcatca taaaggcgtg accggcgaag tggccggtaa agccgatatt      720
ttcctgatgc cgaatattga aaccggcaac gtgatgtata aaacgctgac ctataccacc      780
gacagcaaaa acggcggcat tctggtgggt accagcgcgc cggtggtgct gacctcgcgc      840
gccgacagcc atgaaaccaa aatgaacagc attgcgctgg cggcgctggt ggccggtaat      900
aaataa                                                                906
```

<210> SEQ ID NO 64
<211> LENGTH: 1068
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
atgtatcgtt tactgattat caatcctggc tcgacctcaa ctaaaattgg tatttatgac       60
gatgaaaaag agatatttga gaagacttta cgtcattcag ctgaagagat agaaaaatat      120
aacactatat ttgatcaatt tcagttcaga agaatgtaa ttctcgatgc gttaaaagaa      180
gcaaacattg aagtaagttc tttaaatgct gtagttggac gcggcggact gttaaagcca      240
atagtaagtg aacttatgc agtaaatcaa aaaatgcttg aagaccttaa gtaggcgtt       300 caaggtcagc atgcgtcaaa tcttggtgga attattgcaa atgaaatagc aaaagaaata      360
aatgttccag catacatcgt tgatccagtt gttgtggatg agcttgatga gtttcacgt       420 atatcaggaa tggctgacat tccacgtaaa agtatattcc atgcattaaa tcaaaaagca      480
gttgctagac gctatgcaaa agaagttgga aaaaaatacg aagatcttaa tttaatcgtg      540
gtccacatgg gtggcggtac ttcagtaggt actcataaag atggtagagt aattgaagtt      600
```

```
aataatacac ttgatggaga aggtccattc tcaccagaaa gaagtggtgg cgttccaata        660
ggcgatcttg tacgtttgtg cttcagcaac aaatatactt atgaagaagt aatgaaaaag        720
ataaacggca aaggcggcgt tgttagttac ttaaatacta tcgattttaa ggctgtagtt        780
gataaagctc ttgaaggcga taagaaatgt gcacttatat atgaagcttt cacattccag        840
gtagcaaaag agataggaaa atgttcaacc gttttaaaag gaaatgtaga tgcaataatc        900
ttaacaggcg gaattgcgta caacgagcat gtatgtaatg ccatagagga tagagtaaaa        960
ttcattgcac ctgtagttcg ttatggtgga gaagatgaac ttcttgcact gcagaaggt        1020 ggactgcgcg ttttacgcgg agaagaaaaa gctaaggaat acaaataa                    1068
```

<210> SEQ ID NO 65
<211> LENGTH: 1068
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 65

```
atgtatcgtt tactgattat caatcctggc tcgacctcaa ctaaaattgg tatttatgac        60
gatgaaaaag agatatttga gaagacgtta cgtcattcag ctgaagagat tgaaaaatat       120
aacactatat ttgatcaatt tcagttccgc aagaatgtga ttctcgatgc gttaaaagaa       180
gcaaacattg aagtcagttc tttaaatgct gtagttggac gcggcggact gttaaagcca       240
attgtcagtg gaacttatgc agtaaatcaa aaaatgcttg aagaccttaa agtgggcgtt       300
caaggtcagc atgccagcaa tcttggtggc attattgcca atgaaatcgc aaaagaaatc       360
aatgttccag catacatcgt tgatccggtt gttgtggatg agcttgatga agttagccgt       420
ataagcggaa tggctgacat tccacgtaaa agtatattcc atgcattaaa tcaaaaagca       480
gttgctcgtc gctatgcaaa agaagttggt aaaaaatacg aagatcttaa tttaatcgtg       540
gtccacatgg gtggcggtac ttcagtaggt actcataaag atggtcgcgt gattgaagtt       600
aataatacac ttgatggcga aggtccattc tcaccagaac gtagtggtgg cgttccaatt       660
ggcgatctgg tacgtttgtg cttcagcaac aaatatactt atgaagaagt gatgaaaaag       720
ataaacggca aaggcggcgt tgttagttac ctgaatacta tcgattttaa ggctgtagtt       780
gataaagcgc ttgaaggcga taagaaatgt gcactgattt atgaagcttt caccttccag       840
gtagcaaaag agattggtaa atgttcaacc gttttaaaag gaaatgttga tgccattatc       900
ttaacaggcg gcattgctta caacgagcat gtatgtaatg ccattgagga tcgcgtaaaa       960
ttcattgcac ctgtagttcg ttatggtggc gaagatgaac tgctggcact ggcagaaggt      1020
ggactgcgcg ttttacgcgg cgaagaaaaa gcgaaggaat acaaataa                   1068
```

<210> SEQ ID NO 66
<211> LENGTH: 1068
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 66

```
atgtatcgtc tgctgattat caatcctggc tcgacctcaa ctaaaattgg tatttatgac        60
gatgaaaaag agatatttga gaaacgtta cgtcatagcg ctgaagagat tgaaaaatat        120
aacactattt ttgatcaatt tcagttccgc aagaatgtga ttctcgatgc gctgaaagaa       180
```

```
gcaaacattg aagtcagttc gctgaatgcg gtagttggtc gcggcggtct gctgaagcca      240
attgtcagcg gcacttatgc ggtaaatcaa aaaatgctgg aagacctgaa agtgggcgtt      300
caggggcagc atgccagcaa tcttggtggc attattgcca atgaaatcgc caaagaaatc      360
aatgttccgg catacatcgt tgatccggtt gttgtggatg agctggatga agttagccgt      420
atcagcggaa tggctgacat tccacgtaaa agtatttttcc atgcactgaa tcaaaaagcg     480
gttgcgcgtc gctatgcaaa agaagttggt aaaaaatacg aagatcttaa tctgatcgtg      540
gtgcatatgg gtggcggtac tagcgtcggt actcataaag atggtcgcgt gattgaagtt      600
aataatacac ttgatggcga aggtccattc tcaccagaac gtagcggtgg cgttccaatt      660
ggcgatctgg tacgtttgtg cttcagcaac aaatatacct atgaagaagt gatgaaaaag      720
ataaacggca aggcggcgt tgttagttac ctgaatacta tcgattttaa ggcggtagtt       780
gataaagcgc tggaaggcga taagaaatgt gcactgattt atgaagcgtt caccttccag      840
gtggcaaaag agattggtaa atgttcaacc gttctgaaag caatgttga tgccattatc       900 ctgaccggcg gcattgctta caacgagcat gtttgtaatg ccattgagga tcgcgtaaaa      960
ttcattgcac ctgtggttcg ttatggtggc gaagatgaac tgctggcact ggcagaaggt     1020
ggtctgcgcg ttttacgcgg cgaagaaaaa gcgaaagaat acaaataa                  1068

<210> SEQ ID NO 67
<211> LENGTH: 1068
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atgtatcgtc tgctgattat caacccgggc agcacctcaa ccaaaattgg tatttacgac       60
gatgaaaaag agattttga aaaaacgctg cgtcacagcg cagaagagat tgaaaaatac       120
aacaccattt tcgatcagtt ccagttccgc aaaaacgtga ttctcgatgc gctgaaagaa      180
gccaatattg aagtctcctc gctgaatgcg gtggtcggtc gcggcggtct gctgaaaccg      240
attgtcagcg gcacttatgc ggttaatcag aaaatgctgg aagatctgaa agtgggcgtg      300
caggggcagc atgccagcaa tctcggcggc attatcgcca atgaaatcgc caaagagatc      360
aacgtgccgg cttatatcgt cgatccggtg gtggttgatg aactggatga agtcagccgt      420
atcagcggca tggcggatat tccgcgtaaa agcatttttcc atgcgctgaa tcagaaagcg     480
gttgcgcgtc gctatgccaa agaagtgggt aaaaaatatg aagatctcaa tctgattgtg      540
gtgcatatgg gcggcggcac cagcgtcggt acgcataaag atggtcgcgt gattgaagtg      600
aataacacgc tggatggcga agggccgttc tcgccggaac gtagcggcgg cgtgccgatt      660
ggcgatctgg tgcgtctgtg tttcagcaat aaatacacct acgaagaagt gatgaaaaaa      720
atcaacggca aggcggcgt ggttagctat ctgaatacca tcgattttaa agcggtggtt       780
gataaagcgc tggaaggcga taaaaaatgc gcgctgattt atgaagcgtt taccttccag      840
gtggcgaaag agattggtaa atgttcaacc gtgctgaaag caacgttga tgccattatt       900 ctgaccggcg gcattgctta taacgaacat gtttgtaatg ccattgaaga tcgcgtgaaa      960
tttattgcgc cggtggtgcg ttacggcggc gaagatgaac tgctggcgct ggcggaaggc     1020
ggtctgcgcg tgctgcgcgg cgaagaaaaa gcgaaagagt acaaataa                  1068
```

<210> SEQ ID NO 68
<211> LENGTH: 1407
<212> TYPE: DNA
<213> ORGANISM: Clostridium biejerinckii

<400> SEQUENCE: 68

```
atgaataaag acacactaat acctacaact aaagatttaa aagtaaaaac aaatggtgaa      60
aacattaatt taaagaacta caaggataat tcttcatgtt tcggagtatt cgaaaatgtt     120
gaaaatgcta taagcagcgc tgtacacgca caaaagatat tatcccttca ttatacaaaa     180
gagcaaagag aaaaaatcat aactgagata agaaaggccg cattacaaaa taaagaggtc     240
ttggctacaa tgattctaga agaaacacat atgggaagat atgaggataa aatattaaaa     300
catgaattgg tagctaaata tactcctggt acagaagatt taactactac tgcttggtca     360
ggtgataatg gtcttacagt tgtagaaatg tctccatatg gtgttatagg tgcaataact     420
ccttctacga atccaactga aactgtaata tgtaatagca taggcatgat agctgctgga     480
aatgctgtag tatttaacgg acacccatgc gctaaaaaat gtgttgcctt tgctgttgaa     540
atgataaata aggcaattat ttcatgtggc ggtcctgaaa atctagtaac aactataaaa     600
aatccaacta tggagtctct agatgcaatt attaagcatc cttcaataaa acttctttgc     660
ggaactgggg gtccaggaat ggtaaaaacc ctcttaaatt ctggtaagaa agctataggt     720
gctggtgctg gaaatccacc agttattgta gatgatactg ctgatataga aaaggctggt     780
aggagcatca ttgaaggctg ttcttttgat aataatttac cttgtattgc agaaaaagaa     840
gtatttgttt ttgagaatgt tgcagatgat ttaatatcta acatgctaaa aaataatgct     900
gtaattataa atgaagatca agtatcaaaa ttaatagatt tagtattaca aaaaaataat     960
gaaactcaag aatactttat aaacaaaaaa tgggtaggaa aagatgcaaa attattctta    1020
gatgaaatag atgttgagtc tccttcaaat gttaaatgca taatctgcga agtaaatgca    1080
aatcatccat ttgttatgac agaactcatg atgccaatat tgccaattgt aagagttaaa    1140
gatatagatg aagctattaa atatgcaaag atagcagaac aaaatagaaa acatagtgcc    1200
tatatttatt ctaaaaatat agacaaccta aatagatttg aaagagaaat agatactact    1260
atttttgtaa agaatgctaa atcttttgct ggtgttggtt atgaagcaga aggatttaca    1320
actttcacta ttgctggatc tactggtgag ggaataacct ctgcaaggaa ttttacaaga    1380
caaagaagat gtgtacttgc cggctaa                                        1407
```

<210> SEQ ID NO 69
<211> LENGTH: 468
<212> TYPE: PRT
<213> ORGANISM: Clostridium biejerinckii

<400> SEQUENCE: 69

```
Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
```

```
                    85                  90                  95
Lys Ile Leu Lys His Glu Leu Val Ala Lys Tyr Thr Pro Gly Thr Glu
                100                 105                 110

Asp Leu Thr Thr Thr Ala Trp Ser Gly Asp Asn Gly Leu Thr Val Val
            115                 120                 125

Glu Met Ser Pro Tyr Gly Val Ile Gly Ala Ile Thr Pro Ser Thr Asn
        130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465

<210> SEQ ID NO 70
<211> LENGTH: 1407
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 70
atgaataaag acacactaat acctacaact aaagatttaa aagtaaaaac aaatggtgaa      60
aacattaatt taaagaacta caaggataat tcttcatgtt tcggcgtatt cgaaaatgtt     120
gaaaatgcta taagcagcgc tgtacacgca caaaagatat tatcccttca ttatacaaaa     180
gagcaacgtg aaaaaatcat aactgagata agaaaggccg cattacaaaa taagaggtc      240 ttggctacaa tgattctgga agaaacacat atgggacgtt atgaggataa aatattaaaa     300
catgaattgg tagctaaata tactcctggt acagaagatt taactactac tgcctggtca     360
ggtgataatg gtctgacagt tgtagaaatg tctccatatg gtgttattgg tgcaataact     420
ccttctacga atccaactga aactgtaata tgtaatagca taggcatgat tgctgctgga     480
aatgctgtag tatttaacgg acacccatgc gctaaaaaat gtgttgcctt tgctgttgaa     540
atgataaata aggcaattat ttcatgtggc ggtcctgaaa atctggtaac aactataaaa     600
aatccaacca tggagtctct ggatgcaatt attaagcatc cttcaataaa acttctttgc     660
ggaactgggg tccaggaat ggtaaaaaacc ctgttaaatt ctggtaagaa agctataggt     720
gctggtgctg aaatccacc agttattgtc gatgatactg ctgatataga aaaggctggt     780
cgtagcatca ttgaaggctg ttcttttgat aataatttac cttgtattgc agaaaaagaa     840
gtatttgttt ttgagaatgt tgcagatgat ttaatatcta acatgctaaa aataatgct      900 gtaattataa atgaagatca agtatcaaaa ttaatcgatt tagttattca aaaaaataat     960
gaaactcaag aatactttat aaacaaaaaa tgggtaggaa aagatgcaaa attattcctc    1020
gatgaaatag atgttgagtc tccttcaaat gttaaatgca taatctgcga gtaaatgca    1080 aatcatccat ttgttatgac agaactgatg atgccaatat tgccaattgt acgcgttaaa    1140
gatatcgatg aagctattaa atatgcaaag atagcagaac aaaatagaaa acatagtgcc    1200
tatatttatt ctaaaaatat cgacaacctg aatcgctttg aacgtgaaat agatactact    1260 attttttgtaa agaatgctaa atcttttgct ggtgttggtt atgaagcaga aggatttaca    1320
actttcacta ttgctggatc tactggtgag ggaataaacct ctgcacgtaa ttttacacgc    1380
caacgtcgct gtgtacttgc cggctaa                                        1407

<210> SEQ ID NO 71
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
atgaataaag acacactgat ccctacaact aaagatttaa aagtaaaaac aaatggtgaa      60
aacattaatt taaagaacta caaagataat agcagttgtt tcggcgtatt cgaaaatgtt     120
gaaaatgcta tcagcagcgc tgtacacgca caaaagatat tatcgctgca ttatacaaaa     180
gagcaacgtg aaaaaatcat cactgagata cgtaaggccg cattacaaaa taagaggtg      240 ctggctacaa tgattctgga agaaacacat atgggacgtt atgaggataa aatattaaaa     300
catgaactgg tagctaaata tactcctggt acagaagatt taactactac tgcctggagc     360
ggtgataatg gtctgacagt tgtagaaatg tctccatatg gtgttattgg tgcaataact     420
```

```
ccttctacca atccaactga aactgtaatt tgtaatagca ttggcatgat tgctgctgga    480
aatgctgtag tatttaacgg acacccatgc gctaaaaaat gtgttgcctt tgctgttgaa    540
atgatcaata aggcaattat tagctgtggc ggtccggaaa atctggtaac aactataaaa    600
aatccaacca tggagtctct ggatgccatt attaagcatc cttcaataaa actgctttgc    660
ggaactggcg gtccaggaat ggtaaaaacc ctgttaaatt ctggtaagaa agctattggt    720
gctggtgctg gaaatccacc agttattgtc gatgatactg ctgatattga aaaggctggt    780
cgtagcatca ttgaaggctg ttcttttgat aataatttac cttgtattgc agaaaaagaa    840
gtatttgttt ttgagaatgt tgcagatgat ttaatatcta acatgctgaa aaataatgct    900
gtaattatca atgaagatca ggtatcaaaa ttaatcgatt tagtattaca aaaaaataat    960
gaaactcaag aatactttat caacaaaaaa tgggtaggta agatgcaaa attattcctc    1020 gatgaaatcg atgttgagtc tccttcaaat gttaaatgca ttatctgcga agtgaatgcc    1080
aatcatccat ttgttatgac agaactgatg atgccaatat tgccaattgt gcgcgttaaa    1140
gatatcgatg aagctattaa atatgcaaag attgcagaac aaaatagaaa acatagtgcc    1200
tatatttata gcaaaaatat cgacaacctg aatcgctttg aacgtgaaat cgatactact    1260 attttttgtaa agaatgctaa atcttttgct ggtgttggtt atgaagcaga aggatttacc    1320
actttcacta ttgctggatc tactggtgag ggcataacct ctgcacgtaa ttttacccgc    1380
caacgtcgct gtgtactggc cggctaa                                       1407
```

<210> SEQ ID NO 72
<211> LENGTH: 1407
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
atgaataaag acacgctgat cccgacaact aaagatctga agtaaaaaac caatggtgaa     60
aacattaatc tgaagaacta caaagataat agcagttgtt tcggcgtatt cgaaaatgtt    120
gaaaatgcta tcagcagcgc ggtacacgca caaaagatac tctcgctgca ttataccaaa    180
gagcaacgtg aaaaaatcat cactgagatc cgtaaggccg cattacaaaa taagaggtg    240 ctggcaacaa tgattctgga agaaacacat atgggacgtt atgaggataa atactgaaa    300 catgaactgg tggcgaaata tacgcctggt actgaagatt taaccaccac tgcctggagc    360
ggtgataatg gtctgaccgt tgtggaaatg tcgccttatg gtgttattgg tgcaattacg    420
ccttcaacca atccaactga aacggtaatt tgtaatagca ttggcatgat tgctgctgga    480
aatgcggtag tatttaacgg tcaccctgc gctaaaaaat gtgttgcctt tgctgttgaa    540
atgatcaata aagcgattat tagctgtggc ggtccggaaa atctggtaac cactataaaa    600
aatccaacca tggagtcgct ggatgccatt attaagcatc cttcaatcaa actgctgtgc    660
ggcactggcg gtccaggaat ggtgaaaacc ctgctgaata gcggtaagaa agcgattggt    720
gctggtgctg gaaatccacc agttattgtc gatgatactg ctgatattga aaagcgggt    780 cgtagcatca ttgaaggctg ttcttttgat aataatttac cttgtattgc agaaaaagaa    840
gtatttgttt ttgagaatgt tgccgatgat ctgatctcta acatgctgaa aaataatgcg    900
gtgattatca atgaagatca ggttagcaaa ctgatcgatc tggtattaca aaaaaataat    960
gaaactcaag aatactttat caacaaaaaa tgggtaggta agatgcaaaa actgttcctc    1020
```

```
gatgaaatcg atgttgagtc gccttcaaat gttaaatgca ttatctgcga agtgaatgcc      1080
aatcatccat ttgtgatgac cgaactgatg atgccaattt tgccgattgt gcgcgttaaa      1140
gatatcgatg aagcgattaa atatgcaaag attgcagaac aaaatcgtaa acatagtgcc      1200
tatatttata gcaaaaatat cgacaacctg aatcgctttg aacgtgaaat cgataccact      1260 attttttgtga agaatgctaa atcttttgct ggtgttggtt atgaagcaga aggttttacc      1320
actttcacta ttgctggaag caccggtgaa ggcattacct ctgcacgtaa ttttacccgc      1380
caacgtcgct gtgtactggc cggctaa                                          1407
```

<210> SEQ ID NO 73
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

```
atgaataaag atacgctgat cccgaccacc aaagatctga agtgaaaaac caacggcgaa        60
aatatcaacc tgaaaaacta taagataac agcagttgct ttggcgtgtt tgaaaacgtt       120
gaaaacgcca tctccagcgc ggtgcatgcg caaaaaattc tctcgctgca ttacaccaaa      180
gagcagcgtg aaaaaattat caccgaaatc cgtaaagcgg cgctgcaaaa caagaagtg      240 ctggcaacca tgatcctgga agaaacgcat atggggcgtt atgaagataa aattctgaaa      300
catgaactgg tggcgaaata cacgccgggc actgaagatc tgaccaccac cgcctggagc      360
ggcgataacg gcctgaccgt ggtggagatg tcgccttatg gcgtgattgg cgcgattacg      420
ccgtcaacca acccgaccga aacggtgatt tgtaacagca ttggcatgat gccgcgggt      480 aatgcggtgg tgtttaacgg tcatccctgc gcgaaaaaat gtgtggcgtt tgccgttgag      540
atgatcaaca aagcgattat cagctgcggc ggcccggaaa atctggtgac caccatcaaa      600
aatccgacca tggaatcgct ggatgccatt atcaaacatc cttccatcaa actgctgtgc      660
ggcaccggcg ccccgggcat ggtgaaaacg ctgctgaaca gcggtaaaaa agcgattggc      720
gcgggcgcgg gtaacccgcc ggtgattgtc gatgacaccg ccgatattga aaaagcgggg      780
cgtagcatta ttgaaggctg ttcttttgat aacaacctgc cctgcattgc cgaaaaagaa      840
gtgtttgtct ttgaaaacgt cgccgatgat ctgatcagca atatgctgaa aaacaacgcg      900
gtgattatca tgaagatca ggttagcaaa ctgatcgatc tggtgctgca aaaaaacaac      960
gaaacgcagg aatattttat caacaaaaaa tgggttggta agatgccaa actgtttctc    1020 gatgaaatcg atgttgaatc gccgtctaac gtgaaatgta ttatctgcga agtgaacgcc    1080
aaccatccgt ttgtgatgac cgaactgatg atgccgattc tgccgattgt gcgcgtgaaa    1140
gatatcgatg aagcgattaa atatgccaaa attgccgaac aaaaccgtaa acacagcgcc    1200
tatatttaca gcaaaaatat cgataacctg aaccgctttg aacgtgaaat cgataccacc    1260 attttttgtga aaaatgccaa aagttttgcc ggcgttggtt atgaagcgga aggttttacc    1320
acctttacca ttgccggtag caccggcgaa ggcattacca gcgcccgtaa ttttacccgc    1380
cagcgtcgct gcgtgctggc gggctaa                                        1407
```

<210> SEQ ID NO 74
<211> LENGTH: 1023
<212> TYPE: DNA
<213> ORGANISM: Geobacillus thermoglucosidasius

<400> SEQUENCE: 74

```
atgaaagctg cagtagtaga gcaatttaag gaaccattaa aaattaaaga agtggaaaag    60
ccatctattt catatggcga agtattagtc cgcattaaag catgcggtgt atgccatacg   120
gacttgcacg ccgctcatgg cgattggcca gtaaaaccaa aacttccttt aatccctggc   180
catgaaggag tcggaattgt tgaagaagtc ggtccggggg taacccattt aaaagtggga   240
gaccgcgttg gaattccttg gttatattct gcgtgcggcc attgcgaata ttgtttaagc   300
ggacaagaag cattatgtga acatcaacaa aacgccggct actcagtcga cgggggttat   360
gcagaatatt gcagagctgc gccagattat gtggtgaaaa ttcctgacaa cttatcgttt   420
gaagaagctg ctcctatttt ctgcgccgga gttactactt ataaagcgtt aaaagtcaca   480
ggtacaaaac cgggagaatg ggtagcgatc tatggcatcg gcggccttgg acatgttgcc   540
gtccagtatg cgaaagcgat ggggcttcat gttgttgcag tggatatcgg cgatgagaaa   600
ctggaacttg caaagagct tggcgccgat cttgttgtaa atcctgcaaa agaaaatgcg   660
gcccaattta tgaaagagaa agtcggcgga gtacacgcgg ctgttgtgac agctgtatct   720
aaacctgctt ttcaatctgc gtacaattct atccgcagag cggcacgtg cgtgcttgtc   780
ggattaccgc cggaagaaat gcctattcca atctttgata cggtattaaa cggaattaaa   840
attatcggtt ccattgtcgg cacgcggaaa gacttgcaag aagcgcttca gttcgctgca   900
gaaggtaaag taaaaccat tattgaagtg caacctcttg aaaaaattaa cgaagtattt   960
gacagaatgc taaaggaga attaacggga cgggttgttt taacgttaga aaataataat  1020
taa                                                                1023
```

<210> SEQ ID NO 75
<211> LENGTH: 340
<212> TYPE: PRT
<213> ORGANISM: Geobacillus thermoglucosidasius

<400> SEQUENCE: 75

```
Met Lys Ala Ala Val Val Glu Gln Phe Lys Glu Pro Leu Lys Ile Lys
 1               5                  10                  15

Glu Val Glu Lys Pro Ser Ile Ser Tyr Gly Glu Val Leu Val Arg Ile
            20                  25                  30

Lys Ala Cys Gly Val Cys His Thr Asp Leu His Ala Ala His Gly Asp
        35                  40                  45

Trp Pro Val Lys Pro Lys Leu Pro Leu Ile Pro Gly His Glu Gly Val
    50                  55                  60

Gly Ile Val Glu Glu Val Gly Pro Gly Val Thr His Leu Lys Val Gly
65                  70                  75                  80

Asp Arg Val Gly Ile Pro Trp Leu Tyr Ser Ala Cys Gly His Cys Glu
                85                  90                  95

Tyr Cys Leu Ser Gly Gln Glu Ala Leu Cys Glu His Gln Gln Asn Ala
            100                 105                 110

Gly Tyr Ser Val Asp Gly Gly Tyr Ala Glu Tyr Cys Arg Ala Ala Pro
        115                 120                 125

Asp Tyr Val Val Lys Ile Pro Asp Asn Leu Ser Phe Glu Glu Ala Ala
    130                 135                 140

Pro Ile Phe Cys Ala Gly Val Thr Thr Tyr Lys Ala Leu Lys Val Thr
145                 150                 155                 160

Gly Thr Lys Pro Gly Glu Trp Val Ala Ile Tyr Gly Ile Gly Gly Leu
                165                 170                 175
```

```
Gly His Val Ala Val Gln Tyr Ala Lys Ala Met Gly Leu His Val Val
            180                 185                 190
Ala Val Asp Ile Gly Asp Glu Lys Leu Glu Leu Ala Lys Glu Leu Gly
        195                 200                 205
Ala Asp Leu Val Val Asn Pro Ala Lys Glu Asn Ala Ala Gln Phe Met
    210                 215                 220
Lys Glu Lys Val Gly Gly Val His Ala Ala Val Val Thr Ala Val Ser
225                 230                 235                 240
Lys Pro Ala Phe Gln Ser Ala Tyr Asn Ser Ile Arg Arg Gly Gly Thr
                245                 250                 255
Cys Val Leu Val Gly Leu Pro Pro Glu Glu Met Pro Ile Pro Ile Phe
            260                 265                 270
Asp Thr Val Leu Asn Gly Ile Lys Ile Ile Gly Ser Ile Val Gly Thr
        275                 280                 285
Arg Lys Asp Leu Gln Glu Ala Leu Gln Phe Ala Ala Glu Gly Lys Val
    290                 295                 300
Lys Thr Ile Ile Glu Val Gln Pro Leu Glu Lys Ile Asn Glu Val Phe
305                 310                 315                 320
Asp Arg Met Leu Lys Gly Glu Ile Asn Gly Arg Val Val Leu Thr Leu
                325                 330                 335
Glu Asn Asn Asn
            340

<210> SEQ ID NO 76
<211> LENGTH: 4090
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
atggctatcg aaatcaaagt accggacatc ggggctgatg aagttgaaat caccgagatc      60
ctggtcaaag tgggcgacaa agttgaagcc gaacagtcgc tgatcaccgt agaaggcgac     120
aaagcctcta tggaagttcc gtctccgcag gcgggtatcg ttaaagagat caaagtctct     180
gttggcgata aacccagac cggcgcactg attatgattt cgattccgc cgacggtgca      240
gcagacgctg cacctgctca ggcagaagag aagaaagaag cagctccggc agcagcacca     300
gcggctgcgg cggcaaaaga cgttaacgtt ccggatatcg cagcgacga gttgaagtg      360
accgaaatcc tggtgaaagt tggcgataaa gttgaagctg aacagtcgct gatcaccgta     420
gaaggcgaca aggcttctat ggaagttccg gctccgtttg ctggcaccgt gaaagagatc     480
aaagtgaacg tgggtgacaa agtgtctacc ggctcgctga ttatggtctt cgaagtcgcg     540
ggtgaagcag gcgcggcagc tccggccgct aaacaggaag cagctccggc agcggcccct     600
gcaccagcgg ctggcgtgaa agaagttaac gttccggata tcggcggtga cgaagttgaa     660
gtgactgaag tgatggtgaa agtgggcgac aaagttgccg ctgaacagtc actgatcacc     720
gtagaaggcg acaaagcttc tatggaagtt ccggcgccgt ttgcaggcgt cgtgaaggaa     780
ctgaaagtca cgttggcga taaagtgaaa actggctcgc tgattatgat cttcgaagtt     840
gaaggcgcag cgcctgcggc agctcctgcg aaacaggaag cggcagcgcc ggcaccggca     900
gcaaaagctg aagccccggc agcagcacca gctgcgaaag cggaaggcaa atctgaattt     960
gctgaaaacg acgcttatgt tcacgcgact ccgctgatcc gcgtctggc acgcgagttt    1020
ggtgttaacc ttgcgaaagt gaagggcact ggccgtaaag gtcgtatcct gcgcgaagac    1080
```

-continued

```
gttcaggctt acgtgaaaga agctatcaaa cgtgcagaag cagctccggc agcgactggc    1140
ggtggtatcc ctggcatgct gccgtggccg aaggtggact tcagcaagtt tggtgaaatc    1200
gaagaagtgg aactgggccg catccagaaa atctctggtg cgaacctgag ccgtaactgg    1260
gtaatgatcc cgcatgttac tcacttcgac aaaaccgata tcaccgagtt ggaagcgttc    1320
cgtaaacagc agaacgaaga agcggcgaaa cgtaagctgg atgtgaagat caccccggtt    1380
gtcttcatca tgaaagccgt tgctgcagct cttgagcaga tgcctcgctt caatagttcg    1440
ctgtcggaag acgtcagcg tctgaccctg aagaaataca tcaacatcgg tgtggcggtg    1500
gatacccga acgtctggt tgttccggta ttcaaagacg tcaacaagaa aggcatcatc     1560
gagctgtctc gcgagctgat gactatttct aagaaagcgc gtgacggtaa gctgactgcg    1620
ggcgaaatgc agggcggttg cttcaccatc tccagcatcg gcggcctggg tactacccac    1680
ttcgcgccga ttgtgaacgc gccggaagtg gctatcctcg gcgtttccaa gtccgcgatg    1740
gagccggtgt ggaatggtaa agagttcgtg ccgcgtctga tgctgccgat ttctctctcc    1800
ttcgaccacc gcgtgatcga cggtgctgat ggtgcccgtt tcattaccat cattaacaac    1860
acgctgtctg acattcgccg tctggtgatg taagtaaaag agccggccca acggccggct    1920
tttttctggt aatctcatga atgtattgag gttattagcg aatagacaaa tcggttgccg    1980
tttgttgttt aaaaattgtt aacaattttg taaaataccg acggatagaa cgacccggtg    2040
gtggttaggg tattacttca catccctat ggatttctgg gtgcagcaag gtagcaagcg    2100
ccagaatccc caggagctta cataagtaag tgactgggt gagggcgtga agctaacgcc     2160
gctgcggcct gaaagacgac gggtatgacc gccggagata aatatataga ggtcatgatg    2220
agtactgaaa tcaaaactca ggtcgtggta cttggggcag gccccgcagg ttactccgct    2280
gccttccgtt gcgctgattt aggtctggaa accgtaatcg tagaacgtta caacacccett   2340
ggcggtgttt gtctgaacgt gggttgtatc ccttctaaag cgctgctgca cgtggcaaaa    2400
gttatcgaag aagcgaaagc gctggccgaa cacggcatcg ttttcggcga accgaaaact    2460
gacattgaca agatccgcac ctggaaagaa aaagtcatca ctcagctgac cggtggtctg    2520
gctggcatgg ccaaaggtcg taaagtgaag gtggttaacg gtctgggtaa atttaccggc    2580
gctaacaccc tggaagtgga aggcgaaaac ggcaaaaccg tgatcaactt cgacaacgcc    2640
atcatcgcgg cgggttcccg tccgattcag ctgccgttta tcccgcatga agatccgcgc    2700
gtatgggact ccaccgacgc gctggaactg aaatctgtac cgaaacgcat gctggtgatg    2760
ggcggcggta tcatcggtct ggaaatgggt accgtatacc atgcgctggg ttcagagatt    2820
gacgtggtgg aaatgttcga ccaggttatc ccggctgccg acaaagacgt ggtgaaagtc    2880
ttcaccaaac gcatcagcaa gaaatttaac ctgatgctgg aagccaaagt gactgccgtt    2940
gaagcgaaag aagacggtat ttacgtttcc atggaaggta aaaagcaccg gcggaagcg     3000
cagcgttacg acgcagtgct ggtcgctatc ggccgcgtac cgaatggtaa aaacctcgat    3060
gcaggtaaag ctggcgtgga agttgacgat cgcggcttca tccgcgttga caaacaaatg    3120
cgcaccaacg tgccgcacat ctttgctatc ggcgatatcg tcggtcagcc gatgctggcg    3180
cacaaaggtg tccatgaagg ccacgttgcc gcagaagtta tctccggtct gaaacactac    3240
ttcgatccga aagtgatccc atccatcgcc tacactaaac cagaagtggc atgggtcggt    3300
ctgaccgaga aagaagcgaa agagaaaggc atcagctacg aaaccgccac cttcccgtgg    3360
gctgcttccg gccgtgctat cgcttctgac tgcgcagatg gtatgaccaa actgatcttc    3420
```

```
gacaaagaga cccaccgtgt tatcggcggc gcgattgtcg gcaccaacgg cggcgagctg    3480
ctgggtgaga tcggcctggc tatcgagatg ggctgtgacg ctgaagacat cgccctgacc    3540
atccacgctc acccgactct gcacgagtcc gttggcctgg cggcggaagt gttcgaaggc    3600
agcatcaccg acctgccaaa cgccaaagcg aagaaaaagt aacttttcct ttcaggaaaa    3660
aagcataagc ggctccggga gccgcttttt ttatgcctga tgtttagaac tatgtcactg    3720
ttcataaacc gctacacctc atacatactt taagggcgaa ttctgcagat atccatcaca    3780
ctggcggccg ctcgagcatg catctagcac atccggcaat taaaaaagcg ctaaccacg     3840 ccgcttttttt tacgtctgca atttacctttt ccagtcttct tgctccacgt tcagagagac    3900
gttcgcatac tgctgaccgt tgctcgttat tcagcctgac agtatggtta ctgtcgttta    3960
gacgttgtgg gcggctctcc tgaactttct cccgaaaaac ctgacgttgt tcaggtgatg    4020
ccgattgaac acgctggcgg gcgttatcac gttgctgttg attcagtggg cgctgctgta    4080 cttttttcctt                                                          4090

<210> SEQ ID NO 77
<211> LENGTH: 475
<212> TYPE: PRT
<213> ORGANISM: Escherichia coli

<400> SEQUENCE: 77

Met Met Ser Thr Glu Ile Lys Thr Gln Val Val Leu Gly Ala Gly
 1               5                  10                  15

Pro Ala Gly Tyr Ser Ala Ala Phe Arg Cys Ala Asp Leu Gly Leu Glu
                20                  25                  30

Thr Val Ile Val Glu Arg Tyr Asn Thr Leu Gly Gly Val Cys Leu Asn
                35                  40                  45

Val Gly Cys Ile Pro Ser Lys Ala Leu Leu His Val Ala Lys Val Ile
        50                  55                  60

Glu Glu Ala Lys Ala Leu Ala Glu His Gly Ile Val Phe Gly Glu Pro
65                  70                  75                  80

Lys Thr Asp Ile Asp Lys Ile Arg Thr Trp Lys Glu Lys Val Ile Asn
                85                  90                  95

Gln Leu Thr Gly Gly Leu Ala Gly Met Ala Lys Gly Arg Lys Val Lys
                100                 105                 110

Val Val Asn Gly Leu Gly Lys Phe Thr Gly Ala Asn Thr Leu Glu Val
        115                 120                 125

Glu Gly Glu Asn Gly Lys Thr Val Ile Asn Phe Asp Asn Ala Ile Ile
        130                 135                 140

Ala Ala Gly Ser Arg Pro Ile Gln Leu Pro Phe Ile Pro His Glu Asp
145                 150                 155                 160

Pro Arg Ile Trp Asp Ser Thr Asp Ala Leu Glu Leu Lys Glu Val Pro
                165                 170                 175

Glu Arg Leu Leu Val Met Gly Gly Gly Ile Ile Gly Leu Glu Met Gly
                180                 185                 190

Thr Val Tyr His Ala Leu Gly Ser Gln Ile Asp Val Val Glu Met Phe
        195                 200                 205

Asp Gln Val Ile Pro Ala Ala Asp Lys Asp Ile Val Lys Val Phe Thr
        210                 215                 220

Lys Arg Ile Ser Lys Lys Phe Asn Leu Met Leu Glu Thr Lys Val Thr
225                 230                 235                 240

Ala Val Glu Ala Lys Glu Asp Gly Ile Tyr Val Thr Met Glu Gly Lys
                245                 250                 255
```

```
Lys Ala Pro Ala Glu Pro Gln Arg Tyr Asp Ala Val Leu Val Ala Ile
            260                 265                 270

Gly Arg Val Pro Asn Gly Lys Asn Leu Asp Ala Gly Lys Ala Gly Val
        275                 280                 285

Glu Val Asp Asp Arg Gly Phe Ile Arg Val Asp Lys Gln Leu Arg Thr
290                 295                 300

Asn Val Pro His Ile Phe Ala Ile Gly Asp Ile Val Gly Gln Pro Met
305                 310                 315                 320

Leu Ala His Lys Gly Val His Glu Gly His Val Ala Ala Glu Val Ile
                325                 330                 335

Ala Gly Lys Lys His Tyr Phe Asp Pro Lys Val Ile Pro Ser Ile Ala
            340                 345                 350

Tyr Thr Glu Pro Glu Val Ala Trp Val Gly Leu Thr Glu Lys Glu Ala
        355                 360                 365

Lys Glu Lys Gly Ile Ser Tyr Glu Thr Ala Thr Phe Pro Trp Ala Ala
370                 375                 380

Ser Gly Arg Ala Ile Ala Ser Asp Cys Ala Asp Gly Met Thr Lys Leu
385                 390                 395                 400

Ile Phe Asp Lys Glu Ser His Arg Val Ile Gly Gly Ala Ile Val Gly
                405                 410                 415

Thr Asn Gly Gly Glu Leu Leu Gly Glu Ile Gly Leu Ala Ile Glu Met
            420                 425                 430

Gly Cys Asp Ala Glu Asp Ile Ala Leu Thr Ile His Ala His Pro Thr
        435                 440                 445

Leu His Glu Ser Val Gly Leu Ala Ala Glu Val Phe Glu Gly Ser Ile
        450                 455                 460

Thr Asp Leu Pro Asn Pro Lys Ala Lys Lys Lys
465                 470                 475

<210> SEQ ID NO 78
<211> LENGTH: 475
<212> TYPE: PRT
<213> ORGANISM: Klebsiella pneumoniae

<400> SEQUENCE: 78

Met Met Ser Thr Glu Ile Lys Thr Gln Val Val Leu Gly Ala Gly
1               5                   10                  15

Pro Ala Gly Tyr Ser Ala Ala Phe Arg Cys Ala Asp Leu Gly Leu Glu
                20                  25                  30

Thr Val Ile Val Glu Arg Tyr Ser Thr Leu Gly Gly Val Cys Leu Asn
            35                  40                  45

Val Gly Cys Ile Pro Ser Lys Ala Leu Leu His Val Ala Lys Val Ile
        50                  55                  60

Glu Glu Ala Lys Ala Leu Ala Glu His Gly Ile Val Phe Gly Glu Pro
65                  70                  75                  80

Lys Thr Asp Ile Asp Lys Ile Arg Thr Trp Lys Glu Lys Val Ile Thr
                85                  90                  95

Gln Leu Thr Gly Gly Leu Ala Gly Met Ala Lys Gly Arg Lys Val Lys
            100                 105                 110

Val Val Asn Gly Leu Gly Lys Phe Thr Gly Ala Asn Thr Leu Glu Val
        115                 120                 125

Glu Gly Glu Asn Gly Lys Thr Val Ile Asn Phe Asp Asn Ala Ile Ile
    130                 135                 140

Ala Ala Gly Ser Arg Pro Ile Gln Leu Pro Phe Ile Pro His Glu Asp
```

```
        145                 150                 155                 160
Pro Arg Val Trp Asp Ser Thr Asp Ala Leu Glu Leu Lys Ser Val Pro
                165                 170                 175
Lys Arg Met Leu Val Met Gly Gly Ile Ile Gly Leu Glu Met Gly
            180                 185                 190
Thr Val Tyr His Ala Leu Gly Ser Glu Ile Asp Val Glu Met Phe
        195                 200                 205
Asp Gln Val Ile Pro Ala Ala Asp Lys Asp Val Lys Val Phe Thr
    210                 215                 220
Lys Arg Ile Ser Lys Lys Phe Asn Leu Met Leu Glu Ala Lys Val Thr
225                 230                 235                 240
Ala Val Glu Ala Lys Glu Asp Gly Ile Tyr Val Ser Met Glu Gly Lys
                245                 250                 255
Lys Ala Pro Ala Glu Ala Gln Arg Tyr Asp Ala Val Leu Val Ala Ile
            260                 265                 270
Gly Arg Val Pro Asn Gly Lys Asn Leu Asp Ala Gly Lys Ala Gly Val
        275                 280                 285
Glu Val Asp Asp Arg Gly Phe Ile Arg Val Asp Lys Gln Met Arg Thr
    290                 295                 300
Asn Val Pro His Ile Phe Ala Ile Gly Asp Ile Val Gly Gln Pro Met
305                 310                 315                 320
Leu Ala His Lys Gly Val His Glu Gly His Val Ala Ala Glu Val Ile
                325                 330                 335
Ser Gly Leu Lys His Tyr Phe Asp Pro Lys Val Ile Pro Ser Ile Ala
            340                 345                 350
Tyr Thr Lys Pro Glu Val Ala Trp Val Gly Leu Thr Glu Lys Glu Ala
        355                 360                 365
Lys Glu Lys Gly Ile Ser Tyr Glu Thr Ala Thr Phe Pro Trp Ala Ala
    370                 375                 380
Ser Gly Arg Ala Ile Ala Ser Asp Cys Ala Asp Gly Met Thr Lys Leu
385                 390                 395                 400
Ile Phe Asp Lys Glu Thr His Arg Val Ile Gly Gly Ala Ile Val Gly
                405                 410                 415
Thr Asn Gly Gly Glu Leu Leu Gly Glu Ile Gly Leu Ala Ile Glu Met
            420                 425                 430
Gly Cys Asp Ala Glu Asp Ile Ala Leu Thr Ile His Ala His Pro Thr
        435                 440                 445
Leu His Glu Ser Val Gly Leu Ala Ala Glu Val Phe Glu Gly Ser Ile
    450                 455                 460
Thr Asp Leu Pro Asn Ala Lys Ala Lys Lys
465                 470                 475

<210> SEQ ID NO 79
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
ataataatac atatgaacca tgcgagttac gggcctataa gccaggcgag atatgatcta    60
tatcaatttc tcatctataa tgctttgtta gtatctcgtc gccgactaa taaagagaga   120 gttagtgtga aagctgacaa cccttttgat cttttacttc ctgctgcaat ggccaaagtg   180
```

-continued

```
gccgaagagg cgggtgtcta taaagcaacg aaacatccgc ttaagacttt ctatctggcg      240
attaccgccg gtgttttcat ctcaatcgca ttcaccactg gcacaggcac agaaggtagg      300
tgttacatgt cagaacgttt acacaatgac gtggatccta ttattat                   347
```

<210> SEQ ID NO 80
<211> LENGTH: 4678
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 80

```
aagaggtaaa agaataatgg ctatcgaaat caaagtaccg gacatcgggg ctgatgaagt       60
tgaaatcacc gagatcctgg tcaaagtggg cgacaaagtt gaagccgaac agtcgctgat     120
caccgtagaa ggcgacaaag cctctatgga agttccgtct ccgcaggcgg gtatcgttaa     180
agagatcaaa gtctctgttg gcgataaaac ccagaccggc gcactgatta tgattttcga     240
ttccgccgac ggtgcagcag acgctgcacc tgctcaggca gaagagaaga aagaagcagc     300
tccggcagca gcaccagcgg ctgcggcggc aaaagacgtt aacgttccgg atatcggcag     360
cgacgaagtt gaagtgaccg aaatcctggt gaaagttggc gataaagttg aagctgaaca     420
gtcgctgatc accgtagaag cgacaaggc ttctatggaa gttccggctc cgtttgctgg     480
caccgtgaaa gagatcaaag tgaacgtggg tgacaaagtg tctaccggct cgctgattat     540
ggtcttcgaa gtcgcgggtg aagcaggcgc ggcagctccg gccgctaaac aggaagcagc     600
tccggcagcg gcccctgcac cagcggctgg cgtgaaagaa gttaacgttc cggatatcgg     660
cggtgacgaa gttgaagtga ctgaagtgat ggtgaaagtg ggcgacaaag ttgccgctga     720
acagtcactg atcaccgtag aaggcgacaa agcttctatg gaagttccgg cgccgtttgc     780
aggcgtcgtg aaggaactga agtcaacgt tggcgataaa gtgaaaactg gctcgctgat     840
tatgatcttc gaagttgaag gcgcagcgcc tgcggcagct cctgcgaaac aggaagcggc     900
agcgccggca ccggcagcaa agctgaagc cccggcagca gcaccagctg cgaaagcgga     960
aggcaaatct gaatttgctg aaaacgacgc ttatgttcac gcgactccgc tgatccgccg    1020
tctggcacgc gagtttggtg ttaaccttgc gaaagtgaag ggcactggcc gtaaaggtcg    1080
tatcctgcgc gaagacgttc aggcttacgt gaaagaagct atcaaacgtg cagaagcagc    1140
tccggcagcg actggcggtg gtatccctgg catgctgccg tggccgaagg tggacttcag    1200
caagtttggt gaaatcgaag aagtggaact gggccgcatc cagaaaatct ctggtgcgaa    1260
cctgagccgt aactgggtaa tgatcccgca tgttactcac ttcgacaaaa ccgatatcac    1320
cgagttggaa gcgttccgta acagcagaa cgaagaagcg gcgaaacgta agctggatgt    1380
gaagatcacc ccggttgtct tcatcatgaa agccgttgct gcagctcttg agcagatgcc    1440
tcgcttcaat agttcgctgt cggaagacgg tcagcgtctg acctgaaga aatacatcaa    1500 catcggtgtg gcggtggata ccccgaacgg tctggttgtt ccggtattca aagacgtcaa    1560
caagaaaggc atcatcgagc tgtctcgcga gctgatgact atttctaaga aagcgcgtga    1620
cggtaagctg actgcgggcg aaatgcaggg cggttgcttc accatctcca gcatcggcgg    1680
cctgggtact acccacttcg cgccgattgt gaacgcgccg gaagtggcta tcctcggcgt    1740
ttccaagtcc gcgatggagc cggtgtggaa tggtaaagag ttcgtgccgc gtctgatgct    1800
gccgatttct ctctccttcg accaccgcgt gatcgacggt gctgatggtg cccgtttcat    1860
```

```
taccatcatt aacaacacgc tgtctgacat tcgccgtctg gtgatgtaag taaaagagcc   1920
ggcccaacgg ccggcttttt tctggtaatc tcatgaatgt attgaggtta ttagcgaata   1980
gacaaatcgg ttgccgtttg ttaagccagg cgagatatga tctatatcaa tttctcatct   2040
ataatgcttt gttagtatct cgtcgccgac ttaataaaga gagagttagt cttctatatc   2100
acagcaagaa ggtaggtgtt acatgatgag tactgaaatc aaaactcagg tcgtggtact   2160
tggggcaggc cccgcaggtt actctgcagc cttccgttgc gctgatttag gtctggaaac   2220
cgtcatcgta gaacgttaca gcaccctcgg tggtgtttgt ctgaacgtgg gttgtatccc   2280
ttctaaagcg ctgctgcacg tggcaaaagt tatcgaagaa gcgaaagcgc tggccgaaca   2340
cggcatcgtt ttcggcgaac cgaaaactga cattgacaag atccgcacct ggaaagaaaa   2400
agtcatcact cagctgaccg gtggtctggc tggcatggcc aaaggtcgta aagtgaaggt   2460
ggttaacggt ctgggtaaat ttaccggcgc taacaccctg gaagtggaag gcgaaaacgg   2520
caaaaccgtg atcaacttcg acaacgccat catcgcggcg ggttcccgtc cgattcagct   2580
gccgtttatc ccgcatgaag atccgcgcgt atgggactcc accgacgcgc tggaactgaa   2640
atctgtaccg aaacgcatgc tggtgatggg cggcggtatc atcggtctgg aaatgggtac   2700
cgtataccat cgcgctgggt tcagagattga cgtggtggaa atgttcgacc aggttatccc   2760
ggctgccgac aaagacgtgg tgaaagtctt caccaaacgc atcagcaaga aatttaacct   2820
gatgctggaa gccaaagtga ctgccgttga agcgaaagaa gacggtattt acgtttccat   2880
ggaaggtaaa aaagcaccgg cggaagcgca gcgttacgac gcagtgctgg tcgctatcgg   2940
ccgcgtaccg aatggtaaaa acctcgatgc aggtaaagct ggcgtggaag ttgacgatcg   3000
cggcttcatc cgcgttgaca aacaaatgcg caccaacgtg ccgcacatct ttgctatcgg   3060
cgatatcgtc ggtcagccga tgctggcgca caaaggtgtc catgaaggcc acgttgccgc   3120
agaagttatc tccggtctga aacactactt cgatccgaaa gtgatcccat ccatcgccta   3180
cactaaacca gaagtggcat gggtcggtct gaccgagaaa gaagcgaaag agaaaggcat   3240
cagctacgaa accgccacct cccgtgggc tgcttccggc cgtgctatcg cttctgactg   3300
cgcagatggt atgaccaaac tgatcttcga caaagagacc caccgtgtta tcggcgcgc   3360 gattgtcggc accaacggcg cgagctgct gggtgagatc ggcctggcta tcgagatggg   3420
ctgtgacgct gaagacatcg ccctgaccat ccacgctcac ccgactctgc acagtccgt   3480 tggcctggcg gcggaagtgt tcgaaggcag catcaccgac ctgccaaacg ccaaagcgaa   3540
gaaaaagtaa cttttctttt caggaaaaaa gcataagcgg ctccgggagc cgctttttt   3600 atgcctgatg tttagaacta tgtcactgtt cataaaccgc tacacctcat acatactta   3660 agggcgaatt ctgcagatat ccatcacact ggcggccgct cgagcatgca tctagcacat   3720
ccggcaatta aaaaagcggc taaccacgcc gcttttttta cgtctgcaat ttacctttcc   3780
agtcttcttg ctccacgttc agagagacgt tcgcatactg ctgaccgttg ctcgttattc   3840
agcctgacag tatggttact gtcgtttaga cgttgtgggc ggctctcctg aactttctcc   3900
cgaaaaacct gacgttgttc aggtgatgcc gattgaacac gctggcgggc gttatcacgt   3960
tgctgttgat tcagtgggcg ctgctgtact ttttccttaa acacctggcg ctgctctggt   4020
gatgcggact gaatacgctc acgcgctgcg tctcttcgct gctggttctg cgggttagtc   4080
tgcattttct cgcgaaccgc ctggcgctgc tcaggcgagg cggactgaat gcctcacgc   4140 gctgcctctc ttcgctgctg gatcttcggg ttagtctgca ttctctcgcg aactgcctgg   4200
cgctgctcag gcgaggcgga ctgataacgc tgacgagcgg cgtccttttg ttgctgggtc   4260
```

```
agtggttggc gacggctgaa gtcgtggaag tcgtcatagc tcccatagtg ttcagcttca    4320
ttaaaccgct gtgccgctgc ctgacgttgg gtacctcgtg taatgactgg tgcggcgtgt    4380
gttcgttgct gaaactgatt tgctgccgcc tgacgctggc tgtcgcgcgt tggggcaggt    4440
aattgcgtgg cgctcattcc gccgttgaca tcggtttgat gaaaccgctt tgccatatcc    4500
tgatcatgat agggcacacc attacggtag tttggattgt gccgccatgc catattctta    4560
tcagtaagat gctcaccggt gatacggttg aaattgttga cgtcgatatt gatgttgtcg    4620
ccgttgtgtt gccagccatt accgtcacga tgaccgccat cgtggtgatg ataatcat      4678
```

<210> SEQ ID NO 81
<211> LENGTH: 1114
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (323)..(958)

<400> SEQUENCE: 81

```
caaaaaaccg gagtctgtgc tccggttttt tattatccgc taatcaatta catatgaata     60
tcctccttag ttcctattcc gaagttccta ttctctagaa agtataggaa cttcggcgcg    120
cctacctgtg acggaagatc acttcgcaga ataaataaat cctggtgtcc ctgttgatac    180
cgggaagccc tgggccaact tttggcgaaa atgagacgtt gatcggcacg taagaggttc    240
caactttcac cataatgaaa taagatcact accgggcgta tttttttgagt tgtcgagatt    300 ttcaggagct aaggaagcta aa atg gag aaa aaa atc act gga tat acc acc     352
                         Met Glu Lys Lys Ile Thr Gly Tyr Thr Thr
                          1               5                  10 gtt gat ata tcc caa tgg cat cgt aaa gaa cat ttt gag gca ttt cag     400
Val Asp Ile Ser Gln Trp His Arg Lys Glu His Phe Glu Ala Phe Gln
                15                  20                  25 tca gtt gct caa tgt acc tat aac cag acc gtt cag ctg gat att acg     448
Ser Val Ala Gln Cys Thr Tyr Asn Gln Thr Val Gln Leu Asp Ile Thr
         30                  35                  40 gcc ttt tta aag acc gta aag aaa aat aag cac aag ttt tat ccg gcc     496
Ala Phe Leu Lys Thr Val Lys Lys Asn Lys His Lys Phe Tyr Pro Ala
     45                  50                  55 ttt att cac att ctt gcc cgc ctg atg aat gct cat ccg gaa tta cgt     544
Phe Ile His Ile Leu Ala Arg Leu Met Asn Ala His Pro Glu Leu Arg
 60                  65                  70 atg gca atg aaa gac ggt gag ctg gtg ata tgg gat agt gtt cac cct     592
Met Ala Met Lys Asp Gly Glu Leu Val Ile Trp Asp Ser Val His Pro
 75                  80                  85                  90 tgt tac acc gtt ttc cat gag caa act gaa acg ttt tca tcg ctc tgg     640
Cys Tyr Thr Val Phe His Glu Gln Thr Glu Thr Phe Ser Ser Leu Trp
                 95                 100                 105 agt gaa tac cac gac gat ttc cgg cag ttt cta cac ata tat tcg caa     688
Ser Glu Tyr His Asp Asp Phe Arg Gln Phe Leu His Ile Tyr Ser Gln
            110                 115                 120 gat gtg gcg tgt tac ggt gaa aac ctg gcc tat ttc cct aaa ggg ttt     736
Asp Val Ala Cys Tyr Gly Glu Asn Leu Ala Tyr Phe Pro Lys Gly Phe
        125                 130                 135 att gag aat atg ttt ttc gtc tca gcc aat ccc tgg gtg agt ttc acc     784
Ile Glu Asn Met Phe Phe Val Ser Ala Asn Pro Trp Val Ser Phe Thr
    140                 145                 150
```

-continued

```
agt ttt gat tta aac gtg gcc aat atg gac aac ttc ttc gcc ccc gtt      832
Ser Phe Asp Leu Asn Val Ala Asn Met Asp Asn Phe Phe Ala Pro Val
155                 160                 165                 170 ttc acc atg ggc aaa tat tat acg caa ggc gac aag gtg ctg atg ccg      880
Phe Thr Met Gly Lys Tyr Tyr Thr Gln Gly Asp Lys Val Leu Met Pro
            175                 180                 185 ctg gcg att cag gtt cat cat gcc gtt tgt gat ggc ttc cat gtc ggc      928
Leu Ala Ile Gln Val His His Ala Val Cys Asp Gly Phe His Val Gly
        190                 195                 200 aga tgc tta atg aat aca aca gta ctg cga tgagtggcag ggcggggcgt        978
Arg Cys Leu Met Asn Thr Thr Val Leu Arg
    205                 210 aaggcgcgcc atttaaatga agttcctatt ccgaagttcc tattctctag aaagtatagg   1038
aacttcgaag cagctccagc ctacacccct cttcagggct gactgtttgc ataaaaattc   1098
atctgtatgc acaata                                                   1114
```

<210> SEQ ID NO 82
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Leu Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Cys Leu Met Asn Thr
        195                 200                 205

Thr Val Leu Arg
    210
```

<210> SEQ ID NO 83
<211> LENGTH: 2521
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 83

```
ttatttggtg atattggtac caatatcatg cagcaaacgg tgcaacattg ccgtgtctcg      60
ttgctctaaa agccccaggc gttgttgtaa ccagtcgacc agttttatgt catctgccac     120
tgccagagtc gtcagcaatg tcatggctcg ttcgcgtaaa gcttgcagtt gatgttggtc     180
tgccgttgca tcacttttcg ccggttgttg tattaatgtt gctaattgat agcaatagac     240
catcaccgcc tgcccagat tgagcgaagg ataatccgcc accatcggca caccagtaag      300
aacgtcagcc aacgctaact cttcgttagt caacccggaa tcttcgcgac caaacaccag     360
cgcggcatgg ctcatccatg aagatttttc ctctaacagc ggcaccagtt caactggcgt     420
ggcgtagtaa tgatatttcg cccgactgcg cgcagtggtg gcgacagtga atcgacatc      480
gtgtaacgat tcagccaatg tcgggaaaac tttaatatta tcaataatat caccagatcc     540
atgtgcgacc cagcgggtgg ctggctccag gtgtgcctga ctatcgacaa tccgcagatc     600
gctaaacccc atcgttttca ttgcccgcgc cgctgcccca atattttctg ctctggcggg     660
tgcgaccaga ataatcgtta tacgcatatt gccactcttc ttgatcaaat aaccgcgaac     720
cgggtgatca ctgtcaactt attacgcggt gcgaatttac aaattcttaa cgtaagtcgc     780
agaaaaagcc ctttacttag cttaaaaaag gctaaactat ttcctgactg tactaacggt     840
tgagttgtta aaaaatgcta catatccttc tgtttactta ggataatttt ataaaaaata     900
aatctcgaca attggattca ccacgtttat tagttgtatg atgcaactag ttggattatt     960
aaaataatgt gacgaaagct agcatttaga tacgatgatt tcatcaaact gttaacgtgc    1020
tacaattgaa cttgatatat gtcaacgaag cgtagtttta ttgggtgtcc ggcccctctt    1080
agcctgttat gttgctgtta aaatggttag gatgacagcc gtttttgaca ctgtcgggtc    1140
ctgagggaaa gtacccacga ccaagctaat gatgttgttg acgttgatgg aaagtgcatc    1200
aagaacgcaa ttacgtactt tagtcatgtt acgccgatca tgttaatttg cagcatgcat    1260
caggcaggtc agggactttt gtacttcctg tttcgattta gttggcaatt taggtagcaa    1320
acgaattcat cggctttacc accgtcaaaa aaacggcgc ttttagcgc cgttttatt      1380
tttcaacctt atttccagat acgtaactca tcgtccgttg taacttcttt actggctttc    1440
attttcggca gtgaaaacgc ataccagtcg atattacggg tcacaaacat catgccggcc    1500
agcgccacca ccagcacact ggttcccaac aacagcgcgc tatcggcaga gttgagcagt    1560
ccccacatca caccatccag caacaacagc gcgagggtaa acaacatgct gttgcaccaa    1620
cctttcaata ccgcttgcaa ataaataccg ttcattatcg ccccaatcag actggcgatt    1680
atccatgcca cggtaaaacc ggtatgttca gaaagcgcca gcaagagcaa ataaaacatc    1740
accaatgaaa gccccaccag caaatattgc attgggtgta aacgttgcgc ggtgagcgtt    1800
tcaaaaacaa agaacgccat aaaagtcagt gcaatcagca gaatggcgta cttagtcgcc    1860
cggtcagtta attggtattg atcggctggc gtcgttactg cgacgctaaa cgccgggaag    1920
ttttcccagc cggtatcatt gcctgaagca aaacgctcac cgagattatt agcaaaccag    1980
ctgctttgcc agtgcgcctg aaaacctgac tcgctaactt cccgtttggc tggtagaaaa    2040
tcacctaaaa aactgggatg cggccagttg ctggttaagg tcatttcgct attacgcccg    2100
ccaggcacca cagaaagatc gccggtaccg cttaaattca gggccatatt cagcttcagg    2160
```

```
ttctgcttcc gccagtcccc ttcaggtaaa gggatatgca cgccctgccc gccttgctct    2220
aacccggtgc cgggttcaat ggtcagcgcc gttccgttaa cttcaggcgc tttcaccaca    2280
ccaataccac gcgcatcccc gacgctaatc acaataaatg gcttgcctaa ggtgatattt    2340
ggcgcgttga gttcgctaag acgcgaaaca tcgaaatcgg cttttaacgt taaatcactg    2400
tgccagacct gaccggtata atccctatc ttgcgttctt ccacgttctg attgccatca     2460
accatcaatg actcaggtaa ccaaaaatgg ataaaacttc gtttccgctg cagggtttta    2520
t                                                                     2521
```

<210> SEQ ID NO 84
<211> LENGTH: 3010
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

```
aagccacagc aggatgccca ctgcaacaaa ggtgatcaca ccggaaacgc gatggagaat      60
ggacgctatc gccgtgatgg ggaaccggat ggtctgtagg tccagattaa caggtctttg     120
ttttttcaca tttcttatca tgaataacgc ccacatgctg ttcttattat tccctgggga    180
ctacgggcac agaggttaac tttctgttac ctggagacgt cgggatttcc ttcctccggt    240
ctgcttgcgg gtcagacagc gtcctttcta taactgcgcg tcatgcaaaa cactgcttcc    300
agatgcgaaa acgacacgtt acaacgctgg gtggctcggg attgcagggt gttccggaga    360
cctggcggca gtataggctg ttcacaaaat cattacaatt aacctacata tagtttgtcg    420
ggttttatcc tgaacagtga tccaggtcac gataacaaca tttatttaat ttttaatcat    480
ctaatttgac aatcattcaa caaagttgtt acaaacatta ccaggaaaag catataatgc    540
gtaaaagtta tgaagtcggt atttcaccta agattaactt atgtaacagt gtggaagtat    600
tgaccaattc attcgggaca gttattagtg gtagacaagt ttaataattc ggattgctaa    660
gtacttgatt cgccatttat tcgtcatcaa tggatccttt acctgcaagc gcccagagct    720
ctgtacccag gttttcccct ctttcacaga gcggcgagcc aaataaaaaa cgggtaaagc    780
caggttgatg tgcgaaggca aatttaagtt ccggcagtct tacgcaataa ggcgctaagg    840
agaccttaaa tggctgatac aaaagcaaaa ctcaccctca acggggatac agctgttgaa    900
ctggatgtgc tgaaaggcac gctgggtcaa gatgttattg atatccgtac tctcggttca    960
aaaggtgtgt tcacctttga cccaggcttc acttcaaccg catcctgcga atctaaaatt   1020
acttttattg atggtgatga aggtattttg ctgcaccgcg gtttcccgat cgatcagctg   1080
gcgaccgatt ctaactacct ggaagtttgt tacatcctgc tgaatggtga aaaaccgact   1140
caggaacagt atgacgaatt taaaactacg gtgacccgtc ataccatgat ccacgagcag   1200
attacccgtc tgttccatgc tttccgtcgc gactcgcatc caatggcagt catgtgtggt   1260
attaccggcg cgctggcggc gttctatcac gactcgctgg atgttaacaa tcctcgtcac   1320
cgtgaaattg ccgcgttcct cctgctgtcg aaaatgccga ccatggccgc gatgtgttac   1380
aagtattcca ttggtcagcc atttgtttac ccgcgcaacg atctctccta cgccggtaac   1440
ttcctgaata tgatgttctc cacgccgtgc gaaccgtatg aagttaatcc gattctggaa   1500
cgtgctatgg accgtattct gatcctgcac gctgaccatg aacagaacgc ctctacctcc   1560
accgtgcgta ccgctggctc ttcgggtgcg aacccgtttg cctgtatcgc agcaggtatt   1620
```

```
gcttcactgt ggggacctgc gcacggcggt gctaacgaag cggcgctgaa aatgctggaa    1680
gaaatcagct ccgttaaaca cattccggaa tttgttcgtc gtgcgaaaga caaaaatgat    1740
tctttccgcc tgatgggctt cggtcaccgc gtgtacaaaa attacgaccc gcgcgccacc    1800
gtaatgcgtg aaacctgcca tgaagtgctg aaagagctgg gcacgaagga tgacctgctg    1860
gaagtggcta tggagctgga aaacatcgcg ctgaacgacc cgtactttat cgagaagaaa    1920
ctgtacccga acgtcgattt ctactctggt atcatcctga aagcgatggg tattccgtct    1980
tccatgttca ccgtcatttt cgcaatggca cgtaccgttg gctggatcgc ccactggagc    2040
gaaatgcaca gtgacggtat gaagattgcc cgtccgcgtc agctgtatac aggatatgaa    2100
aaacgcgact ttaaaagcga tatcaagcgt taatggttga ttgctaagtt gtaaatattt    2160
taacccgccg ttcatatggc gggttgattt ttatatgcct aaacacaaaa aattgtaaaa    2220
ataaaatcca ttaacagacc tatatagata tttaaaaaga atagaacagc tcaaattatc    2280
agcaacccaa tactttcaat taaaaacttc atggtagtcg catttataac cctatgaaaa    2340
tgacgtctat ctataccccc ctatatttta ttcatcatac aacaaattca tgataccaat    2400
aatttagttt tgcatttaat aaaactaaca atatttttaa gcaaaactaa aaactagcaa    2460
taatcaaata cgatattctg gcgtagctat acccctattc tatatcctta aaggactctg    2520
ttatgtttaa aggacaaaaa acattggccg cactggccgt atctctgctg ttcactgcac    2580
ctgtttatgc tgctgatgaa ggttctggcg aaattcactt aaggggggag gttattgaag    2640
caccttgtga aattcatcca gaagatattg ataaaaacat agatcttgga caagtcacga    2700
caacccatat aaaccgggag catcatagca ataaagtggc cgtcgacatt cgcttgatca    2760
actgtgatct gcctgcttct gacaacggta gcggaatgcc ggtatccaaa gttggcgtaa    2820
ccttcgatag cacggctaag acaactggtg ctacgccttt gttgagcaac accagtgcag    2880
gcgaagcaac tggggtcggt gtacgactga tggacaaaaa tgacggtaac atcgtattag    2940
gttcagccgc gccagatctt gacctggatg caagctcatc agaacagacg ctgaactttt    3000
tcgcctggat                                                          3010
```

<210> SEQ ID NO 85
<211> LENGTH: 4180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
cgcgatgtcg acgtcacgaa actgaaaaaa ccgctctaca ttctggcgac tgctgatgaa      60
gaaaccagta tggccggagc gcgttatttt gccgaaacta ccgccctgcg cccggattgc     120
gccatcattg gcgaaccgac gtcactacaa ccggtacgcg cacataaagg tcatatctct     180
aacgccatcc gtattcaggg ccagtcgggg cactccagcg atccagcacg cggagttaac     240
gctatcgaac taatgcacga cgccatcggg catattttgc aattgcgcga taacctgaaa     300
gaacgttatc actacgaagc gtttaccgtg ccatacccta cgctcaacct cgggcatatt     360
cacggtggcg acgcttctaa ccgtatttgc gcttgctgtg agttgcatat ggatattcgt     420
ccgctgcctg gcatgacact caatgaactt aatggtttgc tcaacgatgc attggctccg     480
gtgagcgaac gctggccggg tcgtctgacg gtcgacgagc tgcatccgcc gatccctggc     540
tatgaatgcc caccgaatca tcaactggtt gaagtggttg agaaattgct cggagcaaaa     600
```

```
accgaagtgg tgaactactg taccgaagcg ccgtttattc aaacgttatg cccgacgctg    660
gtgttggggc ctggctcaat taatcaggct catcaacctg atgaatatct ggaaacacgg    720
tttatcaagc ccacccgcga actgataacc caggtaattc accattttg ctggcattaa     780
aacgtaggcc ggataaggcg ctcgcgccgc atcggcgct gttgccaaac tccagtgccg      840
caataatgtc ggatgcgatg cttgcgcatc ttatccgacc tacagtgact caaacgatgc    900
ccaaccgtag gccggataag gcgctcgcgc cgcatccggc actgttgcca aactccagtg    960
ccgcaataat gtcggatgcg atacttgcgc atcttatccg accgacagtg actcaaacga   1020
tgcccaactg taggccggat aaggcgctcg cgccgcatcc ggcactgttg ccaaactcca   1080
gtgccgcaat aatgtcggat gcgatacttg cgcatcttat ccgacctaca cctttggtgt   1140
tacttggggc gattttttaa catttccata agttacgctt atttaaagcg tcgtgaattt   1200
aatgacgtaa attcctgcta tttattcgtt tgctgaagcg atttcgcagc atttgacgtc   1260
accgctttta cgtggcttta taaaagacga cgaaaagcaa agcccgagca tattcgcgcc   1320
aatgctagca agaggagaag tcgacatgac agacttaaat aaagtggtaa agaacttga    1380
agctcttggt atttatgacg taaaagaagt tgtttacaat ccaagctacg agcaattgtt   1440
cgaagaagaa actaaaccag gtttagaagg ctttgaaaaa ggtactttaa ctacgactgg   1500
tgcagtggca gtagatacag gtatcttcac aggtcgttct ccaaaagata aatatatcgt   1560
gttagatgaa aaaaccaaag atactgtttg gtggacatct gaaacagcaa aaaacgacaa   1620
caagccaatg aaccaagcta catggcaaag cttaaaagac ttggtaacca ccagctttc    1680
tcgtaaacgc ttatttgtag ttgatggttt ctgtggtgcg agcgaacacg accgtattgc   1740
agtacgtatt gtcactgaag tagcgtggca agcacatttt gtaaaaata tgtttattcg    1800
cccaactgaa gaacaactca aaaattttga accagatttc gttgtaatga atggttctaa   1860
agtaaccaat ccaaactgga agaacaagg tttaaattca gaaaactttg ttgctttcaa    1920
cttgactgaa cgcattcaat taatcggtgg tacttggtac ggcggtgaaa tgaaaaaagg   1980
tatgttctca atcatgaact acttcctacc acttaaaggt gttggtgcaa tgcactgctc   2040
agctaacgtt ggtaaagatg gcgatgtagc aatcttcttc ggcttatctg cacaggtaa    2100
aacaacccctt tcaacggatc caaaacgtga attaatcggt gacgatgaac acggctggga   2160
tgatgtgggt atctttaact ttgaaggtgg ttgctatgcg aaaaccattc acctttcaga   2220
agaaaatgaa ccagatattt accgcgctat ccgtcgcgac gcattattag aaaacgtggt   2280
tgttcgtgca gatggttctg ttgatttcga tgatggttca aaaacagaaa atactcgcgt   2340
gtcttaccca atttatcaca ttgataacat tgtaaaacca gtttctcgtg caggtcacgc   2400
aactaaagtg atttttcttaa ctgcagatgc atttggcgta ttaccaccag tatctaaatt   2460
gacaccagaa caaactaaat actacttctt atctggtttc acagcaaaat tagcaggtac   2520
tgaacgtggt attactgaac caactccaac tttctcagca tgtttcggtg ctgcgttctt   2580
aaccccttcac ccaactcaat atgcagaagt gttagtaaaa cgtatgcaag cagtgggtgc   2640
tgaagcttac ttagtaaata ctggttggaa tggcacaggc aaacgtatct caatcaaaga   2700
tactcgcgga atcattgatg caatcttaga tggctcaatt gaaaaagctg aaatgggcga   2760
attaccaatc tttaacttag ccattcctaa agcattacca ggtgtagatt ctgcaatctt   2820
agatcctcgc gatacttacg cagataaagc acaatggcaa tcaaaagctg aagacttagc   2880
aggtcgtttt gtgaaaaact tgttaaaata tgcaactaac gaagaaggca aagctttaat   2940
tgcagctggt cctaaagctt aatctagaaa gcttcctaga ggcatcaaat aaaacgaaag   3000
```

```
gctcagtcga aagactgggc ctttcgtttt atctgttgtt tgtcggtgaa cgctctcctg    3060
agtaggacga attcacttct gttctaacac cctcgttttc aatatatttc tgtctgcatt    3120
ttattcaaat tctgaatata ccttcagata tccttaagga attgtcgtta cattcggcga    3180
tattttttca agacaggttc ttactatgca ttccacagaa gtccaggcta aacctctttt    3240
tagctggaaa gccctgggtt gggcactgct ctacttttgg ttttctctca ctctgctaca    3300
ggccattatt tacatcagtg gttatagtgg cactaacggc attcgcgact cgctgttatt    3360
cagttcgctg tggttgatcc cggtattcct ctttccgaag cggattaaaa ttattgccgc    3420
agtaatcggc gtggtgctat gggcggcctc tctggcggcg ctgtgctact acgtcatcta    3480
cggtcaggag ttctcgcaga gcgttctgtt tgtgatgttc gaaaccaaca ccaacgaagc    3540
cagcgagtat ttaagccagt atttcagcct gaaaattgtg cttatcgcgc tggcctatac    3600
ggcggtggca gttctgctgt ggacacgcct gcgcccggtc tatattccaa agccgtggcg    3660
ttatgttgtc tcttttgccc tgctttatgg cttgattctg catccgatcg ccatgaatac    3720
gtttatcaaa acaagccgt ttgagaaaac gttggataac ctggcctcgc gtatggagcc    3780
tgccgcaccg tggcaattcc tgaccggcta ttatcagtat cgtcagcaac taaactcgct    3840
aacaaagtta ctgaatgaaa ataatgcctt gccgccactg gctaatttca agatgaatc    3900
gggtaacgaa ccgcgcactt tagtgctggt gattggcgag tcgacccagc gcggacgcat    3960
gagtctgtac ggttatccgc gtgaaaccac gccggagctg gatgcgctgc ataaaaccga    4020
tccgaatctg accgtgttta ataacgtagt tacgtctcgt ccgtacacca ttgaaatcct    4080
gcaacaggcg ctgacctttg ccaatgaaaa gaacccggat ctgtatctga cgcagccgtc    4140
gctgatgaac atgatgaaac aggcgggtta taaaaccttc                         4180
```

<210> SEQ ID NO 86
<211> LENGTH: 4960
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

```
aataggcgta tcacgaggcc ctttcgtctt cacctcgaga attgtgagcg gataacaatt      60
gacattgtga gcggataaca agatactgag cacatcagca ggacgcactg accgaattca     120
attaagctag caagaggaga agtcgagatg aacttacatg aatatcaggc aaaacaactt     180
tttgcccgct atggcttacc agcaccggtg ggttatgcct gtactactcc gcgcgaagca     240
gaagaagccg cttcaaaaat cggtgccggt ccgtgggtag tgaaatgtca ggttcacgct     300
ggtggccgcg gtaaagcggg cggtgtgaaa gttgtaaaca gcaaagaaga catccgtgct     360
tttgcagaaa actggctggg caagcgtctg gtaacgtatc aaacagatgc caatggccaa     420
ccggttaacc agattctggt tgaagcagcg accgatatcg ctaaagagct gtatctcggt     480
gccgttgttg accgtagttc ccgtcgtgtg gtctttatgg cctccaccga aggcggcgtg     540
gaaatcgaaa agtggcggaa agaaactccg cacctgatcc ataagttgc gcttgatccg     600
ctgactggcc cgatgccgta tcagggacgc gagctggcgt tcaaactggg tctggaaggt     660
aaactggttc agcagttcac caaaatcttc atgggcctgg cgaccatttt cctggagcgc     720
gacctggcgt tgatcgaaat caaccccgctg gtcatcacca aacagggcga tctgatttgc     780
ctcgacggca aactgggcgc tgacggcaac gcactgttcc gccagcctga tctgcgcgaa     840
```

-continued

```
atgcgtgacc agtcgcagga agatccgcgt gaagcacagg ctgcacagtg ggaactgaac    900
tacgttgcgc tggacggtaa catcggttgt atggttaacg gcgcaggtct ggcgatgggt    960
acgatggaca tcgttaaact gcacggcggc gaaccggcta acttccttga cgttggcggc   1020
ggcgcaacca aagaacgtgt aaccgaagcg ttcaaaatca tcctctctga cgacaaagtg   1080
aaagccgttc tggttaacat cttcggcggt atcgttcgtt gcgacctgat cgctgacggt   1140
atcatcggcg cggtagcaga agtgggtgtt aacgtaccgg tcgtggtacg tctggaaggt   1200
aacaacgccg aactcggcgc gaagaaactg gctgacagcg gcctgaatat tattgcagca   1260
aaaggtctga cggatgcagc tcagcaggtt gttgccgcag tggagggaa ataatgtcca   1320
ttttaatcga taaaaacacc aaggttatct gccagggctt taccggtagc caggggactt   1380
tccactcaga acaggccatt gcatacggca ctaaaatggt tggcggcgta accccaggta   1440
aaggcggcac cacccacctc ggcctgccgg tgttcaacac cgtgcgtgaa gccgttgctg   1500
ccactggcgc taccgcttct gttatctacg taccagcacc gttctgcaaa gactccattc   1560
tggaagccat cgacgcaggc atcaaactga ttatcaccat cactgaaggc atcccgacgc   1620
tggatatgct gaccgtgaaa gtgaagctgg atgaagcagg cgttcgtatg atcggcccga   1680
actgcccagg cgttatcact ccgggtgaat gcaaaatcgg tatccagcct ggtcacattc   1740
acaaaccggg taaagtgggt atcgtttccc gttccggtac actgacctat gaagcggtta   1800
aacagaccac ggattacggt ttcggtcagt cgacctgtgt cggtatcggc ggtgacccga   1860
tcccgggctc taactttatc gacattctcg aaatgttcga aaagatccg cagaccgaag   1920
cgatcgtgat gatcggtgag atcggcggta gcgctgaaga agaagcagct gcgtacatca   1980
aagagcacgt taccaagcca gttgtgggtt acatcgctgg tgtgactgcg ccgaaaggca   2040
aacgtatggg ccacgcgggt gccatcattg ccggtgggaa agggactgcg gatgagaaat   2100
tcgctgctct ggaagccgca ggcgtgaaaa ccgttcgcag cctggcggat atcggtgaag   2160
cactgaaaac tgttctgaaa taatctagca agaggagaag tcgacatgga aatcaaagaa   2220
atggtgagcc ttgcacgcaa ggctcagaag gagtatcaag ctacccataa ccaagaagca   2280
gttgacaaca tttgccgagc tgcagcaaaa gttatttatg aaaatgcagc tattctggct   2340
cgcgaagcag tagacgaaac cggcatgggc gtttacgaac acaaagtggc caagaatcaa   2400
ggcaaatcca aggtgtttg gtacaacctc cacaataaaa aatcgattgg tatcctcaat   2460
atagacgagc gtaccggtat gatcgagatt gcaaagccta tcggagttgt aggagccgta   2520
acgccgacga ccaacccgat cgttactccg atgagcaata tcatctttgc tcttaagacc   2580
tgcaatgcca tcattattgc cccccacccc agatccaaaa aatgctctgc acacgcagtt   2640
cgtctgatca aagaagctat cgctccgttc aacgtaccgg aaggtatggt tcagatcatc   2700
gaagaaccca gcatcgagaa gacgcaggaa ctcatgggcg ccgtagacgt agtagttgct   2760
acgggtggta tgggcatggt gaagtctgca tattcttcag gaaagccttc tttcggtgtt   2820
ggagccggta acgttcaggt gatcgtggat agcaacatcg atttcgaagc tgctgcagaa   2880
aaaatcatca ccggtcgtgc tttcgacaac ggtatcatct gctcaggcga acagagcatc   2940
atctacaacg aggctgacaa ggaagcagtt ttcacagcat tccgcaacca cggtgcatat   3000
ttctgtgacg aagccgaagg agatcgggct cgtgcagcta tcttcgaaaa tggagccatc   3060
gcgaaagatg tagtaggtca gagcgttgcc ttcattgcca agaaagcaaa catcaatatc   3120
cccgagggta cccgtattct cgttgttgaa gctcgcggcg taggagcaga agacgttatc   3180
```

| | |
|---|---|
| tgtaaggaaa agatgtgtcc cgtaatgtgc gccctcagct acaagcactt cgaagaaggt | 3240 |
| gtagaaatcg cacgtacgaa cctcgccaac gaaggtaacg gccacacctg tgctatccac | 3300 |
| tccaacaatc aggcacacat catcctcgca ggatcagagc tgacggtatc tcgtatcgta | 3360 |
| gtgaatgctc cgagtgccac tacagcaggc ggtcacatcc aaaacggtct tgccgtaacc | 3420 |
| aatacgctcg gatgcggatc atggggtaat aactctatct ccgagaactt cacttacaag | 3480 |
| cacctcctca acatttcacg catcgcaccg ttgaattcaa gcattcacat ccccgatgac | 3540 |
| aaagaaatct gggaactcta atctagcaag aggagaagtc gacatgcaac ttttcaaact | 3600 |
| caagagtgta acacatcact ttgacacttt tgcagaattt gccaaggaat tctgtcttgg | 3660 |
| agaacgcgac ttggtaatta ccaacgagtt catctatgaa ccgtatatga aggcatgcca | 3720 |
| gctcccctgc cattttgtta tgcaggagaa atatgggcaa ggcgagcctt ctgacgaaat | 3780 |
| gatgaataac atcttggcag acatccgtaa tatccagttc gaccgcgtaa tcggtatcgg | 3840 |
| aggaggtacg gttattgaca tctctaaact tttcgttctg aaaggattaa atgatgtact | 3900 |
| cgatgcattc gaccgcaaaa tacctcttat caaagagaaa gaactgatca ttgtgcccac | 3960 |
| aacatgcgga acgggtagcg aggtgacgaa catttctatc gcagaaatca aaagccgtca | 4020 |
| caccaaaatg ggattggctg acgatgccat tgttgcagac catgccatca tcatacctga | 4080 |
| acttctgaag agcttgcctt tccacttcta cgcatgcagt gcaatcgatg ctcttatcca | 4140 |
| tgccatcgag tcatacgtat ctcctaaagc cagtccatat tctcgtctgt tcagtgaggc | 4200 |
| ggcttgggac attatcctgg aagtattcaa gaaaatcgcc gaacacggcc ctgaataccg | 4260 |
| cttcgaaaag ctgggagaaa tgatcatggc cagcaactat gccggtatag ccttcggaaa | 4320 |
| tgcaggagta ggagccgtcc acgcactatc ctaccgttg ggaggcaact atcacgtgcc | 4380 |
| gcatggagaa gcaaactatc agttcttcac agaggtattc aaagtatacc aaagaagaa | 4440 |
| tcctttcggc tatatagtcg aactcaactg gaagctctcc aagatactga actgccagcc | 4500 |
| cgaatacgta tatccgaagc tggatgaact tctcggatgc cttcttacca agaaaccttt | 4560 |
| gcacgaatac ggcatgaagg acgaagaggt aagaggcttt gcggaatcag tgcttaagac | 4620 |
| acagcaaaga ttgctcgcca caactacgt agagcttact gtagatgaga tcgaaggtat | 4680 |
| ctacagaaga ctctactaat ctagaaagct tcctagaggc atcaaataaa acgaaggct | 4740 |
| cagtcgaaag actgggcctt tcgttttatc tgttgtttgt cggtgaacgc tctcctgagt | 4800 |
| aggacaaatc cgccgcccta gacctaggcg ttcggctgcg acacgtcttg agcgattgtg | 4860 |
| taggctggag ctgcttcgaa gttcctatac tttctagaga ataggaactt cggaatagga | 4920 |
| actaaggagg atattcatat ggaccatggc taattcccat | 4960 |

<210> SEQ ID NO 87
<211> LENGTH: 5083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

| | |
|---|---|
| tcgagaaatt tatcaaaaag agtgttgact tgtgagcgga taacaatgat acttagattc | 60 |
| aattgtgagc ggataacaat ttcacacaga attcaattaa gctagcaaga ggagaagtcg | 120 |
| acatggccaa cataagttca ccattcgggc aaaacgaatg gctggttgaa gagatgtacc | 180 |
| gcaagttccg cgacgacccc tcctcggtcg atcccagctg gcacgagttc ctggttgact | 240 |

```
acagcccga  acccacctcc  caaccagctg  ccgaaccaac  ccgggttacc  tcgccactcg    300
ttgccgagcg  ggccgctgcg  gccgccccgc  aggcacccc   caagccggcc  gacaccgcgg    360
ccgcgggcaa  cggcgtggtc  gccgcactgg  ccgccaaaac  tgccgttccc  ccgccagccg    420
aaggtgacga  ggtagcggtg  ctgcgcggcc  ccgccgcggc  cgtcgtcaag  aacatgtccg    480
cgtcgttgga  ggtgccgacg  gcgaccagcg  tccgggcggt  cccggccaag  ctactgatcg    540
acaaccggat  cgtcatcaac  aaccagttga  agcggaccg   cggcggcaag  atctcgttca    600
cgcatttgct  gggctacgcc  ctggtgcagg  cggtgaagaa  attcccgaac  atgaaccggc    660
actacaccga  agtcgacggc  aagcccaccg  cggtcacgcc  ggcgcacacc  aatctcggcc    720
tggcgatcga  cctgcaaggc  aaggacggga  agcgttccct  ggtggtggcc  ggcatcaagc    780
ggtgcgagac  catgcgattc  gcgcagttcg  tcacggccta  cgaagacatc  gtacgccggg    840
cccgcgacgg  caagctgacc  actgaagact  ttgccggcgt  gacgatttcg  ctgaccaatc    900
ccggaaccat  cggcaccgtg  cattcggtgc  cgcggctgat  gcccggccag  ggcgccatca    960
tcggcgtggg  cgccatggaa  taccccgccg  agtttcaagg  cgccagcgag  gaacgcatcg   1020
ccgagctggg  catcggcaaa  ttgatcactt  tgacctccac  ctacgaccac  cgcatcatcc   1080
agggcgcgga  atcgggcgac  ttcctgcgca  ccatccacga  gttgctgctc  tcggatggct   1140
tctgggacga  ggtcttccgc  gaactgagca  tcccatatct  gccggtgcgc  tggagcaccg   1200
acaaccccga  ctcgatcgtc  gacaagaacg  ctcgcgtcat  gaacttgatc  gcggcctacc   1260
gcaaccgcgg  ccatctgatg  gccgataccg  acccgctgcg  gttggacaaa  gctcggttcc   1320
gcagtcaccc  cgacctcgaa  gtgctgaccc  acggcctgac  gctgtgggat  ctcgatcggg   1380
tgttcaaggt  cgacggcttt  gccggtgcgc  agtacaagaa  actgcgcgac  gtgctgggct   1440
tgctgcgcga  tgcctactgc  cgccacatcg  gcgtggagta  cgcccatatc  ctcgaccccg   1500
aacaaaagga  gtggctcgaa  caacgggtcg  agaccaagca  cgtcaaaccc  actgtggccc   1560
aacagaaata  catcctcagc  aagctcaacg  ccgccgagcc  ctttgaaacg  ttcctacaga   1620
ccaagtacgt  cggccagaag  cggttctcgc  tggaaggcgc  cgaaagcgtg  atcccgatga   1680
tggacgcggc  gatcgaccag  tgcgctgagc  acggcctcga  cgaggtggtc  atcgggatgc   1740
cgcaccgggg  ccggctcaac  gtgctggcca  acatcgtcgg  caagccgtac  tcgcagatct   1800
tcaccgagtt  cgagggcaac  ctgaatccgt  cgcaggcgca  cggctccggt  gacgtcaagt   1860
accacctggg  cgccaccggg  ctgtacctgc  agatgttcgg  cgacaacgac  attcaggtgt   1920
cgctgaccgc  caacccgtcg  catctggagg  ccgtcgaccc  ggtgctggag  ggattggtgc   1980
gggccaagca  ggatctgctc  gaccacggaa  gcatcgacag  cgacggccaa  cgggcgttct   2040
cggtggtgcc  gctgatgttg  catggcgatg  ccgcgttcgc  cggtcagggt  gtggtcgccg   2100
agacgctgaa  cctggcgaat  ctgccgggct  accgcgtcgg  cggcaccatc  cacatcatcg   2160
tcaacaacca  gatcggcttc  accaccgcgc  ccgagtattc  caggtccagc  gagtactgca   2220
ccgacgtcgc  aaagatgatc  ggggcaccga  tctttcacgt  caacggcgac  gacccggagg   2280
cgtgtgtctg  ggtggcgcgg  ttggcggtgg  acttccgaca  acggttcaag  aaggacgtcg   2340
tcatcgacat  gctgtgctac  cgccgccgcg  ggcacaacga  gggtgacgac  ccgtcgatga   2400
ccaaccccta  catgtacgac  gtcgtcgaca  ccaagcgcgg  ggcccgcaaa  agctacaccg   2460
aagccctgat  cggacgtggc  gacatctcga  tgaaggaggc  cgaggacgcg  ctgcgcgact   2520
accagggcca  gctggaacgg  gtgttcaacg  aagtgcgcga  gctggagaag  cacgtgtgtc   2580
agccgagcga  gtcggtcgag  tccgaccaga  tgattcccgc  ggggctggcc  actgcggtgg   2640
```

```
acaagtcgct gctggcccgg atcggcgatg cgttcctcgc cttgccgaac ggcttcaccg    2700
cgcacccgcg agtccaaccg gtgctggaga agcgccggga gatggcctat gaaggcaaga    2760
tcgactgggc ctttggcgag ctgctggcgc tgggctcgct ggtggccgaa ggcaagctgg    2820
tgcgcttgtc ggggcaggac agccgccgcg gcaccttctc ccagcggcat tcggttctca    2880
tcgaccgcca cactggcgag gagttcacac cactgcagct gctggcgacc aactccgacg    2940
gcagcccgac cggcggaaag ttcctggtct acgactcgcc actgtcggag tacgccgccg    3000
tcggcttcga gtacggctac actgtgggca atccggacgc cgtggtgctc tgggaggcgc    3060
agttcggcga cttcgtcaac ggcgcacagt cgatcatcga cgagttcatc agctccggtg    3120
aggccaagtg gggccaattg tccaacgtcg tgctgctgtt accgcacggg cacgaggggc    3180
agggaccccga ccacacttct gcccggatcg aacgcttctt gcagttgtgg gcggaaggtt    3240
cgatgaccat cgcgatgccg tcgactccgt cgaactactt ccacctgcta cgccggcatg    3300
ccctggacgg catccaacgc ccgctgatcg tgttcacgcc caagtcgatg ttgcgtcaca    3360
aggccgccgt cagcgaaatc aaggacttca ccgagatcaa gttccgctca gtgctggagg    3420
aacccaccta tgaggacggc atcggagacc gcaacaaggt cagccggatc ctgctgacca    3480
gtggcaagct gtattacgag ctggccgccc gcaaggccaa ggacaaccgc aatgacctcg    3540
cgatcgtgcg gcttgaacag ctcgccccgc tgcccaggcg tcgactgcgt gaaacgctgg    3600
accgctacga gaacgtcaag gagttcttct gggtccaaga ggaaccggcc aaccagggtg    3660
cgtggccgcg attcgggctc gaactacccg agctgctgcc tgacaagttg gccgggatca    3720
agcgaatctc gcgccgggcg atgtcagccc cgtcgtcagg ctcgtcgaag gtgcacgccg    3780
tcgaacagca ggagatcctc gacgaggcgt tcggctaatc tagcaagagg agaagtcgac    3840
atgaagttat taaaattggc acctgatgtt tataaatttg atactgcaga ggagtttatg    3900
aaatacttta aggttggaaa aggtgacttt atacttacta atgaattttt atataaacct    3960
ttccttgaga aattcaatga tggtgcagat gctgtatttc aggagaaata tggactcggt    4020
gaaccttctg atgaaatgat aaacaatata attaaggata ttggagataa acaatataat    4080
agaattattg ctgtaggggg aggatctgta atagatatag ccaaaatcct cagtcttaag    4140
tatactgatg attcattgga tttgtttgag ggaaaagtac ctcttgtaaa aaacaaagaa    4200
ttaattatag ttccaactac atgtggaaca ggttcagaag ttacaaatgt atcagttgca    4260
gaattaaaga aagacatac  taaaaaagga attgcttcag acgaattata tgcaacttat    4320
gcagtacttg taccagaatt tataaaagga cttccatata agttttttgt aaccagctcc    4380
gtagatgcct aatacatgc  aacagaagct tatgtatctc caaatgcaaa tccttatact    4440
gatatgttta gtgtaaaagc tatggagtta attttaaatg gatacatgca aatggtagag    4500
aaaggaaatg attacagagt tgaaataatt gaggattttg ttataggcag caattatgca    4560
ggtatagctt ttgaaaatgc aggagtggga gcggttcacg cactctcata tccaataggc    4620
ggaaattatc atgtgcctca tggagaagca aattatctgt tttttacaga aatatttaaa    4680
acttattatg agaaaaatcc aaatggcaag attaagatg  taaataaact attagcaggc    4740
atactaaaat gtgatgaaag tgaagcttat gacagtttat cacaactttt agataaatta    4800
ttgtcaagaa aaccattaag agaatatgga atgaaagagg aagaaattga acttttgct   4860
gattcagtaa tagaaggaca gcagagactg ttggtaaaca attatgaacc ttttcaagaa    4920
gaagacatag taaacacata taaaaagtta tattaatcta gaaagcttcc tagaggcatc    4980
```

```
aaataaaacg aaaggctcag tcgaaagact gggcctttcg ttttatctgt tgtttgtcgg    5040
tgaacgctct cctgagtagg acaaatccgc cgccctagac cta                      5083

<210> SEQ ID NO 88
<211> LENGTH: 5097
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
tctgtatcag gctgaaaatc ttctctcatc cgccaaaaca gcttcggcgt taagatgcgc      60
gctcaaggac gtaagccgtc gactctcgcc gtgctggcgc aggacacggc taccactcct     120
ttctctgttg atattctgct tgccattgag caaaccgcca gcgagttcgg ctggaatagt     180
tttttaatca atattttttc tgaagatgac gctgcccgcg cggcacgtca gctgcttgcc     240
caccgtccgg atggcattat ctatactaca atggggctgc gacatatcac gctgcctgag     300
tctctgtatg gtgaaaatat tgtattggcg aactgtgtgg cggatgaccc agcgttaccc     360
agttatatcc ctgatgatta cactgcacaa tatgaatcaa cacagcattt gctcgcggcg     420
ggctatcgtc aaccgttatg cttctggcta ccggaaagtg cgttggcaac agggtatcgt     480
cggcagggat ttgagcaggc ctggcgtgat gctggacgag atctggctga ggtgaaacaa     540
tttcacatgg caacaggtga tgatcactac accgatctcg caagtttact caatgcccac     600
ttcaaaccgg gcaaaccaga ttttgatgtt ctgatatgtg gtaacgatcg cgcagccttt     660
gtggcttatc aggttcttct ggcgaagggg gtacgaatcc cgcaggatgt cgccgtaatg     720
ggctttgata tctggttggc gtcgggcat ctgttttta cgccgctgac cacaattcag     780
cttccacatg acattatcgg gcgggaagct gcattgcata ttattgaagg tcgtgaaggg     840
ggaagagtga cgcggatccc ttgcccgctg ttgatccgtt gttccacctg atattatgtt     900
aacccagtag ccagagtgct ccatgttgca gcacagccac tccgtgggag gcataaagcg     960
acagttcccg ttcttctggc tgcggataga ttcgactact catcaccgct tcccgtcgt    1020 taataaatac ttccacggat gatgtatcga taaatatcct tagggcgagc gtgtcacgct    1080
gcgggagggg aatactacgg tagccgtcta aattctcgtg tgggtaatac cgccacaaaa    1140
caagtcgctc agattggtta tcaatataca gccgcattcc agtgccgagc tgtaatccgt    1200
aatgttcggc atcactgttc ttcagcgccc actgcaactg aatctcaact gcttgcgcgt    1260
tttcctgcaa aacatattta ttgctgattg tgcgggaga cagattga tgctgctggc    1320 gtaacgactc agcttcgtgt accgggcgtt gtagaagttt gccattgctc tctgatagct    1380
cgcgcgccag cgtcatgcag cctgcccatc cttcacgttt tgagggcatt ggcgattccc    1440
acatatccat ccagccgata caatacgcc gaccatcctt cgctaaaaag ctttgtggtg    1500
cataaaagtc atgcccgtta tcaagttcag taaaatgccc ggattgtgca aaaagtcgtc    1560
ctggcgacca cattccgggt attacgccac tttgaaagcg atttcggtaa ctgtatccct    1620
cggcattcat tccctgcggg gaaaacatca gataatgctg atcgccaagg ctgaaaaagt    1680
ccggacattc ccacatatag ctttcacccg catcagcgtg ggccagtacg cgatcgaagg    1740
tccattcacg caacgaactg ccgcgataaa gcaggatctg ccccgtgttg cctggatctt    1800
tcgccccgac taccatccac catgtgtcgg cttcacgcca cactttagga tcgcggaagt    1860
gcatgattcc ttctggtgga gtgaggatca caccctgttt ctcgaaatga ataccatccc    1920
```

```
gactggtagc cagacattgt acttcgcgaa ttgcatcgtc attacctgca ccatcgagcc    1980
agacgtgtcc ggtgtagata agtgagagga caccattgtc atcgacagca ctacctgaaa    2040
aacacccgtc tttgtcatta tcgtctcctg gcgctagcgc aataggctca tgctgccagt    2100
ggatcatatc gtcgctggtg gcatgtcccc agtgcattgg ccccccagtgt tcgctcatcg    2160
gatgatgttg ataaaacgcg tgataacgat cgttaaacca gatcaggccg tttggatcgt    2220
tcatccaccc ggcaggaggc gcgaggtgaa aatggggata gaaagtgtta ccccggtgct    2280
catgaagttt tgctagggcg ttttgcgccg catgcaatcg agattgcgtc attttaatca    2340
tcctggttaa gcaaatttgg tgaattgtta acgttaactt ttataaaaat aaagtccctt    2400
actttcataa atgcgatgaa tatcacaaat gttaacgtta actatgacgt tttgtgatcg    2460
aatatgcatg ttttagtaaa tccatgacga ttttgcgaaa aagaggttta tcactatgcg    2520
taactcagat gaatttaagg gaaaaaaatg tcagccaaag tatgggtttt aggggatgcg    2580
gtcgtagatc tcttgccaga atcagacggg cgcctactgc cttgtcctgg cggcgcgcca    2640
gctaacgttg cggtgggaat cgccagatta ggcggaacaa gtgggtttat aggtcgggtg    2700
ggggatgatc cttttggtgc gttaatgcaa agaacgctgc taactgaggg agtcgatatc    2760
acgtatctga agcaagatga atggcaccgg acatccacgg tgcttgtcga tctgaacgat    2820
caaggggaac gttcatttac gtttatggtc cgccccagtg ccgatctttt tttagagacg    2880
acagacttgc cctgctggcg acatggcgaa tggttacatc tctgttcaat tgcgttgtct    2940
gccgagcctt cgcgtaccag cgcatttact gcgatgacgg cgatccggca tgccggaggt    3000
tttgtcagct tcgatcctaa tattcgtgaa gatctatggc aagacgagca tttgctccgc    3060
ttgtgtttgc ggcaggcgct acaactggcg gatgtcgtca agctctcgga agaagaatgg    3120
cgacttatca gtgaaaaaac acagaacgat caggatatat gcgccctggc aaaagagtat    3180
gagatcgcca tgctgttggt gactaaaggt gcagaagggg tggtggtctg ttatcgagga    3240
caagttcacc attttgctgg aatgtctgtg aattgtgtcg atagcacggg ggcgggagat    3300
gcgttcgttg ccgggttact cacaggtctg tcctctacgg gattatctac agatgagaga    3360
gaaatgcgac gaattatcga tctcgctcaa cgttgcggag cgcttgcagt aacggcgaaa    3420
ggggcaatga cagcgctgcc atgtcgacaa gaactggaat agtgagaagt aaacggcgaa    3480
gtcgctctta tctctaaata ggacgtgaat tttttaacga caggcaggta attatggcac    3540
tgaatattcc attcagaaat gcgtactatc gttttgcatc cagttactca tttctctttt    3600
ttatttcctg gtcgctgtgg tggtcgttat acgctatttg gctgaaagga catctagggt    3660
tgacagggac ggaattaggt acactttatt cggtcaacca gtttaccagc attctattta    3720
tgatgttcta cggcatcgtt caggataaac tcggtctgaa gaaaccgctc atctggtgta    3780
tgagtttcat cctggtcttg accggaccgt ttatgattta cgtttatgaa ccgttactgc    3840
aaagcaattt ttctgtaggt ctaattctgg gggcgctatt ttttggcttg ggtatctgg    3900
cgggatgcgg tttgcttgat agcttcaccg aaaaaatggc gcgaaatttt catttcgaat    3960
atggaacagc gcgcgcctgg ggatcttttg gctatgctat tggcgcgttc tttgccggca    4020
tattttttag tatcagtccc catatcaact tctggttggt ctcgctattt ggcgctgtat    4080
ttatgatgat caacatgcgt tttaaagata aggatcacca gtgcgtagcg gcagatgcgg    4140
gaggggtaaa aaaagaggat tttatcgcag ttttcaagga tcgaaacttc tgggttttcg    4200
tcatatttat tgtggggacg tggtcttttct ataacatttt tgatcaacaa cttttttcctg    4260
tcttttattc aggtttattc gaatcacacg atgtaggaac gcgcctgtat ggttatctca    4320
```

```
actcattcca ggtggtactc gaagcgctgt gcatggcgat tattcctttc tttgtgaatc    4380
gggtagggcc aaaaaatgca ttacttatcg gagttgtgat tatggcgttg cgtatccttt    4440
cctgcgcgct gttcgttaac ccctggatta tttcattagt gaagttgtta catgccattg    4500
aggttccact ttgtgtcata tccgtcttca aatacagcgt ggcaaacttt gataagcgcc    4560
tgtcgtcgac gatctttctg attggttttc aaattgccag ttcgcttggg attgtgctgc    4620
tttcaacgcc gactgggata ctctttgacc acgcaggcta ccagacagtt ttcttcgcaa    4680
tttcgggtat tgtctgcctg atgttgctat ttggcatttt cttcttgagt aaaaaacgcg    4740
agcaaatagt tatggaaacg cctgtaccct cagcaatata gacgtaaact tttccggtt    4800 gttgtcgata gctctatatc cctcaaccgg aaaataataa tagtaaaatg cttagccctg    4860
ctaataatcg cctaatccaa acgcctcatt catgttctgg tacagtcgct caaatgtact    4920
tcagatgcgc ggttcgctga tttccaggac attgtcgtca ttcagtgacc tgtcccgtgt    4980
atcacggtcc tgcgaattca tcaaggaatg cattgcggag tgaagtatcg agtcacgcca    5040
tatttcgtca cccgaagatg agttttgaga tattaaggca ggtgactttc actcaca      5097
```